(12) United States Patent
Wang et al.

(10) Patent No.: US 7,335,753 B2
(45) Date of Patent: Feb. 26, 2008

(54) BIFUNCTIONAL HETEROCYCLIC COMPOUNDS AND METHODS OF MAKING AND USING SAME

(75) Inventors: Deping Wang, West Haven, CT (US); Joyce A. Sutcliffe, Brandford, CT (US); Adegboyega K. Oyelere, Hamden, CT (US); Timothy S. McConnell, Cheshire, CT (US); Joseph A. Ippolito, Guilford, CT (US); John N. Abelson, Pasadena, CA (US); Dane M. Springer, Yardley, PA (US); Joseph M. Salvino, Branford, CT (US); Rongliang Lou, Cheshire, CT (US); Joel A. Goldberg, Milford, CT (US); Jay J. Farmer, New Haven, CT (US); Erin M. Duffy, Deep River, CT (US); Ashoke Bhattacharjee, West Haven, CT (US)

(73) Assignee: Rib-X Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 11/359,820

(22) Filed: Feb. 21, 2006

(65) Prior Publication Data

US 2006/0264385 A1    Nov. 23, 2006

Related U.S. Application Data

(63) Continuation of application No. 10/671,326, filed on Sep. 25, 2003, now Pat. No. 7,091,196.

(60) Provisional application No. 60/448,216, filed on Feb. 19, 2003, provisional application No. 60/414,207, filed on Sep. 26, 2002.

(51) Int. Cl.
*A61K 31/7052*   (2006.01)
*A61K 31/7048*   (2006.01)
*A61K 31/4709*   (2006.01)
*A61K 31/4176*   (2006.01)
*A61K 31/4192*   (2006.01)
*A61K 31/422*    (2006.01)
*C07H 17/08*     (2006.01)
*C07D 249/04*    (2006.01)
*C07D 261/04*    (2006.01)
*C07D 403/04*    (2006.01)
*C07D 215/06*    (2006.01)

(52) U.S. Cl. ............... 536/7.4; 514/28; 514/359; 514/314; 514/378; 546/152; 548/255; 548/314.7; 548/240

(58) Field of Classification Search ........... 514/183, 514/375, 236.2, 28, 359, 314, 397, 378; 540/467; 544/137; 548/218, 229, 232, 255, 314.7, 548/240; 546/152; 536/7.4
See application file for complete search history.

(56) References Cited

U.S. PATENT DOCUMENTS

| 3,629,232 | A  | 12/1971 | Jones ............... 260/210 E |
|---|---|---|---|
| 3,681,325 | A  | 8/1972  | Freiberg ............ 260/210 E |
| 4,404,201 | A  | 9/1983  | Haskell et al. ......... 424/246 |
| 4,546,176 | A  | 10/1985 | Machida et al. ........ 544/21 |
| 5,180,719 | A  | 1/1993  | White et al. .......... 514/192 |
| 5,215,980 | A  | 6/1993  | Jones ................. 514/183 |
| 5,232,918 | A  | 8/1993  | Arnould et al. ........ 514/202 |
| 5,281,703 | A  | 1/1994  | White et al. .......... 540/302 |
| 5,336,768 | A  | 8/1994  | Albrecht et al. ....... 540/222 |
| 5,444,051 | A  | 8/1995  | Agouridas et al. ....... 514/29 |
| 5,527,780 | A  | 6/1996  | Agouridas et al. ....... 514/29 |
| 5,543,400 | A  | 8/1996  | Agouridas et al. ....... 514/29 |
| 5,658,888 | A  | 8/1997  | Koga et al. ............ 514/29 |
| 5,693,791 | A  | 12/1997 | Truett ................. 540/222 |
| 5,747,467 | A  | 5/1998  | Agouridas et al. ....... 514/29 |
| 5,780,605 | A  | 7/1998  | Or et al. .............. 536/7.2 |
| 5,866,549 | A  | 2/1999  | Or et al. .............. 514/29 |
| 5,891,643 | A  | 4/1999  | Fesik et al. ........... 435/7.1 |
| 5,905,144 | A  | 5/1999  | Truett ................. 536/22.1 |
| 5,955,440 | A  | 9/1999  | Sauer et al. ........... 514/29 |
| 6,020,521 | A  | 2/2000  | Randolph et al. ....... 560/205 |
| 6,034,069 | A  | 3/2000  | Or et al. .............. 514/29 |
| 6,274,715 | B1 | 8/2001  | Or et al. .............. 536/7.4 |
| 6,288,055 | B1 | 9/2001  | Natarajan et al. ...... 514/210.2 |
| 6,288,234 | B1 | 9/2001  | Griffin ................ 546/190 |
| 6,355,805 | B1 | 3/2002  | Choi et al. ............ 546/301 |
| 6,355,810 | B1 | 3/2002  | Griffin et al. ......... 548/547 |
| 6,362,371 | B1 | 3/2002  | Moran et al. .......... 564/365 |
| 6,395,724 | B1 | 5/2002  | Judice et al. .......... 514/183 |
| 6,420,354 | B1 | 7/2002  | Marquess et al. ....... 514/183 |
| 6,437,119 | B1 | 8/2002  | Truett ................. 540/215 |
| 6,446,032 | B1 | 9/2002  | Schimmel .............. 703/11 |

(Continued)

FOREIGN PATENT DOCUMENTS

DE    196 04 223    8/1997

(Continued)

OTHER PUBLICATIONS

Jones, P.H., and Powley, E.K., "Chemical Modifications of Erythromycin Antibiotics. I. 3'-De(dimethylamino)erythromycin A and B," J. Org. Chem., 33:665-670 (1968).

(Continued)

*Primary Examiner*—Rebecca Anderson
*Assistant Examiner*—Yong Chu
(74) *Attorney, Agent, or Firm*—Ivor R. Elrifi; Heidi A. Erlacher; Mintz Levin Cohn Ferris Glovsky and Popeo PC

(57) ABSTRACT

The invention provides a family of bifunctional heterocyclic compounds useful as anti-infective, anti-proliferative, anti-inflammatory, and prokinetic agents. The invention also provides methods of making the bifunctional heterocyclic compounds, and methods of using such compounds as anti-infective, anti-proliferative agents, anti-inflammatory, and/or prokinetic agents.

21 Claims, No Drawings

U.S. PATENT DOCUMENTS

| | | | |
|---|---|---|---|
| 6,468,979 B1 | 10/2002 | Pellacini et al. | 514/29 |
| 6,479,498 B1 | 11/2002 | Marquess et al. | 514/256 |
| 6,566,509 B1 | 5/2003 | Griffin et al. | 536/7.4 |
| 6,576,615 B2 | 6/2003 | Phan et al. | 514/30 |
| 6,664,240 B2 | 12/2003 | Phan et al. | 514/30 |
| 6,710,034 B2 | 3/2004 | Phan et al. | 514/30 |
| 6,753,415 B2 | 6/2004 | Phan et al. | 536/7.1 |
| 6,878,691 B2 | 4/2005 | Or et al. | 514/29 |
| 7,022,705 B2 * | 4/2006 | Betts | 514/252.05 |
| 7,091,196 B2 * | 8/2006 | Wang et al. | 514/183 |
| 7,129,221 B2 | 10/2006 | Or et al. | 514/28 |
| 2002/0028943 A1 | 3/2002 | Griffin | 546/223 |
| 2003/0092639 A1 | 5/2003 | Phan et al. | 514/28 |
| 2003/0096764 A1 | 5/2003 | Phan et al. | 514/28 |
| 2003/0158093 A1 | 8/2003 | Sun et al. | 514/8 |
| 2003/0176670 A1 | 9/2003 | Griffin et al. | 536/7.4 |
| 2003/0176848 A1 | 9/2003 | Gibson et al. | 604/500 |
| 2003/0181399 A1 | 9/2003 | Wong et al. | 514/35 |
| 2003/0203858 A1 | 10/2003 | Phan et al. | 514/28 |
| 2003/0212010 A1 | 11/2003 | Phan et al. | 514/28 |
| 2004/0014685 A1 | 1/2004 | Mercep et al. | 514/26 |
| 2004/0077612 A1 | 4/2004 | Mercep et al. | 514/175 |
| 2004/0097434 A1 | 5/2004 | Mercep et al. | 514/28 |
| 2004/0157787 A1 | 8/2004 | Or et al. | 514/28 |
| 2004/0235760 A1 | 11/2004 | Phan et al. | 514/28 |
| 2005/0020823 A1 | 1/2005 | Phan et al. | 536/7.1 |
| 2005/0153971 A1 * | 7/2005 | Chen et al. | 514/252.01 |
| 2005/0197334 A1 | 9/2005 | Wang et al. | 514/227.5 |
| 2006/0148869 A1 * | 7/2006 | Chen et al. | 514/376 |
| 2006/0264385 A1 | 11/2006 | Wang et al. | 514/28 |
| 2007/0149463 A1 | 6/2007 | Oyelere et al. | 514/28 |

FOREIGN PATENT DOCUMENTS

| | | |
|---|---|---|
| DE | 100 34 627 A1 | 1/2002 |
| EP | 0 215 355 B1 | 4/1994 |
| EP | 0 213 617 B1 | 8/1994 |
| EP | 0643068 B1 | 8/1998 |
| EP | 0 680 967 B1 | 10/1998 |
| EP | 0 895 999 A1 | 2/1999 |
| EP | 1 132 392 A1 | 9/2001 |
| WO | WO 92/17184 | 10/1992 |
| WO | WO 93/07154 | 4/1993 |
| WO | WO 93/24509 | 12/1993 |
| WO | WO 94/10185 | 5/1994 |
| WO | WO 95/07271 | 3/1995 |
| WO | WO 96/18633 | 6/1996 |
| WO | WO 97/35195 | 9/1997 |
| WO | WO 97/48713 A1 | 12/1997 |
| WO | WO 98/56800 | 12/1998 |
| WO | WO 98/56801 | 12/1998 |
| WO | WO 99/16779 A1 | 4/1999 |
| WO | WO 99/22722 A2 | 5/1999 |
| WO | WO 99/28308 | 6/1999 |
| WO | WO 99/33839 | 7/1999 |
| WO | WO 99/63937 A3 | 12/1999 |
| WO | WO 99/64032 | 12/1999 |
| WO | WO 99/64049 | 12/1999 |
| WO | WO 99/64416 | 12/1999 |
| WO | WO 99/64417 | 12/1999 |
| WO | WO 00/06606 | 2/2000 |
| WO | WO 00/21960 | 4/2000 |
| WO | WO 00/40589 | 7/2000 |
| WO | WO 00/42055 | 7/2000 |
| WO | WO 00/77016 | 12/2000 |
| WO | WO 01/40222 | 6/2001 |
| WO | WO 01/40236 A2 | 6/2001 |
| WO | WO 01/40238 A1 | 6/2001 |
| WO | WO 01/42242 | 6/2001 |
| WO | WO 01/58885 | 8/2001 |
| WO | WO 01/80863 A1 | 11/2001 |
| WO | WO 01/81350 | 11/2001 |
| WO | WO 02/051855 A2 | 7/2002 |
| WO | WO 02/060912 A1 | 8/2002 |
| WO | WO 02/080841 A2 | 10/2002 |
| WO | WO 02/081468 A1 | 10/2002 |
| WO | WO 02/081469 A1 | 10/2002 |
| WO | WO 02/081470 A1 | 10/2002 |
| WO | WO 02/096890 A2 | 12/2002 |
| WO | WO 02/096916 A1 | 12/2002 |
| WO | WO 03/022824 | 3/2003 |
| WO | WO 03/035073 | 5/2003 |
| WO | WO 03/035648 A1 | 5/2003 |
| WO | WO 03/042228 | 5/2003 |
| WO | WO 03/070173 A2 | 8/2003 |
| WO | WO 03/070174 A2 | 8/2003 |
| WO | WO 03/070254 | 8/2003 |
| WO | WO 03/072575 A1 | 9/2003 |
| WO | WO 2004/005309 A2 | 1/2004 |
| WO | WO 2004/005310 A2 | 1/2004 |
| WO | WO 2004/005313 A2 | 1/2004 |
| WO | WO 2004/013153 A2 | 2/2004 |
| WO | WO 2004/043984 | 5/2004 |
| WO | WO 2004/048392 A1 | 6/2004 |
| WO | WO 2004/056817 A1 | 7/2004 |
| WO | WO 2004/056818 A1 | 7/2004 |
| WO | WO 2004/056819 A1 | 7/2004 |
| WO | WO 2004/078770 A1 | 9/2004 |
| WO | WO 2004/080391 | 9/2004 |
| WO | WO 2004/094449 A1 | 11/2004 |
| WO | WO 2004/096221 A1 | 11/2004 |
| WO | WO 2004/108745 A2 | 12/2004 |
| WO | WO 2004/108746 A2 | 12/2004 |
| WO | WO 2005/030786 A1 | 4/2005 |
| WO | WO 2005/042554 A1 | 5/2005 |
| WO | WO 2005/049632 A1 | 6/2005 |
| WO | WO 2005/075494 A1 | 8/2005 |
| WO | WO 2005/085266 A2 | 9/2005 |

OTHER PUBLICATIONS

Stenmark, Heather G., et al., "Biomimetic Synthesis of Macrolide/Ketolide Metabolites through a Selective N-Demethylation Reaction," J. Org. Chem., 65:3875-3876 (2000).

Liang, Chang-Hsing, et al., "Synthesis and Biological Activity of New 5-O-Sugar Modifies Ketolide and 2-Fluoro-Ketolide Antibiotics," Bioorganic & Medicinal Chem, Letters, 15:1307-1310 (2005).

Costa et al. "Hybrids of macrolides and nucleobases or nucleosides" Tetrahedron Letters, vol. 41 (2000), pp. 3371-3375.

Denis et al. "Novel N-demethylation of ketolide : application to the solution phase parallel synthesis of n-desosaninyl-substituted ketolides using ion exchange resins" Tetrahedron Letters, vol. 43 (2002), pp. 4171-4174.

Faghih et al., "Synthesis of 9-Deoxo-4"-deoxy-6,9-epoxyerythromycin Derivatives: Novel and Acid-Stable Motilides," J. Med. Chem, 41: 3402-3408 (1998).

Hwang et al. "1,3-Dipolar cycloaddition of nitride oxides to 1-phenylsulfonyl-1,3-butadienes: synthesis of 3-(4,5-dihydroisoxazol-5-yl)pyrroles" Tetrahedron Lett., vol. 43 (2002), pp. 53-56.

International Search Report for International Application No. PCT/US03/30478, dated Jul. 13, 2004.

Akritopoulou-Zanze et al., "Synthesis and antibacterial activity of novel bifunctional macrolides," Bioorganic & Medicinal Chemistry Letters xxx (2004) xxx-xxx, Available online www.sciencedirect.com.

Hanessian et al., "Quantamycin: A Computer-Simulated New-Generation Inhibitor of Bacterial Ribosomal Binding," *J. Am Chem. Soc.*, 106:6114-6115 (1984).

Hecker et al., "Application of Hygromycin a Structure Activity Relationships to the Antibiotic A201A," *Bioorganic & Medicinal Chemistry Letters*, 3(2):295-298 (1993).

Holmes et al., "Novel Dimeric Penicillin Derived Inhibitors of HIV-I Proteinase: Interaction with the Catalytic Asparates," *Bioorganic & Medicinal Chemistry Letters*, 3(4):503-508 (1993).

Rao et al., "Tight Binding of a Dimeric Derivative of Vancomycin with Dimeric L-Lys-D-Ala-D-Ala," *J. Am Chem. Soc.* 119:10286-10290 (1997).

Shuker et al., "Discovering High-Affinity Ligands for Proteins: SAR by NMR," *Science*, 274 (5292):1531-1543 (2003).

Vince et al., "Chloramphenicol Binding Site with Analogues of Chloramphenicol and Puromycin," Antimicrobial Agents and Chemotherapy, 8(4):439-443 (1975).

Wang et al., "Dimeric Aminoglycosides: Design, Synthesis and RNA Binding," *Bioorganic & Medicinal Chemistry Letters*, 7(14):1951-1956 (1997).

Welch et al., "An Inhibitor of Ribosomal Peptidyl Transferase Using Transition-State Analogy," *Biochemistry*, 34(2): pp. 385-390 (1995).

Zemlicka et al., "Sparsophenicol: A New Synthetic Hybrid Antibiotic Inhibiting Ribosomal Peptide Synthesis," *J. Med. Chem.*, 25:1123-1125 (1982).

Zemlicka et al., "Hybrids of Antibiotics Inhibiting Protein Synthesis. Synthesis and Biological Activity," *J. Med. Chem.*, 36:1239-1244 (1993).

Mereu et al., "Design, synthesis and in vivo activity of 9-(S)-dihydroerythromycin derivatives as potent anti-inflammatory agents", *Bioorg. Med. Chem. Lett.*, 16:5801-5804 (2006).

Mutak et al., "Semisynthetic macrolide antibacterials derived from tylosin. Synthesis and structure-activity relationships of novel desmycosin analogues", *J. Med. Chem.*, 47(2):411-431 (2004).

Phan et al., "Synthesis and antibacterial activity of a novel class of 4'-substituted 16-membered ring macrolides derived from tylosin", *J. Med. Chem.*, 47(12):2965-2968 (2004).

Phillips et al., "Synthesis and antibacterial activity of 5-substituted oxazolidinones", *Bioorg. Med. Chem.*, 11:35-41 (2003).

Randolph et al., "Elimination of antibacterial activities of non-peptide luteinizing hormone-releasing hormone (LHRH) antagonists derived from erythromycin A", *Bioorg. Med. Chem. Lett.*, 14:1599-1602 (2004).

SciFinder Database entry for WO 93/24509, pp. 1-3 (2003).

SciFinder Database entry for WO 94/10185, pp. 1-3 (2003).

Brandt-Rauf et al., *Antimicrobial Agents and Chemotherapy*, p. 88-94 (Jul. 1978).

Gregory et al. *J. Med. Chem.*, 32:1673-1681 (1989).

* cited by examiner

BIFUNCTIONAL HETEROCYCLIC COMPOUNDS AND METHODS OF MAKING AND USING SAME

RELATED APPLICATIONS

This application is a continuation of U.S. application Ser. No. 10/671,326, filed Sep. 25, 2003, which issued as U.S. Pat. No. 7,091,196 B2 on Aug. 15, 2006, and which incorporates by reference and claims priority to U.S. Patent Application Nos. 60/414,207, filed Sep. 26, 2002, and 60/448,216 filed Feb. 19, 2003.

FIELD OF THE INVENTION

The present invention relates generally to the field of anti-infective, anti-proliferative, anti-inflammatory, and pro-kinetic agents, and more particularly, the invention relates to a family of bifunctional heterocyclic compounds useful as such an agent.

BACKGROUND

The evolution of strains of cells or organisms resistant to currently effective therapeutic agents is an ongoing medical problem. For example, the development of cancerous cells resistant to chemotherapeutic drugs has long been recognized as a problem in the oncology field. Once resistant cells develop, the therapeutic regime, in order to remain effective, must be modified to introduce other chemotherapeutic agents. Another example of this resistance problem is the development of strains of microbial, fungal, parasitic and viral pathogens resistant to one or more anti-infective agents. As a result, there is still a need for new anti-proliferative and anti-infective agents that are effective against strains of cells or organisms that have developed resistance to currently available agents.

In the field of anti-infective agents, a variety of different antibiotics have been developed and approved for use in humans over the years. An oxazolidinone ring containing antibiotic known as linezolid (see, compound 1), available under the trade name Zyvox®, has been approved for use as an anti-bacterial agent active against Gram-positive organisms. Unfortunately, linezolid resistant strains of organisms are already being reported (Tsiodras et al. (2001) LANCET 358: 207; Gonzales et al. (2001) LANCET 357: 1179; Zurenko et al. (1999) PROCEEDINGS OF THE 39$^{TH}$ ANNUAL INTERSCIENCE CONFERENCE ON ANTI-BACTERIAL AGENTS AND CHEMOTHERAPY (ICAAC); San Francisco, Calif., USA, September 26-29).

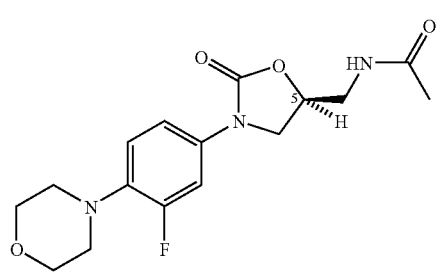

Because linezolid is both a clinically effective and commercially significant anti-microbial agent, investigators have been working to develop other effective linezolid derivatives. Research has indicated that the oxazolidinone ring is important for linezolid activity. The literature commonly describes molecules having small groups substituted at the C-5 of the oxazolidinone ring, and early structure-activity relationships suggested that compounds with larger groups at the C-5 position were less active as anti-bacterial agents. As a consequence, it is believed that, in general, investigators have been reluctant to place large substituents at the C-5 position of oxazolidinone rings in anti-microbial agents.

International patent publication no. WO 01/81350 discloses a series of C-5 substituted oxazolidinones (see, general structure 2) where the acetamido group of linezolid was replaced, for example, with an optionally substituted N-linked 5-membered heteroaryl ring or an N-linked 6-membered heteroaryl ring. The 5-membered heteroaryl ring may contain either (i) one to three further nitrogen heteroatoms, or (ii) a further heteroatom selected from O and S together with an optional further nitrogen heteroatom; wherein the ring is optionally substituted on a C-atom by an oxo or thioxo group; and/or is optionally substituted on a C-atom by one or two $C_{1-4}$ alkyl groups; and/or on an available nitrogen atom (provided that the ring is not thereby quaternized) by $C_{1-4}$ groups. The N-linked 6-membered heteroaryl ring may contain up to three nitrogen heteroatoms in total, wherein the ring is substituted on a suitable C-atom by oxo or thioxo groups, and optionally substituted on any available C-atom by one or two $C_{1-4}$ alkyl groups.

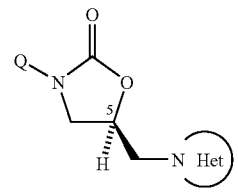

In addition, International patent publication nos. WO 99/64416 and WO 00/21960 also disclose a series of 5-substituted oxazolidiniones (see, general structure 3). In particular, WO 99/64416 discloses compounds having the general structure 3, where X is —O— or —S— and HET is a C-linked 6-membered heteroaryl ring containing 1 or 2 nitrogen atoms. WO 00/21960 discloses compounds having the general structure 3, where X is —N(H)— and HET is a C-linked 5-membered heteroaryl ring containing 2 to 4 heteroatoms independently selected from N, O and S.

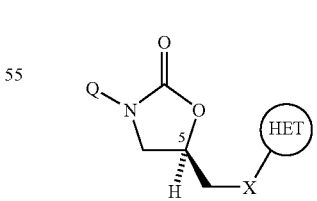

European Patent no. 0 097 469 B1 discloses intermediates of compound 4 which are useful in the synthesis of triazole anti-fungal agents of general structure 5. The intermediates may contain a disubstituted C-5 atom in the oxazolidinone ring, and the nitrogen atom of the oxazolidinone ring is a secondary amine.

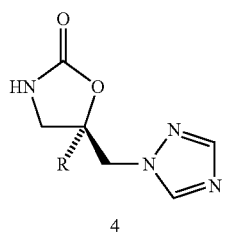

4

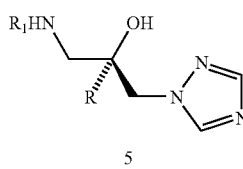

5

Gregory and coworkers disclose the synthesis of a variety of oxazolidinone containing antibacterial agents (Gregory et al. (1989) J. MED. CHEM. 32: 1673-1681). Compound 6, a C-5 substituted five-membered heteroaryl derivative, was inactive as an antibacterial agent. This observation appears to be consistent with other oxazolidinone containing compounds that have the opposite stereochemical configuration at C-5 relative to that found in linezolid.

6

Oxazolidinone compounds similar to those of compound 8 have been formed via decomposition of substituted nitrosoureas 7 and have been useful as anticancer agents (Mulcahy et al. (1989) EUR J. CLIN. ONCOL. 5: 1099-1104; Carmiati et al. (1989) BIOCHEM. PHARMACOL. 38: 2253-2258).

7

8

U.S. Pat. No. 6,034,069 discloses a series of 3'-N-modified 6-O-substituted erythromycin ketolide derivatives similar to compound 9. The aryl group attached to the aminosaccharide moiety (represented by a 3-pyridyl group in 9) was variable, and non-aryl substituents were synthesized as well.

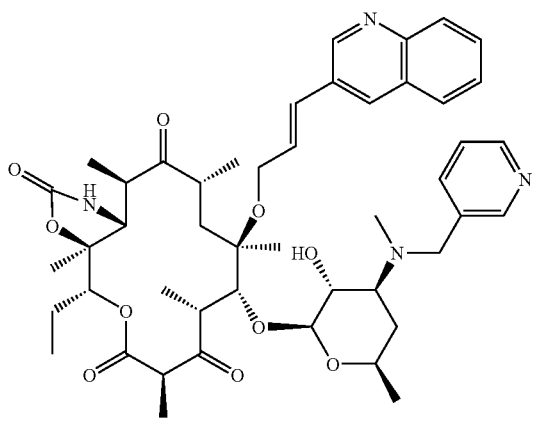

Published German patent application DE 196 04 223 A1 discloses oxazolidinone ring-containing compounds of the general structure 10, where $R_1$ can be, in addition to other structures, a substituted or unsubstituted five-membered ring chosen from thienyl, furyl, pyrrolyl, pyrazolyl, thiazolyl, oxazolyl, imidazolyl and pyrrolidinyl.

10

U.S. Pat. No. 6,362,189 discloses antibiotic compounds having the general formula 11. To the extent that the chemical moiety denoted by the symbol "G" may be an oxazolidinone ring, the ring may be substituted with a thiocarbonyl functionality, namely a —$CH_2NHC(S)R_1$.

11

International patent publication no. WO 99/63937 proposes the synthesis of multivalent macrolide antibiotics comprising a portion of a macrolide antibiotic linked via a linker to a portion of another known antibacterial agent. Two of the compounds proposed, although apparently not made or tested, include those shown below having the formulas 13a and 13b.

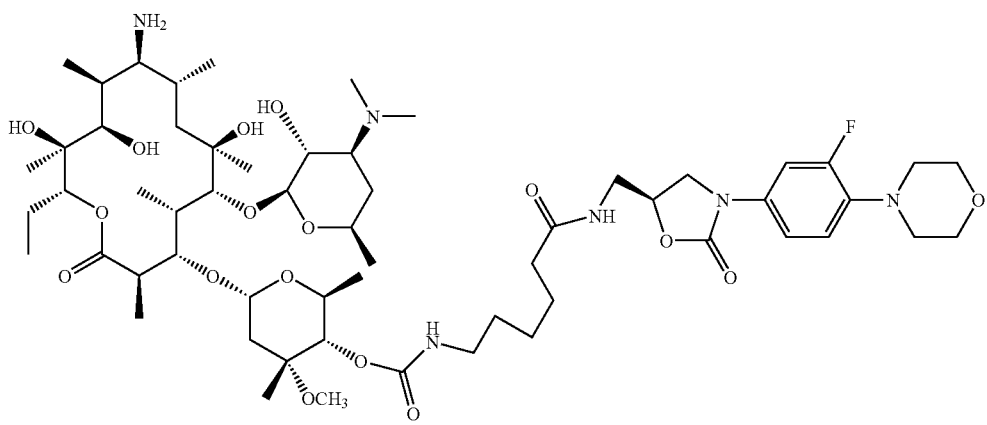

13a

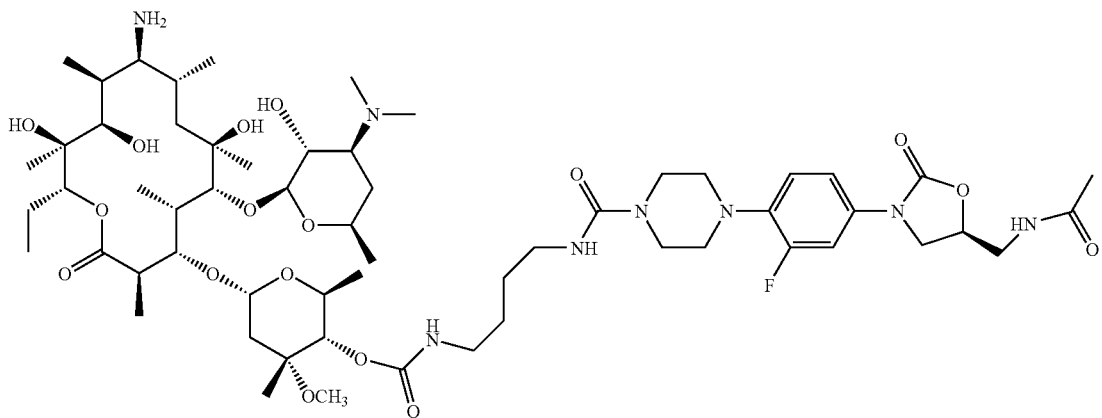

13b

Notwithstanding the foregoing, there is still an ongoing need for new anti-infective and anti-proliferative agents. There is also an ongoing need for new anti-inflammatory agents, and new agents to treat gastrointestinal motility disorders.

SUMMARY OF THE INVENTION

The invention provides a family of compounds useful as anti-infective agents and/or anti-proliferative agents, for example, chemotherapeutic agents, anti-fungal agents, anti-bacterial agents, anti-parasitic agents, anti-viral agents, and/or anti-inflammatory agents, and/or prokinetic (gastrointestinal modulatory) agents, having the formula:

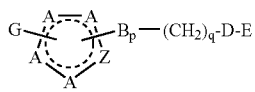

or pharmaceutically acceptable salts, esters, or prodrugs, thereof. In the formula, p and q independently are 0 or 1. Also, A, at each occurrence, independently is a carbon atom, a carbonyl group, or a nitrogen atom. The B, D, E, and G groups can be selected from the respective groups of chemical moieties later defined in the detailed description.

In some embodiments, the invention provides a family of compounds having the formula:

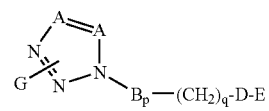

or pharmaceutically acceptable salts, esters or prodrugs thereof. In the formula, p and q independently are 0 or 1. Also, A, at each occurrence, independently is a carbon atom or a nitrogen atom, provided that when one A is a nitrogen atom, the other A is a carbon atom. The B, D, E, and G groups can be selected from the respective groups of chemical moieties later defined in the detailed description.

In other embodiments, the invention provides a family of compounds having the formula:

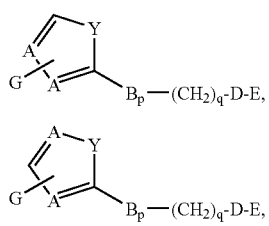

-continued

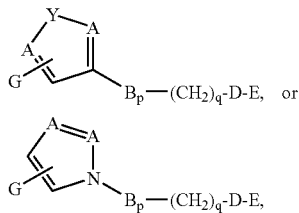

or pharmaceutically acceptable salts, esters or prodrugs thereof. In the formula, p and q independently are 0 or 1. Also, A, at each occurrence, independently is a carbon atom or a nitrogen atom. The B D, E, and G groups can be selected from the respective groups of chemical moieties later defined in the detailed description.

In another aspect, the invention provides a pharmaceutical composition comprising a therapeutically effective amount of one or more of the foregoing compounds and a pharmaceutically acceptable carrier. In yet another aspect, the invention provides a method for treating a microbial infection, a fungal infection, a viral infection, a parasitic disease, a proliferative disease, an inflammatory disease, or a gastrointestinal motility disorder in a mammal by administering effective amounts of the compounds of the invention or pharmaceutical compositions of the invention, for example, via oral, parenteral, or topical routes. In still another aspect, the invention provides methods for synthesizing any one of the foregoing compounds. In another aspect, the invention provides a medical device, for example, a medical stent, which contains or is coated with one or more of the foregoing compounds.

The foregoing and other aspects and embodiments of the invention may be more fully understood by reference to the following detailed description and claims.

DETAILED DESCRIPTION OF THE INVENTION

The present invention provides a family of compounds that can be used as anti-proliferative agents and/or anti-infective agents. The compounds may be used without limitation, for example, as anti-cancer agents, anti-bacterial agents, anti-fungal agents, anti-parasitic agents and/or anti-viral agents. Further, the present invention provides a family of compounds that can be used without limitation as anti-inflammatory agents, for example, for use in treating chronic inflammatory airway diseases, and/or as prokinetic agents, for example, for use in treating gastrointestinal motility disorders such as gastroesophageal reflux disease, gastroparesis (diabetic and post surgical), irritable bowel syndrome, and constipation.

1. Definitions

For the purpose of the present invention, the following definitions have been used throughout.

The carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive. Thus, $C_{1-4}$ alkyl refers to alkyl of 1-4 carbon atoms, inclusive, or methyl, ethyl, propyl, and butyl, and isomeric forms thereof.

The terms "$C_{1-2}$ alkyl", "$C_{1-3}$ alkyl", "$C_{1-4}$ alkyl", "$C_{1-5}$ alkyl", "$C_{1-6}$ alkyl", "$C_{1-8}$ alkyl", "$C_{1-10}$ alkyl", and "$C_{1-16}$ alkyl" refer to an alkyl group having one to two, one to three, one to four, one to five, one to six, one to eight, one to ten, or one to sixteen carbon atoms, respectively such as, for example, methyl, ethyl, propyl, butyl, pentyl, hexyl, heptyl, octyl, nonyl, decyl, undecyl, dodecyl, tridecyl, tetradecyl and their isomeric forms thereof.

The terms "$C_{2-5}$ alkenyl", "$C_{2-6}$ alkenyl", "$C_{2-8}$ alkenyl", and "$C_{2-16}$ alkenyl" refer at at least one double bond alkenyl group having two to five, two to six, two to eight, or two to sixteen carbon atoms, respectively such as, for example, ethenyl, propenyl, butenyl, pentenyl, pentdienyl, hexenyl, hexadienyl, heptenyl, heptdienyl, octenyl, octdienyl, octatrienyl, nonenyl, nonedienyl, nonatrienyl, undecenyl, undecdienyl, dodecenyl, tridecenyl, tetradecenyl and their isomeric forms thereof.

The terms "$C_{2-5}$ alkynyl", "$C_{2-6}$ alkynyl", and "$C_{2-8}$ alkynyl" refer to at least one triple bond alkynyl group having two to five, two to six, or two to eight carbon atoms, respectively such as, for example, ethynyl, propynyl, butynyl, pentynyl, pentdiynyl, hexynyl, hexdiynyl, heptynyl, heptdiynyl, octynyl, octdiynyl, octatriynyl, and their isomeric forms thereof.

The terms "$C_{3-4}$ cycloalkyl", "$C_{3-6}$ cycloalkyl", "$C_{5-6}$ cycloalkyl", "$C_{3-7}$ cycloalkyl", and "$C_{3-8}$ cycloalkyl" refer to a cycloalkyl group having three to four, three to six, five to six, three to seven, or three to eight carbon atoms, respectively such as, for example, cyclopropyl, cyclobutyl, cyclopentyl, cyclohexyl, cycloheptyl, cyclooctyl, and their isomeric forms thereof.

The terms "$C_{1-4}$ alkoxy", "$C_{1-5}$ alkoxy", "$C_{1-6}$ alkoxy", and "$C_{1-8}$ alkoxy", refer to an alkyl group having one to four, one to five, one to six, or one to eight carbon atoms, respectively attached to an oxygen atom such as, for example, methoxy, ethoxy, propyloxy, butyloxy, pentyloxy, hexyloxy, heptyloxy, or octyloxy and their isomeric forms thereof.

The term "$C_{1-6}$ hydroxy" refers to an alkyl group having one to six carbon atoms, and isomeric forms thereof, attached to a hydroxy group.

The terms "$C_{1-3}$ acyl", "$C_{1-4}$ acyl", "$C_{1-5}$ acyl", "$C_{1-6}$ acyl", and "$C_{1-8}$ acyl" refer to a carbonyl group having an alkyl group of one to three, one to four, one to five, one to six, or one to eight carbon atoms, respectively.

The terms "$C_{1-4}$ alkoxycarbonyl", and "$C_{1-6}$ alkoxycarbonyl" refer to an ester group having an alkyl group of one to four, or one to six carbon atoms, respectively.

The terms "$C_{1-6}$ alkylthio" and "$C_{1-8}$ alkylthio" refer to an alkyl group having one to six or one to eight carbon atoms respectively and isomeric forms thereof attached to a sulfur atom.

The term "$C_{1-3}$ alkylamino" refers to alkyl groups having from one to three carbon atoms attached to an amino moiety such as, for example, dimethylamino, methylethylamino, diethylamino, dipropylamino, methylpropylamino, or ethylpropylamino and their isomeric forms thereof.

The term "Het" refers to 5 to 10 membered saturated, unsaturated or aromatic heterocyclic rings containing one or more oxygen, nitrogen, and sulfur forming such groups as, for example, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl, 1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate.

The terms "halo" or "halogen" refers to a fluorine atom, a chlorine atom, a bromine atom, and/or an iodine atom.

The term "hydroxy protecting group" refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known (see, for example, T. H. Greene and P. G. M. Wuts (1999) PROTECTIVE GROUPS IN ORGANIC SYNTHESIS, 3rd edition, John Wiley & Sons, New York). Examples of hydroxy protecting groups include, but are not limited to, acetate, methoxymethyl ether, methylthiomethyl, tert-butyldimethylsilyl, tert-butyldiphenylsilyl, acyl substituted with an aromatic group and the like.

The term "aryl" refers to a mono- or bicyclic carbocyclic ring system having one or two aromatic rings including, but not limited to, phenyl, naphthyl, tetrahydronaphthyl, indanyl, idenyl and the like.

The term "substituted aryl" refers to an aryl group, as defined herein, substituted by independent replacement of one, two, three, four, or five of the hydrogen atoms thereon with substituents independently selected from alkyl, substituted alkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. More specifically, the substituents may be F, Cl, Br, I, OH, $NO_2$, CN, C(O)—$C_{1-6}$ alkyl, C(O)-aryl, C(O)-heteroaryl, $CO_2$-alkyl, $CO_2$-aryl, $CO_2$-heteroaryl, $CONH_2$, CONH—$C_{1-6}$ alkyl, CONH-aryl, CONH-heteroaryl, OC(O)—$C_{1-6}$ alkyl, OC(O)-aryl, OC(O)-heteroaryl, $OCO_2$-alkyl, $OCO_2$-aryl, $OCO_2$-heteroaryl, $OCONH_2$, OCONH—$C_{1-6}$ alkyl, OCONH-aryl, OCONH-heteroaryl, NHC(O)—$C_{1-6}$ alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_{1-6}$ alkyl, NHCONH-aryl, NHCONH-heteroaryl, $SO_2$—$C_{1-6}$ alkyl, $SO_2$-aryl, $SO_2$-heteroaryl, $SO_2NH_2$, $SO_2NH$—$C_{1-6}$ alkyl, $SO_2NH$-aryl, $SO_2NH$-heteroaryl, $C_{1-6}$ alkyl, $C_{3-6}$ cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_{1-6}$ alkoxy, methoxymethoxy, methoxyethoxy, amino, benzylamino, arylamino, heteroarylamino, $C_{1-3}$ alkylamino, thio, aryl-thio, heteroarylthio, benzyl-thio, $C_{1-6}$ alkyl-thio, or methylthiomethyl. In addition, substituted aryl groups include tetrafluorophenyl and pentafluorophenyl.

The term "arylalkyl group" refers to an aryl group attached to an alkyl group. An example of an arylalkyl group is a benzyl group.

The term "substituted arylalkyl group" refers to an aryl group or substituted aryl group attached to an alkyl group or a substituted alkyl group, provided that one or both of the aryl and alkyl groups are substituted.

The term "heteroaryl" refers to a cyclic aromatic radical having from five to ten ring atoms of which one ring atom is selected from S, O and N; zero, one, two, or three ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, triazolyl, tetrazolyl, thiazolyl, isothiazolyl, oxazolyl, isoxazolyl, thiadiazolyl, oxadiazolyl, thiophenyl, furanyl, quinolinyl, isoquinolinyl, and the like.

The term "substituted heteroaryl" refers to a heteroaryl group as defined herein, substituted by independent replacement of one, two, three, four, or five of the hydrogen atoms thereon with F, Cl, Br, I, OH, $NO_2$, CN, C(O)—$C_{1-6}$ alkyl, C(O)-aryl, C(O)-heteroaryl, $CO_2$-alkyl, $CO_2$-aryl, $CO_2$-heteroaryl, $CONH_2$, CONH—$C_{1-6}$ alkyl, CONH-aryl, CONH-heteroaryl, OC(O)—$C_{1-6}$ alkyl, OC(O)-aryl, OC(O)-heteroaryl, $OCO_2$-alkyl, $OCO_2$-aryl, $OCO_2$-heteroaryl, $OCONH_2$, OCONH—$C_{1-6}$ alkyl, OCONH-aryl, OCONH-heteroaryl, NHC(O)—$C_{1-6}$ alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_{1-6}$ alkyl, NHCONH-aryl, NHCONH-heteroaryl, $SO_2$—$C_{1-6}$ alkyl, $SO_2$-aryl, $SO_2$-heteroaryl, $SO_2NH_2$, $SO_2NH$—$C_{1-6}$ alkyl, $SO_2NH$-aryl, $SO_2NH$-heteroaryl, $C_{1-6}$ alkyl, $C_{3-6}$ cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_{1-6}$ alkoxy, methoxymethoxy, methoxyethoxy, amino, benzylamino, arylamino, heteroarylamino, $C_{1-3}$ alkylamino, thio, aryl-thio, heteroarylthio, benzyl-thio, $C_{1-6}$ alkyl-thio, or methylthiomethyl.

The term "heterocyclic" refers to heterocycloalkyl and heteroaryl. The term "substituted heterocyclic," as used herein, refers to substituted heterocycloalkyl and substituted heteroaryl.

The term "macrolide" refers to any compound possessing a 14- or 15-macrocyclic ring, and derivatives thereof (such as keto, oxime, cyclic carbonate derivatives). These include, for example, compounds that are (or are synthetically derived from) known antibacterial agents including, but not limited to, erythromycin, clarithromycin, azithromycin, telithromycin, roxithromycin, pikromycin, flurithromycin, and dirithromycin.

In the formulas herein, a broken or dashed circle within a ring indicates that the ring is either aromatic or non-aromatic. A bond extending from a chemical moiety that is depicted as crossing a bond in a ring, but is not attached directly to a ring atom, indicates that the chemical moiety may be bonded to any atom of the ring. As to any of the above chemical moieties that contain one ore more substituents, it is understood that such moieties do not contain any substitution or substitution patterns that are sterically impractical and/or synthetically unfeasible. In addition, the compounds of this invention include all stereochemical isomers arising from the substitution of these moieties.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. PHARM SCIENCES 66: 1-19 (1977). The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids (such as hydrochloric acid, hydrobromic acid, phosphoric acid, sulfuric acid and perchloric acid), or with organic acids (such as acetic acid, oxalic acid, maleic acid, tartaric acid, citric acid, succinic acid or malonic acid), or by using other methods used in the art (such as ion exchange). Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Other suitable ester groups include, for example, those derived from pharmaceutically acceptable alcohols, such as stright-chain or branched aliphatic alcohols, benzylic alcohols, and amino-alcohols. Examples of particular esters include formates, acetates, propionates, butyrates, acrylates, ethylsuccinates, and methyl, ethyl, propyl, benzyl, and 2-aminoethyl alcohol esters.

The term "pharmaceutically acceptable prodrugs" refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the previously formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

The term "physiologically acceptable cation" refers to common, positively charged species such as (but not limited to) metals such as sodium, potassium, calcium, magnesium, zinc and the like. The cation can also be an organic species such as an amine salt. Non-limiting examples of such amine salts can be the protonated form of methylamine, ethylamine, cyclohexylamine, lysine, N-methylglucamine, diethanolamine, triethanolamine, tris-(hydroxymethyl)aminomethane, piperidine, morpholine, and the like.

The term "electron-withdrawing group" refers to groups well known to those in the art capable of pulling electron density towards the group and away from a source (such as an aromatic ring, an olefin, a carbonyl-like group or a sigma bond between two designated atoms). Examples of such electron-withdrawing groups are, for example, nitro, keto, formyl, acyl, halogens, carboxy, trihaloalkyl, sulfonyl and the like.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

2. Compounds of the Invention

In one aspect, the invention provides compounds having the formula:

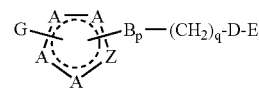

or a pharmaceutically acceptable salt, ester, or prodrug thereof, wherein

A, at each occurrence, independently is carbon, carbonyl, or nitrogen, provided at least one A is carbon;

Z is carbon, nitrogen, oxygen, or sulfur;

B is selected from the group consisting of O, $NR^2$, $S(O)_r$, C=O, C=S, and C=$NOR^3$, p is 0 or 1;

q, at each occurrence, independently is 0 or 1;

r is 0, 1, or 2;

$R^2$, at each occurrence, independently is selected from the group consisting of:

a) hydrogen, b) $S(O)_rR^4$, c) formyl, d) $C_{1-8}$ alkyl, e) $C_{2-8}$ alkenyl, f) $C_{2-8}$ alkynyl, g) $C_{1-8}$ alkoxy, h) $C_{1-8}$ alkylthio, i) $C_{1-8}$ acyl, j) saturated, unsaturated, or aromatic $C_{3-8}$ carbocycle, and k) saturated, unsaturated, or aromatic 5-10 membered heterocycle containing one or more heteroatoms selected from the group consisting of nitrogen, oxygen, and sulfur, wherein any of d)-k) optionally is substituted with one or more moieties selected from the group consisting of carbonyl, aryl, substituted aryl, heteroaryl, substituted heteroaryl, F, Cl, Br, I, CN, $NO_2$, —$NR^3R^3$, —$OR^3$, —$S(O)_rR^4$, —$S(O)_r NR^3R^3$, —$C(O)R^3$, —$C(O)OR^3$, —$OC(O)R^3$, —$C(O)NR^3R^3$, and —$OC(O)NR^3R^3$;

alternatively, two R² groups, taken together with the atom to which they are bonded, form i) 5-8 membered saturated or unsaturated carbocycle, or ii) 5-8 membered saturated or unsaturated heterocycle containing one or more atoms selected from the group consisting of nitrogen, oxygen, and sulfur, wherein i)-ii) optionally is substituted with one or more moieties selected from the group consisting of carbonyl, F, Cl, Br, I, CN, NO$_2$, —NR³R³, —OR³, —S(O)$_r$R⁴, —S(O)$_r$NR³R³, —C(O)R³, —C(O)OR³, —OC(O)R³, —C(O)NR³R³, —OC(O)NR³R³, C$_{1-6}$ acyl, aryl, substituted aryl, heteroaryl, and substituted heteroaryl;

R³, at each occurrence, independently is selected from the group consisting of:
a) hydrogen, b) C$_{1-8}$ alkyl, c) C$_{2-8}$ alkenyl, d) C$_{2-8}$ alkynyl, e) C$_{1-8}$ acyl, f) saturated, unsaturated, or aromatic C$_{3-8}$ carbocycle, and g) saturated, unsaturated, or aromatic 5-10 membered heterocycle containing one or more heteroatoms selected from the group consisting of nitrogen, oxygen, and sulfur, wherein any of b)-h) optionally is substituted with one or more moieties selected from the group consisting of carbonyl, F, Cl, Br, I, CN, NO$_2$, —NR⁶R⁶, —OR⁶, —S(O)$_r$R⁶, —S(O)$_r$NR⁶R⁶, —C(O)R⁶, —C(O)OR⁶, —OC(O)R⁶, —C(O)NR⁶R⁶, —OC(O)NR⁶R⁶, C$_{1-6}$ acyl, aryl, substituted aryl, heteroaryl, and substituted heteroaryl;

alternatively, two R³ groups, taken together with the atom to which they are bonded, form i) a 5-7 membered saturated or unsaturated carbocycle, or ii) a 5-7 membered saturated or unsaturated heterocyocle containing one or more atoms selected from the group consisting of nitrogen, oxygen, and sulfur, wherein i)-ii) optionally is substituted with one or more moieties selected from the group consisting of carbonyl, F, Cl, Br, I, CN, NO$_2$, —NR⁶R⁶, —OR⁶, —S(O)$_r$R⁶, —S(O)$_r$NR⁶R⁶, —C(O)R⁶, —C(O)OR⁶, —OC(O)R⁶, —C(O)NR⁶R⁶, —OC(O)NR⁶R⁶, C$_{1-6}$ acyl, aryl, substituted aryl, heteroaryl, and substituted heteroaryl;

R⁴ is selected from the group consisting of:
a) hydrogen, b) —NR³R³, c) —NR³OR³, d) —NR³NR³R³ e) —NHC(O)R³, f) —C(O)NR³R³, g) —N₃, h) C$_{1-8}$ alkyl, i) C$_{2-8}$ alkenyl, j) C$_{2-8}$ alkynyl, k) saturated, unsaturated, or aromatic C$_{3-8}$ carbocycle, and l) saturated, unsaturated, or aromatic 5-10 membered heterocycle containing one or more heteroatoms selected from the group consisting of nitrogen, oxygen, and sulfur, wherein any of h)-l) optionally is substituted with one or more moieties selected from the group consisting of carbonyl, F, Cl, Br, I, CN, NO$_2$, —NR³R³, —OR³, —SR³, —S(O)$_r$R⁵, —S(O)$_r$NR³R³, —C(O)R³, —C(O)OR³, —OC(O)R³, —C(O)NR³R³, —OC(O)NR³R³, C$_{1-6}$ alkyl, C$_{1-6}$ alkenyl, C$_{1-6}$ alkynyl, C$_{1-6}$ acyl, aryl, substituted aryl, heteroaryl, and substituted heteroaryl;

R⁵ is selected from the group consisting of:
a) hydrogen, b) —NR³R³, c) —NR³OR³, d) —NR³NR³R³ e) —NHC(O)R³, f) —C(O)NR³R³, g) —N₃, h) C$_{1-8}$ alkyl, i) C$_{2-8}$ alkenyl, j) C$_{2-8}$ alkynyl, k) saturated, unsaturated, or aromatic C$_{3-8}$ carbocycle, and l) saturated, unsaturated, or aromatic 5-10 membered heterocycle containing one or more heteroatoms selected from the group consisting of nitrogen, oxygen, and sulfur, wherein any of h)-l) optionally is substituted with one or more moieties selected from the group consisting of F, Cl, Br, I, CN, NO$_2$, —NR³R³, —OR³, —SR³—C(O)R³, —C(O)OR³, —OC(O)R³—C(O)NR³R³, —OC(O)NR³R³, C$_{1-6}$ alkyl, C$_{1-6}$ alkenyl, C$_{1-6}$ alkynyl, C$_{1-6}$ acyl, aryl, substituted aryl, heteroaryl, and substituted heteroaryl; and R⁶, at each occurrence, independently is selected from the group consisting of:
hydrogen, C$_{1-6}$ alkyl, C$_{1-6}$ alkenyl, C$_{1-6}$ alkynyl, C$_{1-6}$ acyl, aryl, substituted aryl, hetreroaryl, substituted heteroaryl;

alternatively, two R⁶ groups taken together are —(CH$_2$)$_s$—, wherein s is 1, 2, 3, 4, or 5;

D-E is selected from the group consisting of:

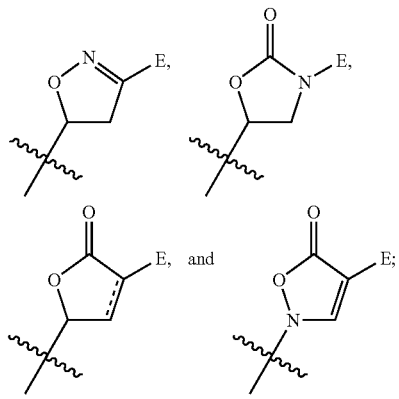

E is selected from the group consisting of:

a)
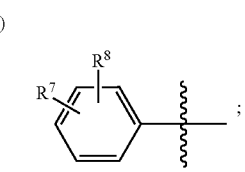

b)
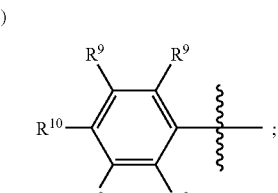

c)
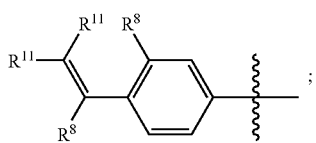

d) 5-10 membered saturated, unsaturated, or aromatic heterocycle containing one or more heteroatoms selected from the group consisting of nitrogen, oxygen, and sulfur, and optionally substituted with one or more R¹³ groups;

e) $C_{5-10}$ saturated, unsaturated, or aromatic carbocycle, optionally substituted with one or more $R^{13}$ groups;
f) $C_{1-8}$ alkyl,
g) $C_{2-8}$ alkenyl,
h) $C_{3-8}$ alkynyl,
i) $C_{1-8}$ alkoxy,
j) $C_{1-8}$ aklylthio,
k) $C_{1-8}$ acyl,
l) $S(O)_rR^5$; and
m) hydrogen,
n) a β-carbolin-3-yl, or indolizinyl bonded via the 6-membered ring, wherein the β-carbolin-3-yl, or indolizinyl optionally is substituted with one to three $R^{30}$ groups;

o) 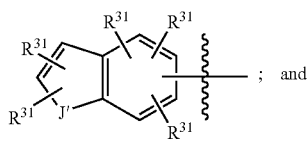 ; and p) 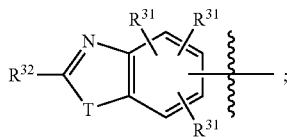 ;

wherein any of f)-k) optionally is substituted with
  i) one or more $R^{13}$ groups;
  ii) 5-6 membered saturated, unsaturated, or aromatic heterocycle containing one or more heteroatoms selected from the group consisting of nitrogen, oxygen, and sulfur, and optionally substituted with one or more $R^{13}$ groups; or
  iii) $C_{5-10}$ saturated, unsaturated, or aromatic carbocycle, optionally substituted with one or more $R^{13}$ groups;
$R^7$ is selected from the group consisting of:
  a) hydrogen, b) carbonyl, c) formyl, d) F, e) Cl, f) Br, g) I, h) CN, i) $NO_2$, j) $OR^3$, k) —$S(O)_rR^5$, l) —$S(O)_iN=R^2$, m) —$C(O)R^2$, n) —$C(O)OR^3$, o) —$OC(O)R^2$, p) —$C(O)NR^2R^2$, q) —$OC(O)NR^2R^2$, r) —$C(=NR^{12})R^2$, s) —$C(R^2)(R^2)OR^3$, t) —$C(R^2)(R^2)OC(O)R^2$, u) —$C(R^2)(OR^3)(CH_2)_rNR^2R^2$, v) —$NR^2R^2$, w) —$NR^2OR^3$, x) —$N(R^2)C(O)R^2$, y) —$N(R^2)C(O)OR^3$, z) —$N(R^2)C(O)NR^2R^2$, aa) —$N(R^2)S(O)_rR^5$, bb) —$C(OR^6)(OR^6)R^2$, cc) —$C(R^2)(R^3)NR^2R^2$, dd) —$C(R^2)(R^3)NR^2R^{12}$, ee) =$NR^{12}$, ff) —$C(S)NR^2R^2$, gg) —$N(R^2)C(S)R^2$, hh) —$OC(S)NR^2R^2$, ii) —$N(R^2)C(S)OR^3$, jj) —$N(R^2)C(S)NR^2R^2$, kk) —$SC(O)R^2$, ll) $C_{1-8}$ alkyl, mm) $C_{2-8}$ alkenyl, nn) $C_{2-8}$ alkynyl, oo) $C_{1-8}$ alkoxy, pp) $C_{1-8}$ alkylthio, qq) $C_{1-8}$ acyl, m) saturated, unsaturated, or aromatic $C_{5-10}$ carbocycle, and ss) saturated, unsaturated, or aromatic 5-10 membered heterocycle containing one or more heteroatoms selected from the group consisting of nitrogen, oxygen, and sulfur,
  wherein any of ll)-ss) optionally is substituted with one or more moieties selected from the group consisting of:
  carbonyl; formyl; F; Cl; Br; I; CN; $NO_2$; $OR^3$; —$S(O)_rR^5$; —$S(O)_iN=R^2$, —$C(O)R^2$; —$C(O)OR^3$; —$OC(O)R^2$; —$C(O)NR^2R^2$; —$OC(O)NR^2R^2$; —$C(=NR^{10})R^2$; —$C(R^2)(R^2)OR^3$; —$C(R^2)(R^2)OC(O)R^2$; —$C(R^2)(OR^3)(CH_2)_rNR^2R^2$; —$NR^2R^2$; —$NR^2OR^3$; —$NR^2C(O)R^2$; —$NR^2C(O)OR^3$; —$NR^2C(O)NR^2R^2$; —$NR^2S(O)_rR^5$; —$C(OR^6)(OR^6)R^2$; —$C(R^2)(R^3)NR^2R^2$; —$C(R^2)(R^3)NR^2R^{12}$; =$NR^{12}$; —$C(S)NR^2R^2$; —$NR^2C(S)R^2$; —$OC(S)NR^2R^2$; —$NR^2C(S)OR^3$; —$NR^2C(S)NR^2R^2$; —$SC(O)R^2$; $C_{2-5}$ alkenyl; $C_{2-5}$ alkynyl; $C_{1-8}$ alkoxy; $C_{1-8}$ alkylthio; $C_{1-8}$ acyl; saturated, unsaturated, or aromatic $C_{5-10}$ carbocycle, optionally substituted with one or more $R^8$ groups; and saturated, unsaturated, or aromatic 5-10 membered heterocycle containing one or more heteroatoms selected from the group consisting of nitrogen, oxygen, and sulfur, and optionally substituted with one or more $R^8$ groups;
$R^8$ is selected from the group consisting of:
  hydrogen; F; Cl; Br; I; CN; $NO_2$; $OR^6$; aryl; substituted aryl; heteroaryl; substituted heteroaryl; and $C_{1-6}$ alkyl, optionally substituted with one or more moieties selected from the group consisting of aryl, substituted aryl, heteroaryl, substituted heteroaryl, F, Cl, Br, I, CN, $NO_2$, and $OR^6$;
alternatively, $R^7$ and $R^8$ taken together are —$O(CH_2)_rO$—;
$R^9$, at each occurrence, independently is selected from the group consisting of:
  hydrogen, F, Cl, Br, I, CN, $OR^3$, $NO_2$, —$NR^2R^2$, $C_{1-6}$ alkyl, $C_{1-6}$ acyl, and $C_{1-6}$ alkoxy;
$R^{10}$ is selected from the group consisting of:
  a) saturated, unsaturated, or aromatic $C_{5-10}$ carbocycle,
  b) saturated, unsaturated, or aromatic 5-10 membered heterocycle containing one or more heteroatoms selected from the group consisting of nitrogen, oxygen, and sulfur,
  c) —X—$C_{1-6}$ alkyl-saturated, unsaturated, or aromatic 5-10 membered heterocycle containing one or more heteroatoms selected from the group consisting of nitrogen, oxygen, and sulfur,
    wherein X is O or $NR^3$,
  d) saturated, unsaturated, or aromatic 10-membered bicyclic ring system optionally containing one or more heteroatoms selected from the group consisting of nitrogen, oxygen, and sulfur,
  e) saturated, unsaturated, or aromatic 13-membered tricyclic ring system optionally containing one or more heteroatoms selected from the group consisting of nitrogen, oxygen, and sulfur, f) 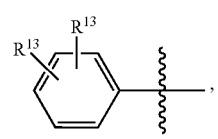

g) 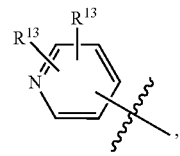

h) 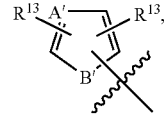

-continued
i) 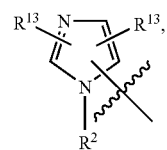
j) 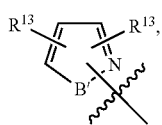
k) 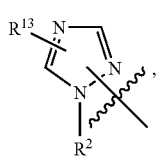
l) 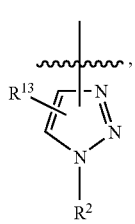
m) 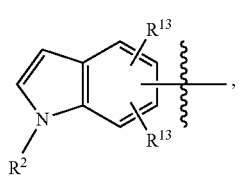
n) 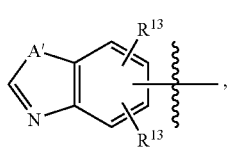
o) 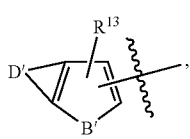
p) 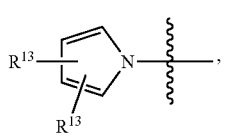
q) 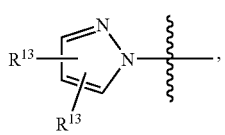
r) 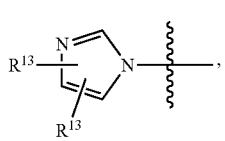
-continued
s) 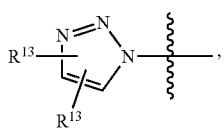
t) 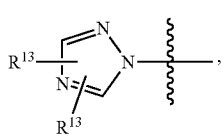
u) 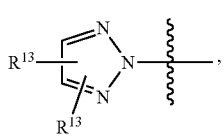
v) 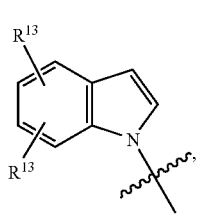
w) a diazinyl group,
x) a triazinyl group,
y) a quinolinyl group,
z) a quinoxalinyl group,
aa) a naphthyridinyl group,
bb) 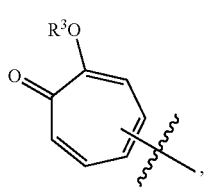
cc) 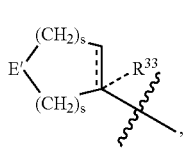
dd) 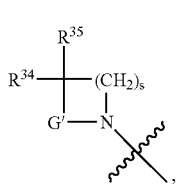
ee) 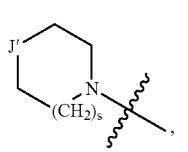

-continued

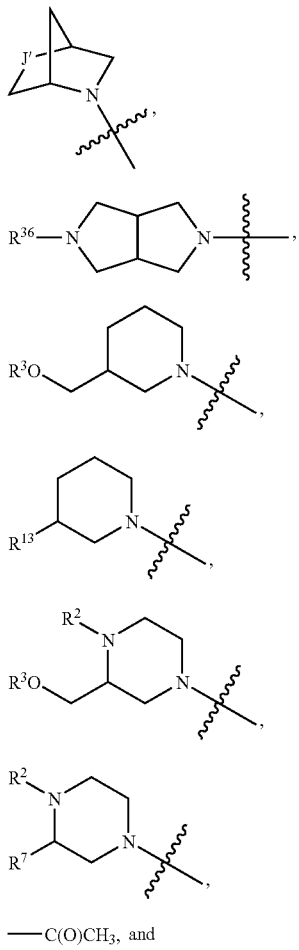

ff)

gg)

hh)

ii)

jj)

kk)

ll) —C(O)CH₃, and mm) R⁹, wherein any of a)-kk) optionally is substituted with one or more R¹³ groups;

alternatively, R¹⁰ and one R⁹ group taken together is

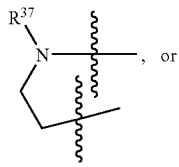, or alternatively, R¹⁰ and one R⁹ group, taken together with the atoms to which they are bonded, form a 5-7 membered saturated or unsaturated carbocycle, optionally substituted with one or more R¹³ groups; or a 5-7 membered saturated or unsaturated heterocyole containing one or more atoms selected from the group consisting of nitrogen, oxygen, and sulfur, and optionally substituted with one or more R¹³ groups;

R¹¹ at each occurrence, independently is selected from the group consisting of:
 hydrogen; an electron-withdrawing group; aryl; substituted aryl; heteroaryl; substituted heteroaryl; and C₁₋₆ alkyl, optionally substituted with F, Cl, or Br;

alternatively, any R¹¹ and R⁸, taken together with the atoms to which they are bonded, form a 5-7 membered saturated or unsaturated carbocycle, optionally substituted with one or more R¹³ groups; or a 5-7 membered saturated or unsaturated heterocycle containing one or more atoms selected from the group consisting of nitrogen, oxygen, and sulfur, and optionally substituted with one or more R¹³ groups;

alternatively, any R¹¹ and R⁸, taken together with the atoms to which they are bonded, form —(CH₂)$_k$— or a 5-, 6-, or 7-membered ring having the formula:

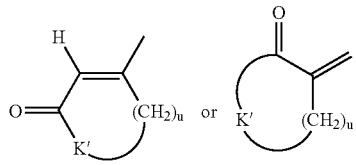

wherein
u is 2, 3, 4, or 5;
R¹² is selected from the group consisting of:
 —NR²R²—OR³, —OC(O)R², —OC(O)OR³, —NR²C(O)R², —NR²C(O)NR²R², —NR²C(S)NR²R², and —NR²C(=NR²)NR²R²;
R¹³, at each occurrence, independently is selected from the group consisting of:
 a) hydrogen, b) carbonyl, c) formyl d) F, e) Cl, f) Br, g) I, h) CN, i) NO₂, j) OR³, k) —S(O)$_r$R⁵, l) —S(O)$_r$N=R³ m) —C(O)R², n) —C(O)OR³ o) —OC(O)R², p) —C(O)NR²R², q) —OC(O)NR²R², r) —C(=NR¹²)R², s) —C(R²)(R²)OR³, t) —C(R²)(R²)OC(O)R², u) —C(R²)(OR³)(CH₂)$_r$NR²R², v) —NR²R², w) —NR²OR³, x) —N(R²)C(O)R², y) —N(R²)C(O)OR³, z) —N(R²)C(O)NR²R², aa) —N(R²)S(O)$_r$R⁵, bb) —C(OR⁶)(OR⁶)R², cc) —C(R²)(R³)NR²R², dd) —C(R²)(R³)NR²R¹², ee) =NR¹², ff) —C(S)NR²R², gg) —N(R²)C(S)R², hh) —OC(S)NR²R², ii) —N(R²)C(S)OR³, jj) —N(R²)C(S)NR²R², kk) —SC(O)R², ll) C₁₋₈ alkyl, mm) C₂₋₈ alkenyl, nn) C₂₋₈ alkynyl, oo) C₁₋₈ alkoxy, pp) C₁₋₈ alkylthio, qq) C₁₋₈ acyl, m) saturated, unsaturated, or aromatic C₅₋₁₀ carbocycle, ss) saturated, unsaturated, or aromatic 5-10 membered heterocycle containing one or more heteroatoms selected from the group consisting of nitrogen, oxygen, and sulfur, tt) saturated, unsaturated, or aromatic 10-membered bicyclic ring system optionally containing one or more heteroatoms selected from the group consisting of nitrogen, oxygen, and sulfur, and uu) saturated, unsaturated, or aromatic 13-membered tricyclic ring system optionally containing one or more heteroatoms selected from the group consisting of nitrogen, oxygen, and sulfur,
 wherein any of ll)-uu) optionally is substituted with one or more moieties selected from the group consisting of:
  carbonyl; formyl; F; Cl; Br; I; CN; NO₂; OR³; —S(O)$_r$R⁵; —S(O)$_r$=R²; —C(O)R²; —C(O)OR³; —OC(O)R²; —C(O)NR²R²; —OC(O)NR²R²; —C(=NR¹²)R²; —C(R²)(R²)OR³; —C(R²)(R²)OC(O)R²; —C(R²)(OR³)(CH₂)$_r$NR²R²; —NR²R²; —NR²OR³; —NR²C(O)R²; —NR²C(O)OR³; —NR²C(O)NR²R²; —NR²S(O)$_r$R⁵; —C(OR⁶)(OR⁶)R²; —C(R²)(R³)

$NR^2R^2$; —$C(R^2)(R^3)NR^2R^{12}$; =$NR^{12}$; —$C(S)NR^2R^2$; —$NR^2C(S)R^2$; —$OC(S)NR^2R^2$; —$NR^2C(S)OR^3$; —$NR^2C(S)NR^2R^2$; —$SC(O)R^2$; $C_{1-8}$ alkyl, $C_{2-8}$ alkenyl; $C_{2-8}$ alkynyl; $C_{1-8}$ alkoxy; $C_{1-8}$ alkylthio; $C_{1-8}$ acyl; saturated, unsaturated, or aromatic $C_{3-10}$ carbocycle optionally substituted with one or more $R^7$ groups; and saturated, unsaturated, or aromatic 3-10 membered heterocycle containing one or more heteroatoms selected from the group consisting of nitrogen, oxygen, and sulfur, and substituted with one or more $R^7$ groups;

A' is CH, N, S, or O;

B' is O, S, or $NR^2$;

D' is an unsaturated 4-atom linker containing one nitrogen atom and three carbon atoms, which forms a pyridyl ring fused with the heteroaryl moiety;

E' is O, $NR^{51}$, or $S(O)_r$;

G' is —$CH_2$—, —$CH_2CH_2$—, —$CH_2(OH)CH_2$—, —$C(O)$—, or —$CH_2CH_2CH_2$—;

J' is —$S(O)_r$—, —O—, or —$NR^{36}$—;

K' is $CH_2$, O, S, or $NR^2$;

$R^{30}$ is selected from the group consisting of:

a) carbonyl, b) formyl, c) F, d) Cl, e) Br, f) CN, g) —$OR^3$, h) —$SR^3$, i) —$CF_3$, j) —$NO_2$, k) —$NR^2R^2$, l) —$NR^{38}R^{38}$, m)

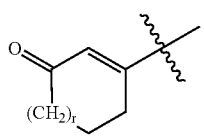

n) $C_{1-6}$ alkyl, o) $C_{2-6}$ alkenyl, p) $C_{2-6}$ alkynyl, q) $C_{1-6}$ alkoxy, r) —$C(O)$—$C_{1-6}$ alkyl, s) $C_{1-6}$ alklylthio, t) $C_{1-6}$ acyl, u) $C_{2-8}$ alkenylphenyl, v) aryl, and w) heteroaryl, wherein any of n)-w) optionally is substituted with one or more $R^{39}$ groups;

$R^{31}$, at each occurrence, independently is selected from the group consisting of:

a) hydrogen, b) carbonyl, c) F, d) Cl, e) Br, f) —CN, g) formyl, h) —$NO_2$, i) —$OR^3$, j) —$NR^2R^2$, k) aryl, l) substituted aryl, m) heteroaryl, n) substituted aryl, o) $C_{1-6}$ alkyl, p) $C_{2-6}$ alkenyl, q) $C_{2-6}$ alkynyl, r) $C_{1-6}$ alkylthio, s) $C_{1-6}$ acyl, t) $C_{1-6}$ alkoxy, and u) —$C(O)C_{1-6}$ alkoxy, wherein any of o)-u) optionally is substituted with one or more moieties from the group consisting of:
—N(phenyl)($CH_2CH_2OH$), —$OCH(CH_3)$($OCH_2CH_3$),
—O-phenyl-[para-NHC(O)$CH_3$], and $R^{13}$;

$R^{32}$, at each occurrence, independently is selected from the group consisting of:

a) hydrogen, b) carbonyl, c) formyl, d) —$OR^{43}$, e) —$NR^{44}R^{44}$, f) —$S(O)_rR^{47}$, g) —$S(O)_rNR^{44}R^{44}$, h) aryl, i) substituted aryl, j) heteroaryl, k) substituted heteroaryl, l) $C_{1-6}$ alkyl, m) $C_{2-6}$ alkenyl, n) $C_{2-6}$ alkynylo) $C_{1-6}$ alkylthio, p) $C_{1-6}$ acyl, q) $C_{1-6}$ alkoxy, r) —$C(O)$—$C_{1-6}$ alkoxy,

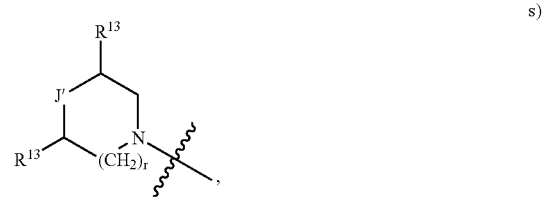

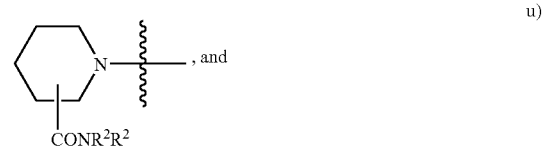

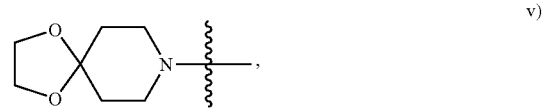

wherein any of n)-w) optionally is substituted with one or more moieties from the group consisting of:
—N(phenyl)($CH_2CH_2OH$), —$OCH(CH_3)$($OCH_2CH_3$), —O-phenyl-[para-NHC(O)$CH_3$] and $R^{13}$;

$R^{33}$ is hydrogen, F, Cl, Br, $C_{1-6}$ alkyl, or $C_{1-6}$ alkyl-aryl;

$R^{34}$ is hydrogen or $CH_3$;

$R^{35}$ is selected from the group consisting of:

hydrogen, —OH, —$CH_3$, —$OCH_3$, —$NHC(O)OR^2$, —$NHC(O)CH_2OR^3$, —$C(O)O$—$C_{1-6}$ alkyl, —$CH_2OH$, —$NHOCH_3$, —$C(O)O$—$C_{1-6}$ alkyl, —$C(O)CH_3$, —$CH_2C(O)CH_3$,

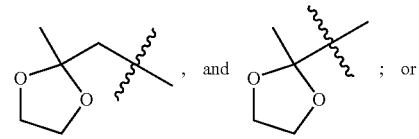

alternatively, $R^{34}$ and $R^{35}$ taken together are a carbonyl, =$NR^{48}$, or

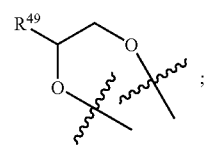

$R^{36}$ is selected from the group consisting of:
—$C(O)OR^3$, —$C(O)C(R^{50})(R^{50})(OR^3)$, —$C(O)R^2$, —$SO_2R^4$, —$C(O)(CH_2)_2C(O)CH_3$, —$C(O)CH_2OH$, —$(CH_2)_2R^2$, —$C(O)CH_2OC(O)R^2$, —$CH_2CN$, —$CH_2CHF_2$, —$SO_2NR^2R^2$, —$NHC(O)CH_2N(CH_3)_2$,

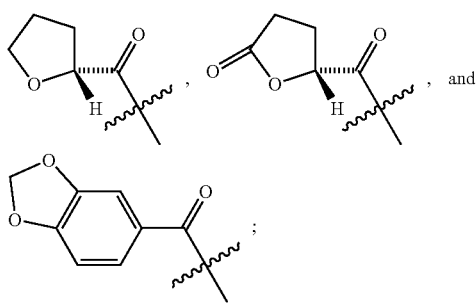

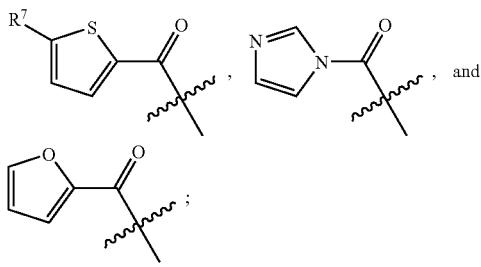

R³⁷ is selected from the group consisting of:
—C(O)CH₃, —C(O)H, —C(O)CHCl₂, —C(O)CH₂OH, —SO₂CH₃, —C(O)CH₂OC(O)CH₃, —C(O)CHF₂, —C(O)CH₂OC(O)H, —C(O)CH₂OCH₂—C≡CH, —C(O)CH₂OCH₂C₆H₅,

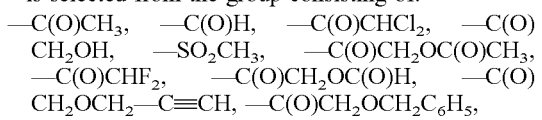

R³⁸, at each occurrence, independently is selected from the group consisting of:
hydrogen, formyl, $C_{1-4}$ alkyl, $C_{1-4}$ acyl, aryl, $C_{3-6}$ cycloalkyl, —P(O)(OR³)(OR³), and —SO₂R⁴;
alternatively, two R³⁸ groups taken together with the atom to which they are bonded form a 5- or 6-membered saturated heterocyclic group containing one or more atoms selected from the group consisting of nitrogen, oxygen, and sulfur, and optionally substituted with phenyl, pyrimidyl, $C_{1-3}$ alkyl, or $C_{1-3}$ acyl;

R³⁹ is selected from the group consisting of:
a) carbonyl, b) formyl, c) F, d) Cl, e) Br, f) I, g) CN, h) —OR³, i) —SR³, j) —CF₃, k) —NO₂, l) —NR²R², m) —C(O)NR²R², n) —NR²R², o) —NR²(SO₂R⁶), p) —SO₂NR²R², q) —S(O)ᵣR⁶, r) —CH=N—R⁴⁰, s) —CH(OH)—SO₃R⁴¹', t) $C_{1-6}$ alkyl, u) $C_{2-6}$ alkenyl, v) $C_{2-6}$ alkynyl, w) $C_{1-6}$ alkoxy, x) —C(O)—$C_{1-6}$ alkyl, y) $C_{1-6}$ alkylthio, z) $C_{1-6}$ acyl, aa) $C_{2-8}$ alkenylphenyl, bb) aryl, and cc) heteroaryl,
wherein any of s)-bb) optionally is substituted with —OH, —N₃, $C_{1-5}$ alkoxy, $C_{1-5}$ acyl, —NR²R²—SR⁴²—OSO₂R⁶, or

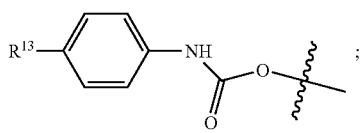

R⁴⁰ is —OH, —OCH₂-aryl, —NHC(O)NH₂, —NHC(S)NH₂, or —NHC(=NH)NR²R²;
R⁴¹ is hydrogen or a sodium ion;

R⁴² is selected from the group consisting of:

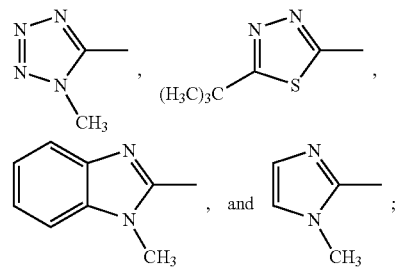

R⁴³ is selected from the group consisting of:
a) $C_{1-8}$ alkyl, b) $C_{3-6}$ cycloalkyl, c) aryl, d) heteroaryl, e) pyridyl, and f)

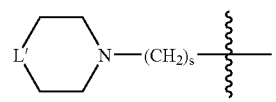

wherein
any of a)-f) optionally is substituted with one or more R¹³ groups, and L' is O, CH₂, or NR²;

R⁴⁴, at each occurrence, independently is selected from the group consisting of:
a) hydrogen, b) $C_{3-6}$ cycloalkyl, c) $C_{1-6}$ acyl, d) $C_{1-8}$ alkyl, e) $C_{1-6}$ alkoxy, f) heteroaryl, g) aryl, h)

h) 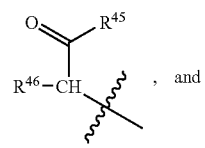

i) 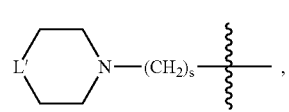

wherein
any of b)-g) optionally is substituted with one or more R¹³ groups, or

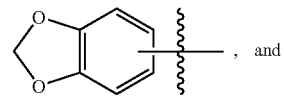

L' is O, CH₂, or NR²;
R⁴⁵ is —OH, $C_{1-4}$ alkoxy, or —NR²R²;
R⁴⁶ is hydrogen or a $C_{1-8}$ alkyl group optionally substituted with one or moieties selected from the group consisting of indolyl, —OR³, —SR³, imidazolyl, $C_{1-8}$ alkylthio, —NR²R², and aryl,
wherein the aryl group optionally is substituted with OH, —C(O)NH₂, —CO₂H, or —C(=NH)NH₂;

R⁴⁷ is selected from the group consisting of:
a) $C_{1-16}$ alkyl, b) $C_{2-16}$ alkenyl, c) aryl, and d) heteroaryl, wherein any of a)-d) optionally is substituted with one or more $R^{13}$ groups;

$R^{48}$ is selected from the group consisting of:
—OH, —OCH$_3$, —NH$_2$, —OC(O)OCH$_3$, —OC(O)CH$_2$OC(O)CH$_3$, —O(CH$_2$)$_2$OH, —OC(O)CH$_2$OCH$_2$C$_6$H$_5$, —O(CH$_2$)$_2$OCH$_2$OCH$_3$, and —OCH$_2$OCH$_3$;

$R^{49}$ is selected from the group consisting of:
hydrogen, —CH$_2$OH, and —CH$_2$OCH$_2$OCH$_3$;

$R^{50}$, at each occurrence, independently is hydrogen or CH$_3$;

alternatively, two $R^{50}$ groups taken together with the carbon atom to which each is bonded are —CH$_2$CH$_2$—;

$R^{51}$ is selected from the group consisting of:
a) hydrogen, b) C$_{1-6}$ alkyl, optionally substituted with one or more hydroxyl groups, halogens, or —CN, c) —(CH$_2$)$_s$-aryl, d) —CO$_2$R$^{52}$, e) —COR$^{53}$, f) —C(O)(CH$_2$)$_s$C(O)R$^{52}$, g) —S(O)$_2$—C$_{1-6}$ alkyl, h) —S(O)$_2$(CH$_2$)$_s$-aryl, and i) —(C(O))$_s$-Het;

$R^{52}$ is selected from the group consisting of:
a) hydrogen, b) C$_{1-6}$ alkyl, optionally substituted with one or more hydroxyl groups, halogens, or —CN, c) —(CH$_2$)$_s$-aryl, and d) —(CH$_2$)$_s$—OR$^{54}$;

$R^{53}$ is selected from the group consisting of:
a) C$_{1-6}$ alkyl, optionally substituted with one or more hydroxyl groups, halogens, or —CN, b) —(CH$_2$)$_s$-aryl, and c) —(CH$_2$)$_s$—OR$^{54}$;

$R^{54}$ is selected from the group consisting of:
a) hydrogen, b) C$_{1-6}$ alkyl, c) —(CH$_2$)$_s$-aryl, and d) —C(O)—C$_{1-6}$ alkyl,
wherein the aryl group is selected from the group consisting of phenyl, pyridyl, and napthyl,
wherein each of the phenyl, pyridyl, and napthyl optionally is substituted with one or more moeities from the group consisting of F, Cl, Br, —CN, —OH, —SH, C$_{1-6}$ alkyl, C$_{1-6}$ alkoxy, and C$_{1-6}$ alkylthio; and G is selected from the group consisting of
a) C$_{1-4}$ alkyl, b) C$_{5-8}$ alkyl, c) C$_{2-8}$ alkenyl, d) C$_{2-8}$ alkynyl, e) C$_{1-8}$ alkoxy, f) C$_{1-8}$ alkylthio, g) C$_{1-8}$ acyl, h) saturated, unsaturated, or aromatic C$_{5-10}$ carbocycle, i) saturated, unsaturated, or aromatic 5-10 membered heterocycle containing one or more heteroatoms selected from the group consisting of nitrogen, oxygen, and sulfur, j)
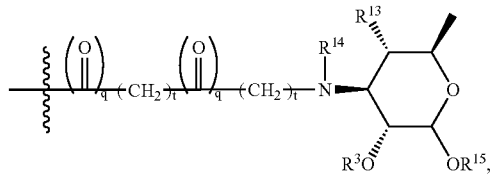

k)
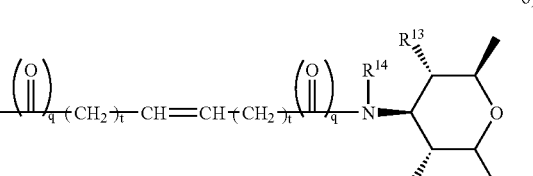

l)
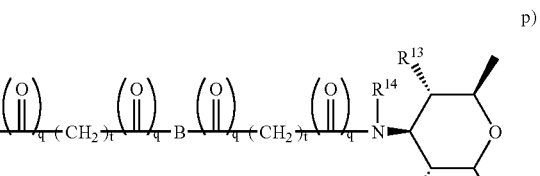

m)
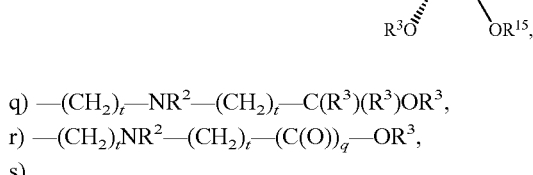

n)
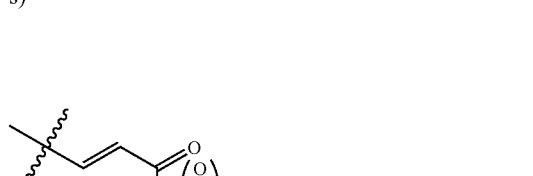

o)
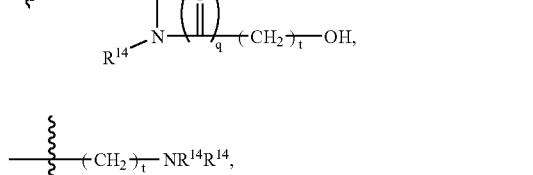

p)
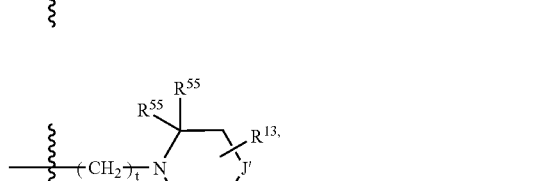

q) —(CH$_2$)$_t$—NR$^2$—(CH$_2$)$_t$—C(R$^3$)(R$^3$)OR$^3$, r) —(CH$_2$)$_t$NR$^2$—(CH$_2$)$_t$—(C(O))$_q$—OR$^3$, s)
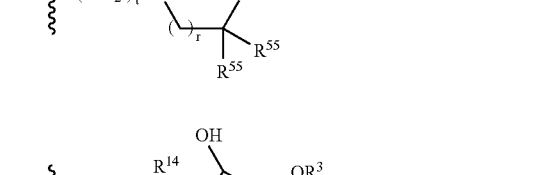

t)
—(CH$_2$)$_t$—NR$^{14}$R$^{14}$, u)
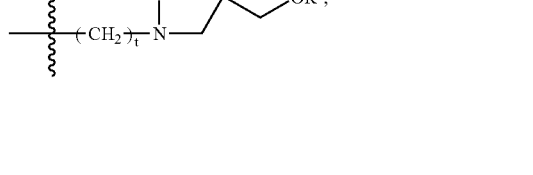

v)
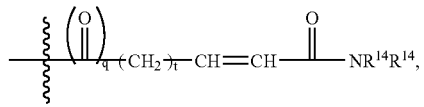

-continued w) 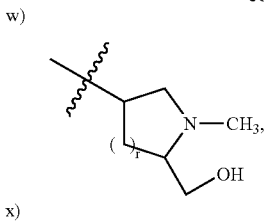

x) 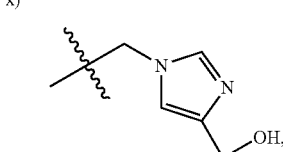

y) 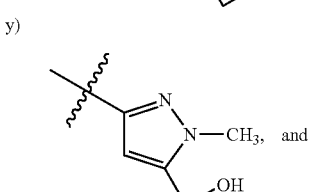

z) 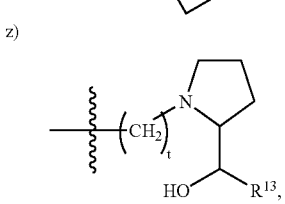

wherein
i) a) is substituted with, and
ii) any of b)-i) optionally is substituted with one or more moieties selected from the group consisting of:
carbonyl; formyl; F; Cl; Br; I; CN; $NO_2$; $OR^3$; $-S(O)_rR^5$; $-S(O)_rN=R^2$; $-C(O)R^2$; $-C(O)OR^3$; $-OC(O)R^2$; $-C(O)NR^2R^2$; $-OC(O)NR^2R^2$; $-C(=NR^{12})R^2$; $-C(R^2)(R^2)OR^3$; $-C(R^2)(R^2)OC(O)R^2$; $-C(R^2)(OR^3)(CH_2)_r NR^2R^2$; $-NR^2R^2$; $-NR^2OR^3$; $-NR^2C(O)R^2$; $-NR^2C(O)OR^3$; $-NR^2C(O)NR^2R^2$; $-NR^2S(O)_rR^5$; $-C(OR^6)(OR^6)R^2$; $-C(R^2)(R^3)NR^2R^2$; $-C(R^2)(R^3)NR^2R^{12}$; $=NR^{12}$; $-C(S)NR^2R^2$; $-NR^2C(S)R^2$; $-OC(S)NR^2R^2$; $-NR^2C(S)OR^3$; $-NR^2C(S)NR^2R^2$; $-SC(O)R^2$; $C_{2-5}$ alkenyl; $C_{2-5}$ alkynyl; $C_{1-8}$ alkoxy; $C_{1-8}$ alkylthio; $C_{1-8}$ acyl; saturated, unsaturated, or aromatic $C_{5-10}$ carbocycle, optionally substituted with one or more $R^{13}$ groups; and saturated, unsaturated, or aromatic 5-10 membered heterocycle containing one or more heteroatoms selected from the group consisting of nitrogen, oxygen, and sulfur, and optionally substituted with one or more $R^{13}$ groups;
t, at each occurrence, independently is 0, 1, 2, or 3;
v is 0, 1, 2, 3, 4, 5, or 6;
K' is O, $NR^2$, or $S(O)_r$;
$R^{55}$, at each occurrence, independently is hydrogen, $-CH_2OH$, or $C_{1-4}$ alkyl;
alternatively, two $R^{55}$ groups taken together are a carbonyl group;
$R^{14}$ is selected from the group consisting of:
a) hydrogen, b) $C_{1-6}$-alkyl, c) $C_{2-6}$ alkenyl, d) $C_{2-6}$ alkynyl, e) $-C(O)-R^3$, f) $-C(O)-C_{1-6}$ alkyl-$R^3$,
g) $-C(O)-C_{2-6}$ alkenyl-$R^3$, h) $-C(O)-C_{2-6}$ alkynyl-$R^3$, i) $-C_{1-6}$ alkyl-J-$R^3$, j) $-C_{2-6}$ alkenyl-J-$R^3$; and k) $-C_{2-6}$ alkynyl-J-$R^3$;
wherein
(i) any of b)-d) optionally is substituted with one or more substituents selected from the group consisting of:
F, Cl, Br, I, aryl, substituted aryl, heteroaryl, substituted heteroaryl, $-OR^3$, $-O-C_{1-6}$ alkyl-$R^2$, $-O-C_{2-6}$ alkenyl-$R^2$, $-O-C_{2-6}$ alkynyl-$R^2$, and $-NR^2R^2$; and
(ii) J is selected from the group consisting of:
$-OC(O)-$, $-OC(O)O-$, $-OC(O)NR^2-$, $-C(O)NR^2-$, $-NR^2C(O)-$, $-NR^2C(O)O-$, $-NR^2C(O)NR^2-$, $-NR^2C(NH)NR^2-$, and $S(O)_r$; and
$R^{15}$ is selected from the group consisting of:
hydrogen; $C_{1-10}$ alkyl, optionally substituted with one or more $R^{13}$ groups; $C_{1-6}$ acyl, optionally substituted with one or more $R^{13}$ groups; aryl; substituted aryl; heteroaryl; substituted heteroaryl; arylalkyl; substituted arylalkyl; and a macrolide;
wherein the macrolide is selected from the group consisting of:

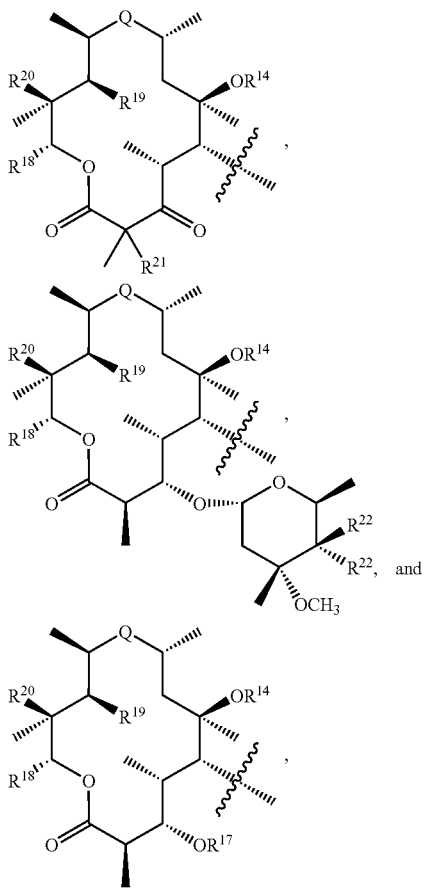

and pharmaceutically acceptable salts, esters and prodrugs thereof, wherein
$R^{17}$ is selected from the group consisting of:
hydrogen, hydroxy protecting group, $R^3$, and $-V-W-R^{13}$, wherein
V is —C(O), —C(O)O—, —C(O)NR$^2$—, or absent, and
W is C$_{1-6}$ alkyl, or absent;
alternatively R$^{17}$ and R$^{14}$, taken together with the atoms to which they are bonded, form:

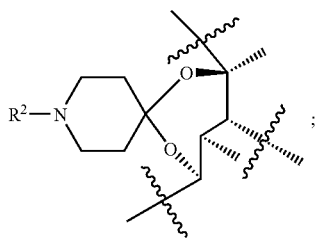
;

Q is selected from the group consisting of:
—NR$^2$—CH$_2$—, —CH$_2$—NR$^2$—, —C(O)—, —C(=NR$^2$)—, —C(=NOR$^3$)—, —C(=N—NR$^2$R$^2$)—, —CH(OR$^3$)—, and —CH(NR$^2$R$^2$)—;
R$^{18}$ is selected from the group consisting of:
i) C$_{1-6}$ alkyl, ii) C$_{2-6}$ alkenyl, and iii) C$_{2-6}$ alkynyl; wherein any of i)-iii) optionally is substituted with one or more moieties selected from the group consisting of —OR$^3$, aryl, substituted aryl, heteroaryl, and substituted heteroaryl;
R$^{19}$ is selected from the group consisting of:
a) —R$^{17}$, b) C$_{1-6}$ alkyl, c) C$_{2-6}$ alkenyl, d) C$_{2-6}$ alkynyl, e) —NR$^2$R$^2$, f) —C(O)R$^3$, g) —C(O)—C$_{1-6}$ alkyl-R$^{13}$, h) —C(O)—C$_{2-6}$ alkenyl-R$^{13}$, and i) —C(O)—C$_{2-6}$ alkynyl-R$^{13}$,
wherein any of b)-d) optionally is substituted with one or more R$^{13}$ groups;
alternatively, R$^{14}$ and R$^{19}$, taken together with the atoms to which they are bonded, form:

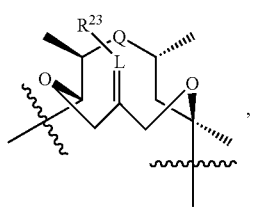
, wherein
L is CH or N, and
R$^{23}$ is —OR$^3$, or R$^3$;
R$^{20}$ is —OR$^{17}$,
alternatively, R$^{19}$ and R$^{20}$, taken together with the atoms to which they are bonded, form a 5-membered ring by attachment to each other through a linker selected from the group consisting of:
—OC(R$^2$)(R$^2$)O—, —OC(O)O—, —OC(O)NR$^2$—, —NR$^2$C(O)O—, —OC(O)NOR$^3$—, —N(OR$^3$)C(O)O—, —OC(O)N—NR$^2$R$^2$—, —N(NR$^2$R$^2$)C(O)O—, —OC(O)CHR$^2$—, —CHR$^2$C(O)O—, —OC(S)O—, —OC(S)NR$^2$—, —NR$^2$C(S)O—, —OC(S)NOR$^3$—, —N(OR$^3$)C(S)O—, —OC(S)N—NR$^2$R$^2$—, —N(NR$^2$R$^2$)C(S)O—, —OC(S)CHR$^2$—, and —CHR$^2$C(S)O—;
alternatively, Q, R$^{19}$, and R$^{20}$, taken together with the atoms to which they are bonded, form:

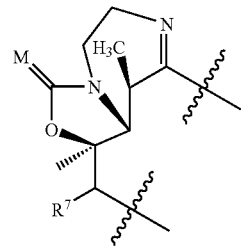

wherein
M is O or NR$^2$;
R$^{21}$ is selected from the group consisting of:
hydrogen, F, Cl, Br, I, and C$_{1-6}$ alkyl;
R$^{22}$, at each occurrence, independently is selected from the group consisting of:
hydrogen, —OR$^3$, —O-hydroxy protecting group, —O—C$_{1-6}$ alkyl-J-R$^{13}$, —O—C$_{2-6}$ alkenyl-J-R$^{13}$, —O—C$_{1-6}$ alkynyl-J-R$^{13}$, and —NR$^2$R$^2$;
alternatively, two R$^{22}$ groups taken together are =O, =N—OR$^3$, or =N—NR$^2$R$^2$; and
R$^2$, R$^3$, R$^{13}$, R$^{14}$, and J are as described hereinabove.
Examples of:

include, but are not limited to, thiophene, furan, 4-oxo-2-imidazolyl, 2-imidazolyl, 4-imidazolyl, 3-isoxazolyl, 4-isoxazolyl, 5-isoxazolyl, 1-pyrazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 1-pyrrolyl, 2-pyrrolyl, 3-pyrrolyl, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,3-triazol-1-yl, 1,2,3-triazol-4-yl, 1,2,3-triazol-5-yl, 1,2,4-triazol-1-yl, 1,2,4-triazol-3-yl, 1,2,4-triazol-5-yl, 1-tetrazol-5-yl, 2-tetrazol-5-yl, 3-isothiazolyl, 4-isothiazolyl and 5-isothiazolyl, 4-oxo-2-thiazolinyl, or 5-methyl-1,3,4-thiadiazol-2-yl, thiazolidine-2,4-dione, oxazolidine-2,4-dione, imidazolidine-2,4-dione, oxazolidin-2-one, thiazolidin-2-one, 3H-oxazol-2-one, 1,3-dihydro-imidazol-2-one, 1,3-dihydro-imidazole-2-thione, 2-thioxo-imidazolidin-4-one, and 4-thioxo-imidazolidin-2-one.

In certain embodiments, the invention provides compounds having the formula:

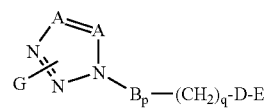

wherein
A, at each occurrence, independently is carbon or nitrogen, provided at least one A is carbon, and p, q, B, D, E, and G are as defined hereinabove.

Other embodiments of the invention include compounds having the formula:

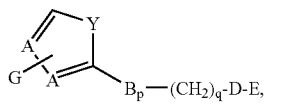

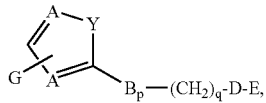

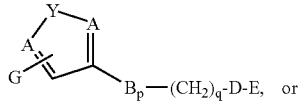

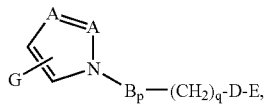

wherein
Y is oxygen or sulfur,
A, at each occurrence, independently is carbon or nitrogen, and
p, q, B, D, E, and G are as defined hereinabove.

In other embodiments, the invention provides compounds having the formula:

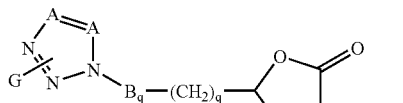

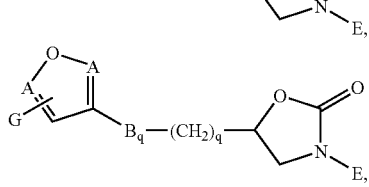

wherein p, q, A, B, E, and G are as defined hereinabove.

Features of these embodiments include compounds having the formula:

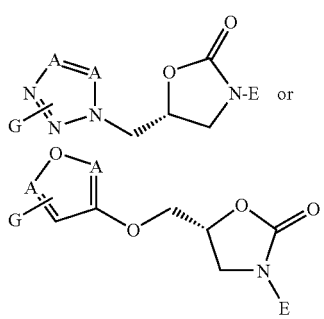

wherein A, E, and G are as defined hereinabove.

In some embodiments, the invention provides compounds having the formula:

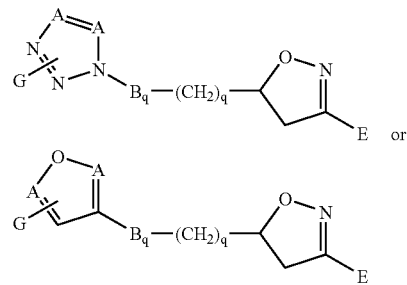

wherein p, q, A, E, and G are as defined hereinabove.

Features of these embodiments include compounds having the formula:

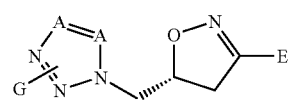

wherein A, E, and G are as defined hereinabove.

In certain embodiments, E has the formula:

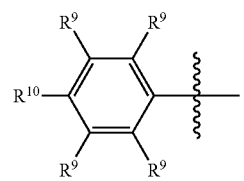

wherein $R^9$ and $R^{10}$, at each occurrence, are as defined hereinabove.

Features of this embodiment include compounds wherein E has the formula:

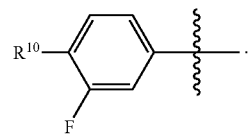

Other features of this embodiment include compounds wherein $R^{10}$ has the formula:

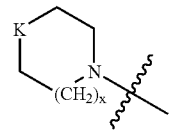

wherein K is selected from the group consisting of O, $NR^2$, and $S(O)_r$, and
x is 0, 1, 2, or 3.

In certain features of this embodiment, K is oxygen, and in other features, t is 1.

Still other features of this embodiment include compounds wherein $R^{10}$ is $-C(O)CH_3$.

Yet another feature of this embodiment includes compounds wherein $R^{10}$ has the formula:

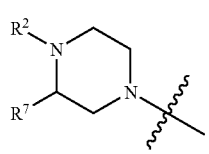

wherein $R^2$ and $R^7$ are as defined hereinabove.

Certain other features of this embodiment include compounds wherein $R^2$ is —C(O)—CH$_2$—OH. In other features, $R^7$ is hydrogen.

In other embodiments according to the invention, in the foregoing compounds, G has the formula:

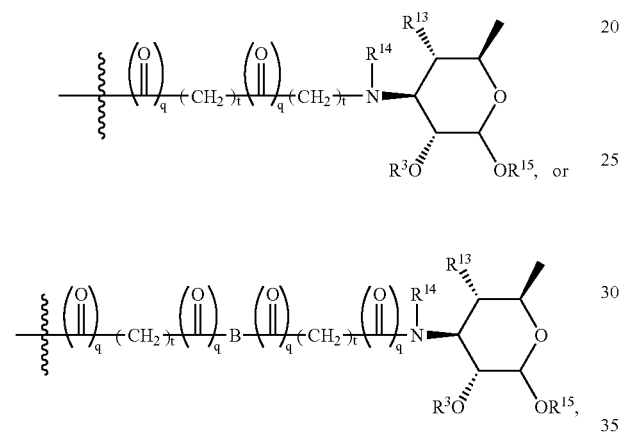

wherein $R^{15}$ is a macrolide.

In other embodiments of the invention, G has the formula selected from the group consisting of:

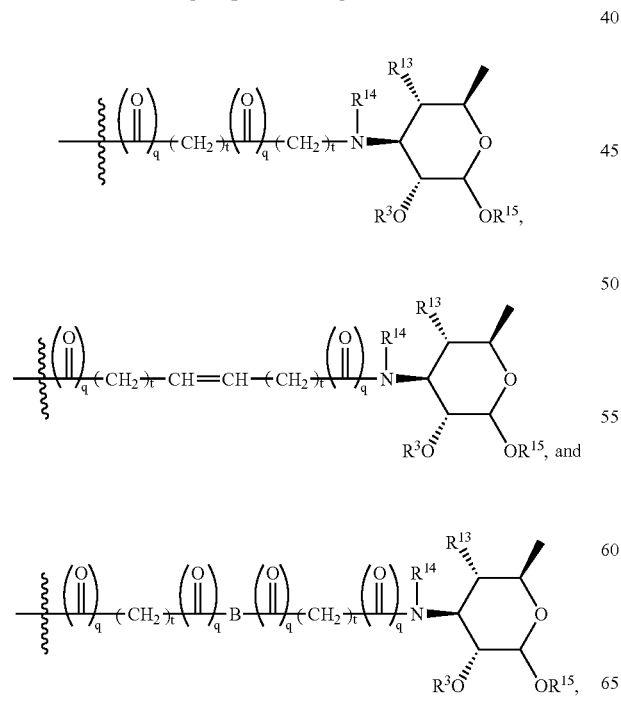

and $R^{15}$ is selected from the group consisting of:

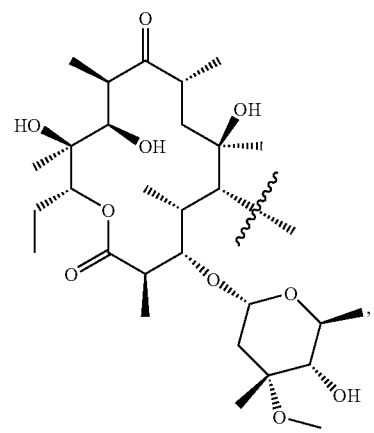

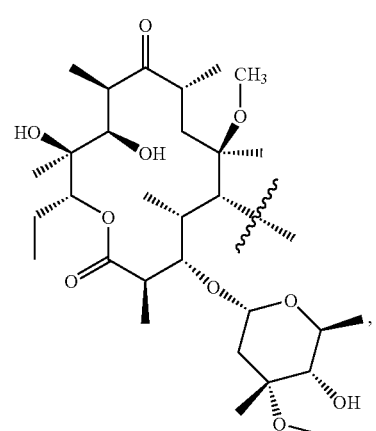

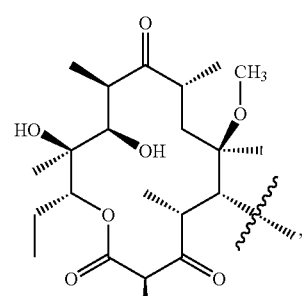

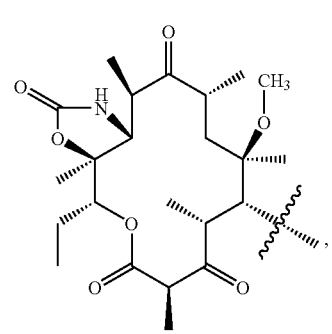

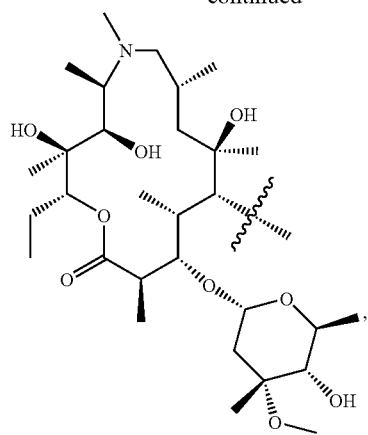
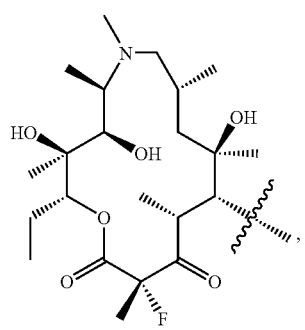
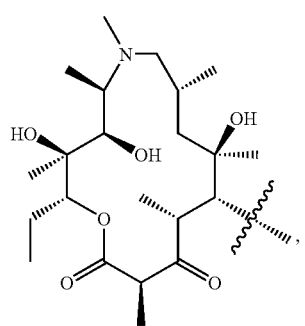
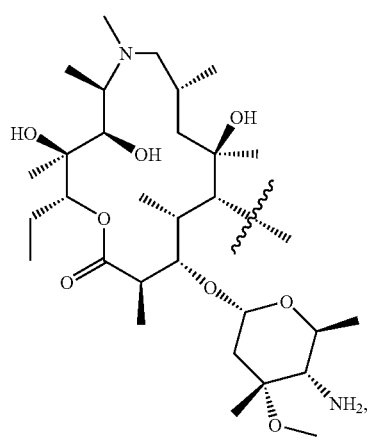
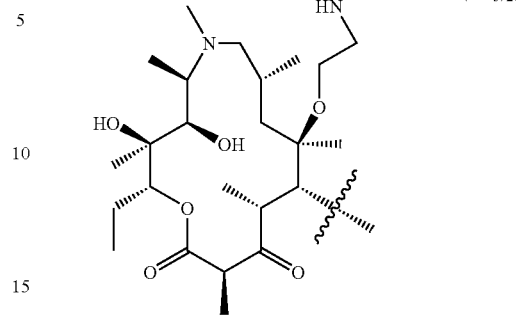
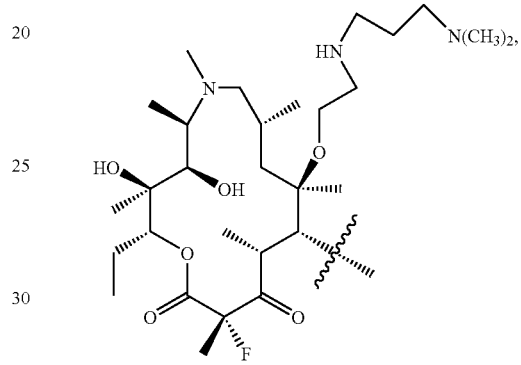
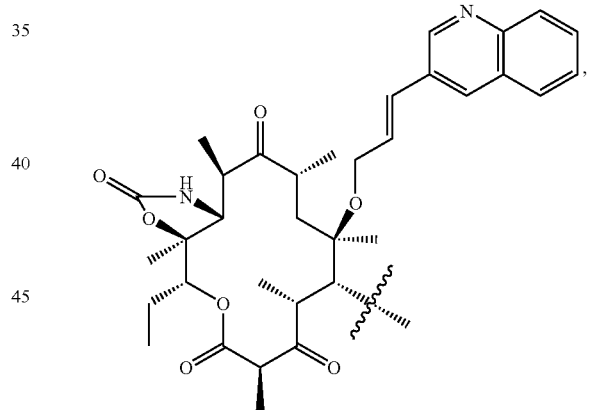
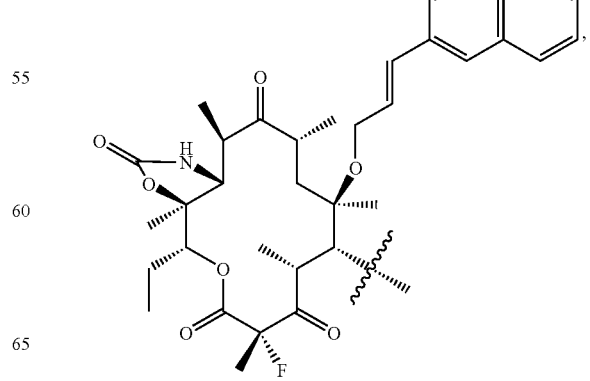

-continued
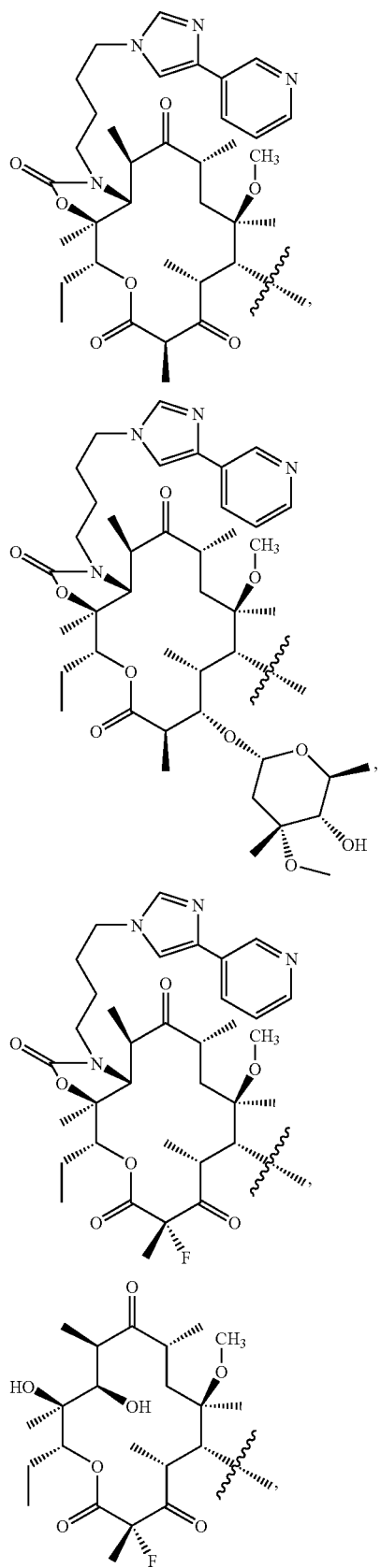
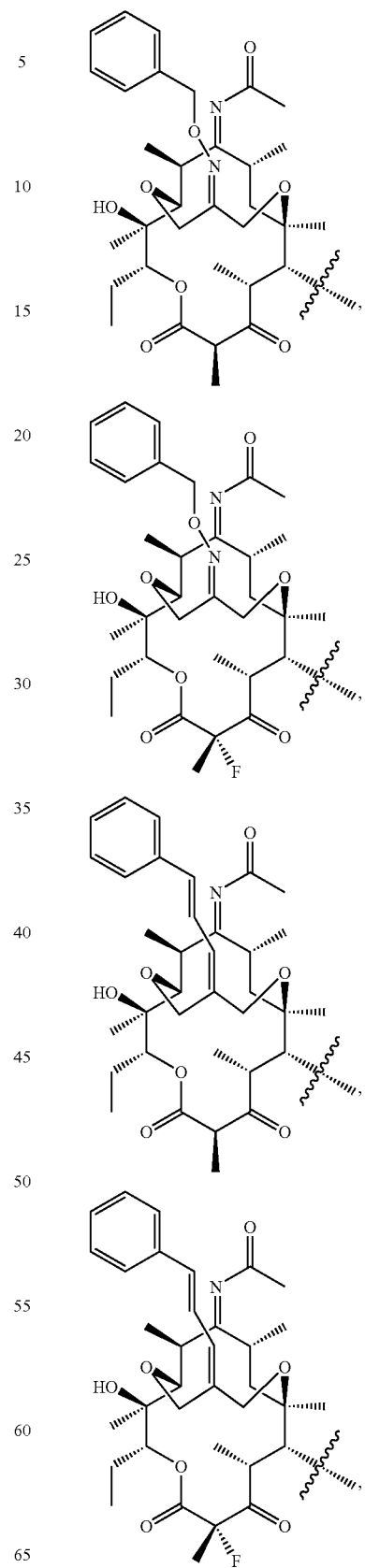

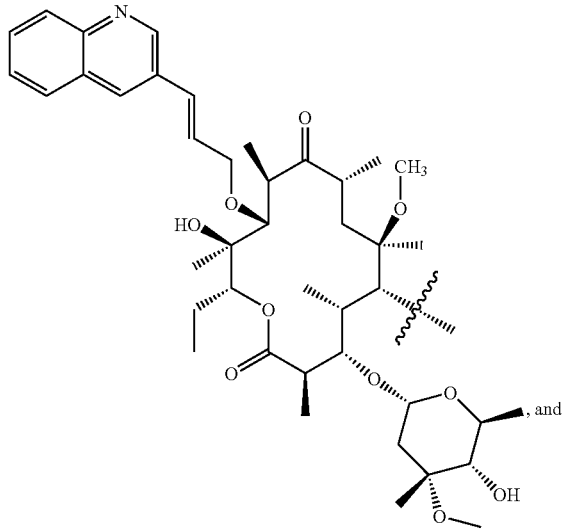
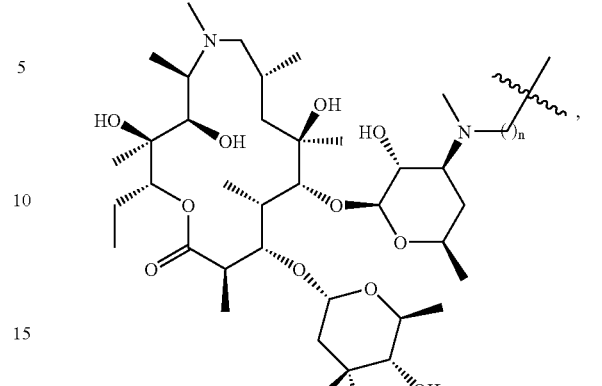
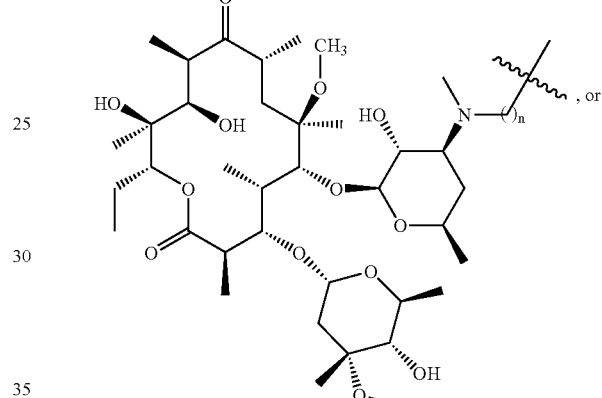
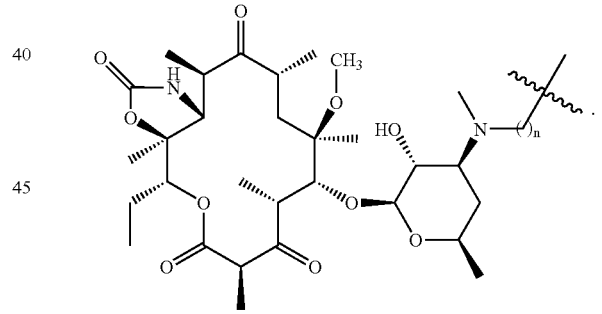
In another embodiments according to the invention, in the foregoing compounds, G has the formula:
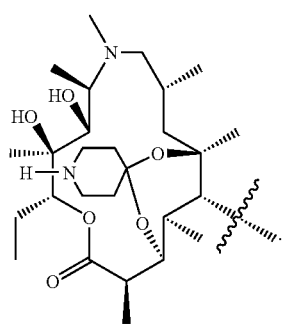
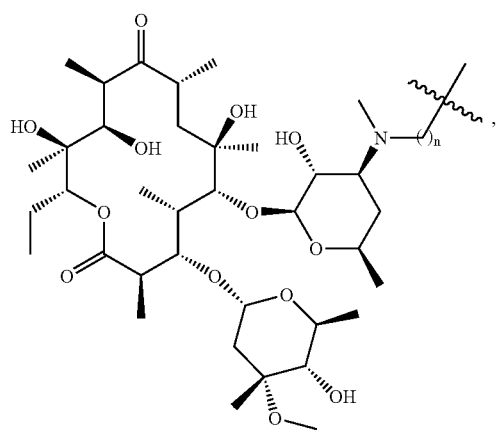
wherein n is 1, 2, 3, or 4.
In still other embodiments, the invention provides compounds having the formula:
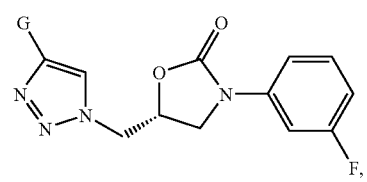
wherein described hereinabove. Features of this embodiment include compounds wherein G is selected from the group consisting of:

41
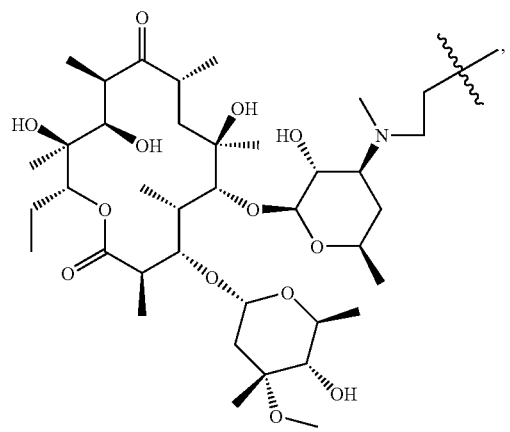
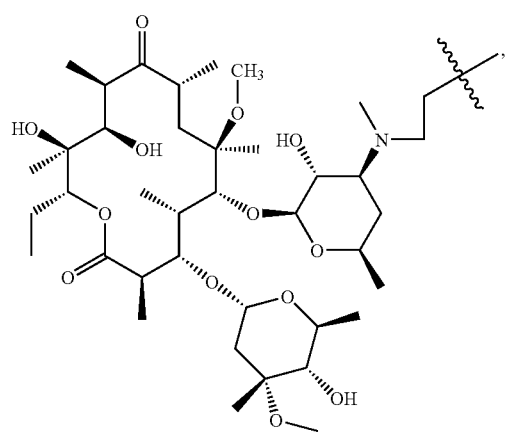
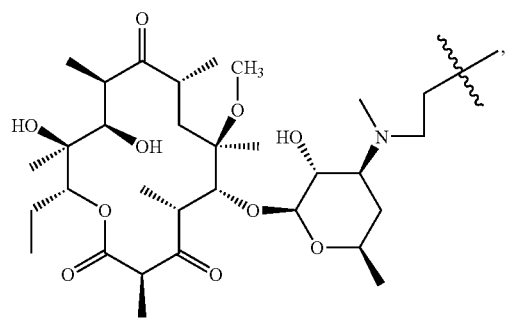
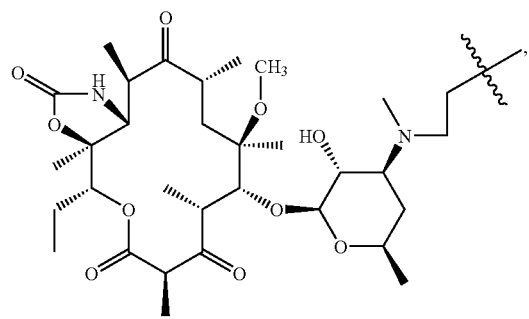
42
-continued
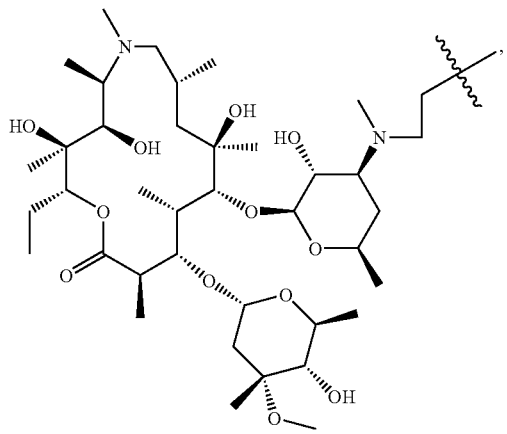
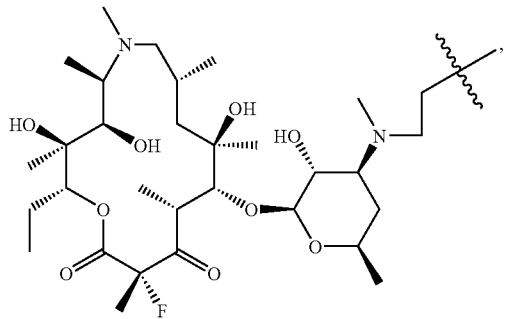
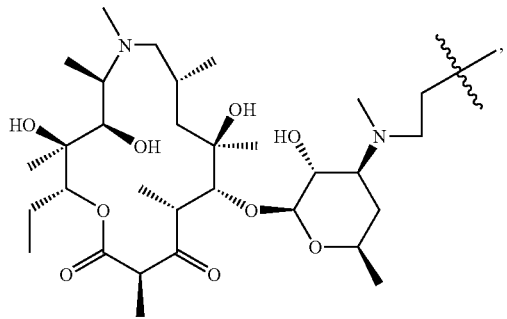
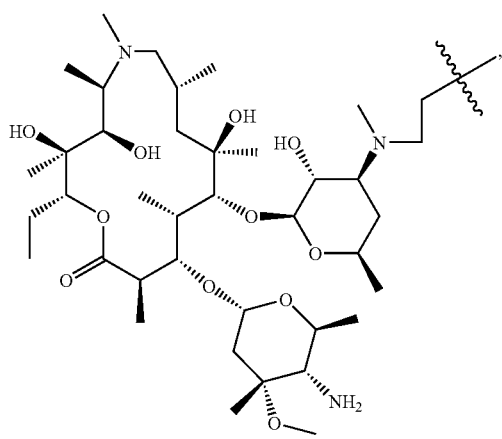

-continued
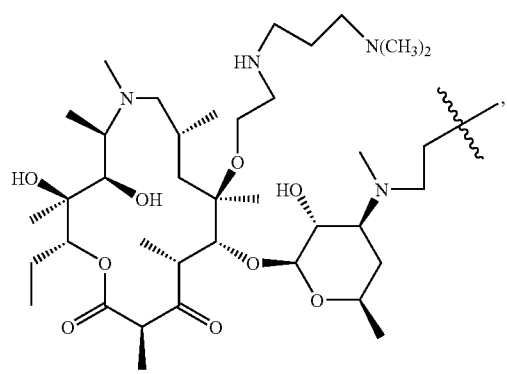
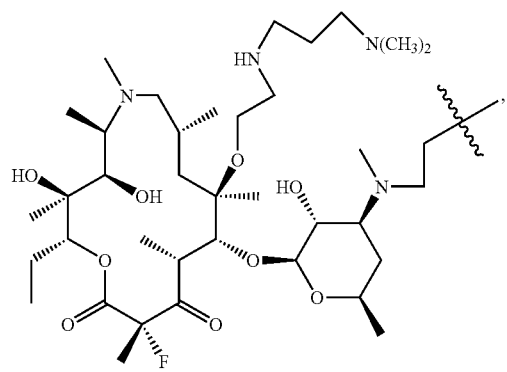
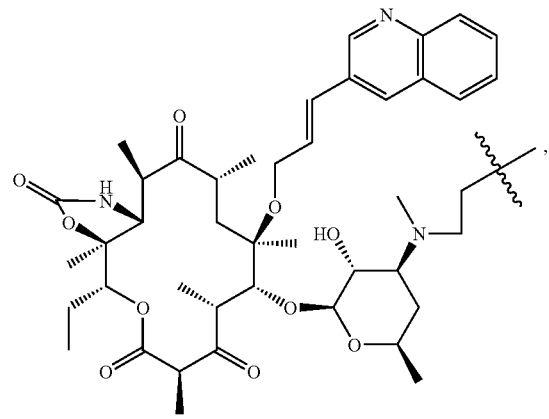
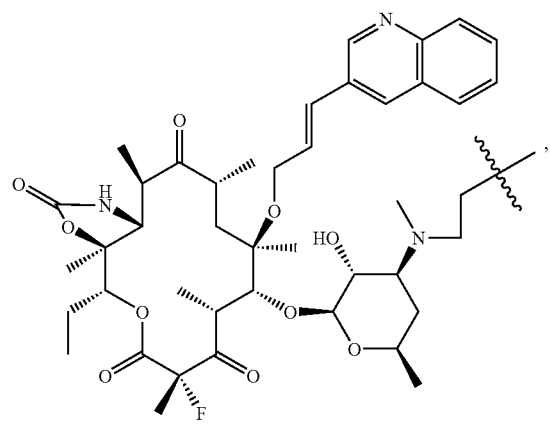
-continued
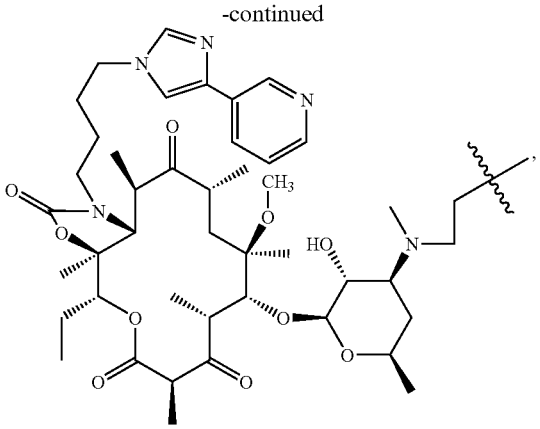
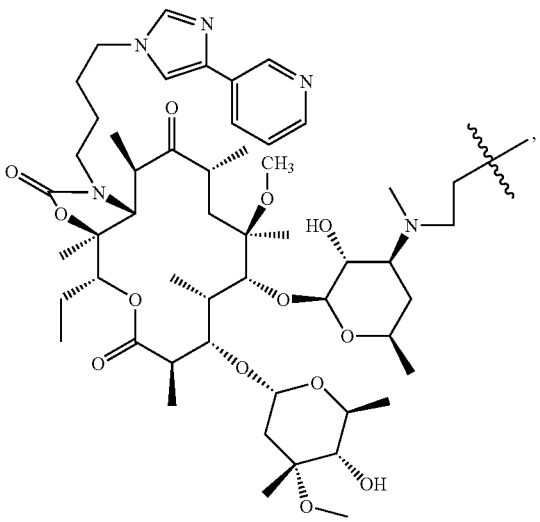
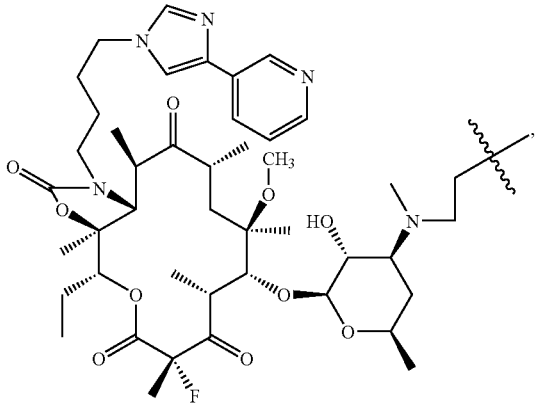
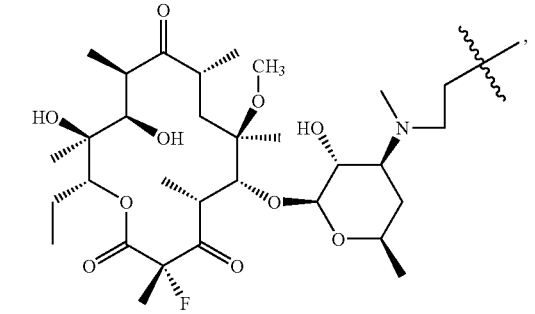

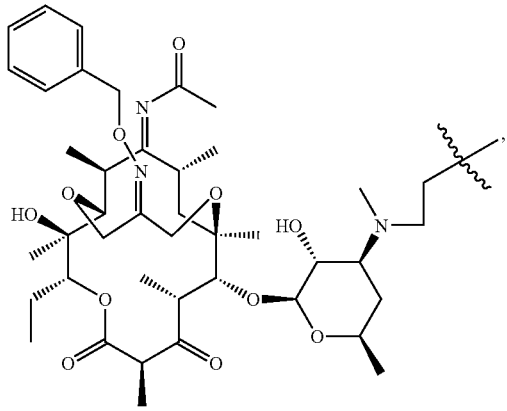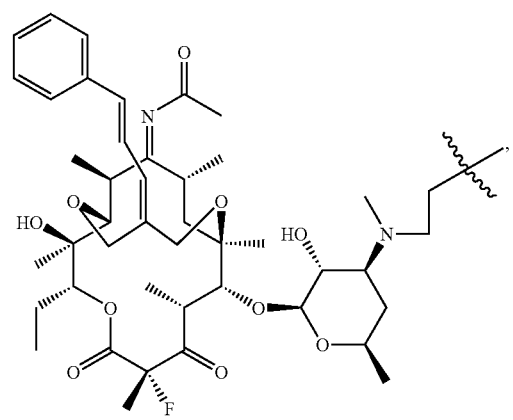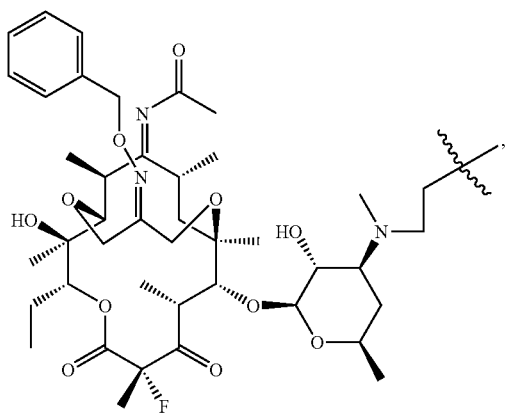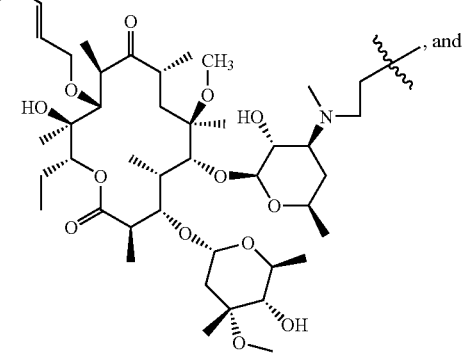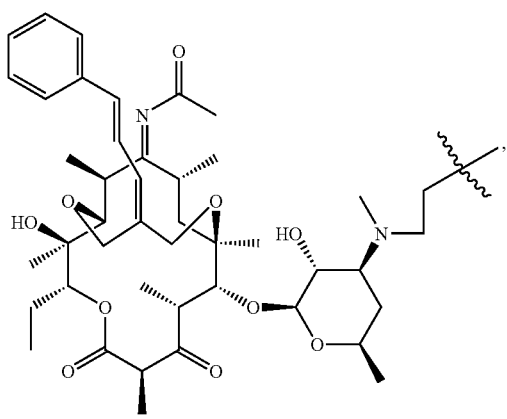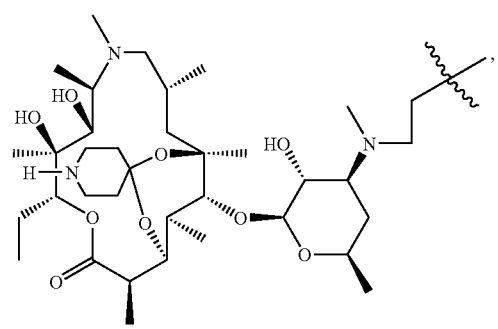
Other embodiments of the invention include compounds having the formula selected from:

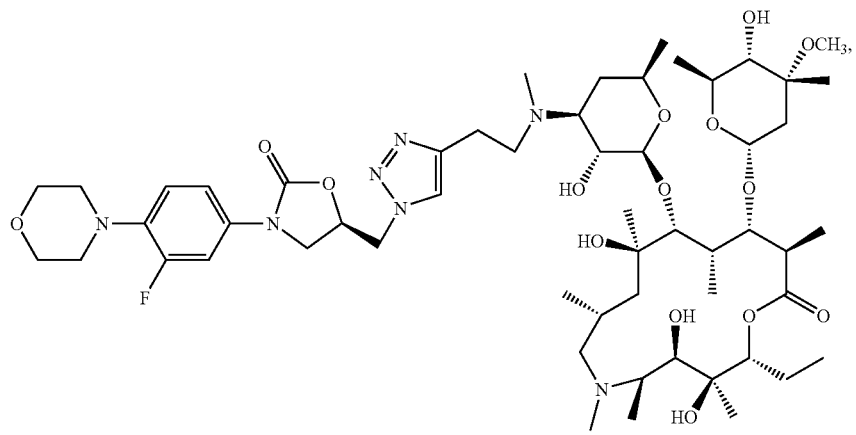
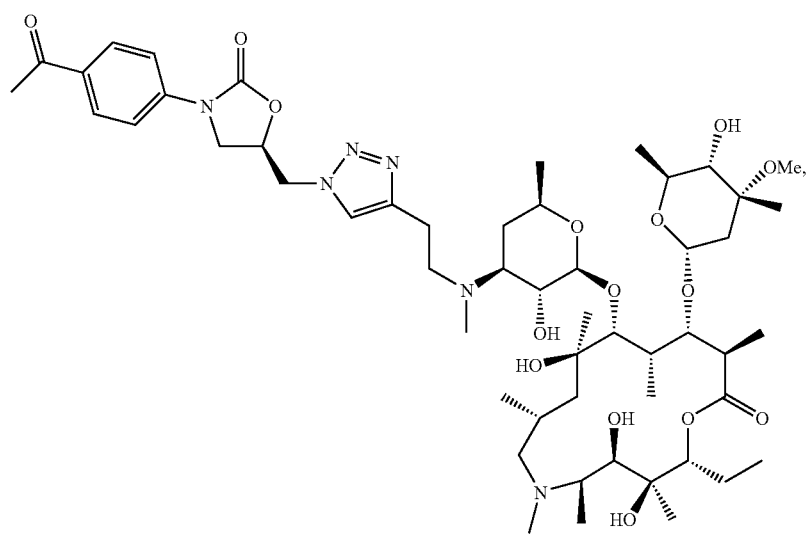
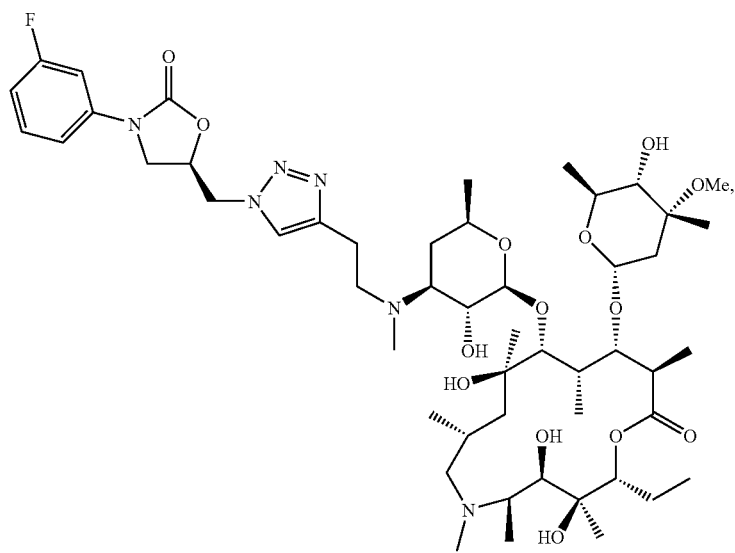

-continued
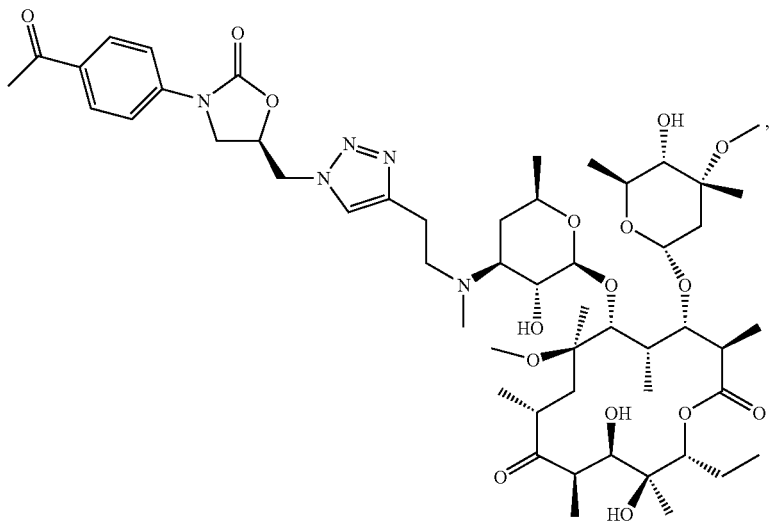
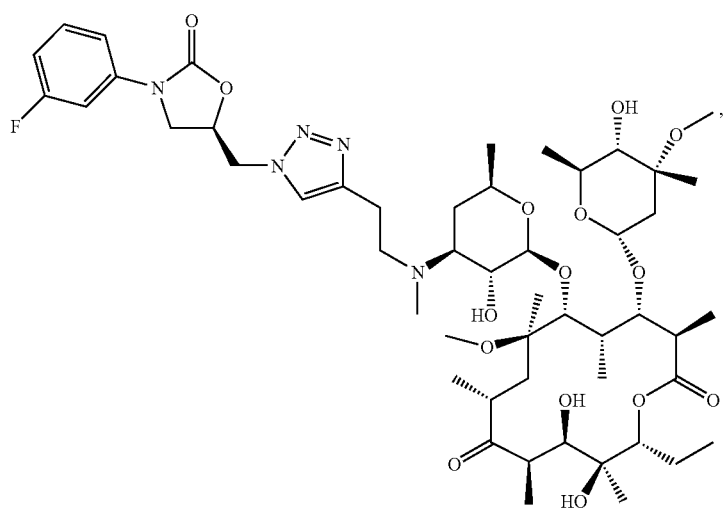
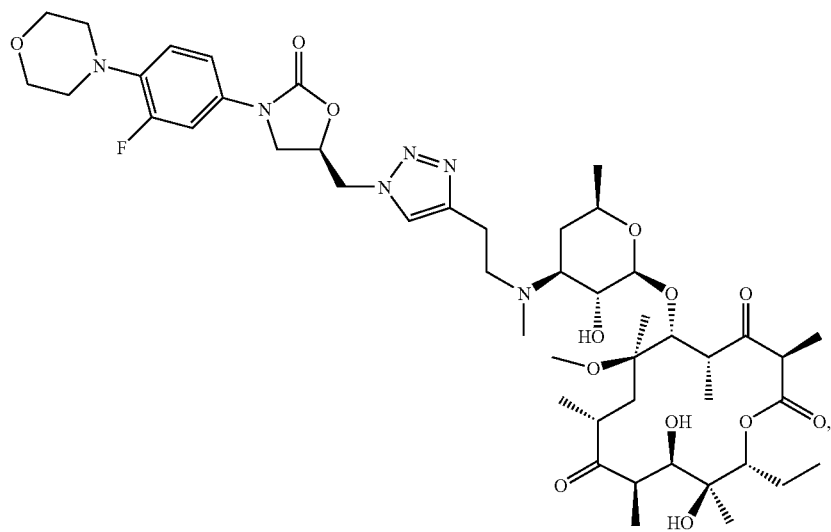

-continued
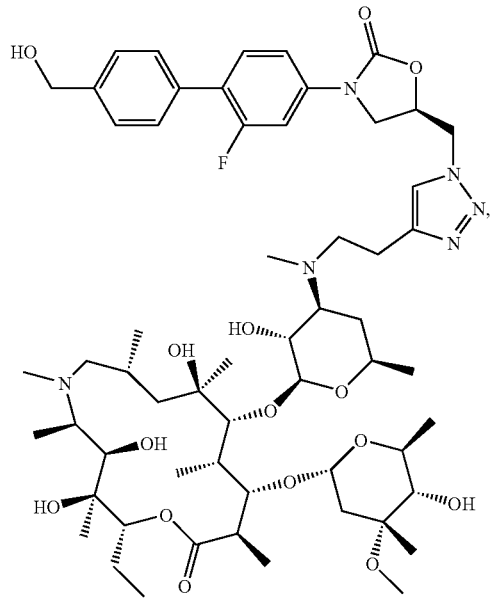
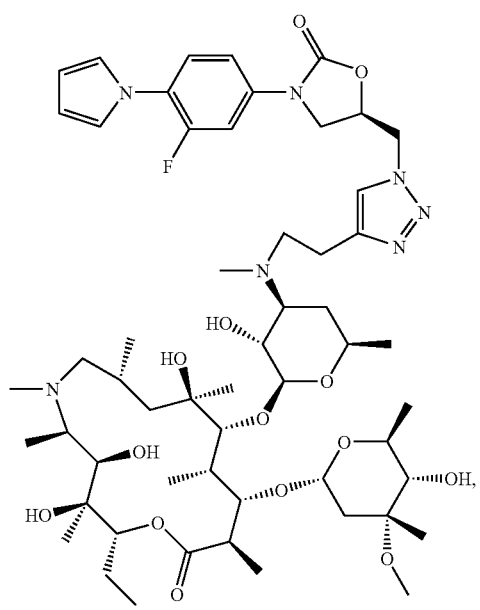

-continued
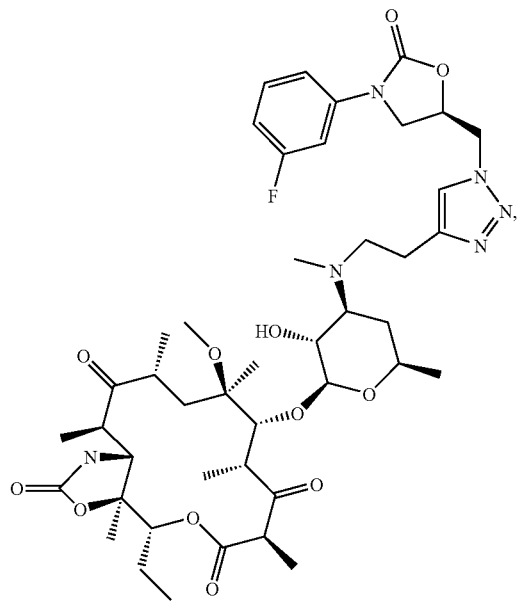
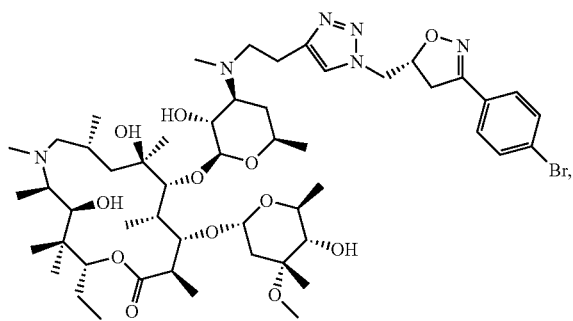
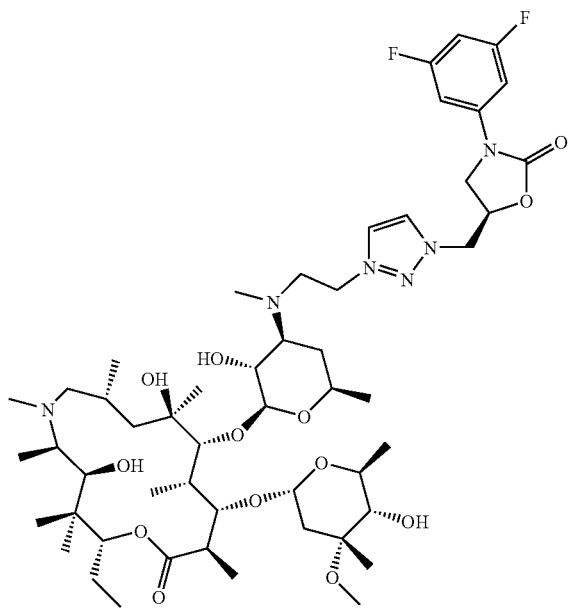

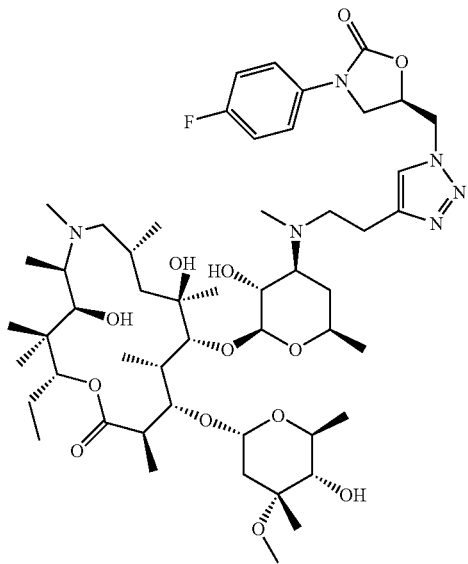
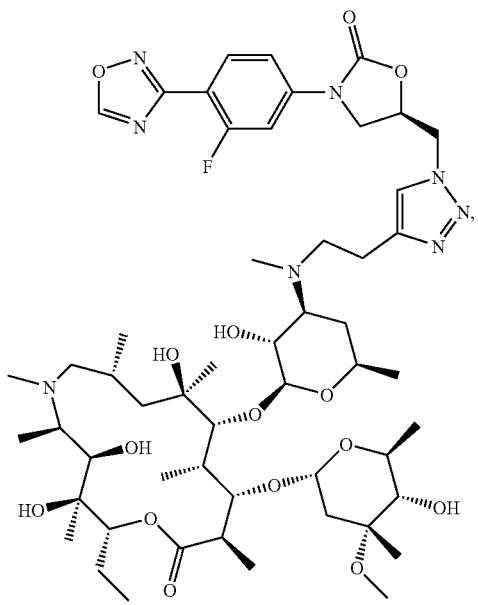

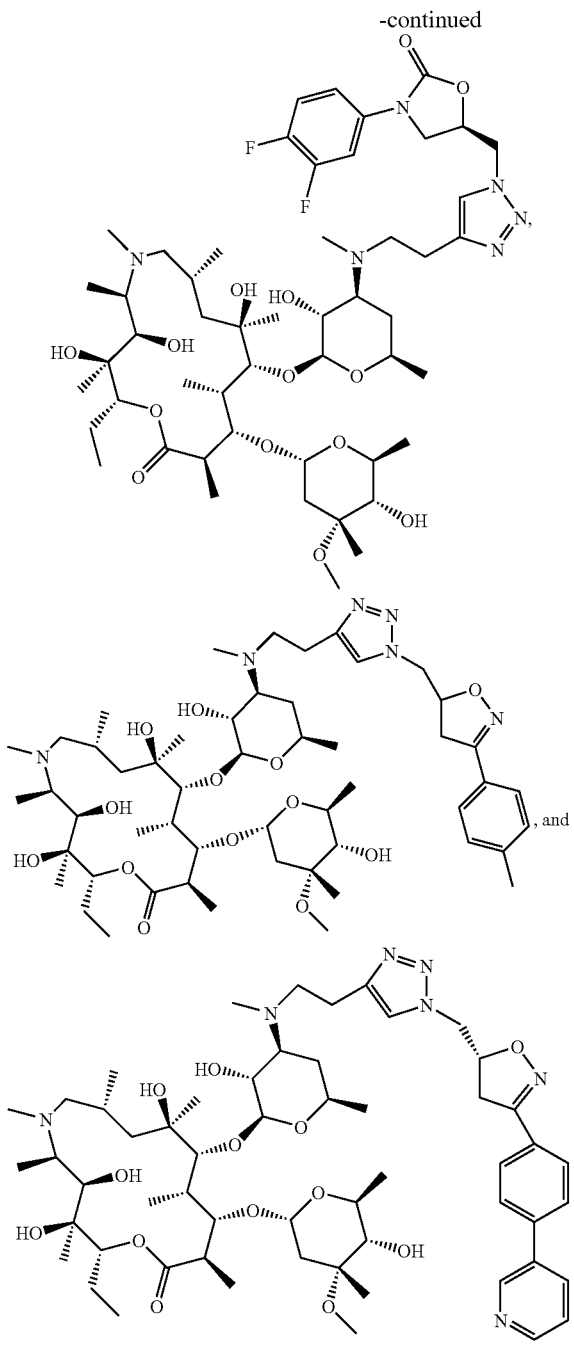

or a pharmaceutically acceptable salt, ester, or prodrug thereof.

In another aspect, the invention provides a pharmaceutical composition comprising a therapeutically effective amount of one or more of the foregoing compounds and a pharmaceutically acceptable carrier. In yet another aspect, the invention provides a method for treating a microbial infection, a fungal infection, a viral infection, a parasitic disease, a proliferative disease, an inflammatory disease, or a gastrointestinal motility disorder in a mammal by administering effective amounts of the compounds of the invention or pharmaceutical compositions of the invention, for example; via oral, parenteral or topical routes. In still another aspect, the invention provides methods for synthesizing any one of the foregoing compounds. In another aspect, the invention provides a medical device, for example, a medical stent, which contains or is coated with one or more of the foregoing compounds.

In another embodiment, the invention further provides a family of hybrid antibiotics comprising a heterocyclic sidechain linked via a heterocyclic linker to at least a portion of a macrolide-based antibiotic. Exemplary heterocyclic sidechains, heterocylic linkers, and macrolides useful in the synthesis of the hybrid antibiotics include, but are not limited to, the chemical moieties shown below:

Heterocyclic Side-Chains
01
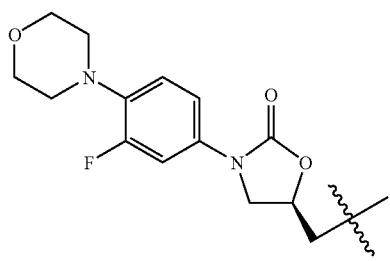
02
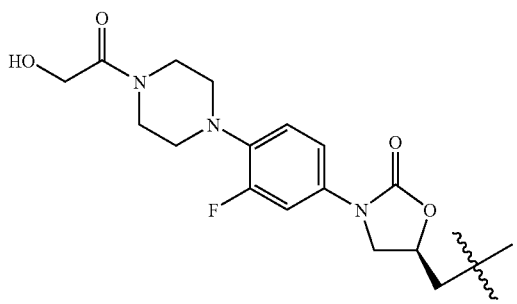
03
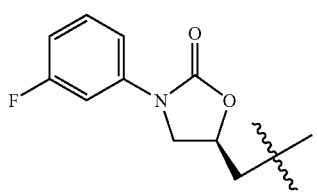
04
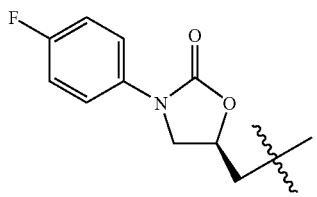
05
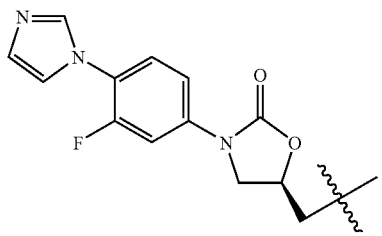
06
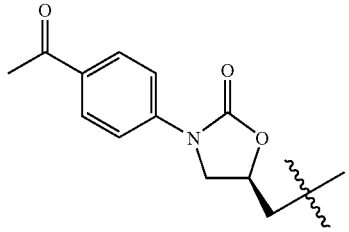
-continued
07
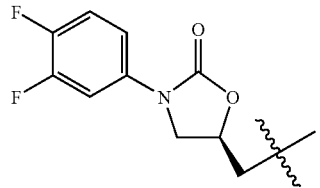
08
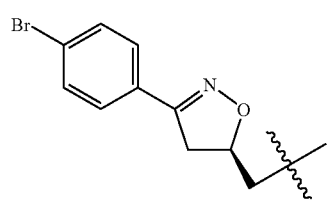
09
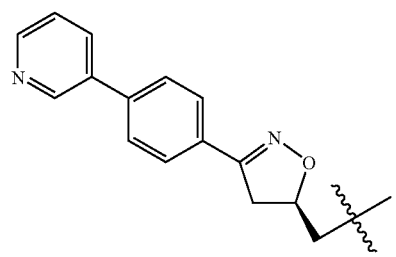
010
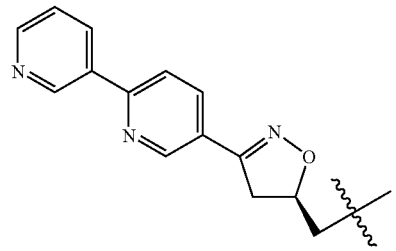
011
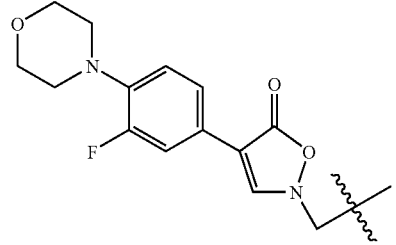
012
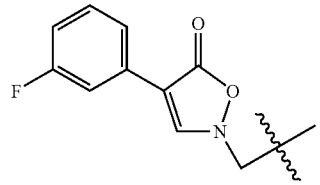

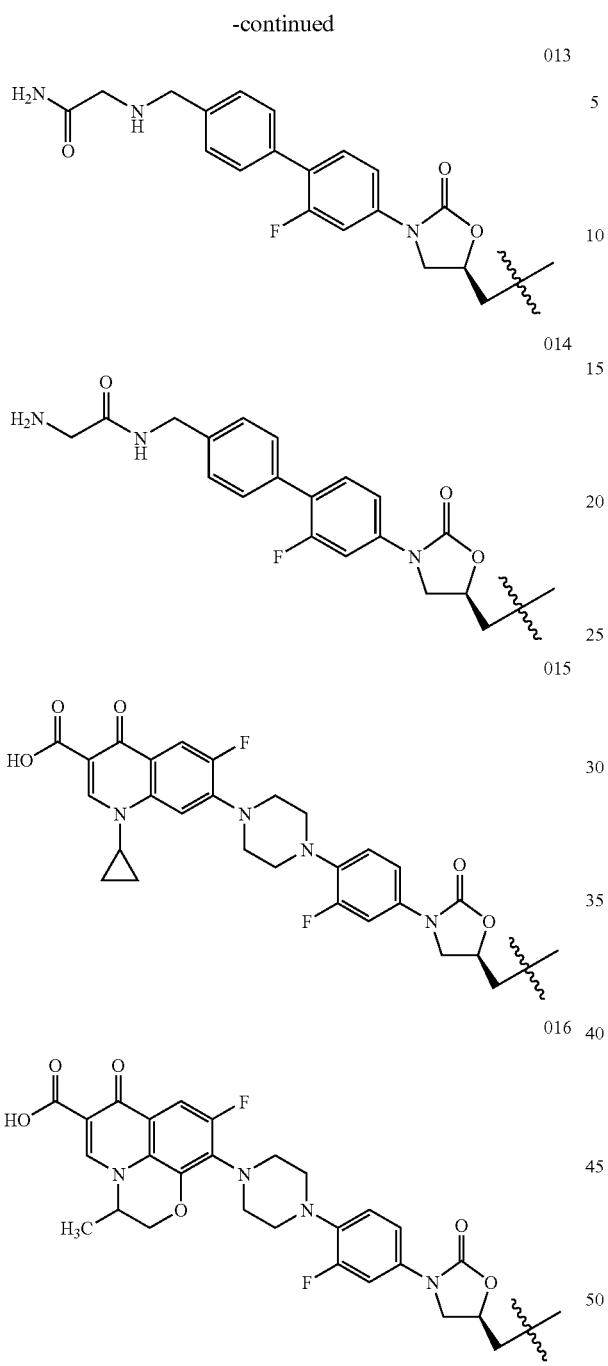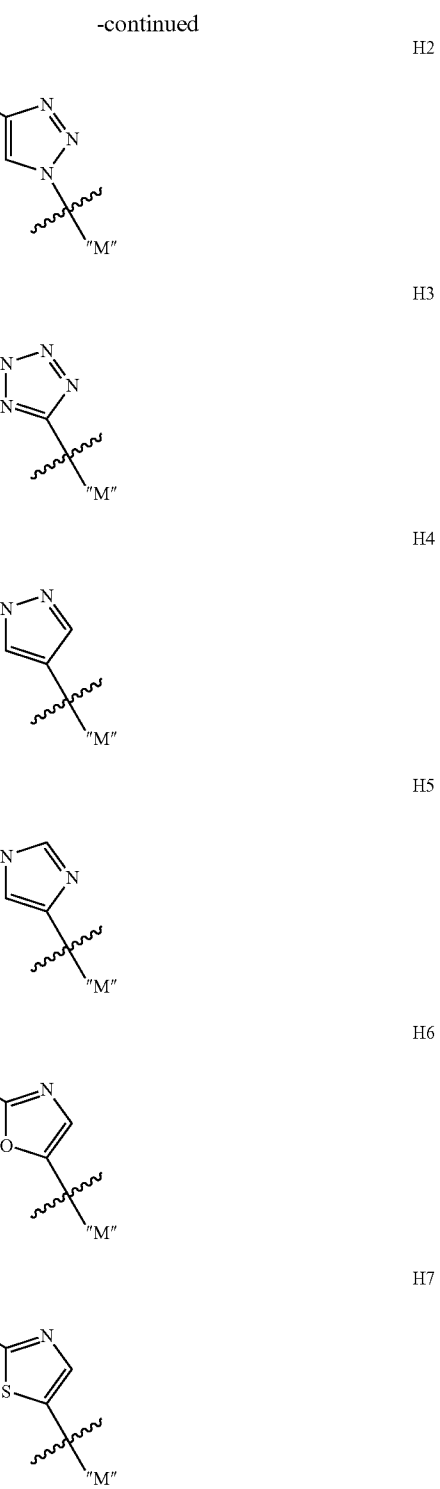
Heterocyclic Linkers
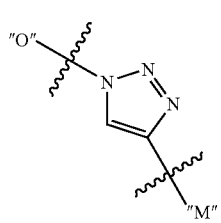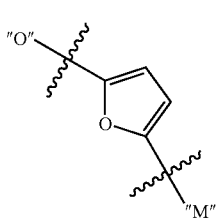

-continued

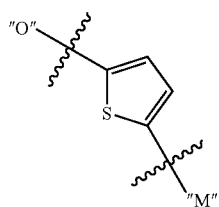
H9

For the above heterocyclic linkers, it should be understood that "O" and "M" are included to depict the orientation of the heterocyclic linker with respect to the other structures that define the compounds of the invention. More specifically, "O" denotes the portion of the compound that includes the heterocyclic side-chain moiety, and "M" denotes the portion of the compound that includes the macrolide moiety.

Macrolides

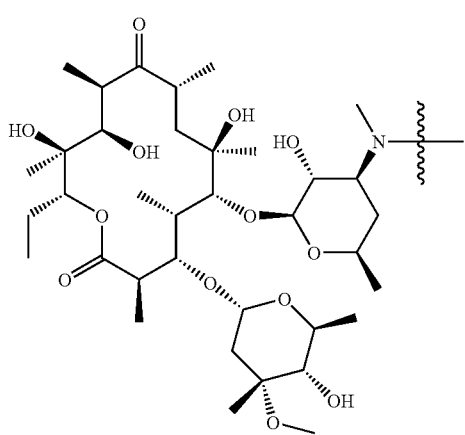
M1

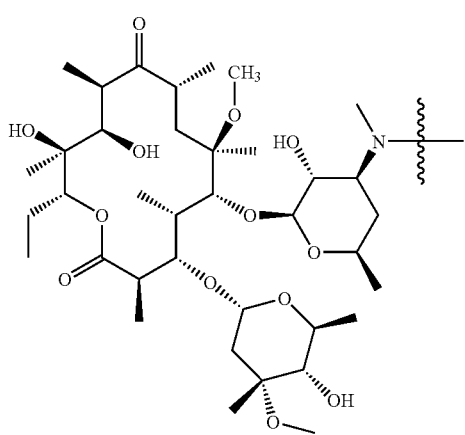
M2

-continued

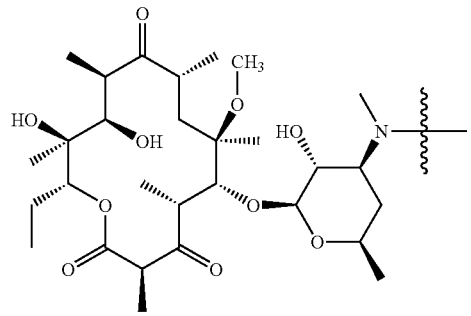
M3

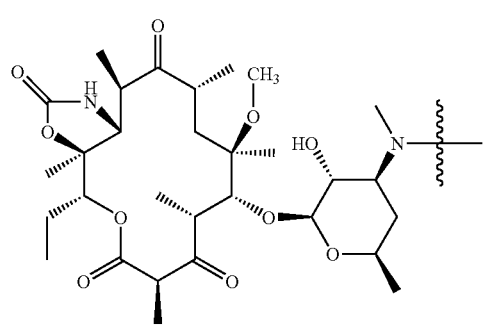
M4

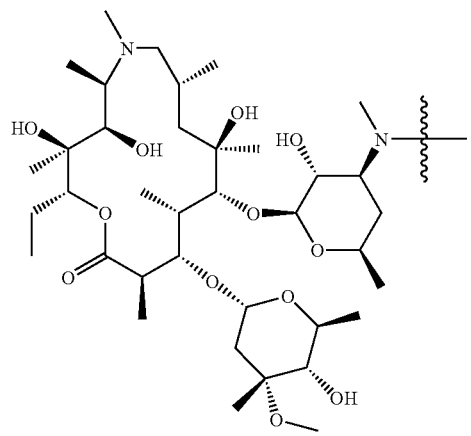
M5

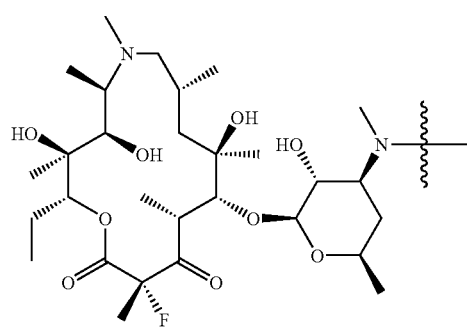
M6

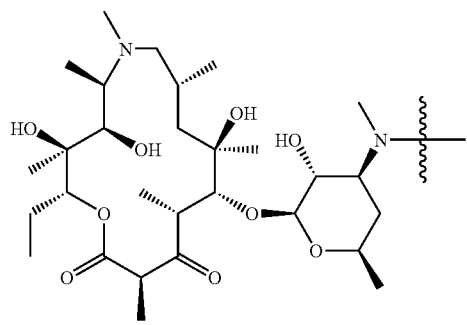
M7
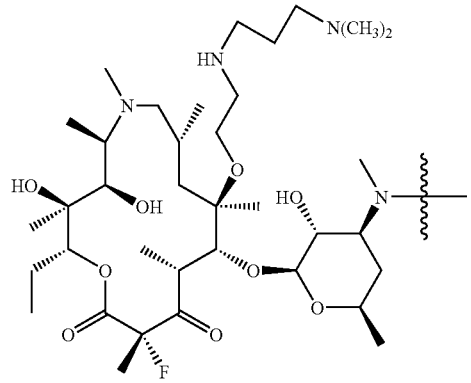
M10
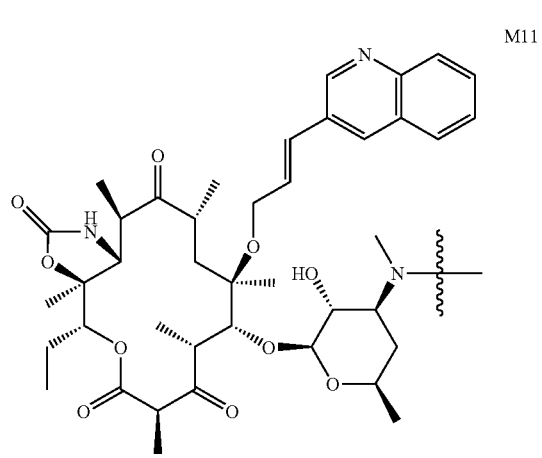
M8
M11
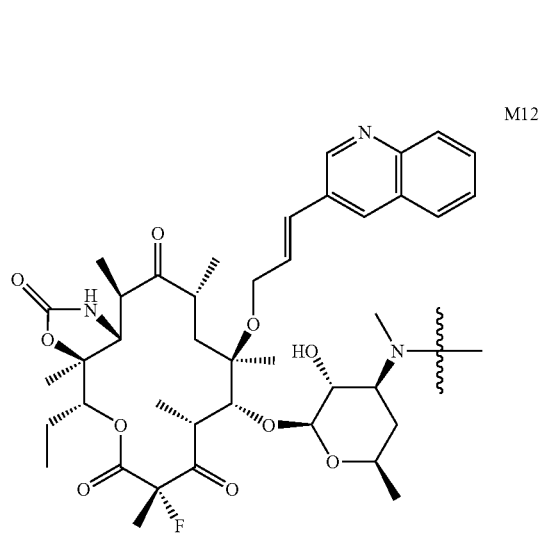
M9
M12

M13
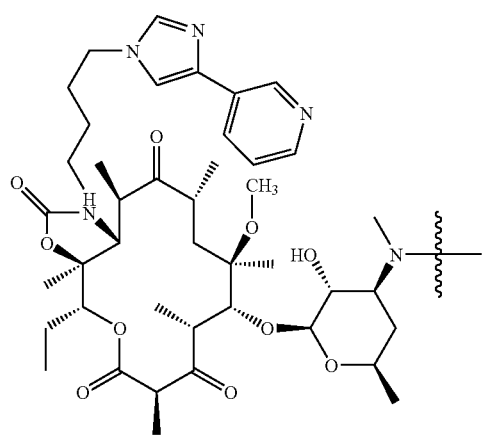
M16
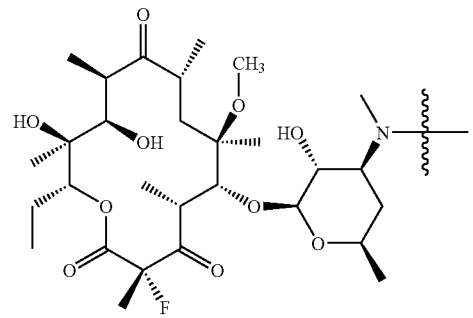
M14
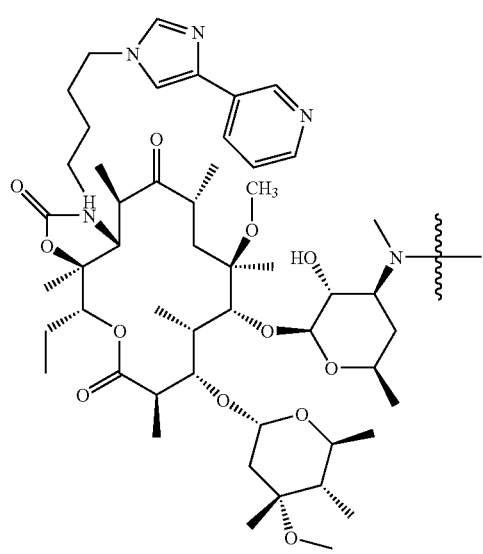
M17
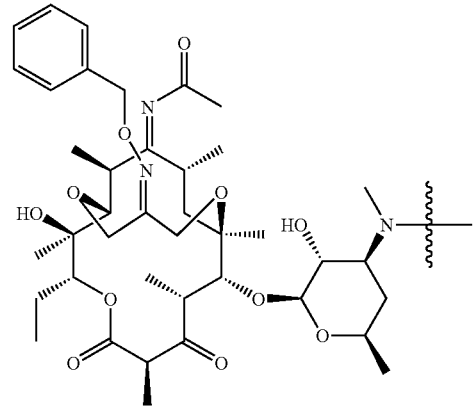
M15
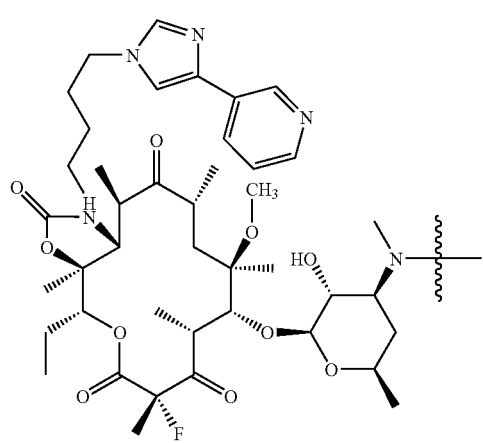
M18
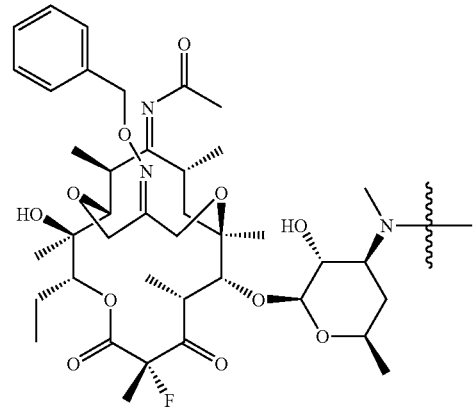

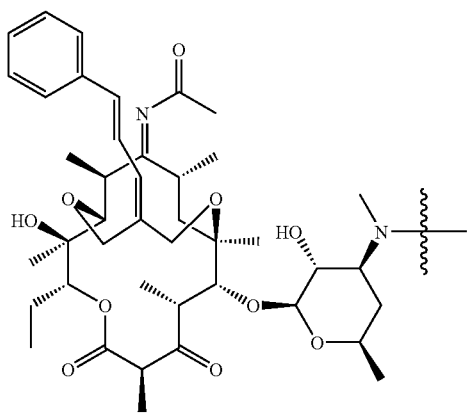
M19
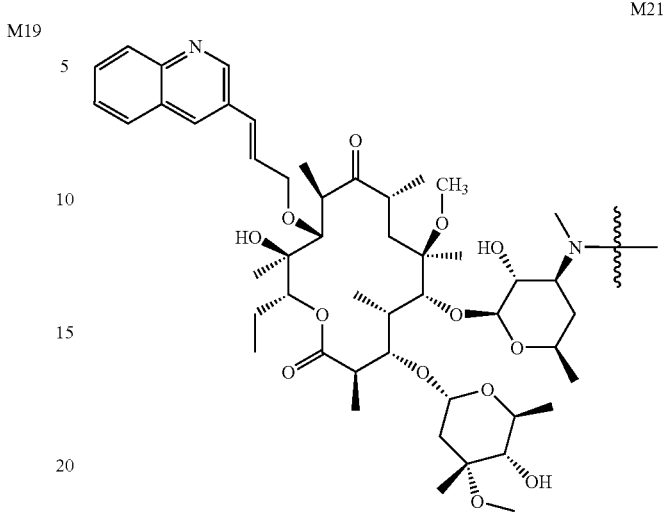
M21
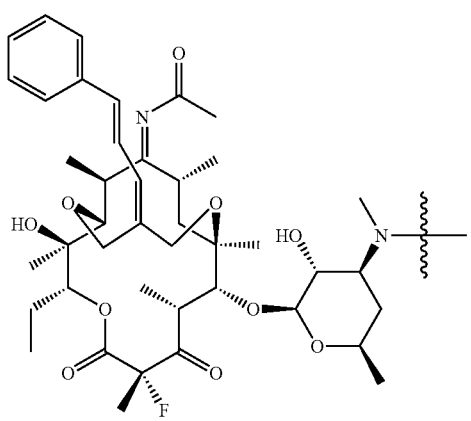
M20
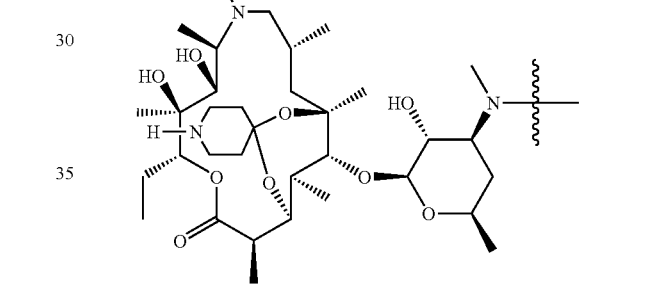
M22
An exemplary scheme showing the linkage of a heterocyclic side-chain to a macrolide via a heterocyclic linker is shown below, where n can be 1, 2, 3, or 4:
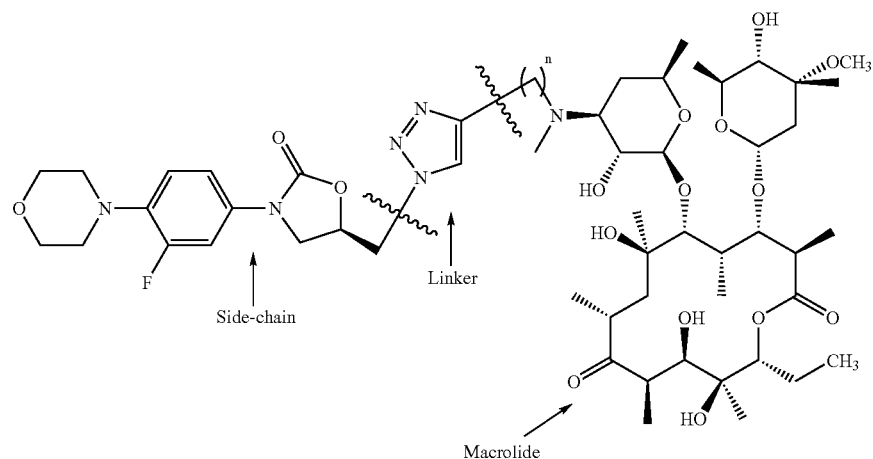

The various heterocyclic side-chains may be linked via the heterocyclic linkers to the macrolides using conventional chemistries known in the art, such as those discussed below. By using the various combinations of chemical moieties provided, the skilled artisan may synthesize one or more of the exemplary compounds listed in Table 1. For each set of examples, the four lower case letter designations denote three compounds where n=1, 2, 3, or 4. For example, as a guide to the following table, compound E1a is the n=1 variant of the structure shown on the same row of the table. Compound E1b is the n=2 derivative, compound E1c is the n=3 derivative, and E1d is the n=4 derivative.

TABLE 1

| Example | O Group | H Group | M Group |
|---|---|---|---|
| E1a–d | O1 | H1 | M1 |
| E2a–d | O1 | H2 | M1 |
| E3a–d | O1 | H3 | M1 |
| E4a–d | O1 | H4 | M1 |
| E5a–d | O1 | H5 | M1 |
| E6a–d | O1 | H6 | M1 |
| E7a–d | O1 | H7 | M1 |
| E8a–d | O1 | H8 | M1 |
| E9a–d | O1 | H9 | M1 |
| E10a–d | O2 | H1 | M1 |
| E11a–d | O2 | H2 | M1 |
| E12a–d | O2 | H3 | M1 |
| E13a–d | O2 | H4 | M1 |
| E14a–d | O2 | H5 | M1 |
| E15a–d | O2 | H6 | M1 |
| E16a–d | O2 | H7 | M1 |
| E17a–d | O2 | H8 | M1 |
| E18a–d | O2 | H9 | M1 |
| E19a–d | O3 | H1 | M1 |
| E20a–d | O3 | H2 | M1 |
| E21a–d | O3 | H3 | M1 |
| E22a–d | O3 | H4 | M1 |
| E23a–d | O3 | H5 | M1 |
| E24a–d | O3 | H6 | M1 |
| E25a–d | O3 | H7 | M1 |
| E26a–d | O3 | H8 | M1 |
| E27a–d | O3 | H9 | M1 |
| E28a–d | O4 | H1 | M1 |
| E29a–d | O4 | H2 | M1 |
| E30a–d | O4 | H3 | M1 |
| E31a–d | O4 | H4 | M1 |
| E32a–d | O4 | H5 | M1 |
| E33a–d | O4 | H6 | M1 |
| E34a–d | O4 | H7 | M1 |
| E35a–d | O4 | H8 | M1 |
| E36a–d | O4 | H9 | M1 |
| E37a–d | O5 | H1 | M1 |
| E38a–d | O5 | H2 | M1 |
| E39a–d | O5 | H3 | M1 |
| E40a–d | O5 | H4 | M1 |
| E41a–d | O5 | H5 | M1 |
| E42a–d | O5 | H6 | M1 |
| E43a–d | O5 | H7 | M1 |
| E44a–d | O5 | H8 | M1 |
| E45a–d | O5 | H9 | M1 |
| E46a–d | O6 | H1 | M1 |
| E47a–d | O6 | H2 | M1 |
| E48a–d | O6 | H3 | M1 |
| E49a–d | O6 | H4 | M1 |
| E50a–d | O6 | H5 | M1 |
| E51a–d | O6 | H6 | M1 |
| E52a–d | O6 | H7 | M1 |
| E53a–d | O6 | H8 | M1 |
| E54a–d | O6 | H9 | M1 |
| E55a–d | O7 | H1 | M1 |
| E56a–d | O7 | H2 | M1 |
| E57a–d | O7 | H3 | M1 |
| E58a–d | O7 | H4 | M1 |
| E59a–d | O7 | H5 | M1 |
| E60a–d | O7 | H6 | M1 |
| E61a–d | O7 | H7 | M1 |
| E62a–d | O7 | H8 | M1 |
| E63a–d | O7 | H9 | M1 |
| E64a–d | O8 | H1 | M1 |
| E65a–d | O8 | H2 | M1 |
| E66a–d | O8 | H3 | M1 |
| E67a–d | O8 | H4 | M1 |
| E68a–d | O8 | H5 | M1 |
| E69a–d | O8 | H6 | M1 |
| E70a–d | O8 | H7 | M1 |
| E71a–d | O8 | H8 | M1 |
| E72a–d | O8 | H9 | M1 |
| E73a–d | O9 | H1 | M1 |
| E74a–d | O9 | H2 | M1 |
| E75a–d | O9 | H3 | M1 |
| E76a–d | O9 | H4 | M1 |
| E77a–d | O9 | H5 | M1 |
| E78a–d | O9 | H6 | M1 |
| E79a–d | O9 | H7 | M1 |
| E80a–d | O9 | H8 | M1 |
| E81a–d | O9 | H9 | M1 |
| E82a–d | O10 | H1 | M1 |
| E83a–d | O10 | H2 | M1 |
| E84a–d | O10 | H3 | M1 |
| E85a–d | O10 | H4 | M1 |
| E86a–d | O10 | H5 | M1 |
| E87a–d | O10 | H6 | M1 |
| E88a–d | O10 | H7 | M1 |
| E89a–d | O10 | H8 | M1 |
| E90a–d | O10 | H9 | M1 |
| E91a–d | O11 | H1 | M1 |
| E92a–d | O11 | H2 | M1 |
| E93a–d | O11 | H3 | M1 |
| E94a–d | O11 | H4 | M1 |
| E95a–d | O11 | H5 | M1 |
| E96a–d | O11 | H6 | M1 |
| E97a–d | O11 | H7 | M1 |
| E98a–d | O11 | H8 | M1 |
| E99a–d | O11 | H9 | M1 |
| E100a–d | O12 | H1 | M1 |
| E101a–d | O12 | H2 | M1 |
| E102a–d | O12 | H3 | M1 |
| E103a–d | O12 | H4 | M1 |
| E104a–d | O12 | H5 | M1 |
| E105a–d | O12 | H6 | M1 |
| E106a–d | O12 | H7 | M1 |
| E107a–d | O12 | H8 | M1 |
| E108a–d | O12 | H9 | M1 |
| E109a–d | O13 | H1 | M1 |
| E110a–d | O13 | H2 | M1 |
| E111a–d | O13 | H3 | M1 |
| E112a–d | O13 | H4 | M1 |
| E113a–d | O13 | H5 | M1 |
| E114a–d | O13 | H6 | M1 |
| E115a–d | O13 | H7 | M1 |
| E116a–d | O13 | H8 | M1 |
| E117a–d | O13 | H9 | M1 |
| E118a–d | O14 | H1 | M1 |
| E119a–d | O14 | H2 | M1 |
| E120a–d | O14 | H3 | M1 |
| E121a–d | O14 | H4 | M1 |
| E122a–d | O14 | H5 | M1 |
| E123a–d | O14 | H6 | M1 |
| E124a–d | O14 | H7 | M1 |
| E125a–d | O14 | H8 | M1 |
| E126a–d | O14 | H9 | M1 |
| E127a–d | O15 | H1 | M1 |
| E128a–d | O15 | H2 | M1 |
| E129a–d | O15 | H3 | M1 |
| E130a–d | O15 | H4 | M1 |
| E131a–d | O15 | H5 | M1 |
| E132a–d | O15 | H6 | M1 |
| E133a–d | O15 | H7 | M1 |
| E134a–d | O15 | H8 | M1 |
| E135a–d | O15 | H9 | M1 |
| E136a–d | O16 | H1 | M1 |
| E137a–d | O16 | H2 | M1 |
| E138a–d | O16 | H3 | M1 |
| E139a–d | O16 | H4 | M1 |

TABLE 1-continued

| Example | O Group | H Group | M Group |
|---|---|---|---|
| E140a–d | O16 | H5 | M1 |
| E141a–d | O16 | H6 | M1 |
| E142a–d | O16 | H7 | M1 |
| E143a–d | O16 | H8 | M1 |
| E144a–d | O16 | H9 | M1 |
| E145a–d | O1 | H1 | M2 |
| E146a–d | O1 | H2 | M2 |
| E147a–d | O1 | H3 | M2 |
| E148a–d | O1 | H4 | M2 |
| E149a–d | O1 | H5 | M2 |
| E150a–d | O1 | H6 | M2 |
| E151a–d | O1 | H7 | M2 |
| E152a–d | O1 | H8 | M2 |
| E153a–d | O1 | H9 | M2 |
| E154a–d | O2 | H1 | M2 |
| E155a–d | O2 | H2 | M2 |
| E156a–d | O2 | H3 | M2 |
| E157a–d | O2 | H4 | M2 |
| E158a–d | O2 | H5 | M2 |
| E159a–d | O2 | H6 | M2 |
| E160a–d | O2 | H7 | M2 |
| E161a–d | O2 | H8 | M2 |
| E162a–d | O2 | H9 | M2 |
| E163a–d | O3 | H1 | M2 |
| E164a–d | O3 | H2 | M2 |
| E165a–d | O3 | H3 | M2 |
| E166a–d | O3 | H4 | M2 |
| E167a–d | O3 | H5 | M2 |
| E168a–d | O3 | H6 | M2 |
| E169a–d | O3 | H7 | M2 |
| E170a–d | O3 | H8 | M2 |
| E171a–d | O3 | H9 | M2 |
| E172a–d | O4 | H1 | M2 |
| E173a–d | O4 | H2 | M2 |
| E174a–d | O4 | H3 | M2 |
| E175a–d | O4 | H4 | M2 |
| E176a–d | O4 | H5 | M2 |
| E177a–d | O4 | H6 | M2 |
| E178a–d | O4 | H7 | M2 |
| E179a–d | O4 | H8 | M2 |
| E180a–d | O4 | H9 | M2 |
| E181a–d | O5 | H1 | M2 |
| E182a–d | O5 | H2 | M2 |
| E183a–d | O5 | H3 | M2 |
| E184a–d | O5 | H4 | M2 |
| E185a–d | O5 | H5 | M2 |
| E186a–d | O5 | H6 | M2 |
| E187a–d | O5 | H7 | M2 |
| E188a–d | O5 | H8 | M2 |
| E189a–d | O5 | H9 | M2 |
| E190a–d | O6 | H1 | M2 |
| E191a–d | O6 | H2 | M2 |
| E192a–d | O6 | H3 | M2 |
| E193a–d | O6 | H4 | M2 |
| E194a–d | O6 | H5 | M2 |
| E195a–d | O6 | H6 | M2 |
| E196a–d | O6 | H7 | M2 |
| E197a–d | O6 | H8 | M2 |
| E198a–d | O6 | H9 | M2 |
| E199a–d | O7 | H1 | M2 |
| E200a–d | O7 | H2 | M2 |
| E201a–d | O7 | H3 | M2 |
| E202a–d | O7 | H4 | M2 |
| E203a–d | O7 | H5 | M2 |
| E204a–d | O7 | H6 | M2 |
| E205a–d | O7 | H7 | M2 |
| E206a–d | O7 | H8 | M2 |
| E207a–d | O7 | H9 | M2 |
| E208a–d | O8 | H1 | M2 |
| E209a–d | O8 | H2 | M2 |
| E210a–d | O8 | H3 | M2 |
| E211a–d | O8 | H4 | M2 |
| E212a–d | O8 | H5 | M2 |
| E213a–d | O8 | H6 | M2 |
| E214a–d | O8 | H7 | M2 |
| E215a–d | O8 | H8 | M2 |
| E216a–d | O8 | H9 | M2 |
| E217a–d | O9 | H1 | M2 |
| E218a–d | O9 | H2 | M2 |
| E219a–d | O9 | H3 | M2 |
| E220a–d | O9 | H4 | M2 |
| E221a–d | O9 | H5 | M2 |
| E222a–d | O9 | H6 | M2 |
| E223a–d | O9 | H7 | M2 |
| E224a–d | O9 | H8 | M2 |
| E225a–d | O9 | H9 | M2 |
| E226a–d | O10 | H1 | M2 |
| E227a–d | O10 | H2 | M2 |
| E228a–d | O10 | H3 | M2 |
| E229a–d | O10 | H4 | M2 |
| E230a–d | O10 | H5 | M2 |
| E231a–d | O10 | H6 | M2 |
| E232a–d | O10 | H7 | M2 |
| E233a–d | O10 | H8 | M2 |
| E234a–d | O10 | H9 | M2 |
| E235a–d | O11 | H1 | M2 |
| E236a–d | O11 | H2 | M2 |
| E237a–d | O11 | H3 | M2 |
| E238a–d | O11 | H4 | M2 |
| E239a–d | O11 | H5 | M2 |
| E240a–d | O11 | H6 | M2 |
| E241a–d | O11 | H7 | M2 |
| E242a–d | O11 | H8 | M2 |
| E243a–d | O11 | H9 | M2 |
| E244a–d | O12 | H1 | M2 |
| E245a–d | O12 | H2 | M2 |
| E246a–d | O12 | H3 | M2 |
| E247a–d | O12 | H4 | M2 |
| E248a–d | O12 | H5 | M2 |
| E249a–d | O12 | H6 | M2 |
| E250a–d | O12 | H7 | M2 |
| E251a–d | O12 | H8 | M2 |
| E252a–d | O12 | H9 | M2 |
| E253a–d | O13 | H1 | M2 |
| E254a–d | O13 | H2 | M2 |
| E255a–d | O13 | H3 | M2 |
| E256a–d | O13 | H4 | M2 |
| E257a–d | O13 | H5 | M2 |
| E258a–d | O13 | H6 | M2 |
| E259a–d | O13 | H7 | M2 |
| E260a–d | O13 | H8 | M2 |
| E261a–d | O13 | H9 | M2 |
| E262a–d | O14 | H1 | M2 |
| E263a–d | O14 | H2 | M2 |
| E264a–d | O14 | H3 | M2 |
| E265a–d | O14 | H4 | M2 |
| E266a–d | O14 | H5 | M2 |
| E267a–d | O14 | H6 | M2 |
| E268a–d | O14 | H7 | M2 |
| E269a–d | O14 | H8 | M2 |
| E270a–d | O14 | H9 | M2 |
| E271a–d | O15 | H1 | M2 |
| E272a–d | O15 | H2 | M2 |
| E273a–d | O15 | H3 | M2 |
| E274a–d | O15 | H4 | M2 |
| E275a–d | O15 | H5 | M2 |
| E276a–d | O15 | H6 | M2 |
| E277a–d | O15 | H7 | M2 |
| E278a–d | O15 | H8 | M2 |
| E279a–d | O15 | H9 | M2 |
| E280a–d | O16 | H1 | M2 |
| E281a–d | O16 | H2 | M2 |
| E282a–d | O16 | H3 | M2 |
| E283a–d | O16 | H4 | M2 |
| E284a–d | O16 | H5 | M2 |
| E285a–d | O16 | H6 | M2 |
| E286a–d | O16 | H7 | M2 |
| E287a–d | O16 | H8 | M2 |
| E288a–d | O16 | H9 | M2 |
| E289a–d | O1 | H1 | M3 |
| E290a–d | O1 | H2 | M3 |
| E291a–d | O1 | H3 | M3 |
| E292a–d | O1 | H4 | M3 |
| E293a–d | O1 | H5 | M3 |

TABLE 1-continued

| Example | O Group | H Group | M Group |
|---|---|---|---|
| E294a–d | O1 | H6 | M3 |
| E295a–d | O1 | H7 | M3 |
| E296a–d | O1 | H8 | M3 |
| E297a–d | O1 | H9 | M3 |
| E298a–d | O2 | H1 | M3 |
| E299a–d | O2 | H2 | M3 |
| E300a–d | O2 | H3 | M3 |
| E301a–d | O2 | H4 | M3 |
| E302a–d | O2 | H5 | M3 |
| E303a–d | O2 | H6 | M3 |
| E304a–d | O2 | H7 | M3 |
| E305a–d | O2 | H8 | M3 |
| E306a–d | O2 | H9 | M3 |
| E307a–d | O3 | H1 | M3 |
| E308a–d | O3 | H2 | M3 |
| E309a–d | O3 | H3 | M3 |
| E310a–d | O3 | H4 | M3 |
| E311a–d | O3 | H5 | M3 |
| E312a–d | O3 | H6 | M3 |
| E313a–d | O3 | H7 | M3 |
| E314a–d | O3 | H8 | M3 |
| E315a–d | O3 | H9 | M3 |
| E316a–d | O4 | H1 | M3 |
| E317a–d | O4 | H2 | M3 |
| E318a–d | O4 | H3 | M3 |
| E319a–d | O4 | H4 | M3 |
| E320a–d | O4 | H5 | M3 |
| E321a–d | O4 | H6 | M3 |
| E322a–d | O4 | H7 | M3 |
| E323a–d | O4 | H8 | M3 |
| E324a–d | O4 | H9 | M3 |
| E325a–d | O5 | H1 | M3 |
| E326a–d | O5 | H2 | M3 |
| E327a–d | O5 | H3 | M3 |
| E328a–d | O5 | H4 | M3 |
| E329a–d | O5 | H5 | M3 |
| E330a–d | O5 | H6 | M3 |
| E331a–d | O5 | H7 | M3 |
| E332a–d | O5 | H8 | M3 |
| E333a–d | O5 | H9 | M3 |
| E334a–d | O6 | H1 | M3 |
| E335a–d | O6 | H2 | M3 |
| E336a–d | O6 | H3 | M3 |
| E337a–d | O6 | H4 | M3 |
| E338a–d | O6 | H5 | M3 |
| E339a–d | O6 | H6 | M3 |
| E340a–d | O6 | H7 | M3 |
| E341a–d | O6 | H8 | M3 |
| E342a–d | O6 | H9 | M3 |
| E343a–d | O7 | H1 | M3 |
| E344a–d | O7 | H2 | M3 |
| E345a–d | O7 | H3 | M3 |
| E346a–d | O7 | H4 | M3 |
| E347a–d | O7 | H5 | M3 |
| E348a–d | O7 | H6 | M3 |
| E349a–d | O7 | H7 | M3 |
| E350a–d | O7 | H8 | M3 |
| E351a–d | O7 | H9 | M3 |
| E352a–d | O7 | H1 | M3 |
| E353a–d | O8 | H2 | M3 |
| E354a–d | O8 | H3 | M3 |
| E355a–d | O8 | H4 | M3 |
| E356a–d | O8 | H5 | M3 |
| E357a–d | O8 | H6 | M3 |
| E358a–d | O8 | H7 | M3 |
| E359a–d | O8 | H8 | M3 |
| E360a–d | O8 | H9 | M3 |
| E361a–d | O9 | H1 | M3 |
| E362a–d | O9 | H2 | M3 |
| E363a–d | O9 | H3 | M3 |
| E364a–d | O9 | H4 | M3 |
| E365a–d | O9 | H5 | M3 |
| E366a–d | O9 | H6 | M3 |
| E367a–d | O9 | H7 | M3 |
| E368a–d | O9 | H8 | M3 |
| E369a–d | O9 | H9 | M3 |
| E370a–d | O10 | H1 | M3 |
| E371a–d | O10 | H2 | M3 |
| E372a–d | O10 | H3 | M3 |
| E373a–d | O10 | H4 | M3 |
| E374a–d | O10 | H5 | M3 |
| E375a–d | O10 | H6 | M3 |
| E376a–d | O10 | H7 | M3 |
| E377a–d | O10 | H8 | M3 |
| E378a–d | O10 | H9 | M3 |
| E379a–d | O11 | H1 | M3 |
| E380a–d | O11 | H2 | M3 |
| E381a–d | O11 | H3 | M3 |
| E382a–d | O11 | H4 | M3 |
| E383a–d | O11 | H5 | M3 |
| E384a–d | O11 | H6 | M3 |
| E385a–d | O11 | H7 | M3 |
| E386a–d | O11 | H8 | M3 |
| E387a–d | O11 | H9 | M3 |
| E388a–d | O12 | H1 | M3 |
| E389a–d | O12 | H2 | M3 |
| E390a–d | O12 | H3 | M3 |
| E391a–d | O12 | H4 | M3 |
| E392a–d | O12 | H5 | M3 |
| E393a–d | O12 | H6 | M3 |
| E394a–d | O12 | H7 | M3 |
| E395a–d | O12 | H8 | M3 |
| E396a–d | O12 | H9 | M3 |
| E397a–d | O13 | H1 | M3 |
| E398a–d | O13 | H2 | M3 |
| E399a–d | O13 | H3 | M3 |
| E400a–d | O13 | H4 | M3 |
| E401a–d | O13 | H5 | M3 |
| E402a–d | O13 | H6 | M3 |
| E403a–d | O13 | H7 | M3 |
| E404a–d | O13 | H8 | M3 |
| E405a–d | O13 | H9 | M3 |
| E406a–d | O14 | H1 | M3 |
| E407a–d | O14 | H2 | M3 |
| E408a–d | O14 | H3 | M3 |
| E409a–d | O14 | H4 | M3 |
| E410a–d | O14 | H5 | M3 |
| E411a–d | O14 | H6 | M3 |
| E412a–d | O14 | H7 | M3 |
| E413a–d | O14 | H8 | M3 |
| E414a–d | O14 | H9 | M3 |
| E415a–d | O15 | H1 | M3 |
| E416a–d | O15 | H2 | M3 |
| E417a–d | O15 | H3 | M3 |
| E418a–d | O15 | H4 | M3 |
| E419a–d | O15 | H5 | M3 |
| E420a–d | O15 | H6 | M3 |
| E421a–d | O15 | H7 | M3 |
| E422a–d | O15 | H8 | M3 |
| E423a–d | O15 | H9 | M3 |
| E424a–d | O16 | H1 | M3 |
| E425a–d | O16 | H2 | M3 |
| E426a–d | O16 | H3 | M3 |
| E427a–d | O16 | H4 | M3 |
| E428a–d | O16 | H5 | M3 |
| E429a–d | O16 | H6 | M3 |
| E430a–d | O16 | H7 | M3 |
| E431a–d | O16 | H8 | M3 |
| E432a–d | O16 | H9 | M3 |
| E433a–d | O1 | H1 | M4 |
| E434a–d | O1 | H2 | M4 |
| E435a–d | O1 | H3 | M4 |
| E436a–d | O1 | H4 | M4 |
| E437a–d | O1 | H5 | M4 |
| E438a–d | O1 | H6 | M4 |
| E439a–d | O1 | H7 | M4 |
| E440a–d | O1 | H8 | M4 |
| E441a–d | O1 | H9 | M4 |
| E442a–d | O2 | H1 | M4 |
| E443a–d | O2 | H2 | M4 |
| E444a–d | O2 | H3 | M4 |
| E445a–d | O2 | H4 | M4 |
| E446a–d | O2 | H5 | M4 |
| E447a–d | O2 | H6 | M4 |

TABLE 1-continued

| Example | O Group | H Group | M Group |
|---------|---------|---------|---------|
| E448a–d | O2 | H7 | M4 |
| E449a–d | O2 | H8 | M4 |
| E450a–d | O2 | H9 | M4 |
| E451a–d | O3 | H1 | M4 |
| E452a–d | O3 | H2 | M4 |
| E453a–d | O3 | H3 | M4 |
| E454a–d | O3 | H4 | M4 |
| E455a–d | O3 | H5 | M4 |
| E456a–d | O3 | H6 | M4 |
| E457a–d | O3 | H7 | M4 |
| E458a–d | O3 | H8 | M4 |
| E459a–d | O3 | H9 | M4 |
| E460a–d | O4 | H1 | M4 |
| E461a–d | O4 | H2 | M4 |
| E462a–d | O4 | H3 | M4 |
| E463a–d | O4 | H4 | M4 |
| E464a–d | O4 | H5 | M4 |
| E465a–d | O4 | H6 | M4 |
| E466a–d | O4 | H7 | M4 |
| E467a–d | O4 | H8 | M4 |
| E468a–d | O4 | H9 | M4 |
| E469a–d | O5 | H1 | M4 |
| E470a–d | O5 | H2 | M4 |
| E471a–d | O5 | H3 | M4 |
| E472a–d | O5 | H4 | M4 |
| E473a–d | O5 | H5 | M4 |
| E474a–d | O5 | H6 | M4 |
| E475a–d | O5 | H7 | M4 |
| E476a–d | O5 | H8 | M4 |
| E477a–d | O5 | H9 | M4 |
| E478a–d | O6 | H1 | M4 |
| E479a–d | O6 | H2 | M4 |
| E480a–d | O6 | H3 | M4 |
| E481a–d | O6 | H4 | M4 |
| E482a–d | O6 | H5 | M4 |
| E483a–d | O6 | H6 | M4 |
| E484a–d | O6 | H7 | M4 |
| E485a–d | O6 | H8 | M4 |
| E486a–d | O6 | H9 | M4 |
| E487a–d | O7 | H1 | M4 |
| E488a–d | O7 | H2 | M4 |
| E489a–d | O7 | H3 | M4 |
| E490a–d | O7 | H4 | M4 |
| E491a–d | O7 | H5 | M4 |
| E492a–d | O7 | H6 | M4 |
| E493a–d | O7 | H7 | M4 |
| E494a–d | O7 | H8 | M4 |
| E495a–d | O7 | H9 | M4 |
| E496a–d | O8 | H1 | M4 |
| E497a–d | O8 | H2 | M4 |
| E498a–d | O8 | H3 | M4 |
| E499a–d | O8 | H4 | M4 |
| E500a–d | O8 | H5 | M4 |
| E501a–d | O8 | H6 | M4 |
| E502a–d | O8 | H7 | M4 |
| E503a–d | O8 | H8 | M4 |
| E504a–d | O8 | H9 | M4 |
| E505a–d | O9 | H1 | M4 |
| E506a–d | O9 | H2 | M4 |
| E507a–d | O9 | H3 | M4 |
| E508a–d | O9 | H4 | M4 |
| E509a–d | O9 | H5 | M4 |
| E510a–d | O9 | H6 | M4 |
| E511a–d | O9 | H7 | M4 |
| E512a–d | O9 | H8 | M4 |
| E513a–d | O9 | H9 | M4 |
| E514a–d | O10 | H1 | M4 |
| E515a–d | O10 | H2 | M4 |
| E516a–d | O10 | H3 | M4 |
| E517a–d | O10 | H4 | M4 |
| E518a–d | O10 | H5 | M4 |
| E519a–d | O10 | H6 | M4 |
| E520a–d | O10 | H7 | M4 |
| E521a–d | O10 | H8 | M4 |
| E522a–d | O10 | H9 | M4 |
| E523a–d | O11 | H1 | M4 |
| E524a–d | O11 | H2 | M4 |
| E525a–d | O11 | H3 | M4 |
| E526a–d | O11 | H4 | M4 |
| E527a–d | O11 | H5 | M4 |
| E528a–d | O11 | H6 | M4 |
| E529a–d | O11 | H7 | M4 |
| E530a–d | O11 | H8 | M4 |
| E531a–d | O11 | H9 | M4 |
| E532a–d | O12 | H1 | M4 |
| E533a–d | O12 | H2 | M4 |
| E534a–d | O12 | H3 | M4 |
| E535a–d | O12 | H4 | M4 |
| E536a–d | O12 | H5 | M4 |
| E537a–d | O12 | H6 | M4 |
| E538a–d | O12 | H7 | M4 |
| E539a–d | O12 | H8 | M4 |
| E540a–d | O12 | H9 | M4 |
| E541a–d | O13 | H1 | M4 |
| E542a–d | O13 | H2 | M4 |
| E543a–d | O13 | H3 | M4 |
| E544a–d | O13 | H4 | M4 |
| E545a–d | O13 | H5 | M4 |
| E546a–d | O13 | H6 | M4 |
| E547a–d | O13 | H7 | M4 |
| E548a–d | O13 | H8 | M4 |
| E549a–d | O13 | H9 | M4 |
| E550a–d | O14 | H1 | M4 |
| E551a–d | O14 | H2 | M4 |
| E552a–d | O14 | H3 | M4 |
| E553a–d | O14 | H4 | M4 |
| E554a–d | O14 | H5 | M4 |
| E555a–d | O14 | H6 | M4 |
| E556a–d | O14 | H7 | M4 |
| E557a–d | O14 | H8 | M4 |
| E558a–d | O14 | H9 | M4 |
| E559a–d | O15 | H1 | M4 |
| E560a–d | O15 | H2 | M4 |
| E561a–d | O15 | H3 | M4 |
| E562a–d | O15 | H4 | M4 |
| E563a–d | O15 | H5 | M4 |
| E564a–d | O15 | H6 | M4 |
| E565a–d | O15 | H7 | M4 |
| E566a–d | O15 | H8 | M4 |
| E567a–d | O15 | H9 | M4 |
| E568a–d | O16 | H1 | M4 |
| E569a–d | O16 | H2 | M4 |
| E570a–d | O16 | H3 | M4 |
| E571a–d | O16 | H4 | M4 |
| E572a–d | O16 | H5 | M4 |
| E573a–d | O16 | H6 | M4 |
| E574a–d | O16 | H7 | M4 |
| E575a–d | O16 | H8 | M4 |
| E576a–d | O16 | H9 | M4 |
| E577a–d | O1 | H1 | M5 |
| E578a–d | O1 | H2 | M5 |
| E579a–d | O1 | H3 | M5 |
| E580a–d | O1 | H4 | M5 |
| E581a–d | O1 | H5 | M5 |
| E582a–d | O1 | H6 | M5 |
| E583a–d | O1 | H7 | M5 |
| E584a–d | O1 | H8 | M5 |
| E585a–d | O1 | H9 | M5 |
| E586a–d | O2 | H1 | M5 |
| E587a–d | O2 | H2 | M5 |
| E588a–d | O2 | H3 | M5 |
| E589a–d | O2 | H4 | M5 |
| E590a–d | O2 | H5 | M5 |
| E591a–d | O2 | H6 | M5 |
| E592a–d | O2 | H7 | M5 |
| E593a–d | O2 | H8 | M5 |
| E594a–d | O2 | H9 | M5 |
| E595a–d | O3 | H1 | M5 |
| E596a–d | O3 | H2 | M5 |
| E597a–d | O3 | H3 | M5 |
| E598a–d | O3 | H4 | M5 |
| E599a–d | O3 | H5 | M5 |
| E600a–d | O3 | H6 | M5 |
| E601a–d | O3 | H7 | M5 |

TABLE 1-continued

| Example | O Group | H Group | M Group |
|---|---|---|---|
| E602a–d | O3 | H8 | M5 |
| E603a–d | O3 | H9 | M5 |
| E604a–d | O4 | H1 | M5 |
| E605a–d | O4 | H2 | M5 |
| E606a–d | O4 | H3 | M5 |
| E607a–d | O4 | H4 | M5 |
| E608a–d | O4 | H5 | M5 |
| E609a–d | O4 | H6 | M5 |
| E610a–d | O4 | H7 | M5 |
| E611a–d | O4 | H8 | M5 |
| E612a–d | O4 | H9 | M5 |
| E613a–d | O5 | H1 | M5 |
| E614a–d | O5 | H2 | M5 |
| E615a–d | O5 | H3 | M5 |
| E616a–d | O5 | H4 | M5 |
| E617a–d | O5 | H5 | M5 |
| E618a–d | O5 | H6 | M5 |
| E619a–d | O5 | H7 | M5 |
| E620a–d | O5 | H8 | M5 |
| E621a–d | O5 | H9 | M5 |
| E622a–d | O6 | H1 | M5 |
| E623a–d | O6 | H2 | M5 |
| E624a–d | O6 | H3 | M5 |
| E625a–d | O6 | H4 | M5 |
| E626a–d | O6 | H5 | M5 |
| E627a–d | O6 | H6 | M5 |
| E628a–d | O6 | H7 | M5 |
| E629a–d | O6 | H8 | M5 |
| E630a–d | O6 | H9 | M5 |
| E631a–d | O7 | H1 | M5 |
| E632a–d | O7 | H2 | M5 |
| E633a–d | O7 | H3 | M5 |
| E634a–d | O7 | H4 | M5 |
| E635a–d | O7 | H5 | M5 |
| E636a–d | O7 | H6 | M5 |
| E637a–d | O7 | H7 | M5 |
| E638a–d | O7 | H8 | M5 |
| E639a–d | O7 | H9 | M5 |
| E640a–d | O8 | H1 | M5 |
| E641a–d | O8 | H2 | M5 |
| E642a–d | O8 | H3 | M5 |
| E643a–d | O8 | H4 | M5 |
| E644a–d | O8 | H5 | M5 |
| E645a–d | O8 | H6 | M5 |
| E646a–d | O8 | H7 | M5 |
| E647a–d | O8 | H8 | M5 |
| E648a–d | O8 | H9 | M5 |
| E649a–d | O9 | H1 | M5 |
| E650a–d | O9 | H2 | M5 |
| E651a–d | O9 | H3 | M5 |
| E652a–d | O9 | H4 | M5 |
| E653a–d | O9 | H5 | M5 |
| E654a–d | O9 | H6 | M5 |
| E655a–d | O9 | H7 | M5 |
| E656a–d | O9 | H8 | M5 |
| E657a–d | O9 | H9 | M5 |
| E658a–d | O10 | H1 | M5 |
| E659a–d | O10 | H2 | M5 |
| E660a–d | O10 | H3 | M5 |
| E661a–d | O10 | H4 | M5 |
| E662a–d | O10 | H5 | M5 |
| E663a–d | O10 | H6 | M5 |
| E664a–d | O10 | H7 | M5 |
| E665a–d | O10 | H8 | M5 |
| E666a–d | O10 | H9 | M5 |
| E667a–d | O11 | H1 | M5 |
| E668a–d | O11 | H2 | M5 |
| E669a–d | O11 | H3 | M5 |
| E670a–d | O11 | H4 | M5 |
| E671a–d | O11 | H5 | M5 |
| E672a–d | O11 | H6 | M5 |
| E673a–d | O11 | H7 | M5 |
| E674a–d | O11 | H8 | M5 |
| E675a–d | O11 | H9 | M5 |
| E676a–d | O12 | H1 | M5 |
| E677a–d | O12 | H2 | M5 |
| E678a–d | O12 | H3 | M5 |
| E679a–d | O12 | H4 | M5 |
| E680a–d | O12 | H5 | M5 |
| E681a–d | O12 | H6 | M5 |
| E682a–d | O12 | H7 | M5 |
| E683a–d | O12 | H8 | M5 |
| E684a–d | O12 | H9 | M5 |
| E685a–d | O13 | H1 | M5 |
| E686a–d | O13 | H2 | M5 |
| E687a–d | O13 | H3 | M5 |
| E688a–d | O13 | H4 | M5 |
| E689a–d | O13 | H5 | M5 |
| E690a–d | O13 | H6 | M5 |
| E691a–d | O13 | H7 | M5 |
| E692a–d | O13 | H8 | M5 |
| E693a–d | O13 | H9 | M5 |
| E694a–d | O14 | H1 | M5 |
| E695a–d | O14 | H2 | M5 |
| E696a–d | O14 | H3 | M5 |
| E697a–d | O14 | H4 | M5 |
| E698a–d | O14 | H5 | M5 |
| E699a–d | O14 | H6 | M5 |
| E700a–d | O14 | H7 | M5 |
| E701a–d | O14 | H8 | M5 |
| E702a–d | O14 | H9 | M5 |
| E703a–d | O15 | H1 | M5 |
| E704a–d | O15 | H2 | M5 |
| E705a–d | O15 | H3 | M5 |
| E706a–d | O15 | H4 | M5 |
| E707a–d | O15 | H5 | M5 |
| E708a–d | O15 | H6 | M5 |
| E709a–d | O15 | H7 | M5 |
| E710a–d | O15 | H8 | M5 |
| E711a–d | O15 | H9 | M5 |
| E712a–d | O16 | H1 | M5 |
| E713a–d | O16 | H2 | M5 |
| E714a–d | O16 | H3 | M5 |
| E715a–d | O16 | H4 | M5 |
| E716a–d | O16 | H5 | M5 |
| E717a–d | O16 | H6 | M5 |
| E718a–d | O16 | H7 | M5 |
| E719a–d | O16 | H8 | M5 |
| E720a–d | O16 | H9 | M5 |
| E721a–d | O1 | H1 | M6 |
| E722a–d | O1 | H2 | M6 |
| E723a–d | O1 | H3 | M6 |
| E724a–d | O1 | H4 | M6 |
| E725a–d | O1 | H5 | M6 |
| E726a–d | O1 | H6 | M6 |
| E727a–d | O1 | H7 | M6 |
| E728a–d | O1 | H8 | M6 |
| E729a–d | O1 | H9 | M6 |
| E730a–d | O2 | H1 | M6 |
| E731a–d | O2 | H2 | M6 |
| E732a–d | O2 | H3 | M6 |
| E733a–d | O2 | H4 | M6 |
| E734a–d | O2 | H5 | M6 |
| E735a–d | O2 | H6 | M6 |
| E736a–d | O2 | H7 | M6 |
| E737a–d | O2 | H8 | M6 |
| E738a–d | O2 | H9 | M6 |
| E739a–d | O3 | H1 | M6 |
| E740a–d | O3 | H2 | M6 |
| E741a–d | O3 | H3 | M6 |
| E742a–d | O3 | H4 | M6 |
| E743a–d | O3 | H5 | M6 |
| E744a–d | O3 | H6 | M6 |
| E745a–d | O3 | H7 | M6 |
| E746a–d | O3 | H8 | M6 |
| E747a–d | O3 | H9 | M6 |
| E748a–d | O4 | H1 | M6 |
| E749a–d | O4 | H2 | M6 |
| E750a–d | O4 | H3 | M6 |
| E751a–d | O4 | H4 | M6 |
| E752a–d | O4 | H5 | M6 |
| E753a–d | O4 | H6 | M6 |
| E754a–d | O4 | H7 | M6 |
| E755a–d | O4 | H8 | M6 |

TABLE 1-continued

| Example | O Group | H Group | M Group |
|---|---|---|---|
| E756a–d | O4 | H9 | M6 |
| E757a–d | O5 | H1 | M6 |
| E758a–d | O5 | H2 | M6 |
| E759a–d | O5 | H3 | M6 |
| E760a–d | O5 | H4 | M6 |
| E761a–d | O5 | H5 | M6 |
| E762a–d | O5 | H6 | M6 |
| E763a–d | O5 | H7 | M6 |
| E764a–d | O5 | H8 | M6 |
| E765a–d | O5 | H9 | M6 |
| E766a–d | O6 | H1 | M6 |
| E767a–d | O6 | H2 | M6 |
| E768a–d | O6 | H3 | M6 |
| E769a–d | O6 | H4 | M6 |
| E770a–d | O6 | H5 | M6 |
| E771a–d | O6 | H6 | M6 |
| E772a–d | O6 | H7 | M6 |
| E773a–d | O6 | H8 | M6 |
| E774a–d | O6 | H9 | M6 |
| E775a–d | O7 | H1 | M6 |
| E776a–d | O7 | H2 | M6 |
| E777a–d | O7 | H3 | M6 |
| E778a–d | O7 | H4 | M6 |
| E779a–d | O7 | H5 | M6 |
| E780a–d | O7 | H6 | M6 |
| E781a–d | O7 | H7 | M6 |
| E782a–d | O7 | H8 | M6 |
| E783a–d | O7 | H9 | M6 |
| E784a–d | O8 | H1 | M6 |
| E785a–d | O8 | H2 | M6 |
| E786a–d | O8 | H3 | M6 |
| E787a–d | O8 | H4 | M6 |
| E788a–d | O8 | H5 | M6 |
| E789a–d | O8 | H6 | M6 |
| E790a–d | O8 | H7 | M6 |
| E791a–d | O8 | H8 | M6 |
| E792a–d | O8 | H9 | M6 |
| E793a–d | O9 | H1 | M6 |
| E794a–d | O9 | H2 | M6 |
| E795a–d | O9 | H3 | M6 |
| E796a–d | O9 | H4 | M6 |
| E797a–d | O9 | H5 | M6 |
| E798a–d | O9 | H6 | M6 |
| E799a–d | O9 | H7 | M6 |
| E800a–d | O9 | H8 | M6 |
| E801a–d | O9 | H9 | M6 |
| E802a–d | O10 | H1 | M6 |
| E803a–d | O10 | H2 | M6 |
| E804a–d | O10 | H3 | M6 |
| E805a–d | O10 | H4 | M6 |
| E806a–d | O10 | H5 | M6 |
| E807a–d | O10 | H6 | M6 |
| E808a–d | O10 | H7 | M6 |
| E809a–d | O10 | H8 | M6 |
| E810a–d | O10 | H9 | M6 |
| E811a–d | O11 | H1 | M6 |
| E812a–d | O11 | H2 | M6 |
| E813a–d | O11 | H3 | M6 |
| E814a–d | O11 | H4 | M6 |
| E815a–d | O11 | H5 | M6 |
| E816a–d | O11 | H6 | M6 |
| E817a–d | O11 | H7 | M6 |
| E818a–d | O11 | H8 | M6 |
| E819a–d | O11 | H9 | M6 |
| E820a–d | O12 | H1 | M6 |
| E821a–d | O12 | H2 | M6 |
| E822a–d | O12 | H3 | M6 |
| E823a–d | O12 | H4 | M6 |
| E824a–d | O12 | H5 | M6 |
| E825a–d | O12 | H6 | M6 |
| E826a–d | O12 | H7 | M6 |
| E827a–d | O12 | H8 | M6 |
| E828a–d | O12 | H9 | M6 |
| E829a–d | O13 | H1 | M6 |
| E830a–d | O13 | H2 | M6 |
| E831a–d | O13 | H3 | M6 |
| E832a–d | O13 | H4 | M6 |
| E833a–d | O13 | H5 | M6 |
| E834a–d | O13 | H6 | M6 |
| E835a–d | O13 | H7 | M6 |
| E836a–d | O13 | H8 | M6 |
| E837a–d | O13 | H9 | M6 |
| E838a–d | O14 | H1 | M6 |
| E839a–d | O14 | H2 | M6 |
| E840a–d | O14 | H3 | M6 |
| E841a–d | O14 | H4 | M6 |
| E842a–d | O14 | H5 | M6 |
| E843a–d | O14 | H6 | M6 |
| E844a–d | O14 | H7 | M6 |
| E845a–d | O14 | H8 | M6 |
| E846a–d | O14 | H9 | M6 |
| E847a–d | O15 | H1 | M6 |
| E848a–d | O15 | H2 | M6 |
| E849a–d | O15 | H3 | M6 |
| E850a–d | O15 | H4 | M6 |
| E851a–d | O15 | H5 | M6 |
| E852a–d | O15 | H6 | M6 |
| E853a–d | O15 | H7 | M6 |
| E854a–d | O15 | H8 | M6 |
| E855a–d | O15 | H9 | M6 |
| E856a–d | O16 | H1 | M6 |
| E857a–d | O16 | H2 | M6 |
| E858a–d | O16 | H3 | M6 |
| E859a–d | O16 | H4 | M6 |
| E860a–d | O16 | H5 | M6 |
| E861a–d | O16 | H6 | M6 |
| E862a–d | O16 | H7 | M6 |
| E863a–d | O16 | H8 | M6 |
| E864a–d | O16 | H9 | M6 |
| E865a–d | O1 | H1 | M7 |
| E866a–d | O1 | H2 | M7 |
| E867a–d | O1 | H3 | M7 |
| E868a–d | O1 | H4 | M7 |
| E869a–d | O1 | H5 | M7 |
| E870a–d | O1 | H6 | M7 |
| E871a–d | O1 | H7 | M7 |
| E872a–d | O1 | H8 | M7 |
| E873a–d | O1 | H9 | M7 |
| E874a–d | O2 | H1 | M7 |
| E875a–d | O2 | H2 | M7 |
| E876a–d | O2 | H3 | M7 |
| E877a–d | O2 | H4 | M7 |
| E878a–d | O2 | H5 | M7 |
| E879a–d | O2 | H6 | M7 |
| E880a–d | O2 | H7 | M7 |
| E881a–d | O2 | H8 | M7 |
| E882a–d | O2 | H9 | M7 |
| E883a–d | O3 | H1 | M7 |
| E884a–d | O3 | H2 | M7 |
| E885a–d | O3 | H3 | M7 |
| E886a–d | O3 | H4 | M7 |
| E887a–d | O3 | H5 | M7 |
| E888a–d | O3 | H6 | M7 |
| E889a–d | O3 | H7 | M7 |
| E890a–d | O3 | H8 | M7 |
| E891a–d | O3 | H9 | M7 |
| E892a–d | O4 | H1 | M7 |
| E893a–d | O4 | H2 | M7 |
| E894a–d | O4 | H3 | M7 |
| E895a–d | O4 | H4 | M7 |
| E896a–d | O4 | H5 | M7 |
| E897a–d | O4 | H6 | M7 |
| E898a–d | O4 | H7 | M7 |
| E899a–d | O4 | H8 | M7 |
| E900a–d | O4 | H9 | M7 |
| E901a–d | O5 | H1 | M7 |
| E902a–d | O5 | H2 | M7 |
| E903a–d | O5 | H3 | M7 |
| E904a–d | O5 | H4 | M7 |
| E905a–d | O5 | H5 | M7 |
| E906a–d | O5 | H6 | M7 |
| E907a–d | O5 | H7 | M7 |
| E908a–d | O5 | H8 | M7 |
| E909a–d | O5 | H9 | M7 |

TABLE 1-continued

| Example | O Group | H Group | M Group |
|---|---|---|---|
| E910a–d | O6 | H1 | M7 |
| E911a–d | O6 | H2 | M7 |
| E912a–d | O6 | H3 | M7 |
| E913a–d | O6 | H4 | M7 |
| E914a–d | O6 | H5 | M7 |
| E915a–d | O6 | H6 | M7 |
| E916a–d | O6 | H7 | M7 |
| E917a–d | O6 | H8 | M7 |
| E918a–d | O6 | H9 | M7 |
| E919a–d | O7 | H1 | M7 |
| E920a–d | O7 | H2 | M7 |
| E921a–d | O7 | H3 | M7 |
| E922a–d | O7 | H4 | M7 |
| E923a–d | O7 | H5 | M7 |
| E924a–d | O7 | H6 | M7 |
| E925a–d | O7 | H7 | M7 |
| E926a–d | O7 | H8 | M7 |
| E927a–d | O7 | H9 | M7 |
| E928a–d | O8 | H1 | M7 |
| E929a–d | O8 | H2 | M7 |
| E930a–d | O8 | H3 | M7 |
| E931a–d | O8 | H4 | M7 |
| E932a–d | O8 | H5 | M7 |
| E933a–d | O8 | H6 | M7 |
| E934a–d | O8 | H7 | M7 |
| E935a–d | O8 | H8 | M7 |
| E936a–d | O8 | H9 | M7 |
| E937a–d | O9 | H1 | M7 |
| E938a–d | O9 | H2 | M7 |
| E939a–d | O9 | H3 | M7 |
| E940a–d | O9 | H4 | M7 |
| E941a–d | O9 | H5 | M7 |
| E942a–d | O9 | H6 | M7 |
| E943a–d | O9 | H7 | M7 |
| E944a–d | O9 | H8 | M7 |
| E945a–d | O9 | H9 | M7 |
| E946a–d | O10 | H1 | M7 |
| E947a–d | O10 | H2 | M7 |
| E948a–d | O10 | H3 | M7 |
| E949a–d | O10 | H4 | M7 |
| E950a–d | O10 | H5 | M7 |
| E951a–d | O10 | H6 | M7 |
| E952a–d | O10 | H7 | M7 |
| E953a–d | O10 | H8 | M7 |
| E954a–d | O10 | H9 | M7 |
| E955a–d | O11 | H1 | M7 |
| E956a–d | O11 | H2 | M7 |
| E957a–d | O11 | H3 | M7 |
| E958a–d | O11 | H4 | M7 |
| E959a–d | O11 | H5 | M7 |
| E960a–d | O11 | H6 | M7 |
| E961a–d | O11 | H7 | M7 |
| E962a–d | O11 | H8 | M7 |
| E963a–d | O11 | H9 | M7 |
| E964a–d | O12 | H1 | M7 |
| E965a–d | O12 | H2 | M7 |
| E966a–d | O12 | H3 | M7 |
| E967a–d | O12 | H4 | M7 |
| E968a–d | O12 | H5 | M7 |
| E969a–d | O12 | H6 | M7 |
| E970a–d | O12 | H7 | M7 |
| E971a–d | O12 | H8 | M7 |
| E972a–d | O12 | H9 | M7 |
| E973a–d | O13 | H1 | M7 |
| E974a–d | O13 | H2 | M7 |
| E975a–d | O13 | H3 | M7 |
| E976a–d | O13 | H4 | M7 |
| E977a–d | O13 | H5 | M7 |
| E978a–d | O13 | H6 | M7 |
| E979a–d | O13 | H7 | M7 |
| E980a–d | O13 | H8 | M7 |
| E981a–d | O13 | H9 | M7 |
| E982a–d | O14 | H1 | M7 |
| E983a–d | O14 | H2 | M7 |
| E984a–d | O14 | H3 | M7 |
| E985a–d | O14 | H4 | M7 |
| E986a–d | O14 | H5 | M7 |
| E987a–d | O14 | H6 | M7 |
| E988a–d | O14 | H7 | M7 |
| E989a–d | O14 | H8 | M7 |
| E990a–d | O14 | H9 | M7 |
| E991a–d | O15 | H1 | M7 |
| E992a–d | O15 | H2 | M7 |
| E993a–d | O15 | H3 | M7 |
| E994a–d | O15 | H4 | M7 |
| E995a–d | O15 | H5 | M7 |
| E996a–d | O15 | H6 | M7 |
| E997a–d | O15 | H7 | M7 |
| E998a–d | O15 | H8 | M7 |
| E999a–d | O15 | H9 | M7 |
| E1000a–d | O16 | H1 | M7 |
| E1001a–d | O16 | H2 | M7 |
| E1002a–d | O16 | H3 | M7 |
| E1003a–d | O16 | H4 | M7 |
| E1004a–d | O16 | H5 | M7 |
| E1005a–d | O16 | H6 | M7 |
| E1006a–d | O16 | H7 | M7 |
| E1007a–d | O16 | H8 | M7 |
| E1008a–d | O16 | H9 | M7 |
| E1009a–d | O1 | H1 | M8 |
| E1010a–d | O1 | H2 | M8 |
| E1011a–d | O1 | H3 | M8 |
| E1012a–d | O1 | H4 | M8 |
| E1013a–d | O1 | H5 | M8 |
| E1014a–d | O1 | H6 | M8 |
| E1015a–d | O1 | H7 | M8 |
| E1016a–d | O1 | H8 | M8 |
| E1017a–d | O1 | H9 | M8 |
| E1018a–d | O2 | H1 | M8 |
| E1019a–d | O2 | H2 | M8 |
| E1020a–d | O2 | H3 | M8 |
| E1021a–d | O2 | H4 | M8 |
| E1022a–d | O2 | H5 | M8 |
| E1023a–d | O2 | H6 | M8 |
| E1024a–d | O2 | H7 | M8 |
| E1025a–d | O2 | H8 | M8 |
| E1026a–d | O2 | H9 | M8 |
| E1027a–d | O3 | H1 | M8 |
| E1028a–d | O3 | H2 | M8 |
| E1029a–d | O3 | H3 | M8 |
| E1030a–d | O3 | H4 | M8 |
| E1031a–d | O3 | H5 | M8 |
| E1032a–d | O3 | H6 | M8 |
| E1033a–d | O3 | H7 | M8 |
| E1034a–d | O3 | H8 | M8 |
| E1035a–d | O3 | H9 | M8 |
| E1036a–d | O4 | H1 | M8 |
| E1037a–d | O4 | H2 | M8 |
| E1038a–d | O4 | H3 | M8 |
| E1039a–d | O4 | H4 | M8 |
| E1040a–d | O4 | H5 | M8 |
| E1041a–d | O4 | H6 | M8 |
| E1042a–d | O4 | H7 | M8 |
| E1043a–d | O4 | H8 | M8 |
| E1044a–d | O4 | H9 | M8 |
| E1045a–d | O5 | H1 | M8 |
| E1046a–d | O5 | H2 | M8 |
| E1047a–d | O5 | H3 | M8 |
| E1048a–d | O5 | H4 | M8 |
| E1049a–d | O5 | H5 | M8 |
| E1050a–d | O5 | H6 | M8 |
| E1051a–d | O5 | H7 | M8 |
| E1052a–d | O5 | H8 | M8 |
| E1053a–d | O5 | H9 | M8 |
| E1054a–d | O6 | H1 | M8 |
| E1055a–d | O6 | H2 | M8 |
| E1056a–d | O6 | H3 | M8 |
| E1057a–d | O6 | H4 | M8 |
| E1058a–d | O6 | H5 | M8 |
| E1059a–d | O6 | H6 | M8 |
| E1060a–d | O6 | H7 | M8 |
| E1061a–d | O6 | H8 | M8 |
| E1062a–d | O6 | H9 | M8 |
| E1063a–d | O7 | H1 | M8 |

TABLE 1-continued

| Example | O Group | H Group | M Group |
| --- | --- | --- | --- |
| E1064a–d | O7 | H2 | M8 |
| E1065a–d | O7 | H3 | M8 |
| E1066a–d | O7 | H4 | M8 |
| E1067a–d | O7 | H5 | M8 |
| E1068a–d | O7 | H6 | M8 |
| E1069a–d | O7 | H7 | M8 |
| E1070a–d | O7 | H8 | M8 |
| E1071a–d | O7 | H9 | M8 |
| E1072a–d | O8 | H1 | M8 |
| E1073a–d | O8 | H2 | M8 |
| E1074a–d | O8 | H3 | M8 |
| E1075a–d | O8 | H4 | M8 |
| E1076a–d | O8 | H5 | M8 |
| E1077a–d | O8 | H6 | M8 |
| E1078a–d | O8 | H7 | M8 |
| E1079a–d | O8 | H8 | M8 |
| E1080a–d | O8 | H9 | M8 |
| E1081a–d | O9 | H1 | M8 |
| E1082a–d | O9 | H2 | M8 |
| E1083a–d | O9 | H3 | M8 |
| E1084a–d | O9 | H4 | M8 |
| E1085a–d | O9 | H5 | M8 |
| E1086a–d | O9 | H6 | M8 |
| E1087a–d | O9 | H7 | M8 |
| E1088a–d | O9 | H8 | M8 |
| E1089a–d | O9 | H9 | M8 |
| E1090a–d | O10 | H1 | M8 |
| E1091a–d | O10 | H2 | M8 |
| E1092a–d | O10 | H3 | M8 |
| E1093a–d | O10 | H4 | M8 |
| E1094a–d | O10 | H5 | M8 |
| E1095a–d | O10 | H6 | M8 |
| E1096a–d | O10 | H7 | M8 |
| E1097a–d | O10 | H8 | M8 |
| E1098a–d | O10 | H9 | M8 |
| E1099a–d | O11 | H1 | M8 |
| E1100a–d | O11 | H2 | M8 |
| E1101a–d | O11 | H3 | M8 |
| E1102a–d | O11 | H4 | M8 |
| E1103a–d | O11 | H5 | M8 |
| E1104a–d | O11 | H6 | M8 |
| E1105a–d | O11 | H7 | M8 |
| E1106a–d | O11 | H8 | M8 |
| E1107a–d | O11 | H9 | M8 |
| E1108a–d | O12 | H1 | M8 |
| E1109a–d | O12 | H2 | M8 |
| E1110a–d | O12 | H3 | M8 |
| E1111a–d | O12 | H4 | M8 |
| E1112a–d | O12 | H5 | M8 |
| E1113a–d | O12 | H6 | M8 |
| E1114a–d | O12 | H7 | M8 |
| E1115a–d | O12 | H8 | M8 |
| E1116a–d | O12 | H9 | M8 |
| E1117a–d | O13 | H1 | M8 |
| E1118a–d | O13 | H2 | M8 |
| E1119a–d | O13 | H3 | M8 |
| E1120a–d | O13 | H4 | M8 |
| E1121a–d | O13 | H5 | M8 |
| E1122a–d | O13 | H6 | M8 |
| E1123a–d | O13 | H7 | M8 |
| E1124a–d | O13 | H8 | M8 |
| E1125a–d | O13 | H9 | M8 |
| E1126a–d | O14 | H1 | M8 |
| E1127a–d | O14 | H2 | M8 |
| E1128a–d | O14 | H3 | M8 |
| E1129a–d | O14 | H4 | M8 |
| E1130a–d | O14 | H5 | M8 |
| E1131a–d | O14 | H6 | M8 |
| E1132a–d | O14 | H7 | M8 |
| E1133a–d | O14 | H8 | M8 |
| E1134a–d | O14 | H9 | M8 |
| E1135a–d | O15 | H1 | M8 |
| E1136a–d | O15 | H2 | M8 |
| E1137a–d | O15 | H3 | M8 |
| E1138a–d | O15 | H4 | M8 |
| E1139a–d | O15 | H5 | M8 |
| E1140a–d | O15 | H6 | M8 |
| E1141a–d | O15 | H7 | M8 |
| E1142a–d | O15 | H8 | M8 |
| E1143a–d | O15 | H9 | M8 |
| E1144a–d | O16 | H1 | M8 |
| E1145a–d | O16 | H2 | M8 |
| E1146a–d | O16 | H3 | M8 |
| E1147a–d | O16 | H4 | M8 |
| E1148a–d | O16 | H5 | M8 |
| E1149a–d | O16 | H6 | M8 |
| E1150a–d | O16 | H7 | M8 |
| E1151a–d | O16 | H8 | M8 |
| E1152a–d | O16 | H9 | M8 |
| E1153a–d | O1 | H1 | M9 |
| E1154a–d | O1 | H2 | M9 |
| E1155a–d | O1 | H3 | M9 |
| E1156a–d | O1 | H4 | M9 |
| E1157a–d | O1 | H5 | M9 |
| E1158a–d | O1 | H6 | M9 |
| E1159a–d | O1 | H7 | M9 |
| E1160a–d | O1 | H8 | M9 |
| E1161a–d | O1 | H9 | M9 |
| E1162a–d | O2 | H1 | M9 |
| E1163a–d | O2 | H2 | M9 |
| E1164a–d | O2 | H3 | M9 |
| E1165a–d | O2 | H4 | M9 |
| E1166a–d | O2 | H5 | M9 |
| E1167a–d | O2 | H6 | M9 |
| E1168a–d | O2 | H7 | M9 |
| E1169a–d | O2 | H8 | M9 |
| E1170a–d | O2 | H9 | M9 |
| E1171a–d | O3 | H1 | M9 |
| E1172a–d | O3 | H2 | M9 |
| E1173a–d | O3 | H3 | M9 |
| E1174a–d | O3 | H4 | M9 |
| E1175a–d | O3 | H5 | M9 |
| E1176a–d | O3 | H6 | M9 |
| E1177a–d | O3 | H7 | M9 |
| E1178a–d | O3 | H8 | M9 |
| E1179a–d | O3 | H9 | M9 |
| E1180a–d | O4 | H1 | M9 |
| E1181a–d | O4 | H2 | M9 |
| E1182a–d | O4 | H3 | M9 |
| E1183a–d | O4 | H4 | M9 |
| E1184a–d | O4 | H5 | M9 |
| E1185a–d | O4 | H6 | M9 |
| E1186a–d | O4 | H7 | M9 |
| E1187a–d | O4 | H8 | M9 |
| E1188a–d | O4 | H9 | M9 |
| E1189a–d | O5 | H1 | M9 |
| E1190a–d | O5 | H2 | M9 |
| E1191a–d | O5 | H3 | M9 |
| E1192a–d | O5 | H4 | M9 |
| E1193a–d | O5 | H5 | M9 |
| E1194a–d | O5 | H6 | M9 |
| E1195a–d | O5 | H7 | M9 |
| E1196a–d | O5 | H8 | M9 |
| E1197a–d | O5 | H9 | M9 |
| E1198a–d | O6 | H1 | M9 |
| E1199a–d | O6 | H2 | M9 |
| E1200a–d | O6 | H3 | M9 |
| E1201a–d | O6 | H4 | M9 |
| E1202a–d | O6 | H5 | M9 |
| E1203a–d | O6 | H6 | M9 |
| E1204a–d | O6 | H7 | M9 |
| E1205a–d | O6 | H8 | M9 |
| E1206a–d | O6 | H9 | M9 |
| E1207a–d | O7 | H1 | M9 |
| E1208a–d | O7 | H2 | M9 |
| E1209a–d | O7 | H3 | M9 |
| E1210a–d | O7 | H4 | M9 |
| E1211a–d | O7 | H5 | M9 |
| E1212a–d | O7 | H6 | M9 |
| E1213a–d | O7 | H7 | M9 |
| E1214a–d | O7 | H8 | M9 |
| E1215a–d | O7 | H9 | M9 |
| E1216a–d | O8 | H1 | M9 |
| E1217a–d | O8 | H2 | M9 |

TABLE 1-continued

| Example | O Group | H Group | M Group |
|---|---|---|---|
| E1218a–d | O8 | H3 | M9 |
| E1219a–d | O8 | H4 | M9 |
| E1220a–d | O8 | H5 | M9 |
| E1221a–d | O8 | H6 | M9 |
| E1222a–d | O8 | H7 | M9 |
| E1223a–d | O8 | H8 | M9 |
| E1224a–d | O8 | H9 | M9 |
| E1225a–d | O9 | H1 | M9 |
| E1226a–d | O9 | H2 | M9 |
| E1227a–d | O9 | H3 | M9 |
| E1228a–d | O9 | H4 | M9 |
| E1229a–d | O9 | H5 | M9 |
| E1230a–d | O9 | H6 | M9 |
| E1231a–d | O9 | H7 | M9 |
| E1232a–d | O9 | H8 | M9 |
| E1233a–d | O9 | H9 | M9 |
| E1234a–d | O10 | H1 | M9 |
| E1235a–d | O10 | H2 | M9 |
| E1236a–d | O10 | H3 | M9 |
| E1237a–d | O10 | H4 | M9 |
| E1238a–d | O10 | H5 | M9 |
| E1239a–d | O10 | H6 | M9 |
| E1240a–d | O10 | H7 | M9 |
| E1241a–d | O10 | H8 | M9 |
| E1242a–d | O10 | H9 | M9 |
| E1243a–d | O11 | H1 | M9 |
| E1244a–d | O11 | H2 | M9 |
| E1245a–d | O11 | H3 | M9 |
| E1246a–d | O11 | H4 | M9 |
| E1247a–d | O11 | H5 | M9 |
| E1248a–d | O11 | H6 | M9 |
| E1249a–d | O11 | H7 | M9 |
| E1250a–d | O11 | H8 | M9 |
| E1251a–d | O11 | H9 | M9 |
| E1252a–d | O12 | H1 | M9 |
| E1253a–d | O12 | H2 | M9 |
| E1254a–d | O12 | H3 | M9 |
| E1255a–d | O12 | H4 | M9 |
| E1256a–d | O12 | H5 | M9 |
| E1257a–d | O12 | H6 | M9 |
| E1258a–d | O12 | H7 | M9 |
| E1259a–d | O12 | H8 | M9 |
| E1260a–d | O12 | H9 | M9 |
| E1261a–d | O13 | H1 | M9 |
| E1262a–d | O13 | H2 | M9 |
| E1263a–d | O13 | H3 | M9 |
| E1264a–d | O13 | H4 | M9 |
| E1265a–d | O13 | H5 | M9 |
| E1266a–d | O13 | H6 | M9 |
| E1267a–d | O13 | H7 | M9 |
| E1268a–d | O13 | H8 | M9 |
| E1269a–d | O13 | H9 | M9 |
| E1270a–d | O14 | H1 | M9 |
| E1271a–d | O14 | H2 | M9 |
| E1272a–d | O14 | H3 | M9 |
| E1273a–d | O14 | H4 | M9 |
| E1274a–d | O14 | H5 | M9 |
| E1275a–d | O14 | H6 | M9 |
| E1276a–d | O14 | H7 | M9 |
| E1277a–d | O14 | H8 | M9 |
| E1278a–d | O14 | H9 | M9 |
| E1279a–d | O15 | H1 | M9 |
| E1280a–d | O15 | H2 | M9 |
| E1281a–d | O15 | H3 | M9 |
| E1282a–d | O15 | H4 | M9 |
| E1283a–d | O15 | H5 | M9 |
| E1284a–d | O15 | H6 | M9 |
| E1285a–d | O15 | H7 | M9 |
| E1286a–d | O15 | H8 | M9 |
| E1287a–d | O15 | H9 | M9 |
| E1288a–d | O16 | H1 | M9 |
| E1289a–d | O16 | H2 | M9 |
| E1290a–d | O16 | H3 | M9 |
| E1291a–d | O16 | H4 | M9 |
| E1292a–d | O16 | H5 | M9 |
| E1293a–d | O16 | H6 | M9 |
| E1294a–d | O16 | H7 | M9 |
| E1295a–d | O16 | H8 | M9 |
| E1296a–d | O16 | H9 | M9 |
| E1297a–d | O1 | H1 | M10 |
| E1298a–d | O1 | H2 | M10 |
| E1299a–d | O1 | H3 | M10 |
| E1300a–d | O1 | H4 | M10 |
| E1301a–d | O1 | H5 | M10 |
| E1302a–d | O1 | H6 | M10 |
| E1303a–d | O1 | H7 | M10 |
| E1304a–d | O1 | H8 | M10 |
| E1305a–d | O1 | H9 | M10 |
| E1306a–d | O2 | H1 | M10 |
| E1307a–d | O2 | H2 | M10 |
| E1308a–d | O2 | H3 | M10 |
| E1309a–d | O2 | H4 | M10 |
| E1310a–d | O2 | H5 | M10 |
| E1311a–d | O2 | H6 | M10 |
| E1312a–d | O2 | H7 | M10 |
| E1313a–d | O2 | H8 | M10 |
| E1314a–d | O2 | H9 | M10 |
| E1315a–d | O3 | H1 | M10 |
| E1316a–d | O3 | H2 | M10 |
| E1317a–d | O3 | H3 | M10 |
| E1318a–d | O3 | H4 | M10 |
| E1319a–d | O3 | H5 | M10 |
| E1320a–d | O3 | H6 | M10 |
| E1321a–d | O3 | H7 | M10 |
| E1322a–d | O3 | H8 | M10 |
| E1323a–d | O3 | H9 | M10 |
| E1324a–d | O4 | H1 | M10 |
| E1325a–d | O4 | H2 | M10 |
| E1326a–d | O4 | H3 | M10 |
| E1327a–d | O4 | H4 | M10 |
| E1328a–d | O4 | H5 | M10 |
| E1329a–d | O4 | H6 | M10 |
| E1330a–d | O4 | H7 | M10 |
| E1331a–d | O4 | H8 | M10 |
| E1332a–d | O4 | H9 | M10 |
| E1333a–d | O5 | H1 | M10 |
| E1334a–d | O5 | H2 | M10 |
| E1335a–d | O5 | H3 | M10 |
| E1336a–d | O5 | H4 | M10 |
| E1337a–d | O5 | H5 | M10 |
| E1338a–d | O5 | H6 | M10 |
| E1339a–d | O5 | H7 | M10 |
| E1340a–d | O5 | H8 | M10 |
| E1341a–d | O5 | H9 | M10 |
| E1342a–d | O6 | H1 | M10 |
| E1343a–d | O6 | H2 | M10 |
| E1344a–d | O6 | H3 | M10 |
| E1345a–d | O6 | H4 | M10 |
| E1346a–d | O6 | H5 | M10 |
| E1347a–d | O6 | H6 | M10 |
| E1348a–d | O6 | H7 | M10 |
| E1349a–d | O6 | H8 | M10 |
| E1350a–d | O6 | H9 | M10 |
| E1351a–d | O7 | H1 | M10 |
| E1352a–d | O7 | H2 | M10 |
| E1353a–d | O7 | H3 | M10 |
| E1354a–d | O7 | H4 | M10 |
| E1355a–d | O7 | H5 | M10 |
| E1356a–d | O7 | H6 | M10 |
| E1357a–d | O7 | H7 | M10 |
| E1358a–d | O7 | H8 | M10 |
| E1359a–d | O7 | H9 | M10 |
| E1360a–d | O8 | H1 | M10 |
| E1361a–d | O8 | H2 | M10 |
| E1362a–d | O8 | H3 | M10 |
| E1363a–d | O8 | H4 | M10 |
| E1364a–d | O8 | H5 | M10 |
| E1365a–d | O8 | H6 | M10 |
| E1366a–d | O8 | H7 | M10 |
| E1367a–d | O8 | H8 | M10 |
| E1368a–d | O8 | H9 | M10 |
| E1369a–d | O9 | H1 | M10 |
| E1370a–d | O9 | H2 | M10 |
| E1371a–d | O9 | H3 | M10 |

TABLE 1-continued

| Example | O Group | H Group | M Group |
|---|---|---|---|
| E1372a–d | O9 | H4 | M10 |
| E1373a–d | O9 | H5 | M10 |
| E1374a–d | O9 | H6 | M10 |
| E1375a–d | O9 | H7 | M10 |
| E1376a–d | O9 | H8 | M10 |
| E1377a–d | O9 | H9 | M10 |
| E1378a–d | O10 | H1 | M10 |
| E1379a–d | O10 | H2 | M10 |
| E1380a–d | O10 | H3 | M10 |
| E1381a–d | O10 | H4 | M10 |
| E1382a–d | O10 | H5 | M10 |
| E1383a–d | O10 | H6 | M10 |
| E1384a–d | O10 | H7 | M10 |
| E1385a–d | O10 | H8 | M10 |
| E1386a–d | O10 | H9 | M10 |
| E1387a–d | O11 | H1 | M10 |
| E1388a–d | O11 | H2 | M10 |
| E1389a–d | O11 | H3 | M10 |
| E1390a–d | O11 | H4 | M10 |
| E1391a–d | O11 | H5 | M10 |
| E1392a–d | O11 | H6 | M10 |
| E1393a–d | O11 | H7 | M10 |
| E1394a–d | O11 | H8 | M10 |
| E1395a–d | O11 | H9 | M10 |
| E1396a–d | O12 | H1 | M10 |
| E1397a–d | O12 | H2 | M10 |
| E1398a–d | O12 | H3 | M10 |
| E1399a–d | O12 | H4 | M10 |
| E1400a–d | O12 | H5 | M10 |
| E1401a–d | O12 | H6 | M10 |
| E1402a–d | O12 | H7 | M10 |
| E1403a–d | O12 | H8 | M10 |
| E1404a–d | O12 | H9 | M10 |
| E1405a–d | O13 | H1 | M10 |
| E1406a–d | O13 | H2 | M10 |
| E1407a–d | O13 | H3 | M10 |
| E1408a–d | O13 | H4 | M10 |
| E1409a–d | O13 | H5 | M10 |
| E1410a–d | O13 | H6 | M10 |
| E1411a–d | O13 | H7 | M10 |
| E1412a–d | O13 | H8 | M10 |
| E1413a–d | O13 | H9 | M10 |
| E1414a–d | O14 | H1 | M10 |
| E1415a–d | O14 | H2 | M10 |
| E1416a–d | O14 | H3 | M10 |
| E1417a–d | O14 | H4 | M10 |
| E1418a–d | O14 | H5 | M10 |
| E1419a–d | O14 | H6 | M10 |
| E1420a–d | O14 | H7 | M10 |
| E1421a–d | O14 | H8 | M10 |
| E1422a–d | O14 | H9 | M10 |
| E1423a–d | O15 | H1 | M10 |
| E1424a–d | O15 | H2 | M10 |
| E1425a–d | O15 | H3 | M10 |
| E1426a–d | O15 | H4 | M10 |
| E1427a–d | O15 | H5 | M10 |
| E1428a–d | O15 | H6 | M10 |
| E1429a–d | O15 | H7 | M10 |
| E1430a–d | O15 | H8 | M10 |
| E1431a–d | O15 | H9 | M10 |
| E1432a–d | O16 | H1 | M10 |
| E1433a–d | O16 | H2 | M10 |
| E1434a–d | O16 | H3 | M10 |
| E1435a–d | O16 | H4 | M10 |
| E1436a–d | O16 | H5 | M10 |
| E1437a–d | O16 | H6 | M10 |
| E1438a–d | O16 | H7 | M10 |
| E1439a–d | O16 | H8 | M10 |
| E1440a–d | O16 | H9 | M10 |
| E1441a–d | O1 | H1 | M11 |
| E1442a–d | O1 | H2 | M11 |
| E1443a–d | O1 | H3 | M11 |
| E1444a–d | O1 | H4 | M11 |
| E1445a–d | O1 | H5 | M11 |
| E1446a–d | O1 | H6 | M11 |
| E1447a–d | O1 | H7 | M11 |
| E1448a–d | O1 | H8 | M11 |
| E1449a–d | O1 | H9 | M11 |
| E1450a–d | O2 | H1 | M11 |
| E1451a–d | O2 | H2 | M11 |
| E1452a–d | O2 | H3 | M11 |
| E1453a–d | O2 | H4 | M11 |
| E1454a–d | O2 | H5 | M11 |
| E1455a–d | O2 | H6 | M11 |
| E1456a–d | O2 | H7 | M11 |
| E1457a–d | O2 | H8 | M11 |
| E1458a–d | O2 | H9 | M11 |
| E1459a–d | O3 | H1 | M11 |
| E1460a–d | O3 | H2 | M11 |
| E1461a–d | O3 | H3 | M11 |
| E1462a–d | O3 | H4 | M11 |
| E1463a–d | O3 | H5 | M11 |
| E1464a–d | O3 | H6 | M11 |
| E1465a–d | O3 | H7 | M11 |
| E1466a–d | O3 | H8 | M11 |
| E1467a–d | O3 | H9 | M11 |
| E1468a–d | O4 | H1 | M11 |
| E1469a–d | O4 | H2 | M11 |
| E1470a–d | O4 | H3 | M11 |
| E1471a–d | O4 | H4 | M11 |
| E1472a–d | O4 | H5 | M11 |
| E1473a–d | O4 | H6 | M11 |
| E1474a–d | O4 | H7 | M11 |
| E1475a–d | O4 | H8 | M11 |
| E1476a–d | O4 | H9 | M11 |
| E1477a–d | O5 | H1 | M11 |
| E1478a–d | O5 | H2 | M11 |
| E1479a–d | O5 | H3 | M11 |
| E1480a–d | O5 | H4 | M11 |
| E1481a–d | O5 | H5 | M11 |
| E1482a–d | O5 | H6 | M11 |
| E1483a–d | O5 | H7 | M11 |
| E1484a–d | O5 | H8 | M11 |
| E1485a–d | O5 | H9 | M11 |
| E1486a–d | O6 | H1 | M11 |
| E1487a–d | O6 | H2 | M11 |
| E1488a–d | O6 | H3 | M11 |
| E1489a–d | O6 | H4 | M11 |
| E1490a–d | O6 | H5 | M11 |
| E1491a–d | O6 | H6 | M11 |
| E1492a–d | O6 | H7 | M11 |
| E1493a–d | O6 | H8 | M11 |
| E1494a–d | O6 | H9 | M11 |
| E1495a–d | O7 | H1 | M11 |
| E1496a–d | O7 | H2 | M11 |
| E1497a–d | O7 | H3 | M11 |
| E1498a–d | O7 | H4 | M11 |
| E1499a–d | O7 | H5 | M11 |
| E1500a–d | O7 | H6 | M11 |
| E1501a–d | O7 | H7 | M11 |
| E1502a–d | O7 | H8 | M11 |
| E1503a–d | O7 | H9 | M11 |
| E1504a–d | O8 | H1 | M11 |
| E1505a–d | O8 | H2 | M11 |
| E1506a–d | O8 | H3 | M11 |
| E1507a–d | O8 | H4 | M11 |
| E1508a–d | O8 | H5 | M11 |
| E1509a–d | O8 | H6 | M11 |
| E1510a–d | O8 | H7 | M11 |
| E1511a–d | O8 | H8 | M11 |
| E1512a–d | O8 | H9 | M11 |
| E1513a–d | O9 | H1 | M11 |
| E1514a–d | O9 | H2 | M11 |
| E1515a–d | O9 | H3 | M11 |
| E1516a–d | O9 | H4 | M11 |
| E1517a–d | O9 | H5 | M11 |
| E1518a–d | O9 | H6 | M11 |
| E1519a–d | O9 | H7 | M11 |
| E1520a–d | O9 | H8 | M11 |
| E1521a–d | O9 | H9 | M11 |
| E1522a–d | O10 | H1 | M11 |
| E1523a–d | O10 | H2 | M11 |
| E1524a–d | O10 | H3 | M11 |
| E1525a–d | O10 | H4 | M11 |

TABLE 1-continued

| Example | O Group | H Group | M Group |
|---|---|---|---|
| E1526a–d | O10 | H5 | M11 |
| E1527a–d | O10 | H6 | M11 |
| E1528a–d | O10 | H7 | M11 |
| E1529a–d | O10 | H8 | M11 |
| E1530a–d | O10 | H9 | M11 |
| E1531a–d | O11 | H1 | M11 |
| E1532a–d | O11 | H2 | M11 |
| E1533a–d | O11 | H3 | M11 |
| E1534a–d | O11 | H4 | M11 |
| E1535a–d | O11 | H5 | M11 |
| E1536a–d | O11 | H6 | M11 |
| E1537a–d | O11 | H7 | M11 |
| E1538a–d | O11 | H8 | M11 |
| E1539a–d | O11 | H9 | M11 |
| E1540a–d | O12 | H1 | M11 |
| E1541a–d | O12 | H2 | M11 |
| E1542a–d | O12 | H3 | M11 |
| E1543a–d | O12 | H4 | M11 |
| E1544a–d | O12 | H5 | M11 |
| E1545a–d | O12 | H6 | M11 |
| E1546a–d | O12 | H7 | M11 |
| E1547a–d | O12 | H8 | M11 |
| E1548a–d | O12 | H9 | M11 |
| E1549a–d | O13 | H1 | M11 |
| E1550a–d | O13 | H2 | M11 |
| E1551a–d | O13 | H3 | M11 |
| E1552a–d | O13 | H4 | M11 |
| E1553a–d | O13 | H5 | M11 |
| E1554a–d | O13 | H6 | M11 |
| E1555a–d | O13 | H7 | M11 |
| E1556a–d | O13 | H8 | M11 |
| E1557a–d | O13 | H9 | M11 |
| E1558a–d | O14 | H1 | M11 |
| E1559a–d | O14 | H2 | M11 |
| E1560a–d | O14 | H3 | M11 |
| E1561a–d | O14 | H4 | M11 |
| E1562a–d | O14 | H5 | M11 |
| E1563a–d | O14 | H6 | M11 |
| E1564a–d | O14 | H7 | M11 |
| E1565a–d | O14 | H8 | M11 |
| E1566a–d | O14 | H9 | M11 |
| E1567a–d | O15 | H1 | M11 |
| E1568a–d | O15 | H2 | M11 |
| E1569a–d | O15 | H3 | M11 |
| E1570a–d | O15 | H4 | M11 |
| E1571a–d | O15 | H5 | M11 |
| E1572a–d | O15 | H6 | M11 |
| E1573a–d | O15 | H7 | M11 |
| E1574a–d | O15 | H8 | M11 |
| E1575a–d | O15 | H9 | M11 |
| E1576a–d | O16 | H1 | M11 |
| E1577a–d | O16 | H2 | M11 |
| E1578a–d | O16 | H3 | M11 |
| E1579a–d | O16 | H4 | M11 |
| E1580a–d | O16 | H5 | M11 |
| E1581a–d | O16 | H6 | M11 |
| E1582a–d | O16 | H7 | M11 |
| E1583a–d | O16 | H8 | M11 |
| E1584a–d | O16 | H9 | M11 |
| E1585a–d | O1 | H1 | M12 |
| E1586a–d | O1 | H2 | M12 |
| E1587a–d | O1 | H3 | M12 |
| E1588a–d | O1 | H4 | M12 |
| E1589a–d | O1 | H5 | M12 |
| E1590a–d | O1 | H6 | M12 |
| E1591a–d | O1 | H7 | M12 |
| E1592a–d | O1 | H8 | M12 |
| E1593a–d | O1 | H9 | M12 |
| E1594a–d | O2 | H1 | M12 |
| E1595a–d | O2 | H2 | M12 |
| E1596a–d | O2 | H3 | M12 |
| E1597a–d | O2 | H4 | M12 |
| E1598a–d | O2 | H5 | M12 |
| E1599a–d | O2 | H6 | M12 |
| E1600a–d | O2 | H7 | M12 |
| E1601a–d | O2 | H8 | M12 |
| E1602a–d | O2 | H9 | M12 |
| E1603a–d | O3 | H1 | M12 |
| E1604a–d | O3 | H2 | M12 |
| E1605a–d | O3 | H3 | M12 |
| E1606a–d | O3 | H4 | M12 |
| E1607a–d | O3 | H5 | M12 |
| E1608a–d | O3 | H6 | M12 |
| E1609a–d | O3 | H7 | M12 |
| E1610a–d | O3 | H8 | M12 |
| E1611a–d | O3 | H9 | M12 |
| E1612a–d | O4 | H1 | M12 |
| E1613a–d | O4 | H2 | M12 |
| E1614a–d | O4 | H3 | M12 |
| E1615a–d | O4 | H4 | M12 |
| E1616a–d | O4 | H5 | M12 |
| E1617a–d | O4 | H6 | M12 |
| E1618a–d | O4 | H7 | M12 |
| E1619a–d | O4 | H8 | M12 |
| E1620a–d | O4 | H9 | M12 |
| E1621a–d | O5 | H1 | M12 |
| E1622a–d | O5 | H2 | M12 |
| E1623a–d | O5 | H3 | M12 |
| E1624a–d | O5 | H4 | M12 |
| E1625a–d | O5 | H5 | M12 |
| E1626a–d | O5 | H6 | M12 |
| E1627a–d | O5 | H7 | M12 |
| E1628a–d | O5 | H8 | M12 |
| E1629a–d | O5 | H9 | M12 |
| E1630a–d | O6 | H1 | M12 |
| E1631a–d | O6 | H2 | M12 |
| E1632a–d | O6 | H3 | M12 |
| E1633a–d | O6 | H4 | M12 |
| E1634a–d | O6 | H5 | M12 |
| E1635a–d | O6 | H6 | M12 |
| E1636a–d | O6 | H7 | M12 |
| E1637a–d | O6 | H8 | M12 |
| E1638a–d | O6 | H9 | M12 |
| E1639a–d | O7 | H1 | M12 |
| E1640a–d | O7 | H2 | M12 |
| E1641a–d | O7 | H3 | M12 |
| E1642a–d | O7 | H4 | M12 |
| E1643a–d | O7 | H5 | M12 |
| E1644a–d | O7 | H6 | M12 |
| E1645a–d | O7 | H7 | M12 |
| E1646a–d | O7 | H8 | M12 |
| E1647a–d | O7 | H9 | M12 |
| E1648a–d | O8 | H1 | M12 |
| E1649a–d | O8 | H2 | M12 |
| E1650a–d | O8 | H3 | M12 |
| E1651a–d | O8 | H4 | M12 |
| E1652a–d | O8 | H5 | M12 |
| E1653a–d | O8 | H6 | M12 |
| E1654a–d | O8 | H7 | M12 |
| E1655a–d | O8 | H8 | M12 |
| E1656a–d | O8 | H9 | M12 |
| E1657a–d | O9 | H1 | M12 |
| E1658a–d | O9 | H2 | M12 |
| E1659a–d | O9 | H3 | M12 |
| E1660a–d | O9 | H4 | M12 |
| E1661a–d | O9 | H5 | M12 |
| E1662a–d | O9 | H6 | M12 |
| E1663a–d | O9 | H7 | M12 |
| E1664a–d | O9 | H8 | M12 |
| E1665a–d | O9 | H9 | M12 |
| E1666a–d | O10 | H1 | M12 |
| E1667a–d | O10 | H2 | M12 |
| E1668a–d | O10 | H3 | M12 |
| E1669a–d | O10 | H4 | M12 |
| E1670a–d | O10 | H5 | M12 |
| E1671a–d | O10 | H6 | M12 |
| E1672a–d | O10 | H7 | M12 |
| E1673a–d | O10 | H8 | M12 |
| E1674a–d | O10 | H9 | M12 |
| E1675a–d | O11 | H1 | M12 |
| E1676a–d | O11 | H2 | M12 |
| E1677a–d | O11 | H3 | M12 |
| E1678a–d | O11 | H4 | M12 |
| E1679a–d | O11 | H5 | M12 |

TABLE 1-continued

| Example | O Group | H Group | M Group |
|---|---|---|---|
| E1680a–d | O11 | H6 | M12 |
| E1681a–d | O11 | H7 | M12 |
| E1682a–d | O11 | H8 | M12 |
| E1683a–d | O11 | H9 | M12 |
| E1684a–d | O12 | H1 | M12 |
| E1685a–d | O12 | H2 | M12 |
| E1686a–d | O12 | H3 | M12 |
| E1687a–d | O12 | H4 | M12 |
| E1688a–d | O12 | H5 | M12 |
| E1689a–d | O12 | H6 | M12 |
| E1690a–d | O12 | H7 | M12 |
| E1691a–d | O12 | H8 | M12 |
| E1692a–d | O12 | H9 | M12 |
| E1693a–d | O13 | H1 | M12 |
| E1694a–d | O13 | H2 | M12 |
| E1695a–d | O13 | H3 | M12 |
| E1696a–d | O13 | H4 | M12 |
| E1697a–d | O13 | H5 | M12 |
| E1698a–d | O13 | H6 | M12 |
| E1699a–d | O13 | H7 | M12 |
| E1700a–d | O13 | H8 | M12 |
| E1701a–d | O13 | H9 | M12 |
| E1702a–d | O14 | H1 | M12 |
| E1703a–d | O14 | H2 | M12 |
| E1704a–d | O14 | H3 | M12 |
| E1705a–d | O14 | H4 | M12 |
| E1706a–d | O14 | H5 | M12 |
| E1707a–d | O14 | H6 | M12 |
| E1708a–d | O14 | H7 | M12 |
| E1709a–d | O14 | H8 | M12 |
| E1710a–d | O14 | H9 | M12 |
| E1711a–d | O15 | H1 | M12 |
| E1712a–d | O15 | H2 | M12 |
| E1713a–d | O15 | H3 | M12 |
| E1714a–d | O15 | H4 | M12 |
| E1715a–d | O15 | H5 | M12 |
| E1716a–d | O15 | H6 | M12 |
| E1717a–d | O15 | H7 | M12 |
| E1718a–d | O15 | H8 | M12 |
| E1719a–d | O15 | H9 | M12 |
| E1720a–d | O16 | H1 | M12 |
| E1721a–d | O16 | H2 | M12 |
| E1722a–d | O16 | H3 | M12 |
| E1723a–d | O16 | H4 | M12 |
| E1724a–d | O16 | H5 | M12 |
| E1725a–d | O16 | H6 | M12 |
| E1726a–d | O16 | H7 | M12 |
| E1727a–d | O16 | H8 | M12 |
| E1728a–d | O16 | H9 | M12 |
| E1729a–d | O1 | H1 | M13 |
| E1730a–d | O1 | H2 | M13 |
| E1731a–d | O1 | H3 | M13 |
| E1732a–d | O1 | H4 | M13 |
| E1733a–d | O1 | H5 | M13 |
| E1734a–d | O1 | H6 | M13 |
| E1735a–d | O1 | H7 | M13 |
| E1736a–d | O1 | H8 | M13 |
| E1737a–d | O1 | H9 | M13 |
| E1738a–d | O2 | H1 | M13 |
| E1739a–d | O2 | H2 | M13 |
| E1740a–d | O2 | H3 | M13 |
| E1741a–d | O2 | H4 | M13 |
| E1742a–d | O2 | H5 | M13 |
| E1743a–d | O2 | H6 | M13 |
| E1744a–d | O2 | H7 | M13 |
| E1745a–d | O2 | H8 | M13 |
| E1746a–d | O2 | H9 | M13 |
| E1747a–d | O3 | H1 | M13 |
| E1748a–d | O3 | H2 | M13 |
| E1749a–d | O3 | H3 | M13 |
| E1750a–d | O3 | H4 | M13 |
| E1751a–d | O3 | H5 | M13 |
| E1752a–d | O3 | H6 | M13 |
| E1753a–d | O3 | H7 | M13 |
| E1754a–d | O3 | H8 | M13 |
| E1755a–d | O3 | H9 | M13 |
| E1756a–d | O4 | H1 | M13 |
| E1757a–d | O4 | H2 | M13 |
| E1758a–d | O4 | H3 | M13 |
| E1759a–d | O4 | H4 | M13 |
| E1760a–d | O4 | H5 | M13 |
| E1761a–d | O4 | H6 | M13 |
| E1762a–d | O4 | H7 | M13 |
| E1763a–d | O4 | H8 | M13 |
| E1764a–d | O4 | H9 | M13 |
| E1765a–d | O5 | H1 | M13 |
| E1766a–d | O5 | H2 | M13 |
| E1767a–d | O5 | H3 | M13 |
| E1768a–d | O5 | H4 | M13 |
| E1769a–d | O5 | H5 | M13 |
| E1770a–d | O5 | H6 | M13 |
| E1771a–d | O5 | H7 | M13 |
| E1772a–d | O5 | H8 | M13 |
| E1773a–d | O5 | H9 | M13 |
| E1774a–d | O6 | H1 | M13 |
| E1775a–d | O6 | H2 | M13 |
| E1776a–d | O6 | H3 | M13 |
| E1777a–d | O6 | H4 | M13 |
| E1778a–d | O6 | H5 | M13 |
| E1779a–d | O6 | H6 | M13 |
| E1780a–d | O6 | H7 | M13 |
| E1781a–d | O6 | H8 | M13 |
| E1782a–d | O6 | H9 | M13 |
| E1783a–d | O7 | H1 | M13 |
| E1784a–d | O7 | H2 | M13 |
| E1785a–d | O7 | H3 | M13 |
| E1786a–d | O7 | H4 | M13 |
| E1787a–d | O7 | H5 | M13 |
| E1788a–d | O7 | H6 | M13 |
| E1789a–d | O7 | H7 | M13 |
| E1790a–d | O7 | H8 | M13 |
| E1791a–d | O7 | H9 | M13 |
| E1792a–d | O8 | H1 | M13 |
| E1793a–d | O8 | H2 | M13 |
| E1794a–d | O8 | H3 | M13 |
| E1795a–d | O8 | H4 | M13 |
| E1796a–d | O8 | H5 | M13 |
| E1797a–d | O8 | H6 | M13 |
| E1798a–d | O8 | H7 | M13 |
| E1799a–d | O8 | H8 | M13 |
| E1800a–d | O8 | H9 | M13 |
| E1801a–d | O9 | H1 | M13 |
| E1802a–d | O9 | H2 | M13 |
| E1803a–d | O9 | H3 | M13 |
| E1804a–d | O9 | H4 | M13 |
| E1805a–d | O9 | H5 | M13 |
| E1806a–d | O9 | H6 | M13 |
| E1807a–d | O9 | H7 | M13 |
| E1808a–d | O9 | H8 | M13 |
| E1809a–d | O9 | H9 | M13 |
| E1810a–d | O10 | H1 | M13 |
| E1811a–d | O10 | H2 | M13 |
| E1812a–d | O10 | H3 | M13 |
| E1813a–d | O10 | H4 | M13 |
| E1814a–d | O10 | H5 | M13 |
| E1815a–d | O10 | H6 | M13 |
| E1816a–d | O10 | H7 | M13 |
| E1817a–d | O10 | H8 | M13 |
| E1818a–d | O10 | H9 | M13 |
| E1819a–d | O11 | H1 | M13 |
| E1820a–d | O11 | H2 | M13 |
| E1821a–d | O11 | H3 | M13 |
| E1822a–d | O11 | H4 | M13 |
| E1823a–d | O11 | H5 | M13 |
| E1824a–d | O11 | H6 | M13 |
| E1825a–d | O11 | H7 | M13 |
| E1826a–d | O11 | H8 | M13 |
| E1827a–d | O11 | H9 | M13 |
| E1828a–d | O12 | H1 | M13 |
| E1829a–d | O12 | H2 | M13 |
| E1830a–d | O12 | H3 | M13 |
| E1831a–d | O12 | H4 | M13 |
| E1832a–d | O12 | H5 | M13 |
| E1833a–d | O12 | H6 | M13 |

TABLE 1-continued

| Example | O Group | H Group | M Group |
|---|---|---|---|
| E1834a–d | O12 | H7 | M13 |
| E1835a–d | O12 | H8 | M13 |
| E1836a–d | O12 | H9 | M13 |
| E1837a–d | O13 | H1 | M13 |
| E1838a–d | O13 | H2 | M13 |
| E1839a–d | O13 | H3 | M13 |
| E1840a–d | O13 | H4 | M13 |
| E1841a–d | O13 | H5 | M13 |
| E1842a–d | O13 | H6 | M13 |
| E1843a–d | O13 | H7 | M13 |
| E1844a–d | O13 | H8 | M13 |
| E1845a–d | O13 | H9 | M13 |
| E1846a–d | O14 | H1 | M13 |
| E1847a–d | O14 | H2 | M13 |
| E1848a–d | O14 | H3 | M13 |
| E1849a–d | O14 | H4 | M13 |
| E1850a–d | O14 | H5 | M13 |
| E1851a–d | O14 | H6 | M13 |
| E1852a–d | O14 | H7 | M13 M13 |
| E1853a–d | O14 | H8 | M13 |
| E1854a–d | O14 | H9 | M13 |
| E1855a–d | O15 | H1 | M13 |
| E1856a–d | O15 | H2 | M13 |
| E1857a–d | O15 | H3 | M13 |
| E1858a–d | O15 | H4 | M13 |
| E1859a–d | O15 | H5 | M13 |
| E1860a–d | O15 | H6 | M13 |
| E1861a–d | O15 | H7 | M13 |
| E1862a–d | O15 | H8 | M13 |
| E1863a–d | O15 | H9 | M13 |
| E1864a–d | O16 | H1 | M13 |
| E1865a–d | O16 | H2 | M13 |
| E1866a–d | O16 | H3 | M13 |
| E1867a–d | O16 | H4 | M13 |
| E1868a–d | O16 | H5 | M13 |
| E1869a–d | O16 | H6 | M13 |
| E1870a–d | O16 | H7 | M13 |
| E1871a–d | O16 | H8 | M13 |
| E1872a–d | O16 | H9 | M13 |
| E1873a–d | O1 | H1 | M14 |
| E1874a–d | O1 | H2 | M14 |
| E1875a–d | O1 | H3 | M14 |
| E1876a–d | O1 | H4 | M14 |
| E1877a–d | O1 | H5 | M14 |
| E1878a–d | O1 | H6 | M14 |
| E1879a–d | O1 | H7 | M14 |
| E1880a–d | O1 | H8 | M14 |
| E1881a–d | O1 | H9 | M14 |
| E1882a–d | O2 | H1 | M14 |
| E1883a–d | O2 | H2 | M14 |
| E1884a–d | O2 | H3 | M14 |
| E1885a–d | O2 | H4 | M14 |
| E1886a–d | O2 | H5 | M14 |
| E1887a–d | O2 | H6 | M14 |
| E1888a–d | O2 | H7 | M14 |
| E1889a–d | O2 | H8 | M14 |
| E1890a–d | O2 | H9 | M14 |
| E1891a–d | O3 | H1 | M14 |
| E1892a–d | O3 | H2 | M14 |
| E1893a–d | O3 | H3 | M14 |
| E1894a–d | O3 | H4 | M14 |
| E1895a–d | O3 | H5 | M14 |
| E1896a–d | O3 | H6 | M14 |
| E1897a–d | O3 | H7 | M14 |
| E1898a–d | O3 | H8 | M14 |
| E1899a–d | O3 | H9 | M14 |
| E1900a–d | O4 | H1 | M14 |
| E1901a–d | O4 | H2 | M14 |
| E1902a–d | O4 | H3 | M14 |
| E1903a–d | O4 | H4 | M14 |
| E1904a–d | O4 | H5 | M14 |
| E1905a–d | O4 | H6 | M14 |
| E1906a–d | O4 | H7 | M14 |
| E1907a–d | O4 | H8 | M14 |
| E1908a–d | O4 | H9 | M14 |
| E1909a–d | O5 | H1 | M14 |
| E1910a–d | O5 | H2 | M14 |
| E1911a–d | O5 | H3 | M14 |
| E1912a–d | O5 | H4 | M14 |
| E1913a–d | O5 | H5 | M14 |
| E1914a–d | O5 | H6 | M14 |
| E1915a–d | O5 | H7 | M14 |
| E1916a–d | O5 | H8 | M14 |
| E1917a–d | O5 | H9 | M14 |
| E1918a–d | O6 | H1 | M14 |
| E1919a–d | O6 | H2 | M14 |
| E1920a–d | O6 | H3 | M14 |
| E1921a–d | O6 | H4 | M14 |
| E1922a–d | O6 | H5 | M14 |
| E1923a–d | O6 | H6 | M14 |
| E1924a–d | O6 | H7 | M14 |
| E1925a–d | O6 | H8 | M14 |
| E1926a–d | O6 | H9 | M14 |
| E1927a–d | O7 | H1 | M14 |
| E1928a–d | O7 | H2 | M14 |
| E1929a–d | O7 | H3 | M14 |
| E1930a–d | O7 | H4 | M14 |
| E1931a–d | O7 | H5 | M14 |
| E1932a–d | O7 | H6 | M14 |
| E1933a–d | O7 | H7 | M14 |
| E1934a–d | O7 | H8 | M14 |
| E1935a–d | O7 | H9 | M14 |
| E1936a–d | O8 | H1 | M14 |
| E1937a–d | O8 | H2 | M14 |
| E1938a–d | O8 | H3 | M14 |
| E1939a–d | O8 | H4 | M14 |
| E1940a–d | O8 | H5 | M14 |
| E1941a–d | O8 | H6 | M14 |
| E1942a–d | O8 | H7 | M14 |
| E1943a–d | O8 | H8 | M14 |
| E1944a–d | O8 | H9 | M14 |
| E1945a–d | O9 | H1 | M14 |
| E1946a–d | O9 | H2 | M14 |
| E1947a–d | O9 | H3 | M14 |
| E1948a–d | O9 | H4 | M14 |
| E1949a–d | O9 | H5 | M14 |
| E1950a–d | O9 | H6 | M14 |
| E1951a–d | O9 | H7 | M14 |
| E1952a–d | O9 | H8 | M14 |
| E1953a–d | O9 | H9 | M14 |
| E1954a–d | O10 | H1 | M14 |
| E1955a–d | O10 | H2 | M14 |
| E1956a–d | O10 | H3 | M14 |
| E1957a–d | O10 | H4 | M14 |
| E1958a–d | O10 | H5 | M14 |
| E1959a–d | O10 | H6 | M14 |
| E1960a–d | O10 | H7 | M14 |
| E1961a–d | O10 | H8 | M14 |
| E1962a–d | O10 | H9 | M14 |
| E1963a–d | O11 | H1 | M14 |
| E1964a–d | O11 | H2 | M14 |
| E1965a–d | O11 | H3 | M14 |
| E1966a–d | O11 | H4 | M14 |
| E1967a–d | O11 | H5 | M14 |
| E1968a–d | O11 | H6 | M14 |
| E1969a–d | O11 | H7 | M14 |
| E1970a–d | O11 | H8 | M14 |
| E1971a–d | O11 | H9 | M14 |
| E1972a–d | O12 | H1 | M14 |
| E1973a–d | O12 | H2 | M14 |
| E1974a–d | O12 | H3 | M14 |
| E1975a–d | O12 | H4 | M14 |
| E1976a–d | O12 | H5 | M14 |
| E1977a–d | O12 | H6 | M14 |
| E1978a–d | O12 | H7 | M14 |
| E1979a–d | O12 | H8 | M14 |
| E1980a–d | O12 | H9 | M14 |
| E1981a–d | O13 | H1 | M14 |
| E1982a–d | O13 | H2 | M14 |
| E1983a–d | O13 | H3 | M14 |
| E1984a–d | O13 | H4 | M14 |
| E1985a–d | O13 | H5 | M14 |
| E1986a–d | O13 | H6 | M14 |
| E1987a–d | O13 | H7 | M14 |

TABLE 1-continued

| Example | O Group | H Group | M Group |
|---|---|---|---|
| E1988a–d | O13 | H8 | M14 |
| E1989a–d | O13 | H9 | M14 |
| E1990a–d | O14 | H1 | M14 |
| E1991a–d | O14 | H2 | M14 |
| E1992a–d | O14 | H3 | M14 |
| E1993a–d | O14 | H4 | M14 |
| E1994a–d | O14 | H5 | M14 |
| E1995a–d | O14 | H6 | M14 |
| E1996a–d | O14 | H7 | M14 |
| E1997a–d | O14 | H8 | M14 |
| E1998a–d | O14 | H9 | M14 |
| E1999a–d | O15 | H1 | M14 |
| E2000a–d | O15 | H2 | M14 |
| E2001a–d | O15 | H3 | M14 |
| E2002a–d | O15 | H4 | M14 |
| E2003a–d | O15 | H5 | M14 |
| E2004a–d | O15 | H6 | M14 |
| E2005a–d | O15 | H7 | M14 |
| E2006a–d | O15 | H8 | M14 |
| E2007a–d | O15 | H9 | M14 |
| E2008a–d | O16 | H1 | M14 |
| E2009a–d | O16 | H2 | M14 |
| E2010a–d | O16 | H3 | M14 |
| E2011a–d | O16 | H4 | M14 |
| E2012a–d | O16 | H5 | M14 |
| E2013a–d | O16 | H6 | M14 |
| E2014a–d | O16 | H7 | M14 |
| E2015a–d | O16 | H8 | M14 |
| E2016a–d | O16 | H9 | M14 |
| E2017a–d | O1 | H1 | M15 |
| E2018a–d | O1 | H2 | M15 |
| E2019a–d | O1 | H3 | M15 |
| E2020a–d | O1 | H4 | M15 |
| E2021a–d | O1 | H5 | M15 |
| E2022a–d | O1 | H6 | M15 |
| E2023a–d | O1 | H7 | M15 |
| E2024a–d | O1 | H8 | M15 |
| E2025a–d | O1 | H9 | M15 |
| E2026a–d | O2 | H1 | M15 |
| E2027a–d | O2 | H2 | M15 |
| E2028a–d | O2 | H3 | M15 |
| E2029a–d | O2 | H4 | M15 |
| E2030a–d | O2 | H5 | M15 |
| E2031a–d | O2 | H6 | M15 |
| E2032a–d | O2 | H7 | M15 |
| E2033a–d | O2 | H8 | M15 |
| E2034a–d | O2 | H9 | M15 |
| E2035a–d | O3 | H1 | M15 |
| E2036a–d | O3 | H2 | M15 |
| E2037a–d | O3 | H3 | M15 |
| E2038a–d | O3 | H4 | M15 |
| E2039a–d | O3 | H5 | M15 |
| E2040a–d | O3 | H6 | M15 |
| E2041a–d | O3 | H7 | M15 |
| E2042a–d | O3 | H8 | M15 |
| E2043a–d | O3 | H9 | M15 |
| E2044a–d | O4 | H1 | M15 |
| E2045a–d | O4 | H2 | M15 |
| E2046a–d | O4 | H3 | M15 |
| E2047a–d | O4 | H4 | M15 |
| E2048a–d | O4 | H5 | M15 |
| E2049a–d | O4 | H6 | M15 |
| E2050a–d | O4 | H7 | M15 |
| E2051a–d | O4 | H8 | M15 |
| E2052a–d | O4 | H9 | M15 |
| E2053a–d | O5 | H1 | M15 |
| E2054a–d | O5 | H2 | M15 |
| E2055a–d | O5 | H3 | M15 |
| E2056a–d | O5 | H4 | M15 |
| E2057a–d | O5 | H5 | M15 |
| E2058a–d | O5 | H6 | M15 |
| E2059a–d | O5 | H7 | M15 |
| E2060a–d | O5 | H8 | M15 |
| E2061a–d | O5 | H9 | M15 |
| E2062a–d | O6 | H1 | M15 |
| E2063a–d | O6 | H2 | M15 |
| E2064a–d | O6 | H3 | M15 |
| E2065a–d | O6 | H4 | M15 |
| E2066a–d | O6 | H5 | M15 |
| E2067a–d | O6 | H6 | M15 |
| E2068a–d | O6 | H7 | M15 |
| E2069a–d | O6 | H8 | M15 |
| E2070a–d | O6 | H9 | M15 |
| E2071a–d | O7 | H1 | M15 |
| E2072a–d | O7 | H2 | M15 |
| E2073a–d | O7 | H3 | M15 |
| E2074a–d | O7 | H4 | M15 |
| E2075a–d | O7 | H5 | M15 |
| E2076a–d | O7 | H6 | M15 |
| E2077a–d | O7 | H7 | M15 |
| E2078a–d | O7 | H8 | M15 |
| E2079a–d | O7 | H9 | M15 |
| E2080a–d | O8 | H1 | M15 |
| E2081a–d | O8 | H2 | M15 |
| E2082a–d | O8 | H3 | M15 |
| E2083a–d | O8 | H4 | M15 |
| E2084a–d | O8 | H5 | M15 |
| E2085a–d | O8 | H6 | M15 |
| E2086a–d | O8 | H7 | M15 |
| E2087a–d | O8 | H8 | M15 |
| E2088a–d | O8 | H9 | M15 |
| E2089a–d | O9 | H1 | M15 |
| E2090a–d | O9 | H2 | M15 |
| E2091a–d | O9 | H3 | M15 |
| E2092a–d | O9 | H4 | M15 |
| E2093a–d | O9 | H5 | M15 |
| E2094a–d | O9 | H6 | M15 |
| E2095a–d | O9 | H7 | M15 |
| E2096a–d | O9 | H8 | M15 |
| E2097a–d | O9 | H9 | M15 |
| E2098a–d | O10 | H1 | M15 |
| E2099a–d | O10 | H2 | M15 |
| E2100a–d | O10 | H3 | M15 |
| E2101a–d | O10 | H4 | M15 |
| E2102a–d | O10 | H5 | M15 |
| E2103a–d | O10 | H6 | M15 |
| E2104a–d | O10 | H7 | M15 |
| E2105a–d | O10 | H8 | M15 |
| E2106a–d | O10 | H9 | M15 |
| E2107a–d | O11 | H1 | M15 |
| E2108a–d | O11 | H2 | M15 |
| E2109a–d | O11 | H3 | M15 |
| E2110a–d | O11 | H4 | M15 |
| E2111a–d | O11 | H5 | M15 |
| E2112a–d | O11 | H6 | M15 |
| E2113a–d | O11 | H7 | M15 |
| E2114a–d | O11 | H8 | M15 |
| E2115a–d | O11 | H9 | M15 |
| E2116a–d | O12 | H1 | M15 |
| E2117a–d | O12 | H2 | M15 |
| E2118a–d | O12 | H3 | M15 |
| E2119a–d | O12 | H4 | M15 |
| E2120a–d | O12 | H5 | M15 |
| E2121a–d | O12 | H6 | M15 |
| E2122a–d | O12 | H7 | M15 |
| E2123a–d | O12 | H8 | M15 |
| E2124a–d | O12 | H9 | M15 |
| E2125a–d | O13 | H1 | M15 |
| E2126a–d | O13 | H2 | M15 |
| E2127a–d | O13 | H3 | M15 |
| E2128a–d | O13 | H4 | M15 |
| E2129a–d | O13 | H5 | M15 |
| E2130a–d | O13 | H6 | M15 |
| E2131a–d | O13 | H7 | M15 |
| E2132a–d | O13 | H8 | M15 |
| E2133a–d | O13 | H9 | M15 |
| E2134a–d | O14 | H1 | M15 |
| E2135a–d | O14 | H2 | M15 |
| E2136a–d | O14 | H3 | M15 |
| E2137a–d | O14 | H4 | M15 |
| E2138a–d | O14 | H5 | M15 |
| E2139a–d | O14 | H6 | M15 |
| E2140a–d | O14 | H7 | M15 |
| E2141a–d | O14 | H8 | M15 |

TABLE 1-continued

| Example | O Group | H Group | M Group |
|---|---|---|---|
| E2142a–d | O14 | H9 | M15 |
| E2143a–d | O15 | H1 | M15 |
| E2144a–d | O15 | H2 | M15 |
| E2145a–d | O15 | H3 | M15 |
| E2146a–d | O15 | H4 | M15 |
| E2147a–d | O15 | H5 | M15 |
| E2148a–d | O15 | H6 | M15 |
| E2149a–d | O15 | H7 | M15 |
| E2150a–d | O15 | H8 | M15 |
| E2151a–d | O15 | H9 | M15 |
| E2152a–d | O16 | H1 | M15 |
| E2153a–d | O16 | H2 | M15 |
| E2154a–d | O16 | H3 | M15 |
| E2155a–d | O16 | H4 | M15 |
| E2156a–d | O16 | H5 | M15 |
| E2157a–d | O16 | H6 | M15 |
| E2158a–d | O16 | H7 | M15 |
| E2159a–d | O16 | H8 | M15 |
| E2160a–d | O16 | H9 | M15 |
| E2161a–d | O1 | H1 | M16 |
| E2162a–d | O1 | H2 | M16 |
| E2163a–d | O1 | H3 | M16 |
| E2164a–d | O1 | H4 | M16 |
| E2165a–d | O1 | H5 | M16 |
| E2166a–d | O1 | H6 | M16 |
| E2167a–d | O1 | H7 | M16 |
| E2168a–d | O1 | H8 | M16 |
| E2169a–d | O1 | H9 | M16 |
| E2170a–d | O2 | H1 | M16 |
| E2171a–d | O2 | H2 | M16 |
| E2172a–d | O2 | H3 | M16 |
| E2173a–d | O2 | H4 | M16 |
| E2174a–d | O2 | H5 | M16 |
| E2175a–d | O2 | H6 | M16 |
| E2176a–d | O2 | H7 | M16 |
| E2177a–d | O2 | H8 | M16 |
| E2178a–d | O2 | H9 | M16 |
| E2179a–d | O3 | H1 | M16 |
| E2180a–d | O3 | H2 | M16 |
| E2181a–d | O3 | H3 | M16 |
| E2182a–d | O3 | H4 | M16 |
| E2183a–d | O3 | H5 | M16 |
| E2184a–d | O3 | H6 | M16 |
| E2185a–d | O3 | H7 | M16 |
| E2186a–d | O3 | H8 | M16 |
| E2187a–d | O3 | H9 | M16 |
| E2188a–d | O4 | H1 | M16 |
| E2189a–d | O4 | H2 | M16 |
| E2190a–d | O4 | H3 | M16 |
| E2191a–d | O4 | H4 | M16 |
| E2192a–d | O4 | H5 | M16 |
| E2193a–d | O4 | H6 | M16 |
| E2194a–d | O4 | H7 | M16 |
| E2195a–d | O4 | H8 | M16 |
| E2196a–d | O4 | H9 | M16 |
| E2197a–d | O5 | H1 | M16 |
| E2198a–d | O5 | H2 | M16 |
| E2199a–d | O5 | H3 | M16 |
| E2200a–d | O5 | H4 | M16 |
| E2201a–d | O5 | H5 | M16 |
| E2202a–d | O5 | H6 | M16 |
| E2203a–d | O5 | H7 | M16 |
| E2204a–d | O5 | H8 | M16 |
| E2205a–d | O5 | H9 | M16 |
| E2206a–d | O6 | H1 | M16 |
| E2207a–d | O6 | H2 | M16 |
| E2208a–d | O6 | H3 | M16 |
| E2209a–d | O6 | H4 | M16 |
| E2210a–d | O6 | H5 | M16 |
| E2211a–d | O6 | H6 | M16 |
| E2212a–d | O6 | H7 | M16 |
| E2213a–d | O6 | H8 | M16 |
| E2214a–d | O6 | H9 | M16 |
| E2215a–d | O7 | H1 | M16 |
| E2216a–d | O7 | H2 | M16 |
| E2217a–d | O7 | H3 | M16 |
| E2218a–d | O7 | H4 | M16 |
| E2219a–d | O7 | H5 | M16 |
| E2220a–d | O7 | H6 | M16 |
| E2221a–d | O7 | H7 | M16 |
| E2222a–d | O7 | H8 | M16 |
| E2223a–d | O7 | H9 | M16 |
| E2224a–d | O8 | H1 | M16 |
| E2225a–d | O8 | H2 | M16 |
| E2226a–d | O8 | H3 | M16 |
| E2227a–d | O8 | H4 | M16 |
| E2228a–d | O8 | H5 | M16 |
| E2229a–d | O8 | H6 | M16 |
| E2230a–d | O8 | H7 | M16 |
| E2231a–d | O8 | H8 | M16 |
| E2232a–d | O8 | H9 | M16 |
| E2233a–d | O9 | H1 | M16 |
| E2234a–d | O9 | H2 | M16 |
| E2235a–d | O9 | H3 | M16 |
| E2236a–d | O9 | H4 | M16 |
| E2237a–d | O9 | H5 | M16 |
| E2238a–d | O9 | H6 | M16 |
| E2239a–d | O9 | H7 | M16 |
| E2240a–d | O9 | H8 | M16 |
| E2241a–d | O9 | H9 | M16 |
| E2242a–d | O10 | H1 | M16 |
| E2243a–d | O10 | H2 | M16 |
| E2244a–d | O10 | H3 | M16 |
| E2245a–d | O10 | H4 | M16 |
| E2246a–d | O10 | H5 | M16 |
| E2247a–d | O10 | H6 | M16 |
| E2248a–d | O10 | H7 | M16 |
| E2249a–d | O10 | H8 | M16 |
| E2250a–d | O10 | H9 | M16 |
| E2251a–d | O11 | H1 | M16 |
| E2252a–d | O11 | H2 | M16 |
| E2253a–d | O11 | H3 | M16 |
| E2254a–d | O11 | H4 | M16 |
| E2255a–d | O11 | H5 | M16 |
| E2256a–d | O11 | H6 | M16 |
| E2257a–d | O11 | H7 | M16 |
| E2258a–d | O11 | H8 | M16 |
| E2259a–d | O11 | H9 | M16 |
| E2260a–d | O12 | H1 | M16 |
| E2261a–d | O12 | H2 | M16 |
| E2262a–d | O12 | H3 | M16 |
| E2263a–d | O12 | H4 | M16 |
| E2264a–d | O12 | H5 | M16 |
| E2265a–d | O12 | H6 | M16 |
| E2266a–d | O12 | H7 | M16 |
| E2267a–d | O12 | H8 | M16 |
| E2268a–d | O12 | H9 | M16 |
| E2269a–d | O13 | H1 | M16 |
| E2270a–d | O13 | H2 | M16 |
| E2271a–d | O13 | H3 | M16 |
| E2272a–d | O13 | H4 | M16 |
| E2273a–d | O13 | H5 | M16 |
| E2274a–d | O13 | H6 | M16 |
| E2275a–d | O13 | H7 | M16 |
| E2276a–d | O13 | H8 | M16 |
| E2277a–d | O13 | H9 | M16 |
| E2278a–d | O14 | H1 | M16 |
| E2279a–d | O14 | H2 | M16 |
| E2280a–d | O14 | H3 | M16 |
| E2281a–d | O14 | H4 | M16 |
| E2282a–d | O14 | H5 | M16 |
| E2283a–d | O14 | H6 | M16 |
| E2284a–d | O14 | H7 | M16 |
| E2285a–d | O14 | H8 | M16 |
| E2286a–d | O14 | H9 | M16 |
| E2287a–d | O15 | H1 | M16 |
| E2288a–d | O15 | H2 | M16 |
| E2289a–d | O15 | H3 | M16 |
| E2290a–d | O15 | H4 | M16 |
| E2291a–d | O15 | H5 | M16 |
| E2292a–d | O15 | H6 | M16 |
| E2293a–d | O15 | H7 | M16 |
| E2294a–d | O15 | H8 | M16 |
| E2295a–d | O15 | H9 | M16 |

TABLE 1-continued

| Example | O Group | H Group | M Group |
|---|---|---|---|
| E2296a–d | O16 | H1 | M16 |
| E2297a–d | O16 | H2 | M16 |
| E2298a–d | O16 | H3 | M16 |
| E2299a–d | O16 | H4 | M16 |
| E2300a–d | O16 | H5 | M16 |
| E2301a–d | O16 | H6 | M16 |
| E2302a–d | O16 | H7 | M16 |
| E2303a–d | O16 | H8 | M16 |
| E2304a–d | O16 | H9 | M16 |
| E2305a–d | O1 | H1 | M17 |
| E2306a–d | O1 | H2 | M17 |
| E2307a–d | O1 | H3 | M17 |
| E2308a–d | O1 | H4 | M17 |
| E2309a–d | O1 | H5 | M17 |
| E2310a–d | O1 | H6 | M17 |
| E2311a–d | O1 | H7 | M17 |
| E2312a–d | O1 | H8 | M17 |
| E2313a–d | O1 | H9 | M17 |
| E2314a–d | O2 | H1 | M17 |
| E2315a–d | O2 | H2 | M17 |
| E2316a–d | O2 | H3 | M17 |
| E2317a–d | O2 | H4 | M17 |
| E2318a–d | O2 | H5 | M17 |
| E2319a–d | O2 | H6 | M17 |
| E2320a–d | O2 | H7 | M17 |
| E2321a–d | O2 | H8 | M17 |
| E2322a–d | O2 | H9 | M17 |
| E2323a–d | O3 | H1 | M17 |
| E2324a–d | O3 | H2 | M17 |
| E2325a–d | O3 | H3 | M17 |
| E2326a–d | O3 | H4 | M17 |
| E2327a–d | O3 | H5 | M17 |
| E2328a–d | O3 | H6 | M17 |
| E2329a–d | O3 | H7 | M17 |
| E2330a–d | O3 | H8 | M17 |
| E2331a–d | O3 | H9 | M17 |
| E2332a–d | O4 | H1 | M17 |
| E2333a–d | O4 | H2 | M17 |
| E2334a–d | O4 | H3 | M17 |
| E2335a–d | O4 | H4 | M17 |
| E2336a–d | O4 | H5 | M17 |
| E2337a–d | O4 | H6 | M17 |
| E2338a–d | O4 | H7 | M17 |
| E2339a–d | O4 | H8 | M17 |
| E2340a–d | O4 | H9 | M17 |
| E2341a–d | O5 | H1 | M17 |
| E2342a–d | O5 | H2 | M17 |
| E2343a–d | O5 | H3 | M17 |
| E2344a–d | O5 | H4 | M17 |
| E2345a–d | O5 | H5 | M17 |
| E2346a–d | O5 | H6 | M17 |
| E2347a–d | O5 | H7 | M17 |
| E2348a–d | O5 | H8 | M17 |
| E2349a–d | O5 | H9 | M17 |
| E2350a–d | O6 | H1 | M17 |
| E2351a–d | O6 | H2 | M17 |
| E2352a–d | O6 | H3 | M17 |
| E2353a–d | O6 | H4 | M17 |
| E2354a–d | O6 | H5 | M17 |
| E2355a–d | O6 | H6 | M17 |
| E2356a–d | O6 | H7 | M17 |
| E2357a–d | O6 | H8 | M17 |
| E2358a–d | O6 | H9 | M17 |
| E2359a–d | O7 | H1 | M17 |
| E2360a–d | O7 | H2 | M17 |
| E2361a–d | O7 | H3 | M17 |
| E2362a–d | O7 | H4 | M17 |
| E2363a–d | O7 | H5 | M17 |
| E2364a–d | O7 | H6 | M17 |
| E2365a–d | O7 | H7 | M17 |
| E2366a–d | O7 | H8 | M17 |
| E2367a–d | O7 | H9 | M17 |
| E2368a–d | O8 | H1 | M17 |
| E2369a–d | O8 | H2 | M17 |
| E2370a–d | O8 | H3 | M17 |
| E2371a–d | O8 | H4 | M17 |
| E2372a–d | O8 | H5 | M17 |
| E2373a–d | O8 | H6 | M17 |
| E2374a–d | O8 | H7 | M17 |
| E2375a–d | O8 | H8 | M17 |
| E2376a–d | O8 | H9 | M17 |
| E2377a–d | O9 | H1 | M17 |
| E2378a–d | O9 | H2 | M17 |
| E2379a–d | O9 | H3 | M17 |
| E2380a–d | O9 | H4 | M17 |
| E2381a–d | O9 | H5 | M17 |
| E2382a–d | O9 | H6 | M17 |
| E2383a–d | O9 | H7 | M17 |
| E2384a–d | O9 | H8 | M17 |
| E2385a–d | O9 | H9 | M17 |
| E2386a–d | O10 | H1 | M17 |
| E2387a–d | O10 | H2 | M17 |
| E2388a–d | O10 | H3 | M17 |
| E2389a–d | O10 | H4 | M17 |
| E2390a–d | O10 | H5 | M17 |
| E2391a–d | O10 | H6 | M17 |
| E2392a–d | O10 | H7 | M17 |
| E2393a–d | O10 | H8 | M17 |
| E2394a–d | O10 | H9 | M17 |
| E2395a–d | O11 | H1 | M17 |
| E2396a–d | O11 | H2 | M17 |
| E2397a–d | O11 | H3 | M17 |
| E2398a–d | O11 | H4 | M17 |
| E2399a–d | O11 | H5 | M17 |
| E2400a–d | O11 | H6 | M17 |
| E2401a–d | O11 | H7 | M17 |
| E2402a–d | O11 | H8 | M17 |
| E2403a–d | O11 | H9 | M17 |
| E2404a–d | O12 | H1 | M17 |
| E2405a–d | O12 | H2 | M17 |
| E2406a–d | O12 | H3 | M17 |
| E2407a–d | O12 | H4 | M17 |
| E2408a–d | O12 | H5 | M17 |
| E2409a–d | O12 | H6 | M17 |
| E2410a–d | O12 | H7 | M17 |
| E2411a–d | O12 | H8 | M17 |
| E2412a–d | O12 | H9 | M17 |
| E2413a–d | O13 | H1 | M17 |
| E2414a–d | O13 | H2 | M17 |
| E2415a–d | O13 | H3 | M17 |
| E2416a–d | O13 | H4 | M17 |
| E2417a–d | O13 | H5 | M17 |
| E2418a–d | O13 | H6 | M17 |
| E2419a–d | O13 | H7 | M17 |
| E2420a–d | O13 | H8 | M17 |
| E2421a–d | O13 | H9 | M17 |
| E2422a–d | O14 | H1 | M17 |
| E2423a–d | O14 | H2 | M17 |
| E2424a–d | O14 | H3 | M17 |
| E2425a–d | O14 | H4 | M17 |
| E2426a–d | O14 | H5 | M17 |
| E2427a–d | O14 | H6 | M17 |
| E2428a–d | O14 | H7 | M17 |
| E2429a–d | O14 | H8 | M17 |
| E2430a–d | O14 | H9 | M17 |
| E2431a–d | O15 | H1 | M17 |
| E2432a–d | O15 | H2 | M17 |
| E2433a–d | O15 | H3 | M17 |
| E2434a–d | O15 | H4 | M17 |
| E2435a–d | O15 | H5 | M17 |
| E2436a–d | O15 | H6 | M17 |
| E2437a–d | O15 | H7 | M17 |
| E2438a–d | O15 | H8 | M17 |
| E2439a–d | O15 | H9 | M17 |
| E2440a–d | O16 | H1 | M17 |
| E2441a–d | O16 | H2 | M17 |
| E2442a–d | O16 | H3 | M17 |
| E2443a–d | O16 | H4 | M17 |
| E2444a–d | O16 | H5 | M17 |
| E2445a–d | O16 | H6 | M17 |
| E2446a–d | O16 | H7 | M17 |
| E2447a–d | O16 | H8 | M17 |
| E2448a–d | O16 | H9 | M17 |
| E2449a–d | O1 | H1 | M18 |

TABLE 1-continued

| Example | O Group | H Group | M Group |
|---|---|---|---|
| E2450a–d | O1 | H2 | M18 |
| E2451a–d | O1 | H3 | M18 |
| E2452a–d | O1 | H4 | M18 |
| E2453a–d | O1 | H5 | M18 |
| E2454a–d | O1 | H6 | M18 |
| E2455a–d | O1 | H7 | M18 |
| E2456a–d | O1 | H8 | M18 |
| E2457a–d | O1 | H9 | M18 |
| E2458a–d | O2 | H1 | M18 |
| E2459a–d | O2 | H2 | M18 |
| E2460a–d | O2 | H3 | M18 |
| E2461a–d | O2 | H4 | M18 |
| E2462a–d | O2 | H5 | M18 |
| E2463a–d | O2 | H6 | M18 |
| E2464a–d | O2 | H7 | M18 |
| E2465a–d | O2 | H8 | M18 |
| E2466a–d | O2 | H9 | M18 |
| E2467a–d | O3 | H1 | M18 |
| E2468a–d | O3 | H2 | M18 |
| E2469a–d | O3 | H3 | M18 |
| E2470a–d | O3 | H4 | M18 |
| E2471a–d | O3 | H5 | M18 |
| E2472a–d | O3 | H6 | M18 |
| E2473a–d | O3 | H7 | M18 |
| E2474a–d | O3 | H8 | M18 |
| E2475a–d | O3 | H9 | M18 |
| E2476a–d | O4 | H1 | M18 |
| E2477a–d | O4 | H2 | M18 |
| E2478a–d | O4 | H3 | M18 |
| E2479a–d | O4 | H4 | M18 |
| E2480a–d | O4 | H5 | M18 |
| E2481a–d | O4 | H6 | M18 |
| E2482a–d | O4 | H7 | M18 |
| E2483a–d | O4 | H8 | M18 |
| E2484a–d | O4 | H9 | M18 |
| E2485a–d | O5 | H1 | M18 |
| E2486a–d | O5 | H2 | M18 |
| E2487a–d | O5 | H3 | M18 |
| E2488a–d | O5 | H4 | M18 |
| E2489a–d | O5 | H5 | M18 |
| E2490a–d | O5 | H6 | M18 |
| E2491a–d | O5 | H7 | M18 |
| E2492a–d | O5 | H8 | M18 |
| E2493a–d | O5 | H9 | M18 |
| E2494a–d | O6 | H1 | M18 |
| E2495a–d | O6 | H2 | M18 |
| E2496a–d | O6 | H3 | M18 |
| E2497a–d | O6 | H4 | M18 |
| E2498a–d | O6 | H5 | M18 |
| E2499a–d | O6 | H6 | M18 |
| E2500a–d | O6 | H7 | M18 |
| E2501a–d | O6 | H8 | M18 |
| E2502a–d | O6 | H9 | M18 |
| E2503a–d | O7 | H1 | M18 |
| E2504a–d | O7 | H2 | M18 |
| E2505a–d | O7 | H3 | M18 |
| E2506a–d | O7 | H4 | M18 |
| E2507a–d | O7 | H5 | M18 |
| E2508a–d | O7 | H6 | M18 |
| E2509a–d | O7 | H7 | M18 |
| E2510a–d | O7 | H8 | M18 |
| E2511a–d | O7 | H9 | M18 |
| E2512a–d | O8 | H1 | M18 |
| E2513a–d | O8 | H2 | M18 |
| E2514a–d | O8 | H3 | M18 |
| E2515a–d | O8 | H4 | M18 |
| E2516a–d | O8 | H5 | M18 |
| E2517a–d | O8 | H6 | M18 |
| E2518a–d | O8 | H7 | M18 |
| E2519a–d | O8 | H8 | M18 |
| E2520a–d | O8 | H9 | M18 |
| E2521a–d | O9 | H1 | M18 |
| E2522a–d | O9 | H2 | M18 |
| E2523a–d | O9 | H3 | M18 |
| E2524a–d | O9 | H4 | M18 |
| E2525a–d | O9 | H5 | M18 |
| E2526a–d | O9 | H6 | M18 |
| E2527a–d | O9 | H7 | M18 |
| E2528a–d | O9 | H8 | M18 |
| E2529a–d | O9 | H9 | M18 |
| E2530a–d | O10 | H1 | M18 |
| E2531a–d | O10 | H2 | M18 |
| E2532a–d | O10 | H3 | M18 |
| E2533a–d | O10 | H4 | M18 |
| E2534a–d | O10 | H5 | M18 |
| E2535a–d | O10 | H6 | M18 |
| E2536a–d | O10 | H7 | M18 |
| E2537a–d | O10 | H8 | M18 |
| E2538a–d | O10 | H9 | M18 |
| E2539a–d | O11 | H1 | M18 |
| E2540a–d | O11 | H2 | M18 |
| E2541a–d | O11 | H3 | M18 |
| E2542a–d | O11 | H4 | M18 |
| E2543a–d | O11 | H5 | M18 |
| E2544a–d | O11 | H6 | M18 |
| E2545a–d | O11 | H7 | M18 |
| E2546a–d | O11 | H8 | M18 |
| E2547a–d | O11 | H9 | M18 |
| E2548a–d | O12 | H1 | M18 |
| E2549a–d | O12 | H2 | M18 |
| E2550a–d | O12 | H3 | M18 |
| E2551a–d | O12 | H4 | M18 |
| E2552a–d | O12 | H5 | M18 |
| E2553a–d | O12 | H6 | M18 |
| E2554a–d | O12 | H7 | M18 |
| E2555a–d | O12 | H8 | M18 |
| E2556a–d | O12 | H9 | M18 |
| E2557a–d | O13 | H1 | M18 |
| E2558a–d | O13 | H2 | M18 |
| E2559a–d | O13 | H3 | M18 |
| E2560a–d | O13 | H4 | M18 |
| E2561a–d | O13 | H5 | M18 |
| E2562a–d | O13 | H6 | M18 |
| E2563a–d | O13 | H7 | M18 |
| E2564a–d | O13 | H8 | M18 |
| E2565a–d | O13 | H9 | M18 |
| E2566a–d | O14 | H1 | M18 |
| E2567a–d | O14 | H2 | M18 |
| E2568a–d | O14 | H3 | M18 |
| E2569a–d | O14 | H4 | M18 |
| E2570a–d | O14 | H5 | M18 |
| E2571a–d | O14 | H6 | M18 |
| E2572a–d | O14 | H7 | M18 |
| E2573a–d | O14 | H8 | M18 |
| E2574a–d | O14 | H9 | M18 |
| E2575a–d | O15 | H1 | M18 |
| E2576a–d | O15 | H2 | M18 |
| E2577a–d | O15 | H3 | M18 |
| E2578a–d | O15 | H4 | M18 |
| E2579a–d | O15 | H5 | M18 |
| E2580a–d | O15 | H6 | M18 |
| E2581a–d | O15 | H7 | M18 |
| E2582a–d | O15 | H8 | M18 |
| E2583a–d | O15 | H9 | M18 |
| E2584a–d | O16 | H1 | M18 |
| E2585a–d | O16 | H2 | M18 |
| E2586a–d | O16 | H3 | M18 |
| E2587a–d | O16 | H4 | M18 |
| E2588a–d | O16 | H5 | M18 |
| E2589a–d | O16 | H6 | M18 |
| E2590a–d | O16 | H7 | M18 |
| E2591a–d | O16 | H8 | M18 |
| E2592a–d | O16 | H9 | M18 |
| E2593a–d | O1 | H1 | M19 |
| E2594a–d | O1 | H2 | M19 |
| E2595a–d | O1 | H3 | M19 |
| E2596a–d | O1 | H4 | M19 |
| E2597a–d | O1 | H5 | M19 |
| E2598a–d | O1 | H6 | M19 |
| E2599a–d | O1 | H7 | M19 |
| E2600a–d | O1 | H8 | M19 |
| E2601a–d | O1 | H9 | M19 |
| E2602a–d | O2 | H1 | M19 |
| E2603a–d | O2 | H2 | M19 |

TABLE 1-continued

| Example | O Group | H Group | M Group |
|---|---|---|---|
| E2604a–d | O2 | H3 | M19 |
| E2605a–d | O2 | H4 | M19 |
| E2606a–d | O2 | H5 | M19 |
| E2607a–d | O2 | H6 | M19 |
| E2608a–d | O2 | H7 | M19 |
| E2609a–d | O2 | H8 | M19 |
| E2610a–d | O2 | H9 | M19 |
| E2611a–d | O3 | H1 | M19 |
| E2612a–d | O3 | H2 | M19 |
| E2613a–d | O3 | H3 | M19 |
| E2614a–d | O3 | H4 | M19 |
| E2615a–d | O3 | H5 | M19 |
| E2616a–d | O3 | H6 | M19 |
| E2617a–d | O3 | H7 | M19 |
| E2618a–d | O3 | H8 | M19 |
| E2619a–d | O3 | H9 | M19 |
| E2620a–d | O4 | H1 | M19 |
| E2621a–d | O4 | H2 | M19 |
| E2622a–d | O4 | H3 | M19 |
| E2623a–d | O4 | H4 | M19 |
| E2624a–d | O4 | H5 | M19 |
| E2625a–d | O4 | H6 | M19 |
| E2626a–d | O4 | H7 | M19 |
| E2627a–d | O4 | H8 | M19 |
| E2628a–d | O4 | H9 | M19 |
| E2629a–d | O5 | H1 | M19 |
| E2630a–d | O5 | H2 | M19 |
| E2631a–d | O5 | H3 | M19 |
| E2632a–d | O5 | H4 | M19 |
| E2633a–d | O5 | H5 | M19 |
| E2634a–d | O5 | H6 | M19 |
| E2635a–d | O5 | H7 | M19 |
| E2636a–d | O5 | H8 | M19 |
| E2637a–d | O5 | H9 | M19 |
| E2638a–d | O6 | H1 | M19 |
| E2639a–d | O6 | H2 | M19 |
| E2640a–d | O6 | H3 | M19 |
| E2641a–d | O6 | H4 | M19 |
| E2642a–d | O6 | H5 | M19 |
| E2643a–d | O6 | H6 | M19 |
| E2644a–d | O6 | H7 | M19 |
| E2645a–d | O6 | H8 | M19 |
| E2646a–d | O6 | H9 | M19 |
| E2647a–d | O7 | H1 | M19 |
| E2648a–d | O7 | H2 | M19 |
| E2649a–d | O7 | H3 | M19 |
| E2650a–d | O7 | H4 | M19 |
| E2651a–d | O7 | H5 | M19 |
| E2652a–d | O7 | H6 | M19 |
| E2653a–d | O7 | H7 | M19 |
| E2654a–d | O7 | H8 | M19 |
| E2655a–d | O7 | H9 | M19 |
| E2656a–d | O8 | H1 | M19 |
| E2657a–d | O8 | H2 | M19 |
| E2658a–d | O8 | H3 | M19 |
| E2659a–d | O8 | H4 | M19 |
| E2660a–d | O8 | H5 | M19 |
| E2661a–d | O8 | H6 | M19 |
| E2662a–d | O8 | H7 | M19 |
| E2663a–d | O8 | H8 | M19 |
| E2664a–d | O8 | H9 | M19 |
| E2665a–d | O9 | H1 | M19 |
| E2666a–d | O9 | H2 | M19 |
| E2667a–d | O9 | H3 | M19 |
| E2668a–d | O9 | H4 | M19 |
| E2669a–d | O9 | H5 | M19 |
| E2670a–d | O9 | H6 | M19 |
| E2671a–d | O9 | H7 | M19 |
| E2672a–d | O9 | H8 | M19 |
| E2673a–d | O9 | H9 | M19 |
| E2674a–d | O10 | H1 | M19 |
| E2675a–d | O10 | H2 | M19 |
| E2676a–d | O10 | H3 | M19 |
| E2677a–d | O10 | H4 | M19 |
| E2678a–d | O10 | H5 | M19 |
| E2679a–d | O10 | H6 | M19 |
| E2680a–d | O10 | H7 | M19 |
| E2681a–d | O10 | H8 | M19 |
| E2682a–d | O10 | H9 | M19 |
| E2683a–d | O11 | H1 | M19 |
| E2684a–d | O11 | H2 | M19 |
| E2685a–d | O11 | H3 | M19 |
| E2686a–d | O11 | H4 | M19 |
| E2687a–d | O11 | H5 | M19 |
| E2688a–d | O11 | H6 | M19 |
| E2689a–d | O11 | H7 | M19 |
| E2690a–d | O11 | H8 | M19 |
| E2691a–d | O11 | H9 | M19 |
| E2692a–d | O12 | H1 | M19 |
| E2693a–d | O12 | H2 | M19 |
| E2694a–d | O12 | H3 | M19 |
| E2695a–d | O12 | H4 | M19 |
| E2696a–d | O12 | H5 | M19 |
| E2697a–d | O12 | H6 | M19 |
| E2698a–d | O12 | H7 | M19 |
| E2699a–d | O12 | H8 | M19 |
| E2700a–d | O12 | H9 | M19 |
| E2701a–d | O13 | H1 | M19 |
| E2702a–d | O13 | H2 | M19 |
| E2703a–d | O13 | H3 | M19 |
| E2704a–d | O13 | H4 | M19 |
| E2705a–d | O13 | H5 | M19 |
| E2706a–d | O13 | H6 | M19 |
| E2707a–d | O13 | H7 | M19 |
| E2708a–d | O13 | H8 | M19 |
| E2709a–d | O13 | H9 | M19 |
| E2710a–d | O14 | H1 | M19 |
| E2711a–d | O14 | H2 | M19 |
| E2712a–d | O14 | H3 | M19 |
| E2713a–d | O14 | H4 | M19 |
| E2714a–d | O14 | H5 | M19 |
| E2715a–d | O14 | H6 | M19 |
| E2716a–d | O14 | H7 | M19 |
| E2717a–d | O14 | H8 | M19 |
| E2718a–d | O14 | H9 | M19 |
| E2719a–d | O15 | H1 | M19 |
| E2720a–d | O15 | H2 | M19 |
| E2721a–d | O15 | H3 | M19 |
| E2722a–d | O15 | H4 | M19 |
| E2723a–d | O15 | H5 | M19 |
| E2724a–d | O15 | H6 | M19 |
| E2725a–d | O15 | H7 | M19 |
| E2726a–d | O15 | H8 | M19 |
| E2727a–d | O15 | H9 | M19 |
| E2728a–d | O16 | H1 | M19 |
| E2729a–d | O16 | H2 | M19 |
| E2730a–d | O16 | H3 | M19 |
| E2731a–d | O16 | H4 | M19 |
| E2732a–d | O16 | H5 | M19 |
| E2733a–d | O16 | H6 | M19 |
| E2734a–d | O16 | H7 | M19 |
| E2735a–d | O16 | H8 | M19 |
| E2736a–d | O16 | H9 | M19 |
| E2737a–d | O1 | H1 | M20 |
| E2738a–d | O1 | H2 | M20 |
| E2739a–d | O1 | H3 | M20 |
| E2740a–d | O1 | H4 | M20 |
| E2741a–d | O1 | H5 | M20 |
| E2742a–d | O1 | H6 | M20 |
| E2743a–d | O1 | H7 | M20 |
| E2744a–d | O1 | H8 | M20 |
| E2745a–d | O1 | H9 | M20 |
| E2746a–d | O2 | H1 | M20 |
| E2747a–d | O2 | H2 | M20 |
| E2748a–d | O2 | H3 | M20 |
| E2749a–d | O2 | H4 | M20 |
| E2750a–d | O2 | H5 | M20 |
| E2751a–d | O2 | H6 | M20 |
| E2752a–d | O2 | H7 | M20 |
| E2753a–d | O2 | H8 | M20 |
| E2754a–d | O2 | H9 | M20 |
| E2755a–d | O3 | H1 | M20 |
| E2756a–d | O3 | H2 | M20 |
| E2757a–d | O3 | H3 | M20 |

TABLE 1-continued

| Example | O Group | H Group | M Group |
|---|---|---|---|
| E2758a–d | O3 | H4 | M20 |
| E2759a–d | O3 | H5 | M20 |
| E2760a–d | O3 | H6 | M20 |
| E2761a–d | O3 | H7 | M20 |
| E2762a–d | O3 | H8 | M20 |
| E2763a–d | O3 | H9 | M20 |
| E2764a–d | O4 | H1 | M20 |
| E2765a–d | O4 | H2 | M20 |
| E2766a–d | O4 | H3 | M20 |
| E2767a–d | O4 | H4 | M20 |
| E2768a–d | O4 | H5 | M20 |
| E2769a–d | O4 | H6 | M20 |
| E2770a–d | O4 | H7 | M20 |
| E2771a–d | O4 | H8 | M20 |
| E2772a–d | O4 | H9 | M20 |
| E2773a–d | O5 | H1 | M20 |
| E2774a–d | O5 | H2 | M20 |
| E2775a–d | O5 | H3 | M20 |
| E2776a–d | O5 | H4 | M20 |
| E2777a–d | O5 | H5 | M20 |
| E2778a–d | O5 | H6 | M20 |
| E2779a–d | O5 | H7 | M20 |
| E2780a–d | O5 | H8 | M20 |
| E2781a–d | O5 | H9 | M20 |
| E2782a–d | O6 | H1 | M20 |
| E2783a–d | O6 | H2 | M20 |
| E2784a–d | O6 | H3 | M20 |
| E2785a–d | O6 | H4 | M20 |
| E2786a–d | O6 | H5 | M20 |
| E2787a–d | O6 | H6 | M20 |
| E2788a–d | O6 | H7 | M20 |
| E2789a–d | O6 | H8 | M20 |
| E2790a–d | O6 | H9 | M20 |
| E2791a–d | O7 | H1 | M20 |
| E2792a–d | O7 | H2 | M20 |
| E2793a–d | O7 | H3 | M20 |
| E2794a–d | O7 | H4 | M20 |
| E2795a–d | O7 | H5 | M20 |
| E2796a–d | O7 | H6 | M20 |
| E2797a–d | O7 | H7 | M20 |
| E2798a–d | O7 | H8 | M20 |
| E2799a–d | O7 | H9 | M20 |
| E2800a–d | O8 | H1 | M20 |
| E2801a–d | O8 | H2 | M20 |
| E2802a–d | O8 | H3 | M20 |
| E2803a–d | O8 | H4 | M20 |
| E2804a–d | O8 | H5 | M20 |
| E2805a–d | O8 | H6 | M20 |
| E2806a–d | O8 | H7 | M20 |
| E2807a–d | O8 | H8 | M20 |
| E2808a–d | O8 | H9 | M20 |
| E2809a–d | O9 | H1 | M20 |
| E2810a–d | O9 | H2 | M20 |
| E2811a–d | O9 | H3 | M20 |
| E2812a–d | O9 | H4 | M20 |
| E2813a–d | O9 | H5 | M20 |
| E2814a–d | O9 | H6 | M20 |
| E2815a–d | O9 | H7 | M20 |
| E2816a–d | O9 | H8 | M20 |
| E2817a–d | O9 | H9 | M20 |
| E2818a–d | O10 | H1 | M20 |
| E2819a–d | O10 | H2 | M20 |
| E2820a–d | O10 | H3 | M20 |
| E2821a–d | O10 | H4 | M20 |
| E2822a–d | O10 | H5 | M20 |
| E2823a–d | O10 | H6 | M20 |
| E2824a–d | O10 | H7 | M20 |
| E2825a–d | O10 | H8 | M20 |
| E2826a–d | O10 | H9 | M20 |
| E2827a–d | O11 | H1 | M20 |
| E2828a–d | O11 | H2 | M20 |
| E2829a–d | O11 | H3 | M20 |
| E2830a–d | O11 | H4 | M20 |
| E2831a–d | O11 | H5 | M20 |
| E2832a–d | O11 | H6 | M20 |
| E2833a–d | O11 | H7 | M20 |
| E2834a–d | O11 | H8 | M20 |
| E2835a–d | O11 | H9 | M20 |
| E2836a–d | O12 | H1 | M20 |
| E2837a–d | O12 | H2 | M20 |
| E2838a–d | O12 | H3 | M20 |
| E2839a–d | O12 | H4 | M20 |
| E2840a–d | O12 | H5 | M20 |
| E2841a–d | O12 | H6 | M20 |
| E2842a–d | O12 | H7 | M20 |
| E2843a–d | O12 | H8 | M20 |
| E2844a–d | O12 | H9 | M20 |
| E2845a–d | O13 | H1 | M20 |
| E2846a–d | O13 | H2 | M20 |
| E2847a–d | O13 | H3 | M20 |
| E2848a–d | O13 | H4 | M20 |
| E2849a–d | O13 | H5 | M20 |
| E2850a–d | O13 | H6 | M20 |
| E2851a–d | O13 | H7 | M20 |
| E2852a–d | O13 | H8 | M20 |
| E2853a–d | O13 | H9 | M20 |
| E2854a–d | O14 | H1 | M20 |
| E2855a–d | O14 | H2 | M20 |
| E2856a–d | O14 | H3 | M20 |
| E2857a–d | O14 | H4 | M20 |
| E2858a–d | O14 | H5 | M20 |
| E2859a–d | O14 | H6 | M20 |
| E2860a–d | O14 | H7 | M20 |
| E2861a–d | O14 | H8 | M20 |
| E2862a–d | O14 | H9 | M20 |
| E2863a–d | O15 | H1 | M20 |
| E2864a–d | O15 | H2 | M20 |
| E2865a–d | O15 | H3 | M20 |
| E2866a–d | O15 | H4 | M20 |
| E2867a–d | O15 | H5 | M20 |
| E2868a–d | O15 | H6 | M20 |
| E2869a–d | O15 | H7 | M20 |
| E2870a–d | O15 | H8 | M20 |
| E2871a–d | O15 | H9 | M20 |
| E2872a–d | O16 | H1 | M20 |
| E2873a–d | O16 | H2 | M20 |
| E2874a–d | O16 | H3 | M20 |
| E2875a–d | O16 | H4 | M20 |
| E2876a–d | O16 | H5 | M20 |
| E2877a–d | O16 | H6 | M20 |
| E2878a–d | O16 | H7 | M20 |
| E2879a–d | O16 | H8 | M20 |
| E2880a–d | O16 | H9 | M20 |
| E2881a–d | O1 | H1 | M21 |
| E2882a–d | O1 | H2 | M21 |
| E2883a–d | O1 | H3 | M21 |
| E2884a–d | O1 | H4 | M21 |
| E2885a–d | O1 | H5 | M21 |
| E2886a–d | O1 | H6 | M21 |
| E2887a–d | O1 | H7 | M21 |
| E2888a–d | O1 | H8 | M21 |
| E2889a–d | O1 | H9 | M21 |
| E2890a–d | O2 | H1 | M21 |
| E2891a–d | O2 | H2 | M21 |
| E2892a–d | O2 | H3 | M21 |
| E2893a–d | O2 | H4 | M21 |
| E2894a–d | O2 | H5 | M21 |
| E2895a–d | O2 | H6 | M21 |
| E2896a–d | O2 | H7 | M21 |
| E2897a–d | O2 | H8 | M21 |
| E2898a–d | O2 | H9 | M21 |
| E2899a–d | O3 | H1 | M21 |
| E2900a–d | O3 | H2 | M21 |
| E2901a–d | O3 | H3 | M21 |
| E2902a–d | O3 | H4 | M21 |
| E2903a–d | O3 | H5 | M21 |
| E2904a–d | O3 | H6 | M21 |
| E2905a–d | O3 | H7 | M21 |
| E2906a–d | O3 | H8 | M21 |
| E2907a–d | O3 | H9 | M21 |
| E2908a–d | O4 | H1 | M21 |
| E2909a–d | O4 | H2 | M21 |
| E2910a–d | O4 | H3 | M21 |
| E2911a–d | O4 | H4 | M21 |

TABLE 1-continued

| Example | O Group | H Group | M Group |
|---|---|---|---|
| E2912a–d | O4 | H5 | M21 |
| E2913a–d | O4 | H6 | M21 |
| E2914a–d | O4 | H7 | M21 |
| E2915a–d | O4 | H8 | M21 |
| E2916a–d | O4 | H9 | M21 |
| E2917a–d | O5 | H1 | M21 |
| E2918a–d | O5 | H2 | M21 |
| E2919a–d | O5 | H3 | M21 |
| E2920a–d | O5 | H4 | M21 |
| E2921a–d | O5 | H5 | M21 |
| E2922a–d | O5 | H6 | M21 |
| E2923a–d | O5 | H7 | M21 |
| E2924a–d | O5 | H8 | M21 |
| E2925a–d | O5 | H9 | M21 |
| E2926a–d | O6 | H1 | M21 |
| E2927a–d | O6 | H2 | M21 |
| E2928a–d | O6 | H3 | M21 |
| E2929a–d | O6 | H4 | M21 |
| E2930a–d | O6 | H5 | M21 |
| E2931a–d | O6 | H6 | M21 |
| E2932a–d | O6 | H7 | M21 |
| E2933a–d | O6 | H8 | M21 |
| E2934a–d | O6 | H9 | M21 |
| E2935a–d | O7 | H1 | M21 |
| E2936a–d | O7 | H2 | M21 |
| E2937a–d | O7 | H3 | M21 |
| E2938a–d | O7 | H4 | M21 |
| E2939a–d | O7 | H5 | M21 |
| E2940a–d | O7 | H6 | M21 |
| E2941a–d | O7 | H7 | M21 |
| E2942a–d | O7 | H8 | M21 |
| E2943a–d | O7 | H9 | M21 |
| E2944a–d | O8 | H1 | M21 |
| E2945a–d | O8 | H2 | M21 |
| E2946a–d | O8 | H3 | M21 |
| E2947a–d | O8 | H4 | M21 |
| E2948a–d | O8 | H5 | M21 |
| E2949a–d | O8 | H6 | M21 |
| E2950a–d | O8 | H7 | M21 |
| E2951a–d | O8 | H8 | M21 |
| E2952a–d | O8 | H9 | M21 |
| E2953a–d | O9 | H1 | M21 |
| E2954a–d | O9 | H2 | M21 |
| E2955a–d | O9 | H3 | M21 |
| E2956a–d | O9 | H4 | M21 |
| E2957a–d | O9 | H5 | M21 |
| E2958a–d | O9 | H6 | M21 |
| E2959a–d | O9 | H7 | M21 |
| E2960a–d | O9 | H8 | M21 |
| E2961a–d | O9 | H9 | M21 |
| E2962a–d | O10 | H1 | M21 |
| E2963a–d | O10 | H2 | M21 |
| E2964a–d | O10 | H3 | M21 |
| E2965a–d | O10 | H4 | M21 |
| E2966a–d | O10 | H5 | M21 |
| E2967a–d | O10 | H6 | M21 |
| E2968a–d | O10 | H7 | M21 |
| E2969a–d | O10 | H8 | M21 |
| E2970a–d | O10 | H9 | M21 |
| E2971a–d | O11 | H1 | M21 |
| E2972a–d | O11 | H2 | M21 |
| E2973a–d | O11 | H3 | M21 |
| E2974a–d | O11 | H4 | M21 |
| E2975a–d | O11 | H5 | M21 |
| E2976a–d | O11 | H6 | M21 |
| E2977a–d | O11 | H7 | M21 |
| E2978a–d | O11 | H8 | M21 |
| E2979a–d | O11 | H9 | M21 |
| E2980a–d | O12 | H1 | M21 |
| E2981a–d | O12 | H2 | M21 |
| E2982a–d | O12 | H3 | M21 |
| E2983a–d | O12 | H4 | M21 |
| E2984a–d | O12 | H5 | M21 |
| E2985a–d | O12 | H6 | M21 |
| E2986a–d | O12 | H7 | M21 |
| E2987a–d | O12 | H8 | M21 |
| E2988a–d | O12 | H9 | M21 |
| E2989a–d | O13 | H1 | M21 |
| E2990a–d | O13 | H2 | M21 |
| E2991a–d | O13 | H3 | M21 |
| E2992a–d | O13 | H4 | M21 |
| E2993a–d | O13 | H5 | M21 |
| E2994a–d | O13 | H6 | M21 |
| E2995a–d | O13 | H7 | M21 |
| E2996a–d | O13 | H8 | M21 |
| E2997a–d | O13 | H9 | M21 |
| E2998a–d | O14 | H1 | M21 |
| E2999a–d | O14 | H2 | M21 |
| E3000a–d | O14 | H3 | M21 |
| E3001a–d | O14 | H4 | M21 |
| E3002a–d | O14 | H5 | M21 |
| E3003a–d | O14 | H6 | M21 |
| E3004a–d | O14 | H7 | M21 |
| E3005a–d | O14 | H8 | M21 |
| E3006a–d | O14 | H9 | M21 |
| E3007a–d | O15 | H1 | M21 |
| E3008a–d | O15 | H2 | M21 |
| E3009a–d | O15 | H3 | M21 |
| E3010a–d | O15 | H4 | M21 |
| E3011a–d | O15 | H5 | M21 |
| E3012a–d | O15 | H6 | M21 |
| E3013a–d | O15 | H7 | M21 |
| E3014a–d | O15 | H8 | M21 |
| E3015a–d | O15 | H9 | M21 |
| E3016a–d | O16 | H1 | M21 |
| E3017a–d | O16 | H2 | M21 |
| E3018a–d | O16 | H3 | M21 |
| E3019a–d | O16 | H4 | M21 |
| E3020a–d | O16 | H5 | M21 |
| E3021a–d | O16 | H6 | M21 |
| E3022a–d | O16 | H7 | M21 |
| E3023a–d | O16 | H8 | M21 |
| E3024a–d | O16 | H9 | M21 |
| E3025a–d | O1 | H1 | M22 |
| E3026a–d | O1 | H2 | M22 |
| E3027a–d | O1 | H3 | M22 |
| E3028a–d | O1 | H4 | M22 |
| E3029a–d | O1 | H5 | M22 |
| E3030a–d | O1 | H6 | M22 |
| E3031a–d | O1 | H7 | M22 |
| E3032a–d | O1 | H8 | M22 |
| E3033a–d | O1 | H9 | M22 |
| E3034a–d | O2 | H1 | M22 |
| E3035a–d | O2 | H2 | M22 |
| E3036a–d | O2 | H3 | M22 |
| E3037a–d | O2 | H4 | M22 |
| E3038a–d | O2 | H5 | M22 |
| E3039a–d | O2 | H6 | M22 |
| E3040a–d | O2 | H7 | M22 |
| E3041a–d | O2 | H8 | M22 |
| E3042a–d | O2 | H9 | M22 |
| E3043a–d | O3 | H1 | M22 |
| E3044a–d | O3 | H2 | M22 |
| E3045a–d | O3 | H3 | M22 |
| E3046a–d | O3 | H4 | M22 |
| E3047a–d | O3 | H5 | M22 |
| E3048a–d | O3 | H6 | M22 |
| E3049a–d | O3 | H7 | M22 |
| E3050a–d | O3 | H8 | M22 |
| E3051a–d | O3 | H9 | M22 |
| E3052a–d | O4 | H1 | M22 |
| E3053a–d | O4 | H2 | M22 |
| E3054a–d | O4 | H3 | M22 |
| E3055a–d | O4 | H4 | M22 |
| E3056a–d | O4 | H5 | M22 |
| E3057a–d | O4 | H6 | M22 |
| E3058a–d | O4 | H7 | M22 |
| E3059a–d | O4 | H8 | M22 |
| E3060a–d | O4 | H9 | M22 |
| E3061a–d | O5 | H1 | M22 |
| E3062a–d | O5 | H2 | M22 |
| E3063a–d | O5 | H3 | M22 |
| E3064a–d | O5 | H4 | M22 |
| E3065a–d | O5 | H5 | M22 |

TABLE 1-continued

| Example | O Group | H Group | M Group |
|---|---|---|---|
| E3066a–d | O5 | H6 | M22 |
| E3067a–d | O5 | H7 | M22 |
| E3068a–d | O5 | H8 | M22 |
| E3069a–d | O5 | H9 | M22 |
| E3070a–d | O6 | H1 | M22 |
| E3071a–d | O6 | H2 | M22 |
| E3072a–d | O6 | H3 | M22 |
| E3073a–d | O6 | H4 | M22 |
| E3074a–d | O6 | H5 | M22 |
| E3075a–d | O6 | H6 | M22 |
| E3076a–d | O6 | H7 | M22 |
| E3077a–d | O6 | H8 | M22 |
| E3078a–d | O6 | H9 | M22 |
| E3079a–d | O7 | H1 | M22 |
| E3080a–d | O7 | H2 | M22 |
| E3081a–d | O7 | H3 | M22 |
| E3082a–d | O7 | H4 | M22 |
| E3083a–d | O7 | H5 | M22 |
| E3084a–d | O7 | H6 | M22 |
| E3085a–d | O7 | H7 | M22 |
| E3086a–d | O7 | H8 | M22 |
| E3087a–d | O7 | H9 | M22 |
| E3088a–d | O8 | H1 | M22 |
| E3089a–d | O8 | H2 | M22 |
| E3090a–d | O8 | H3 | M22 |
| E3091a–d | O8 | H4 | M22 |
| E3092a–d | O8 | H5 | M22 |
| E3093a–d | O8 | H6 | M22 |
| E3094a–d | O8 | H7 | M22 |
| E3095a–d | O8 | H8 | M22 |
| E3096a–d | O8 | H9 | M22 |
| E3097a–d | O9 | H1 | M22 |
| E3098a–d | O9 | H2 | M22 |
| E3099a–d | O9 | H3 | M22 |
| E3100a–d | O9 | H4 | M22 |
| E3101a–d | O9 | H5 | M22 |
| E3102a–d | O9 | H6 | M22 |
| E3103a–d | O9 | H7 | M22 |
| E3104a–d | O9 | H8 | M22 |
| E3105a–d | O9 | H9 | M22 |
| E3106a–d | O10 | H1 | M22 |
| E3107a–d | O10 | H2 | M22 |
| E3108a–d | O10 | H3 | M22 |
| E3109a–d | O10 | H4 | M22 |
| E3110a–d | O10 | H5 | M22 |
| E3111a–d | O10 | H6 | M22 |
| E3112a–d | O10 | H7 | M22 |
| E3113a–d | O10 | H8 | M22 |
| E3114a–d | O10 | H9 | M22 |
| E3115a–d | O11 | H1 | M22 |
| E3116a–d | O11 | H2 | M22 |
| E3117a–d | O11 | H3 | M22 |
| E3118a–d | O11 | H4 | M22 |
| E3119a–d | O11 | H5 | M22 |
| E3120a–d | O11 | H6 | M22 |
| E3121a–d | O11 | H7 | M22 |
| E3122a–d | O11 | H8 | M22 |
| E3123a–d | O11 | H9 | M22 |
| E3124a–d | O12 | H1 | M22 |
| E3125a–d | O12 | H2 | M22 |
| E3126a–d | O12 | H3 | M22 |
| E3127a–d | O12 | H4 | M22 |
| E3128a–d | O12 | H5 | M22 |
| E3129a–d | O12 | H6 | M22 |
| E3130a–d | O12 | H7 | M22 |
| E3131a–d | O12 | H8 | M22 |
| E3132a–d | O12 | H9 | M22 |
| E3133a–d | O13 | H1 | M22 |
| E3134a–d | O13 | H2 | M22 |
| E3135a–d | O13 | H3 | M22 |
| E3136a–d | O13 | H4 | M22 |
| E3137a–d | O13 | H5 | M22 |
| E3138a–d | O13 | H6 | M22 |
| E3139a–d | O13 | H7 | M22 |
| E3140a–d | O13 | H8 | M22 |
| E3141a–d | O13 | H9 | M22 |
| E3142a–d | O14 | H1 | M22 |
| E3143a–d | O14 | H2 | M22 |
| E3144a–d | O14 | H3 | M22 |
| E3145a–d | O14 | H4 | M22 |
| E3146a–d | O14 | H5 | M22 |
| E3147a–d | O14 | H6 | M22 |
| E3148a–d | O14 | H7 | M22 |
| E3149a–d | O14 | H8 | M22 |
| E3150a–d | O14 | H9 | M22 |
| E3151a–d | O15 | H1 | M22 |
| E3152a–d | O15 | H2 | M22 |
| E3153a–d | O15 | H3 | M22 |
| E3154a–d | O15 | H4 | M22 |
| E3155a–d | O15 | H5 | M22 |
| E3156a–d | O15 | H6 | M22 |
| E3157a–d | O15 | H7 | M22 |
| E3158a–d | O15 | H8 | M22 |
| E3159a–d | O15 | H9 | M22 |
| E3160a–d | O16 | H1 | M22 |
| E3161a–d | O16 | H2 | M22 |
| E3162a–d | O16 | H3 | M22 |
| E3163a–d | O16 | H4 | M22 |
| E3164a–d | O16 | H5 | M22 |
| E3165a–d | O16 | H6 | M22 |
| E3166a–d | O16 | H7 | M22 |
| E3167a–d | O16 | H8 | M22 |
| E3168a–d | O16 | H9 | M22 |

3. Synthesis of the Compounds of the Invention

In another aspect, the invention provides methods for making the compounds of the invention. The following schemes depict some exemplary chemistries available for synthesizing the compounds of the invention. It will be appreciated, however, that the desired compounds may be synthesized using other alternative chemistries known in the art.

Scheme 1 illustrates the synthesis of oxazolidinones substituted at C-5 with 1,2,3-triazolylmethyl derivatives. Isocyanates 14 can react with lithium bromide and glycidyl butyrate at elevated temperature to produce oxazolidinone intermediates of type 15 (Gregory et al. (1989) J. MED. CHEM. 32:1673). Hydrolysis of the resulting butyrate ester of compound 15 produces alcohol 17. Alcohol 17 can also be synthesized from carbamates such as the benzyl carbamate 16. The carbamate nitrogen of compound 16 then is deprotonated, and alkylated with glycidyl butyrate to produce (after in situ hydrolysis of the butyl ester) hydroxymethyl derivative 17. While the R enantiomer depicted throughout Scheme 1 generally is the most biologically useful derivative for antibacterial agents, it is contemplated that compounds derived from either the R or the S enantiomer, or any mixture of R and S enantiomers, may be useful in the practice of the invention.

Alcohols 17 can be converted to useful intermediates such as mesylates 18a (by treatment with methanesulfonyl chloride and triethylamine in an appropriate solvent) and azide 19 (by subsequent displacement of the mesylate by sodium azide in DMF). Azide 19 can also be produced from tosylate 18b (or a brosylate or nosylate), or an alkyl halide of type 18c (made from alcohol 17 via methods known to those skilled in the art). Azide 19 can be heated in the presence of substituted acetylenes 20 to produce C-5 substituted 1,2,3-triazolylmethyl oxazolidinone derivatives of type 21 and 22. It is to be understood that alternative chemical conditions could be employed by those skilled in the art to effect this transformation.

Scheme 1

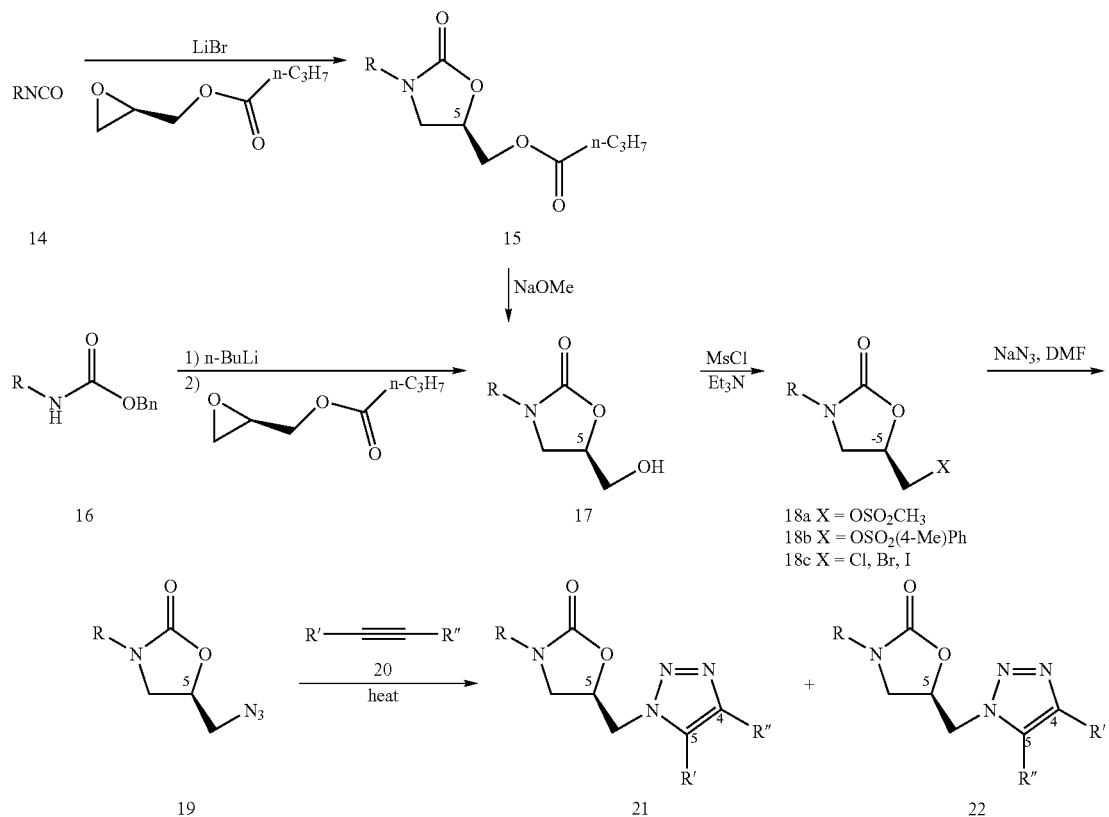

It is understood that unsymmetrical acetylene derivatives can react to produce a mixture of regioisomeric cycloaddition products, represented by 21 and 22, and that the reaction conditions can be adjusted by processes known to those skilled in the art to produce more selectively one regioisomer or the other. For example, Scheme 2 depicts the reaction of mono-substituted acetylene 23 with azide 19 to produce two regioisomeric triazoles, 24 and 25. The major isomer is most often the anti isomer 24 since the reaction leading to this product proceeds at a faster rate. Under certain circumstances, the more sterically disfavored syn isomer is also formed, but at an appreciably diminished rate. The addition of copper(I)iodide is a useful additive for this reaction, and often leads to increased proportions of the major "anti" adduct 24 (Tornoe, C. W. et al. (2002) J. ORG. CHEM. 67: 3057). Increased proportions of the minor isomer 25 may be produced by minor modification of the reaction scheme. Azide 19 can react with the trimethylsilyl substituted acetylene 26 to produce the anti isomer 27 and the syn isomer 28. Desilylation with tetrabutylammonium fluoride can produce triazole 24 and 25, with increased proportions of 25 obtainable from the more abundant precursor triazole 27.

Scheme 2

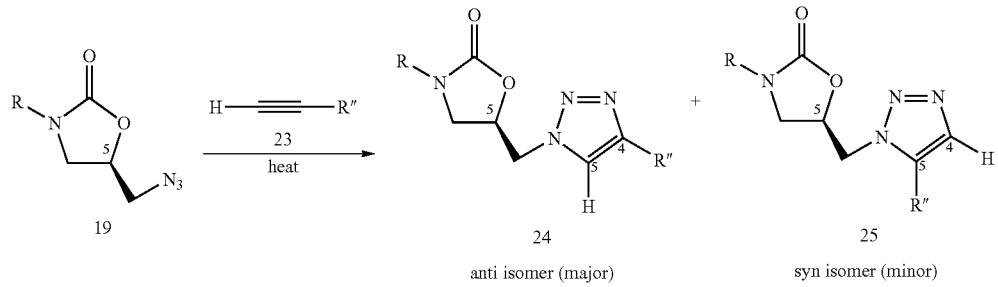

-continued

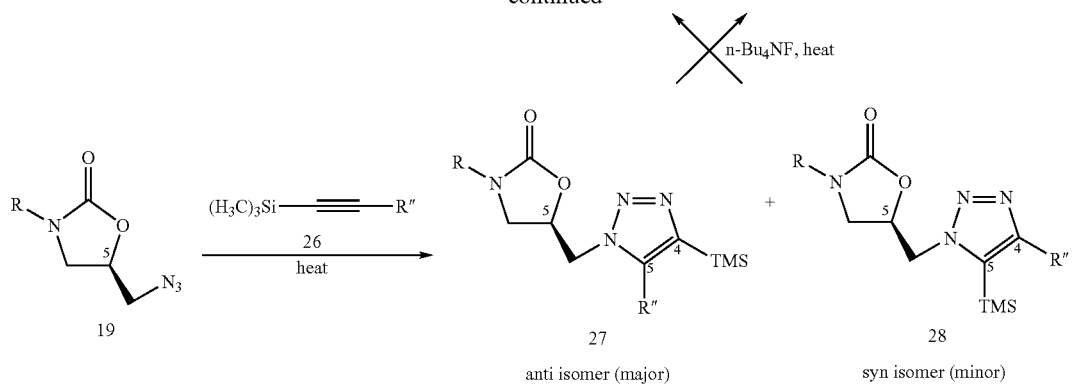

An alternate approach toward the synthesis of some of the compounds of the present invention is shown in Scheme 3. Aromatic halide 29, when activated, can react with the anion derived from treatment of carbamate 33 with an appropriate base to produce 3-aryl substituted oxazolidinone derivatives 31 via nucleophilic aromatic substitution. Suitable bases include, for example, n-BuLi, LiN(Si(CH$_3$)$_3$)$_2$, and NaH. Carbamate 33 can be synthesized by exposure of 32 to carbonyldiimidazole in DMF, followed by in situ silylation of the hydroxymethyl group of the initial product with an appropriate silyl chloride. Desilylation of derivatives of type 31 produces alcohols 17 that can be converted to the targets of the present invention by the processes described within the schemes.

des-methyl desosamine derivative 37. Desosamine derivative 37 is available from the degradation of erythromycin. Alkylation of 37 with alkynes 35 produces triazole-linked sugar compounds of type 38. The dimethyl amino group of the desosamine sugar of macrolide antibiotics can be mono-demethylated to produce the corresponding secondary amine (U.S. Pat. No. 3,725,385, Flynn et al. (1954) J. AM. CHEM. SOC. 76: 3121; Ku et al. (1997) BIOORG. MED. CHEM. LETT. 7: 1203; Stenmark et al. (2000) J. ORG. CHEM. 65: 3875). For example, amine 39 (an intermediate in the synthesis of amino sugar 37), or a suitably protected derivative of 39 such as the per-silylated compound (formed by pre-treatment with bis-trimethylsilylacetamide, hexamethyldisilazane or other agents known in the art) can be

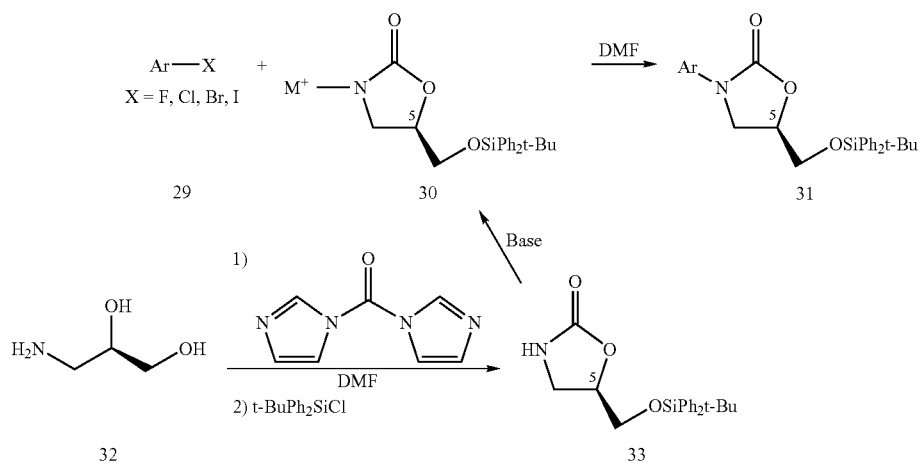

Scheme 4a illustrates the synthesis of some alkynes of type 23 required for the synthesis of some of the compounds of the present invention. Secondary alkyl amines (or cycloalkyl amines) can be alkylated with electrophiles comprised of an alkyne connected by a variable bond or linker to a carbon bearing a leaving group, for example, a halide or sulfonate group (35), to produce alkynes of type 36. The substituted alkynes can be used in cycloaddition reactions with azides to yield triazole-linked target compounds. The amino group undergoing such an alkylation can be derived from amino saccharides, for example (but not limited to), the alkylated with alkynes of type 35. This alkylation reaction produces intermediates of type 40, that can react with azides of type 19 to yield target compounds.

An alternative route is available for the production of desosamine derivatives 38. Alkynes 40 can be hydrolyzed with strong acid to produce amines 38. It is understood that, given appropriate reaction conditions known to those skilled in the art, any macrolide antibacterial agent (naturally occurring, semi-synthetic or synthesized) is capable of serving as starting material for the processes depicted in Scheme 4a.

Scheme 4a

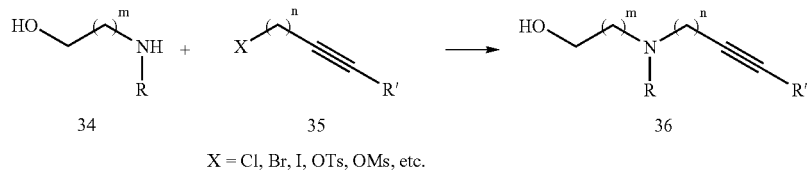

X = Cl, Br, I, OTs, OMs, etc.

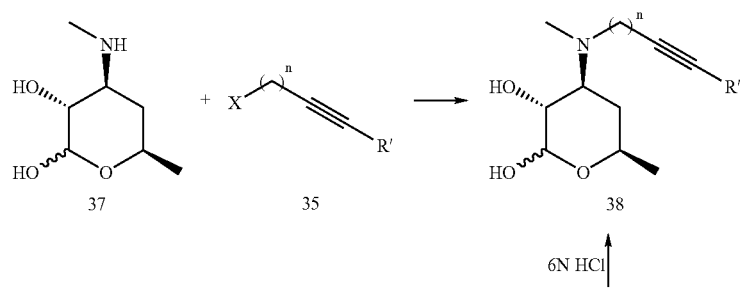

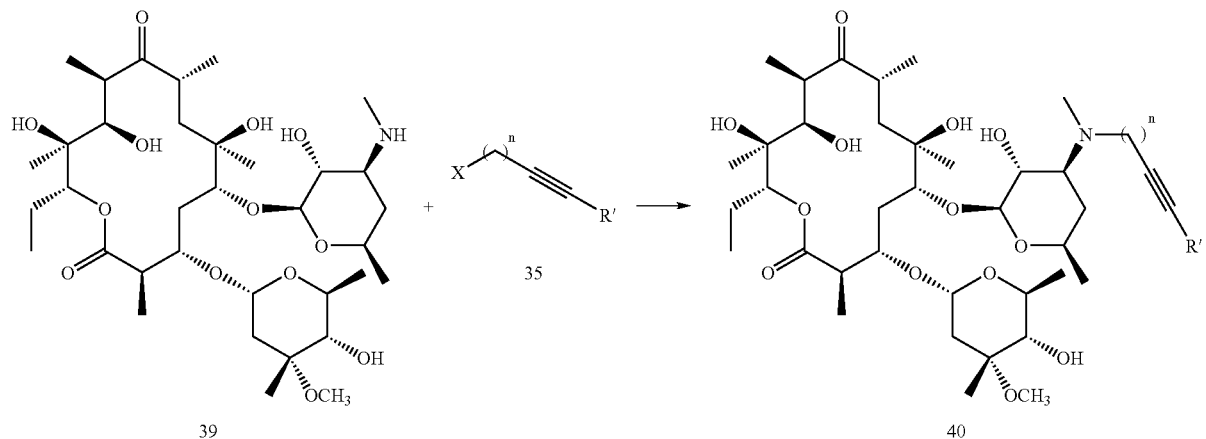

Scheme 4b illustrates the synthesis of compounds of the present invention that contain extra keto groups in the alkyl link between the 5-membered heterocyclic ring and the macrolide moiety. Azides 19 can react with propiolate esters to produce the ester-substituted products. (It is to be understood that mixtures of regioisomeric cycloadducts may form in this reaction, however, only the anti adduct is depicted in Scheme 4b.) Hydrolysis of the ester yields the acid, which can be converted using known chemistry (Ramtohul et al. (2000) J. ORG. CHEM. 67: 3169) to the bromoacetyl triazole. Heating this bromoacetyl derivative with 39 (or a suitably protected version of 39) can yield products that contain a keto link with one methylene group between the ketone and the macrolide group. The bromoacetyl intermediate can be converted via lithio-dithiane chemistry, subsequent hydrolysis, and reduction to an alcohol. The tosylate (or halide) of this alcohol can be made, and this electrophile can be used to alkylate 39 to give products with two methylene groups between the ketone and the macrolide group.

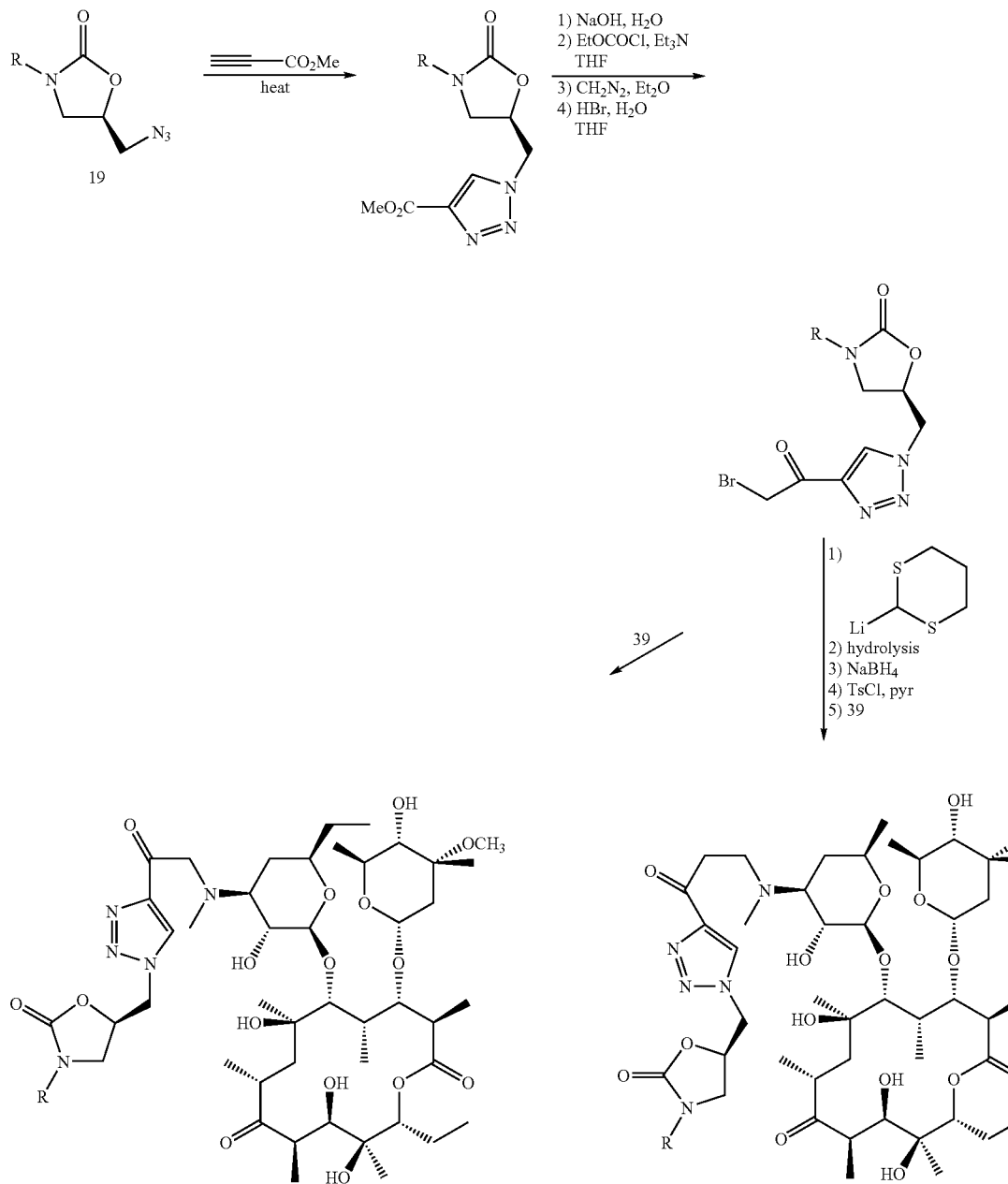

Scheme 5 illustrates another method to synthesize regioisomeric triazole-linked derivatives of the invention. Carbon-linked triazole derivatives of type 44 and 45 can be produced by first displacing a leaving group (for example, a sulfonate or a halide) from electrophiles 18a-c, with either lithium acetylide 41a or lithium trimethylsilylacetylide 41b to produce alkynes 42. The cycloaddition reaction of alkynes 42 with appropriate azides 43 can yield regioisomeric triazoles 44 and 45. (It will be understood that alternative chemical conditions could be employed to produce compounds 44 and 45 such as the use of copper(I)iodide instead of heat).

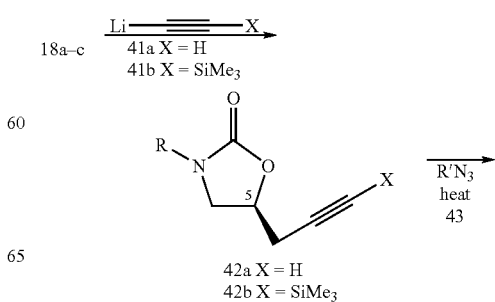

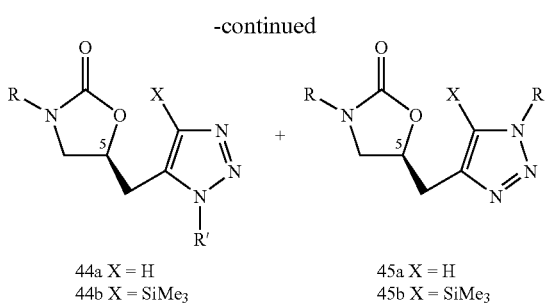

44a X = H
44b X = SiMe₃

45a X = H
45b X = SiMe₃

A specific example of the utility of the chemistry expressed in Scheme 5 is shown in Scheme 6. Des-methyl erythromycin derivative 39 (or a suitably protected derivative thereof) can be alkylated with a bromoalcohol, and the alcohol function of the product converted to a leaving group such as a tosylate. The tosylate can be displaced with sodium azide to yield azide 46. Cycloadditon of 46 and alkyne 42a can produce final targets of type 47. Alternative alkylsulfonates or halides can be used as the starting material for the synthesis of azide 46 (i.e., different leaving groups). Other macrolide entities can be used in place of the des-methyl erythromycin derivative 39 to produce a variety of alternative products.

Another method that can be used to synthesize carbon-linked triazole derivatives of type 47 is illustrated in Scheme 7. Alkyne 42a can react with trimethylsilylazide (or with sodium azide, ammonium chloride and copper(I)iodide, or other conditions known in the art) to produce two possible regioisomeric products, triazoles 48 and 49. Either of these (or the mixture) can be desilylated with n-Bu₄NF to produce triazole 50. Des-methyl erythromycin derivative 39 (or an alternate des-methyl amino macrolide derivative) can be converted to tosylate 51 (or another sulfonate or halide electrophile), and then the electrophile can serve to alkylate triazole 50 to produce either the N-1 substituted triazole 47, or the N-2 substituted triazole 53, or a mixture of both. In the event that a mixture is produced, both compounds may be separated from one another. It is contemplated that other macrolides may be transformed by the chemistry of Scheme 7 to produce other compounds of interest.

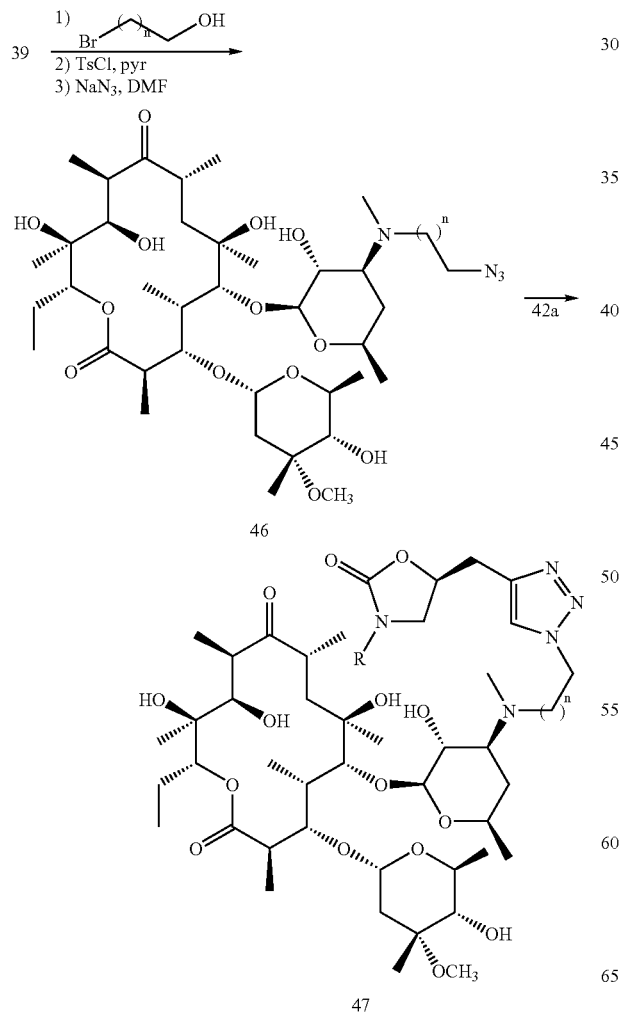

Scheme 6

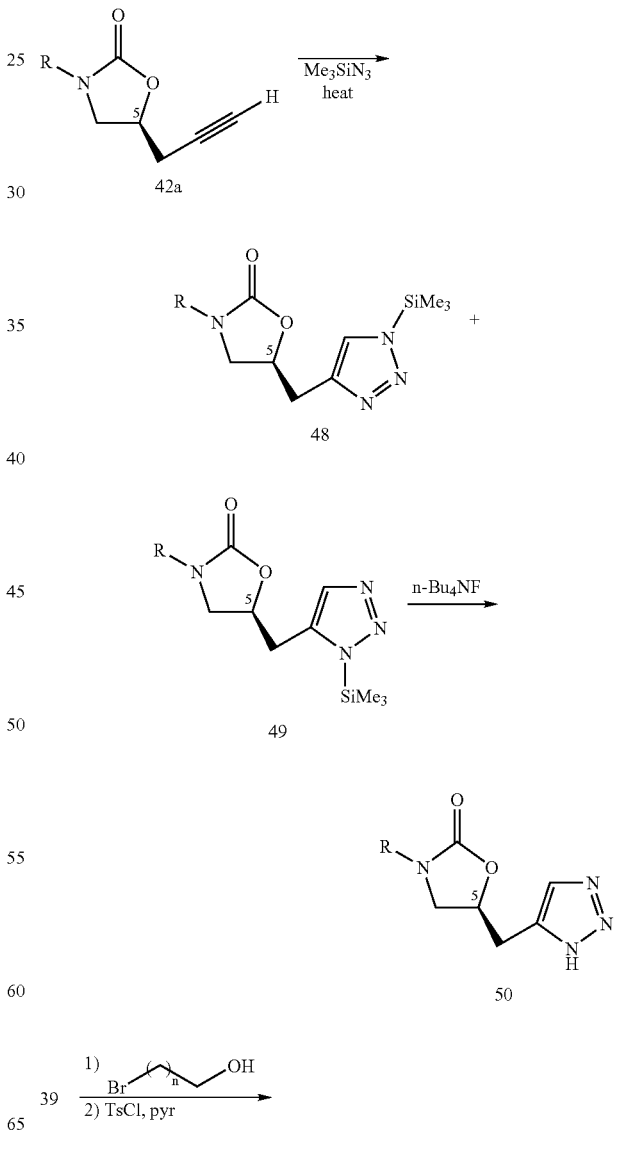

Scheme 7 cycloadducts, where the anti isomer often predominates. As an example, des-methyl erythromycin 39 can be alkylated with ω-halo or ω-sulfonate nitriles to yield nitriles 57. These derivatives can react with azides of type 19 to produce target tetrazoles of type 59 and 60. It is to be understood that the R' group of nitrites 54 may contain the macrolide moiety, or suitable substituted alkyl groups containing an alcohol or protected alcohol that could be converted to a leaving group prior to a final alkylation step with a macrolide amine. Thus, the tetrazoles 55 and 56 could be produced that have as their R' groups alkyl chains bearing a hydroxy group that can be converted into a sulfonate or halide leaving group prior to alkylation with amines similar to 39 to afford products of type 59 and 60. The hydroxy group may be unmasked from a protected hydroxyl group in the compounds 55 and 56 prior to further conversions as mentioned above to afford targets of type 59 and 60.

Scheme 8a illustrates the synthesis of oxazolidinones substituted at C-5 with tetrazolylmethyl derivatives. Azides of type 19 can react with nitrites 54 to produce tetrazoles of type 55 and 56. In a similar fashion to the chemistry described in Scheme 1, this reaction can yield regioisomeric -continued

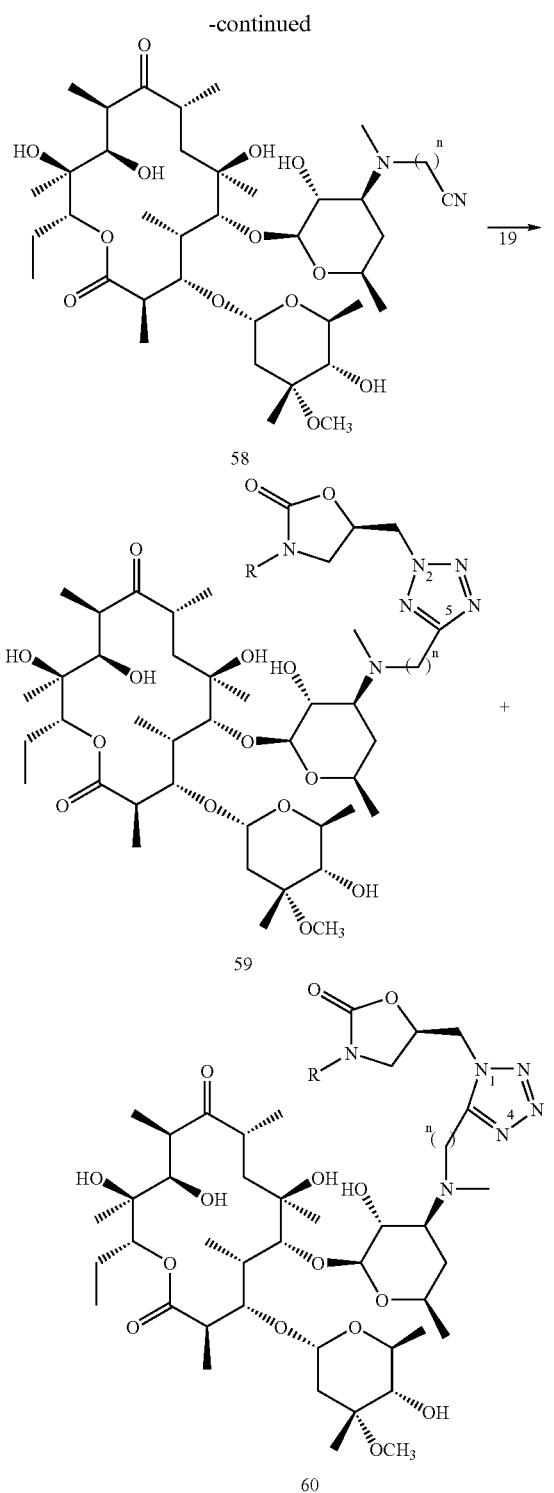

Scheme 8b depicts another strategy to synthesize tetrazoles of type 59 and 60. Azides 19 could undergo cycloaddition to functionalized nitrites of type 57a to afford tetrazole intermediates 55a and 56a. If 55a and 56a contain an appropriate electrophilic group such as a halide or sulfonate, it can react directly with macrolide amines of type 39 (or a suitably protected derivative thereof) to yield targets of type 59 and 60. Alternatively, silyloxy-substituted nitriles 57a could be used during the cycloaddition reaction to afford intermediates of type 55a and 56a where X is a silyloxy group. The silylether protecting group could then be removed from 55a and 56a, and the resultant alcohol converted to an appropriate electrophile (Such as a halide or sulfonate) that would then be suitable for alkylation of macrolide amines of type 39 to give the desired targets.

Scheme 8b

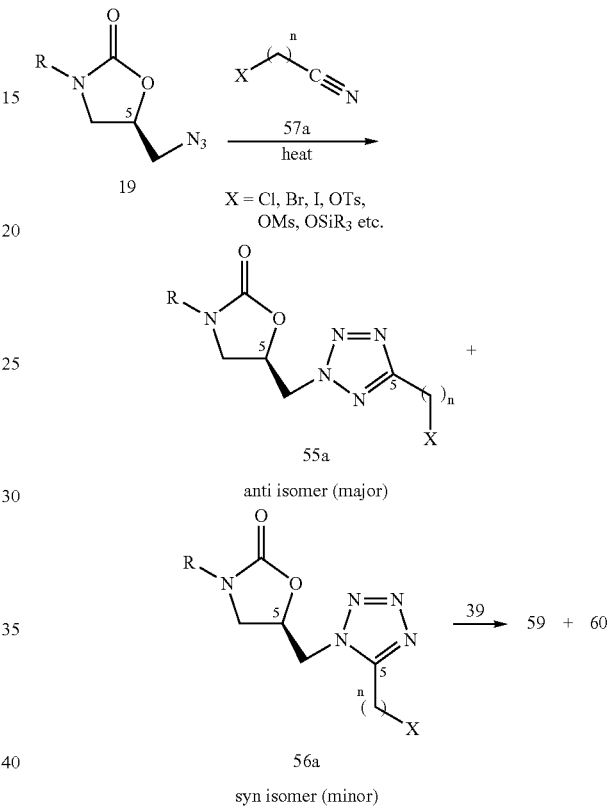

It will be understood that if the alkyl group bearing substituent X in 55a and 56a contains a hydroxyl group, the group could be oxidized to an aldehyde by methods well known to those skilled in the art. Such aldehydes could be used to produce targets of type 59 and 60 via the use of reductive amination conditions employed on these aldehydes and macrolide amines similar to amine 39 (or suitably protected variants thereof).

Scheme 9 illustrates one method of synthesizing pyrazole derivatives of the present invention. Known trityl-protected organolithium derivative 61 (Elguero et al. (1997) SYNTHESIS 563) can be alkylated with electrophiles of type 18a-c to produce pyrazoles of type 62. Cleavage of the trityl group can be accomplished using a variety of acidic reagents, for example, trifluoroacetic acid (TFA), to produce pyrazole 63. Alkylation of 63 with a bromoalcohol of appropriate length, followed by tosylation (or alternate sulfonation or halide formation) can produce electrophiles 64. Alkylation of 39 with 64 produces targets of type 65. The lithium anions derived from heterocycles such as 61 may optionally be converted to copper (or other metallic) derivatives to facilitate their displacement reactions with sulfonates and halides. These anions may also be allowed to react with suitably protected macrolides, such as the per-silylated derivative of 51.

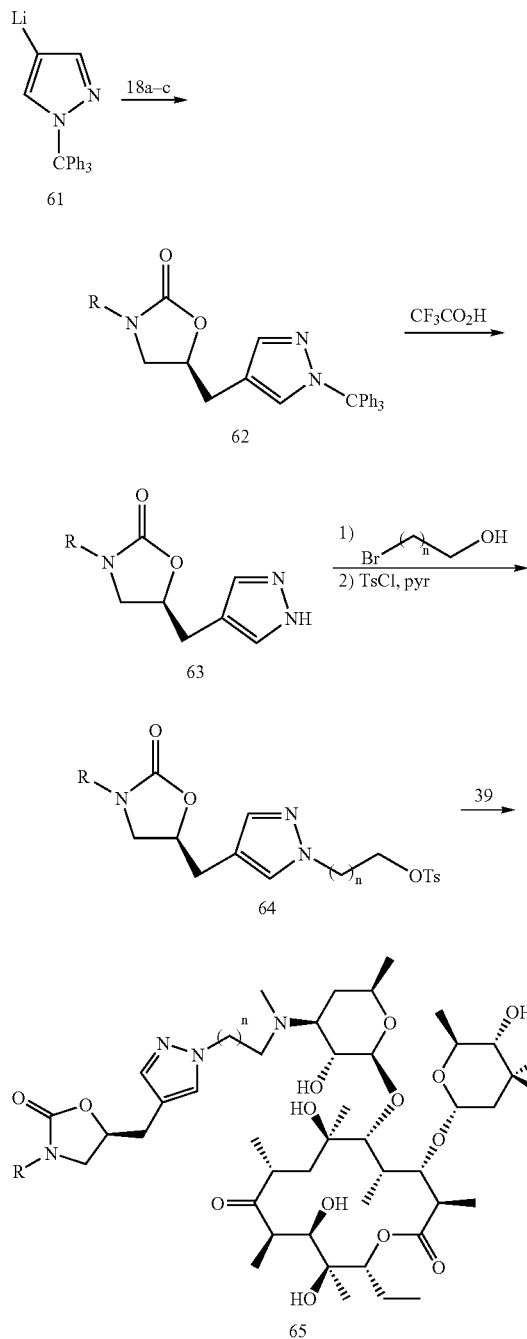

protecting group. The free pyrazoles can undergo direct alkylation with electrophiles 18a-c in a suitable solvent, for example, dimethylformamide, or can be first converted via deprotonation with a suitable base, for example, sodium hydride or n-butyllithium, to the corresponding anion, if a more reactive nucleophile is required. The resultant pyrazole derivatives 67 can be desilylated and converted to tosylates 68 (if a sulfonate strategy is employed), which can serve as electrophiles for subsequent reaction with macrolide aminosaccharides, for example, amine 39, to produce the resultant target 69.

Another approach to intermediates of type 67 can start with alkylation of the known dianion 70 (Hahn et al. (1991) J. HETEROCYCLIC CHEMISTRY 28: 1189) with an appropriate bifunctional linker to produce compounds related to pyrazole 71, which can subsequently be alkylated (with or without prior deprotonation) with electrophiles 18a-c to produce intermediates 67. The n=1 derivatives in this series can be synthesized by trapment of compound 61 with DMF to produce the corresponding aldehyde, and then reduction to the alcohol. Alternatively, methoxymethyl (MOM) chloride or bromide can serve as the alkylating reagent for 61, and hydrolysis of the trityl and MOM groups of the product would yield 4-hydroxymethyl-1,2-pyrazole. The dianion of this pyrazole can be alkylated on nitrogen to produce an alcohol that serves as the precursor for a n=1 tosylate (or other leaving group).

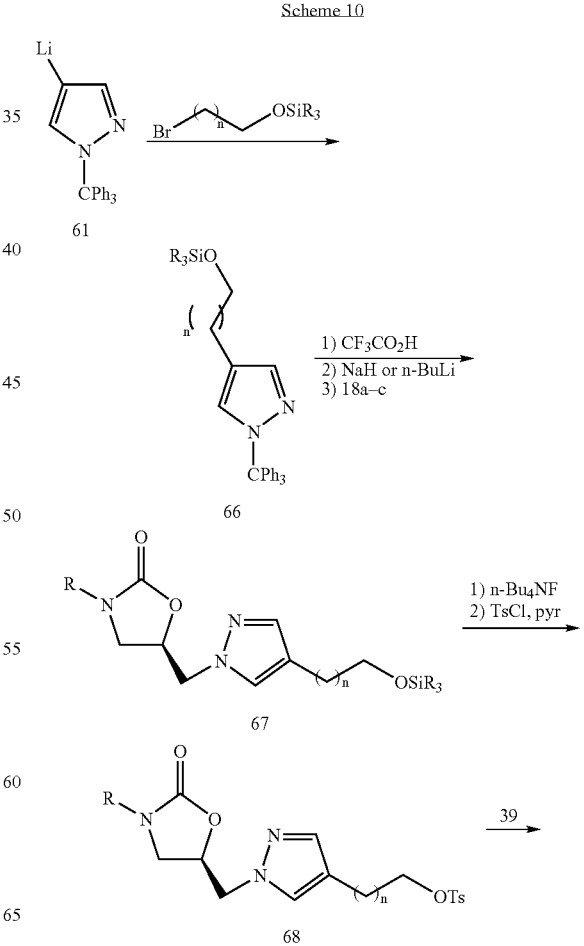

Scheme 10 depicts another method of synthesizing pyrazoles of the present invention. Anions 61 can be alkylated with a bifunctional linker of variable length such as an alkyl halide containing a silyloxy derivative. Alternatively an α,ω dihaloalkyl derivative can be used as the alkylating agent, or a mixed halo-sulfonate can be employed for this purpose. The resulting substituted pyrazoles 66 can be converted to the free pyrazoles by TFA cleavage of the triphenylmethyl -continued

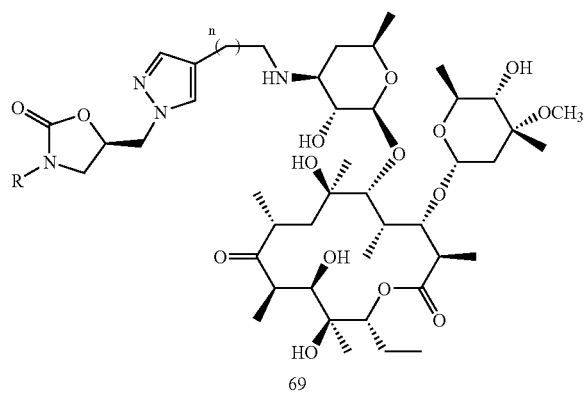
69

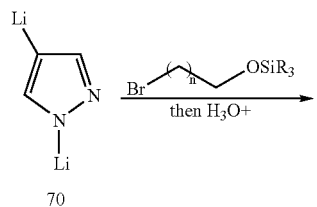
70

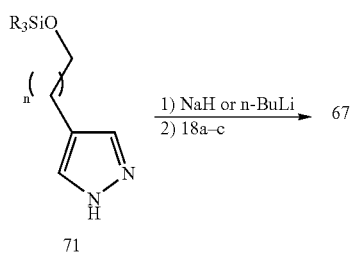
71

Scheme 11 shows an alternate approach for synthesizing pyrazole derivatives of type 69. Alkylation of the anion of a β-dicarbonyl system with appropriate electrophiles similar to tosylate 51 can yield (in the specific example of β-dicarbonyl derivative 72a) products of type 73. Treatment of these intermediates with hydrazine can produce pyrazoles of type 74. Direct alkylation of 74 with electrophiles 18a-c can proceed to produce targets 69. Alternatively, the hydroxyl residues of 74 (and other sensitive functional groups of other macrolide derivatives such as intermediates 39 and 51) can be protected with suitable protecting groups (such as those highlighted in Greene, T. W. and Wuts, P. G. M. supra). and the hydrogen atom on the nitrogen atom of the pyrazole derivative deprotonated with a suitable base, for example, sodium hydride or n-butyllithium. The resulting anion can then be alkylated with electrophiles 18a-c, and the resulting product deprotected to produce targets 69. The use of protecting groups well known to those skilled in the art for the macrolide portions of these intermediates may be required for many of the subsequent reactions shown in the schemes below that involve heteroaryl anion alkylations.

Scheme 11

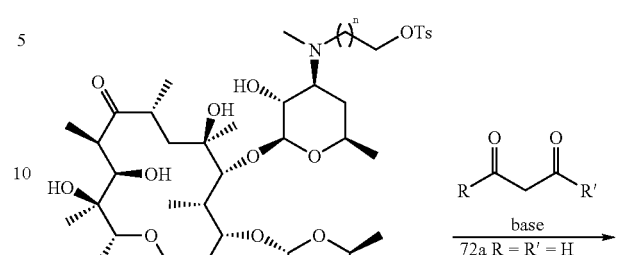
51

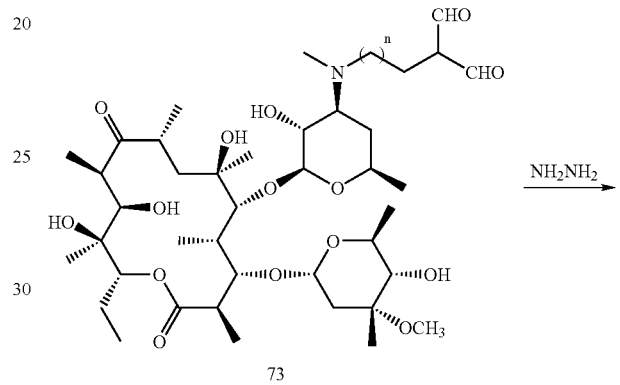
73

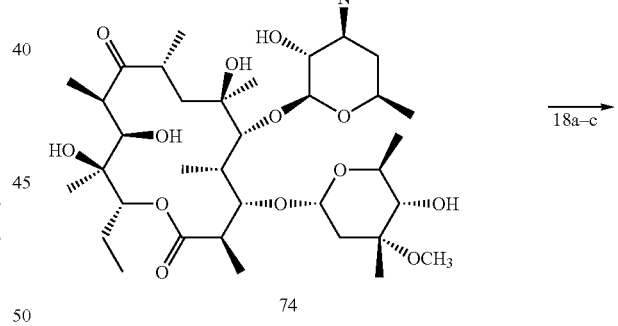
74

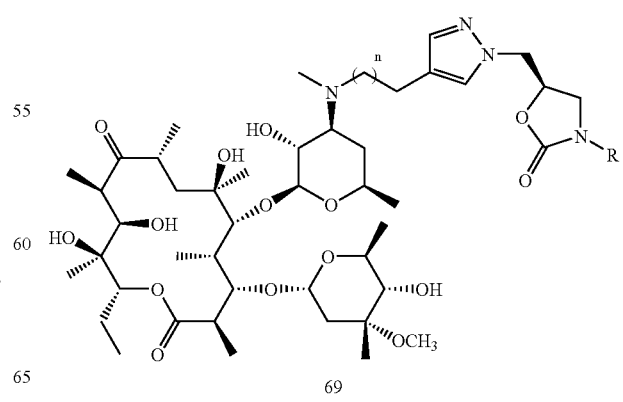
69

Scheme 12 exemplifies a synthesis of imidazoles of the present invention. The known dianion 75 (Katritzky et al. (1989) J. CHEM. SOC. PERKIN TRANS. 1: 1139) can react with electrophiles 18a-c to produce after protic work-up imidazoles of type 76. Direct alkylation of 76 by heating with electrophiles related to 51 in an appropriate organic solvent can yield 1,4-disubstituted imidazoles 77. Alternatively, the imidazole anion formed via deprotonation of the imidazole hydrogen atom of 76 with a suitable base and then alkylation with 51 can also produce 77.

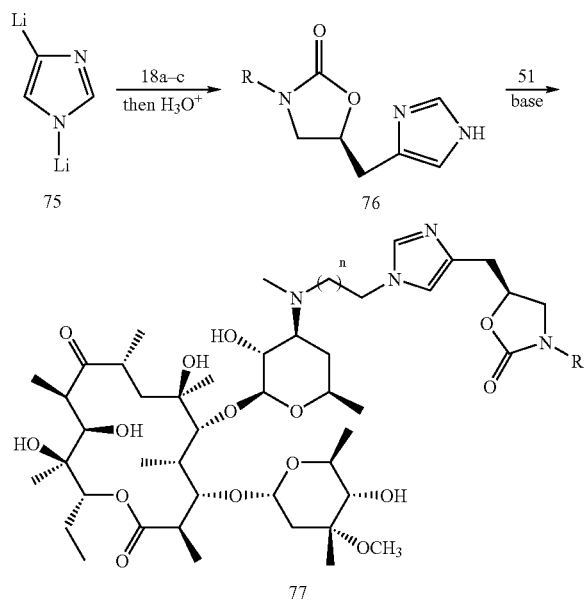

Scheme 13 illustrates another synthesis of imidazoles of the present invention. 4-Bromoimidazole can be deprotonated using, for example, sodium hydride or lithium diisopropylamide, or another suitable organic base, to give anion 78 (or the corresponding lithio derivative). Alkylation of 78 with 18a-c can yield bromoimidazole 79 which can then be subjected to metal-halogen exchange and alkylated with 51 (or a suitably protected derivative of 51) to produce isomeric 1,4-disubstituted imidazoles 80.

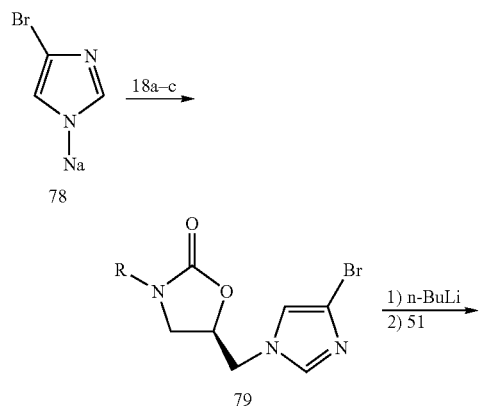

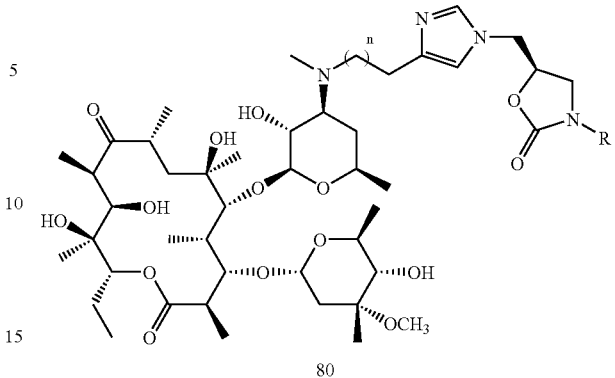

Scheme 14 depicts chemistry suitable for the synthesis of other target imidazole derivatives. The silylethoxymethyl (SEM) protected imidazole can be lithiated at C-2 (Shapiro et al. (1995) HETEROCYCLES 41: 215) and can react with electrophiles 18a-c to produce imidazole intermediates 82. Lithiation of imidazole intermediates 82 at C-4 of the imidazole, followed by alkylation with electrophiles of type 51 (or a suitably protected version such as the per-silylated derivative), and then deprotection of the SEM can produce imidazoles 83.

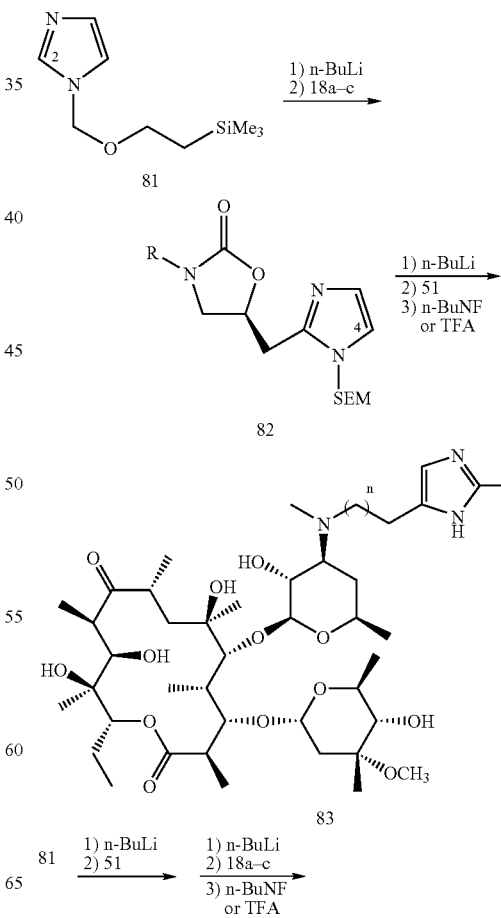

-continued

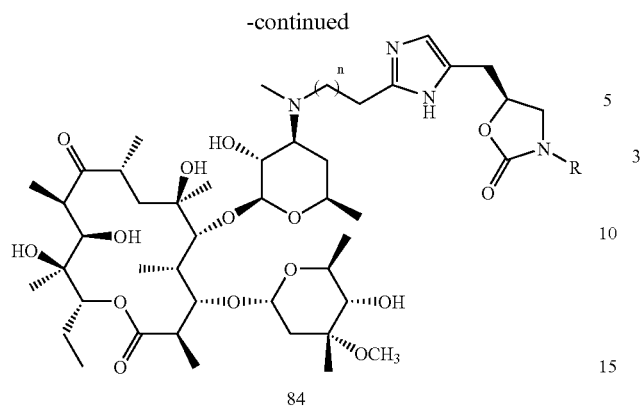

84

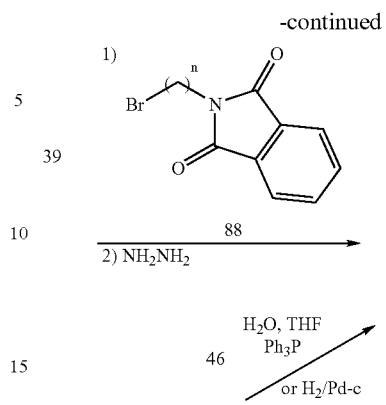

Scheme 15 shows how tosylmethyl isocyanide can be used to make imidazoles of the present invention (Vanelle et al. (2000) EUR. J. MED. CHEM. 35: 157; Horne et al. (1994) HETEROCYCLES 39: 139). Alcohols 17 can be oxidized to produce aldehydes 85 using an appropriate agent such as the Dess-Martin periodinane, or oxalyl chloride/dimethylsulfoxide/triethylamine (Swern oxidation). A variety of chromium complexes can also be used for this oxidation, including, for example, pyridinium dichromate (PDC), pyridinium chlorochromate (PCC), chromium trioxide, and tetrapropylammonium perruthenate. Wittig homologation of 85 can provide aldehyde 86, which can then be converted by tosylmethyl isocyanide to produce intermediate 87. The reaction of 87 with amines 89 (formed via alkylation of amines 39 with bromoalkyl phthalimides 88 followed by hydrazine cleavage, or reduction of azides 46) can produce imidazoles 77.

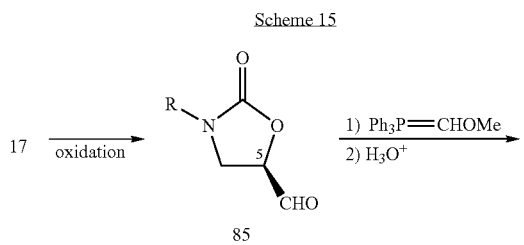

Scheme 15

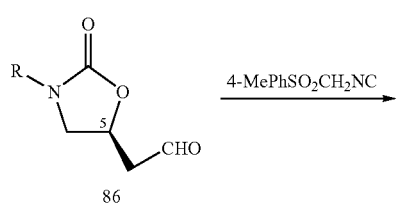

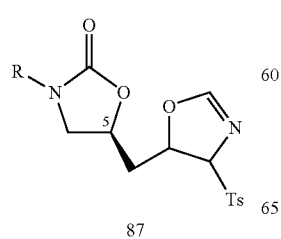

87

Scheme 16 delineates how 1,3 thiazole and 1,3 oxazole derivatives of the present invention can be synthesized. Known dibromo thiazoles and oxazoles 90a and 90b can be selectively metallated at C-2 and alkylated with electrophiles 18a-c to produce intermediates 91a and 91b (Pinkerton et al. (1972) J. HETEROCYCLIC CHEMISTRY 9: 67). Transmetallation with zinc chloride can be employed in the case of the oxazole anion if the anion displays any tendency to ring open prior to its reaction with certain electrophiles. The bromo azoles 91 can be metallated to form the corresponding anion which can undergo alkylation with sulfonates 51 (or the related halides) to produce the final targets 92. Reordering of the sequence of electrophiles in this process permits access to the isomeric thiazoles and oxazoles 93.

Scheme 16

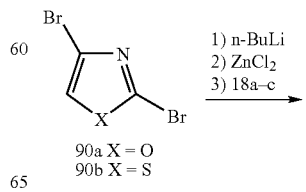

90a X = O
90b X = S

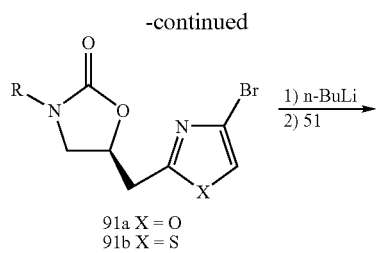
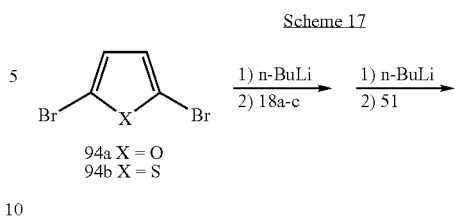

Scheme 17

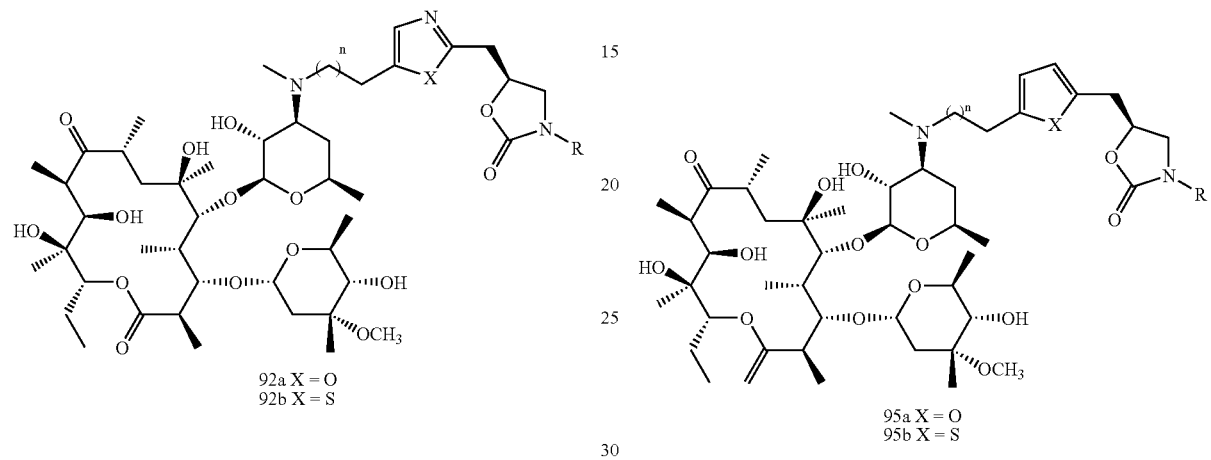

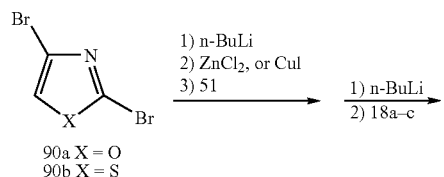

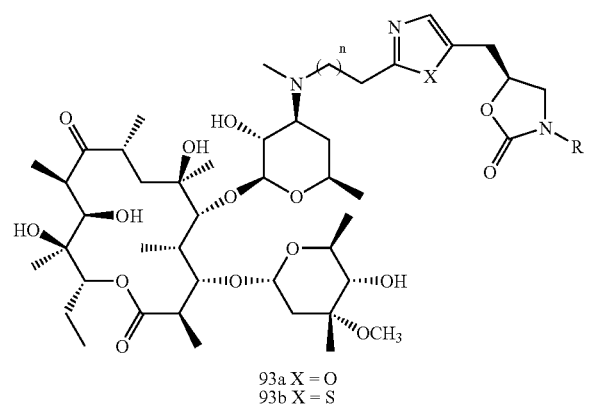

Scheme 17 shows the synthesis of 2,5 disubstituted furan and thiophene derivatives of the invention. Commercially available dibromofuran 94a and dibromothiophene 94b can be monolithiated (Cherioux et al. (2001) ADVANCED FUNCTIONAL MATERIALS 11: 305) and alkylated with electrophiles 18a-c. The monobromo intermediates obtained from this reaction can be lithiated again and then alkylated with electrophiles of type 51 (or a protected version of 51) to produce the final targets 95.

Scheme 18 depicts the synthesis of 2,4 disubstituted furan and thiophene derivatives of the invention. Commercially available furan aldehyde 96a, and the known thiophene aldehyde 96b, can be reduced to the corresponding alcohols and the resulting alcohols converted to a leaving group such as tosylates 97. Alternate sulfonates and halides can be synthesized and used in this fashion. The tosylates 97 can alkylate amine 39 (or a protected version thereof), and the heteroaryl bromide can be converted to a suitable organometallic agent (by reagents such as n-BuLi, or i-Pr$_2$Mg/CuCN). This intermediate organometallic agent can be alkylated with electrophiles 18a-c to produce targets of type 98 where n=1. As the scheme shows, a reordering of steps can be employed involving reduction, silylation, lithiation and then initial alkylation with 18a-c. Desilylation of the alkylation product, followed by tosylation of the alcohol, provides an intermediate that can then be alkylated with amine 39 to produce targets 98. Simple homologation protocols, using the reagents depicted in Scheme 18 or others known to those skilled in the art, can convert the aldehydes 96 to longer chain tosylates such as 99 and 100. The use of these tosylates in the alkylation with 39, and subsequent metal-halogen exchange and alkylation with 18a-c, can yield compounds of type 98 where n=2 and 3. It will be appreciated that longer chain tosylates can be produced using chemistries similar to that depicted in Scheme 18, and that other bifunctional linkers can be used to produce compounds of type 98.

Scheme 18

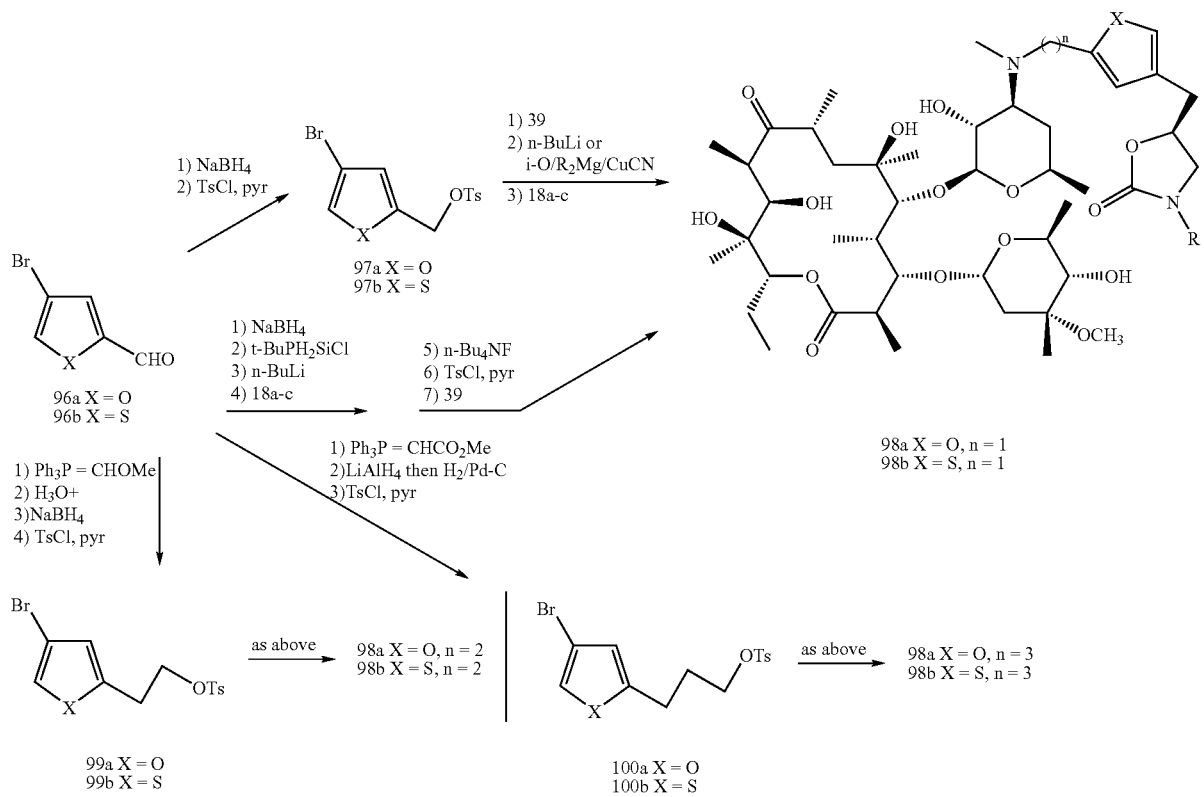

Chemistries similar to that employed above in Scheme 18 can convert known thiophene aldehyde 101 (Eras et al. (1984) J. HETEROCYCLIC CHEMISTRY 21: 215) to produce products of type 104 (Scheme 19). The known acid 102 (Wang et al. (1996) TETRAHEDRON 52: 12137) can be converted to aldehyde 103 by reduction with, for example, borane or lithium aluminum hydride, followed by oxidation of the resultant hydroxymethyl intermediate with, for example, PDC, PCC, or another suitable reagent. Aldehyde 103 can then be converted to produce compounds of type 104.

Scheme 19

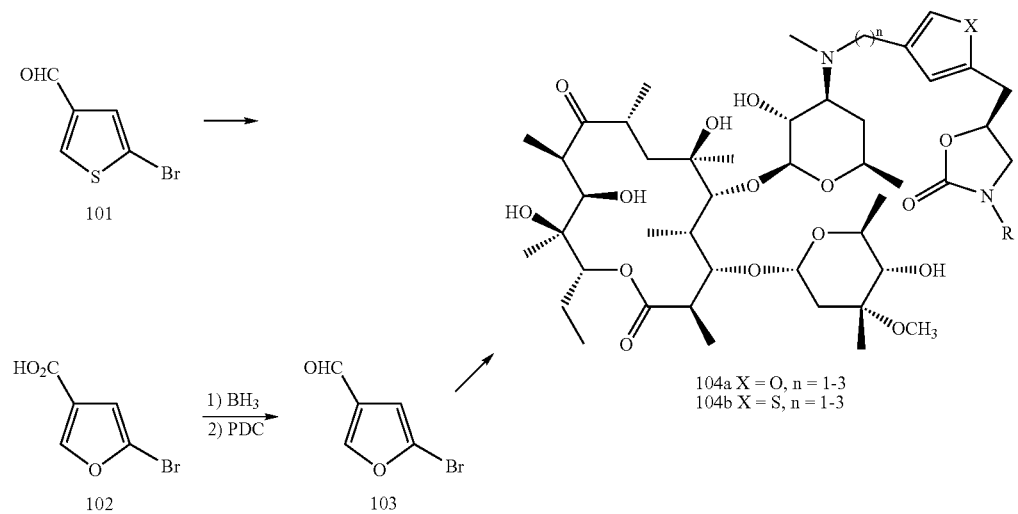

Scheme 20 illustrates the synthesis of 2,5 disubstituted pyrroles of the invention. The BOC-protected dibromopyrrole 105 can be lithiated and alkylated sequentially (Chen et al. (1987) TETRAHEDRON LETT. 28: 6025; Chen et al. (1992) ORG. SYNTH. 70: 151; and Martina et al. (1991) SYNTHESIS 613), and allowed to react with electrophiles 18a-c and 51 (or a suitably protected analogue of 51) to produce, after final BOC deprotection with TFA, disubstituted pyrroles of type 106.

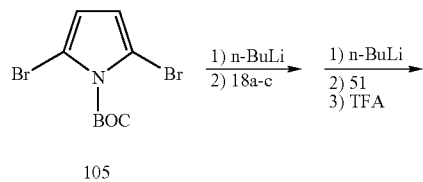

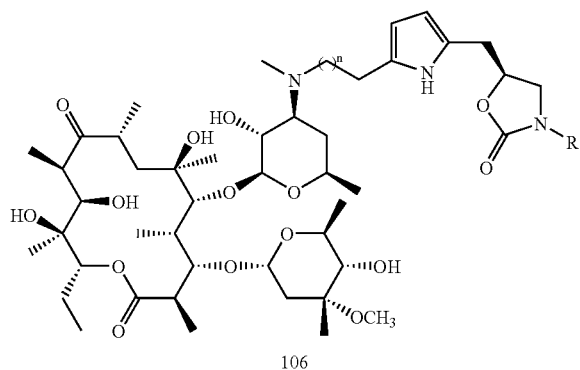

Scheme 21 shows the synthesis of 2,4 disubstituted pyrroles of the invention. Commercially available pyrrole ester 107 can be protected with a suitable protecting group, for example, the BOC group, and the ester function hydrolyzed to the corresponding acid. The resulting acid can then be reduced to the alcohol using, for example, borane to yield an alcohol that can be converted to tosylate 108. Amine 39 (or a suitably protected version of 39, formed for example by silylation of the hydroxyl groups with bis-trimethylsilylacetamide or another silylating reagent) can be alkylated with tosylate 108 to produce an intermediate bromopyrrole. The bromopyrrole can then be converted to an organometallic reagent that can then react with electrophiles 18a-c. The resulting product can then be deprotected with TFA to produce pyrroles 109. The alcohol formed after borane reduction of the acid derived from 107 can then be homologated to tosylates 110 and 111 by chemistries similar to that shown below in Scheme 23. The use of these tosylates in the alkylation strategy can produce target pyrroles of type 109 where n=2 and 3.

An alternative approach is to protect the alcohol functions prior to tosylation, and perform the alkylation of the organometallic derived from the halopyrrole with 18a-c first. For example, silyloxy derivative 112 can be produced from 107, and the organometallic derivative derived from it alkylated with 18a-c to yield silyl ethers 113. Subsequent desilylation and conversion to tosylates 114 provides an electrophile that can be used in the alkylation reaction with 39. A final BOC cleavage can then give pyrroles 109. It is understood that the alcohol precursor of 112 can be homologated, using chemistries similar to that shown below in Scheme 23 and other schemes) to other alkanols that can be tosylated for further reactions with amine 39 (or related macrolide derived amines). Furthermore, the alcohol derived from silyl cleavage of 113 can serve as the starting material for this type of homologation efforts to produce the alkyl tosylates (or halides) required for making targets 109 where n is variable.

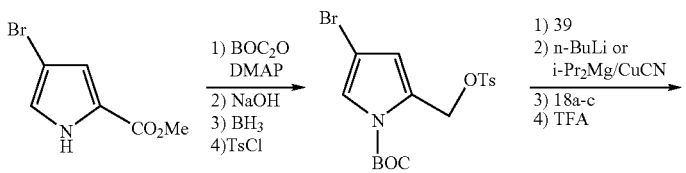

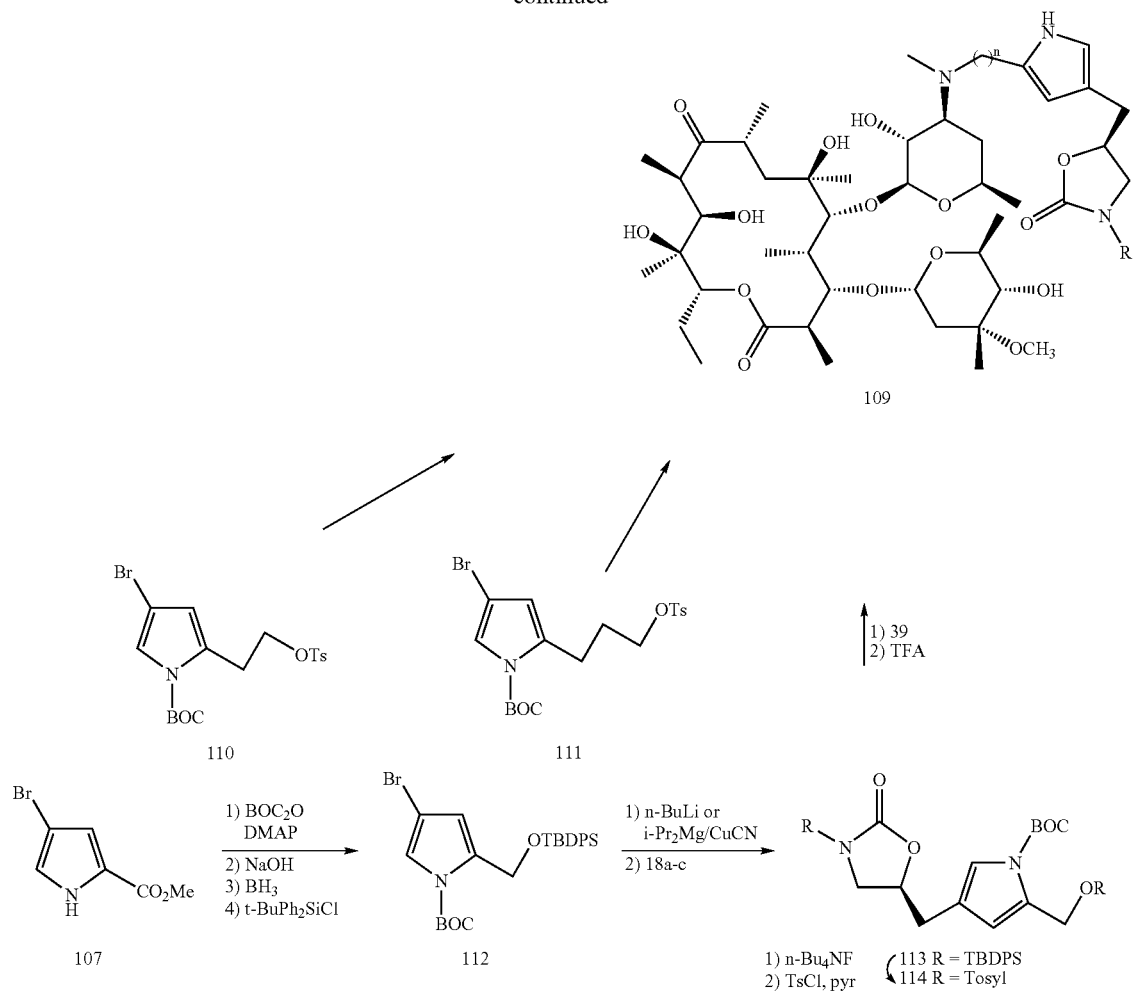

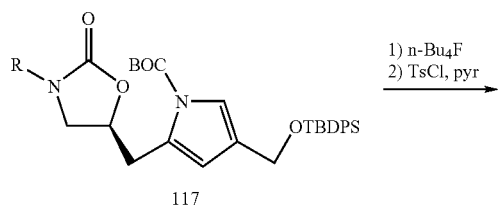

Scheme 22 shows the synthesis of isomeric 2,4 disubstituted pyrroles of the invention. Commercially available pyrrole acid 115 can be protected as the BOC derivative, and the acid function reduced to an alcohol, which can then be protected to produce the silyl ether 116. Deprotonation of 116 with n-butyllithium can occur at the 5 position of the pyrrole ring, and this anion (or that derived from transmetallation with an appropriate metal) can be alkylated with electrophiles 18a-c to produce pyrrole 117. Desilylation of 117, followed by tosylation, alkylation with amine 39, and TFA deprotection of the BOC group can yield pyrroles 119.

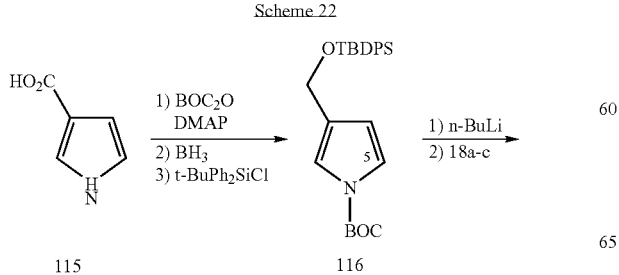

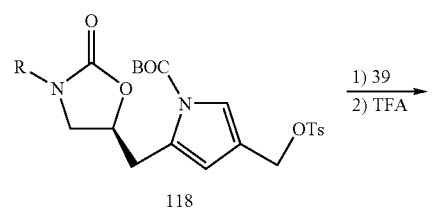

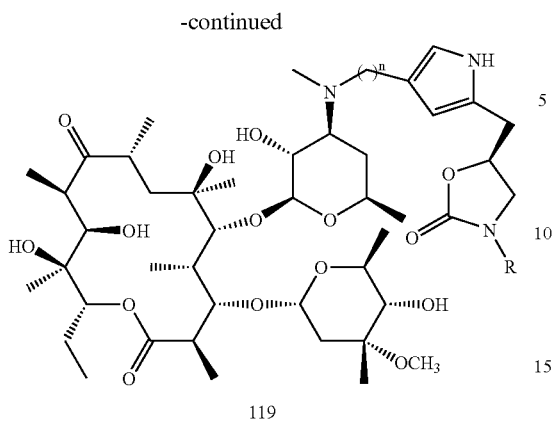

119

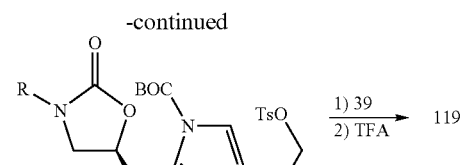

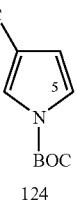

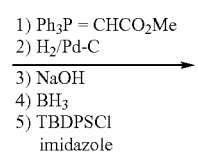

124

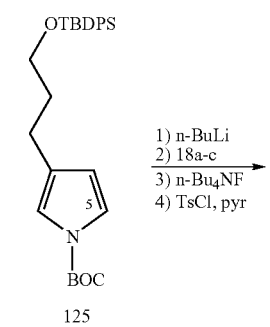

125

Scheme 23 illustrates the synthesis of longer chain tosylates of type 123 and 126 used to alkylate amines of type 39 to produce pyrroles 119. The alcohol 120 derived from protection of 115 followed by borane reduction can be oxidized to aldehyde 124. The Wittig reaction of aldehyde 124 with methoxymethyl triphenylphosphorane is followed by an acid hydrolysis step to produce the homologated aldehyde 121. Reduction and silyl protection can yield 122, which can then be deprotonated, alkylated and then converted to tosylate 123. Aldehyde 124 can undergo a Wittig reaction with carbomethoxymethyl triphenylphosphorane. The Wittig product then is reduced to an alkanol that can then be silylated to produce 125. Conversion of 125 to pyrroles 119 can then occur using the same chemistry employed to provide 119 from 122.

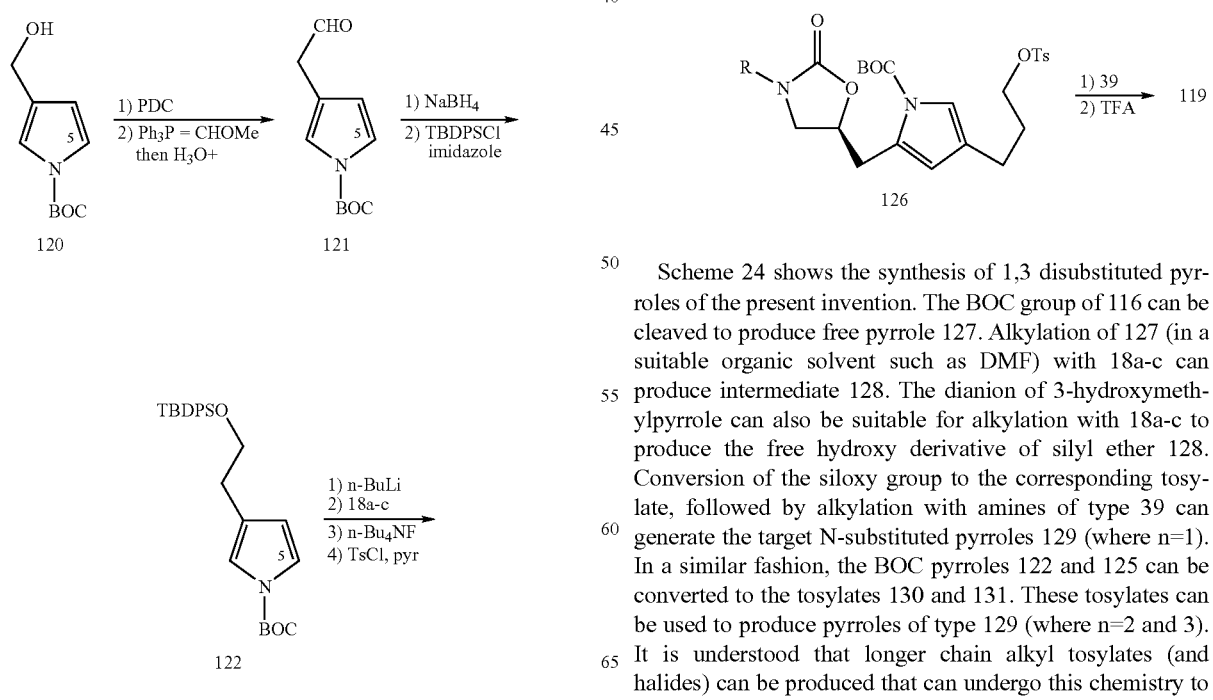

Scheme 24 shows the synthesis of 1,3 disubstituted pyrroles of the present invention. The BOC group of 116 can be cleaved to produce free pyrrole 127. Alkylation of 127 (in a suitable organic solvent such as DMF) with 18a-c can produce intermediate 128. The dianion of 3-hydroxymethylpyrrole can also be suitable for alkylation with 18a-c to produce the free hydroxy derivative of silyl ether 128. Conversion of the siloxy group to the corresponding tosylate, followed by alkylation with amines of type 39 can generate the target N-substituted pyrroles 129 (where n=1). In a similar fashion, the BOC pyrroles 122 and 125 can be converted to the tosylates 130 and 131. These tosylates can be used to produce pyrroles of type 129 (where n=2 and 3). It is understood that longer chain alkyl tosylates (and halides) can be produced that can undergo this chemistry to produce pyrroles 129 where n is >3.

Scheme 24

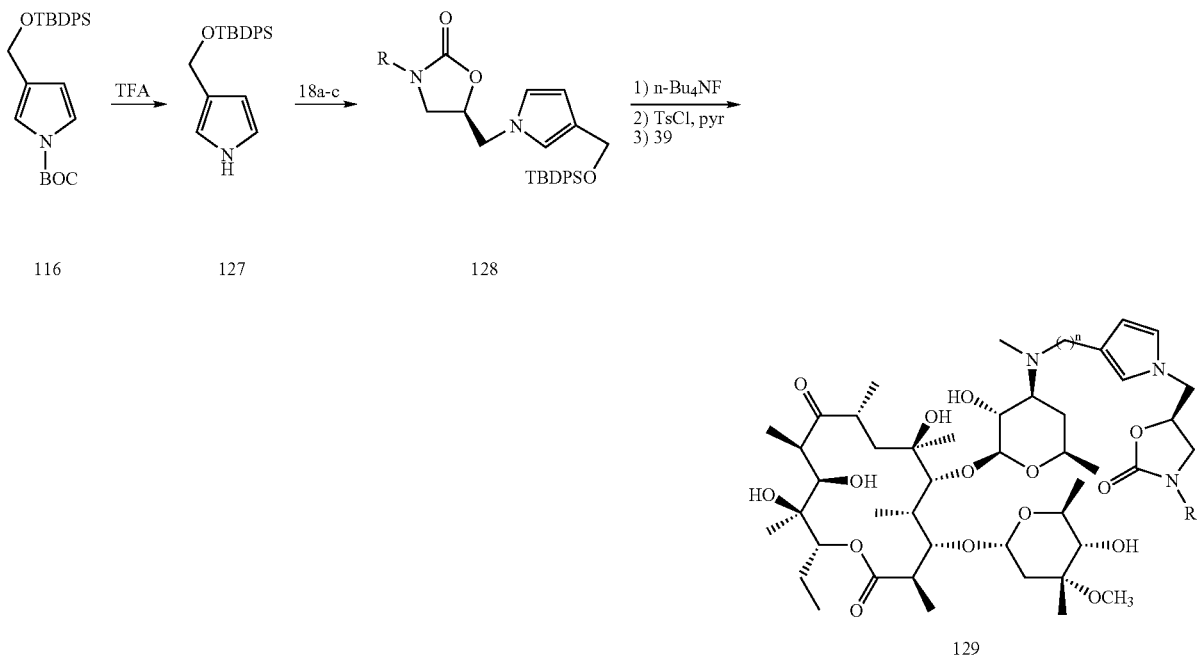

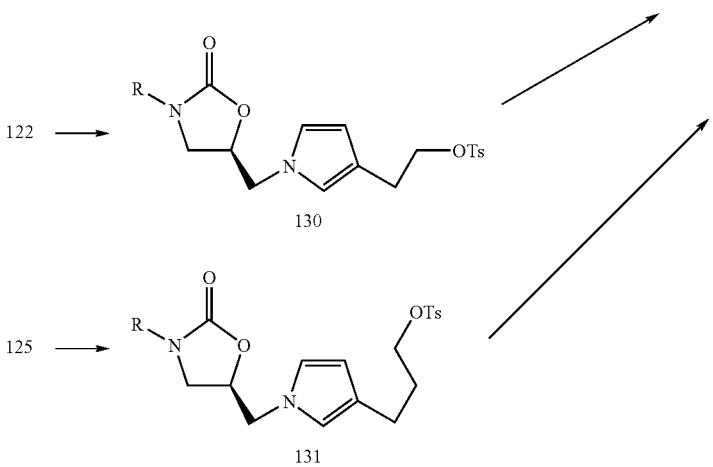

Scheme 25 illustrates the use of hydantoin-like groups as the 5-membered heterocyclic linker between the G groups and the $R_1$ moieties of the present invention. Electrophiles of type 18a-c can alkylate anions derived from hydantoins to produce compounds of the present invention. For example, 3-substituted hydantoins of type 132 can be purchased and treated with an appropriate base to generate the corresponding imide anion. The resulting anions can be alkylated with electrophiles similar (but not limited) to intermediates 18a-c to produce hydantoin derivatives 134. Alternatively, 1-substituted hydantoins of type 133 can be purchased or prepared, and treated with base and electrophile to yield isomeric hydantoin derivatives 135. It is understood that such hydantoins can have, for example, at optional locations, thiocarbonyl functionalities in place of the illustrated carbonyl groups. Such compounds can be prepared by treatment of the oxy-hydantoins with Lawesson's reagent, elemental sulfur, phosphorus pentasulfide, and other reagents commonly used in the art to perform this transformation.

Alternatively, such thiohydantoins can be synthesized selectively by sequential synthetic steps known in the art. The R' group of 132 and 133 may represent a protecting group function, for example, benzyl, alkoxybenzyl, benzyloxycarbonyl, t-butoxycarbonyl, that is compatible with the alkylation step. Such a protecting group can subsequently be removed from products 134 and 135, yielding products where the R' group is a hydrogen atom. These intermediates can be used to produce various target molecules by their treatment with base and then subsequent exposure to appropriate electrophiles.

Scheme 25

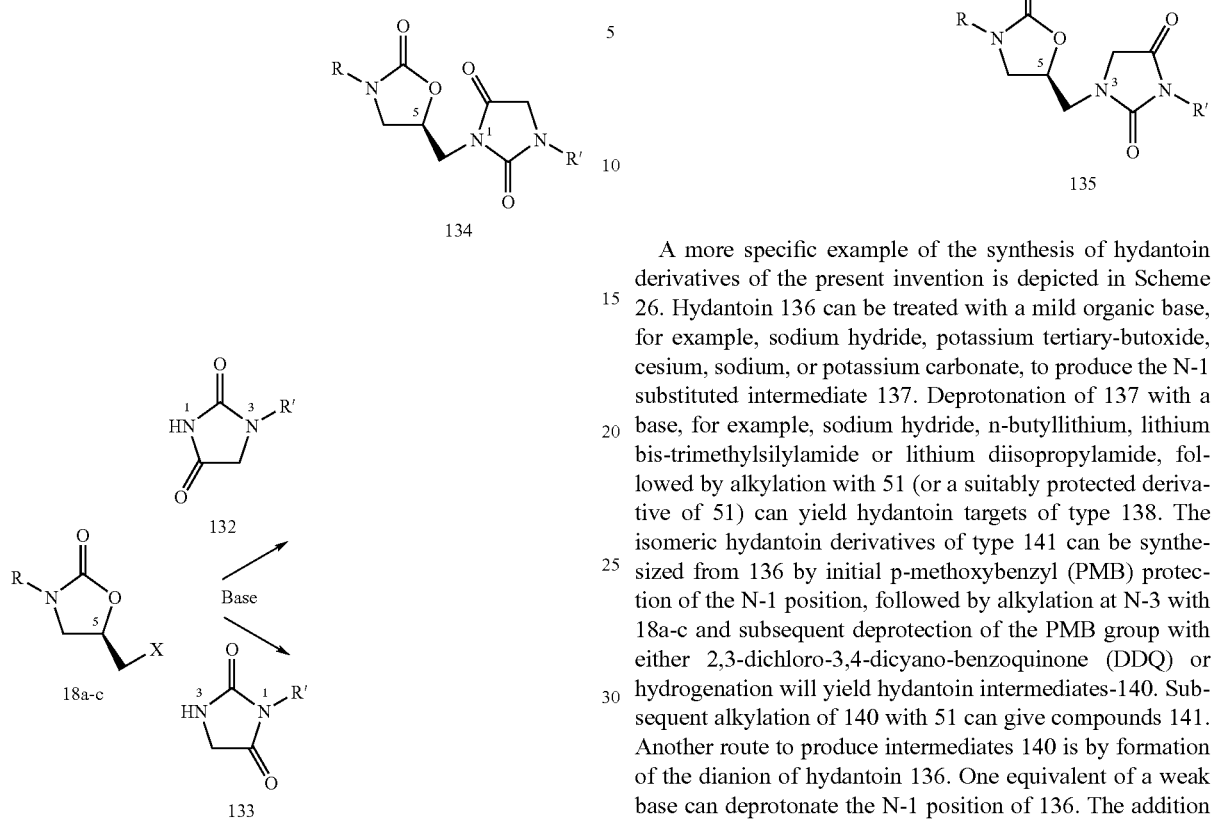

A more specific example of the synthesis of hydantoin derivatives of the present invention is depicted in Scheme 26. Hydantoin 136 can be treated with a mild organic base, for example, sodium hydride, potassium tertiary-butoxide, cesium, sodium, or potassium carbonate, to produce the N-1 substituted intermediate 137. Deprotonation of 137 with a base, for example, sodium hydride, n-butyllithium, lithium bis-trimethylsilylamide or lithium diisopropylamide, followed by alkylation with 51 (or a suitably protected derivative of 51) can yield hydantoin targets of type 138. The isomeric hydantoin derivatives of type 141 can be synthesized from 136 by initial p-methoxybenzyl (PMB) protection of the N-1 position, followed by alkylation at N-3 with 18a-c and subsequent deprotection of the PMB group with either 2,3-dichloro-3,4-dicyano-benzoquinone (DDQ) or hydrogenation will yield hydantoin intermediates-140. Subsequent alkylation of 140 with 51 can give compounds 141. Another route to produce intermediates 140 is by formation of the dianion of hydantoin 136. One equivalent of a weak base can deprotonate the N-1 position of 136. The addition of another equivalent of a strong base, for example, n-butyllithium, to the initial anion can deprotonate it again, this time at N-3. Alkylation can occur at the more reactive position (N-3) to again produce hydantoins 140.

Scheme 26

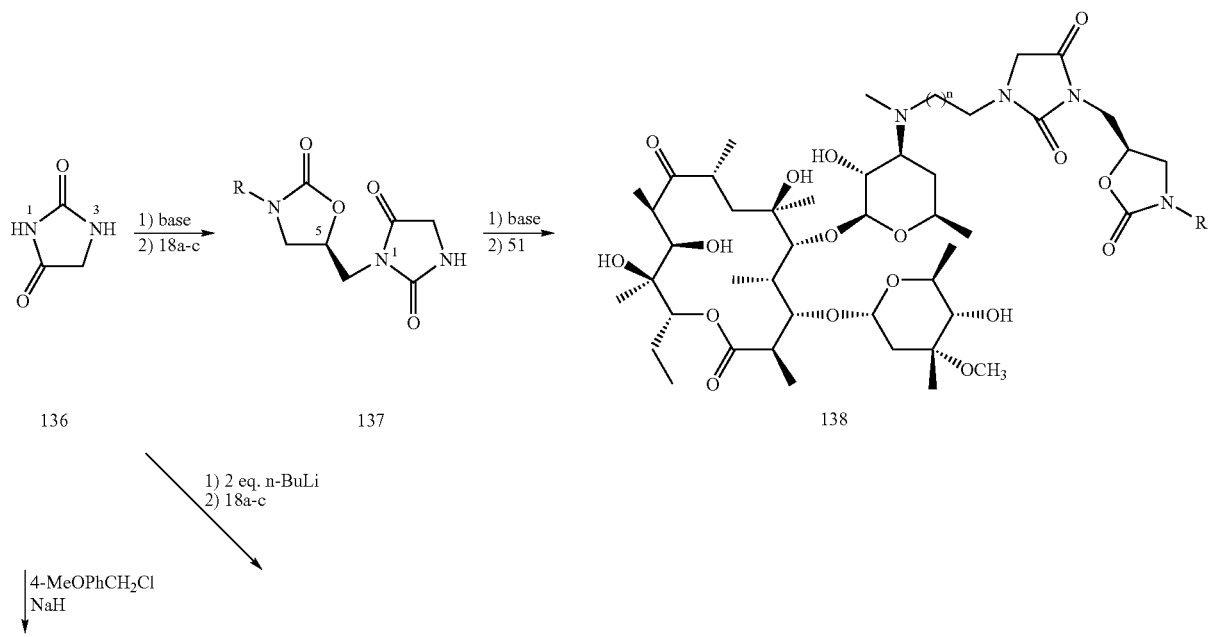

-continued

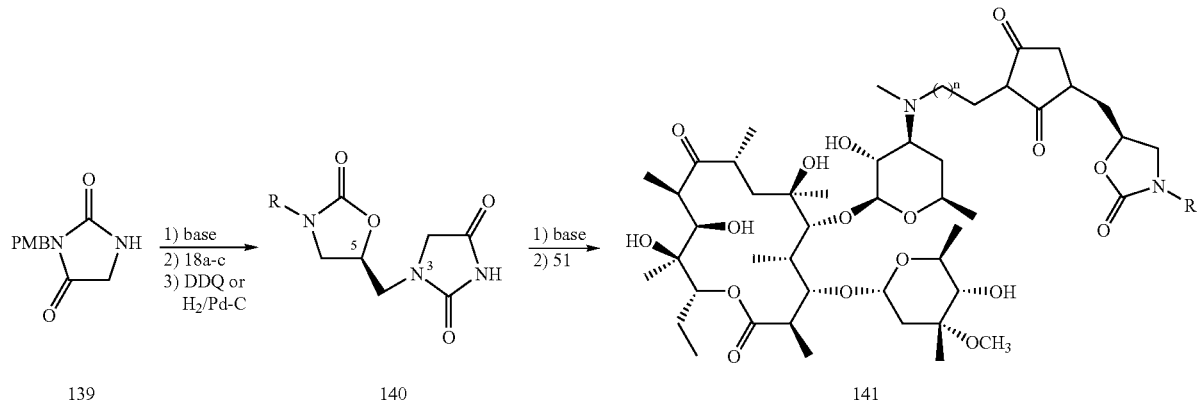

Scheme 27 illustrates how isoxazolidinone derivatives of type 515 of the present invention can be synthesized. Macrolide 171 (or any other macrolide amine) can be converted to alkyl azide 510 (where $n \geq 2$) via use of an appropriate alkyl halide or sulfonate electrophile of type 511. A variety of isoxazolidinone derivatives of type 512 (for syntheses of these types of derivatives see US Patent Application 20020094984) can be alkylated with propargyl electrophiles of type 513 to yield alkynes of type 514. The cycloaddition of azides 510 and alkynes 514 yields target isoxazolidinone derivatives 515. It is to be understood that alternative macrolides and isoxazolidinone derivatives can be used in this chemistry, and alternate chain lengths of the various electophiles can be utilized to produce other compounds of the present invention. It is intended that such alternate targets are within the scope of the present invention.

Scheme 27

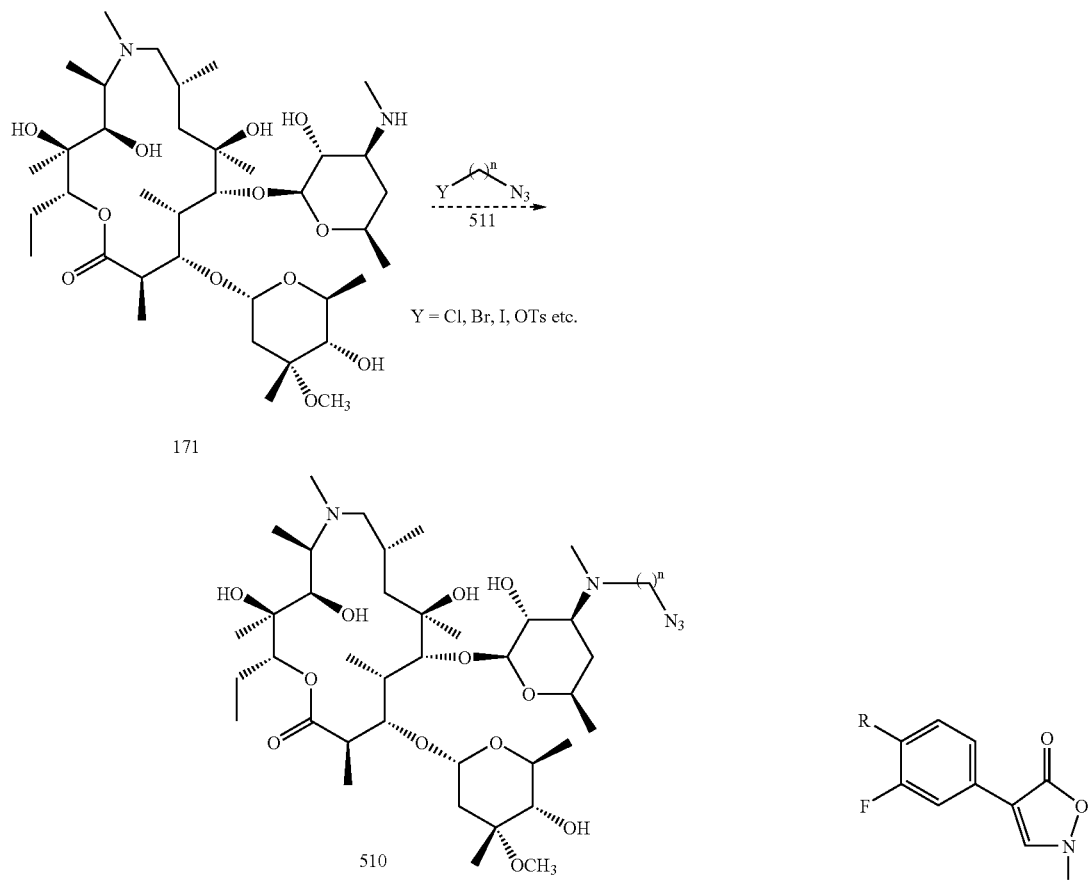

-continued

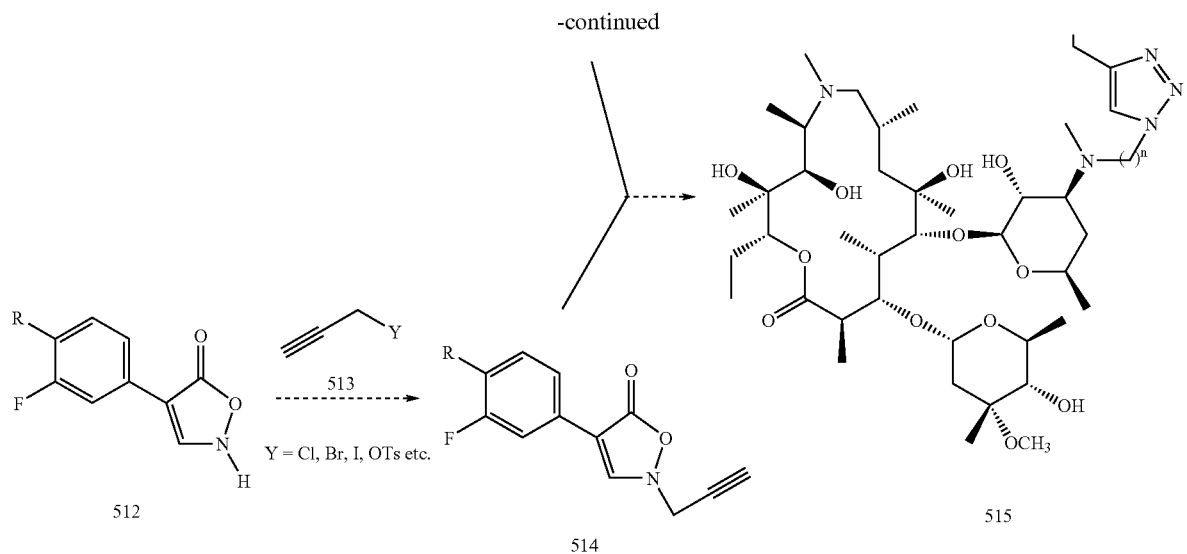

In addition to the foregoing, compounds disclosed in the following publications, patents and patent applications are suitable intermediates for preparation of the compounds of this invention:

Tucker, J. A. et al., *J. Med. Chem.*, 1998, 41, 3727; Gregory, W. A. et al., *J. Med. Chem.*, 1990, 33, 2569; Genin, M. J. et al., *J. Med. Chem.*, 1998, 41, 5144; Brickner, S. J. et al., *J. Med. Chem.*, 1996, 39, 673. Barbachyn, M. R. et al., *J. Med. Chem.*, 1996, 39, 680; Barbachyn, M. R. et al., *Bioorg. Med. Chem. Lett.*, 1996, 6, 1003; Barbachyn, M. R. et al., *Bioorg. Med Chem. Lett.*, 1996, 6, 1009; Grega, K. C. et al., *J. Org. Chem.*, 1995, 60, 5255; Park, C.-H. et al., *J. Med. Chem.*, 1992, 35, 1156; Yu, D. et al., *Bioorg. Med. Chem. Lett.*, 2002, 12, 857; Weidner-Wells, M. A. et al., *Bioorg Med. Chem.*, 2002, 10, 2345; and Cacchi, S. et al., *Org. Lett.*, 2001, 3, 2539. U.S. Pat. Nos. 4,801,600; 4,948,801; 5,736,545; 6,362,189; 5,523,403; 4,461,773; 6,365,751; 6,124,334; 6,239,152; 5,981,528; 6,194,441; 6,147,197; 6,034,069; 4,990,602; 6,124,269; and 6,271,383. U.S. Pat. Application 2001/0046992, PCT Application and publications WO96/15130; WO95/14684; WO 99/28317; WO 98/01447; WO 98/01446; WO 97/31917; WO 97/27188; WO 97/10223; WO 97/09328; WO 01/46164; WO 01/09107; WO 00/73301; WO 00/21960; WO 01/81350; WO 97/30995; WO 99/10342; WO 99/10343; WO 99/64416; WO 00/232917; and WO 99/64417, European Patents EP 0312000 B1; EP 0359418 A1; EP 00345627; EP 1132392; and EP 0738726 A1.

4. Characterization of Compounds of the Invention

Compounds designed, selected and/or optimized by methods described above, once produced, may be characterized using a variety of assays known to those skilled in the art to determine whether the compounds have biological activity. For example, the molecules may be characterized by conventional assays, including but not limited to those assays described below, to determine whether they have a predicted activity, binding activity and/or binding specificity.

Furthermore, high-throughput screening may be used to speed up analysis using such assays. As a result, it may be possible to rapidly screen the molecules described herein for activity, for example, as anti-cancer, anti-bacterial, anti-fungal, anti-parasitic or anti-viral agents. Also, it may be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies. A variety of binding assays may be useful in screening new molecules for their binding activity. One approach includes surface plasmon resonance (SPR) which can be used to evaluate the binding properties molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor RTM from Pharmacia Biosensor, Piscatawy, N.J.) provides a focused beam of polychromatic light to the interface between a gold film (provided as a disposable biosensor "chip") and a buffer compartment that can be regulated by the user. A 100 nm thick "hydrogel" composed of carboxylated dextran which provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies which are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest may also be characterized as a modulator (for example, an inhibitor of protein synthesis) of the functional activity of the ribosome or ribosomal subunit.

Furthermore, more specific protein synthesis inhibition assays may be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3$H leucine or $^{35}$S methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

Furthermore, the compounds may be assayed for antiproliferative or anti-infective properties on a cellular level. For example, where the target organism is a micro-organism, the activity of compounds of interest may be assayed by growing the micro-organisms of interest in media either containing or lacking the compound. Growth inhibition may be indicative that the molecule may be acting as a protein synthesis inhibitor. More specifically, the activity of the compounds of interest against bacterial pathogens may be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays may be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition. NCCLS Document M100-S12/M7 (ISBN 1-56238-394-9).

The compounds may be assayed for anti-inflammatory properties on a cellular level, for example, to determine the inhibition of cytokine production. Further, the compounds may be assessed for calcium flux in CHO cells expressing the human motilin receptor or in animal models for prokinetic behavior such as the rabbit duodenum strip model known to display contractility when a motilin agonist is applied.

5. Formulation and Administration

The compounds of the invention may be useful in the prevention or treatment of a variety of human or other animal disorders, including for example, bacterial infection, fungal infections, viral infections, parasitic diseases, and cancer. It is contemplated that, once identified, the active molecules of the invention may be incorporated into any suitable carrier prior to use. The dose of active molecule, mode of administration and use of suitable carrier will depend upon the intended recipient and target organism. The formulations, both for veterinary and for human medical use, of compounds according to the present invention typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations may conveniently be presented in dosage unit form and may be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's *Pharmaceutical Sciences*, (Gennaro, A., ed.), Mack Pub., (1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, hydrogenated naphthalenes, and the like. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration may be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug may also be administered in the form of a bolus, electuary or paste. A tablet may be made by compressing or moulding the drug optionally with one or more accessory ingredients. Compressed tablets may be prepared by compressing, in a suitable machine, the drug in a free-flowing form such as a powder or granules, optionally mixed by a binder, lubricant, inert diluent, surface active or dispersing agent. Moulded tablets may be made by moulding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration may be in the form of a sterile aqueous preparation of the drug which may be in microcrystalline form, for example, in the form of an aqueous microcrystalline suspension. Liposomal formulations or biodegradable polymer systems may also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect may be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intrvenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in therapeutically effective amounts, e.g., amounts which provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

The active compound may be administered directly to a tissue locus by applying the compound to a medical device that is placed in contact with the tissue. For example, an active compound may be applied to a stent at the site of vascular injury. Stents can be prepared by any of the methods well known in the pharmaceutical art. See, e.g., Fattori, R. and Piva, T., "Drug-Eluting Stents in Vascular Intervention," *Lancet*, 2003, 361, 247-249; Morice, M. C., "A New Era in the Treatment of Coronary Disease?" *European Heart Journal*, 2003, 24, 209-211; and Toutouzas, K. et al., "Sirolimus-Eluting Stents: A Review of Experimental and Clinical Findings," *Z. Kardiol.*, 2002, 91(3), 49-57. The stent may be fabricated from stainless steel or another bio-compatible metal, or it may be made of a bio-compatible polymer. The active compound may be linked to the stent surface, embedded and released from polymer materials coated on the stent, or surrounded by and released through a carrier which coats or spans the stent. The stent may be used to administer single or multiple active compounds to tissues adjacent to the stent.

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a drug as well as tailoring the dosage and/or therapeutic regimen of treatment with the drug.

In therapeutic use for treating, or combating, bacterial infections in mammals, the compounds or pharmaceutical compositions thereof will be administered orally, parenterally and/or topically at a dosage to obtain and maintain a concentration, that is, an amount, or blood-level or tissue level of active component in the animal undergoing treatment which will be anti-microbially effective. The term "effective amount" is understood to mean that the compound of the invention is present in or on the recipient in an amount sufficient to elicit biological activity, for example, anti-microbial activity, anti-fungal activity, anti-viral activity, anti-parasitic activity, anti-proliferative activity, anti-inflammatory activity or ameliorating a symptom of a gastrointestinal motility disorder. Generally, an effective amount of dosage of active component will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered may be increased beyond the above upper level in order to rapidly achieve the desired blood-level or tissue level, or the initial dosage may be smaller than the optimum and the daily dosage may be progressively increased during the course of treatment depending on the particular situation. If desired, the daily dose may also be divided into multiple doses for administration, for example, 2-4 four times per day.

In light of the foregoing, the specific examples presented below are illustrative only and are not intended to limit the scope of the invention. Other generic and specific configurations will be apparent to those persons skilled in the art.

6. EXAMPLES

Some of the abbreviations used in the following experimental details of the synthesis of the examples are defined below:
hr=hour(s)
min=minute(s)
mol=mole(s)
mmol=millimole(s)
M=molar
μM=micromolar
g=gram(s)
μg=microgram(s)
rt=room temperature
L=liter(s)
mL=milliliter(s)
Et$_2$O=diethyl ether
THF=tetrahydrofuran
DMSO=dimethyl sulfoxide
EtOAc=ethyl acetate
Et$_3$N=triethylamine
i-Pr$_2$NEt=diisopropylethylamine
CH$_2$Cl$_2$=methylene chloride
CHCl$_3$=chloroform
CDCl$_3$=deuterated chloroform
CCl$_4$=carbon tetrachloride
MeOH=methanol
CD$_3$OD=deuterated methanol
EtOH=ethanol
DMF=dimethylformamide
BOC=t-butoxycarbonyl
CBZ=benzyloxycarbonyl
TBS=t-butyldimethylsilyl
TBSCl=t-butyldimethylsilyl chloride
TFA=trifluoroacetic acid
DBU=diazabicycloundecene
TBDPSCl=t-butyldiphenylchlorosilane
Hunig's Base=N,N-diisopropylethylamine
DMAP=N,N-diisopropylethylamine
CuI=copper (I) iodide
MsCl=methanesulfonyl chloride
NaN$_3$=sodium azide
Na$_2$SO$_4$=sodium sulfate
NaNCO$_3$=sodium bicarbonate
NaOH=sodium hydroxide
MgSO$_4$=magnesium sulfate
K$_2$CO$_3$=potassium carbonate
KOH=potassium hydroxide
NH$_4$OH=ammonium hydroxide
NH$_4$Cl=ammonium chloride
SiO$_2$=silica
Pd—C=palladium on carbon
Pd(dppf)Cl$_2$=dichloro[1,1'-bis(diphenylphosphino)ferrocene]palladium (II)

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

Example 1

Exemplary Oxazolidinone Derivatives

Exemplary compounds synthesized in accordance with the invention are listed in Table 2.

TABLE 2

| Compound Number | Structure |
|---|---|
| 142 | 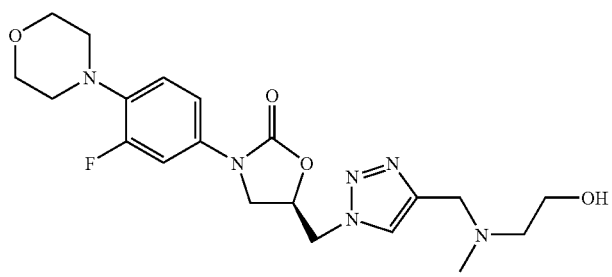 |

TABLE 2-continued
| Compound Number | Structure |
|---|---|
| 143 | 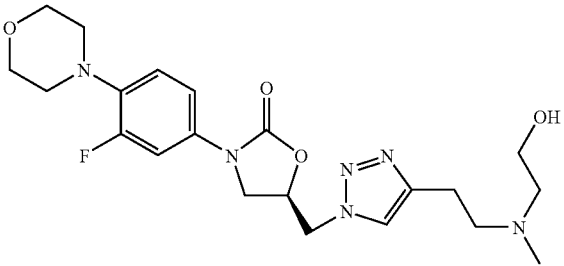 |
| 144 | 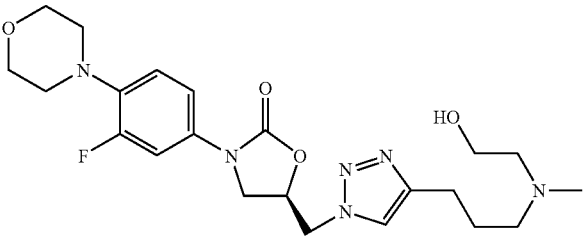 |
| 145 | 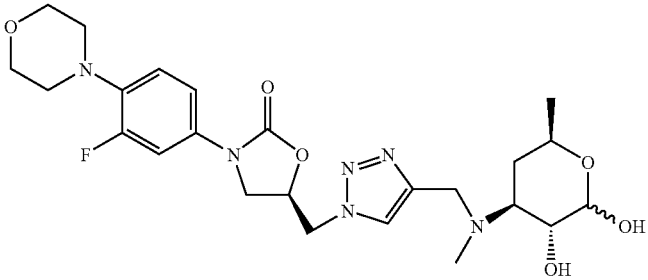 |
| 146 | 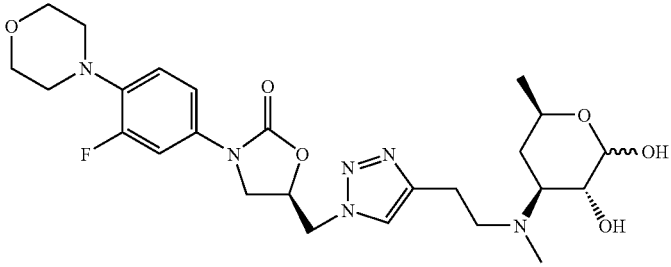 |
| 147 | 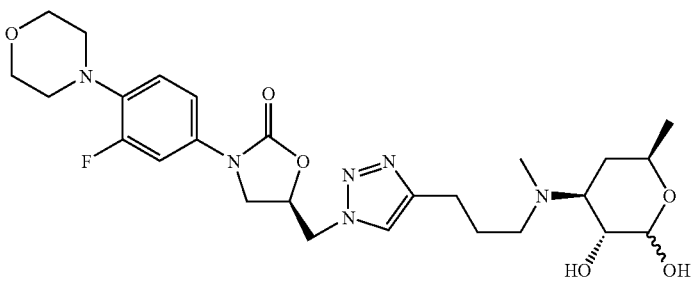 |

TABLE 2-continued

| Compound Number | Structure |
| --- | --- |
| 148 | 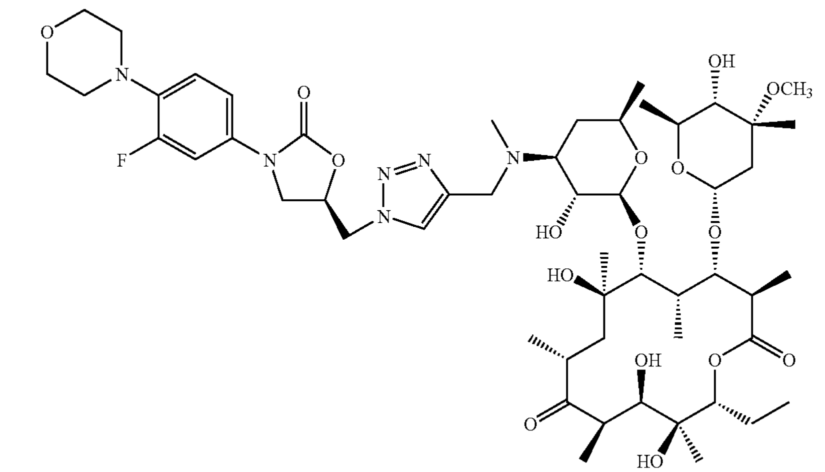 |
| 149 | 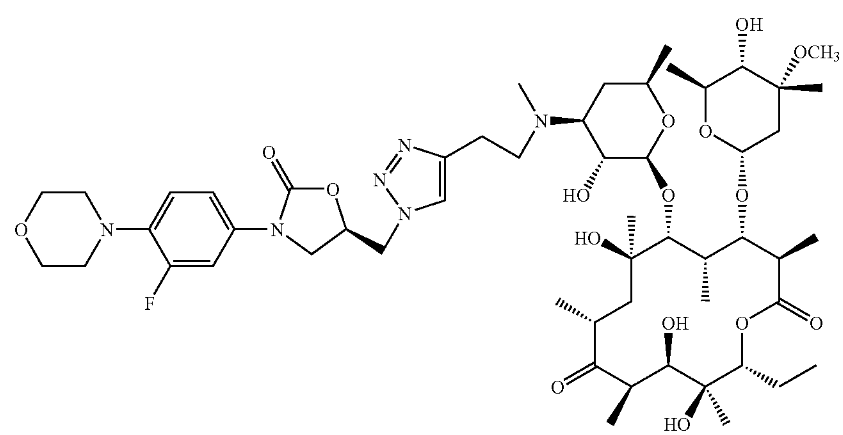 |
| 150 | 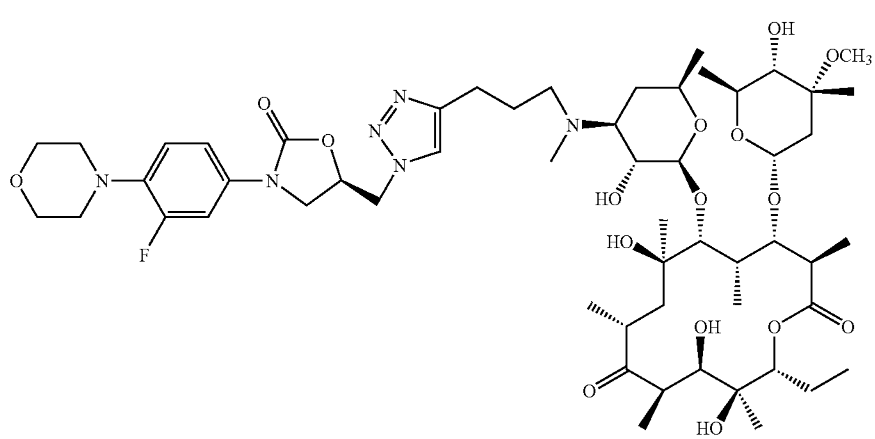 |

TABLE 2-continued
| Compound Number | Structure |
|---|---|
| 151 | 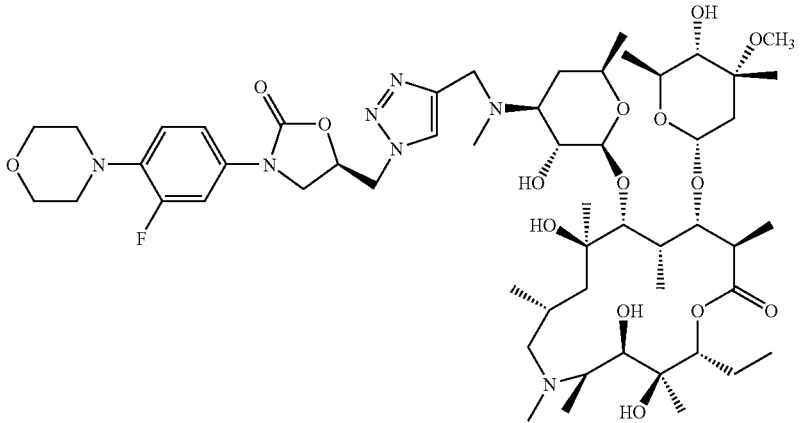 |
| 152 | 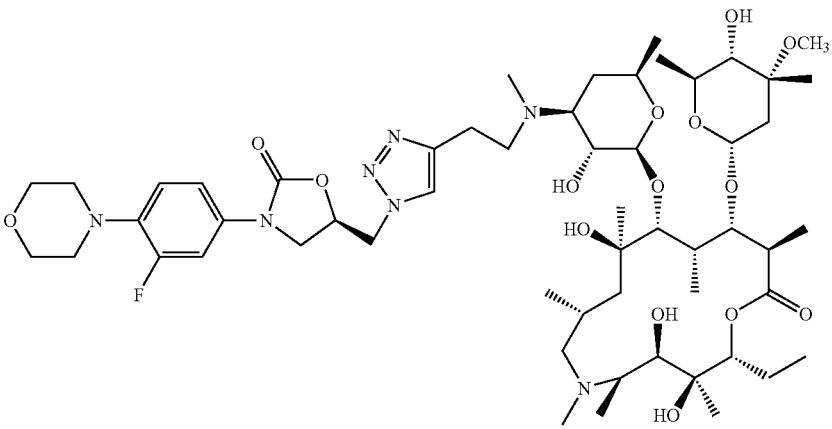 |
| 153 | 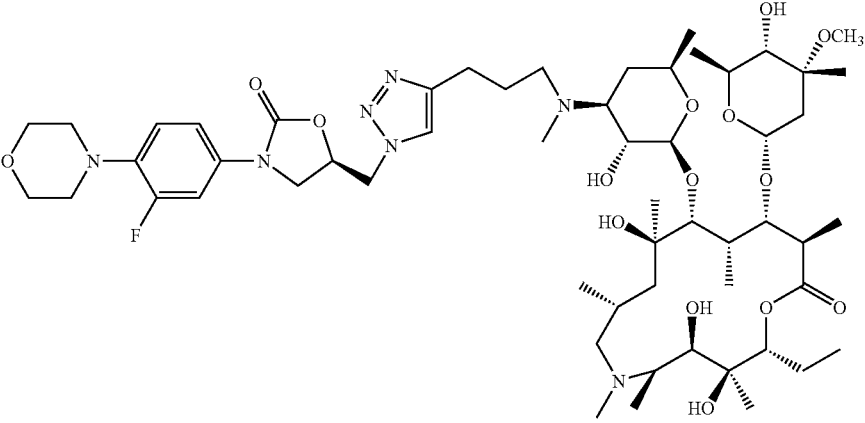 |

TABLE 2-continued

| Compound Number | Structure |
|---|---|
| 175 | 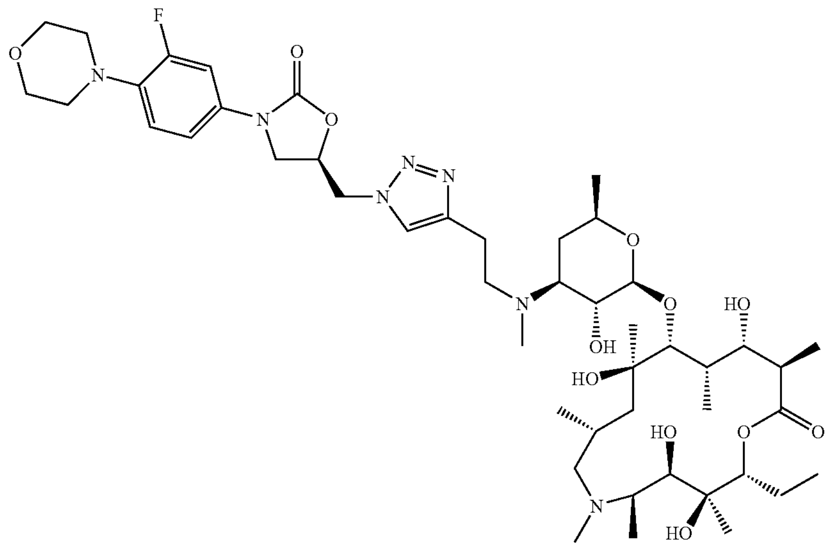 |
| 176 | 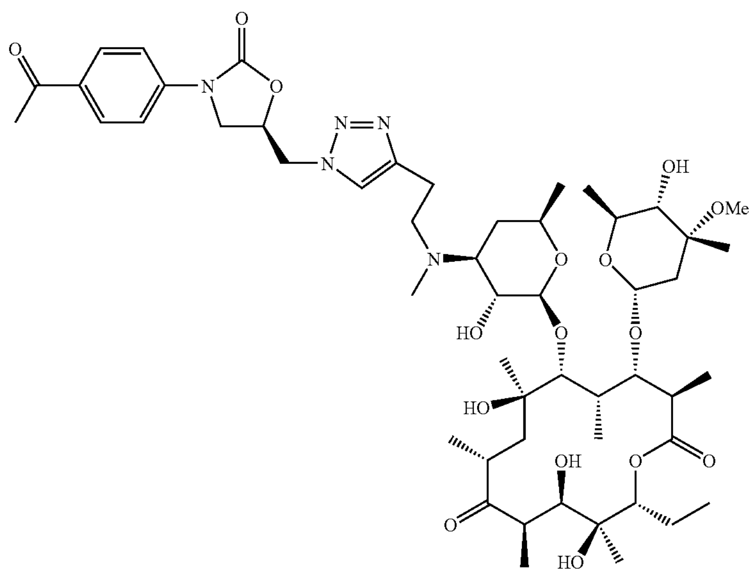 |
| 177 | 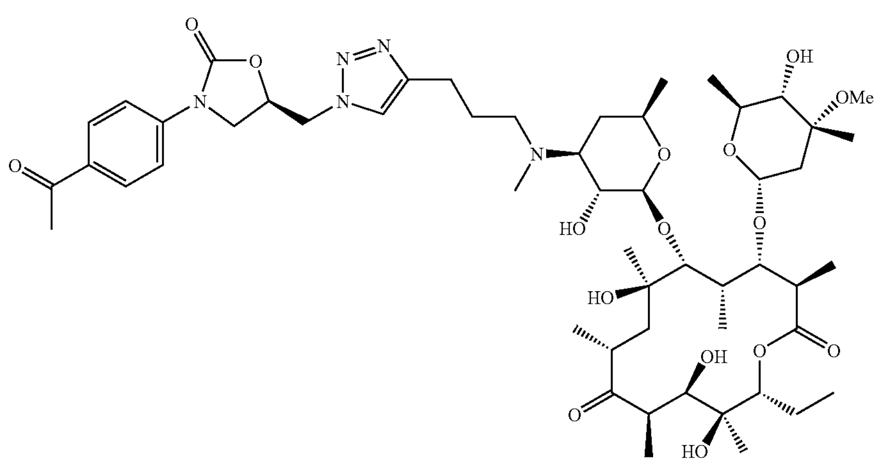 |

TABLE 2-continued

| Compound Number | Structure |
|---|---|
| 178 | 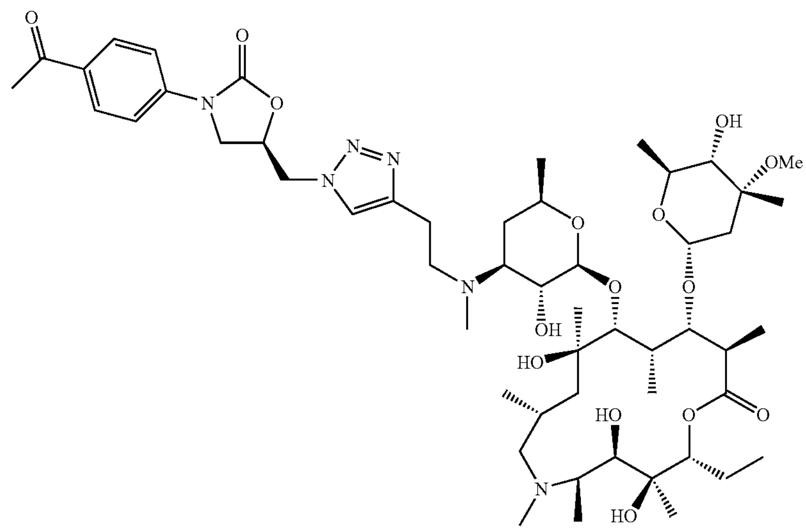 |
| 179 | 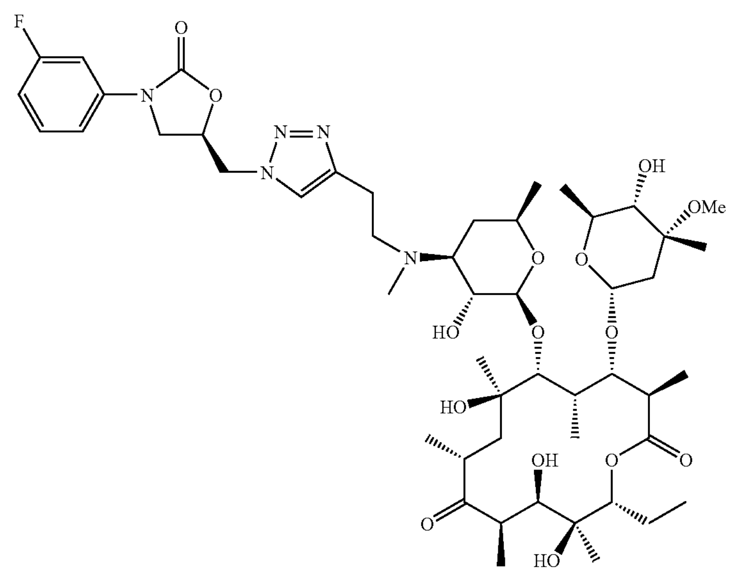 |

TABLE 2-continued
| Compound Number | Structure |
|---|---|
| 180 | 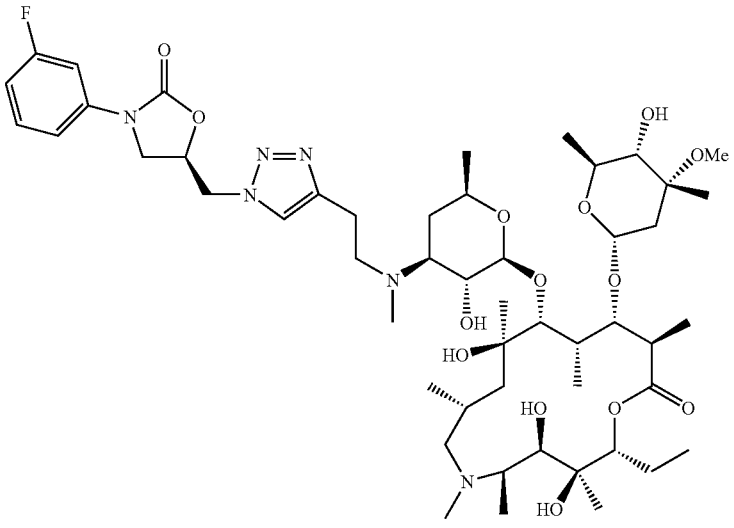 |
| 181 | 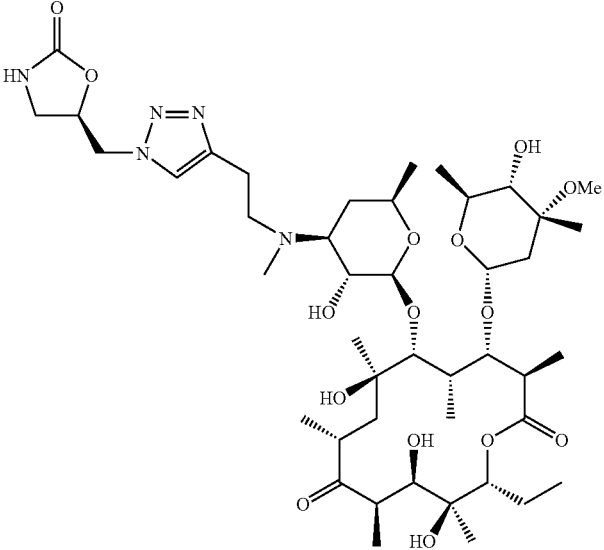 |

TABLE 2-continued

| Compound Number | Structure |
| --- | --- |
| 182 | 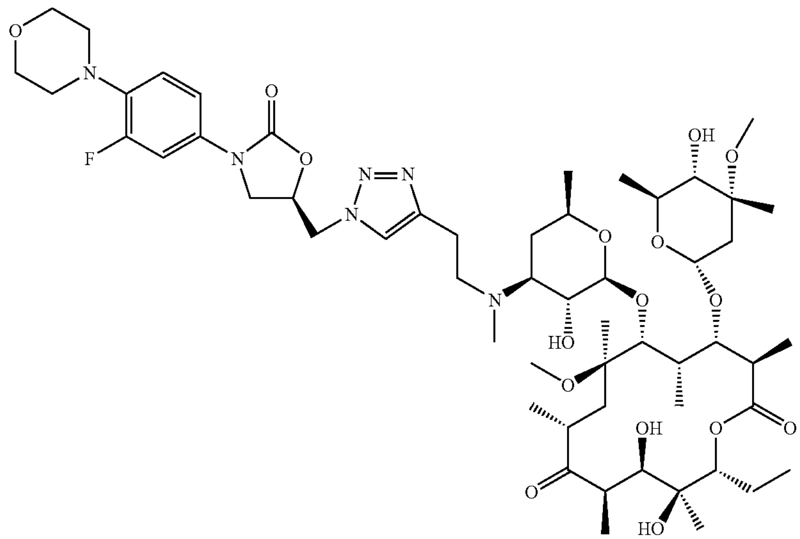 |
| 183 | 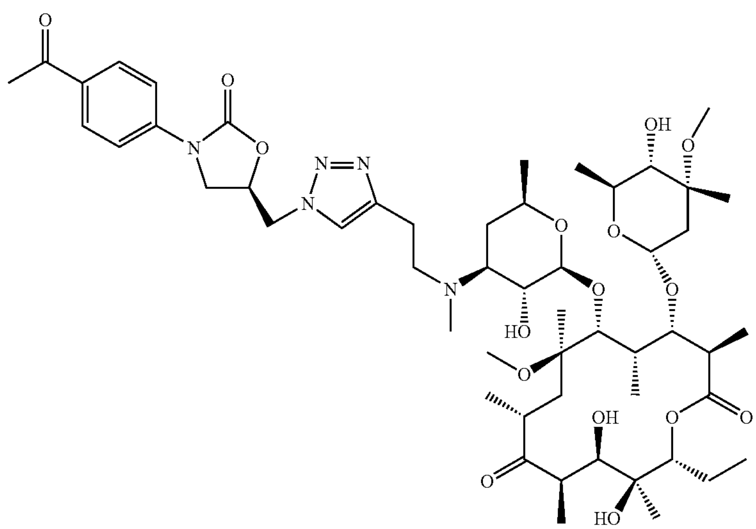 |
| 184 | 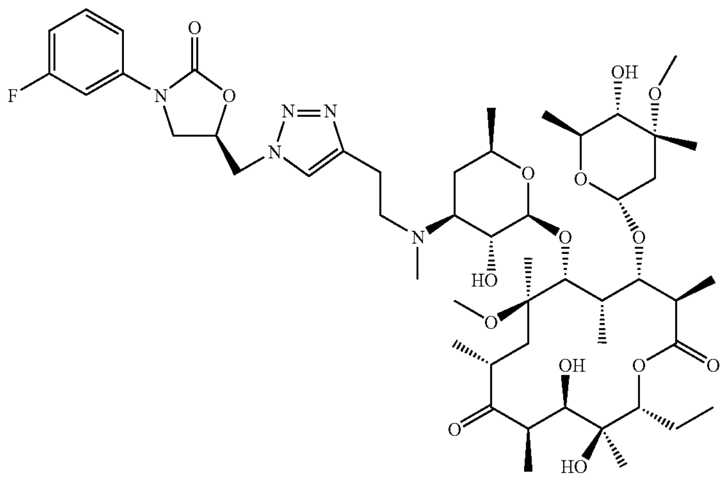 |

TABLE 2-continued

| Compound Number | Structure |
|---|---|
| 185 | 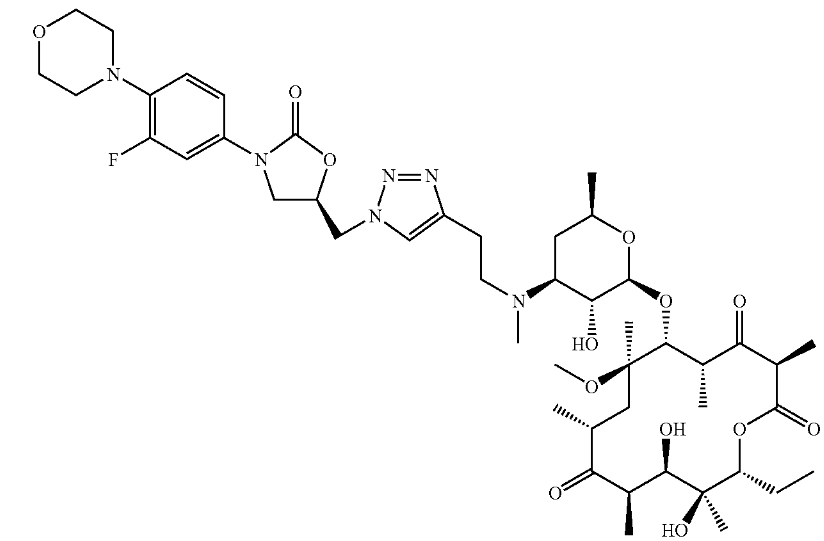 |
| 186 | 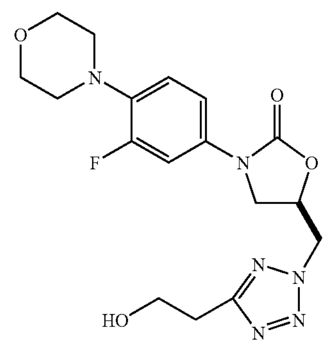 |
| 187 | 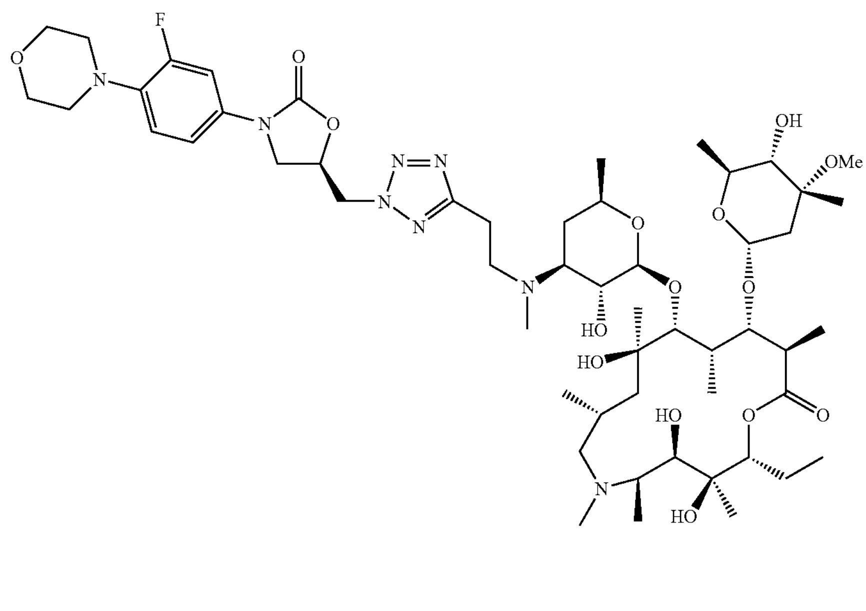 |

TABLE 2-continued
| Compound Number | Structure |
| --- | --- |
| 203 | 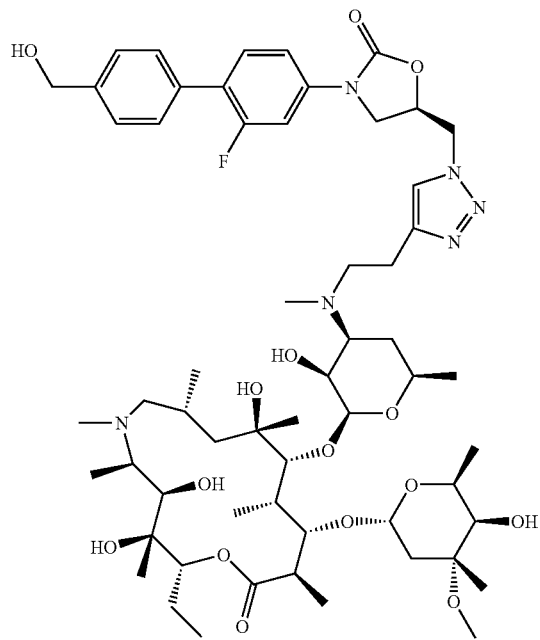 |
| 204 | 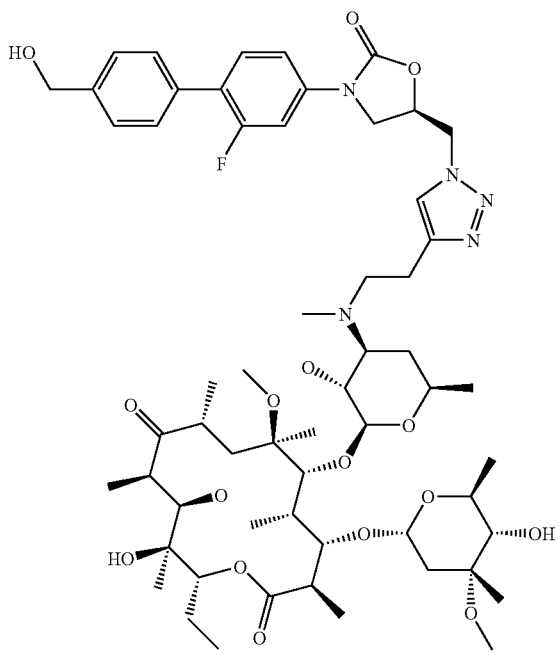 |

TABLE 2-continued

| Compound Number | Structure |
| --- | --- |
| 205 | 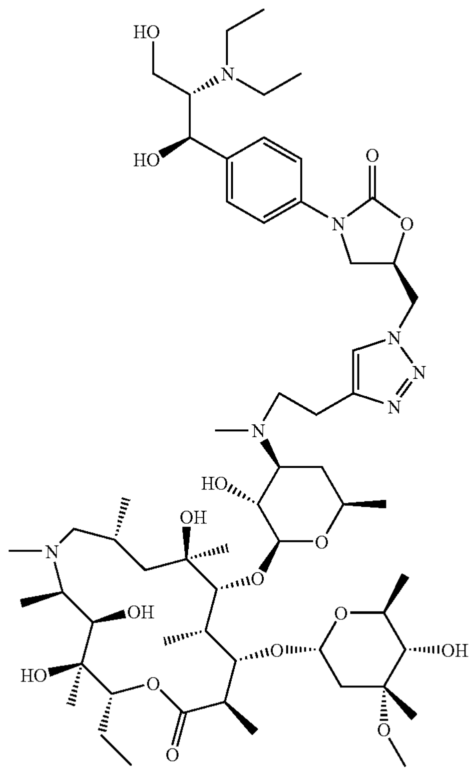 |
| 206 | 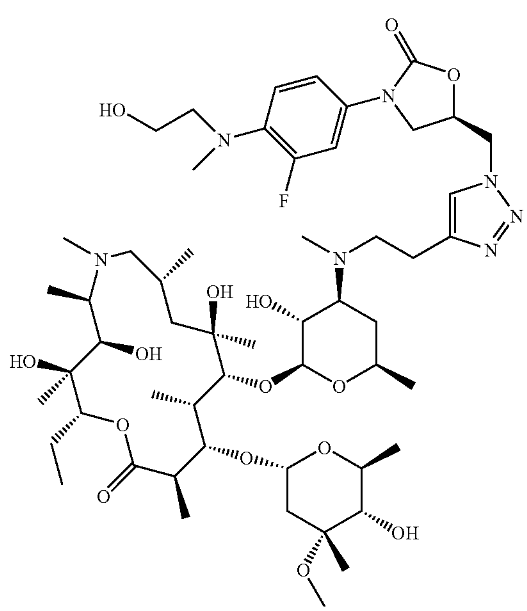 |

TABLE 2-continued
| Compound Number | Structure |
| --- | --- |
| 207 | 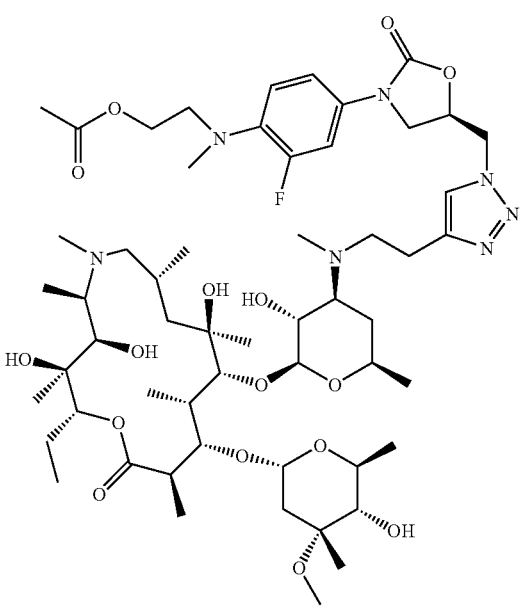 |
| 208 | 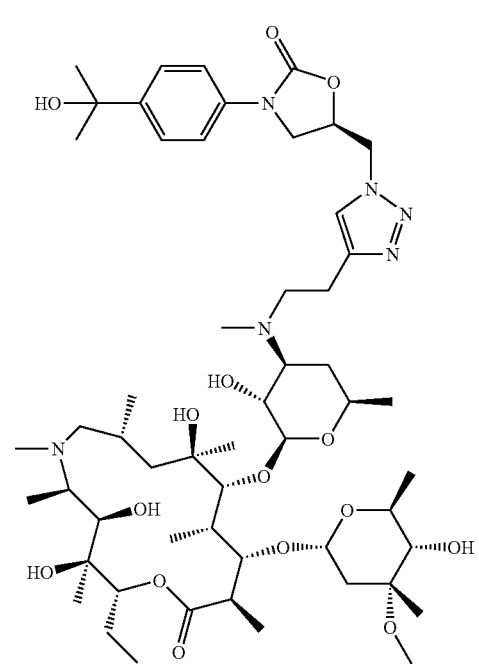 |

TABLE 2-continued
| Compound Number | Structure |
|---|---|
| 209 | 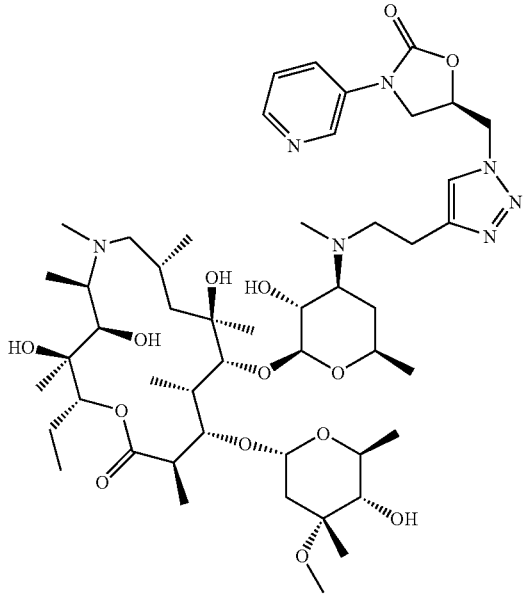 |
| 210 | 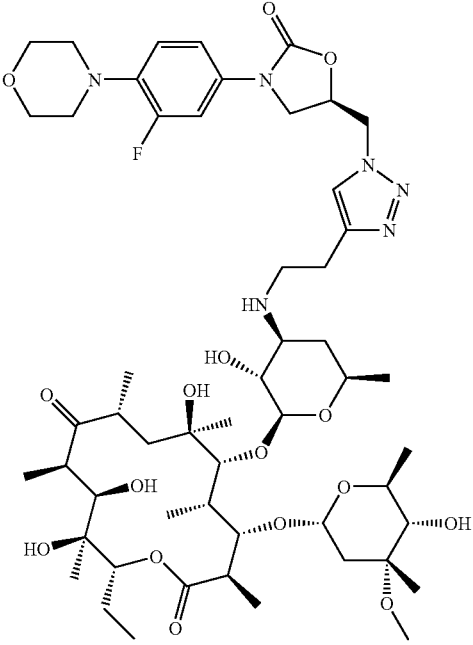 |

TABLE 2-continued
| Compound Number | Structure |
| --- | --- |
| 211 | 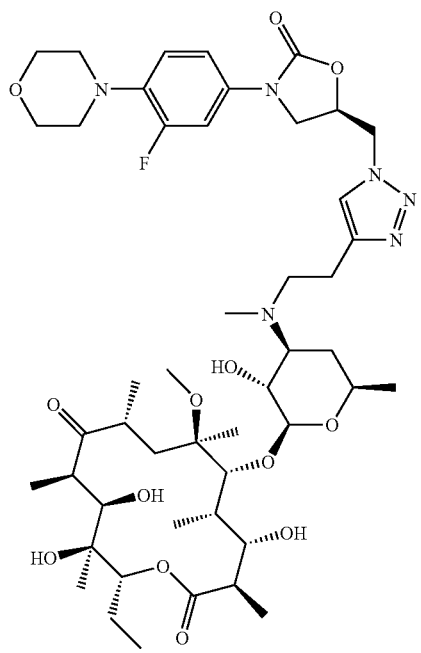 |
| 212 | 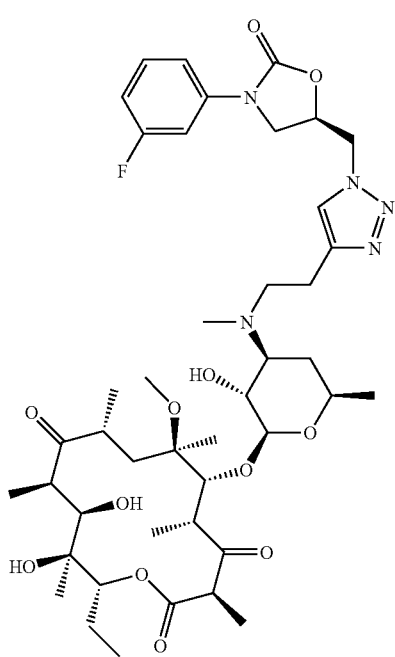 |

TABLE 2-continued
| Compound Number | Structure |
|---|---|
| 213 | 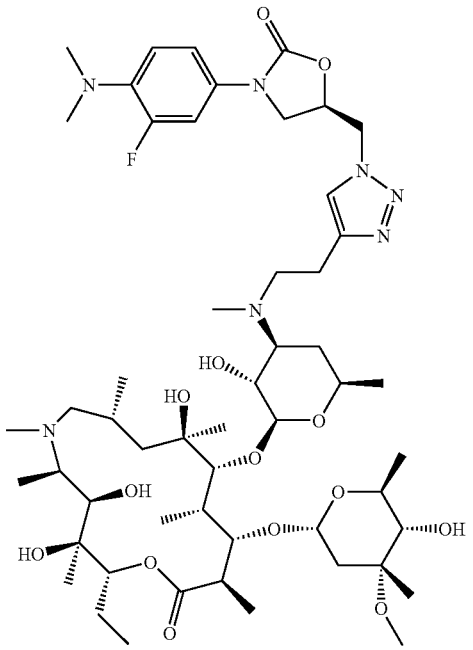 |
| 214 | 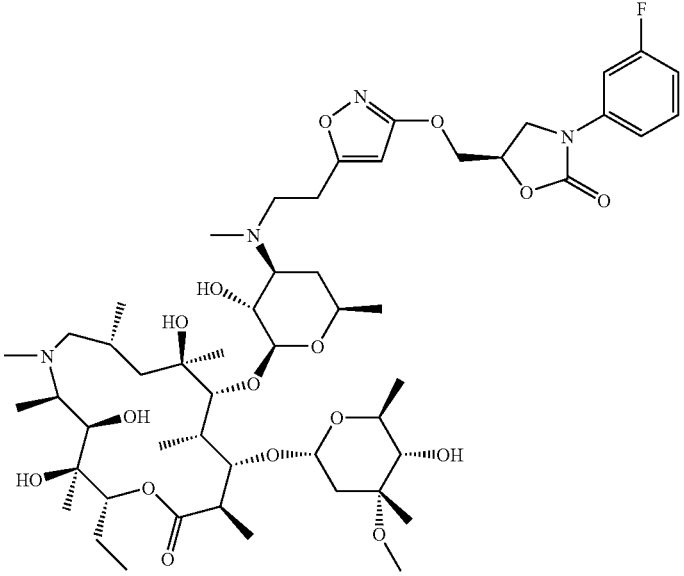 |

TABLE 2-continued
| Compound Number | Structure |
|---|---|
| 215 | 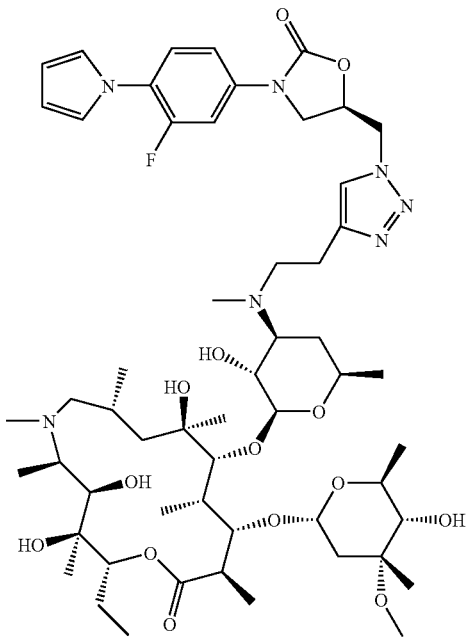 |
| 216 | 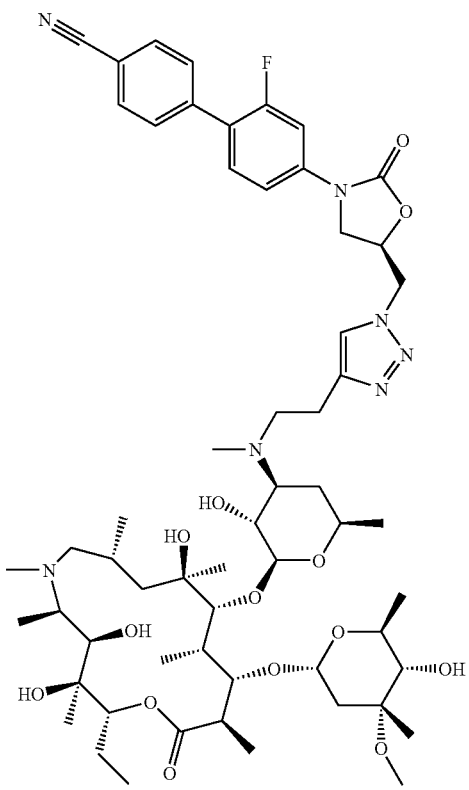 |

TABLE 2-continued

| Compound Number | Structure |
|---|---|
| 217 | 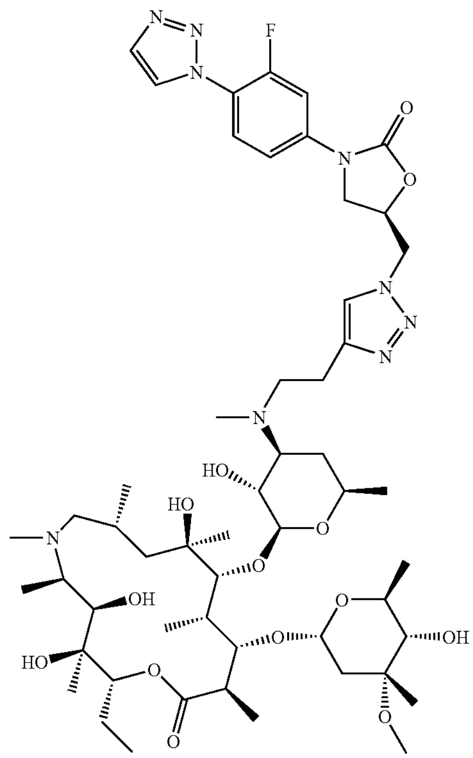 |
| 218 | 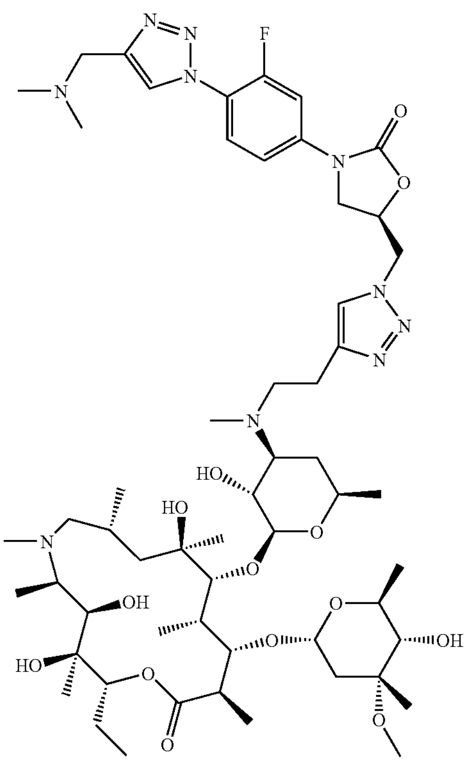 |

TABLE 2-continued
| Compound Number | Structure |
|---|---|
| 219 | 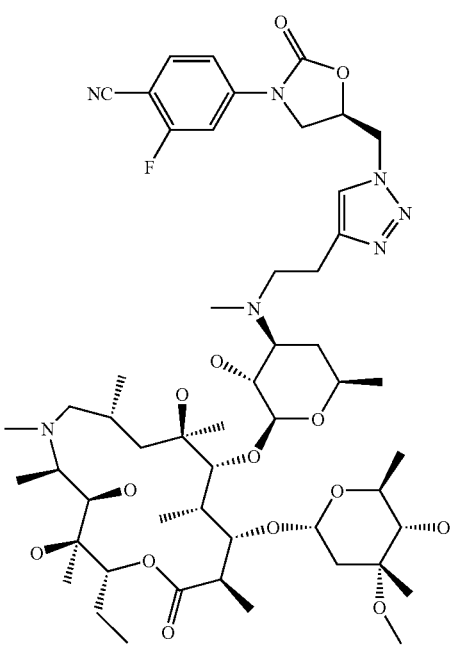 |
| 220 | 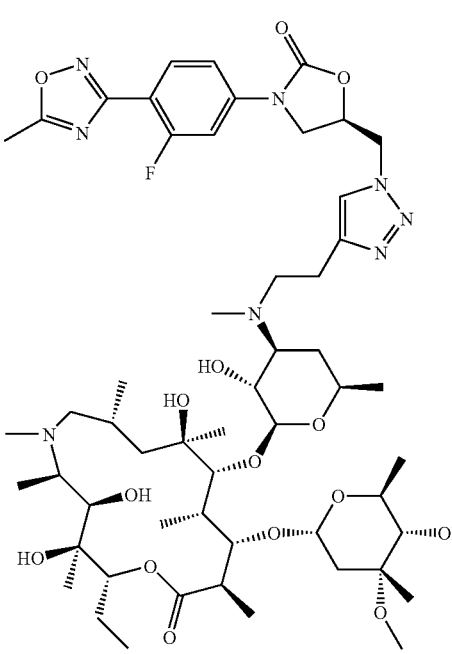 |

TABLE 2-continued

| Compound Number | Structure |
| --- | --- |
| 221 | 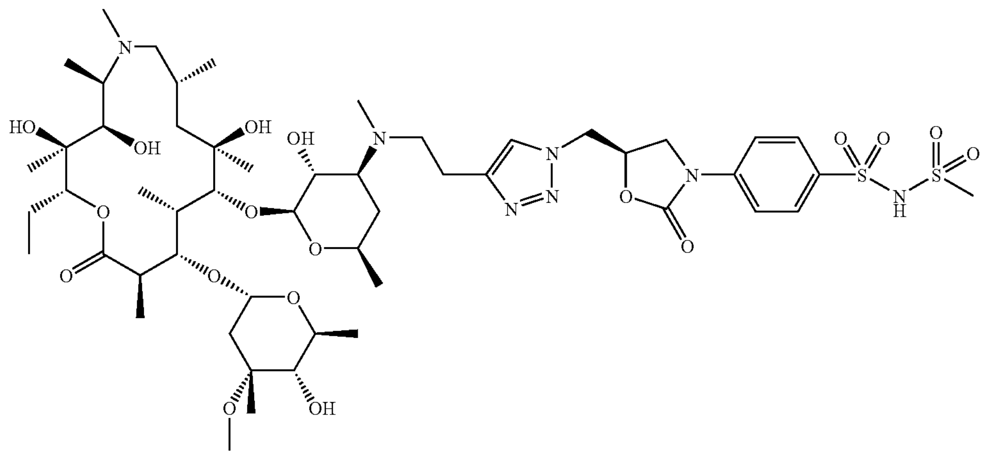 |
| 222 | 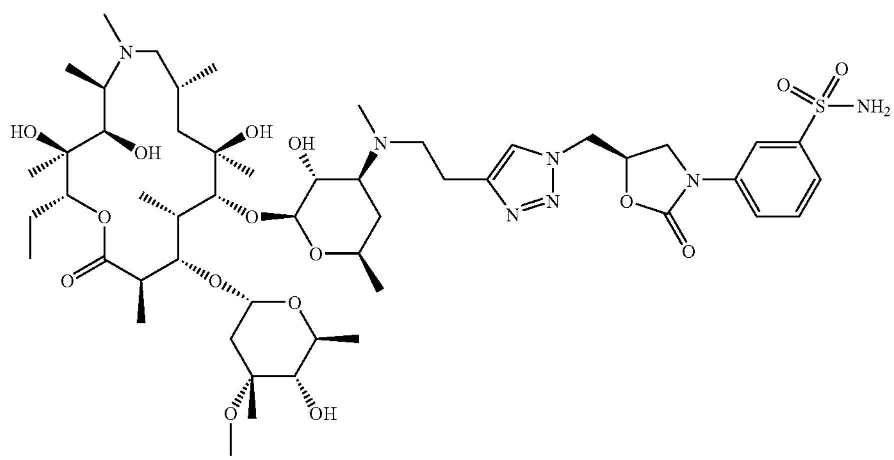 |
| 223 | 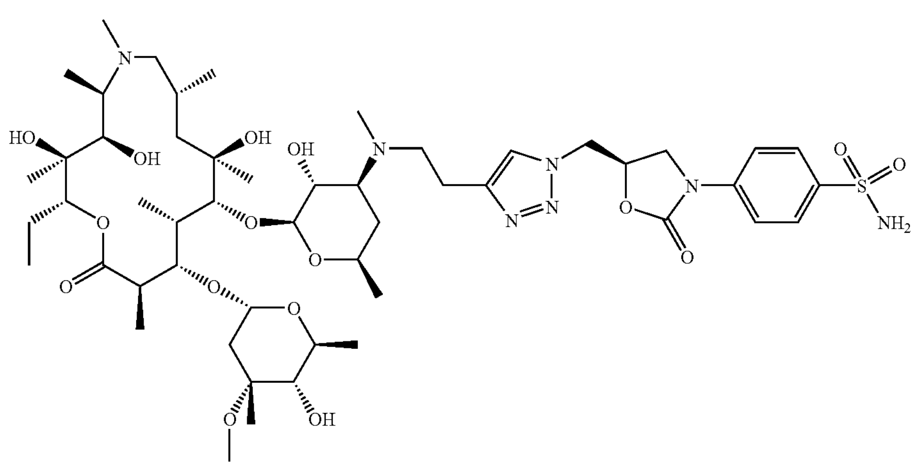 |

TABLE 2-continued

| Compound Number | Structure |
|---|---|
| 224 | 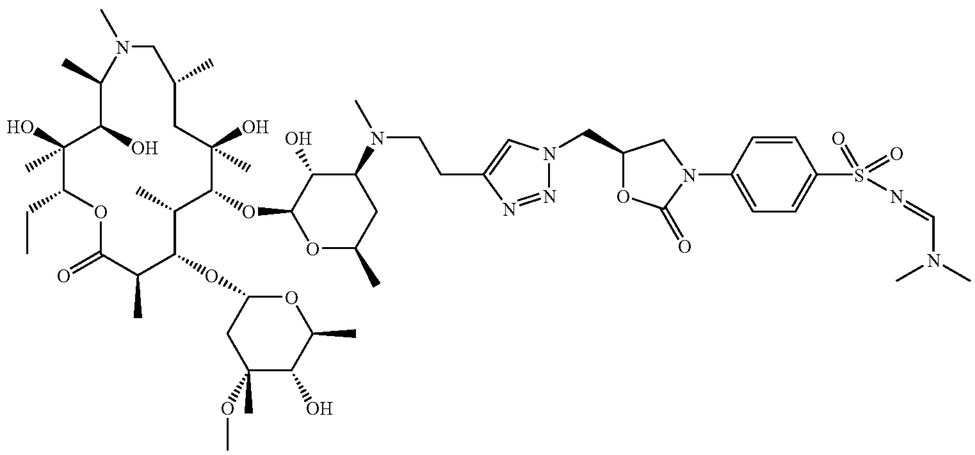 |
| 225 | 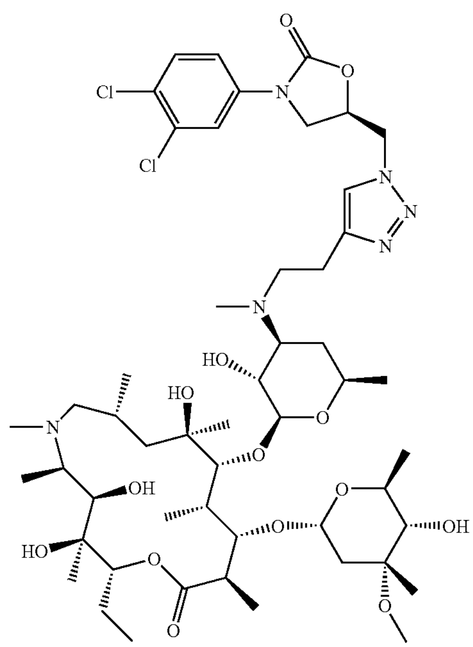 |

US 7,335,753 B2
TABLE 2-continued
| Compound Number | Structure |
| --- | --- |
| 226 | 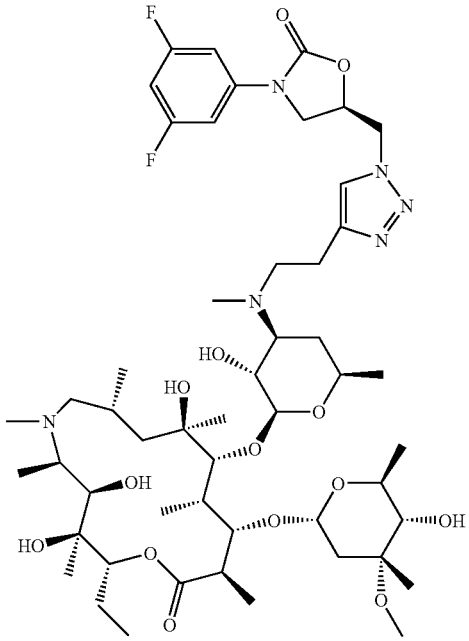 |
| 227 | 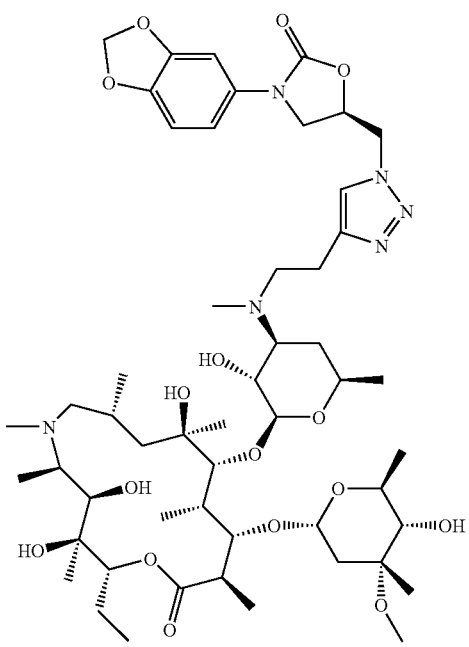 |

TABLE 2-continued

| Compound Number | Structure |
| --- | --- |
| 228 | 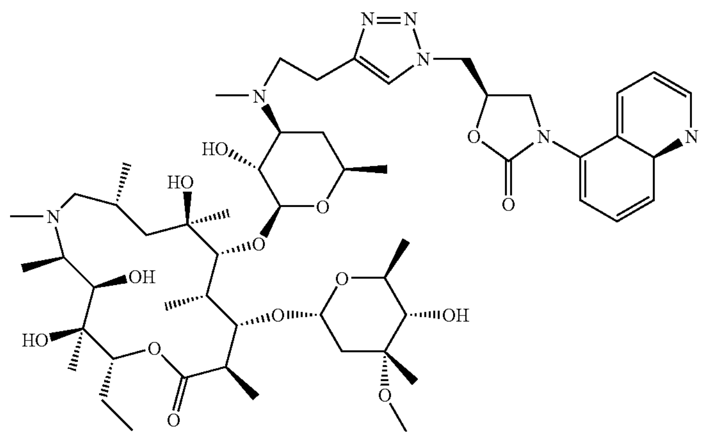 |
| 229 | 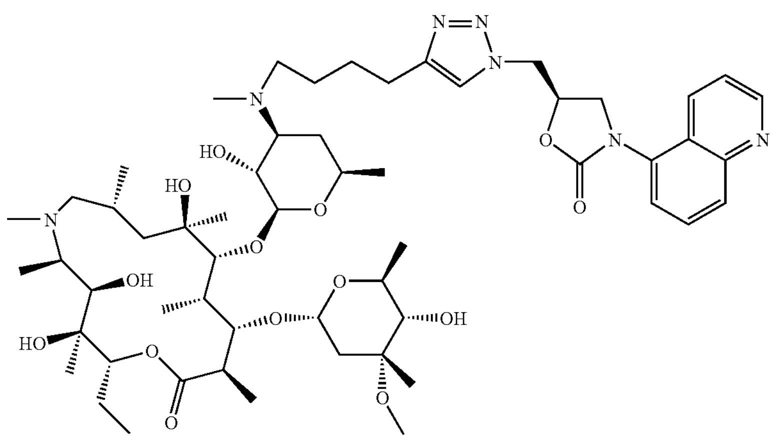 |
| 230 | 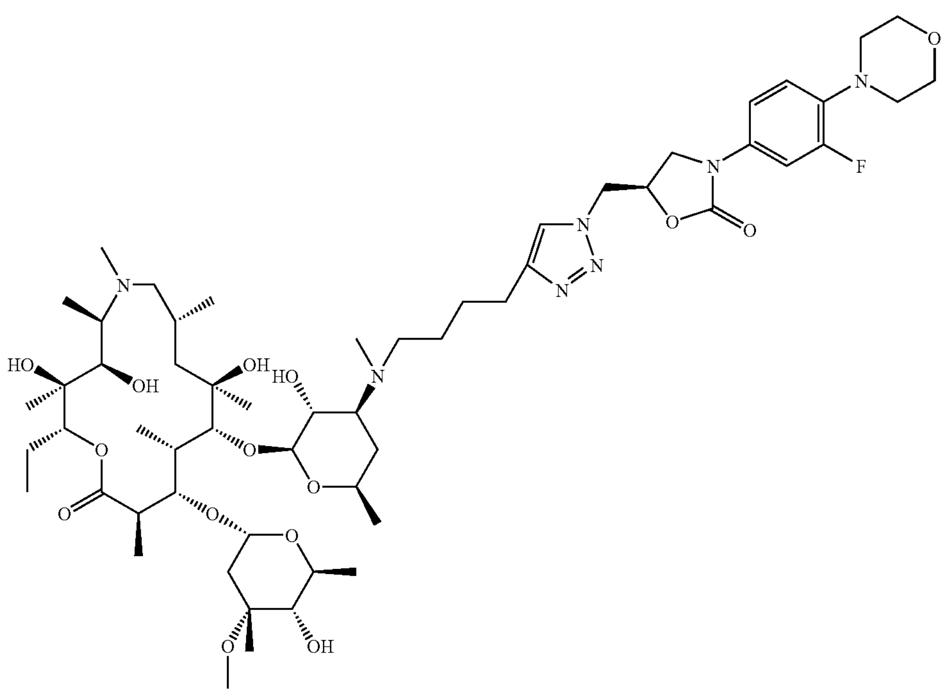 |

TABLE 2-continued
| Compound Number | Structure |
| --- | --- |
| 231 | 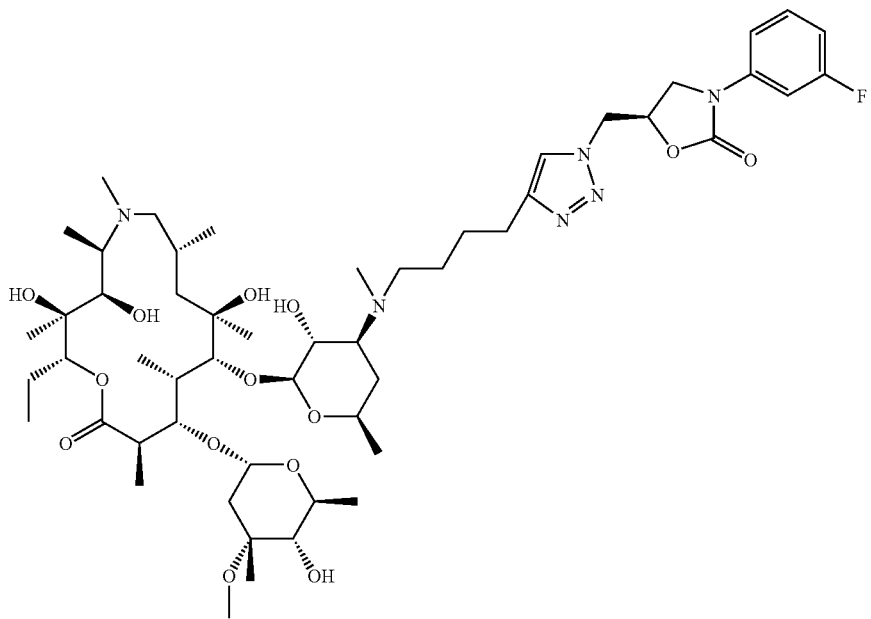 |
| 232 | 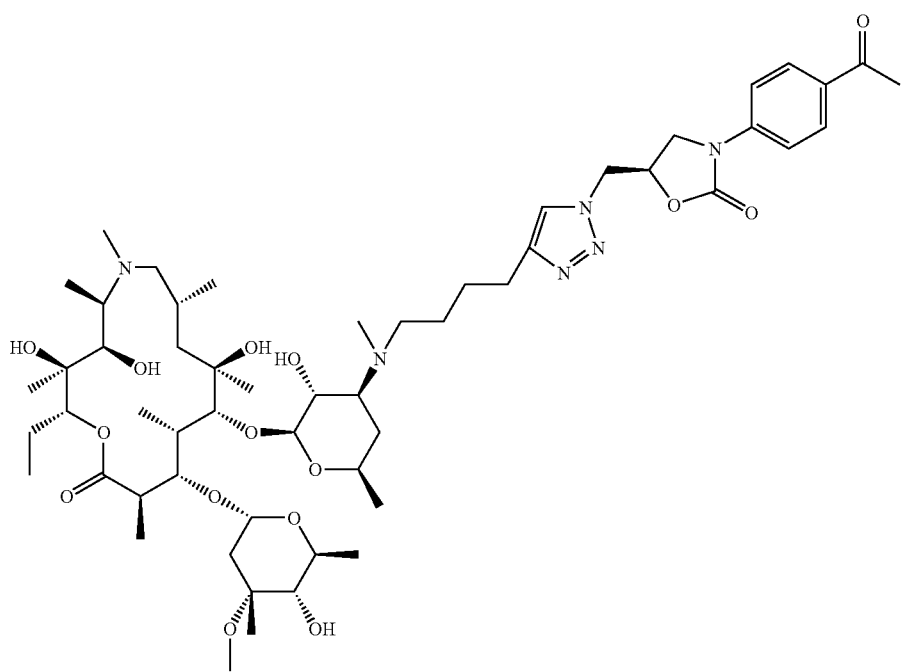 |

TABLE 2-continued
| Compound Number | Structure |
|---|---|
| 233 | 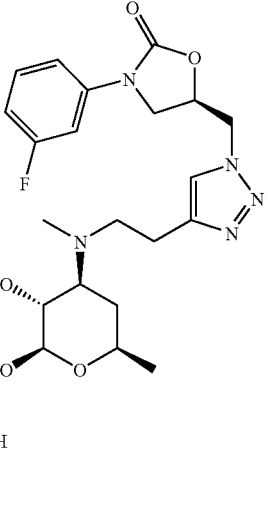 |
| 234 | 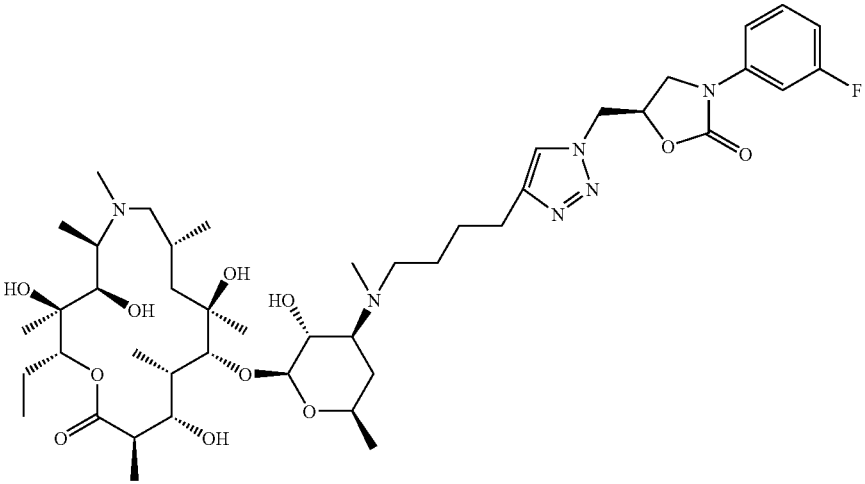 |
| 235 | 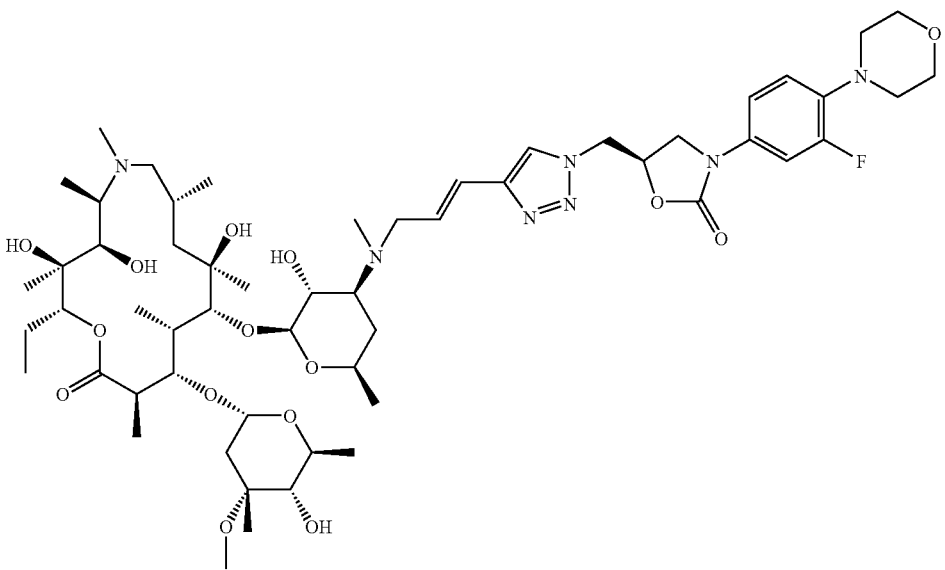 |

TABLE 2-continued
| Compound Number | Structure |
| --- | --- |
| 236 | 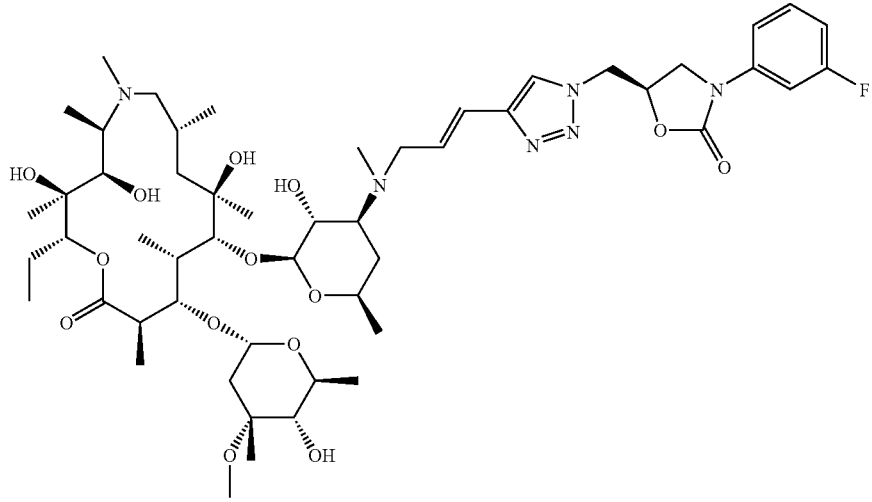 |
| 237 | 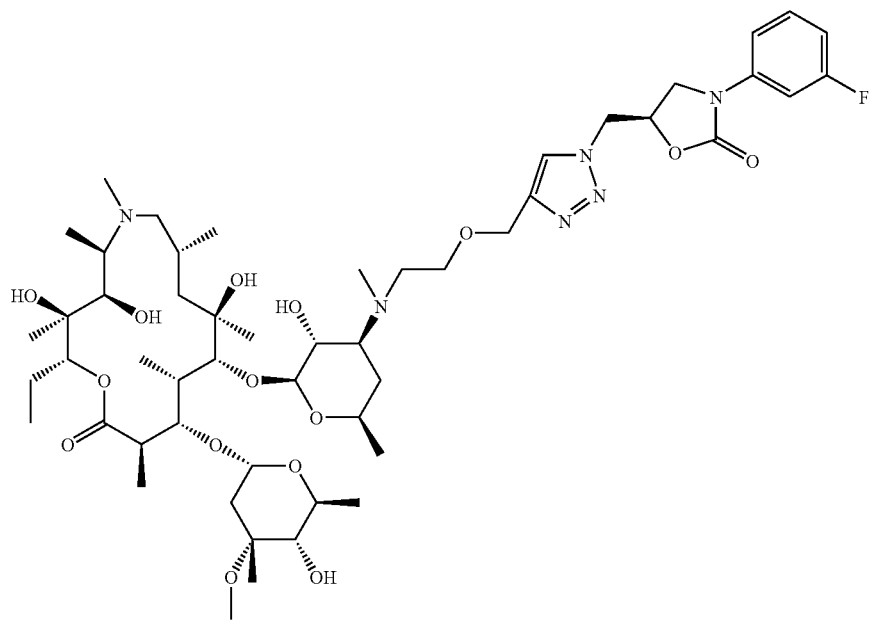 |

TABLE 2-continued
| Compound Number | Structure |
|---|---|
| 238 | 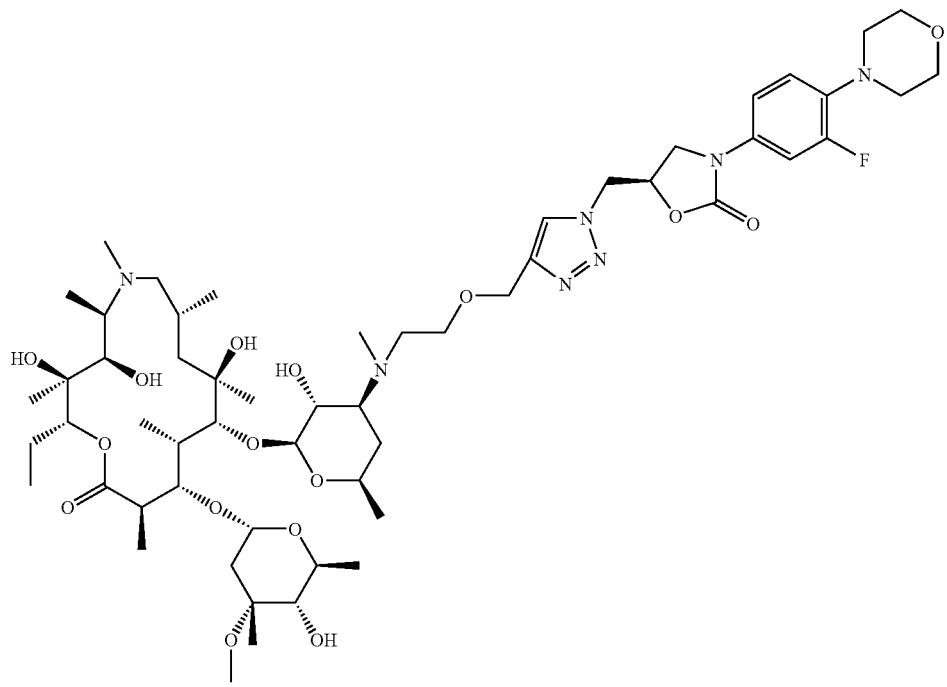 |
| 239 | 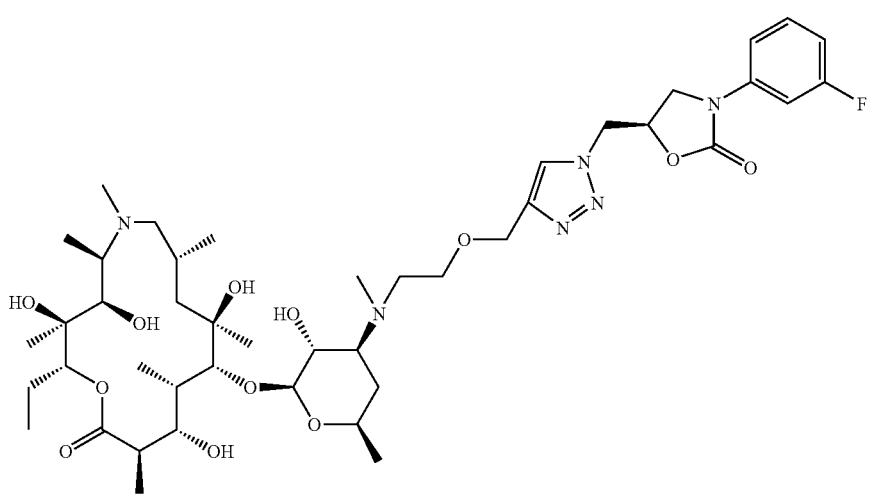 |

TABLE 2-continued
| Compound Number | Structure |
|---|---|
| 240 | 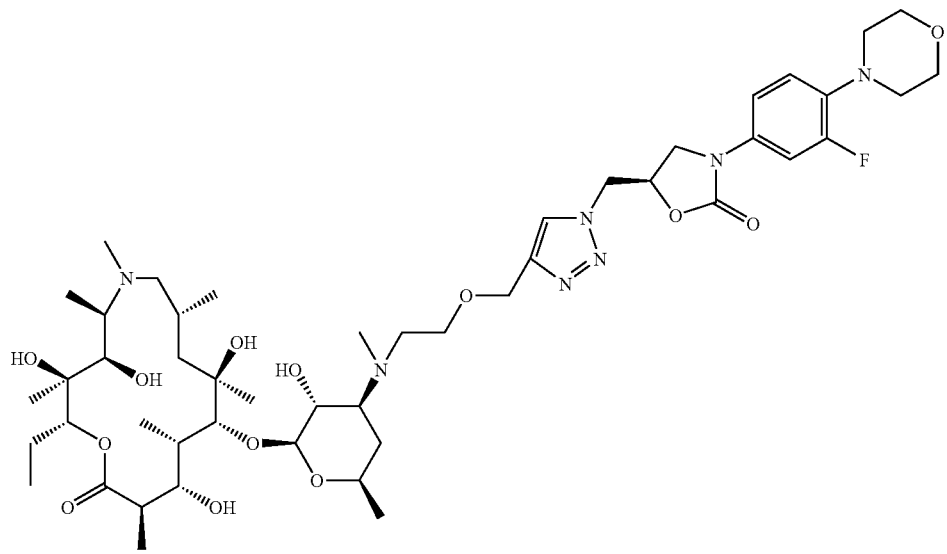 |
| 241 | 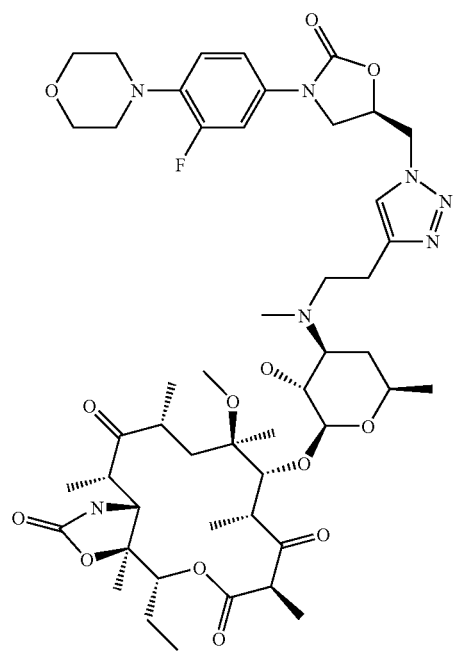 |

TABLE 2-continued

| Compound Number | Structure |
|---|---|
| 242 | 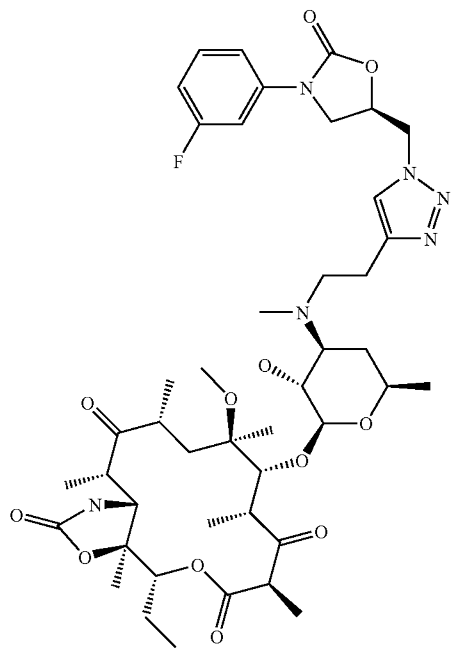 |
| 243 | 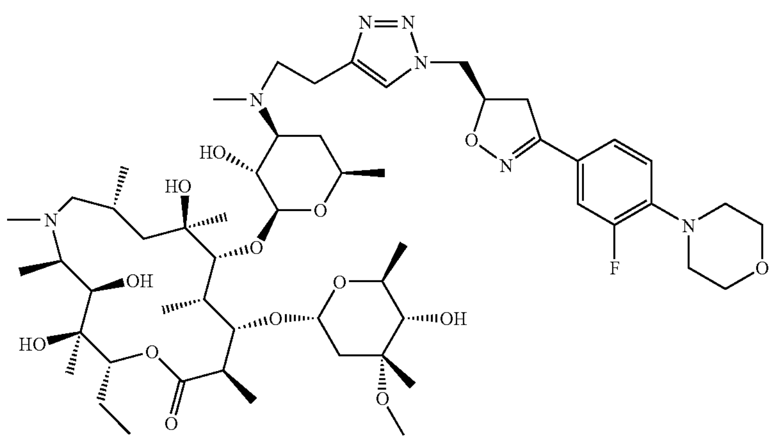 |
| 244 | 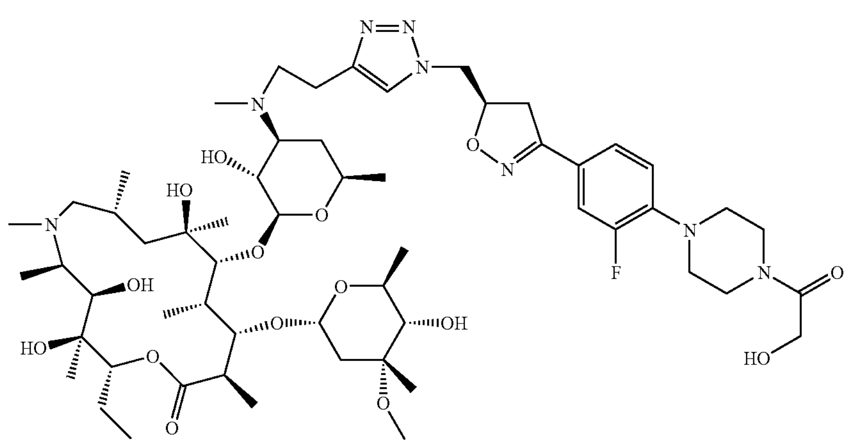 |

TABLE 2-continued
| Compound Number | Structure |
|---|---|
| 245 | 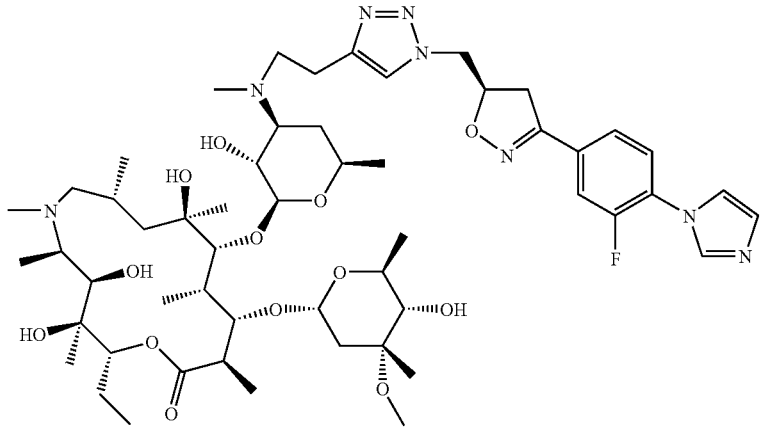 |
| 246 | 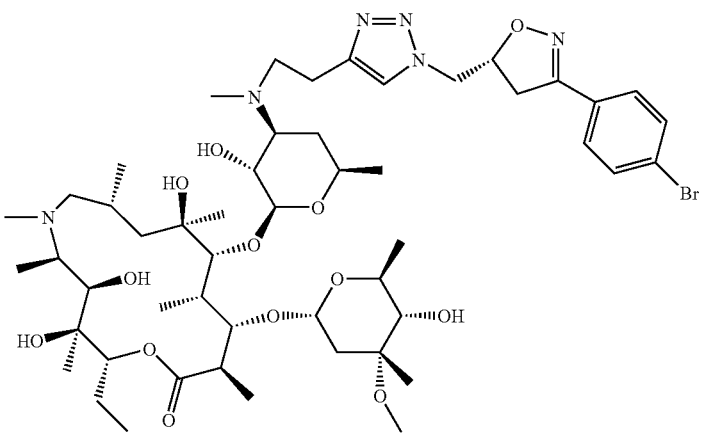 |
| 247 | 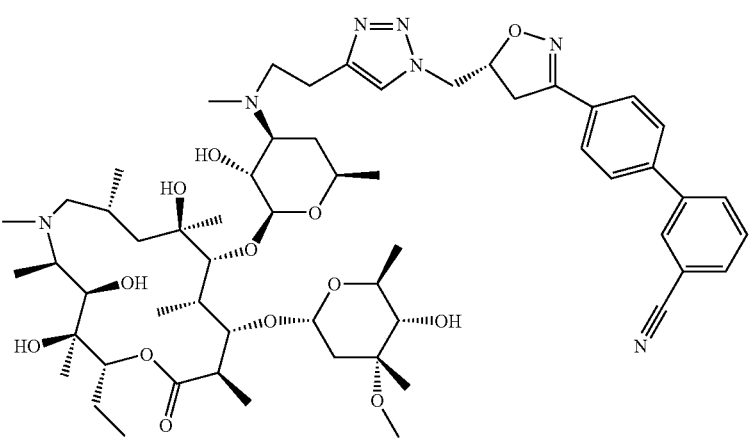 |

TABLE 2-continued

| Compound Number | Structure |
| --- | --- |
| 248 | 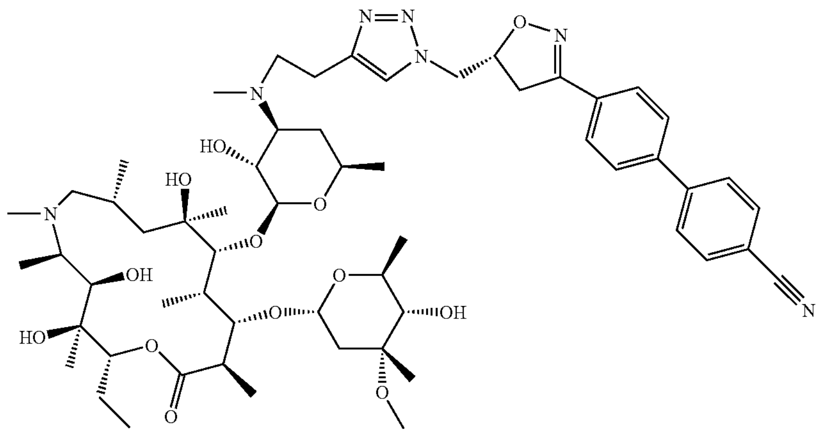 |
| 249 | 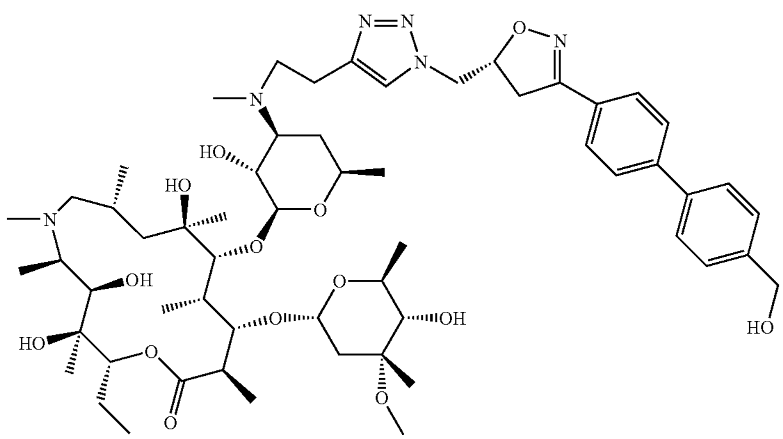 |
| 250 | 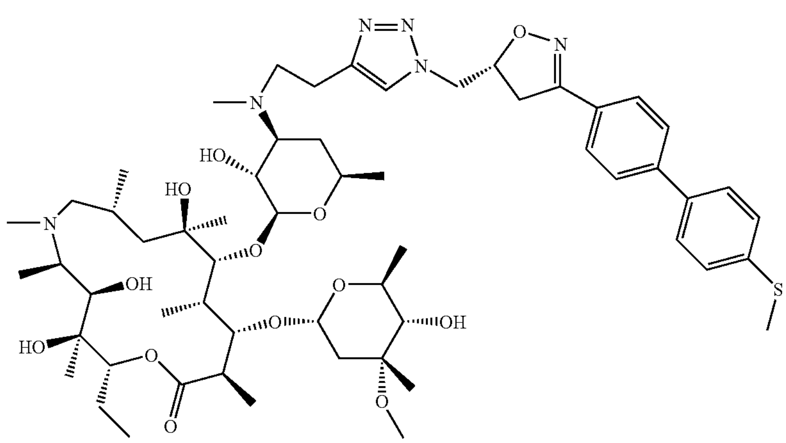 |

TABLE 2-continued
| Compound Number | Structure |
|---|---|
| 251 | 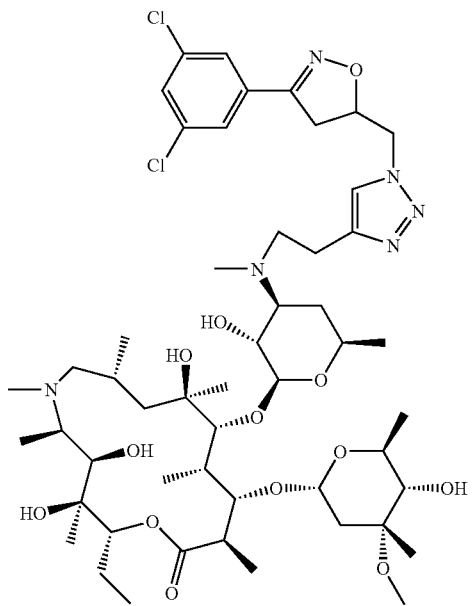 |
| 252 | 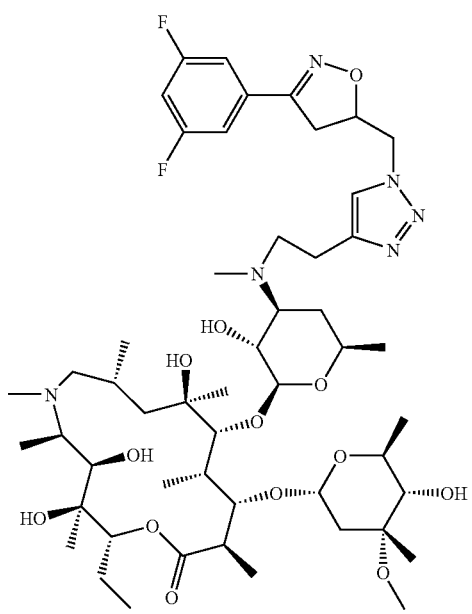 |

TABLE 2-continued
| Compound Number | Structure |
|---|---|
| 361 | 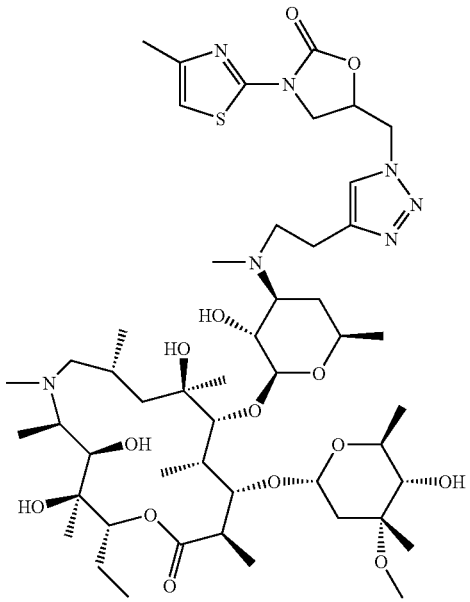 |
| 362 | 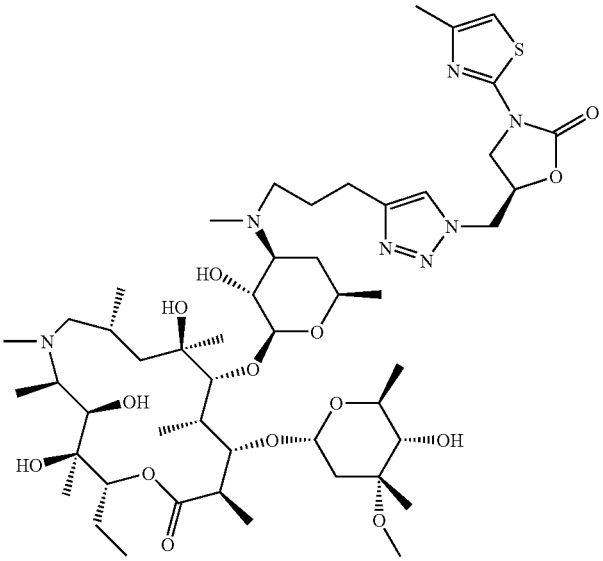 |

/ TABLE 2-continued

| Compound Number | Structure |
| --- | --- |
| 363 | 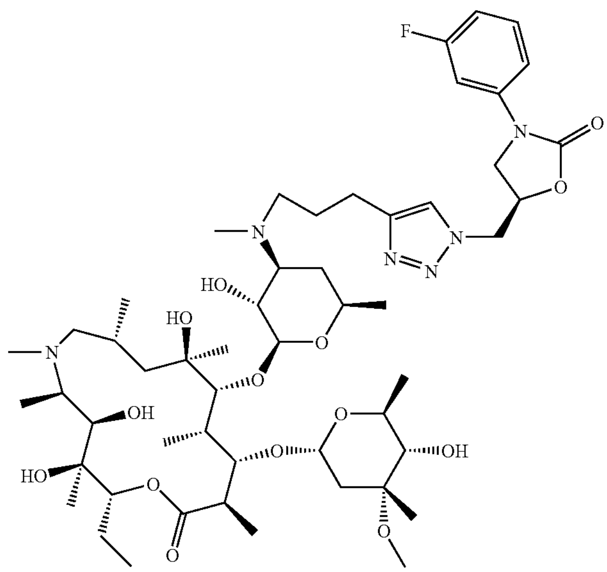 |
| 364 | 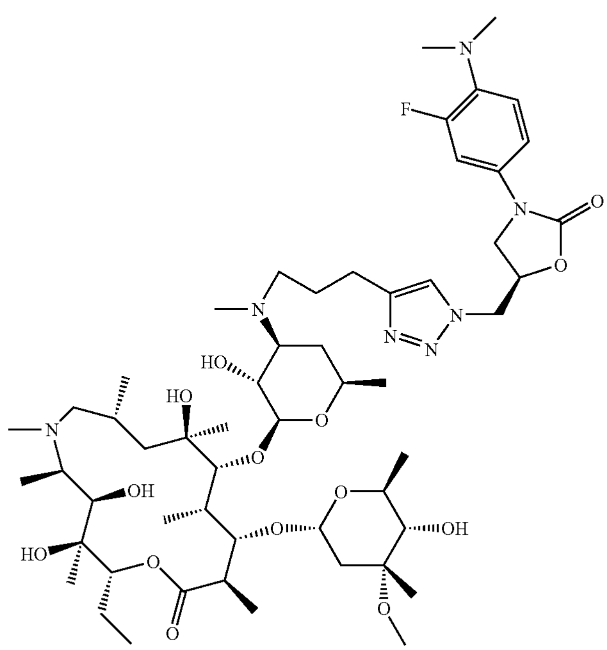 |

TABLE 2-continued
| Compound Number | Structure |
|---|---|
| 365 | 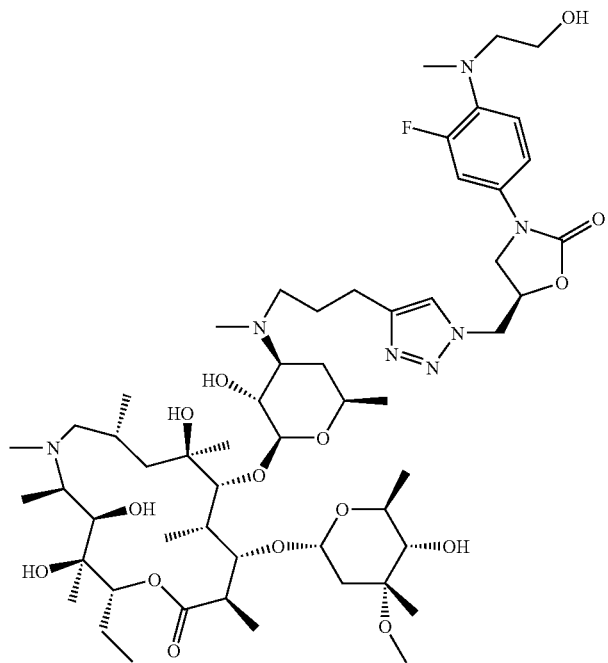 |
| 366 | 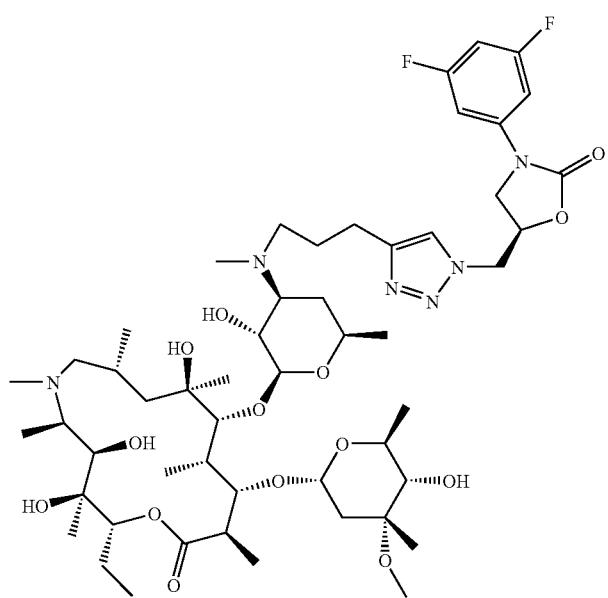 |

TABLE 2-continued
| Compound Number | Structure |
|---|---|
| 367 | 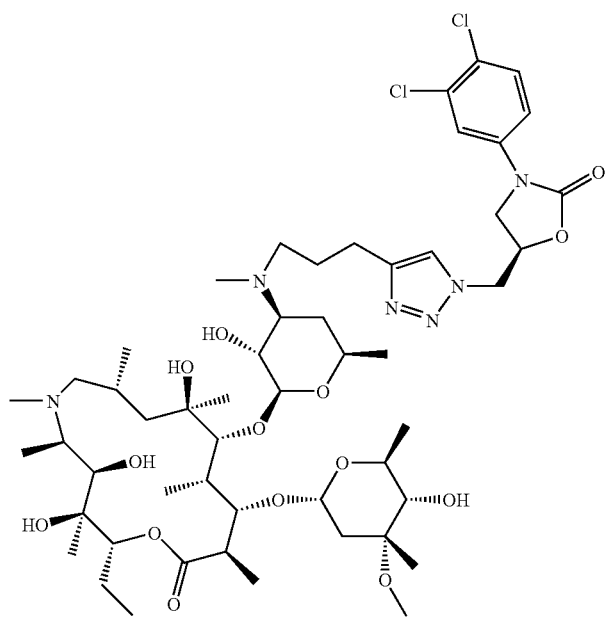 |
| 368 | 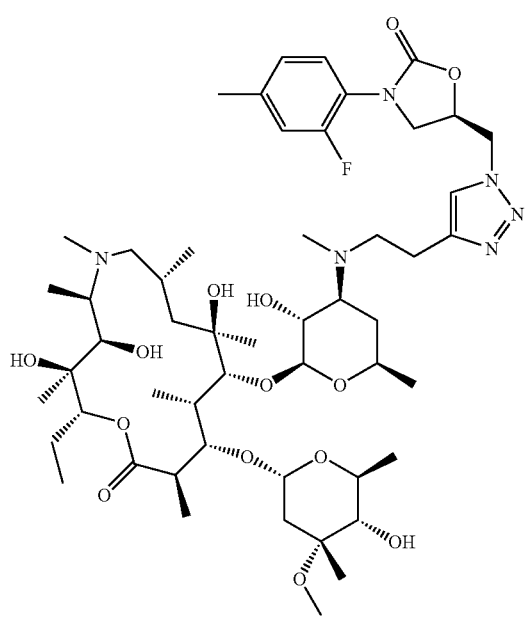 |

TABLE 2-continued
| Compound Number | Structure |
|---|---|
| 369 | 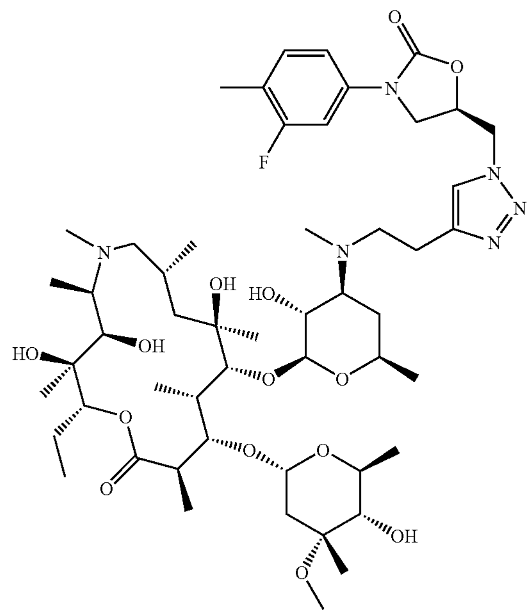 |
| 370 | 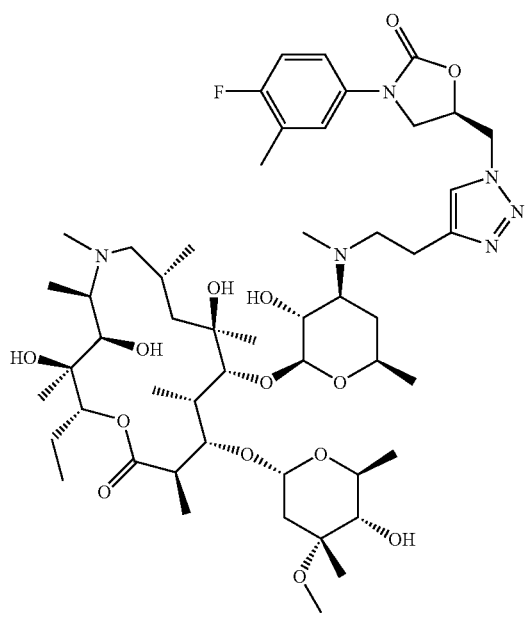 |

TABLE 2-continued
| Compound Number | Structure |
| --- | --- |
| 371 | 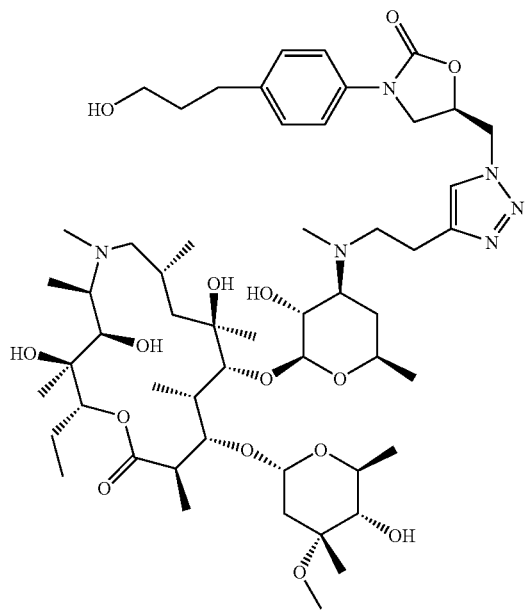 |
| 372 | 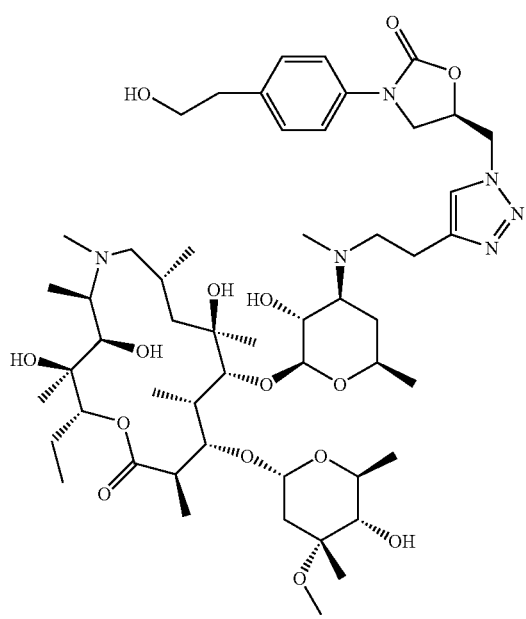 |

TABLE 2-continued
| Compound Number | Structure |
|---|---|
| 373 | 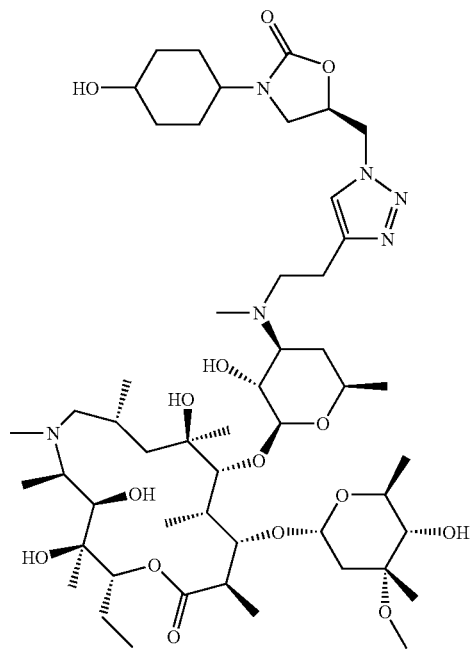 |
| 374 | 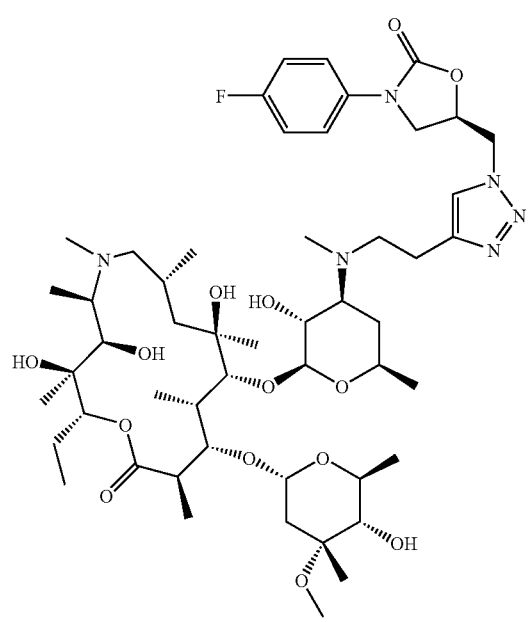 |

TABLE 2-continued
| Compound Number | Structure |
|---|---|
| 375 | 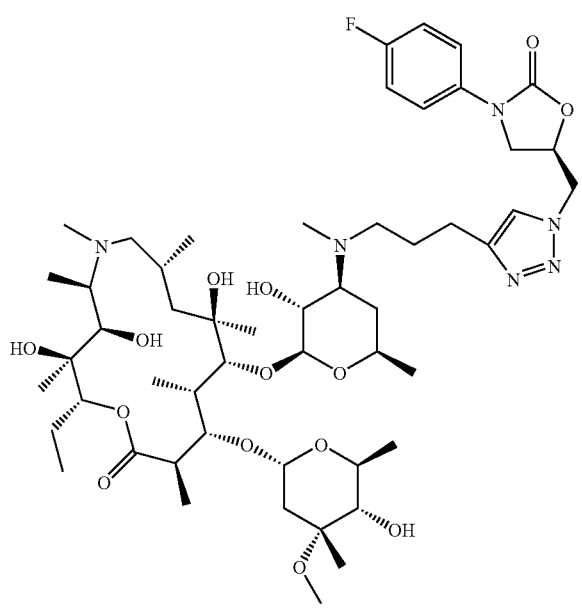 |
| 376 | 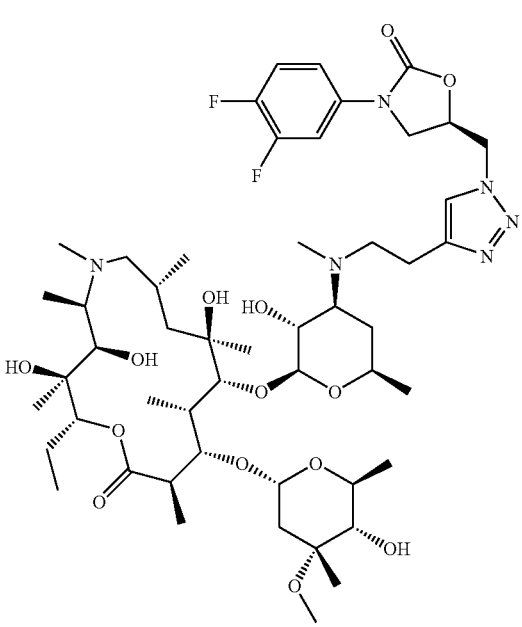 |

TABLE 2-continued
| Compound Number | Structure |
|---|---|
| 377 | 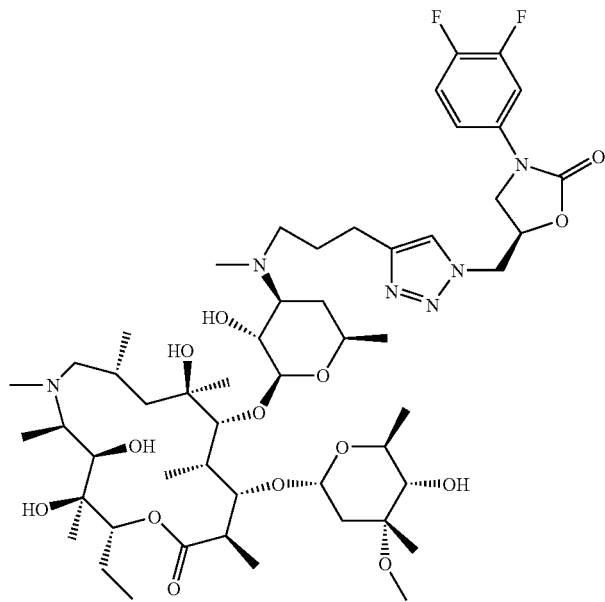 |
| 378 | 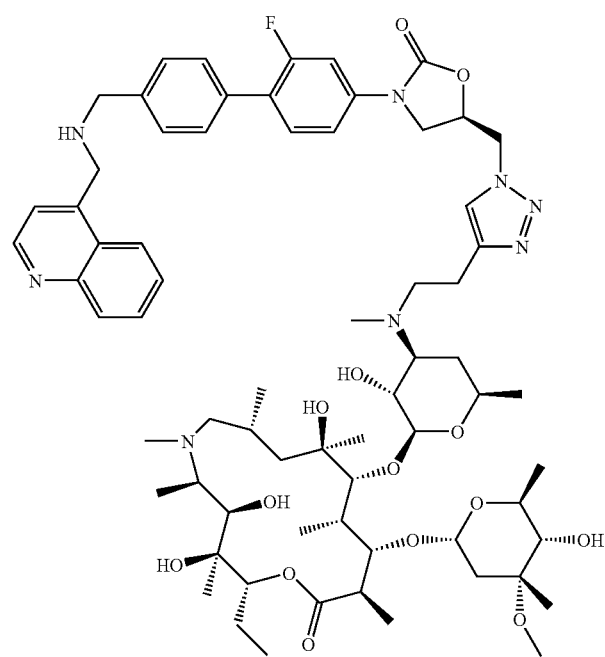 |

TABLE 2-continued
| Compound Number | Structure |
|---|---|
| 379 | 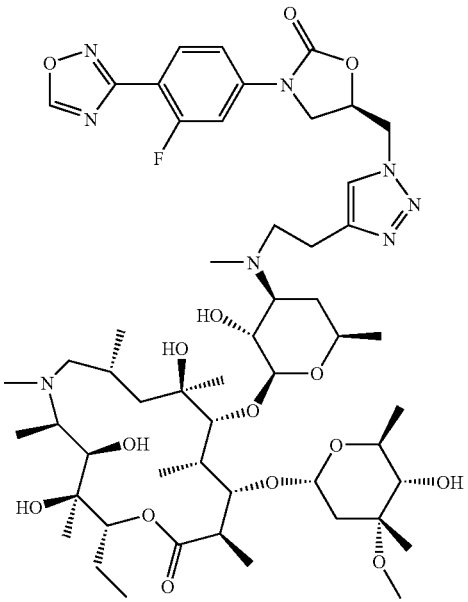 |
| 380 | 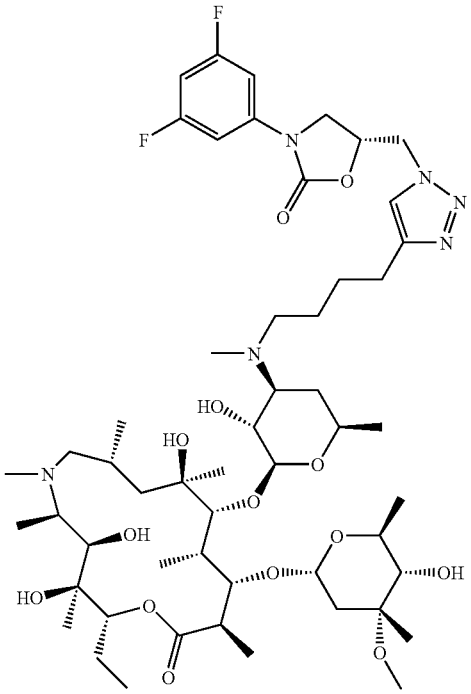 |

TABLE 2-continued
| Compound Number | Structure |
|---|---|
| 381 | 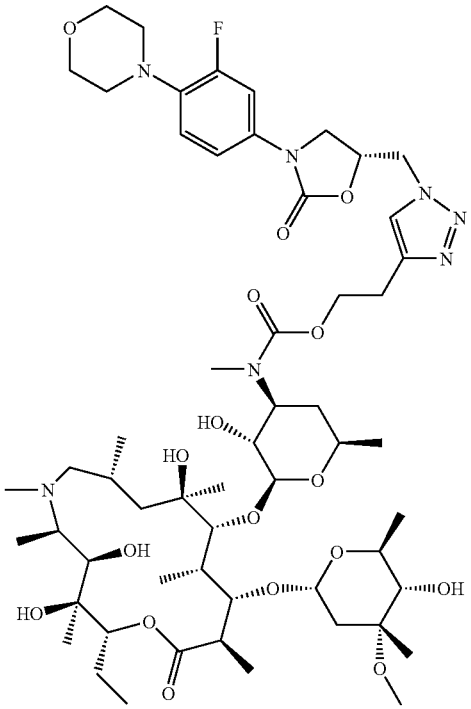 |
| 382 | 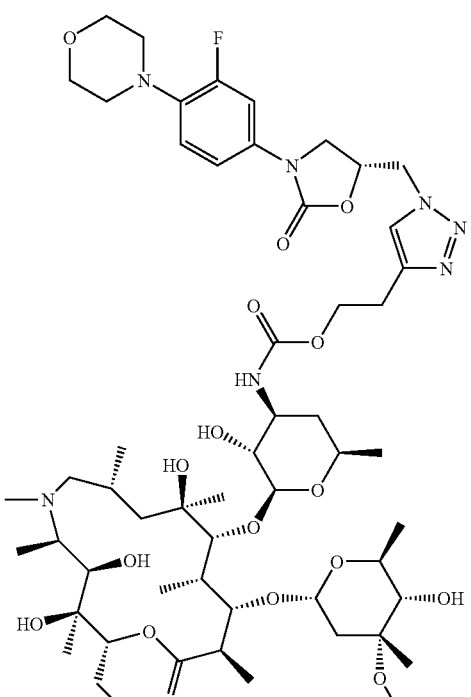 |

TABLE 2-continued

| Compound Number | Structure |
| --- | --- |
| 383 | 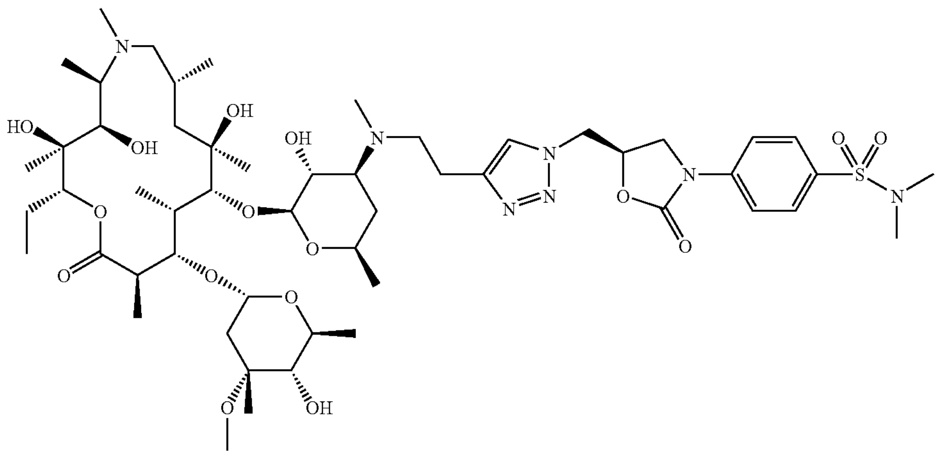 |
| 384 | 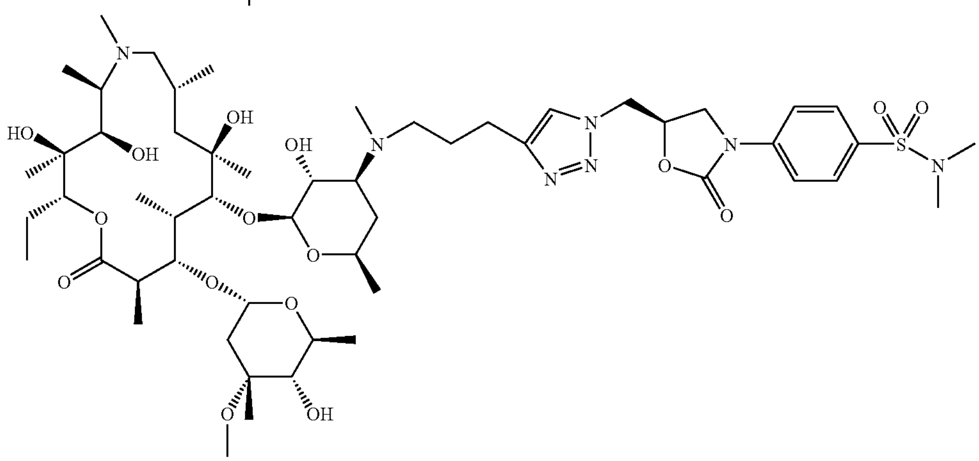 |
| 385 | 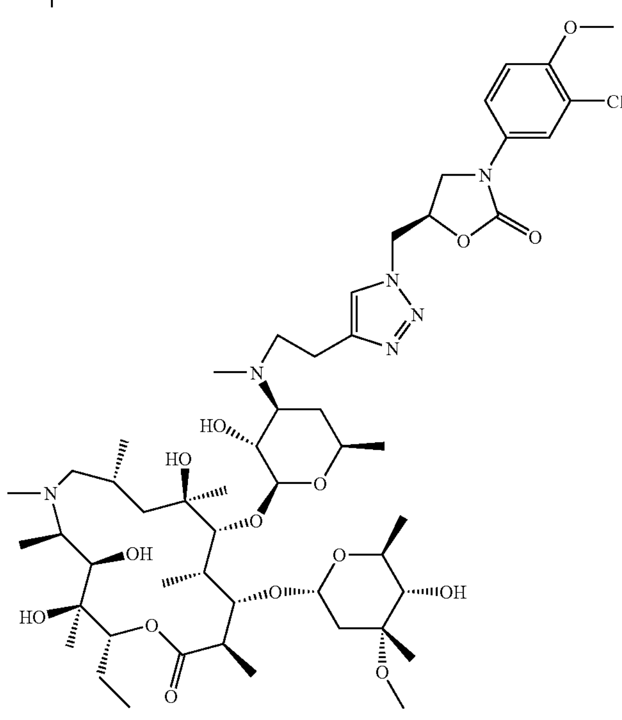 |

TABLE 2-continued
| Compound Number | Structure |
| --- | --- |
| 386 | 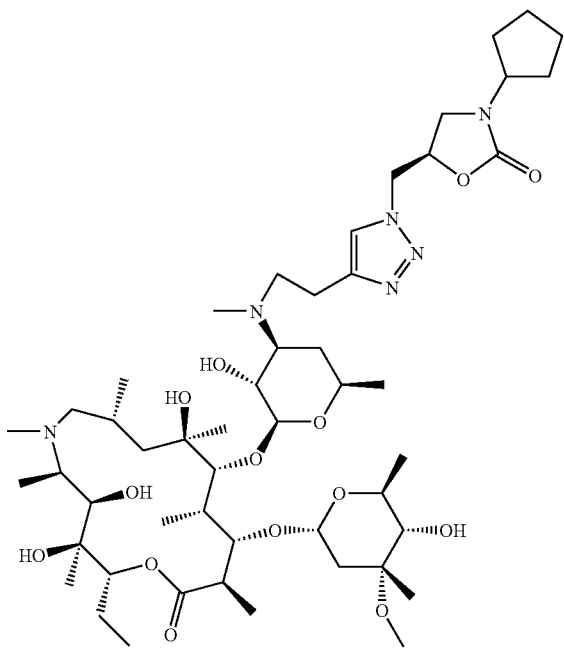 |
| 387 | 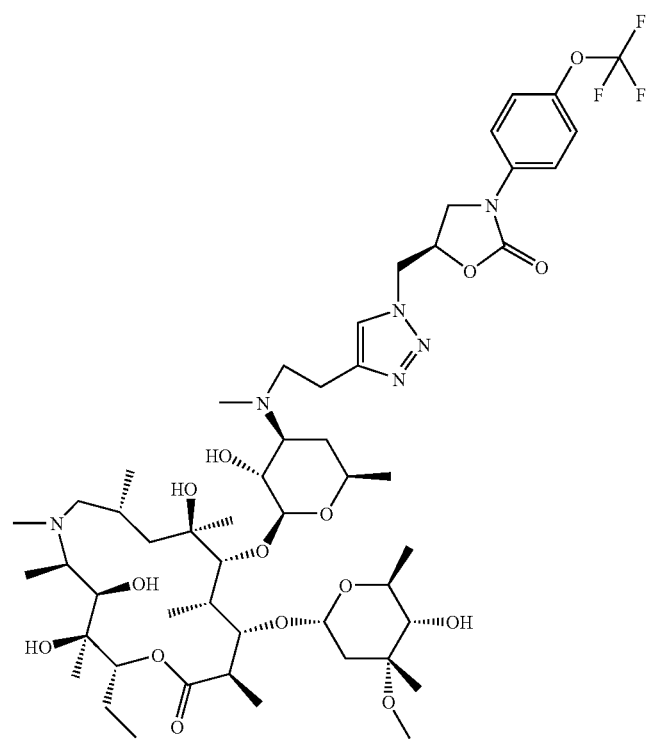 |

TABLE 2-continued
| Compound Number | Structure |
| --- | --- |
| 388 | 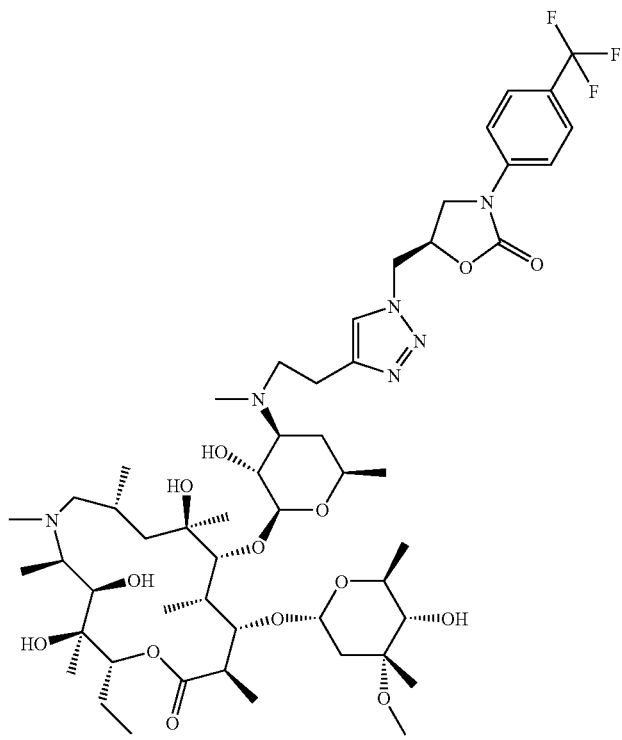 |
| 389 | 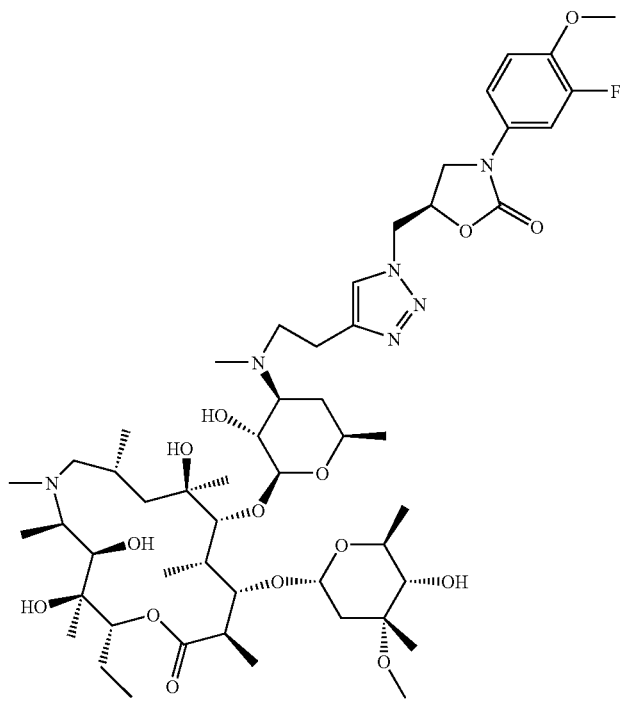 |

TABLE 2-continued

| Compound Number | Structure |
|---|---|
| 390 | 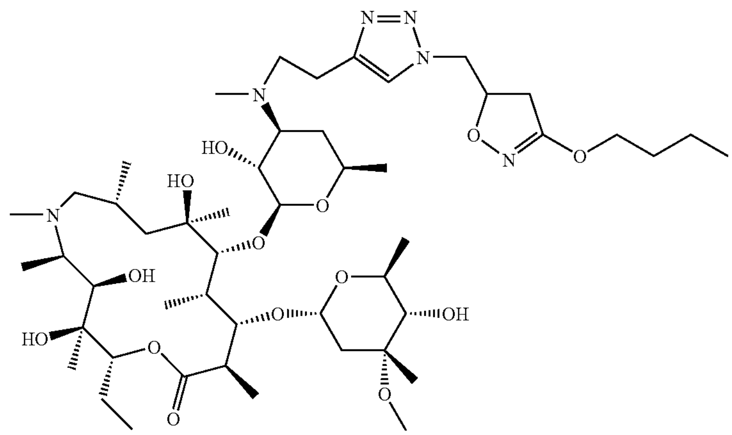 |
| 391 | 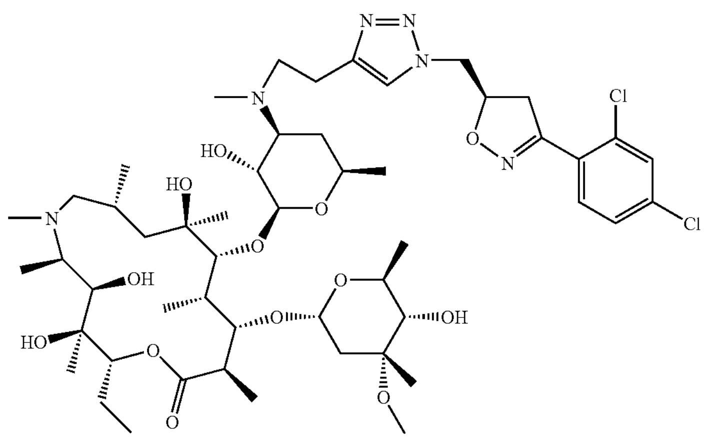 |
| 392 | 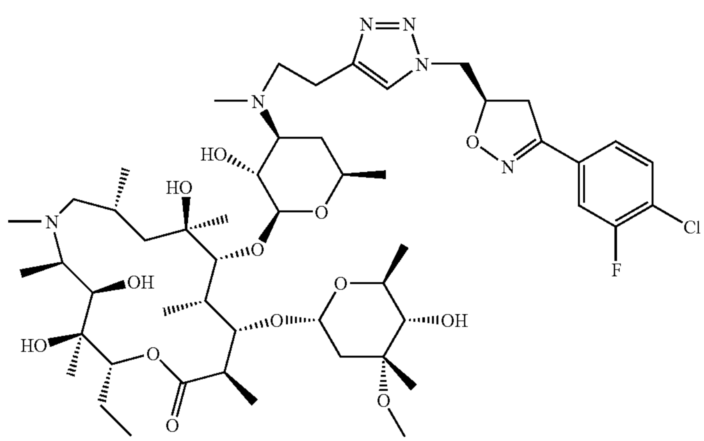 |

TABLE 2-continued
| Compound Number | Structure |
|---|---|
| 393 | 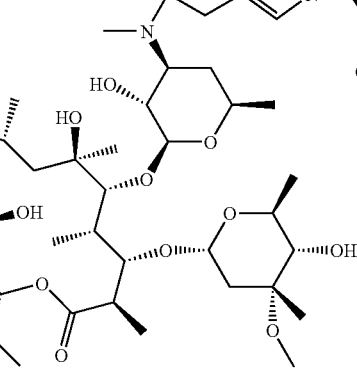 |
| 394 | 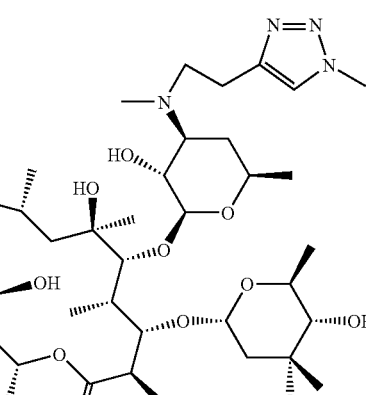 |
| 395 | 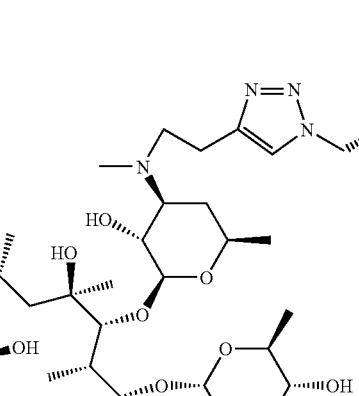 |

TABLE 2-continued
| Compound Number | Structure |
|---|---|
| 396 | 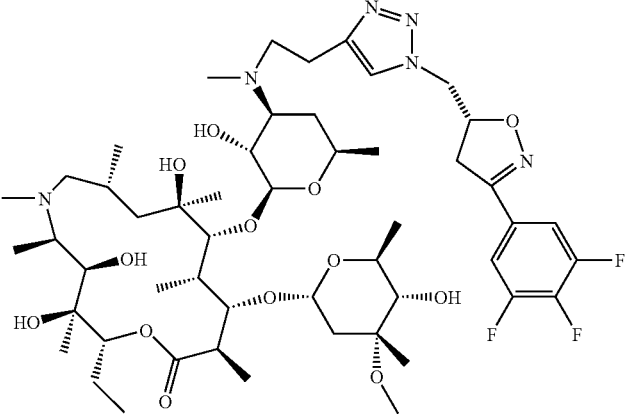 |
| 397 | 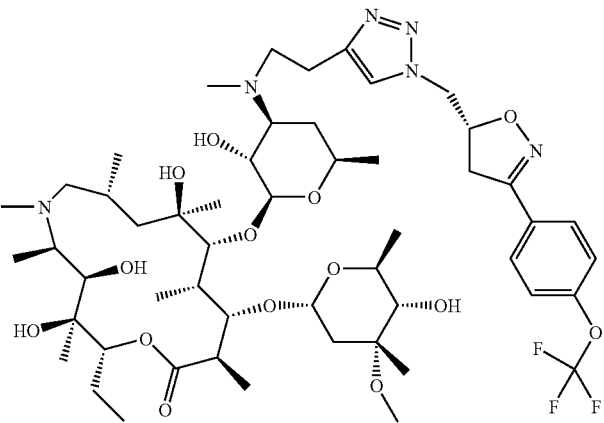 |
| 398 | 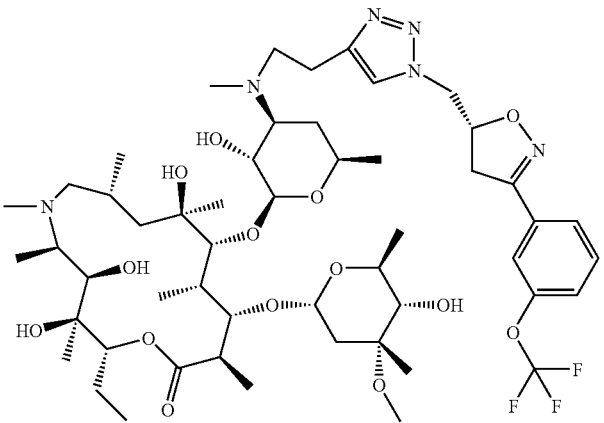 |

TABLE 2-continued

| Compound Number | Structure |
|---|---|
| 399 | 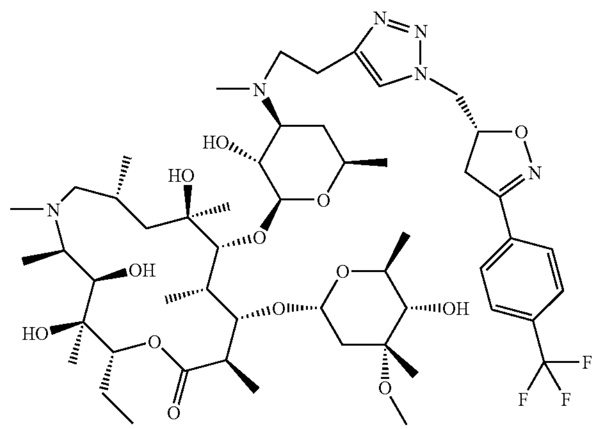 |
| 400 | 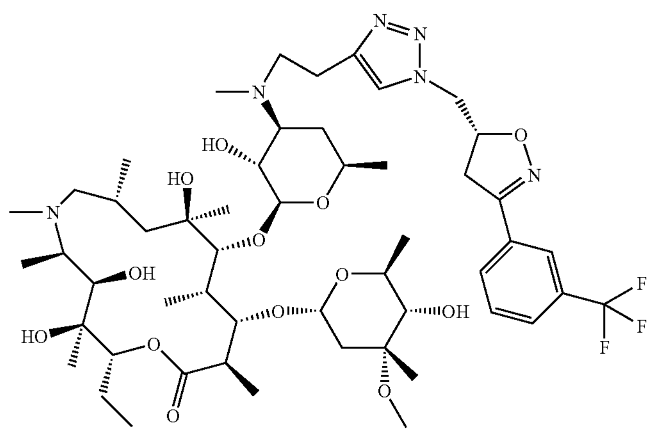 |
| 401 | 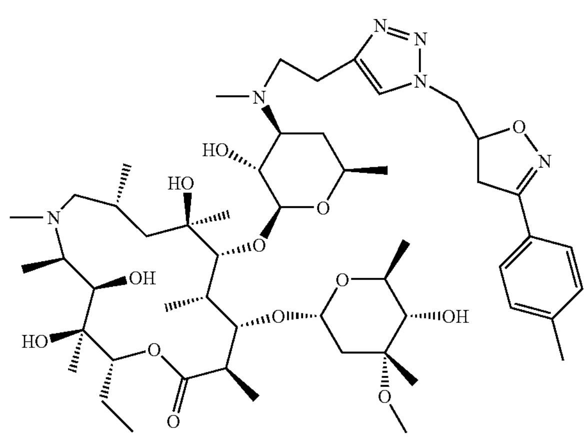 |

TABLE 2-continued

| Compound Number | Structure |
| --- | --- |
| 402 | 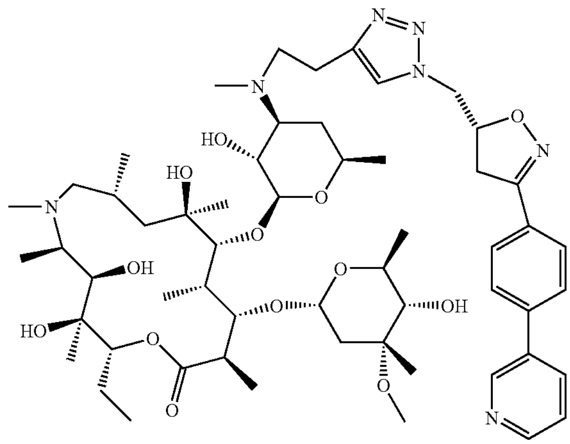 |
| 403 | 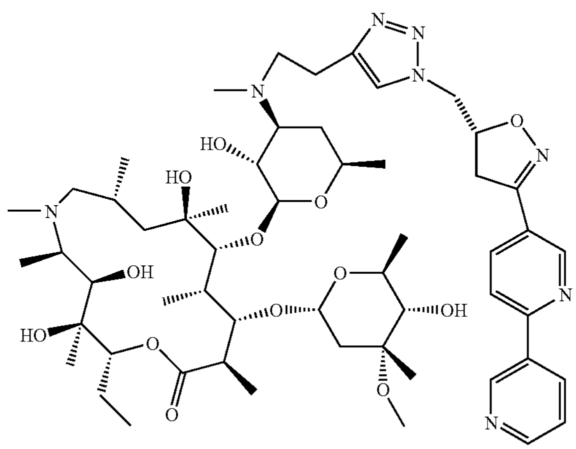 |
| 404 | 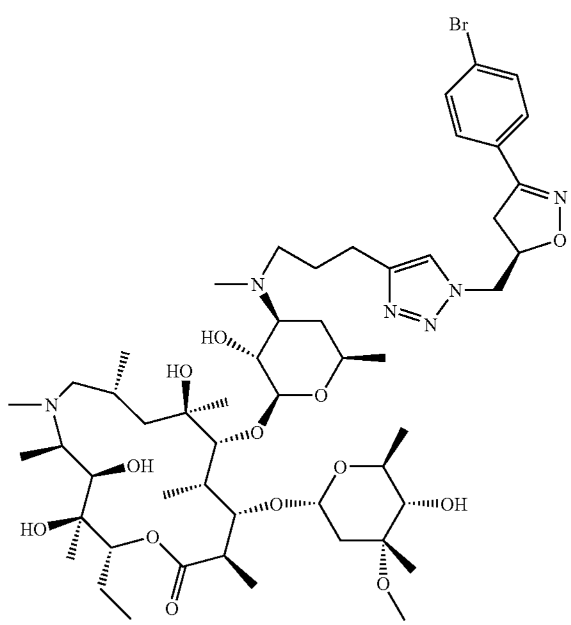 |

TABLE 2-continued
| Compound Number | Structure |
|---|---|
| 405 | 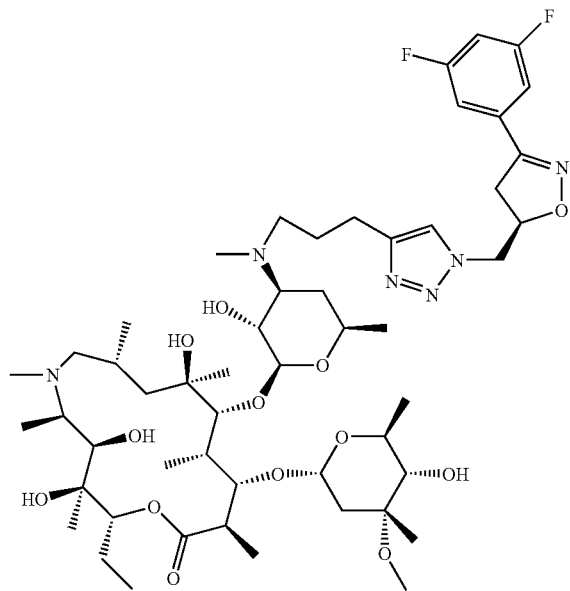 |
| 406 | 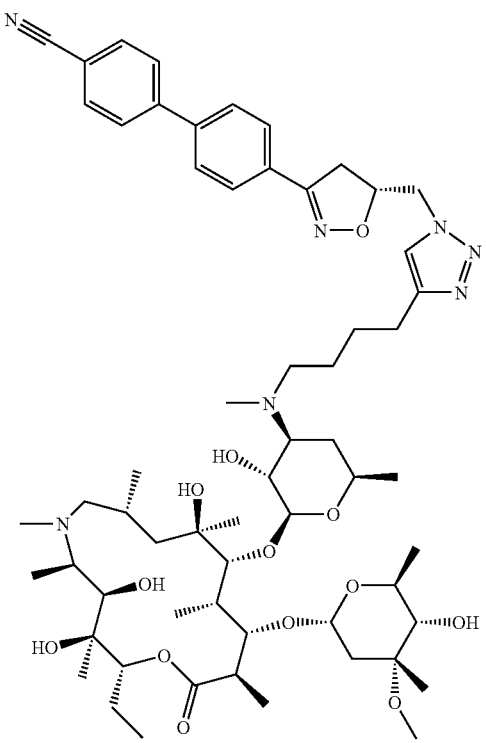 |

TABLE 2-continued
| Compound Number | Structure |
| --- | --- |
| 407 | 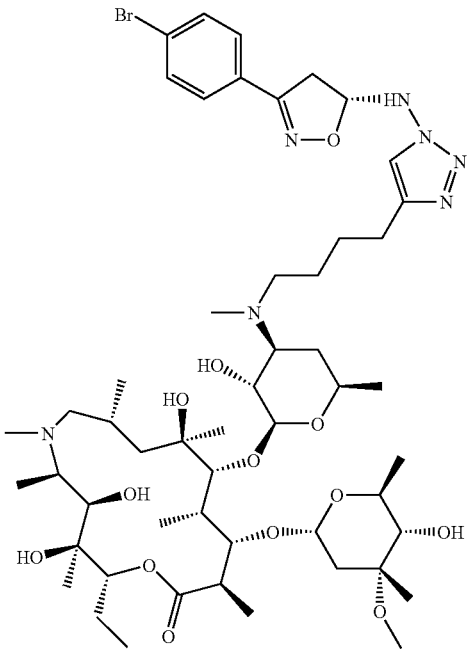 |
| 408 | 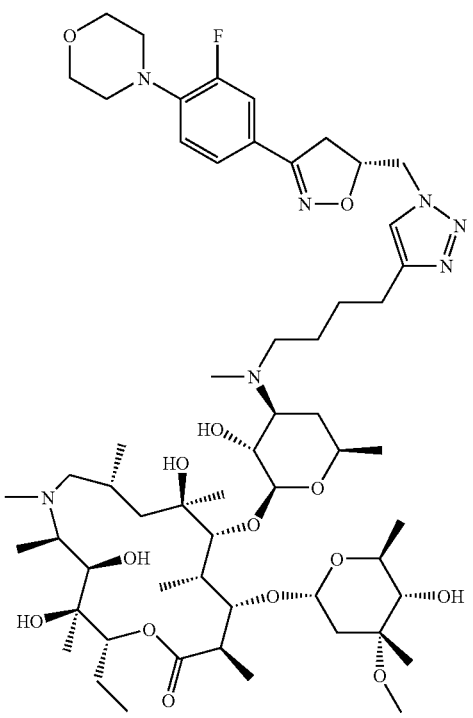 |

TABLE 2-continued
| Compound Number | Structure |
|---|---|
| 409 | 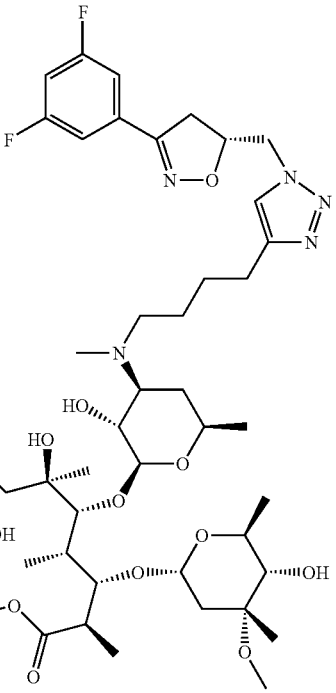 |
| 410 | 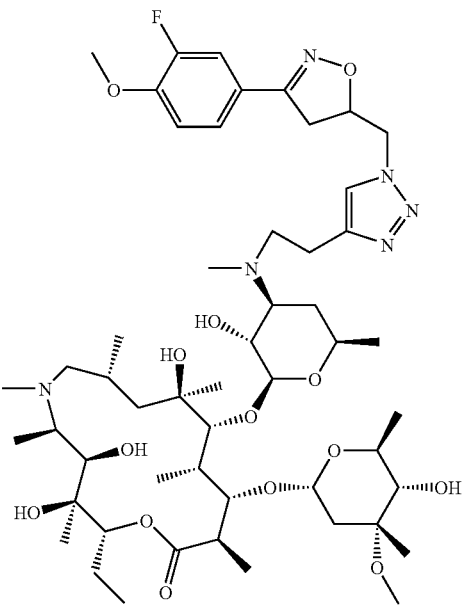 |

TABLE 2-continued
| Compound Number | Structure |
|---|---|
| 411 | 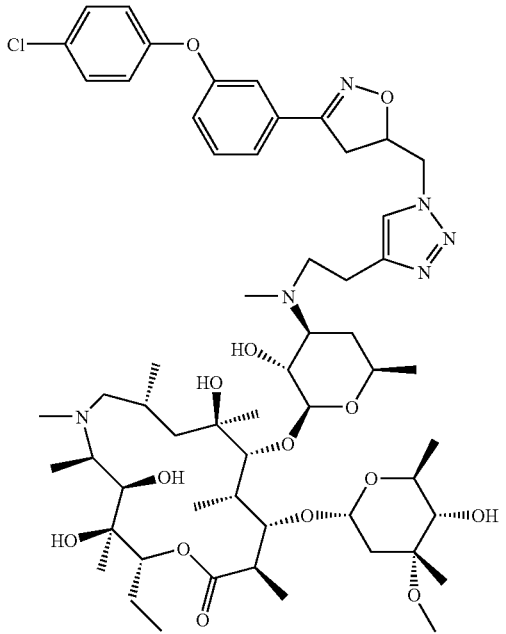 |
| 412 | 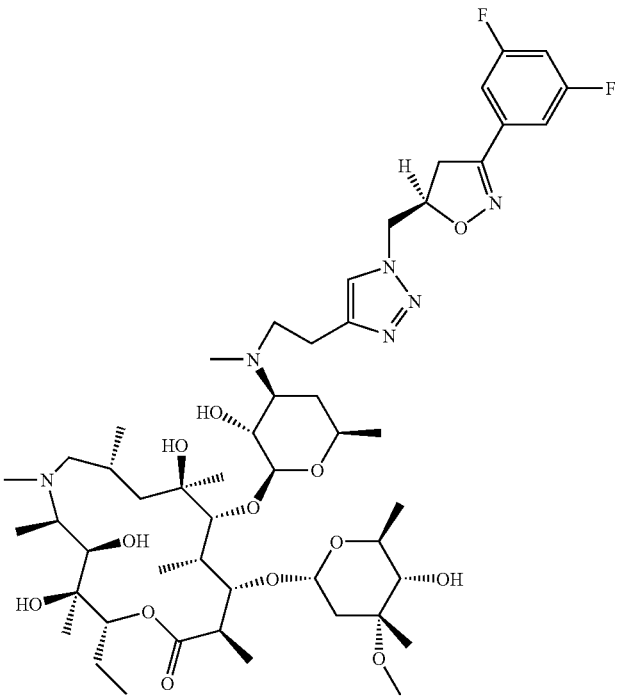 |

TABLE 2-continued

| Compound Number | Structure |
| --- | --- |
| 413 | 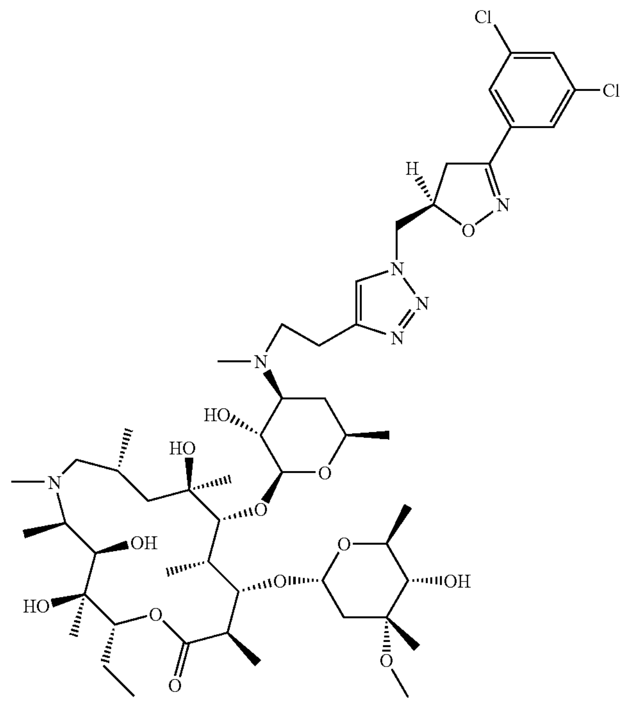 |
| 414 | 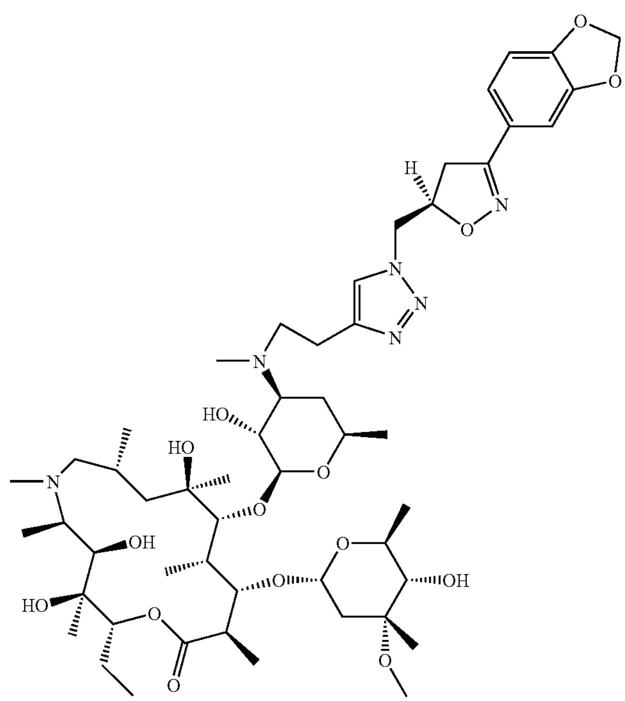 |

TABLE 2-continued

| Compound Number | Structure |
|---|---|
| 415 | 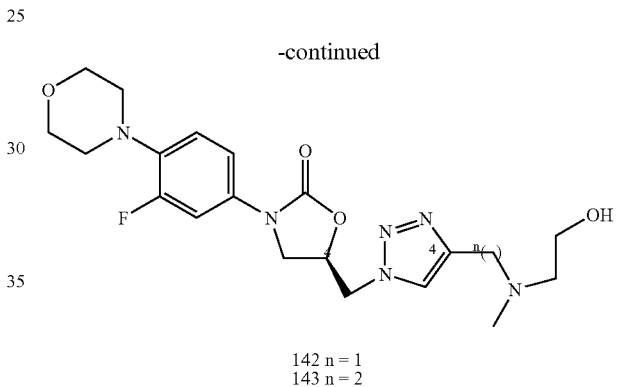 |

Example 2

Synthesis of Compounds 142 and 143

Scheme 28 below depicts the synthesis of compounds 142 and 143 using the chemistries previously exemplified. Briefly, 2-methylamino-ethanol was alkylated with propargyl bromide 154 and tosylate 155 to produce alkynes 156 and 157, respectively. Alkynes 156 and 157 were heated in the presence of the azide intermediate 158 (Brickner, S. J. et al. (1996) J. MED. CHEM 39: 673) to produce compounds 142 and 143, respectively.

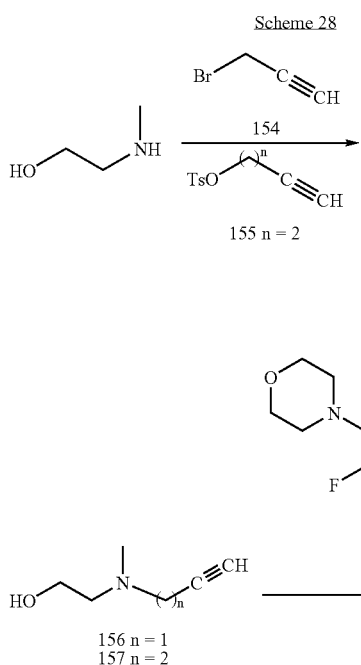

Scheme 28

Synthesis of Tosylate 155

3-Butyn-1-ol (1.8 g, 25 mmol) was dissolved in methylene chloride ($CH_2Cl_2$) (40 mL) and triethylamine ($Et_3N$) (4.18 mL, 30 mmol). The solution was stirred at 0° C. followed by addition of p-toluenesulfonyl chloride (5.05 g, 26.25 mmol). The reaction was allowed to warm to room temperature over a period of 1 hour and stirring was continued overnight. Thin layer chromatography (TLC) analysis (hexanes/ethyl acetate (EtOAc) 6:1) after 20 hours of reaction showed a complete consumption of 3-butyn-1-ol. The precipitated triethylamine hydrochloride was filtered off and the filtrate washed with water ($H_2O$) (30 mL) and brine (30 mL). The organic layer was dried over sodium sulfate ($Na_2SO_4$) and the solvent evaporated away to give 155 as a light-yellow oil (5.45 g, 97%). The crude oil was used without further purification; however, it could be purified on a silica gel column, first eluting with 8% EtOAc in hexanes followed by 40% EtOAc in hexanes.

Synthesis of Alkyne 157

A suspension of O-tosyl-3-butyn-1-ol (2.8 g, 12.5 mmol), 2-methylaminoethanol (0.93 mL, 11.4 mmol) and sodium bicarbonate ($NaHCO_3$) was heated at 50° C. for 20 hours. $NaHCO_3$ was filtered, the solvent was evaporated, and the resulting residue was partitioned between $H_2O$ (30 mL) and EtOAc (30 mL). The layers were separated and the aqueous layer was back extracted with EtOAc (4×20 mL). The combined organic layer was dried over Na₂SO₄ and the solvent evaporated away to give an oil), residue. The oily crude was purified on silica gel column eluting with 5:1 CH₂Cl₂/methanol (MeOH) to give compound 157 as an oil (0.54 g, 37%).

Synthesis of Alkyne 156

Alkyne 156 was made from 2-methylaminoethanol and propargyl bromide as described for alkyne 157 above.

Synthesis of Triazole 142

Azide 158 (0.15 g, 0.47 mmol) and alkyne 156 (0.212 g, 1.5 mmol) were dissolved in anhydrous tetrahydrofuran (THF) (10 mL) and Hunig's base (2 mL, 11.6 mmol). To this solution was added copper iodide (CuI) (0.136 g, 0.7 mmol) and the resulting suspension stirred at room temperature for 16 hours. TLC (chloroform (CHCl₃)/MeOH 10:1) showed a quantitative consumption of azide 158. Methylene chloride (30 mL) was added, the suspension was filtered and solvent was evaporated from the filtrate. The residue was purified on silica gel eluting with 6-13% MeOH in CH₂Cl₂ to provide triazole 142 (0.11 g, 50.6%). Data for 142: ¹H-NMR (500 MHz, CDCl₃) δ 7.78 (s, 1H), 7.30 (dd, J=15, 3 Hz, 1H), 6.98 (dd, J=9, 2 Hz, 1H), 6.88 (t, J=10 Hz, 1H), 5.08 (m, 1H), 4.77 (m, 2H), 4.15 (t, J=10 Hz, 1H), 3.94 (m, 1H), 3.85 (t, J=5 Hz, 4H), 3.76 (bs, 2H), 3.60 (m, 2H), 3.03 (t, J=4 Hz, 4H), 2.53 (m, 2H), 2.26 (s, 3H).

Synthesis of Triazole 143

Azide 158 (0.383 g, 1.2 mmol) and alkyne 157 (0.24 g, 1.9 mmol) were dissolved in anhydrous THF (12 mL) and Hunig's base (3 mL, 17.4 mmol). To this solution was added CuI (0.43 g, 2.2 mmol) and the resulting suspension was stirred at room temperature for 3 hours. TLC (CH₂Cl₂/MeOH 9:1) showed that the reaction was complete within 3 hours with no further consumption of azide 158 upon stirring overnight. Methylene chloride (50 mL) was added, the suspension was filtered and solvent was evaporated from the filtrate. The residue was purified on silica gel eluting with 10-20% MeOH in CH₂Cl₂ to provide triazole 143 (0.108 g, 20%). Data for 143: ¹H-NMR (500 MHz, CDCl₃/CD₃OD) δ 7.78 (s, 1H), 7.33 (dd, J=15, 3 Hz, 1H), 7.02 (dd, J=9, 2 Hz, 1H), 6.95 (t, J=9 Hz, 1H) 5.10 (m, 1H), 4.76 (m, 2H), 4.19 (t, J=9 Hz, 1H). 3.93 (m, 1H), 3.87 (t, J=5 Hz, 414), 3.65 (m, 2H), 3.06 (t, J=5 Hz, 4H), 2.90 (t, J=4 Hz, 2H), 2.75 (t, J=5 Hz, 2H), 2.62 (t, J=6 Hz, 2H), 2.34 (s, 3H).

Example 3

Synthesis of Compound 144

Scheme 29 below depicts the synthesis of compound 144 using the chemistries previously exemplified. Cycloaddition of azide 158 and alkyne 159 produced triazole 160. Tosylation of the alcohol of triazole 160, followed by alkylation with 2-methylamino-ethanol, produced 4-substituted triazole 144.

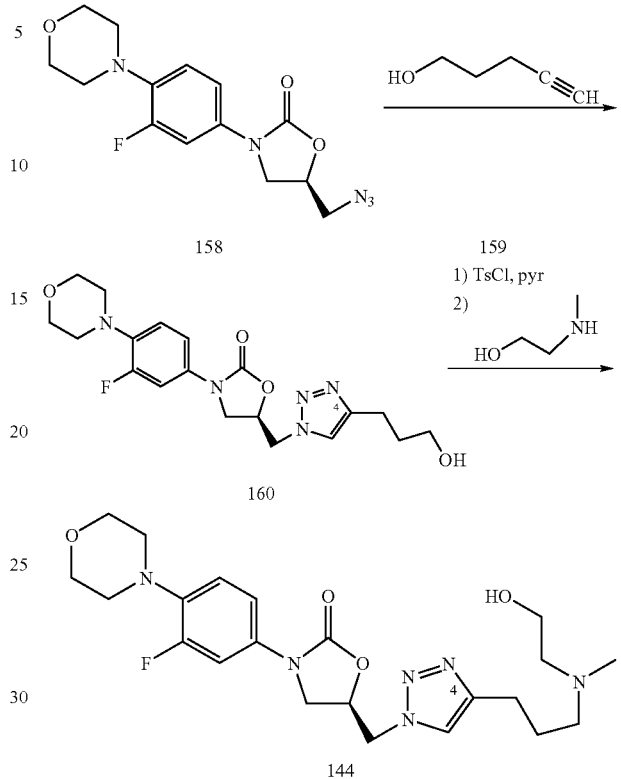

Scheme 29

Synthesis of Alcohol 160

Azide 158 (0.15 g, 0.47 mmol) and 4-pentyn-1-ol (0.034 g, 0.39 mmol) were dissolved in anhydrous THF (10 mL) and Hunig's base (2 mL, 11.6 mmol). To this solution was added CuI (0.136 g, 0.7 mmol) and the resulting suspension was stirred at room temperature for 16 hours. TLC (CHCl₃/MeOH 10:1) showed a quantitative consumption of azide 158. Methylene chloride (30 mL) was added, the suspension was filtered and solvent was evaporated from the filtrate. The residue was purified on silica gel eluting with 5-7% MeOH in CH₂Cl₂ to provide 160 (0.077 g, 48.7%).

Synthesis of Triazole 144

Compound 160 (0.072 g, 0.178 mmol) was dissolved in CH₂Cl₂ (2 mL) and Et₃N (0.09 mL, 0.63 mmol). To this solution was added p-toluenesulfonlyl chloride (0.0366 g, 0.19 mmol) and stirring continued at room temperature for 20 hours during which a quantitative consumption of compound 160 was noticed by TLC (CH₂Cl₂/MeOH 9: 1). The reaction was quenched with 10:1H₂O/THF within 30 minutes and then partitioned between 10% NaHCO₃ (20 mL) and CH₂Cl₂ (20 mL). The two layers were separated; and the organic layer washed with saturated brine (3×15 mL) and dried over Na₂SO₄. Solvent was evaporated to give an oily residue.

The crude product above was dissolved in THF (3 mL) and Hunig's base (0.31 mL, 1.8 mmol). To this solution was added 2-(methylamino)ethanol (0.037 mL, 0.45 mmol) and stirring was continued at room temperature for 20 hours. The reaction was partitioned between 5% MeOH in CH$_2$Cl$_2$ (30 mL) and saturated brine (20 mL). The two layers were separated and the resulting organic layer was washed with saturated brine (2×20 mL), dried over Na$_2$SO$_4$ and the solvent was evaporated. The crude product was purified on silica gel eluting with 15-35% MeOH in CH$_2$Cl$_2$ to CH$_2$Cl$_2$/MeOH/ammonium hydroxide (NH$_4$OH) 3:1:0.05 to provide compound 144 (0.041 g, 50%). Data for 144: $^1$H-NMR (500 MHz, CDCl$_3$/CD$_3$OD) δ 7.77 (s, 1H), 7.34 (dd, J=15, 3 Hz, 1H), 7.04 (dd, J=9, 2.5 Hz, 1H), 6.98 (t, J=9 Hz, 1H), 5.12 (m, 1H), 4.77 (m, 2H), 4.20 (t, J=9 Hz, 1H), 3.96 (m, 1H), 3.86 (t, J=5 Hz, 4H), 3.63 (m, 2H), 3.05 (t, J=5 Hz, 4H), 2.71 (t, J=6 Hz, 2H), 2.52 (t, J=6 Hz, 2H), 2.42 (t, J=8 Hz, 2H), 2.26 (s, 3H), 1.83 (m, 2H).

Example 4

Synthesis of Compounds 145-147

Scheme 30 below depicts the synthesis of compounds 145-147 using chemistries previously exemplified. Desmethyl erythromycin amine 39 was alkylated with propargyl bromide 154 or the tosylates 155 and 161 to produce alkynes 162, 163 and 164, respectively. Hydrolysis of alkynes 162, 163 and 164 produces alkynes 165, 166 and 167, respectively, which were then used in a cycloaddition reaction with azide 158 to produce the 4-substituted triazole compounds 145, 146 and 147, respectively.

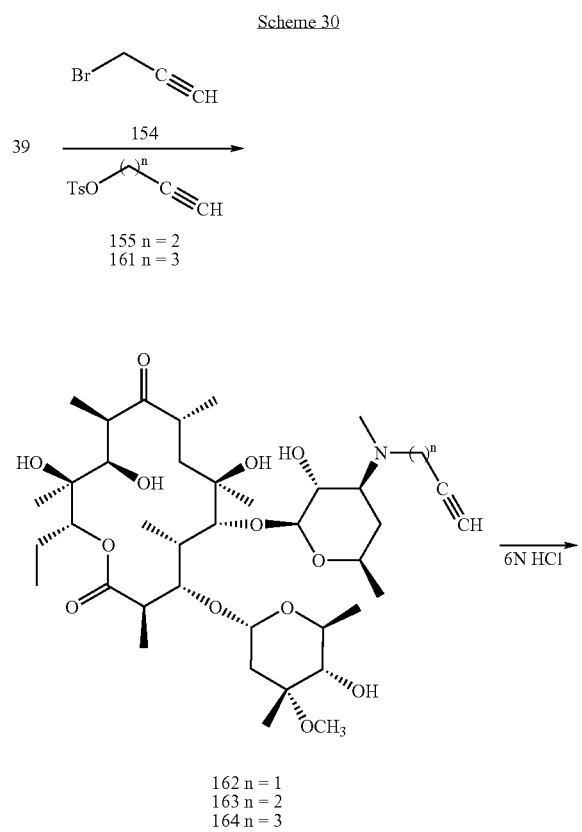

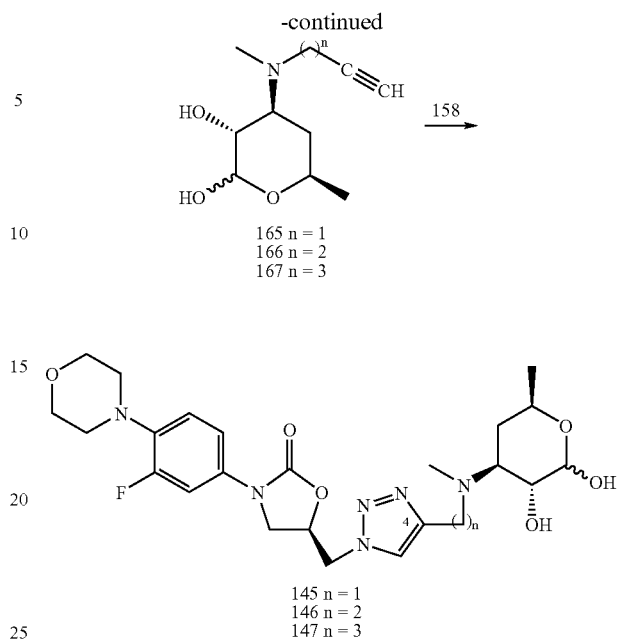

Synthesis of Tosylate 161

Tosylate 161 was made from 4-pentyn-1-ol using the same protocol described for the synthesis of tosylate 155 above.

Synthesis of Alkyne 165

Alkyne 162 (800 mg) was stirred with 6N hydrochloric acid (HCl) overnight at ambient temperature and heated to 100° C. for 2 hours. The dark solution was cooled to room temperature and extracted with CH$_2$Cl$_2$ (3×8 mL) and ethyl ether (Et$_2$O) (3×8 mL). The aqueous phase was concentrated to obtain a foamy solid, which was redissolved in water (8 mL) and neutralized with NaHCO$_3$. The solution was extracted with EtOAc (3×10 mL), dried with Na$_2$SO$_4$, concentrated and purified by flash chromatography (silica gel, 5% MeOH—CHCl$_3$) to give the alkyne 165 (85 mg, 40%) as a mixture of anomers.

Synthesis of Alkyne 166 and 167

The same procedure used for the synthesis of alkyne 165 from 162 was used to synthesize alkyne 166 from 163, and alkyne 167 from 164. The alkynes 166 and 167 were used in subsequent chemistry without further purification.

Synthesis of Triazole 145

To a solution of alkyne 165 (80 mg, 0.0402 mmol), azide 158 (155 mg, 0.482 mmol), and Hunig's base (2.1 mL, 12.06 mmol) in THF (5 mL) was added CuI (156 mg, 0.804 mmol) and the mixture was stirred overnight at ambient temperature. The reaction mixture was diluted with 10% MeOH—CHCl$_3$ (50 mL), washed with brine (2×50 mL), dried with Na$_2$SO$_4$, and concentrated under reduced pressure. The crude mixture was purified by flash chromatography (silica gel, 10% MeOH—CHCl$_3$) to give compound 145 (80 mg, 40%). Data for 145: $^1$H-NMR (500 MHz, CDCl$_3$; partial structure) δ 7.72 (s, 1H), 7.28 (d, 1H), 6.95-6.84 (m, 2H, m).

Synthesis of Triazoles 146 and 147

The same procedure used for the synthesis of triazole 145 from 165 was used to synthesize triazole 146 from alkyne 166, and triazole 147 from alkyne 167.

Example 5

Synthesis of Compounds 148-150

Scheme 31 below depicts the synthesis of compounds 148-150 using one exemplary method. Alkynes 162, 163 and 164 were reacted with azide 158 to produce a mixture of the 4-substituted triazoles 148, 149, and 150, respectively.

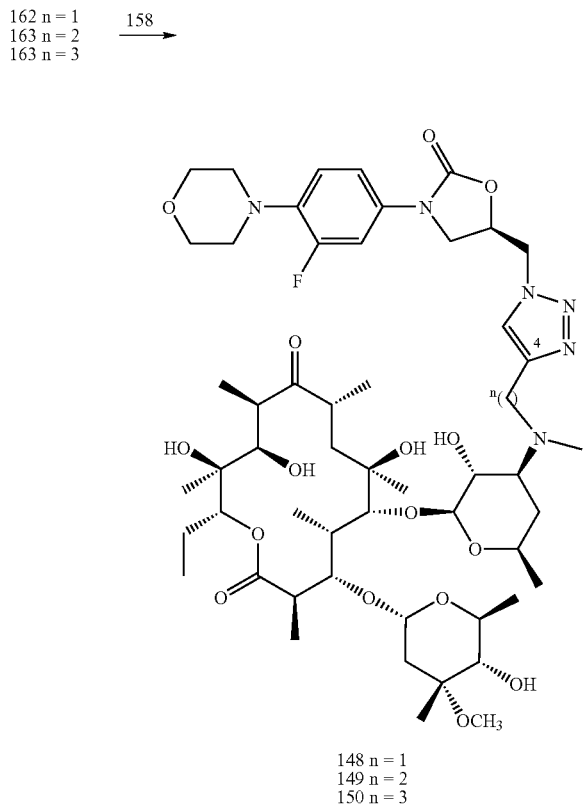

Scheme 31

162 n = 1
163 n = 2
163 n = 3

158 →

148 n = 1
149 n = 2
150 n = 3

Scheme 32 below depicts the synthesis of compounds 149 and 150 using an alternative exemplary method. Azide 158 was reacted with tosylates 155 and 161 to produce triazole tosylates 168 and 169, respectively. The reaction of compounds 168 and 169 with amine 39 produced compounds 149 and 150, respectively.

Scheme 32

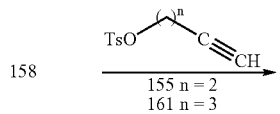

158 → 
155 n = 2
161 n = 3

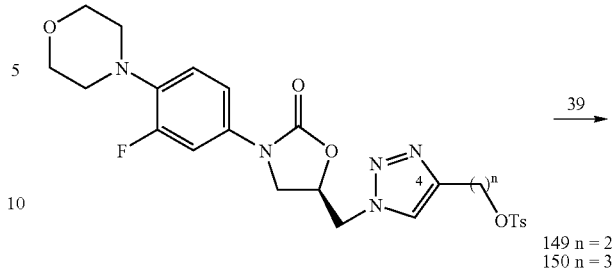

149 n = 2
150 n = 3

Synthesis of Amine 39

Compound 39 was made from erythromycin A employing the procedure described in U.S. Pat. No. 3,725,385.

Synthesis of Alkyne 163

A mixture of des(N-methyl)erythromycin 39 (1.0 g, 1.4 mmol) and tosylate 155 (1.25 g, 5.6 mmol) in anhydrous THF (15 mL) and Hunig's base (2.2 mL, 11.9 mmol) was kept stirring at 55° C. for 48 hours. The reaction was poured into $CH_2Cl_2$ (50 mL), extracted with 2% aqueous $NH_4OH$ (3×30 mL) and saturated brine (1×30 mL). The organic layer was dried over $Na_2SO_4$ and the solvent was evaporated away. The crude was purified on silica gel column eluting with $CH_2Cl_2$/MeOH 10:1 to give 163 (0.35 g, 32%).

Synthesis of Alkyne 164

Alkyne 164 was made from des(N-methyl)erythromycin 39 and tosylate 161 using the same procedure described for alkyne 163.

Synthesis of Alkyne 162

Alkyne 162 was made from des(N-methyl)erythromycin 39 and propargyl bromide using the same procedure described for alkyne 163.

Synthesis of Tosylate 168

Azide 158 (1.5 g, 4.7 mmol) and tosylate 155 (0.875 g, 3.9 mmol) were dissolved in anhydrous THF (25 mL) and Hunig's base (10 mL, 57.4 mmol). To this solution was added CuI (1.36 g, 7.0 mmol) and the resulting suspension was stirred at room temperature for 2 hours. TLC ($CHCl_3$/MeOH 10:1) showed a quantitative consumption of azide 158. The reaction was poured into $CH_2Cl_2$ (60 mL), extracted with saturated $NaHCO_3$ (3×30 mL) and saturated brine (2×30 mL). The organic layer was dried over $Na_2SO_4$ and the solvent was evaporated away. The crude was purified on silica gel column eluting with 0-3% MeOH in $CH_2Cl_2$ to give 168 (1.34 g, 63%).

Synthesis of Triazole 149

Method A: Alkyne 163 (0.80 g, 1.036 mmol) and azide 158 (0.50 g, 1.6 mmol) were dissolved in anhydrous THF (10 mL) and Hunig's base (2.2 mL, 11.6 mmol). To this solution was added CuI (0.403 g, 2.07 mmol) and the resulting suspension stirred at room temperature for 2 hours. $CH_2Cl_2$ (60 mL) was added, the solution was extracted with saturated $NaHCO_3$ (3×30 mL), $NH_4Cl$ (3×30 mL) and saturated brine (30 mL). The organic layer was dried over $Na_2SO_4$ and the solvent was evaporated. The crude was purified on silica gel eluting with $CH_2Cl_2$/MeOH 15:1 to 10:1 to provide triazole 149 (0.91 g, 80%).

Method B: A mixture of des(N-methyl)erythromycin 39 (0.25 g, 0.342 mmol) and tosylate 168 (0.28 g, 0.51 mmol) in anhydrous THF (5 mL) and Hunig's base (0.65 mL, 3.51 mmol) was stirred at 55° C. for 48 hours. The reaction was poured into $CH_2Cl_2$ (30 mL), extracted with saturated $NaHCO_3$ (3×20 mL) and saturated brine (1×20 mL). The organic layer was dried over $Na_2SO_4$ and the solvent evaporated. The crude product was purified on silica gel column eluting with $CH_2Cl_2$/MeOH 15:1 to 10:1 to give triazole 149 (0.151 g, 40%). Data for 149: $^1$H-NMR, partial, (500 MHz, $CDCl_3$) δ 7.60 (s, 1H), 7.29 (dd, J=14, 3 Hz, 1H), 6.95 (dd, J=10, 3 Hz, 1H), 6.86 (t, J=9 Hz, 1H), 5.00 (m, 2H), 4.85 (d, J=5H, 1H), 4.67 (m, 2H), 4.37 (d, J=7 Hz, 1H), 4.08 (t, J=10 Hz, 1H), 3.52 (d, J=8 Hz, 1H), 3.44 (m, 1H), 2.66 (m, 2H), 0.82 (t, J=8 Hz, 3H).

Synthesis of Triazole 148

Triazole 148 was made from alkyne 162 and azide 158 using method A as described for triazole 149.

Synthesis of Triazole 150

Triazole 150 was made from alkyne 164 and azide 158 using both methods A and B described for triazole 149. Data for 150: $^1$H-NMR, partial, (500 MHz, $CDCl_3$) δ 7.49 (s, 1H), 7.26 (dd, J=15, 3 Hz, 1H), 6.91 (dd, J=10, 3 Hz, 1H), 6.84 (t, J=9 Hz, 1H), 5.00 (m, 2H), 4.85 (d, J=5H, 1H), 4.67 (m, 2H), 4.38 (d, J=8 Hz, 1H), 4.07 (t, J=10 Hz, 1H), 3.52 (d, J=8 Hz, 1H), 3.44 (m, 1H), 2.69 (m, 2H), 0.78 (t, J=8 Hz, 3H).

Example 6

Synthesis of Compounds 151-153

Scheme 33 below depicts the synthesis of compounds 151-153 using the chemistries previously exemplified. Demethylation of azithromycin 170 selectively produced amine 171. Amine 171 was alkylated with bromide 154 and tosylates 155 and 161 to produce alkynes 172, 173 and 174, respectively. Cycloaddition of alkynes 172, 173 and 174 with azide 158 produced compounds 151, 152 and 153, respectively.

Scheme 33

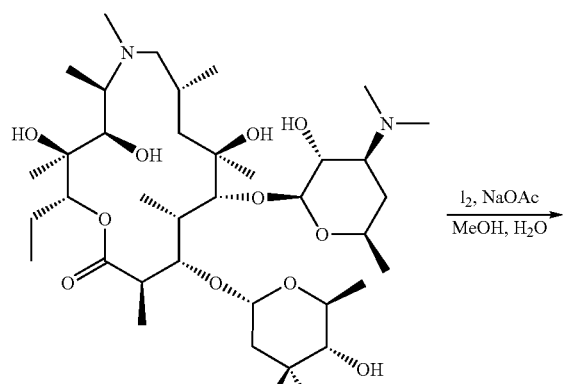

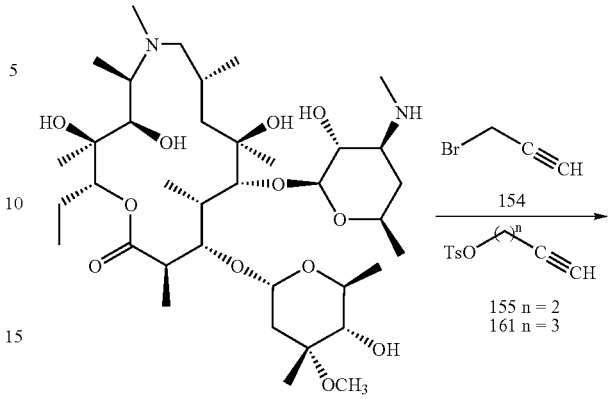

Synthesis of des(N-methyl)azithromycin 171

Azithromycin 170 (0.80 g, 1.02 mmol) and sodium acetate (NaOAc) (0.712 g, 8.06 mmol) were dissolved in 80% aqueous MeOH (25 mL). The solution was kept at 50° C. followed by addition of iodine ($I_2$) (0.272 g, 1.07 mmol) in three batches within 3 minutes. The reaction was maintained at a pH between 8-9 by adding 1N sodium hydroxide (NaOH) (1 mL) at 10 min and 45 minute intervals. The solution turned colorless within 45 minutes, however, stirring was continued for 2 hours. TLC ($CH_2Cl_2$/MeOH/ $NH_4OH$ 10:1:0.05) after 2 hours showed a single major product (Rf=0.66). The reaction was cooled to room temperature, poured into $H_2O$ (75 mL) containing $NH_4OH$ (1.5 mL) and extracted with $CHCl_3$ (3×30 mL). The combined organic layer was washed with $H_2O$ (30 mL) containing $NH_4OH$ (1.5 mL), dried over $Na_2SO_4$ and the solvent evaporated to give a white residue. The crude was purified on silica gel column eluting with $CH_2Cl_2$/MeOH/$NH_4OH$ 18:1:0.05 to 10:1:0.05 to provide amine 171 (0.41 g, 55%).

Synthesis of Alkyne 172

Alkyne 172 was made from des(N-methyl)azithromycin 171 and propargyl bromide using the same procedure described for the synthesis of compound 163.

Synthesis of Alkyne 173

Alkyne 173 was made from des (N-methyl)azithromycin 171 and tosylate 155 using the same procedure described for the synthesis of compound 163.

Synthesis of Triazole 151

Triazole 151 was made from alkyne 172 and azide 158 using method A as described for the synthesis of compound 149.

Synthesis of Triazole 152

Triazole 152 was made from alkyne 173 and azide 158 using method A as described for the synthesis of compound 149. Data for 152: $^1$H-NMR (300 MHz, CDCl$_3$, partial): δ 7.63 (s, 1H), 7.34 (dd, J=14, 2 Hz, 1H), 6.98 (dd, J=9, 2 Hz, 1H), 6.90 (t, J=9 Hz, 1H), 5.11 (d, J=4 Hz, 1H), 4.96 (m, 1H), 4.71 (m, 3H), 4.44 (d, J=7 Hz, 1H), 4.30 (d, J=2 Hz, 1H), 4.10 (m, 2H), 3.86 (m, 5H), 3.04 (m, 5H), 0.90 (t, J=7 Hz, 3H).

Synthesis of Triazole 153

Triazole 153 was made from alkyne 174 and azide 158 using method A as described for compound 149. Data for 153: $^1$H-NMR, partial, (500 MHz, CDCl$_3$) δ 7.50 (s, 1H), 7.29 (dd, J=15, 3 Hz, 1H), 6.94 (dd, J=10, 3 Hz, 1H), 6.87 (t, J=9 Hz, 1H), 5.13 (m, 1H), 5.00 (m, 1H), 4.71 (m, 2H), 4.43 (d, J=7 Hz, 1H), 4.26 (bs, 1H), 3.61 (d, J=8 Hz, 1H), 0.78 (t, J=8 Hz, 3H).

Synthesis of Alkyne 174

Alkyne 174 was made from des(N-methyl)azithromycin 171 and tosylate 161 using the same procedure described for compound 163.

Example 7

Synthesis of Compound 175

Triazole 152 was hydrolyzed with dilute acid to afford the des-cladinose derivative 175.

Synthesis of Triazole 175

Compound 152 (0.120 g, 0.108 mmol) was dissolved in 0.25N HCl (10 mL) and the solution was kept stirring at room temperature for 24 h. The reaction was extracted with CH$_2$Cl$_2$ (2×20 mL) and the organic layer was discarded. The aqueous layer was basified with conc. NH$_4$OH and then extracted with CH$_2$Cl$_2$ (3×30 mL). The combined organic layer was extracted with saturated brine (1×20 mL), and dried over Na$_2$SO$_4$. TLC (CH$_2$Cl$_2$/MeOH/NH$_4$OH 10:1: 0.05) showed >95% conversion to a new lower Rf product (Rf=0.56). The solvent was evaporated to provide 175 as a white solid (0.101 g, 98%). Data for 175: $^1$H-NMR (300 MHz, CDCl$_3$, partial): δ 7.58 (s, 1H), 7.26 (dd, J=14, 2 Hz, 1H), 6.91 (dd, J=10, 2 Hz, 1H), 6.82 (t, J=9 Hz, 1H), 4.97 (m, 1H), 4.63-4.66 (m, 3H), 4.36 (d, J=7 Hz, 1H), 4.02 (bs, 1H), 3.78 (t, J=4 Hz, 4H), 2.96 (t, J=5 Hz, 4H), 0.83 (t, J=7 Hz, 3H).

Example 8

Synthesis of Compounds 176-178

Scheme 34 below depicts the synthesis of compounds 176-178 using the chemistries previously exemplified. Azide 188 was treated with alkyne 163 to afford triazole 176. The same azide was used to make triazoles 177 and 178 from alkynes 164 and 173 respectively.

Scheme 34

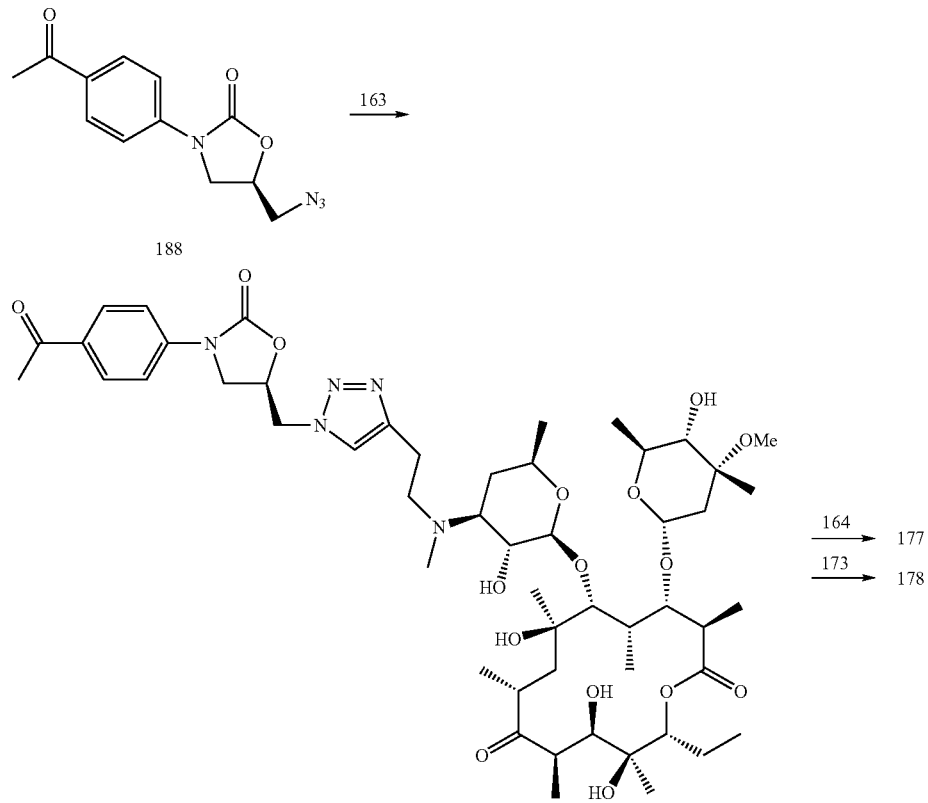

Synthesis of Azide 188

The known azide 188 can be synthesized following the procedure reported in the literature (Gregory, W. A. et al. *J. Med. Chem.* 1989, 32, 1673).

Synthesis of Triazole 176

This compound was made from alkyne 163 and azide 188 using method A as described for compound 149. Data for 176: $^1$H-NMR (300 MHz, CDCl$_3$, partial): δ 7.90 (d, J=9 Hz, 2H), 7.59 (s, 1H), 7.50 (d, J=9 Hz, 2H), 5.01-5.15 (m, 2H), 4.84 (d, J=4 Hz, 1H), 4.71 (m, 2H), 4.36 (d, J=7 Hz, 1H), 4.20 (t, J=7 Hz, 1H) 3.93-4.02 (m, 4H), 3.79 (bs, 1H), 0.79 (t, J=7 Hz, 3H).

Synthesis of Triazole 177

This compound was made from alkyne 164 and azide 188 using method A as described for compound 149. Data for 177: $^1$H-NMR (300 MHz, CDCl$_3$, partial): δ 7.98 (d, J=9 Hz, 2H), 7.53-7.56 (m, 3H), 5.07-5.19 (m, 2H), 4.89 (d, J=4 Hz, 1H), 4.75 (m, 2H), 4.43 (d, J=7 Hz, 1H), 4.22 (t, J=7 Hz, 1H), 4.01 (m, 1H), 3.92 (s, 1H), 3.83 (s, 1H), 0.86 (t, J=7 Hz, 3H).

Synthesis of Triazole 178

This compound was made from alkyne 173 and azide 188 using method A as described for compound 149. Data for 178: $^1$H-NMR (300 MHz, CDCl$_3$, partial): δ 7.90 (d, J=9 Hz, 2H), 7.55 (s, 1H), 7.48 (d, J=8 Hz, 2H), 4.97-5.02 (m, 2H), 4.61-4.67 (m, 3H), 4.36 (d, J=7 Hz, 1H), 3.95-4.21 (m, 5H), 3.58 (m, 2H), 3.36 (m, 1H), 3.14-3,25 (m, 5H), 0.82 (t, J=7 Hz, 3H).

Example 9

Synthesis of Compounds 179-180

Scheme 35 below depicts the synthesis of compounds 179 and 180 using the chemistries previously exemplified. Azide 189 was treated with alkyne 163 to afford triazole 179. The same azide was used to make triazole 180 from alkyne 173.

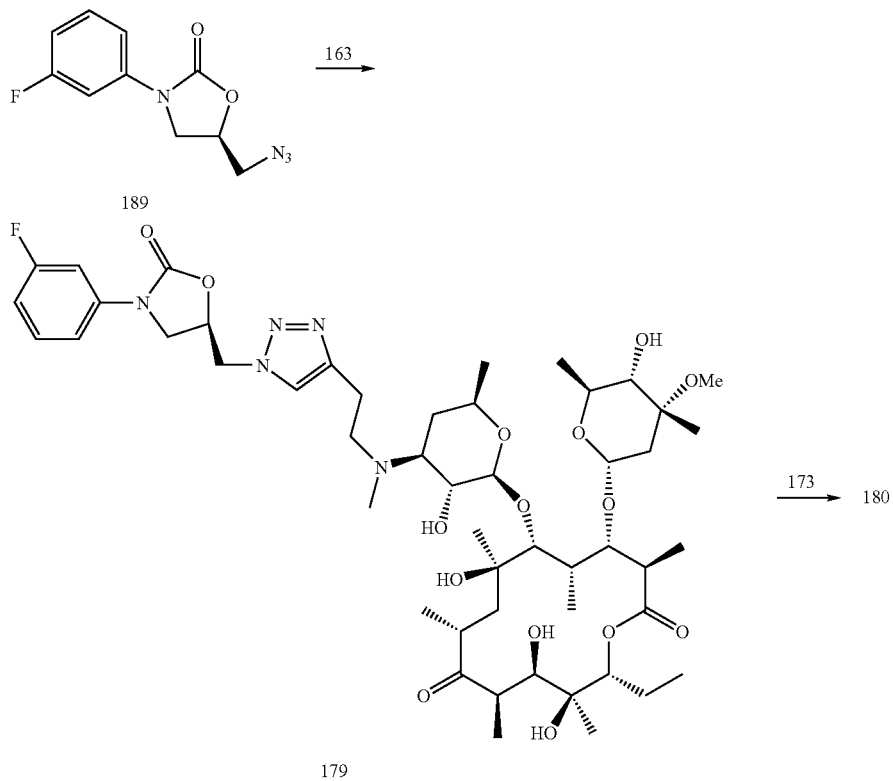

Scheme 35

Synthesis of Azide 189

The azide was synthesized from 3-fluoroaniline using the chemistry reported in the literature (Brickner, S. J. et al *J. Med. Chem.* 1996, 39, 673).

Synthesis of Triazole 179

This compound was made from alkyne 163 and azide 189 using method A as described for compound 149. Data for 179: $^1$H-NMR (300 MHz, CDCl$_3$, partial): δ 7.55 (s, 1H), 7.28-7.36 (m, 1H), 7.09 (dd, J=8 Hz, 1.6 Hz, 1H), 6.83 (m, 1H), 5.04-5.12 (m, 2H), 4.88 (d, J=5 Hz, 1H), 4.72 (m, 2H), 4.39 (d, J=7 Hz, 1H), 4.16 (t, J=7 Hz, 1H), 3.82 (s, 1H), 0.83 (t, J=7 Hz, 3H).

Synthesis of Triazole 180

This compound was made from alkyne 173 and azide 189 using method A as described for compound 149. Data for 180: $^1$H-NMR (300 MHz, CDCl$_3$, partial): δ 7.55 (s, 1H), 7.22-7.29 (m, 1H), 7.02 (d, J=8 Hz, 1H), 6.77 (m, 1H), 5.01 (m, 2H), 4.63-4.66 (m, 3H), 4.21-4.37 (m, 3H), 3.86 (m, 1H), 3.60 (m, 2H), 3.41 (m, 1H), 0.82 (t, J=8 Hz, 3H).

Example 10

Synthesis of Compound 181

Scheme 36 below depicts the synthesis of compound 181 from azide 194 and alkyne 163. The synthesis of azide 194 began with the conversion of tert-butylamine to benzylcarbamate 190. Carbamate 190 was treated with n-butyllithium and R-glycidyl butyrate to afford alcohol 191. Mesylation to give 192 was followed by cleavage of the t-butyl group with trifluoroacetic acid to provide mesylate 193. Displacement of the mesylate with sodium azide yielded azide 194. The azide was treated with alkyne 163 to afford triazole 181.

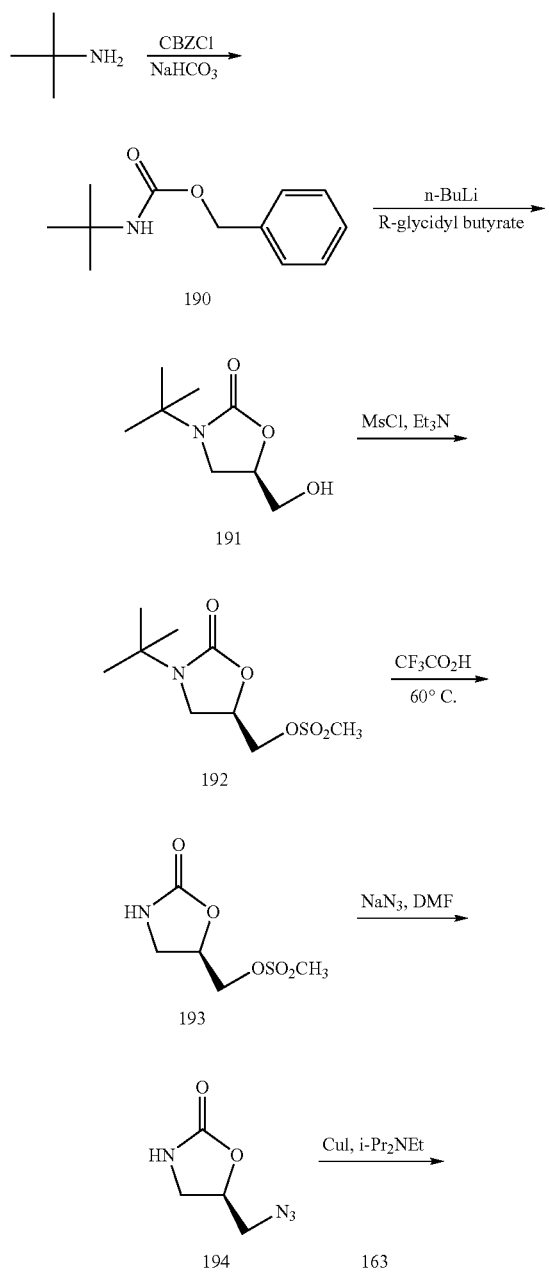

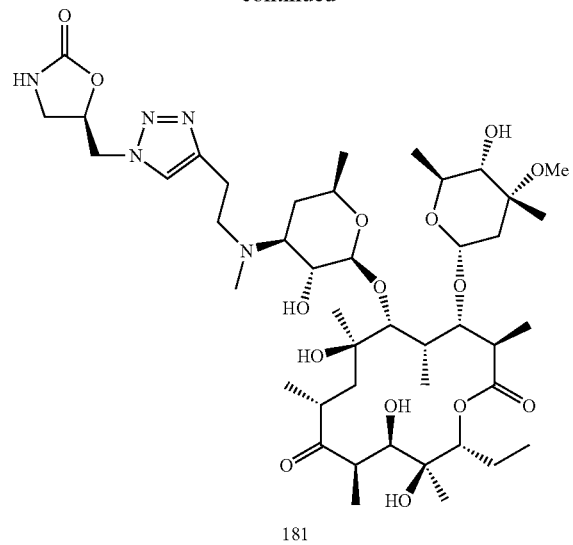

Synthesis of Carbamate 190

Sodium bicarbonate (34.48 g., 410.4 mmol) was dissolved in water (680 mL) and tert-butylamine (29 mL, 273.6 mmol) was added. The mixture was cooled to 0° C., and benzyl chloroformate (37 mL) was added. The mixture was stirred 5 min at 0° C., the cold bath removed, and then stirring was continued at room temperature overnight (~16 hours). The mixture was evaporated, and partitioned with a 1:1 mixture of ethyl acetate and water. The organic layer was washed with water, 1N HCl, and then brine. The organic layer was dried with $Na_2SO_4$, and evaporated to yield 190 (48.45 g., 85% yield) of suitable purity for use in subsequent reactions. Data for 190: $^1$HNMR (300 MHz, $CDCl_3$): δ 7.37-7.26 (m, 5H), 5.04 (s, 2H), 4.77 (brs, 1H), 1.31 (s, 9H).

Synthesis of Alcohol 191

Carbamate 190 (40 g., 193 mmol) was dissolved in 540 mL tetrahydrofuran, and the solution cooled to -78° C. n-Butyllithium (2.5M in hexane, 85 mL, 212.4 mmol) was added slowly, and the mixture allowed to stir for 45 ml at -78° C. R-Glycidyl butyrate (32.6 mL, 212.4 mmol) was added, and the mixture was stirred for 1 h at -78° C. The bath was removed and the reaction allowed to stir overnight at room temperature. The mixture had become thick with solids, and an additional 150 mL of tetrahydrofuran was added, and stirring was continued for another hour. The reaction was quenched with 25 mL saturated ammonium chloride solution, and partitioned with ethyl acetate and water. The aqueous layer was extracted thrice with ethyl acetate, and the combined organic layer was washed with brine, dried ($Na_2SO_4$), and evaporated to yield 191 (15.21 g., 46% yield) of suitable purity for use in subsequent reactions. Data for 191: $^1$HNMR (300 MHz, $CDCl_3$): δ 4.29 (dd, J=9, 2 Hz, 1H), 4.19 (dd (app), J=8, 8 Hz, 1H), 3.94-3.87 (m, 1H), 3.84-3.76 (m, 1H), 3.71-3.61 (m, 1H), 2.50-2.42 (m, 1H), 1.44 (s, 9H).

Synthesis of Mesylate 192

Alcohol 191 (9.00 g., 52.0 mmol) was dissolved in 215 mL methylene chloride, and the mixture cooled to 0° C. Triethylamine (14.5 mL, 104 mmol) was added, followed by methanesulfonyl chloride (4.43 mL, 57.2 mmol). The mixture was allowed to warm to room temperature and stirred overnight. Methylene chloride (120 mL) was added, and the mixture washed twice with 1N HCl, then twice with 10% aqueous sodium carbonate, and then brine. The organic phase was dried ($Na_2SO_4$), and evaporated to half its volume. Hexane was added, and the solvents evaporated to form a white precipitate. Before the solution was allowed to evaporate to dryness, more hexane was added and evaporation continued. Again, before the solution was allowed to evaporate to dryness, it was filtered and the solid collected. The precipitate was dried to afford mesylate 192 (11.16 g., 85% yield). Data for 192: $^1$HNMR (300 MHz, $CDCl_3$): δ 4.39-4.34 (m, 1H), 4.25-4.23 (m, 2H), 4.18-4.12 (m, 2H), 3.10 (s, 3H), 1.47 (s, 9H).

Synthesis of Mesylate 193

A solution of mesylate 192 (562 mg, 2.20 mmol) in trifluoroacetic acid (8.0 mL) was heated at 60° C. for 4 h. The reaction mixture was cooled to room temperature, and the solvent was evaporated. The remaining residue was thrice dissolved in chloroform (50 mL) and evaporated to afford mesylate 193 (450 mg, 100% yield) as a tan solid. Data for 193: $^1$HNMR (300 MHz, DMSO): δ 7.86 (brs, 1H), 4.34-4.27 (m, 1H), 4.12-4.08 (m, 2H) 4.05-3.98 (m, 2H), 3.14 (s, 3H).

Synthesis of Azide 194

A solution of mesylate 193 (400 mg, 2.10 mmol) in dimetlhylformamide (4.0 mL) was treated with sodium azide (195 mg, 3.00 mmol) and the mixture heated to 80° C. for 3 h. The reaction mixture was cooled to room temperature, diluted with ethyl acetate (100 mL), and washed with brine (2×50 mL). Drying ($Na_2SO_4$), and evaporation provided azide 194 (105 mg, 35% yield) as a yellow oil of suitable purity for use in subsequent reactions. Data for 194: $^1$HNMR (300 MHz, $CDCl_3$): δ 6.29 (s, 1H), 4.45-4.40 (m, 1H), 4.13-4.07 (m, 1H), 3.97-3.78 (m, 1H), 3.48-3.35 (m, 2H).

Synthesis of Triazole 181

A solution of alkyne 163 (135 mg, 0.180 mmol) in tetrahydrofuran (3.0 mL) was treated with azide 194 (50 mg, 0.350 mmol), i-$Pr_2$NEt (1.00 mL, 5.30 mmol) and copper (I) iodide (50 mg, 0.270 mmol), and the mixture was stirred under argon at room temperature for 15 h. The reaction mixture was diluted with methylene chloride (100 mL), washed with saturated aqueous $NH_4Cl$ (50 mL), and brine (50 mL). The organic phase was dried ($Na_2SO_4$), and evaporated. The residue was chromatographed on silica gel using a 5-20% gradient of methanol in 1:1 ethyl acetate/methylene chloride as eluant to provide 80 mg of crude product. The crude was dissolved in methylene chloride (100 mL) and washed with saturated aqueous $NH_4Cl$ (3×100 mL) and dried again. Preparative thin layer chromatography (1:4.5:4.5 methanol/methylene chloride/ethyl acetate as eluant) provided triazole 181 (9.0 mg, 6% yield) as a white film. Data for 181: MS (ESI) m/z 914 (M+H)$^+$. $^1$HNMR (300 MHz, $CDCl_3$, partial): δ 7.54 (s, 1H), 6.12 (s, 1H), 5.01-4.95 (m, 1H), 4.79 (d, J=4 Hz, 1H), 4.19-4.11 (m, 2H), 4.08-4.02 (m, 2H), 3.83 (s, 1H), 3.74 (s, 1H)), 3.48-3.30 (m, 4H), 3.23 (s, 3H), 3.09-2.90 (m, 4H), 2.87-2.73 (m, 4H), 2.70-2.50 (m, 2H), 2.28 (s, 3H), 0.80 (t (app), J=7 Hz, 3H).

Example 11

Synthesis of Compounds 182-184

Scheme 37 below depicts the synthesis of compounds 182-184 starting from clarithromycin (195). Clarithromycin is demethylated to afford secondary amine 196 which was subsequently alkylated with tosylate 155 to provide alkyne 197. Alkyne 197 was treated with azides 158, 188, and 189 to yield triazoles 182, 183, and 184 respectively.

Scheme 37

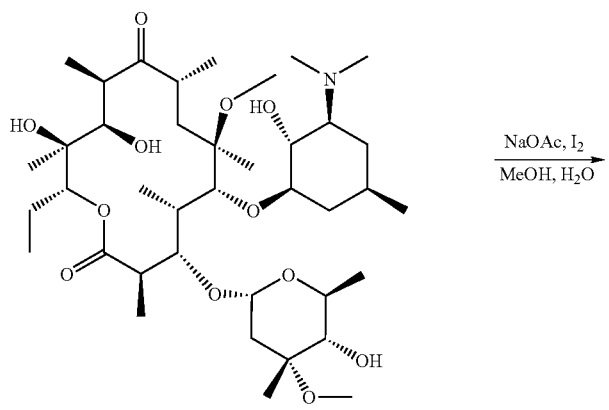

195

NaOAc, $I_2$
―――――――→
MeOH, $H_2O$

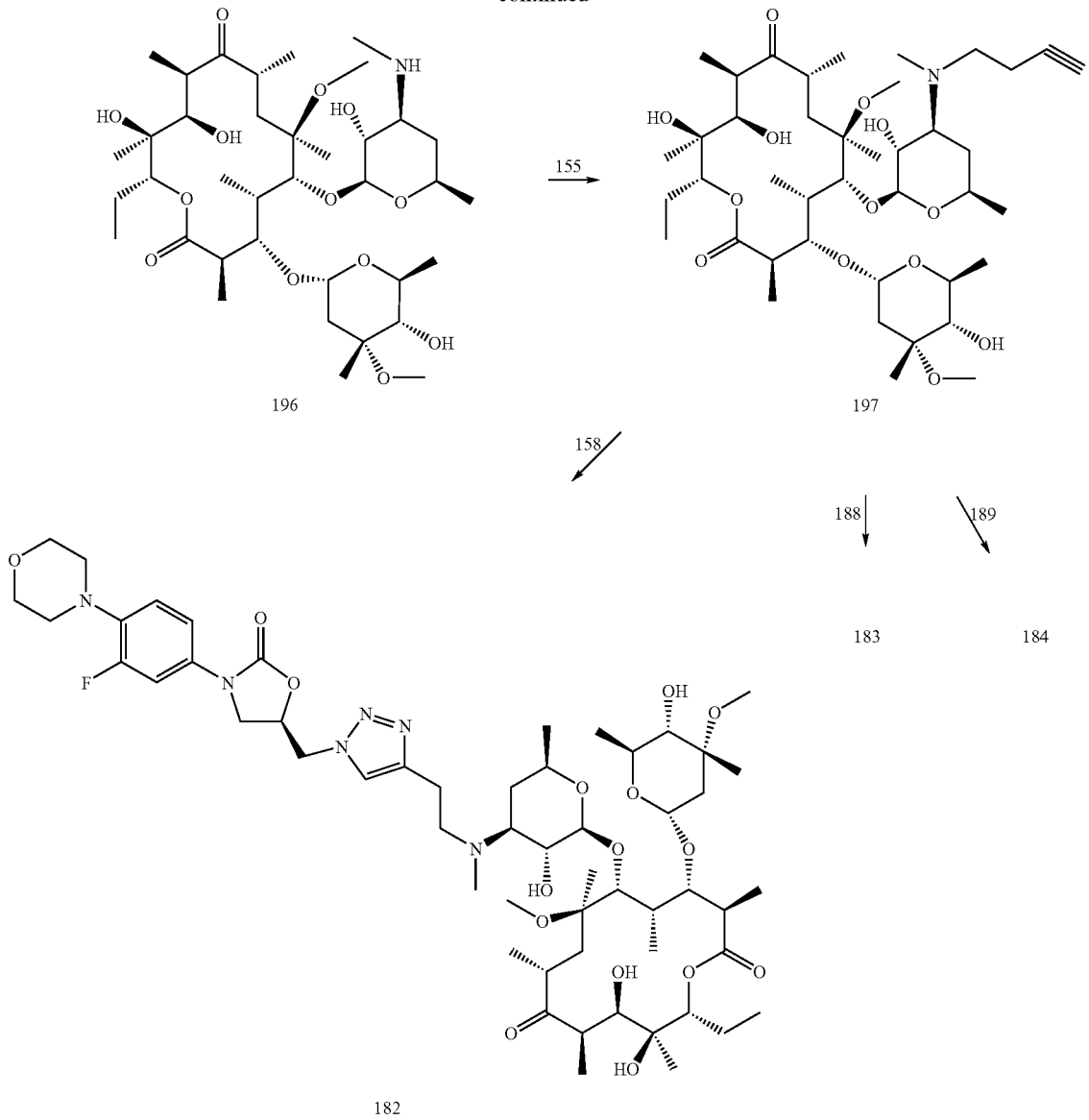

Synthesis of Amine 196

To a mixture of clarithromycin (195) (1.00 g, 1.3 mmol) and NaOAc-3H$_2$O (0.885 g, 6.5 mmol) was added MeOH—H$_2$O (20 mL, 4:1), and the mixture heated to 55-60° C. Iodine (0.330 g, 1.3 mmol) was added portionwise and the reaction stirred at 55-60° C. for 3 h. The reaction mixture was poured into 50 CHCl$_3$ containing 1 mL ammonium hydroxide. It was extracted with CHCl$_3$ (4×50 mL), washed with water (70 mL) containing 5 mL ammonium hydroxide, dried (anhydrous Na$_2$SO$_4$), concentrated and purified by flash chromatography (silica gel, CHCl$_3$:MeOH:NH$_4$OH 100:10:0.1) to afford 196. Yield: 0.9 g (92%).

Synthesis of Alkyne 197

To a solution of N-desmethyl clarithromycin 196 (3.00 g, 4.08 mmol) and tosylate 155 (1.40 g, 6.13 mmol) in THF (45 mL) was added Hunig's base (15 mL) and the mixture was refluxed for 48 h. The reaction mixture was concentrated under reduced pressure and redissolved in CHCl$_3$ (100 mL). The organic layer was washed with brine (3×100 mL), dried (over Na$_2$SO$_4$), and concentrated under reduced pressure. After purification by flash; chromatography (silica gel, 5% MeOH in CHCl$_3$), 2.50 g (78% yield) of pure product 197 was obtained. Data for 197: $^1$HNMR (300 MHz, CDCl$_3$, partial): δ 0.85 (t, 3H), 2.25 (s, 3H), 3.00 (s, 3H), 3.20 (s, 1H), 3.25 (m, 1H), 3.30 (s, 3H), 3.50 (m, 1H), 3.55 (s, 1H), 3.65 (d, 1H), 3.75 (m, 3H), 4.00 (s, 1H), 4.05 (m, 1H), 4.45 (d, 1H), 4.95 (d, 1H), 5.10 (dd, 1H).

Synthesis of Triazole 182

To a solution of alkyne 197 (0.100 g, 0.127 mmol), azide 158 (0.082 g, 0.254 mmol), and Hunig's Base (0.417 mL) in THF (1.5 mL) was added CuI (0.030 g, 0.16 mmol), and the reaction mixture was stirred at room temperature for 2 hours. The reaction mixture was diluted with CHCl$_3$ (50 mL), washed with saturated NH$_4$Cl (3×50 mL), dried over anhydrous Na$_2$SO$_4$ and concentrated under reduced pressure. The crude reaction mixture was purified on a silica gel column eluting with 3% 2M NH₃-MeOH in CH₂Cl₂ to afford 1,4 triazole isomer 182 (0.125 g). Data for 182: ¹HNMR (300 MHz, CDCl₃, partial): δ 0.85 (t, 3H), 2.25 (s, 3H), 3.65 (d, 1H), 4.10 (t, 1H), 4.40 (d, 1H), 4.70 (dd, 2H), 4.90 (d, 1H), 5.10-4.95 (m, 2H), 6.88 (t, 1H), 7.00 (dt, 1H), 7.35 (dd, 1H), 7.60 (s, 1H).

Synthesis of Triazole 183

The same protocol used above to synthesize target 182 was used for the cycloaddition of alkyne 197 (0.100 g, 0.127 mmol) and azide 188 (0.066 g, 0.254 mmol) to afford target 183. Data for 183: ¹HNMR (300 MHz, CDCl₃, partial): δ 0.85 (t, 3H), 2.20 (s, 3H), 2.55 (s, 3H), 3.00 (s, 3H), 3.30 (s, 3H), 3.70 (d, 1H-3.95-4.05 (m, 3H), 4.20 (t, 1H), 4.45 (d, 1H), 4.70 (dd, 2H), 4.90 (d, 1H), 5.10-5.00 (m, 2H), 7.55 (d, 2H), 7.60 (s, 1H), 7.95 (d, 2H).

Synthesis of Triazole 184

Cycloaddition of alkyne 197 (0.050 g, 0.0636 mmol) with azide 189 (0.030 g, 0.127 mmol), using the same procedure for the synthesis of 182, afforded target 184 (0.0253 g). Data for 184: MS (ESI) m/z 1022.3 (M+H)⁺; ¹HNMR (300 MHz, CDCl₃, partial): δ 0.86 (t, 1H), 2.25 (s, 3H), 3.00 (s, 3H), 3.30 (s, 3H), 3.50 (m, 1H), 3.65 (s, 1H), 4.10 (t, 1H), 4.40 (d, 1H), 4.70 (dd, 2H), 4.85 (d, 1H), 5.00 (m, 2H), 6.85 (bt, 1H), 7.10 (bd, 1H), 7.35 (bt, 2H), 7.60 (s, 1H).

Example 12

Synthesis of Compound 185

Scheme 38 below depicts the synthesis of compound 185 starting from alkyne 197. Alkyne 197 is hydrolyzed with dilute acid to afford the des-cladinose derivative 198. The hydroxyl on the desosamine sugar of 198 was acetylated to afford alcohol 199 which was then oxidized to ketolide derivative 200. Deacylation of 200 provided alkyne 201, which was then treated with azide 158 to provide triazole 185.

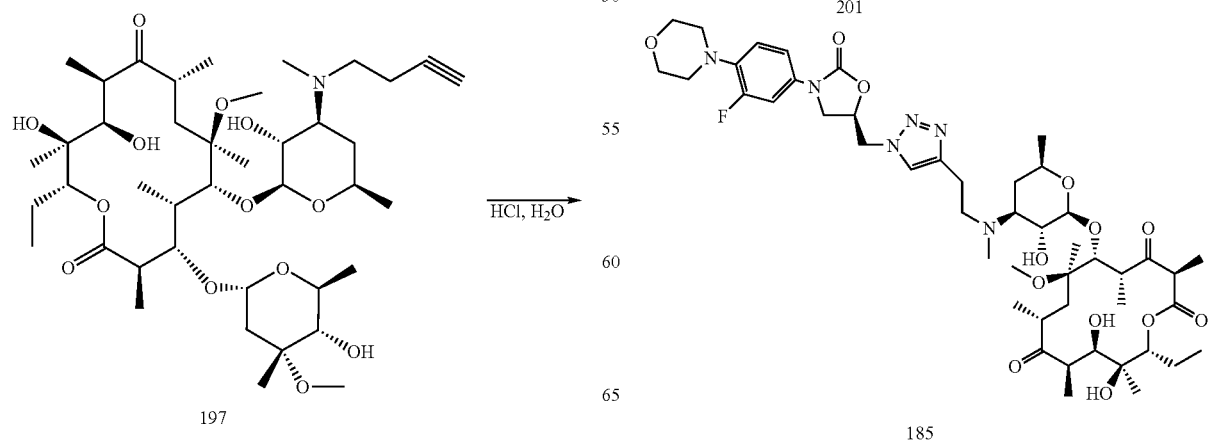

Synthesis of Alcohol 198

To the alkyne 197 (0.700 g) was added 10 mL 0.9N HCl and the mixture was stirred for 4 h at room temperature. The reaction mixture was saturated with sodium chloride and was adjusted to pH 8 using aqueous NH$_4$OH solution. The solution was extracted with ethyl acetate (3×30 mL), dried (with Na$_2$SO$_4$), and concentrated under reduced pressure. Purification of the crude reaction mixture by flash chromatography (silica gel, 60% ethyl acetate in hexane) afforded 0.200 g (35% yield) of the descladinose derivative 198. Data for 198: $^1$HNMR (300 MHz, CDCl$_3$, partial): δ 0.82 (t, 3H), 2.25 (s, 3H), 3.00 (s, 3H), 3.25 (dd, 1H), 3.55 (m, 2H), 3.70 (s, 1H), 3.85 (s, 1H), 3.95 (s, 1H), 4.40 (d, 1H), 5.15 (dd, 1H).

Synthesis of Acetate 199

To a solution of 198 (0.200 g, 0.32 mmol) in acetone (2 mL) was added acetic anhydride (0.050 mL, 0.5 mmol) and the mixture was stirred overnight at room temperature. The reaction was quenched with water and extracted with ethyl acetate (3×50 mL). The combined organic fractions were washed with saturated sodium bicarbonate (3×50 mL), dried (anhydrous Na$_2$SO$_4$), and concentrated under reduced pressure. The crude reaction mixture was purified by flash chromatography (silica gel, 50% ethyl acetate in hexane) to yield 0.100 g (50% yield) of acetate 199. Data for 199: $^1$HNMR(300 MHz, CDCl$_3$, partial): δ 0.84 (t, 3H), 2.00 (s, 3H), 2.20 (s, 3H), 2.90 (s, 3H), 3.00 (q, 1H), 3.25 (s, 1H, 3.47 (m, 2H), 3.70 (bs, 1H), 3.82 (bs, 1H), 3.97 (s, 1H), 4.60 (d, 1H), 4.77 (dd, 1H), 5.15 (dd, 1H).

Synthesis of Ketolide 200

To a solution of acetate 199 (0.090 g, 0.134 mmol), EDC.HCl (0.172 g, 0.90 mmol), and DMSO (0.171 mL, 2.41 mmol) in CH$_2$Cl$_2$ (1.5 mL) was added dropwise a solution of pyridinium trifluoroacetate (0.174 g, 0.90 mmol) in CH$_2$Cl$_2$ (1 mL) at 15° C. The reaction mixture was slowly warmed up to room temperature and stirred for 3 h. The reaction was quenched with water (2 mL), and allowed to stir for 30 min. The mixture was then poured into CHCl$_3$ (50 mL), and the organic layer was washed with water (2×50 mL), dried (over anhydrous Na$_2$SO$_4$), and concentrated under reduced pressure. The crude material was purified by flash chromatography (silica gel, 30% ethyl acetate in hexane) to yield 0.070 g (78%) of the ketolide 200. Data for 200: MS (ESI) m/z 668 (M+H)$^+$; $^1$HNMR (300 MHz, CDCl$_3$, partial): δ 0.86 (t, 3H), 2.00 (s, 3H), 2.24 (s, 3H), 2.70 (s, 3H), 2.95-3.10 (m, 1H), 3.15-3.05 (m, 1H), 3.45-3.65 (m, 4H), 3.80 (q, 1H), 3.90 (s, 1H), 4.28 (d, 1H), 4.40 (d, 1H), 4.76 (dd, 1H), 5.10 (dd, 1H).

Synthesis of Alkyne 201

A solution of ketolide 200 (0.230 g) in MeOH (10 mL) was heated at 50° C. for 48 h. The solvent was removed under reduced pressure to yield pure deacetylated product 201 (0.190 g, 88%). Data for 201: MS (ESI) m/z 626 (M+H)$^+$; $^1$HNMR (300 MHz, CDCl$_3$, partial): δ 0.85 (t, 3H), 2.25 (s, 3H), 2.70 (s, 3H), 2.97 (q, 1H), 3.10 (t, 1H), 3.18 (dd, 1H), 3.5 (m, 1H), 3.80-3.97 (m, 2H), 4.32 (m, 2H), 5.15 (dd, 1H).

Synthesis of Triazole 185

To a solution of 201 (0.050 g, 0.080 mmol), azide 158 (0.050 g, 0.16 mmol), and Hunig's Base (0.417 mL) in THF (1.5 mL) was added CuI (0.030 g, 0.16 mmol), and the reaction mixture was stirred at room temperature for 2 h. It was diluted with CHCl$_3$ (50 mL), washed with saturated NH$_4$Cl (3×50 mL), dried (anhydrous Na$_2$SO$_4$) and concentrated under reduced pressure. The crude reaction mixture was purified by flash chromatography (silica gel, 3% 2M NH$_3$-MeOH in CH$_2$Cl$_2$) to afford 185 (0.043 g). Data for 185: MS (ESI) m/z 947.4 (M+H)$^+$; $^1$HNMR (300 MHz, CDCl$_3$, partial): δ 0.86 (t, 3H), 2.25 (s, 3H), 2.70 (s, 3H), 4.10 (t, 1H), 4.30 (t, 2H), 4.70 (dd, 2H), 5.00 (m, 1H), 5.10 (dd, 1H), 6.90 (t, 1H), 6.95 (dt, 1H), 7.25 (dd, 1H) 7.60 (s, 1H).

Example 13

Synthesis of Compounds 186 and 187

Scheme 39 below depicts the synthesis of compounds 186 and 187. Azide 158 is treated 3-hydroxypropionitrile to yield tetrazole 186. Tetrazole 186 was converted to tosylate 202 which then served to alkylate amine 171 to afford tetrazole 187.

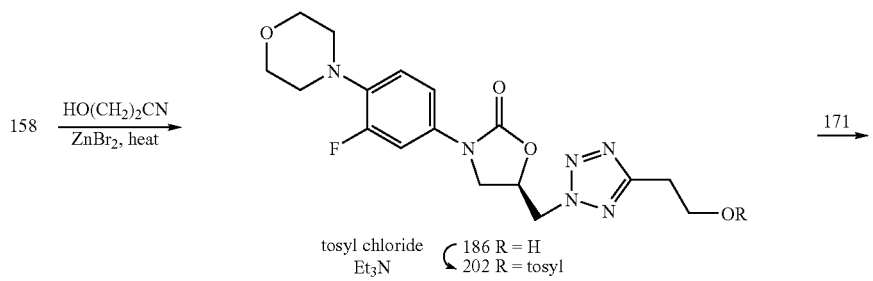

Scheme 39

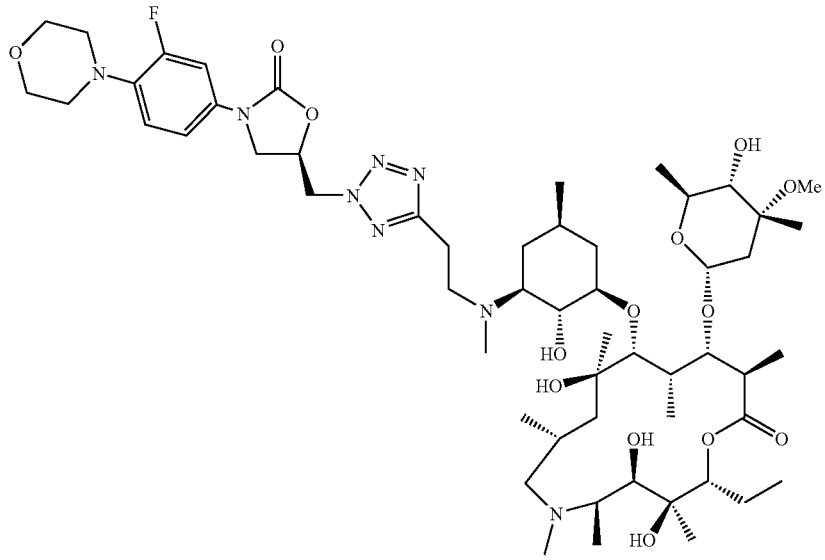

187

Synthesis of Tetrazole 186

A suspension of azide 158 (0.300 g, 0.940 mmol), 3-hydroxypropionitrile (1.0 mL, 14.2 mmol) and zinc bromide (ZnBr$_2$) (0.212 g, 0.940 mmol) in 2-propanol/H$_2$O (4:1) was heated under reflux for 40 h. The reaction was poured into CH$_2$Cl$_2$ (50 mL) and H$_2$O (20 mL) and carefully partitioned (caution: emulsion problem). The aqueous layer was back-extracted with CH$_2$Cl$_2$ (3×30 mL). The combined organic layer was dried over Na$_2$SO$_4$ and the solvent vas evaporated. The crude was purified on silica gel column eluting with 0-10% MeOH in CH$_2$Cl$_2$ to provide 186 (0.037 g, 10%). $^1$H-NMR (300 MHz, CDCl$_3$, partial): δ 7.41 (dd, J=14, 3 Hz, 1H), 7.05-7.13 (m, 2H), 6.93 (t, J=9 Hz, 1H), 4.78 (m, 1H), 3.65-4.04 (m, 10H), 3.04 (t, J=5 Hz, 4H), 2.48 (t, J=6 Hz, 2H).

Synthesis of Tosylate 202

Tetrazole 186 (0.028 g, 0.071 mmol) was dissolved in CH$_2$Cl$_2$ (2 mL) and Et$_3$N (0.015 mL, 0.107 mmol). To this solution was added p-toluenesulfonyl chloride (0.034 g, 0.179 mmol) and stirring was continued at room temperature for 24 h during which time a quantitative consumption of 186 was noticed by TLC (CH$_2$Cl$_2$/MeOH 9:1, R$_f$=0.52). The reaction was quenched with H$_2$O/THF 10:1 within 30 min and then partitioned between 10% NaHCO$_3$ (15 mL) and CH$_2$Cl$_2$ (20 mL). The two layers were separated; the organic layer was washed with saturated brine (3×15 mL) and dried over Na$_2$SO$_4$. The solvent was evaporated, and the crude was purified on a silica gel column eluting with 0-3% MeOH in CH$_2$Cl$_2$ to provide 202 (0.031 g, 80%).

Synthesis of Tetrazole 187

Compound 187 was made from des(N-methyl)-azithromycin 171 and tosyltetrazole 202 using method B as described for compound 149. Data for 187: $^1$H-NMR (300 MHz, CDCl$_3$, partial): δ 7.40 (dd, J=14, 3 Hz, 1H), 6.98 (dd, J=9, 2 Hz, 1H), 6.84 (t, J=9 Hz, 1H), 5.05 (m, 1H), 4.62-4.65 (m, 3H), 4.34 (d, J=7 Hz, 1H), 4.19 (bs, 1H), 3.80 (t, J=5-Hz, 4H), 2.98 (t, J=5 Hz, 4H), 0.82 (t, J=7 Hz, 3H).

Example 14

Synthesis of Compounds 203 and 204

Scheme 40 below depicts the synthesis of compounds 203 and 204. Known azide 253 (see: International Patent Application WO 03/035648) was coupled to 4-hydroxymethylphenylboronic acid to yield biaryl azide 254. Cycloaddition of 254 to alkynes 173 and 197 delivers macrolide targets 203 and 204 respectively.

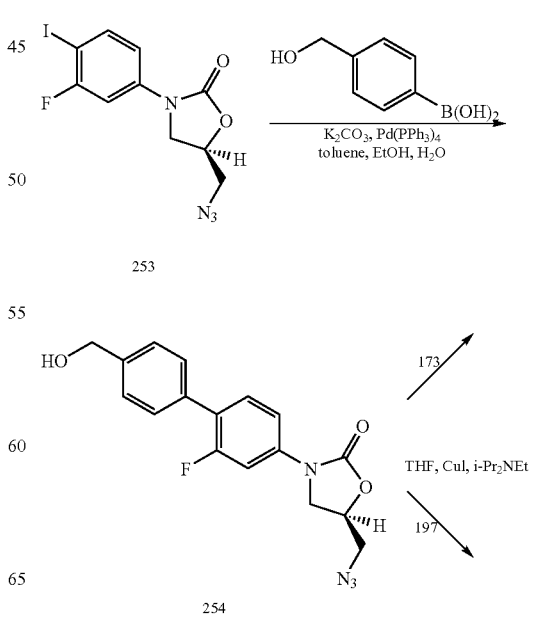

Scheme 40

Synthesis of Biaryl Azide 254

Azide 253 (0.300 g, 0.830 mmol), and 4-hydroxymethylphenylboronic acid (0.152 g, 1.00 mmol) were dissolved in toluene. Potassium carbonate (0.345 g, 2.50 mmol), tetrakis(triphenylphosphine)palladium (0.040 g, 0.035 mmol), ethanol (3 mL) and water (3 mL) were added, and the reaction was degassed thrice before being heated to reflux for two hours. The reaction was allowed to cool to room temperature, and then was partitioned between ethyl acetate (10 mL) and water (10 mL). The layers were separated, and the aqueous phase extracted with ethyl acetate (2×10 mL). The combined organic layers were washed with water (10 mL) and brine (10 mL). The organic layer was dried with MgSO$_4$, and evaporated. The crude was purified on silica gel column eluting with 20-50% EtOAc in CH$_2$Cl$_2$ to provide 254 (0.163 g, 0.476 mmol; 57% yield).

Synthesis of Triazole 203

This compound was obtained from the reaction of alkyne 173 (0.075 g, 0.095 mmol) with azide 254 (0.049 g, 0.143 mmol) in the presence of CuI (0.029 g, 0.143 mmol) in THF (3 mL) and i-Pr$_2$NEt (0.6 mL) at room temperature within 6 h. The crude reaction was concentrated and then purified on silica gel eluting with CH$_2$Cl$_2$/MeOH/NH$_4$OH 30:1:0.05 to 25:1:0.05 to 20:1:0.05 to 18:1:0.05 to 15:1:0.05 to give 203 as a white solid. Data for 203: MS (ESI) m/z 1129.4 (M+H)$^+$; $^1$H-NMR (300 MHz, CDCl$_3$, partial): δ 7.65 (s, 1H), 7.53-7.33 (m, 6H), 7.19 (d, J=8 Hz, 1H), 5.03 (m, 2H), 4.70-4.76 (m, 5H), 4.42 (d, J=7 Hz, 1H), 4.28 (d, J=3 Hz, 1H), 4.06 (m, 3H), 3.67 (m, 2H), 3.43 (m, 1H), 0.82 (m, 7H).

Synthesis of Triazole 204

A solution of alkyne 197 (100 mg, 0.127 mmol) in tetrahydrofuran (3.0 mL) was treated with azide 254 (50 mg, 0.15 mmol), i-Pr$_2$NEt (0.664 mL, 3.81 mmol) and copper (I) iodide (48.4 mg, 0.254 mmol), and the mixture was stirred under argon at room temperature for 15 h. The reaction mixture was diluted with methylene chloride (50 mL), washed with saturated aqueous NH$_4$Cl (3×50 mL), and brine (2×50 mL). The organic phase was dried (Na$_2$SO$_4$), and evaporated. The residue was chromatographed on silica gel using a 4-10% gradient of methanol in chloroform as eluant to provide 69 mg of pure product 204 as a white powder. Data for 204: MS (ESI) m/z 1128.5 (M+H)$^+$, 1150.4 (M+Na)$^+$. $^1$HNMR (300 MHz, CDCl$_3$, partial): δ 7.72 (s, 1H), 7.52-7.38 (m, 6H), 7.17 (dd, J=8, 2 Hz, 1H) 5.06-5.03 (m, 2H), 4.92 (d, J=4 Hz, 1H), 4.42 (d, J=7 Hz, 1H), 4.18 (t, 1H), 0.82 (t, J=7 Hz, 3H).

Example 15

Synthesis of Compound 205

Scheme 41 depicts the synthesis of compound 205. Available amine 255 was bis-silylated and the amine alkylated to afford diethyl amine derivative 256. The nitro group of 256 was reduced and the resultant amine converted to the benzyl carbamate 257. Conversion of 257 via standard methods to the oxazolidinone 258 was followed by formation of the azides 259 and 260. Azide 260 was treated with alkyne 173 to afford the triazole cycloadduct which was subsequently desilylated to afford compound 205.

Scheme 41

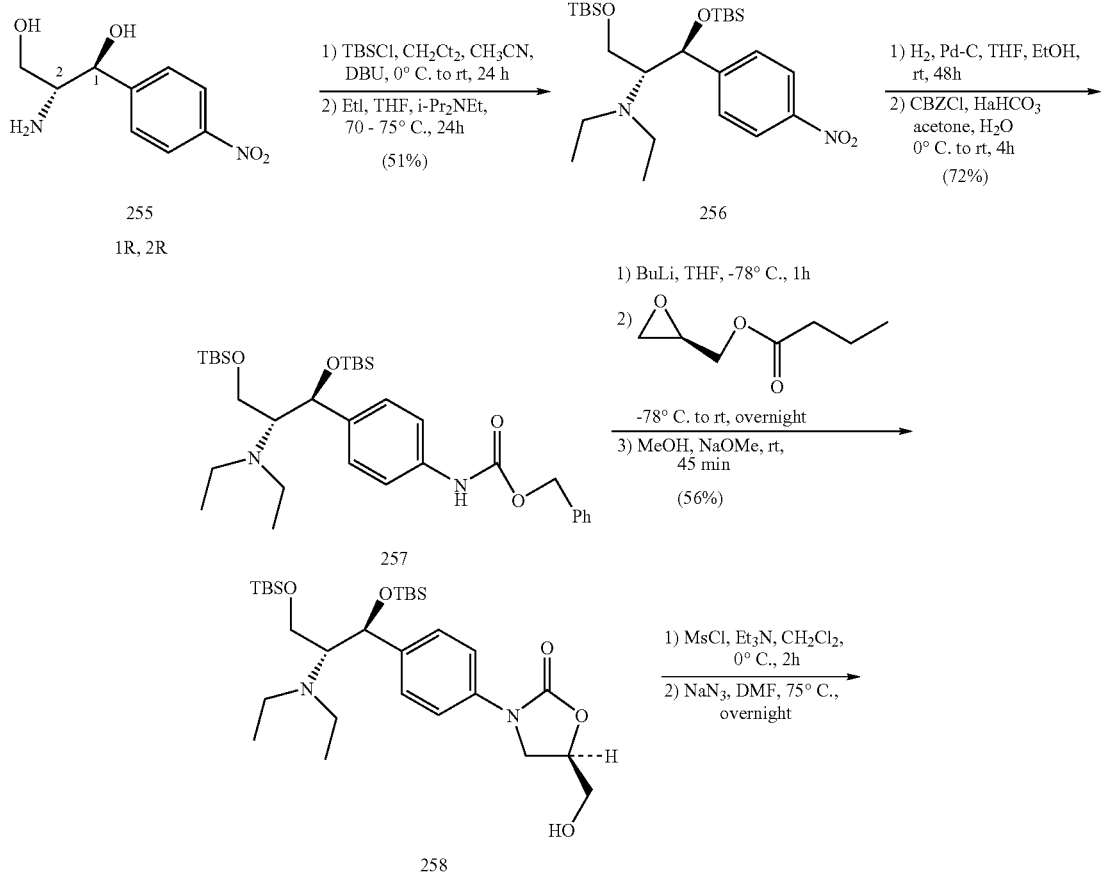

-continued

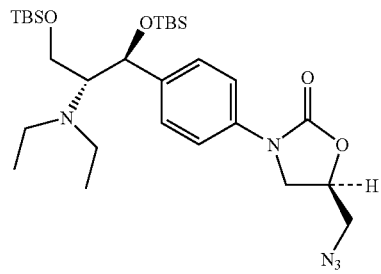

259

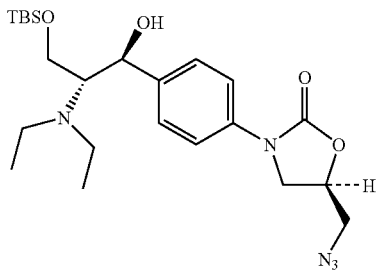

260

1) 173, CuI, THF
   i-Pr₂NEt, rt, 2h
2) TEMED-HF
   CH₃CN, CH₂Cl₂
   rt, 3h

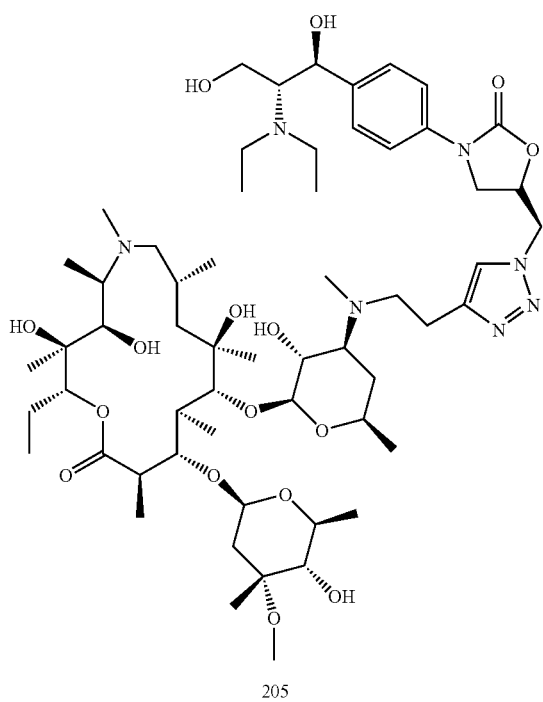

205

Synthesis of Amine 256

To a suspension of amine 255 (2.00 g, 9.33 mmol) in a 1.0 M $CH_2Cl_2$ solution of TBSCl (22.40 mL, 22.40 mmol) and anhydrous $CH_3CN$ (10 mL) was added DBU (2.96 mL, 19.56 mmol) at 0° C. A clear homogenous solution resulted within a few minutes of the DBU addition and the reaction was stirred at room temperature for 24 h. The reaction was poured into $CH_2Cl_2$ (60 mL) and extracted with saturated $NaHCO_3$ (3×30 mL), saturated $NH_4Cl$ (2×30 mL), saturated brine, and then the organic phase was dried over $Na_2SO_4$. The solvent was evaporated to give a light yellow oil which was used without further purification.

To a solution of the crude product obtained above (2.00 g, 4.54 mmol) in THF (25 mL) and i-Pr₂NEt (10 mL) was added iodoethane (5.00 mL, 61.35 mmol) and the mixture was heated between 70° C. to 75° C. for 48 h. The reaction was worked-up as described in the first step above. The crude was purified on silica gel eluting with hexanes/EtOAc 12:1 to 8:1 to give compound 256 as a light yellow oil (1.16 g, 51%). Data for 256: $^1$H-NMR, (300 MHz, $CDCl_3$): δ 8.08 (d, J=9 Hz, 2H), 7.41 (d, J=9 Hz, 2H), 4.99 (d, J=3 Hz, 1H), 3.79 (m, 1H), 3.65 (m, 1H), 2.59 (m, 2H), 2.48 (m, 1H), 2.37 (m, 2H), 0.86 (s, 9H), 0.84 (s, 9H), 0.63 (t, J=7 Hz, 6H), 0.00 (bs, 9H), −0.29 (s, 3H).

Synthesis of Carbamate 257

Compound 256 (1.16 g, 2.34 mmol) was dissolved in absolute EtOH (30 mL) and THF (6 mL). To this solution was added Pd—C (10 wt %, Degussa, 0.11 g) and the reaction was kept under a hydrogen environment using a balloon. TLC after stirring for 48 h revealed a complete consumption of starting material. The reaction was filtered and the filtrate evaporated to give a yellow oil. The crude oil was dissolved in acetone (30 mL) and water (10 mL). The resulting mixture was kept at 0° C. while $NaHCO_3$ (0.46 g, 5.5 mmol) and CBZCl (0.42 mL, 2.81 mmol) were added. The reaction was allowed to warm up to room temperature and stirred for 4 h. The reaction was poured into CH₂Cl₂ (60 mL) and extracted with saturated NaHCO₃ (3×30 mL), saturated NH₄Cl (2×30 mL), and the organic phase was dried over Na₂SO₄. The solvent was evaporated to give a yellow oil. The crude was purified on silica gel column, eluting with 1-4% MeOH in CH₂Cl₂ to give 257 as a yellow oil (1.02 g, 72%). Data for 257: ¹H-NMR (300 MHz, CDCl₃): δ 7.37-28 (m, 9H), 5.17 (s, 2H), 4.84 (d, J=4 Hz, 1H), 3.77 (m, 1H), 3.60 (m, 1H), 2.69-2.43 (m, 5H), 0.88 (s, 9H), 0.85 (s, 9H), 0.75 (t, J=7 Hz, 6H), 0.00 (bs, 9H), −0.29 (s, 3H).

Synthesis of Alcohol 258

Carbamate 257 (1.02 g, 1.69 mmol) was dissolved in anhydrous THF (10 mL) and the solution was cooled to −78° C. n-Butyllithium (2.5 M in Hexanes) (0.87 mL, 2.18 mmol) was added and the reaction was maintained at −78° C. for 1 h. (R)-Glycidyl butyrate (0.31 mL, 2.184 mmol) was added, the reaction was allowed to warm up to room temperature and stirred for about 16 h. The reaction was partitioned between saturated NH₄Cl (30 mL) and CH₂Cl₂ (50 mL). The organic layer was washed with saturated NH₄Cl (2×30 mL), saturated brine (1×30 mL), and then dried over Na₂SO₄. The solvent was evaporated, and the residue was dissolved in MeOH (20 mL) containing a catalytic amount of sodium methoxide, and the solution was stirred at room temperature for 45 min. The solvent was evaporated, the crude was taken up into CH₂Cl₂ (50 mL) and extracted with saturated NH₄Cl (2×30 mL). The organic phase was dried over Na₂SO₄ and concentrated. The residue was purified on silica gel column, eluting with 5-6% MeOH in CH₂Cl₂ to give 258 as a white foam (0.53 g, 56%). Data for 258: ¹H-NMR (300 MHz, CDCl₃): δ 7.52 (d, J=9 Hz, 2H), 7.41 (d, J=9 Hz, 2H), 4.87 (d, J=3 Hz, 1H), 4.70 (m, 1H), 4.02-3.92 (m, 3H), 3.76 (m, 2H), 3.62 (m, 1H), 2.63-2.43 (m, 5H), 0.88 (s, 9H), 0.85 (s, 9H), 0.74 (t, J=7 Hz, 6H), 0.00 (bs, 9H), −0.28 (s, 3H).

Synthesis of Azides 259 and 260

To a solution of oxazolidinone 258 (0.53 g, 0.935 mmol) in anhydrous CH₂Cl₂ (15 mL) and Et₃N (0.28 mL, 2.00 mmol) at 0° C. was added MsCl (0.14 mL, 1.8 mmol). The reaction was stirred at 0° C. for 2 h and the reaction was poured into saturated NaHCO₃ (30 mL) and CH₂Cl₂ (50 mL) and the two layers were separated. The organic layer was extracted with H₂O (2×30 mL), saturated brine (1×30 mL), and dried over Na₂SO₄. The solvent was evaporated to give a yellow oil. The crude was taken up in DMF (10 mL), NaN₃ (0.24 g, 3.74 mmol) was added, and the reaction was heated at 75° C. for 24 h. Water (40 mL) was added and the reaction was extracted with EtOAc (3×40 mL). The combined organic layer was extracted with saturated brine (1×50 mL) and dried over Na₂SO₄. The solvent was evaporated and the crude was purified on a silica gel column, eluting with 1-6% MeOH in CH₂Cl₂ to give azide 259 (0.378 g) and azide 260 (0.027 g). Data for azide 259: ¹H-NMR (300 MHz, CDCl₃): δ 7.54 (d, J=9 Hz, 2H), 7.41 (d, J=9 Hz, 2H), 4.87 (d, J=3 Hz, 1H), 4.70 (m, 1H), 4.02-3.92 (m, 3H), 3.77-3.74 (m, 2H), 3.62 (m, 1H), 2.63-2.43 (m, 5H), 0.88 (s, 9H), 0.85 (s, 9H), 0.71 (t, J=7 Hz, 6H), 0.00 (bs, 9H), −0.28 (s, 3H). Data for azide 260: MS (ESI) m/z 478.1 (M+H)⁺; ¹H-NMR (300 MHz, CDCl₃): δ 7.59 (d, J=9 Hz, 2H), 7.49 (d, J=9 Hz, 2H), 4.86 (m, 1H), 4.46 (d, J=10 Hz, 1H), 4.20 (t, J=9 Hz, 1H), 3.95 (m, 1H), 3.81-3.61 (m, 4H), 2.98-2.94 (m, 2H), 2.79-2.71 (m, 3H), 1.22 (t, J=7 Hz, 6H), 0.93 (s, 9H), 0.00 (s, 3H), 0.00 (s, 3H).

Synthesis of Compound 205

Alkyne 173 (0.038 g, 0.045 mmol) and azide 260 (0.027 g, 0.057 mmol) were subjected to the cycloaddition reaction in the presence of CuI (0.029 g, 0.143 mmol) in THF (3 mL) and i-Pr₂NEt (0.6 mL) at room temperature for 2 h. The reaction was poured into a mixture containing saturated NH₄Cl/NH₄OH (pH=9.5, 30 mL) and extracted with CH₂Cl₂ (3×30 mL). The combined organic layer was dried over Na₂SO₄ and the solvent evaporated. The crude was purified on silica gel eluting with CH₂Cl₂/MeOH/NH₄OH 15:1:0.05 to give a white solid (0.048 g).

The product obtained above (0.047 g) was dissolved in CH₂Cl₂ (2 mL) and a freshly prepared solution of 1.34 M N,N,N'N'-tetramethylethylenediamine hydrofluoride (TE-MED.HF) in acetonitrile (0.5 mL, 0.67 mmol) was added. Stirring was continued for 3 h and the reaction was concentrated. The crude was purified on a silica gel column, eluting with CHCl₃/MeOH/NH₄OH 15:1:0.05 to give a slightly impure white solid. This was re-purified on a second silica gel column eluting with CH₂Cl₂/MeOH/NH₄OH 18:1:0.04 to 16:1:0.04 to give 205 as a white solid (0.018 g). Data for 205: MS (ESI) m/z 1172.5 (M+Na)⁺; ¹H-NMR (300 MHz, CDCl₃, partial): δ 7.61 (s, 1H), 7.25-7.17 (m, 4H), 4.89 (m, 2H), 4.58 (m, 3H), 4.17 (d, J=9 Hz, 1H), 4.04 (m, 2H), 3.76 (m, 1H), 3.46-3.31 (m, 4H), 2.85 (d, J=9 Hz, 1H), 0.75 (m, 7H).

Example 16

Synthesis of Compounds 206 and 207

Scheme 42 depicts the synthesis of targets 206 and 207. The aromatic substitution reaction of 3,4-difluoronitrobenzene and 2-(methylamino)ethanol provided nitroaniline 261. The alcohol of 261 was protected and the nitro group was reduced to afford amine 262. Conversion of 262 to carbamate 263 was followed by synthesis of the oxazolidinone 264. Alcohol 264 was converted to azides 265 and 266, and the latter was acylated to afford azide 267. The cycloaddition of 266 and 267 with alkyne 173 afforded targets 206 and 207 respectively.

Scheme 42

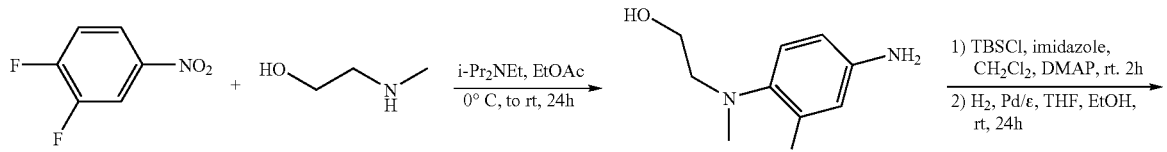

261

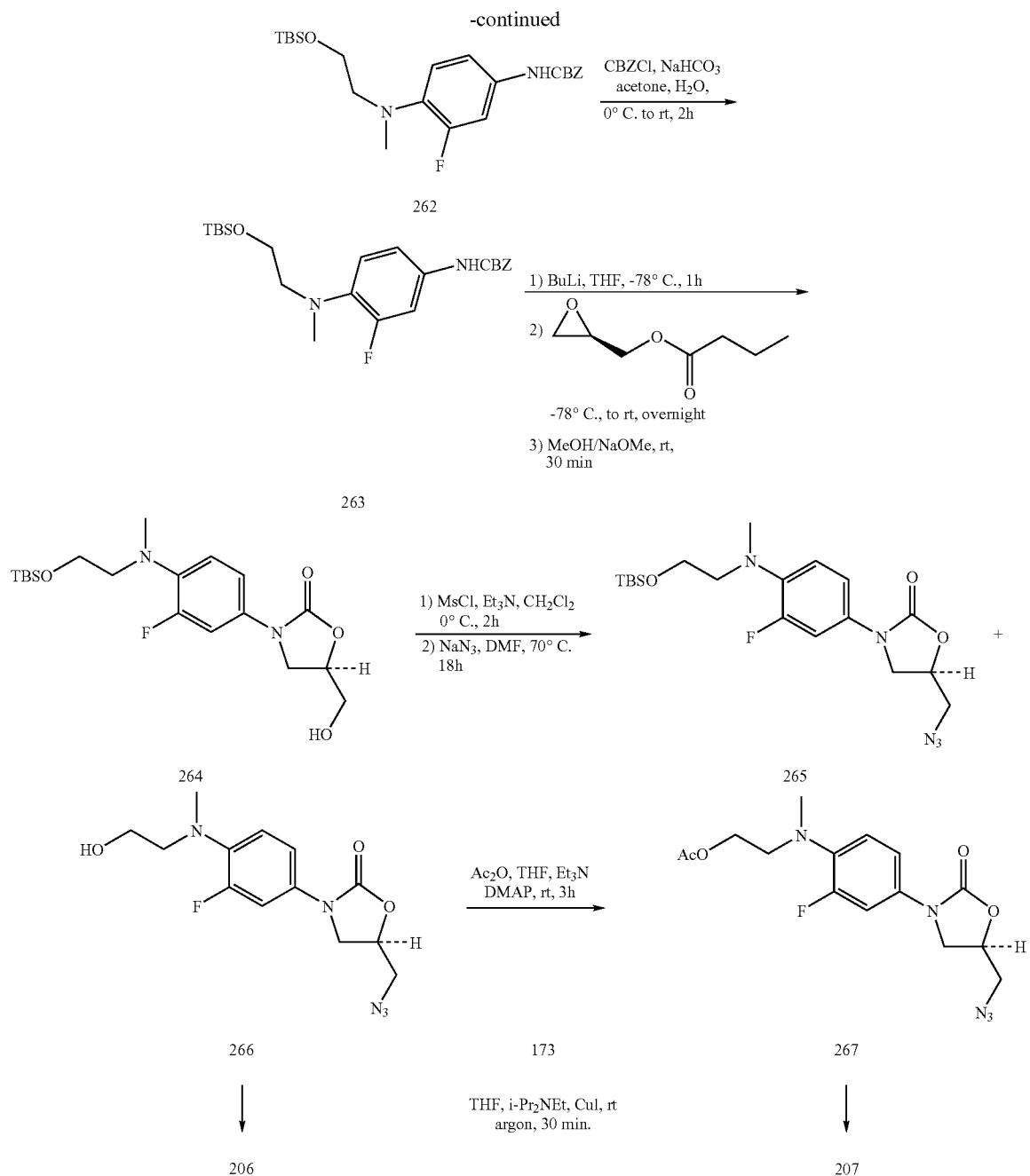

Synthesis of Amine 261

To a solution of 3,4-difluoronitrobenzene (2.4 mL, 29.72 mmol) in EtOAc (20 mL) and i-Pr$_2$NEt (5.1 mL, 29.30 mmol) was slowly added 2-(methylamino)ethanol (3 mL, 27.10 mmol) at 0° C. The reaction was allowed to warm up to room temperature and stirring was continued overnight. The reaction was poured into EtOAc (30 mL) and extracted with H$_2$O (50 mL). The aqueous layer was basified with KOH pellets (pH 10.0) and extracted with CH$_2$Cl$_2$ (3×30 mL). The combined organic layer was dried over Na$_2$SO$_4$ and the solvent evaporated to give a yellow solid residue. The crude was dissolved in 6 N HCl (60 mL) at 0° C., extracted with CH$_2$Cl$_2$ (3×30 mL), and the organic layer was back extracted with 6 N HCl (25 mL). The combined acid layer was basified with KOH pellets at 0° C. and extracted with CH$_2$Cl$_2$ (4×40 mL). The organic phase was dried over Na$_2$SO$_4$ and the solvent evaporated to give 261 as a yellow solid (R$_f$=0.56, CH$_2$Cl$_2$/MeOH, 4.59 g, 79%). Data for 261: MS (ESI) m/z 214.7 (M+H)$^+$.

Synthesis of Amine 262

Compound 261 (4.5 g, 21 mmol), imidazole (2.91 g, 42 mmol) and DMAP (0.26 g, 2.1 mmol) were dissolved in anhydrous CH$_2$Cl$_2$ (50 mL). To this solution was added TBSCl (3.33 g, 22.10 mmol) and stirring was continued for 2 h. CH$_2$Cl$_2$ (30 mL) was added and the mixture was extracted with saturated NaHCO$_3$ (2×50 mL) and saturated brine (1×50 mL). The organic phase was dried over Na$_2$SO$_4$ and evaporated to give a yellow oil. The oil was dissolved in absolute EtOH (50 mL) and THF (10 mL). To this solution was added Pd—C (10 wt %, Degussa, 0.50 g) and the reaction was kept under a hydrogen environment using a balloon. TLC after stirring for 24 h revealed a complete consumption of starting material. The reaction was filtered and the filtrate evaporated to give 262 as a red oil which was used in further reactions without further purification. Data for 262: MS (ESI) m/z 298.7 (M+H)$^+$.

Synthesis of Oxazolidinone 264

Crude oil 262 was dissolved in acetone (60 mL) and water (20 mL). The resulting mixture was kept at 0° C., and NaHCO$_3$ (4.13 g, 49.40 mmol) and CBZCl (3.77 mL, 25.22 mmol) were added. The reaction was allowed to warm up to room temperature and stirring continued for 2 h. The reaction was poured into CH$_2$Cl$_2$ (120 mL) and extracted with saturated NaHCO$_3$ (2×50 mL) and saturated brine (1×50 mL). The organic phase was dried over Na$_2$SO$_4$ and evaporated to give carbamate 263 as a red oily residue.

The crude 263 above was dissolved in anhydrous THF (50 mL) and the solution was cooled to −78° C. n-Butyllithium (2.5 M in Hexanes) (10.8 mL, 27 mmol) was added and the reaction was maintained at −78° C. for 1 h. (R)-Glycidyl butyrate (3.83 mL, 27 mmol) was added, the reaction was allowed to warm up to room temperature, and stirring was continued for about 16 h. The reaction was poured into EtOAc (100 mL), extracted with saturated NaHCO$_3$ (2×60 mL) and saturated brine (1×60 mL). The organic phase was dried over Na$_2$SO$_4$ and evaporated. The residue was dissolved in MeOH (50 mL) containing sodium methoxide (25% wt/vol in MeOH, 0.3 mL) and the solution was stirred at room temperature for 30 min. The solvent was evaporated, and the crude was poured into EtOAc (100 mL), and washed with saturated NaHCO$_3$ (1×60 mL) and saturated brine (1×60 mL). The organic phase was dried over Na$_2$SO$_4$ and evaporated to give a brown oily residue. The residue was purified on a silica gel column, eluting with CH$_2$Cl$_2$/MeOH 25:1 to 20:1 to give 264 as a brown solid (5.93 g, 71%). Data for 264: MS (ESI) m/z 399.0 (M+H)$^+$.

Synthesis of Azides 265 and 266

To a solution of oxazolidinone 264 (3.00 g, 7.54 mmol) in anhydrous CH$_2$Cl$_2$ (40 mL) and Et$_3$N (2.16 ml, 15.45 mmol) at 0° C. was added MsCl (1.03 mL, 13.20 mmol). The reaction was stirred at 0° C. for 2 h and then was poured into saturated NaHCO$_3$ (60 mL) and CH$_2$Cl$_2$ (100 mL) and the two layers separated. The organic layer was extracted with H$_2$O (2×40 mL), saturated brine (1×40 mL) and dried over Na$_2$SO$_4$. The solvent was evaporated to give a brown oil. The crude was taken up in DMF (25 mL), then NaN$_3$ (2.00 g, 30.16 mmol) was added and the reaction was kept at 70° C. for 18 h. Water (60 mL) and EtOAc (100 mL) were added and the two layers separated. The aqueous layer was extracted with EtOAc (2×50 mL), and the combined organic layer was dried over Na$_2$SO$_4$ and evaporated. The crude was purified on a silica gel column, eluting with CH$_2$Cl$_2$/MeOH 30:1 to 24:1 to 20:1 to give azide 265 (2.16 g, 68%, white solid) and azide 266 (0.33 g, 14%, brown foam). Data for azide 265: MS (ESI) m/z 424.0 (M+H)$^+$; $^1$H-NMR (300 MHz, CDCl$_3$): δ 7.35 (dd, J=15, 3 Hz, 1H), 7.06 (dd, J=9, 2 Hz, 1H), 6.88 (m, 1H), 4.75 (m, 1H), 4.02 (t, J=9 Hz, 1H), 3.81-3.74 (m, 3H), 3.67 (dd, J=13, 5 Hz, 1H), 3.57 (dd, J=13, 4 Hz, 1H), 3.28 (t, J=6 Hz, 2H), 2.90 (s, 3H), 0.85 (s, 9H), 0.01 (s, 6H). Data for azide 266: MS (ESI) m/z 309.8 (M+H)$^+$; $^1$H-NMR (300 MHz, CDCl$_3$): δ 7.37 (dd, J=15, 3 Hz, 1H), 7.06 (dd, J=9, 3 Hz, 1H), 6.94 (t, J=6 Hz, 1H), 4.77 (m, 1H), 4.03 (t, J=9 Hz, 1H), 3.80-3.56 (m, 5H), 3.20 (t, J=6 Hz, 2H), 2.81 (s, 3H).

Synthesis of Azide 267

To a solution of azide 266 (0.16 g, 0.52 mmol) in THF (5 mL) and Et$_3$N (0.10 mL, 0.68 mmol) was added Ac$_2$O (0.065 mL, 0.68 mmol) and a few grains of DMAP at room temperature. Stirring was continued for 3 h, then the reaction was quenched with aqueous MeOH, poured into NaHCO$_3$ (30 mL), and extracted with CH$_2$Cl$_2$ (50 mL). The CH$_2$Cl$_2$ layer was extracted once with saturated brine (30 mL) and dried over Na$_2$SO$_4$. The solvent was evaporated to give 267 as a brown oil (0.182 g, 99%). MS (ESI) m/z 351.9 (M+H)$^+$.

Synthesis of Triazole 206

This compound was obtained from the reaction of alkyne 173 (0.315 g, 0.40 mmol) with azide 266 (0.16 g, 0.52 mmol) in the presence of CuI (0.057 g, 0.30 mmol) in THF (10 mL) and i-Pr$_2$NEt (0.1 mL) at room temperature within 30 min under argon. Saturated NH$_4$Cl (30 mL) was added, and stirring was continued for 5 min. The reaction was basified with NH$_4$OH to pH 9.0. CH$_2$Cl$_2$ (40 mL) was added, the two layers were separated, and the aqueous layer was extracted with CH$_2$Cl$_2$ (2×25 mL). The combined organic layer was dried over Na$_2$SO$_4$ and the solvent evaporated. The crude was purified on silica gel eluting with CH$_2$Cl$_2$/MeOH/NH$_4$OH 18:1:0.05 to 15:1:0.05 to 12:1:0.05 to give 206 as a white solid (0.426 g, 97%). Data for 206: MS (ESI) m/z 1096.4 (M+H)$^+$; $^1$H-NMR (300 MHz, CDCl$_3$, partial): δ 7.61 (s, 1H), 7.24 (dd, J=15, 2 Hz, 1H), 6.90 (m, 2H), 5.00 (m, 2H), 4.69 (m, 3H), 4.43 (d, J=7 Hz, 1H), 4.24 (m, 2H), 3.88 (m, 1H), 3.74 (t, J=5 Hz, 2H), 0.88 (m, 7H).

Synthesis of Triazole 207

This compound was obtained from the reaction of alkyne 173 (0.315 g, 0.40 mmol) with azide 267 (0.182 g, 0.52 mmol) as described for triazole 206 above. The crude was purified on silica gel, first eluting with CH$_2$Cl$_2$/MeOH 18:1 to remove unreacted 267, then with CH$_2$Cl$_2$/MeOH 15:1 to 12:1 to 10:1 containing a trace amount of NH$_4$OH to give 207 as a white solid (0.42 g, 92%). Data for 207: MS (ESI) m/z 1138.3 (M+H)$^+$; $^1$H-NMR (300 MHz, CDCl$_3$, partial): δ 7.62 (s, 1H), 7.29 (dd, J=15, 2 Hz, 1H), 6.93 (m, 1H), 6.85 (t, J=9 Hz, 1H), 5.01 (m, 2H), 4.66 (m, 3H), 4.22 (t, J=6 Hz, 2H), 3.89 (m, 1H), 3.38 (t, J=6 Hz, 2H), 0.89 (m, 7H).

Example 17

Synthesis of Triazole 208

Scheme 43 depicts the synthesis of triazole 208. Azide 188 was converted to benzylic alcohol 268, which was subsequently converted to triazole 208 using the copper-catalyzed cycloaddition chemistry described above.

305

Scheme 43

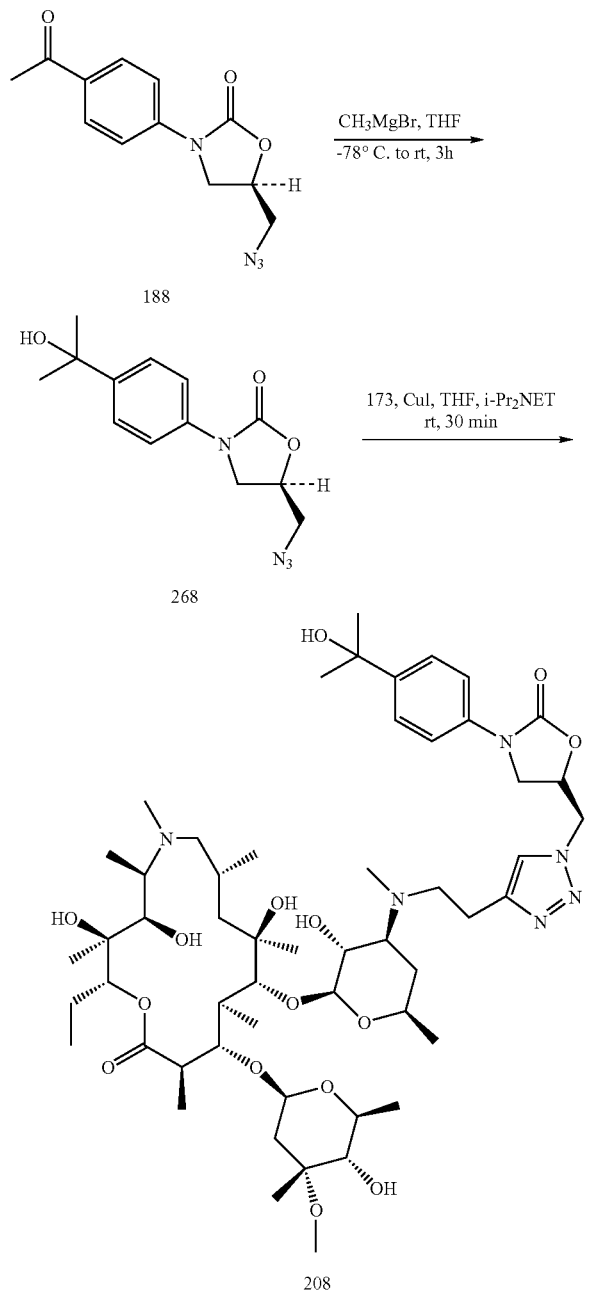

Synthesis of Azide 268

A solution of azide 188 (0.38 g, 1.43 mmol) in anhydrous THF (5 mL) was cooled to −78° C. To this solution was slowly added 1 M methyl magnesiumbromide (CH₃MgBr) in butyl ether (1.5 mL, 1.50 mmol) within 20 min. The reaction was allowed to warm up to room temperature and stirring was continued for 3 h. The reaction was quenched with H₂O (20 mL) and extracted with CH₂Cl₂ (40 mL). The organic layer was extracted with saturated brine (25 mL), dried over Na₂SO₄ and the solvent evaporated. The crude was purified on silica gel eluting with EtOAc/Hexanes 3:1 to

306

5:1 to give azide 268 as a white foam (0.178 g, 45%). Data for 268: MS (ESI) m/z 276.8 (M+H)⁺.

Synthesis of Triazole 208

This compound was obtained from the reaction of alkyne 173 (0.20 g, 0.25 mmol) with azide 268 (0.095 g, 0.34 mmol) as described for triazole 206 above except that the reaction was first quenched with saturated NH₄Cl/NH₄OH 5:1 (pH=9.5, 30 mL) before the usual CH₂Cl₂ extraction. The crude was purified on silica gel, first eluting with CH₂Cl₂/MeOH 12:1, then with CH₂Cl₂/MeOH/NH₄OH 15:1:0.05 to 12:1:0.05 to give 208 as a white solid (0.056 g). Data for 208: MS (ESI) m/z 1063.4 (M+H)⁺; ¹H-NMR (300 MHz, CDCl₃, partial): δ 7.63 (s, 1H), 7.48 (d, J=9 Hz, 2H), 7.37 (d, J=9 Hz, 2H), 5.03 (m, 2H), 4.72 (11, 3H), 4.44 (d, J=7 Hz, 1H), 4.30 (d, J=5 Hz, 1H), 4.16 (t, J=9 Hz, 1H), 3.92 (m, 1H), 3.67 (m, 2H), 0.90 (m, 7H).

Example 18

Synthesis of Triazole 209

Scheme 44 shows the synthesis of triazole 209. 3-Aminopyridine was converted to carbamate 269 which was subsequently transformed to azide 271 using chemistry similar to that reported above. Cycloaddition of 271 with alkyne 173 yielded triazole 209.

Scheme 44

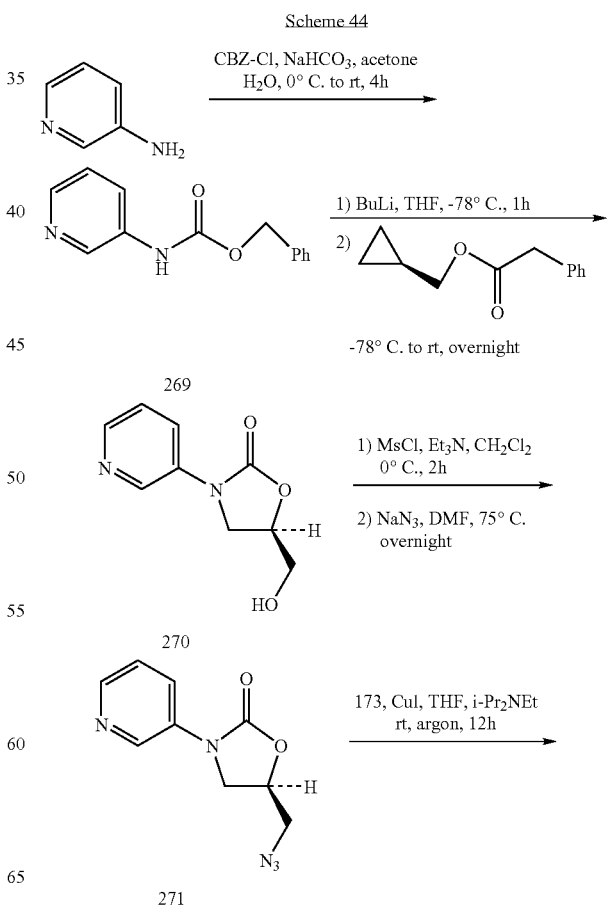

-continued

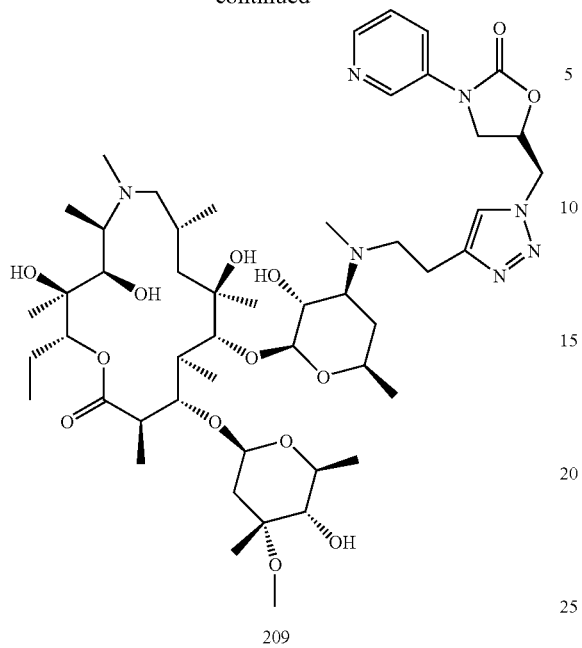

209

Synthesis of Alcohol 270

Oxazolidinone 270 was synthesized from 3-aminopyridine using the chemistry reported for the conversion of amine 262 to alcohol 264 (Example 16). The crude was purified on silica gel column, eluting with $CH_2Cl_2$/MeOH 19:1 to give 270 as a white solid (46%). Data for 270: MS (ESI) m/z 194.7 $(M+H)^+$.

Synthesis of Azide 271

Azide 271 was synthesized from alcohol 270 as described for the synthesis of azides 259 and 260 (Example 15) except that the sodium azide reaction with the intermediate mesylated derivative of 270 was complete within 2 h. The reaction was worked-up with saturated $NaHCO_3$ (30 mL) and EtOAc (4×40 mL). The organic phase was dried over $Na_2SO_4$ and evaporated. The crude was purified on silica gel, eluting with $CH_2Cl_2$/MeOH 17:1 to give 271 as a colorless, thick oil (81%). Data for 271: MS (ESI) m/z 220.0 $(M+H)^+$; $^1$H-NMR (300 MHz, $CDCl_3$): δ 8.60 (d, J=2 Hz, 1H), 8.35 (dd, J=5, 1 Hz, 1H), 8.07 (m, 1H), 7.28 (dd, J=8, 5 Hz, 1H), 4.83 (m, 1H), 4.11 (t, J=9 Hz, 1H), 3.87 (dd, J=9,6 Hz, 1H), 3.72 (dd, J=14,4 Hz, 1H), 3.57 (dd, J=14, 5 Hz, 1H).

Synthesis of Triazole 209

This compound was obtained from the reaction of alkyne 173 (0.17 g, 0.22 mmol) with azide 271 (0.080 g, 0.36 mmol) as described for triazole 206 above (Example 16) except that the reaction was allowed to stir for 12 h. The crude was purified on silica gel, first eluting with $CH_2Cl_2$/MeOH 17:1, then with $CH_2Cl_2$/MeOH/$NH_4OH$ 17:1:0.05 to 15:1:0.05 to 12:1:0.05 to 10:1:0.05 to give 209 as a white solid (0.117 g, 54%). Data for 209: MS (ESI) m/z 1006.5 $(M+H)^+$; $^1$H-NMR (300 MHz, $CDCl_3$, partial): δ 8.67 (d, J=3 Hz, 1H), 8.36 (dd, J=5, 1 Hz, 1H), 7.84 (m, 1H), 7.62 (s, 1H), 7.28 (m, 1H), 5.16-5.05 (m, 2H), 4.75 (d, J=4 Hz, 2H), 4.45 (d, J=7 Hz, 1H), 3.64 (t, J=7 Hz, 1H), 0.88 (m, 7H).

Example 19

Synthesis of Triazole 210

Triazole 210 was synthesized by dealkylation of compound 149 (Scheme 45).

Scheme 45

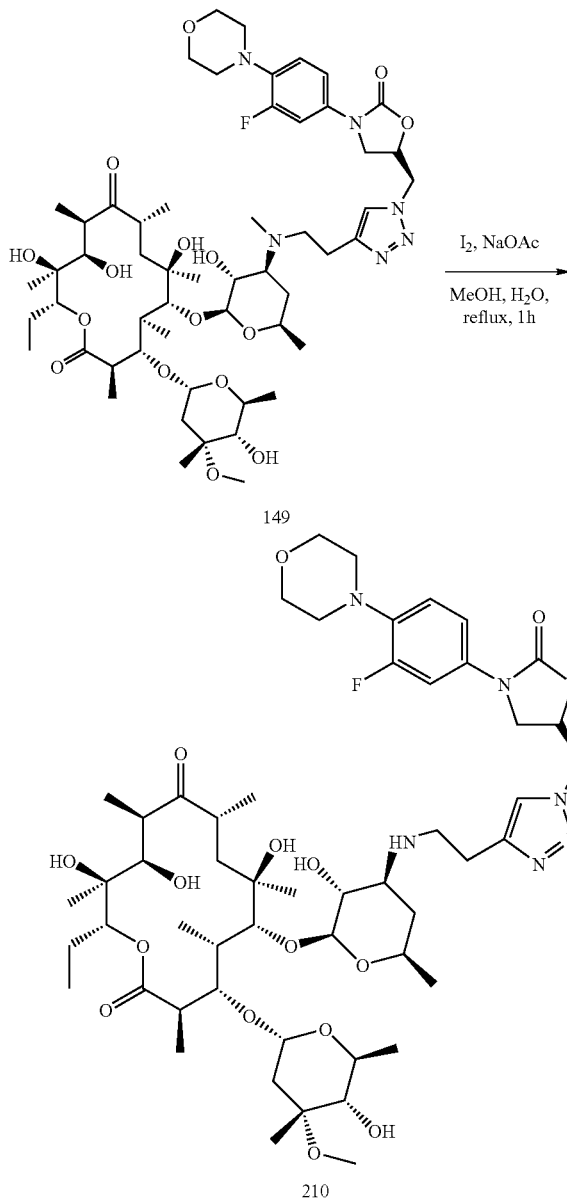

Synthesis of Triazole 210

Compound 149 (0.20 g, 0.183 mmol) and NaOAc (0.15 g, 1.83 mmol) were dissolved in 80% aqueous MeOH (5 mL), and the mixture was heated under gentle reflux for 1 h. The reaction was allowed to cool to room temperature and $H_2O$/$NH_4OH$ 8:1 (9 mL) was added. The mixture was extracted with $CH_2Cl_2$ (3×20 mL), the combined organic layer was extracted with $H_2O$/$NH_4OH$ 5:1 (20 mL), dried over $Na_2SO_4$ and the solvent evaporated. The crude was purified on silica gel eluting with $CH_2Cl_2$/MeOH/$H_2O$ (containing a trace of $NH_4OH$) 20:1:0.05 to 18:1:0.05 to 15:1:0.05 to 12:1:0.05 to give 210 as a white solid (0.049 g). Data for 210: MS (ESI) m/z 1079.4 $(M+Na)^+$; $^1$H-NMR (300

MHz, CDCl₃, partial): δ 7.55 (s, 1H), 7.25 (dd, J=14, 2 Hz, 1H), 6.91 (dd, J=9, 2 Hz, 1H), 6.82 (t, J=9 Hz, 1H), 4.96 (m, 2H), 4.81 (d, J=4 Hz, 1H), 4.64 (m, 2H), 4.31 (d, J=7 Hz, 1H), 4.05 (t, J=9 Hz, 1H), 3.47 (d, J=7 Hz, 2H), 2.29-2.25 (m, 2H), 0.78 (t, J=7 Hz, 3H).

Example 20

Synthesis of Triazole 211

A solution of alkyne 198 (136 mg, 0.216 mmol) in tetrahydrofuran (3.0 mL) was treated with azide 158 (104 mg, 0.325 mmol), i-Pr₂NEt (1.1 mL, 6.58 mmol) and copper (1) iodide (82 mg, 0.432 mmol), and the mixture was stirred under argon at room temperature for 15 h. The reaction mixture was diluted with methylene chloride (50 mL), washed with saturated aqueous NH₄Cl (3×50 mL), and brine (2×50 mL). The organic phase was dried (Na₂SO₄), and evaporated. The residue was chromatographed on silica gel using a 4-10% gradient of methanol in methylene chloride as eluant to provide 211 as a white solid (0.112 g, 0.118 mmol, 56%). Data for 211: MS (ESI) m/z 949.3 (M+H)⁺; ¹HNMR (300 MHz, CDCl₃, partial): δ 7.68 (s, 1H), 7.33 (dd, J=2, 14 Hz, 1H), 6.97 (dd, J=2,9 Hz, 1H), 6.89 (t, J=9 Hz, 1H), 5.16 (dd, J=3, 11 Hz, 1H), 5.09-4.99 (m, 1H), 4.72 (ddd, J=4, 15, 18 Hz, 2H), 4.36 (d, J=7 Hz, 1H), 4.13 (t, J=9 Hz, 2H), 0.83 (t, J=7 Hz, 3H).

Example 21

Synthesis of Triazole 212

To a mixture of alkyne 201 (48 mg, 0.076 mmol), azide 189 (19.9 mg, 0.084 mmol) and copper (I) iodide (8 mg, 0.038 mmol) was added THF (3 mL) and the mixture was repeatedly degassed and flushed with argon. Then i-Pr₂NEt (0.1 mL) was introduced and the mixture was stirred at room temperature for 1 h. The reaction mixture was poured into NH₄Cl (30 mL) and stirred for few minutes. Then NH₄OH (3 mL) was added and the mixture was extracted with methylene chloride (3×40 ml). The combined organic layers were dried (Na₂SO₄), concentrated and flash chromatographed over silica gel (methylene chloride: MeOH: NH₄OH=48:2:0.05) to provide 212 (55 mg, 0.06 mmol-9%). Data for 212: MS (ESI) m/z 862.3 (M+H)⁺; ¹HNMR (300 MHz, CDCl₃, partial): δ 7.60 (s, 1H), 7.32 (m, 1H), 7.09 (dd, J=3, 9 Hz, 1H), 6.85 (brt, 1H), 0.86 (t, J=7 Hz, 3H).

Example 22

Synthesis of Triazole 213

Scheme 46 illustrates the synthesis of triazole 213. 3,4-Difluoronitrobenzene is converted to nitroaniline 272 via an aromatic substitution reaction. The nitro group of 272 is reduced to afford aniline 273 which is transformed to carbamate 274. Oxazolidinone formation to provide 275 is followed by conversion to the azide to yield 277. Cycloaddition of azide 277 with alkyne 173 afforded triazole 213.

Scheme 46

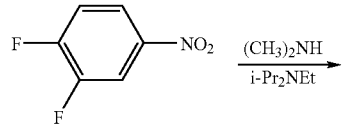

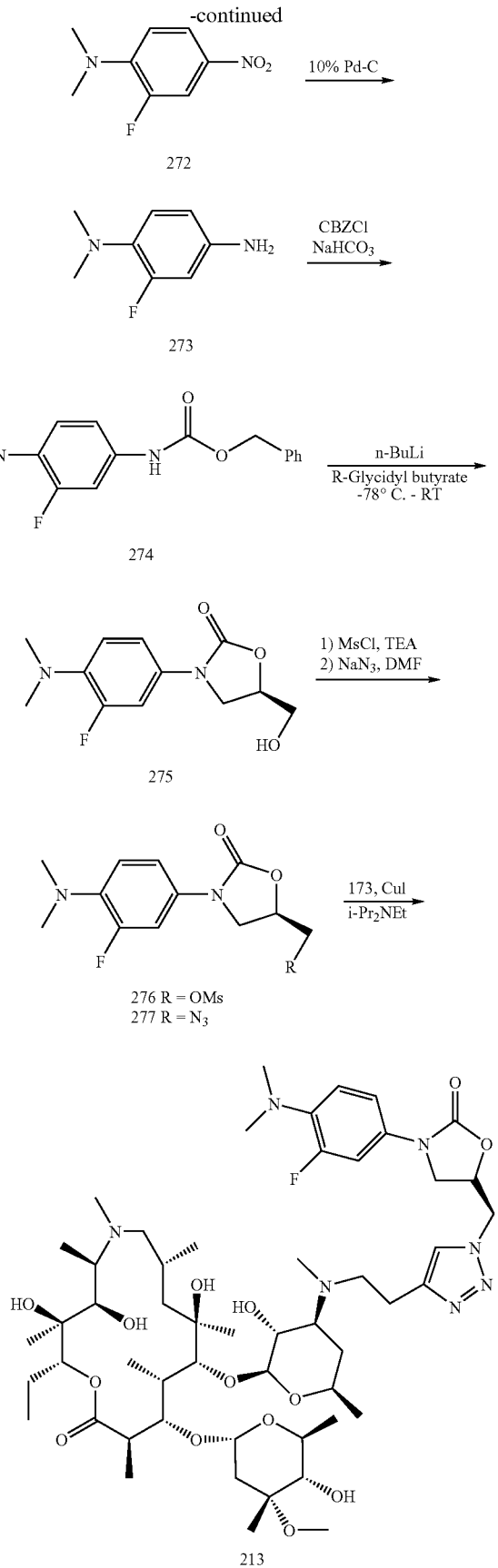

Synthesis of Nitroaniline 272

3,4-Difluoronitrobenzene (3 mL, 27.1 mmol) was added to a solution of dimethyl amine (15 mL, 29.8 mmol) and i-Pr$_2$NEt (5.2 ml, 29.8 mmol) in ethyl acetate (20 mL) at 0° C. and the mixture was stirred at room temperature overnight. The yellow solution was concentrated and redissolved in methylene chloride (100 mL) and then washed with water (50 mL). The aqueous layer was basified with KOH pellets and back extracted with methylene chloride (2×50 mL). The combined organic layer after evaporation afforded a yellow solid which was dissolved in 6N HCl (60 mL) at 0° C. and washed with methylene chloride (3×60 mL). The solution was basified with KOH pellets (pH 10) and extracted with methylene chloride (3×100 mL). The combined organic phase was dried (Na$_2$SO$_4$) and concentrated to provide 272 (1.8 g). Data for 272: $^1$HNMR (300 MHz, CDCl$_3$): δ 7.95 (dd, J=2, 8 Hz, 1H), 7.88 (dd, J=3, 14 Hz, 1H), 6.72 (t, J=9 Hz, 1H), 3.10 (s, 6H).

Synthesis of Aniline 273

To a solution of nitroaniline 272 (1.7 g, 9.2 mmol) in EtOH and THF (2:1, 30 mL) was added 10% Pd—C (0.2 g) and the mixture was stirred overnight at room temperature under hydrogen atmosphere. It was filtered through a Whatman filter paper and the residue was washed with methylene chloride (4×25 mL). The combined organic layer was evaporated to provide 273 (1.3 g). Data for 273: $^1$HNMR (300 MHz, CDCl$_3$): δ 6.81 (t, J=11 Hz, 1H), 6.46-6.37 (m, 2H), 2.73 (s, 6H).

Synthesis of Carbamate 274

To a solution of aniline 273 (1.3 g, 8.4 mmol) in a mixture of acetone (20 mL) and water (5 mL) was added NaHCO$_3$ (1.76 g, 21 mmol) at 0° C. and the mixture was stirred for few minutes. Then benzyl chloroformate (1.5 mL, 10.1 mmol) was added dropwise and the mixture was stirred at 0° C. for 1 h. The reaction mixture was concentrated and dissolved in methylene chloride (50 mL). The organic layer was washed with brine (3×50 mL), dried (Na$_2$SO$_4$) and concentrated to provide 274 (2.4 g) of suitable purity for use in subsequent reactions. Data for 274: $^1$HNMR (300 MHz, CDCl$_3$): δ 7.38-7.12 (m, 6H), 6.95 (brd, J=8 Hz, 1H), 6.84 (t, J=9 Hz, 1H), 6.57 (brs, 1H), 5.18 (s, 2H), 2.78 (s, 6H).

Synthesis of Oxazolidinone 275

To a solution of carbamate 274 (2.4 g, 8.3 mmol) in THF (80 mL) was added n-BuLi (4.32 mL, 2.5 M in hexane, 10.79 mmol) at −78° C. and the mixture was stirred for 1 h. (R)-Glycidyl butyrate (1.5 mL, 10.87 mmol) was added and the reaction warmed to room temperature and allowed to stir overnight. The reaction was carefully poured into saturated NH$_4$Cl (70 mL) and extracted with EtOAc (3×100 mL). The combined organic layers were washed with brine (1×200 mL), dried (Na$_2$SO$_4$) and concentrated. Flash chromatography over silica gel (60%-100% EtOAc in hexanes) provided 275 (2 g) 275 as a white solid. Data for 275: $^1$HNMR (300 MHz, CDCl$_3$): δ 7.38 (dd, J=3, 15 Hz, 1H), 7.10 (dd, J=3, 9 Hz 1H), 6.88 (t, J=12 Hz, 1H), 4.75-4.71 (m, 1H), 4.02-3.93 (m, 3H), 3.79-3.75 (m, 1H), 2.81 (s, 6H).

Synthesis of Azide 277

To alcohol 275 (900 mg, 3.54 mmol) in methylene chloride (35 mL) at 0° C. was added triethylamine (0.5 mL, 3.58 mmol) and methanesulfonyl chloride (0.41 mL, 5.31 mmol). After stirring for 1 h at 0° C., the reaction was poured into water (100 mL) and extracted with methylene chloride (3×100 mL). The combined organic layers were washed with water (2×100 mL), dried (Na$_2$SO$_4$) and concentrated to yield 1.1 g of pure product 276. To a solution of mesylate 276 (1.1 g, 3.3 mmol) in DMF (15 mL) was added sodium azide (646 mg, 9.9 mmol) and the reaction was heated at 75° C. overnight. The reaction was poured into water (100 mL) and extracted with EtOAc (3×100 mL). The combined organic layers were washed with water (3×100 mL), dried (Na$_2$SO$_4$) and concentrated to provide a solid. The material was further purified by flash chromatography over silica gel (50% EtOAc in hexanes) to yield 858 mg of pure azide 277. Data for 277: $^1$HNMR (300 MHz, CDCl$_3$): δ 7.38 (dd, J=3, 15 Hz, 1H), 7.10 (dd, J=3, 9 Hz 1H), 6.89 (t, J=9 Hz, 1H), 4.78-4.75 (m, 1H), 4.01 (t, J=9 Hz, 1H), 3.81 (dd, J=6, 9 Hz, 1H), 3.69 (dd, J=5, 13 Hz, 1H), 3.58 (dd, J=5, 13 Hz, 1H), 2.82 (s, 3H).

Synthesis of Triazole 213

To a mixture of alkyne 173 (200 mg, 0.254 mmol), azide 277 (85 mg, 0.305 mmol) and copper (1) iodide (24 mg, 0.127 mmol) was added THF (10 mL) and the mixture was repeatedly degassed and flushed with argon. Then i-Pr$_2$NEt (0.1 mL) was introduced and the mixture was stirred at room temperature for 1 h. The reaction mixture was poured into NH$_4$Cl (30 mL) and stirred for few minutes. Then NH$_4$OH (3 mL) was added and the mixture extracted with methylene chloride (3×40 ml). The combined organic layers were dried (Na$_2$SO$_4$), concentrated and flash chromatographed over silica gel (methylene chloride: MeOH:NH$_4$OH=12:1;0.05) to provide 223 mg of triazole 213. Data for 213: MS (ESI) m/z 1066.5 (M+H)$^+$; $^1$HNMR (300 MHz, CDCl$_3$, partial): δ 7.63 (s, 1H), 7.27 (dd, J=2, 8 Hz, 1H), 6.94 (dd, J=2, 9 Hz, 1H), 6.84 (t, J=9 Hz, 1H), 5.30-5.04 (m, 2H), 0.89 (t, J=7 Hz, 3H).

Example 23

Synthesis of Isoxazole 214

Scheme 47 exemplifies the synthesis of isoxazole 214. Known alkyne 278 (Zacharie, B. et al. *J. Med. Chem.* 1997, 40, 2883) was converted by hydroxylamine to hydroxyisoxazole 279. The Mitsunobu reaction of 279 with alcohol 280 (synthesized from 3-fluoroaniline using the chemistry reported in the literature (Brickner, S. J. et al. *J. Med. Chem.* 1996, 39, 673)) afforded isoxazole 281. Desilylation of 281 afforded alcohol 282 which was subsequently converted to tosylate 283. Alkylation of amine 171 with tosylate 283 yielded isoxazole 214.

Scheme 47

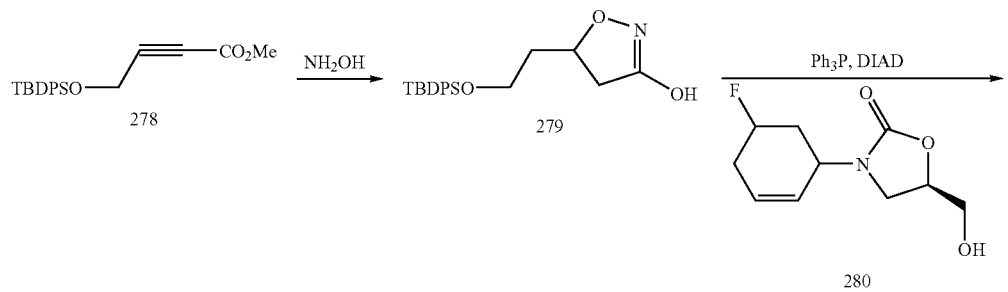

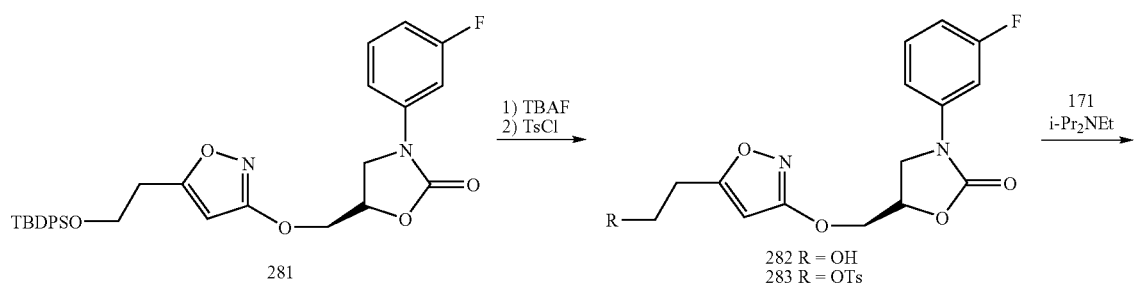

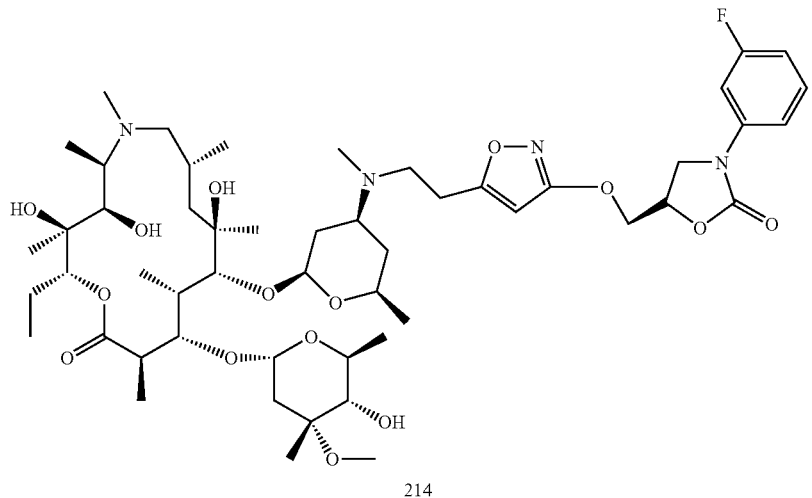

Synthesis of Hydroxyisoxazole 279

To a solution of hydroxylamine hydrochloride (208 mg, 3.0 mmol) in MeOH (5 mL) was added 10% NaOH (3.14 mL, 7.85 mmol) solution followed by a solution of alkyne 278 (900 mg, 2.5 mmol) in MeOH (1.5 mL). The mixture was stirred overnight at room temperature and was then acidified with 6N HCl (pH 2), saturated with sodium sulphate. The mixture was extracted with diethyl ether (3×50 mL). The combined organic layers were washed with water (3×100 mL), dried (Na$_2$SO$_4$), concentrated and chromatographed over silica gel (20% EtOAc in hexanes) to provide 280 mg pure isoxazole 279 as a white solid. Data for 279: MS (ESI) m/z 408.9 (M+CH$_3$CN)$^+$; $^1$HNMR (300 MHz, CDCl$_3$): δ 7.62 (brd, 4H), 7.46-7.35 (m, 6H), 5.76 (s, 1H), 3.91 (t, J=6 Hz, 2H), 2.86 (t, J=7 Hz, 2H), 1.03 (s, 9H).

Synthesis of Isoxazole 281

To a solution of isoxazole 279 (100 mg, 0.272 mmol), alcohol 280 (86 mg, 0.408 mmol) and triphenyl phosphine (114 mg, 0.435 mmol) in THF (8 mL) was added diisopropyl azodicarboxylate (0.08 mL, 0.408 mmol) at −20° C. The solution was warmed to room temperature and stirred for 3 h. The mixture was concentrated and chromatographed over silica gel (25-30% EtOAc in hexanes) to provide 140 mg of 281. Data for 281: MS (ESI) m/z 583.0 (M+Na)$^+$; $^1$HNMR (300 MHz, CDCl$_3$): δ 7.61 (dd, J=3, 9 Hz, 4H), 7.48-7.32 (m, 9H), 6.85 (brt, 1H), 5.72 (s, 1H), 5.02-4.94 (m, 1H), 4.53

(dd, J=4, 12 Hz, 1H), 4.46 (dd, J=5, 12 Hz, 1H), 4.16-4.09 (m, 2H), 3.93 (t, J=6 Hz, 2H), 2.87 (t, J=6 Hz, 2H), 1.03 (s, 9H).

Synthesis of Isoxazole 282

To a Solution of silyl ether 281 (140 mg, 0.25 mmol) in THF (5 mL) was added tetrabutylammonium fluoride (0.5 mL, 1M in THF) at 0° C. and the mixture was stirred overnight at room temperature. The reaction mixture was concentrated and dissolved in EtOAc (50 mL). The organic layer was washed with brine (2×50 mL), dried (Na$_2$SO$_4$), concentrated and chromatographed over silica gel (70% EtOAc in hexanes) to provide 70 mg of 282. Data for 282: MS (ESI) m/z 322.8 (M+H)$^+$; $^1$HNMR (300 MHz, CDCl$_3$): δ 7.45 (ddd, J=2, 5, 11 Hz, 1H), 7.30-7.21 (m, 2H), 6.88-6.82 (m, 1H), 5.78 (s, 1H), 5.04-4.96 (m, 1H), 4.52 (dd, J=4, 12 Hz, 1H), 4.43 (dd, J=5, 11 Hz, 1H), 4.15 (t, J=9 Hz, 1H), 3.96 (dd, J=6, 9 Hz, 1H), 3.91 (t, J=6 Hz, 2H), 2.91 (t, J=6 Hz).

Synthesis of Tosylate 283 p-Toluenesulfonyl chloride (71.5 mg, 0.375 mmol) was added to a solution of isoxazole 282 (60 mg, 0.187 mmol), triethylamine (0.065 mL, 0.468 mmol) and DMAP (cat.) in methylene chloride (5 mL) at 0° C. The mixture was then allowed to stir at room temperature for 4 h. The reaction mixture was diluted with EtOAc (30 mL) and washed with brine (3×30 mL), dried (Na$_2$SO$_4$), concentrated and chromatographed over silica gel (50% EtOAc in hexanes) to yield 77.6 mg of pure tosylate 283. Data for 283: MS (ESI) m/z 476.9 (M+H)$^+$, 498.9 (M+Na)$^+$; $^1$HNMR (300 MHz, CDCl$_3$): δ 7.76 (d, J=9 Hz, 2H), 7.46 (ddd, J=2, 5, 11 Hz, 1H), 7.38-7.23 (m, 4H), 6.89-6.83 (m, 1H), 5.73 (s, 1H), 5.04-4.96 (m, 1H), 4.52 (dd, J=4, 12 Hz, 1H), 4.44 (dd, J=5, 11 Hz, 1H), 4.26 (t, J=6 Hz, 2H), 4.16 (t, J=9 Hz, 1H), 3.96 (dd, J=6,9 Hz, 1H), 3.02 (t, J=6 Hz, 2H), 2.45 (s, 3H).

Synthesis of Isoxazole 214

A suspension of N-desmethylazithromycin 171 (100 mg, 0.136 mmol), tosylate 283 (52 mg, 0.109 mmol), i-Pr$_2$NEt (3 mL) and NaI (cat.) in THF (4 mL) was heated to reflux for 72 h. The reaction mixture was concentrated and chromatographed over silica gel (methylene chloride:MeOH: NH$_4$OH=12:1:0.01) to yield 7 mg of 214. Data for 214: MS (ESI) m/z 1039.1 (M+H)$^+$, 1061.5 (M+Na)$^+$; $^1$HNMR (300 MHz, CDCl$_3$, partial): δ 7.46 (ddd, J=2, 5, 11 Hz, 1H), 7.38-7.23 (m, 2H), 6.86 (brt, 1H), 5.72 (s, 1H), 5.08 (d, J=5 Hz, 1H), 5.02-4.96 (m, 1H), 4.68 (d, J=8 Hz, 1H), 4.53 (dd, J=4, 11 Hz, 1H), 4.46 (dd, J=5, 9 Hz, 1H), 0.90 (t, J=6 Hz, 3H).

Example 24

Synthesis of Triazole 215

Scheme 48 exemplifies the synthesis of triazole 215. The cycloaddition of known azide 284 (see U.S. Pat. No. 6,124,334) and alkyne 173 afforded triazole 215:

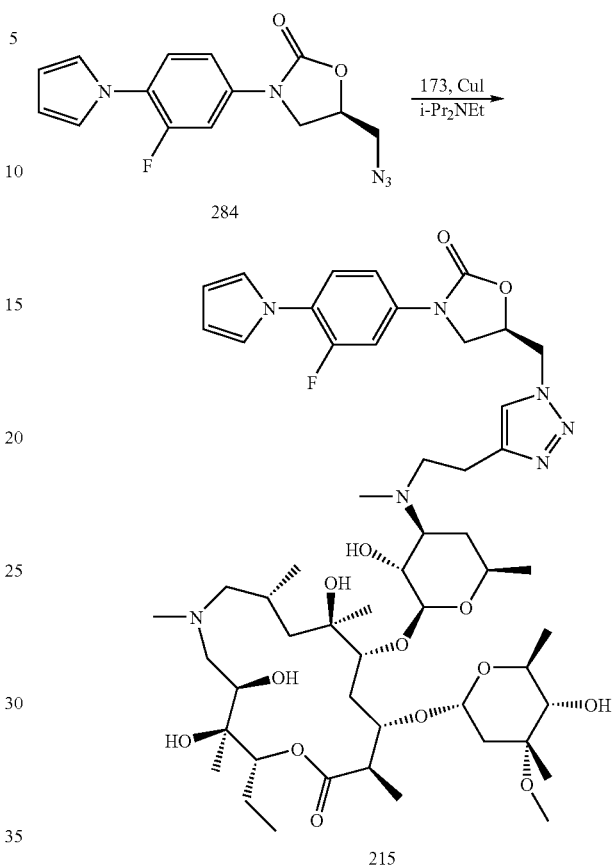

Synthesis of Triazole 215

A solution of alkyne 173 (0.100 g, 0.13 mmol) and azide 284 (0.046 g, 0.19 mmol) in tetrahydrofuran (1.3 mL) was treated with N,N-diisopropylethylamine (0.670 mL, 3.8 mmol) and copper (I) iodide (36 mg, 0.19 mmol) and the mixture was stirred under argon at 23° C. for 2.5 h. The reaction mixture was diluted with saturated aqueous ammonium hydroxide (10 mL) and extracted with dichloromethane (4×30 mL). The combined organic fractions were dried (Na$_2$SO$_4$), evaporated, and the residue purified by flash chromatography (SiO$_2$, ammonium hydroxide/methanol/dichloromethane 0.05:1:9) to provide 215 (53 mg, 0.048 mmol, 38%) as a white powder. Data for 215: MS (ESI) m/z 545.0 (M+2H)$^{2+}$; $^1$HNMR (300 MHz, CDCl$_3$, partial): δ 7.81 (s, 1H), 7.61-7.54 (m, 1H), 7.39-7.33 (m, 1H), 7.21-7.15 (m, 1H), 6.99 (d, J=2 Hz, 2H), 6.34 (d, J=1 Hz, 2H), 3.29 (s, 3H), 3.26 (s, 3H), 0.89-0.78 (m, 6H).

Example 25

Synthesis of Triazole 216

Scheme 49 depicts the synthesis of triazole 216. The known alcohol 285 (see International Patent Application WO0306440) is converted by standard chemistry to azide 287. This azide is coupled to 4-cyanophenylboronic acid using the Suzuki reaction to afford biaryl azide 288. Cycloaddition of 288 with alkyne 173 afforded triazole 216.

Scheme 49

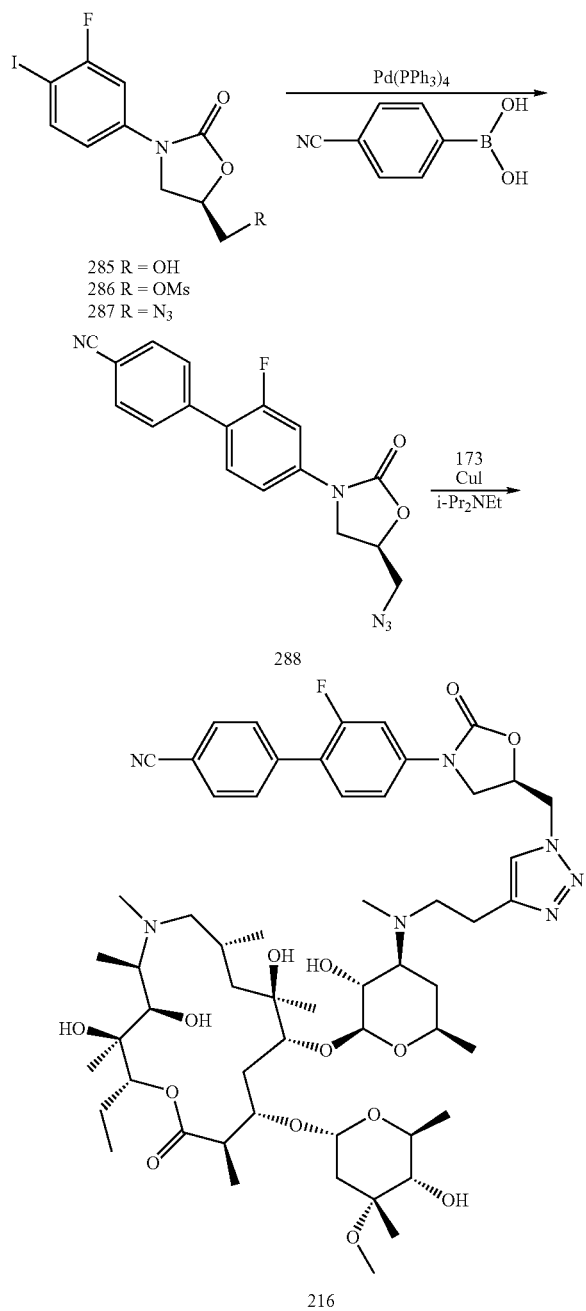

5.07-5.00 (m, 1H), 4.53-4.48 (m, 2H), 4.22-4.19 (m, 1H), 3.83 (dd, J=9, 6 Hz, 1H), 3.26 (s, 3H).

Synthesis of Azide 287

A solution of mesylate 286 (7.00 g, 16.8 mmol) in dimethylformamide (50 mL) was treated with sodium azide (1.5 g, 23 mmol) and stirred at 50° C. under argon for 18 h. The reaction mixture was cooled to 20° C., poured into $H_2O$ (400 mL) and stirred at 0° C. The resulting precipitate was filtered, washed with $H_2O$ and dried under reduced pressure to provide azide 287 as a white powder (4.0 g, 11 mmol, 66%). Data for 287: $^1$HNMR (300 MHz, CDCl$_3$): δ 7.71 (dd, J=9, 7 Hz, 1H), 7.48 (dd, J=10, 2 Hz, 1H), 7.06 (dd, J=9, 2 Hz, 1H), 4.89-4.77 (m, 1H), 4.09-4.04 (m, 1H), 3.84 (dd, J=9, 6 Hz, 1H), 3.73 (dd, J=13, 5 Hz, 1H), 3.61 (dd, J=13, 5 Hz, 1H).

Synthesis of Azide 288

A solution of azide 287 (0.36 g, 1.0 mmol) in toluene/ethanol/$H_2O$ (3:1:1, 10 mL) was treated with potassium carbonate (0.41 g, 3.0 mmol), 4-cyanophenylboronic acid (0.18 g, 1.2 mmol) and tetrakis(triphenylphosphine)palladium (0.005 g, 0.05 mmol), and the mixture was stirred under argon at 80° C. for 0.5 h. The reaction mixture was cooled to room temperature, diluted with ethyl acetate (50 mL), washed with $H_2O$ (3×50 mL), dried (Na$_2$SO$_4$), and evaporated. Flash chromatography (SiO$_2$, hexanes/ethyl acetate 1:1) provided azide 288 (0.23 g, 0.67 mmol, 67%) as a white powder. Data for 288: $^1$HNMR (300 MHz, CDCl$_3$): δ 7.72-7.69 (m, 2H), 7.64-7.60 (m, 2H), 7.55 (dd, J=13, 2 Hz), 7.46-7.41 (m, 1H), 7.35 (dd, J=9, 2 Hz), 4.87-4.78 (m, 1H), 4.14-4.08 (m, 1H), 3.89 (dd, J=9, 6 Hz, 1H), 3.73 (dd, J=13, 5 Hz, 1H) 3.61 (dd, J=13, 5 Hz, 1H).

Synthesis of Triazole 216

A solution of alkyne 173 (0.19 g, 0.24 mmol) and azide 288 (0.10 g, 0.30 mmol) in tetrahydrofuran (5.0 mL) was treated with N,N-diisopropylethylamine (0.042 mL, 0.24 mmol) and copper (I) iodide (19 mg, 0.10 mmol) and the mixture was stirred under argon at 23° C. for 0.5 h. The reaction mixture was diluted with saturated aqueous ammonium hydroxide (10 mL) and extracted with dichloromethane (3×30 mL). The combined organic fractions were dried (Na$_2$SO$_4$) and evaporated, and the residue purified by flash chromatography (SiO$_2$, ammonium hydroxide/methanol/dichloromethane (0.05:1:9) to provide 216 (110 mg, 0.098 mmol, 41%) as a white powder. Data for 216: MS (ESI) m/z 1125 (M+H)$^+$; $^1$HNMR (300 MHz, CDCl$_3$, partial): δ 7.72-7.69 (m, 2H), 7.62 (s, 1H), 7.60 (m, 2H), 7.49-7.44 (m, 1H), 7.42-7.37 (m, 1H), 7.22-7.19 (m, 1H), 3.31 (s, 3H), 2.34 (s, 3H), 2.30 (s, 3H), 0.88-0.86 (m, 6H).

Synthesis of Mesylate 286

A solution of alcohol 285 (2.5 g, 7.4 mmol) in methylene chloride (40 mL) was cooled to 0° C. under argon and treated with Et$_3$N (1.80 mL, 13.2 mmol) and methanesulfonyl chloride (0.57 mL, 7.4 mmol). The reaction mixture was warmed to 23° C. for 0.5 h then washed with 1 M hydrochloric acid (50 mL), saturated aqueous sodium bicarbonate (50 mL) and saturated aqueous sodium chloride (50 mL). Drying (Na$_2$SO$_4$) and evaporation provided mesylate 286 (2.8 g, 6.7 mmol, 91%) as a white powder Data for 286: $^1$HNMR (300 MHz, DMSO-d$_6$): δ 7.85 (dd, J=9, 8 Hz, 1H), 7.57 (dd, J=11, 2 Hz, 1H), 7.22 (dd, J=9, 2 Hz, 1H),

Example 26

Synthesis of Triazoles 217 and 218

Scheme 50 details the synthesis of triazoles 217 and 218. The known carbamate 289 (see *J. Med. Chem.* 2000, 43, 953) was deprotected to afford aniline 290. Diazotization of 290 afforded azide 291, which was subsequently converted by cycloaddition chemistry with available alkynes to triazoles 292 and 295. Manipulation of these intermediates to azides 294 and 297 as followed by cycloaddition with alkyne 173 to afford triazoles 217 and 218 respectively.

Scheme 50
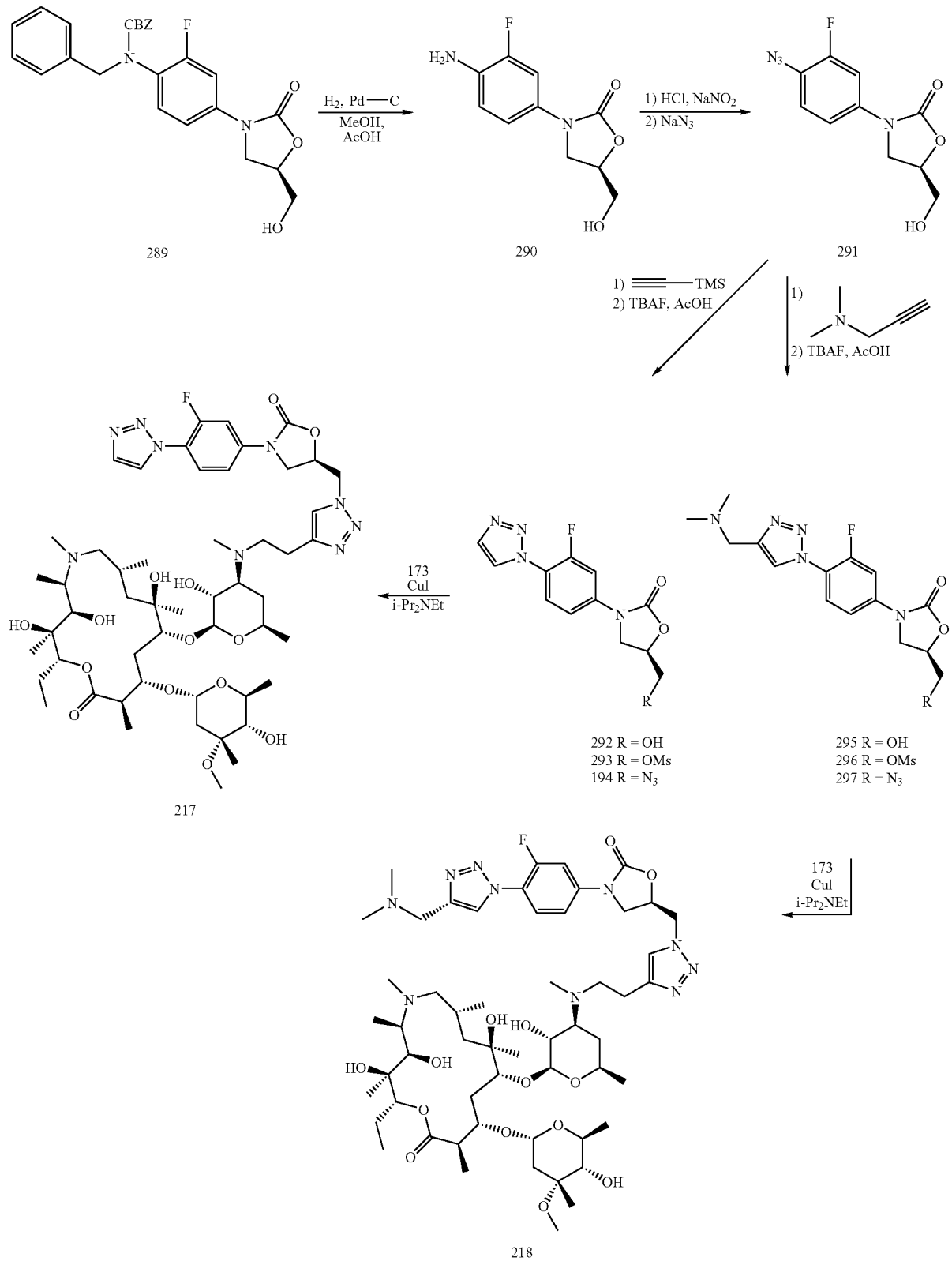

Synthesis of Aniline 290

A solution of carbamate 289 (3.6 g, 7.9 mmol) in methanol (120 mL) was treated with acetic acid (30 mL) and 10% Pd—C (1.0 g) and the mixture was stirred under a balloon of hydrogen for 12 h at 23° C. The reaction mixture was filtered through a plug of $SiO_2$ and evaporated under reduced pressure, providing 290 (1.5 g, 6.6 mmol, 84%) as a pink-white solid. Data for 290: $^1$HNMR (300 MHz, DMSO-$d_6$): δ 7.32 (dd, J=14, 3, Hz, 1H), 6.99-6.95 (m, 1H), 6.75 (dd, J=10, 9 Hz, 1H), 4.99 (s, 2H), 4.66-4.58 (m, 1H), 4.01-3.94 (m, 1H). 3.72 (dd, J=9, 6 Hz, 1H), 3.63 (dd, J=12, 4 Hz, 1H), 3.50 (dd, J=12, 4 Hz, 1H).

Synthesis of Azide 291

A suspension of aniline 290 (0.56 g, 2.5 mmol) in $H_2O$ (10 mL) was cooled to 0° C. and treated with concentrated hydrochloric acid (1.0 mL, 12.4 mmol) and sodium nitrite (0.19 g, 2.8 mmol). A solution of sodium azide (0.24 g, 3.8 mmol) in $H_2O$ (1.0 mL) was added after 1 h, and stirring at 0° C. was continued for an additional 1 h. The reaction mixture was diluted with saturated aqueous sodium bicarbonate (20 mL) and extracted with ethyl acetate (100 mL). The organic fraction was washed with $H_2O$ (100 mL) dried ($Na_2SO_4$) and evaporated to an orange film. Data for 291: $^1$HNMR (300 MHz, $CD_3OD$): δ 7.51 (dd, J=14, 3 Hz, 1H), 7.19 (m, 1H), 7.03 (m, 1H), 4.70-4.61 (m, 1H), 4.02-3.96 (m, 1H), 3.79 (m, 1H), 3.74 (m, 1H).

Synthesis of Triazole 292

A solution of azide 291 (0.14 g, 0.56 mmol) and trimethylsilylacetylene (0.47 mL, 3.3 mmol) in dimethylformamide (4 mL) was stirred at 60° C. for 16 h. The reaction mixture was cooled to 23° C., concentrated under reduced pressure to a volume of 2.0 mL, and treated with tetrabutylamonium fluoride (1.5 mL of a 1.0 M solution in tetrahydrofuran) and acetic acid (0.1 mL) and the mixture was stirred for 12 h. Ethyl acetate (100 mL) was added and the solution was washed with $H_2O$ (3×75 mL), dried ($Na_2SO_4$) and evaporated to provide 292 (87 mg, 0.31 mmol, 56%) as a brown foam that was used directly in the next step.

Synthesis of Azide 294

A solution of alcohol 292 (94 mg, 0.34 mmol) in dichloromethane (3.5 mL) was cooled to 0° C. and treated with triethylamine (0.095 mL, 0.68 mmol) and methanesulfonyl chloride (0.029 mL, 0.37 mmol). The reaction mixture was stirred at 23° C. for 1 h, then diluted with ethyl acetate (150 mL) and washed with 1 M hydrochloric acid (2×75 mL), 10% aqueous sodium carbonate (75 mL), dried ($Na_2SO_4$), and evaporated. Flash chromatography ($SiO_2$, 50-100% ethyl acetate/hexanes) provided mesylate 293 (50 mg, 0.14 mmol, 41%) as a yellow film. Data for 293: MS (ESI) m/z 357 (M+H)$^+$; $^1$HNMR (300 MHz, $CDCl_3$): δ 8.11-8.09 (m, 1H), 8.04-7.98 (m, 1H), 7.88 (m, 1H), 7.85 (dd, J=13, 2 Hz, 1H), 7.32-7.27 (m, 1H), 5.04-4.96 (m, 1H), 4.54 (dd, J=12, 4 Hz, 1H), 4.47 (dd, J=12, 4 Hz, 1H), 4.26-4.20 (m, 1H), 4.03 (dd, J=9, 6 Hz, 1H), 3.12 (s, 3H), 2.36 (s, 6H).

A solution of mesylate 293 (0.050 g, 0.15 mmol) in dimethylformamide (1.5 mL) was treated with sodium azide (0.018 g, 0.28 mmol) and stirred at 60° C. under argon for 12 h. The reaction mixture was cooled to 20° C., diluted with ethyl acetate (75 mL), washed with $H_2O$ (3×50 mL), dried ($Na_2SO_4$), and evaporated under reduced pressure providing azide 294 as a yellow film (41 mg).

Synthesis of Triazole 217

A solution of crude azide 294 obtained above (0.038 g, 0.13 mmol) and alkyne 173 (0.079 g, 0.10 mmol) in tetrahydrofuran (5.0 mL) was treated with diisopropylethylamine (0.050 mL, 0.29 mmol) and copper (I) iodide (18 mg, 0.094 mmol) and stirred under argon at 23° C. for 1 h. The reaction mixture was diluted with saturated aqueous ammonium hydroxide (10 mL) and extracted with dichloromethane (3×30 mL). The combined organic fractions were dried ($Na_2SO_4$), evaporated, and the residue purified by flash chromatography ($SiO_2$, ammonium hydroxide/methanol/dichloromethane (0.05:1:9) to provide triazole 217 (32 mg, 0.029 mmol, 29%) as a yellow foam. Data for 217: MS (ESI) m/z 546 (M+2H)$^{2+}$; $^1$HNMR (300 MHz, $CDCl_3$, partial): δ 8.01 (d, J=1 Hz, 1H), 7.88-7.83 (m, 1H), 7.79 (d, J=1 Hz, 1H), 7.68 (s, 1H), 7.60 (m, 1H), 7.20 (m, 1H), 3.26 (s, 3H), 2.30 (s, 3H), 2.22 (s, 3H), 0.88-0.84 (m, 6H).

Synthesis of Triazole 295

A solution of azide 291 (0.14 g, 0.56 mmol) and N,N-dimethylpropargylamine (0.30 mL, 2.6 mmol) in dimethylformamide (4 mL) was treated with copper (1) iodide (0.030 g, 0.16 mmol) and stirred at 20° C. for 1 h. The reaction mixture was diluted with ethyl acetate (100 mL) and washed with 10% ammonium hydroxide (2×100 mL) and saturated aqueous sodium chloride (100 mL), dried ($Na_2SO_4$) and evaporated. Flash chromatography of the crude material ($SiO_2$, ammonium hydroxide/methanol/dichloromethane (0.05:1:9) provided triazole 295 (18 mg, 0.054 mmol, 9.6%) as a yellow film. Data for 295: $^1$HNMR (300 MHz, $CDCl_3$): δ 8.02-8.01 (m, 1H), 7.86-7.81 (m, 1H), 7.71 (dd, J=14, 2 Hz, 1H), 7.33-7.27 (m, 1H), 4.83-4.76 (m, 1H), 4.15-4.04 (m, 2H), 4.02 (dd, J=9, 4 Hz, 1H), 3.78 (dd, J=13, 3 Hz, 1H), 3.73-3.71 (m, 2H), 2.36 (s, 6H).

Synthesis of Azide 297

A solution of alcohol 295 (17 mg, 0.050 mmol) in dichloromethane (0.5 mL) was cooled to 0° C. and treated with triethylamine (0.014 mL, 0.10 mmol) and methanesulfonyl chloride (0.0043 mL, 0.056 mmol). The reaction mixture was stirred at 23° C. for 1 h, then diluted with ethyl acetate (100 mL) and washed with 10% aqueous sodium carbonate (2×100 mL), dried ($Na_2SO_4$) and evaporated. Flash chromatography ($SiO_2$, ammonium hydroxide/methanol/dichromethane (0.05:1:9) provided mesylate 296 (17 mg, 0.041 mmol, 82%) as a yellow film. Data for 296: MS (ESI) m/z 414 (M+H)$^+$; $^1$HNMR (300 MHz, $CDCl_3$): δ 8.02-8.01 (m, 1H), 8.05-7.95 (m, 1H), 7.83 (dd, J=13, 2 Hz, 1H), 7.31-7.27 (m, 1H), 5.04-4.97 (m, 1H), 4.54 (dd, J=12, 4 Hz, 1H), 4.47 (dd, J=12, 4 Hz, 1H), 4.03 (dd, J=9, 6 Hz, 1H), 3.70 (s, 2H), 3.12 (s, 3H), 2.36 (s, 6H).

A solution of the above mesylate 296 (0.017 g, 0.042 mmol) in dimethylformamide (0.40 mL) was treated with sodium azide (0.006 g, 0.848 mmol) and stirred at 60° C. under argon for 12 h. The reaction mixture was cooled to 20° C., diluted with ethyl acetate (75 mL), washed with $H_2O$ (3×50 mL), dried ($Na_2SO_4$), and evaporated under reduced pressure providing azide 297 as a white foam (15 mg).

Synthesis of Triazole 218

A solution of crude azide 297 (0.012 g, 0.033 mmol) and alkyne 173 (0.021 g, 0.027 mmol) in tetrahydrofuran (1.4 mL) was treated with diisopropylethylamine (0.014 mL, 0.13 mmol) and copper (I) iodide (4.7 mg, 0.025 mmol) and stirred under argon at 23° C. for 1 h. The reaction mixture was diluted with saturated aqueous ammonium hydroxide (10 mL) and extracted with dichloromethane (3×30 mL). The combined organic fractions were dried ($Na_2SO_4$), evaporated, and the residue purified by flash chromatography ($SiO_2$, ammonium hydroxide/methanol/dichloromethane (0.05:1:9) to provide triazole 218 (12 mg, 0.010 mmol, 39%) as a yellow foam. Data for 218: MS (ESI) m/z 574 (M+2H)$^{2+}$; $^1$HNMR (300 MHz, CDCl$_3$, partial): δ 8.11 (m, 1H), 7.89-7.84 (m, 1H), 7.67 (s, 1H), 7.58 (m, 1H), 7.20 (m, 1H), 3.22 (s, 3H), 2.38 (s, 6H), 2.31 (s, 3H), 2.23 (s, 3H), 0.88-0.84 (m, 6H).

Example 27

Synthesis of Triazoles 219 and 220

Scheme 51 details the synthesis of thiazoles 219 and 220. Iodoaryl alcohol 285 is converted to nitrile 298 which is then transformed to azide 300 via mesylate 299. Cycloaddition of azide 300 and alkyne 173 yielded triazole 219. Nitrile 298 was manipulated to oxadiazole 301, which served as the precursor to azide 302. Cycloaddition of 302 with 173 afforded triazole 220.

with methylene chloride (100 mL), and washed with saturated aqueous ammonium chloride (100 mL) and saturated aqueous sodium chloride (100 mL). Drying (Na$_2$SO$_4$) and evaporation provided 298 (2.9 g, 12.3 mmol, 76%) as a white powder. Data for 298: $^1$HNMR (300 MHz, CD$_3$OD): δ 7.68 (dd, J=12, 2 Hz, 1H), 7.62 (dd, J=9, 8 Hz, 1H), 7.39 (dd, J=9, 2 Hz, 1H), 4.71-4.65 (m, 1H), 4.08-4.02 (m, 1H), 3.86 (dd, J=9, 6 Hz, 1H), 3.77 (dd, J=13, 3 Hz, 1H), 3.60 (dd, J=13, 4 Hz, 1H).

Synthesis of Azide 300

A solution of nitrile alcohol 298 (600 mg, 2.50 mmol) in methylene chloride (14 mL) was cooled to 0° C. under argon and treated with triethylamine (0.70 mL, 5.0 mmol) and methanesulfonyl chloride (0.22 mL, 2.8 mmol). The reaction mixture was warmed to 23° C. for 0.5 h and subsequently

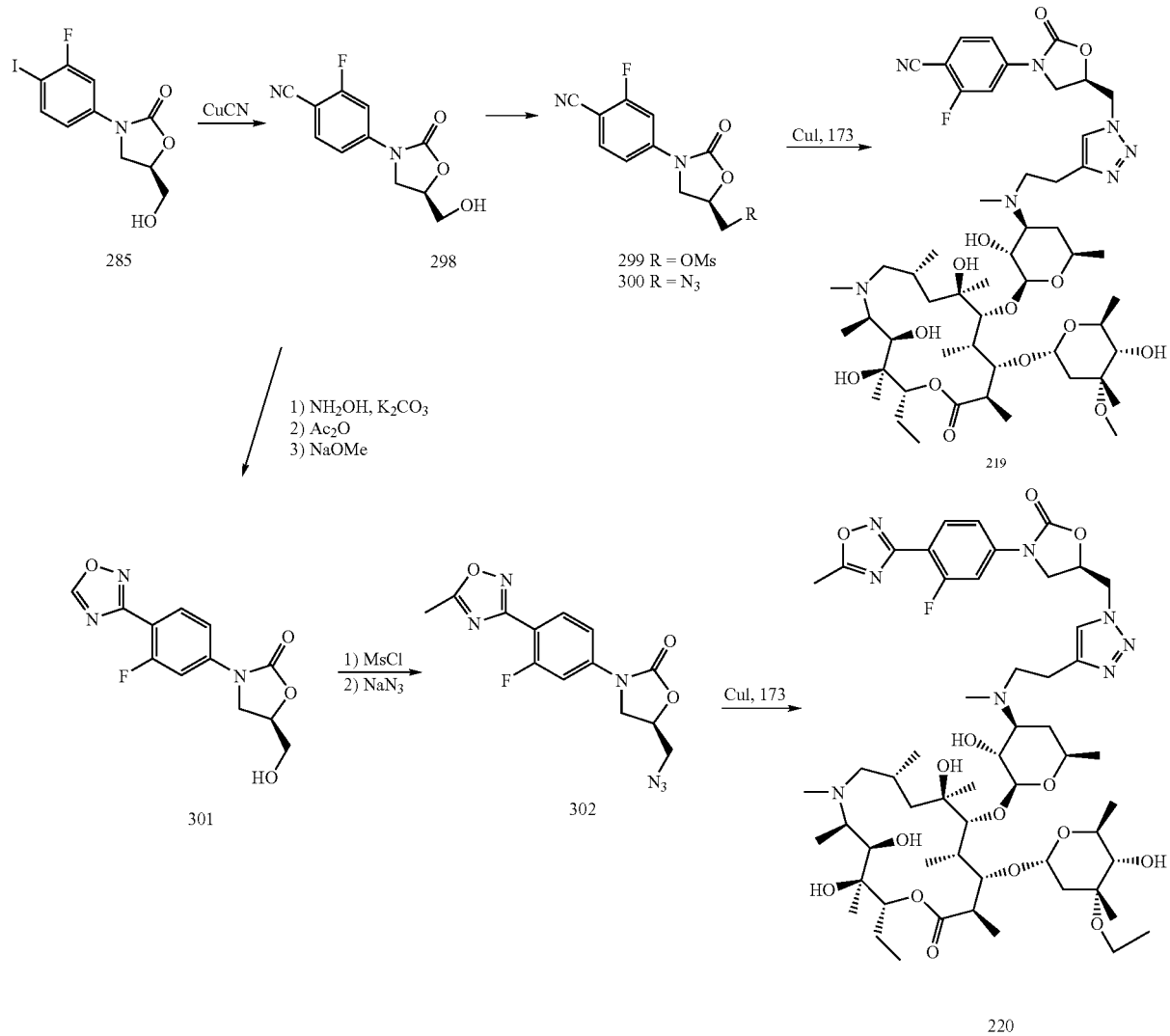

Scheme 51

Synthesis of Nitrile 298

A solution of alcohol 285 (5.4 g, 16.1 mmol) in dimethylformamide (16 mL) was treated with copper (I) cyanide (1.60 g, 17.7 mmol) and stirred at 145° C. under argon for 18 h. The reaction mixture was cooled to 23° C. and diluted diluted with methylene chloride (50 mL), washed with 1 M hydrochloric acid (15 mL), saturated aqueous sodium bicarbonate (15 mL), and saturated aqueous sodium chloride (15 mL). Drying (Na$_2$SO$_4$) and evaporation provided mesylate 299 (0.62 g, 2.0 mmol, 80%) as a white powder. Data for 299: ¹HNMR (300 MHz, CDCl₃): δ 7.63 (dd, J=12, 2 Hz, 1H), 7.56 (dd, J=9, 7 Hz, 1H), 7.31 (dd, J=9, 2 Hz, 1H), 5.01-4.94 (m, 1H), 4.51 (dd, J=12, 3 Hz, 1H), 4.43 (dd, J=12, 4 Hz, 1H), 4.22-4.15 (m, 1H), 3.96 (dd, J=9, 6 Hz, 1H), 3.45 (dd, J=15, 7 Hz, 1H), 3.06 (s, 3H).

A solution of mesylate 299 (0.61 g, 1.9 mmol) in dimethylformamide (15 mL) was treated with sodium azide (0.26 g, 4.0 mmol) and stirred at 75° C. under argon for 1 h. The reaction mixture was cooled to 23° C., diluted with water (100 mL) and extracted with methylene chloride (3×50 mL). The combined organic layer was washed with water (100 mL). The solvent was evaporated and the residue redissolved in ethyl acetate (50 mL) and washed with water (100 mL). Drying (Na₂SO₄) and evaporation provided azide 300 (0.38 g, 1.5 mmol, 79%) as a brown oil. Data for 300: ¹HNMR (300 MHz, CDCl₃): δ 7.61-7.52 (m, 2H), 7.28 (dd, J=9, 2 Hz, 1H), 4.84-4.76 (m, 1H), 4.08-4.02 (m, 1H), 3.83 (dd, J=9, 6 Hz, 1H), 3.72 (dd, J=13, 4 Hz, 1H), 3.55 (dd, J=13, 4 Hz, 1H).

Synthesis of Triazole 219

A solution of alkyne 173 (0.15 g, 0.19 mmol) and azide 300 (0.060 g, 0.21 mmol) in tetrahydrofuran (1.5 mL) was treated with N,N-diisopropylethylamine (0.066 mL, 0.38 mmol) and copper (I) iodide (19 mg, 0.10 mmol) and stirred under argon at 23° C. for 1 h. The reaction mixture was diluted with saturated aqueous ammonium hydroxide (10 mL) and extracted with dichloromethane (4×30 mL). The combined organic fractions were dried (Na₂SO₄), evaporated, and the residue purified by flash chromatography (SiO₂, ammonium hydroxide/methanol/dichloromethane (0.05:1:9) to provide 219 (100 mg, 0.095 mmol, 50%) as a white powder. Data for 219: ¹HNMR (300 MHz, CDCl₃, partial): δ 7.62-7.55 (m, 3H), 7.24 (dd, J=9, 2 Hz, 1H), 3.34 (s, 3H), 2.32 (s, 3H), 2.24 (s, 3H), 1.02 (d, J=7 Hz, 3H), 0.92-0.80 (m, 6H).

Synthesis of Oxadiazole 301

A solution of nitrile 298 (2.00 g, 8.50 mmol) in methanol (42.5 mL) was treated with potassium carbonate (1.18 g, 8.50 mmol) and hydroxylamine hydrochloride (1.18 g, 17.0 mmol) and heated to reflux for 18 h. The reaction mixture was cooled to 23° C., diluted with ethyl acetate (100 mL) and washed with water (4×100 mL). Drying (Na₂SO₄) and evaporation afforded a brown powder. A solution of crude this hydroxyamidine (1.00 g, 3.7 mmol) in pyridine (17.5 mL) under argon was cooled to 0° C. and treated dropwise with a solution of acetic anhydride (0.70 mL, 7.4 mmol) in pyridine (17.5 mL). The reaction mixture was heated to 120° C. for 1 h and then cooled to 23° C. The reaction mixture was then diluted with ethyl acetate (50 mL) and washed with 1 M hydrochloric acid (30 mL), saturated aqueous sodium bicarbonate (30 mL), and saturated aqueous sodium chloride (30 mL) and dried (Na₂SO₄). Flash chromatography (SiO₂, 50-75% ethyl acetate/hexanes) afforded the intermediate acetate-protected oxadiazole (0.28 g, 0.84 mmol, 22%) as a white powder. Data for intermediate oxadiazole: MS (ESI) m/z 335.9 (M+H)⁺; ¹NMR (300 MHz, CDCl₃: δ 8.07-8.02 (m, 1H), 7.62 (dd, J=13, 2 Hz, 1H), 7.39 (dd, J=9, 2 Hz, 1H), 4.97-4.89 (m, 1H), 4.41 (dd, J=12, 4 Hz, 1H), 4.33 (dd, J=12, 5 Hz, 1H), 4.21-4.15 (m, 1H), 3.88 (dd, J=9, 6 Hz, 1H), 2.68 (s, 3H), 2.11 (s, 3H).

A solution of the oxadiazole acetate obtained above (0.25 g, 0.75 mmol) in methanol (0.75 mL) was treated with sodium methoxide (0.005 mg, 0.08 mmol) and stirred at 23° C. for 1 h. The reaction mixture was quenched with 1 M hydrochloric acid (0.15 mL) and the solvent was evaporated in vacuo to provide oxadiazole 301 (0.21 g, 0.72 mmol, 95%) as a white powder. Data for 301: ¹HNMR (300 MHz, CDCl₃): δ 8.06-8.00 (m, 1H), 7.63 (dd, J=13, 2 Hz, 1H), 7.39 (dd, J=9, 2 Hz, 1H), 4.81 (m, 1H), 4.07 (m, 3H), 3.78 (dd, J=13, 4 Hz, 1H), 2.68 (s, 1H).

Synthesis of Azide 302

A solution of alcohol 301 (0.18 g, 0.61 mmol) in methylene chloride (3.5 mL) was cooled to 0° C. under argon and treated with triethylamine (0.18 mL, 1.2 mmol) and methanesulfonyl chloride (0.050 mL, 0.68 mmol). The reaction mixture was warmed to 23° C. for 0.5 h and diluted with methylene chloride (20 mL), washed with 1 M hydrochloric acid (110 mL)), saturated aqueous sodium bicarbonate (10 mL), and saturated aqueous sodium chloride (10 mL). Drying (Na₂SO₄) and evaporation provided the intermediate mesylate (0.19 g, 0.51 mmol, 84%) as a white powder: ¹HNMR (300 MHz, CDCl₃, partial): δ 8.02-7.96 (m, 1H), 7.62-7.45 (m, 1H), 4.94-4.87 (m, 1H), 4.46 (dd, J=12, 4 Hz, 1H), 4.39 (dd, J=12, 4 Hz, 1H), 4.17-4.11 (m, 1H), 3.95 (dd, J=9, 6 Hz, 1H), 3.05 (s, 3H), 2.61 (s, 3H).

A solution of the above mesylate (0.18 g, 0.49 mmol) in dimethylformamide (3.7 mL) was treated with sodium azide (64 mg, 0.98 mmol) and stirred at 75° C. under argon for 2 h. The reaction mixture was cooled to 23° C., poured into H₂O (50 mL), and stirred at 0° C. The resulting precipitate was filtered, washed with H₂O, and dried under reduced pressure to provide azide 302 (80 mg, 0.25 mmol, 51%) as a white powder. Data for 302: ¹HNMR (300 MHz, CDCl₃): δ 8.05 (m, 1H), 7.62 (dd, J=13, 2 Hz, 1H), 7.41-7.39 (m, 1H), 4.88-4.81 (m, 1H), 4.16-4.10 (m, 1H), 3.92 (dd, J=9, 6 Hz, 1H), 3.76 (dd, J=13, 5 Hz, 1H), 3.63 (dd, J=13, 4 Hz, 1H), 2.68 (s, 3H).

Synthesis of Triazole 220

A solution of alkyne 173 (0.13 g, 0.16 mmol) and azide 302 (0.060 g, 0.19 mmol) in tetrahydrofuran (1.2 mL) was treated with N,N-diisopropylethylamine (0.044 mL, 0.32 mmol) and copper (1) iodide (15 mg, 0.080 mmol) and stirred under argon at 23° C. for 0.5 h. The reaction mixture was diluted with saturated aqueous ammonium hydroxide (10 mL) and extracted with dichloromethane (4×30 mL). The combined organic fractions were dried (Na₂SO₄), evaporated, and the residue purified by flash chromatography (SiO₂, ammonium hydroxide/methanol/dichloromethane (0.05:1:9)) to provide 220 (70 mg, 0.063 mmol, 40%) as a white powder. Data for 220: MS (ESI) m/z 1105.5 (M+H)⁺; ¹HNMR (300 MHz, CDCl₃, partial): δ 8.04-7.98 (m, 1H), 7.65 (s, 1H), 7.57-7.53 (m, 1H), 7.27-7.24 (m, 1H), 4.81-4.68 (m, 1H), 4.76-4.73 (m, 1H), 4.43 (d, J=7 Hz, 1H), 3.35 (s, 3H), 0.99-0.81 (m, 6H).

Example 28

Synthesis of Triazole 221

Scheme 52 details the synthesis of triazole 221. p-Nitrobenzenesulfonyl chloride was treated with ammonia to provide sulfonamide 303. The nitro group was reduced to provide aniline 304 which was converted to carbamate 305. Oxazolidinone formation to yield alcohol 306 was followed by standard manipulations to afford azide 308. Cycloaddition of 308 with alkyne 173 yielded triazole 221.

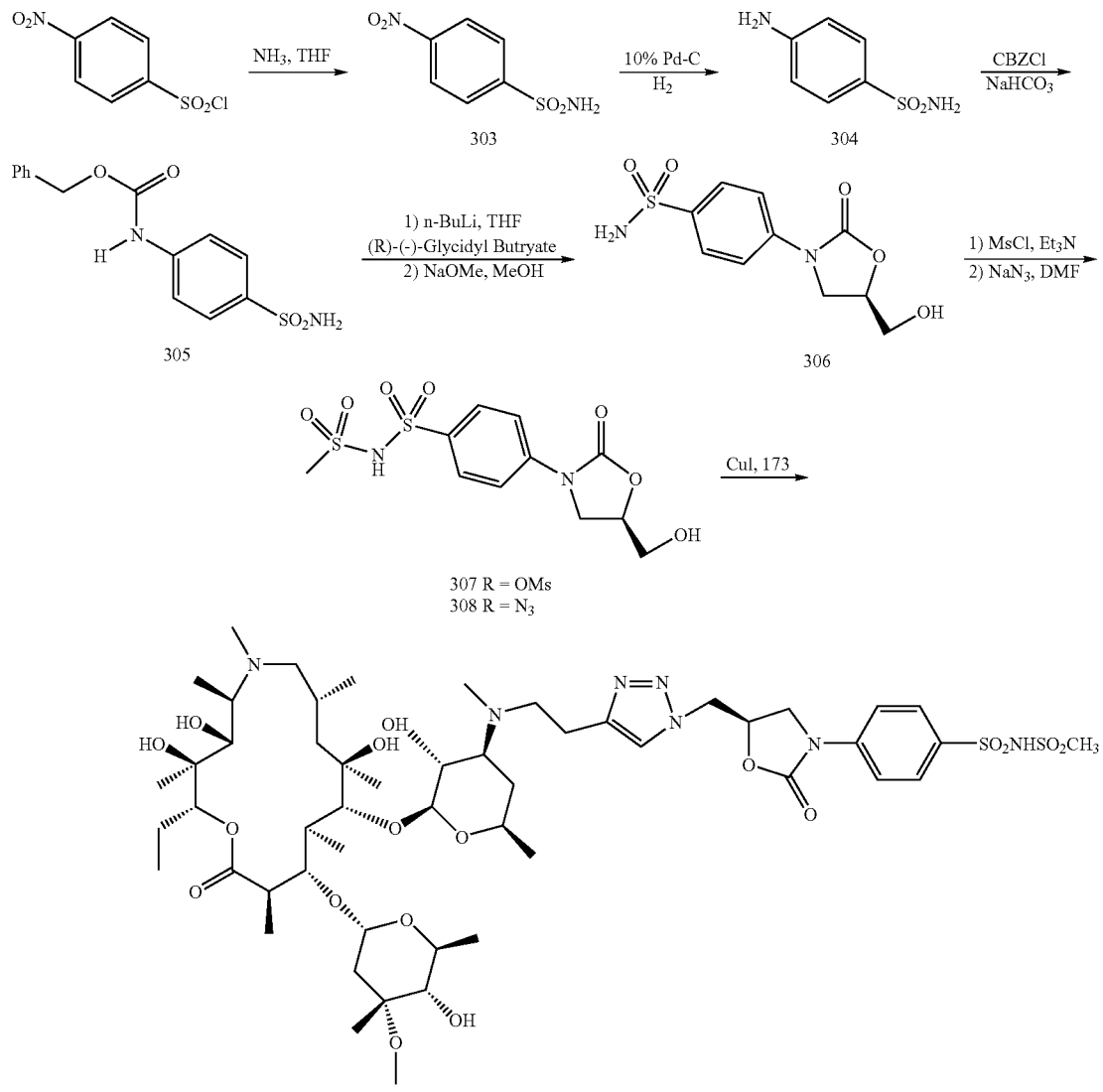

Scheme 52

Synthesis of Sulfonamide 303

4-Nitrobenzenesulfonyl chloride (2.22 g, 10 mmol) was added to a solution of concentrated ammonium hydroxide (3 mL) in THF (5 mL) at 0° C. The reaction was stirred at 0° C. for 1 h and then at room temperature for additional 1 h. The THF was removed under vaccum, more water was added, and the precipitate was collected by filtration and dried to afford 303 (1.90 g, 94% yield).

Synthesis of Aniline 304

To a solution of 4-nitrobenzenesulfonamide 303 (1.9 g, 9.4 mmol) in methanol (20 mL) was added 10% Pd—C (0.19 g) and the resulted mixture was stirred at room temperature for 12 h under 1 atm hydrogen atmosphere. The Pd—C was removed by filtration n celite. The filtered solution was evaporated to provide 304 (1.4 g, 87% yield) as a white solid. Data for 304: $^1$HNMR (300 MHz, CDCl$_3$—CD$_3$OD): δ 7.63 (d, J=9 Hz, 2H), 6.70 (d, J=9 Hz, 2H).

Synthesis of Carbamate 305

Benzyl chloroformate (1.4 mL, 9.6 mmol) was added dropwise to a solution of aniline 304 (1.38 g, 8.0 mmol), and NaHCO$_3$ (2.69 g, 21 mmol) in a mixture of THF (5 mL) and water (3 mL) at 0° C. After stirring at same temperature 2 h, the reaction mixture was diluted with ethyl acetate (30 mL). The organic layer was washed with brine (3×50 mL), dried (MgSO$_4$) and concentrated to provide 2.35 g of white solid 305 in a yield of 96%. Data for 305: $^1$HNMR (300 MHz, CD$_3$OD): δ 7.80 (d, J=9 Hz, 2H) 7.61 (d, J=9 Hz, 2H), 7.43-7.33 (m, 5H), 5.20 (s, 2H).

Synthesis of Alcohol 306

To a solution of carbamate 305 (440 mg, 1.44 mmol) in THF (10 mL) was added n-BuLi (2.0 mL, 2.5 M in hexane, 5.03 mmol) at −78° C. and the mixture was stirred for 30 min. (R)-(−)-Glycidyl butyrate (0.25 mL, 1.73 mmol) was added, the reaction was stirred at −78° C. for 3 h, and then warmed to room temperature and stirred overnight. The reaction was carefully quenched with saturated NH₄Cl and extracted with EtOAc. The organic phase was washed with brine, dried (MgSO₄) and concentrated. The residue was dissolved in 10 mL of methanol and sodium methoxide (0.2 mL, 30% wt/wt in methanol) was added. After stirring at room temperature for 2 h, the mixture was concentrated and purified by chromatography (25:1:0.05/CH₂Cl₂:MeOH:NH₃.H₂O) to afford 100 mg of desired oxazolidinone 306 in a yield of 26%. Data for 306: ¹HNMR (300 MHz, CD₃OD): δ 7.90 (d, J=9 Hz, 2H), 7.78 (d, J=9 Hz, 2H), 4.77 (m, 1H), 4.18 (t, J=9 Hz, 1H), 3.99 (dd, J=6, 9 Hz, 1H), 3.87 (dd, J=3, 12 Hz, 1H), 3.71 (dd, J=3, 12 Hz, 1H).

Synthesis of Azide 308

To a solution of alcohol 306 (106 mg, 0.39 mmol), Et₃N (129 mg, 1.28 mmol) and 4-dimethylaminopyridine (1 mg) in CH₂Cl₂ (10 mL) and DMF (2 mL) was added methanesulfonyl chloride (150 mg, 1.31 mmol) at 0° C., and the mixture was stirred for 2 h. The reaction mixture was concentrated and purified by chromatography on silica gel (10:1:0.05/CH₂Cl₂:MeOH: NH₃.H₂O) to afford mesylate 307 (135 mg, 81% yield). Data for 307: ¹HNMR (300 MHz, CDCl₃): δ 7.85 (d, J=9 Hz, 2H), 7.54 (d, J=9 Hz, 2H), 4.96 (m, 1H), 4.50 (dd, J=3, 12 Hz, 1H), 4.42 (dd, J=3, 12 Hz, 1H), 4.16 (t, J=9 Hz, 1H), 3.89 (dd, J=6, 9 Hz, 1H), 2.90 (s, 3H), 2.80 (s, 3H).

A mixture of 307 (135 mg, 0.30 mmol) and sodium azide (101 mg, 1.56 mmol) in DMF (1 mL) was heated at 80° C. for 2 h. The reaction mixture was diluted with CH₂Cl₂ (10 mL), filtered, concentrated and purified by flash chromatography to afford crude azide 308 (118 mg), which was of sufficient purity to be used in subsequent reactions. Data for 308: ¹HNMR (300 MHz, CDCl₃—CD₃OD): δ 7.73 (d, J=8 Hz, 2H), 7.43 (d, J=8 Hz, 2H), 4.67 (m, 1H), 3.97 (t, J=9 Hz, 1H), 3.71 (dd, J=7, 8 Hz, 1H), 3.57 (dd, J=3, 13 Hz, 1H), 3.41 (dd, J=4, 13 Hz, 1H), 2.76 (s, 3H).

Synthesis of Triazole 221

A mixture of alkyne 173 (118 mg, 0.15 mmol), azide 308 (118 mg, prepared as above) and copper (I) iodide (28.5 mg, 0.15 mmol) in THF (5 mL) was repeatedly degassed and flushed with argon. i-Pr₂NEt (0.26 mL) was introduced and the mixture was stirred at room temperature for 2 h. The reaction mixture was poured into saturated NH₄Cl (30 mL) and stirred for 15 minutes. The mixture was extracted with CH₂Cl₂, washed with brine, dried over MgSO₄ and concentrated. The crude material was chromatographed on silica gel (10:1:0.05 CH₂Cl₂/MeOH/NH₃.H₂O) to provide triazole 221 (108 mg, 62% yield) as a white foam. Data for 221: MS (ESI) m/z 1162.3 (M+H)⁺; ¹HNMR (300 MHz, CDCl₃-DMSO, partial): δ 7.91 (d, J=9 Hz, 2H), 7.85 (s, 1H), 7.51 (d, J=9 Hz, 2H), 3.35 (s, 3H), 3.33 (s, 3H), 3.32 (s, 3H), 0.89 (t, J=8 Hz, 3H).

Example 29

Synthesis of Triazole 222

Scheme 53 details the synthesis of triazole 222. Sulfonamide 309 was protected as the sulfonamidine 310 prior to conversion to oxazolidinone alcohol 311. Alcohol 311 was transformed to azide 314 via functional group interconversion followed by hydrolysis of the amidine protecting group. Cycloaddition of 314 with alkyne 173 provided triazole 222.

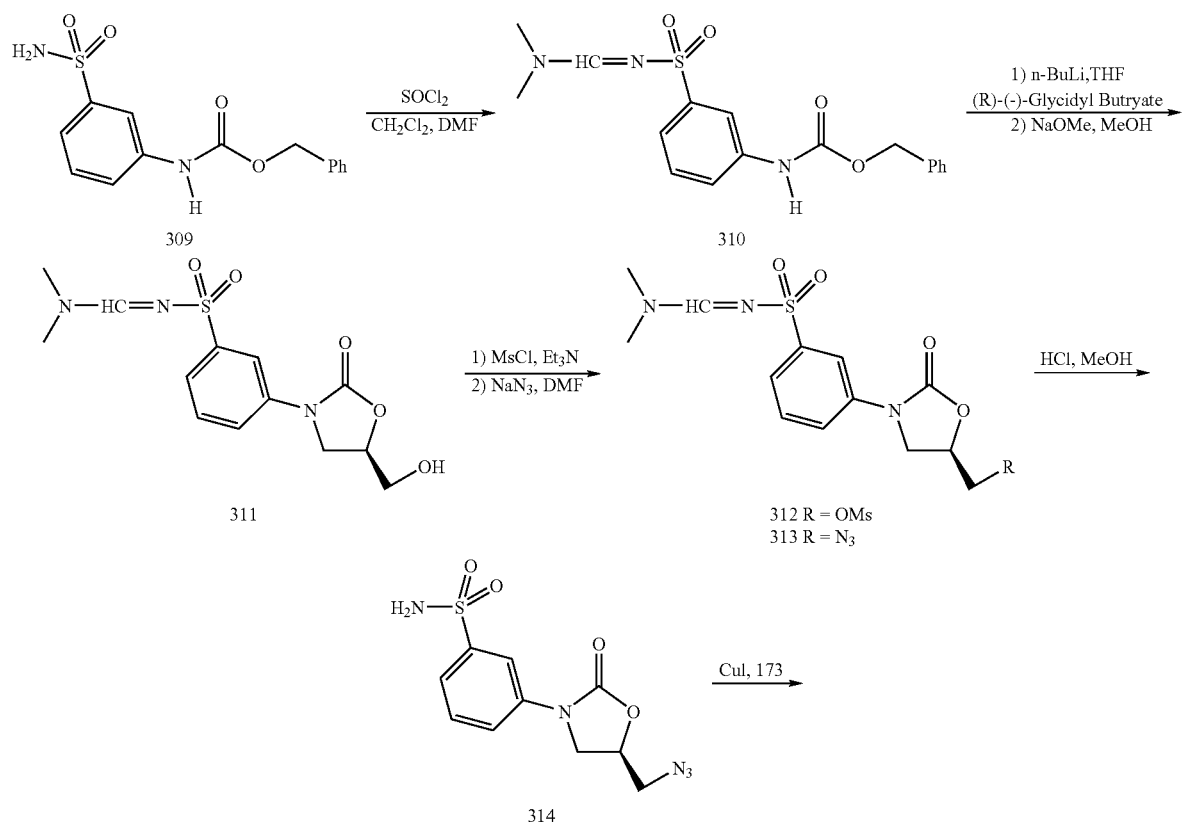

Scheme 53

-continued

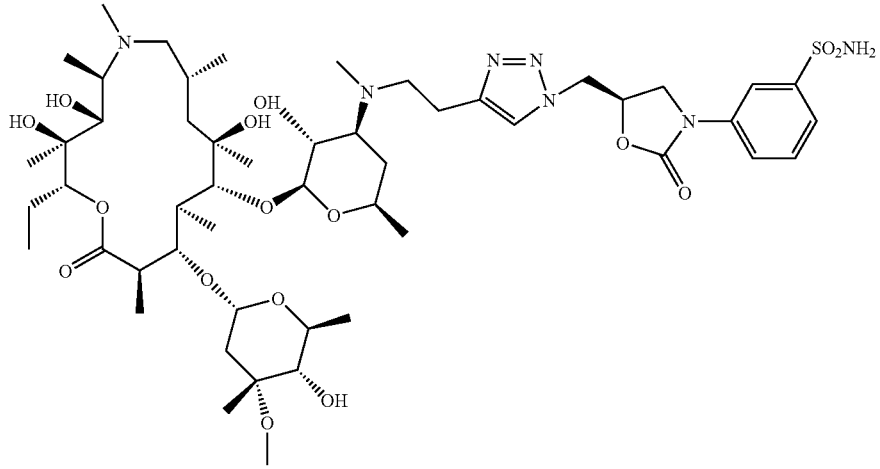

222

Synthesis of Sulfonamidine 310

A solution of sulfonamide 309 (1.10 g, 3.59 mmol, prepared from 3-nitrobenzenesulfonyl chloride by using similar procedures described for the preparation of 305), thionyl chloride (1.30 mL, 17.97 mmol) and DMF (5 mL) in $CH_2Cl_2$ (20 mL) was refluxed for 0.5 h. The reaction was cooled with an ice-bath and neutralized with saturated $NaHCO_3$. The organic phase was separated, washed with brine, dried over $MgSO_4$ and evaporated to provide 310 as a white solid (1.25 g, 96% yield). Data for 310: $^1$HNMR (300 MHz, $CDCl_3$): δ 8.12 (s, 1H), 7.81 (t, J=4 Hz, 1H), 7.74 (m, 1H), 7.59 (m, 1H), 7.44-7.35 (m, 6H), 6.98 (br s, 1H), 5.22 (s, 2H), 3.12 (s, 3H), 3.02 (s, 3H).

Synthesis of Alcohol 311

To a solution of 310 (724 mg, 2.0 mmol) in THF (16 mL) was added n-BuLi (1.5 mL, 2.5 M in hexane, 3.5 mmol) at −78° C. and the mixture was stirred for 30 min. (R)-(−)-Glycidyl butyrate (0.35 mL, 2.5 mmol) was added, the reaction was stirred at −78° C. for 3 h, and then warmed to room temperature and stirred overnight. The reaction was carefully quenched with saturated $NH_4Cl$ and extracted with EtOAc. The organic phase was washed with brine, dried ($MgSO_4$) and concentrated. The residue was dissolved in 10 mL of methanol and sodium methoxide (0.2 mL, 30% wt/wt in methanol) was added. After stirring at room temperature for 2 h, the mixture was concentrated and purified by chromatography on silica gel (25:1:0.05/$CH_2Cl_2$:MeOH: $NH_3.H_2O$) to afford 311 as a white solid (350 mg, 53% yield). Data for 311: $^1$HNMR (300 MHz, $CDCl_3$): δ 8.06 (s, 1H), 7.87 (dd, J=2, 8 Hz, 1H), 7.79 (t, J=2 Hz, 1H), 7.57 (m, 1H), 7.39 (t, J=8 Hz, 1H), 4.70 (m, 1H), 3.99 (m, 2H), 3.92 (dd, J=3, 12 Hz, 1H), 3.70 (dd, J=4, 12 Hz, 1H), 3.08 (s, 3H), 2.96 (s, 3H).

Synthesis of Azide 314

To a solution of alcohol 311 (170 mg, 0.52 mmol) and $Et_3N$ (58 mg, 0.57 mmol) in $CH_2Cl_2$ (10 mL) was added methanesulfonyl chloride (72 mg, 0.62 mmol) at 0° C. and the mixture was stirred for 30 min. The $CH_2Cl_2$ solution was washed with brine, dried ($MgSO_4$) and concentrated to afford mesylate 312 (200 mg, 95% yield). Data for 312: $^1$HNMR (300 MHz, $CDCl_3$): δ 8.05 (s, 1H), 7.79 (m, 2H), 7.56 (d, J=8 Hz, 1H), 7.39 (t, J=8 Hz, 1H), 4.90 (m, 1H), 4.45 (dd, J=4, 12 Hz, 1H), 4.37 (dd, J=4, 12 Hz, 1H), 4.14 (t, J=9 Hz, 1H), 3.91 (dd, J=6, 9 Hz, 1H), 3.08 (s, 3H), 3.03 (s, 3H), 2.95 (s, 3H).

A mixture of mesylate 312 (105 mg, 0.26 mmol) and sodium azide (67 mg, 1.04 mmol) in DMF (2 mL) was heated at 80° C. for 2 h. The reaction was then diluted with ethyl acetate, washed with brine, dried ($MgSO_4$) and evaporated to provide azide 313 as a white solid (80 mg, 87% yield). Data for 313: $^1$HNMR (300 MHz, $CDCl_3$): δ 8.06 (s, 1H), 7.84 (m, 1H), 7.78 (t, J=2 Hz, 1H), 7.56 (d, J=8 Hz, 1H), 7.40 (t, J=8 Hz, 1H), 4.77 (m, 1H), 4.07 (t, J=9 Hz, 1H), 3.84 (dd, J=6, 9 Hz, 1H), 3.67 (dd, J=4, 13 Hz, 1H), 3.53 (dd, J=4, 13 Hz, 1H), 3.08 (s, 3H), 2.95 (s, 3H).

To a solution of azide 313 (80 mg, 0.23 mmol) in methanol (5 mL) was added concentrated HCl (0.5 mL). After refluxing for 4 h, the reaction was cooled with an ice-bath and neutralized with saturated $NaHCO_3$. The resulting mixture was extracted with $CH_2Cl_2$, washed with brine, dried over $MgSO_4$ and evaporated to provide 314 (58 mg, 86% yield). Data for 314: $^1$HNMR (300 MHz, $CDCl_3$-$CD_3OD$): δ 7.86 (m, 1H), 7.68 (d, J=8 Hz, 1H), 7.55 (d, J=8 Hz, 1H), 7.39 (t, J=8 Hz, 1H), 4.75 (m, 1H), 4.04 (t, J=9 Hz, 1H), 3.80 (dd, J=6, 9 Hz, 1H), 3.64 (dd, J=4, 13 Hz, 1H), 3.47 (dd, J=4, 13 Hz, 1H).

Synthesis of Triazole 222

To a solution of alkyne 173 (79 mg mg, 0.10 mmol), azide 314 (36 mg, 0.112 mmol) and copper (1) iodide (38 mg, 0.2 mmol) in THF (5 mL) under argon was added i-$Pr_2NEt$ (0.18 mL). After stirring at room temperature for 2 h, the reaction mixture was poured into saturated $NH_4Cl$ (30 mL) and stirred for 15 minutes. The mixture was extracted with $CH_2Cl_2$, washed with brine, dried over $MgSO_4$ and concentrated. The crude material was chromatographed on silica (10:1 $CH_2Cl_2$/MeOH) to provide triazole 222 (65 mg, 60% yield) as a white foam. Data for 222: MS (ESI) m/z 1084.4 $(M+H)^+$; $^1$HNMR (300 MHz, $CDCl_3$-DMSO, partial): 8-7.76 (s, 1H), 7.71 (d, J=8 Hz, 1H), 7.59 (s, 1H), 7.57 (s, 1H), 7.36 (t, J=8 Hz, H), 0.81 (t, J=7 Hz, 3H).

Example 30

Synthesis of Triazoles 223 and 224

Scheme 54 details the synthesis of triazoles 223 and 224. Sulfonamide 305 was protected as sulfonamidine 315 prior to conversion to oxazolidinone alcohol 316. Transformation of 316 to azide 319 as described previously was followed by cycloaddition of 319 with alkyne 173 to produce triazole 223. The cycloaddition of intermediate azide 318 with alkyne 173 afforded triazole 224.

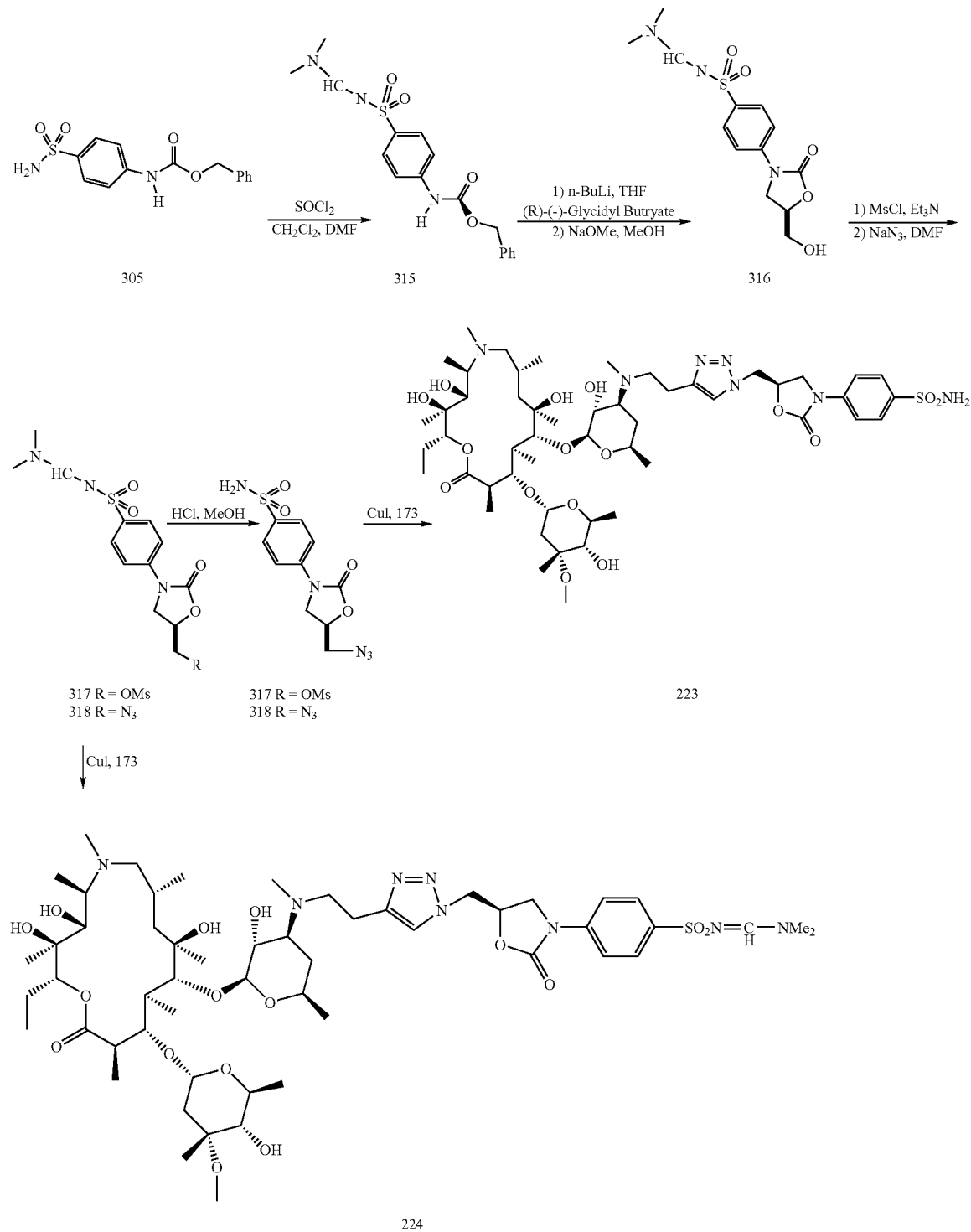

Synthesis of Sulfonamidine 315

Sulfonamidine 315 was synthesized using the same procedure described for the preparation of 310; 0.92 g of 305 afforded 1.02 g of 315 (94% yield). Data for 315: $^1$HNMR (300 MHz, CDCl$_3$): δ 8.10 (s, 1H), 7.81 (d, J=9 Hz, 2H), 7.47 (d, J=9 Hz, 2H), 7.41-7.34 (m, 5H), 6.89 (br s, 1H), 5.20 (s, 2H), 3.11 (s, 3H), 3.00 (s, 3H).

Synthesis of Alcohol 316

Alcohol 316 was synthesized using the same procedure described for the preparation of 311; 0.97 g of 315 afforded 0.60 g of 316 (69% yield). Data for 316: $^1$HNMR (300 MHz, CDCl$_3$-CD$_3$OD): δ 8.03 (s, 1H), 7.79 (d, J=9 Hz, 2H), 7.59 (d, J=9 Hz, 2H), 4.68 (m, 1H), 3.98 (m, 2H), 3.84 (dd, J=4, 13 Hz, 1H), 3.64 (dd, J=4, 13 Hz, 1H), 3.08 (s, 3H), 2.95 (s, 3H).

Synthesis of Azide 318

Mesylate 317 was synthesized using the same procedure described for the preparation of 312; 176 mg of 316 afforded 210 mg of 317 (96% yield). Data for 317: $^1$HNMR (300 MHz, CDCl$_3$): δ 8.06 (s, 1H), 7.83 (d, J=9 Hz, 21-1), 7.57 (d, J=9 Hz, 21-1), 4.90 (m, 1H), 4.41 (m, 2H), 4.13 (t, J=9 Hz, 1H), 3.94 (dd, J=6, 9 Hz, 1H), 3.10 (s, 3H), 3.06 (s, 3H), 2.95 (s, 3H).

Azide 318 was synthesized using the same procedure described for the preparation of 313; 210 mg of 317 afforded 180 mg of 318 (98% yield). Data for 318: $^1$HNMR (300 MHz, CDCl$_3$): δ 8.04 (s, 1H), 7.82 (d, J=9 Hz, 2H), 7.60 (d, J=9 Hz, 2H), 4.90 (m, 1H), 4.08 (t, J=9 Hz, 1H), 3.85 (dd, J=6, 9 Hz, 1H), 3.70 (dd, J=4, 13 Hz, 1H), 3.55 (dd, J=4, 13 Hz, 1H), 3.09 (s, 3H), 2.96 (s, 3H).

Synthesis of Azide 319

Azide 319 was synthesized using the same procedure described for the preparation of 314; 150 mg of 318 afforded 118 mg of 319 (93% yield). Data for 319: $^1$HNMR (300 MHz, CDCl$_3$-CD$_3$OD): δ 7.78 (d, J=9 Hz, 2H), 7.56 (d, J=9 Hz, 2H), 4.74 (m, 1H), 4.04 (t, J=9 Hz, 1H), 3.80 (dd, J=6, 9 Hz, 1H), 3.64 (dd, J=4, 13 Hz, 1H), 3.48 (dd, J=4, 13 Hz, 1H).

Synthesis of Triazole 223

Triazole 223 was synthesized using the same procedure described for the preparation of 222; the reaction of alkyne 173 (118 mg, 0.15 mmol) and azide 319 (54 mg, 0.18 mmol) afforded 150 mg of 223 (92% yield). Data for 223: MS (ESI) m/z 1084.4 (M+H)$^+$; $^1$HNMR (300 MHz, CDCl$_3$, partial): δ 7.77 (d, J=9 Hz, 2H), 7.55 (s, 114), 7.45 (d, J=9 Hz, 2H), 3.26 (s, 3H), 0.82 (t, J=8 Hz, 3H).

Synthesis of Triazole 224

Triazole 224 was synthesized using the same procedure described for the preparation of 222; the reaction of alkyne 173 (79 mg, 0.10 mmol) and azide 318 (43 mg, 0.12 mmol) afforded 93 mg of 224 (82% yield). Data for 224: MS (ESI) m/z 1139.7 (M+H)$^+$; $^1$HNMR (300 MHz, CDCl$_3$, partial): δ 8.04 (s, 1H), 7.78 (d, J=9 Hz, 2H), 7.54 (s, 1H), 7.45 (d, J=9 Hz, 2H), 3.27 (s, 3H), 3.07 (s, 3H), 2.94 (s, 3H), 0.82 (t, J=8 Hz, 3H).

Example 31

Synthesis of Triazoles 225-227

Scheme 55 details the synthesis of triazole 225. 3,4-Dichloroaniline was converted to carbamate 320 before being carried further through alcohol 321 to azide 323. The cycloaddition of 323 with alkyne 173 gave triazole 225. Triazoles 226 and 227 were synthesized from the requisite anilines using the same sequence as described in Scheme 55.

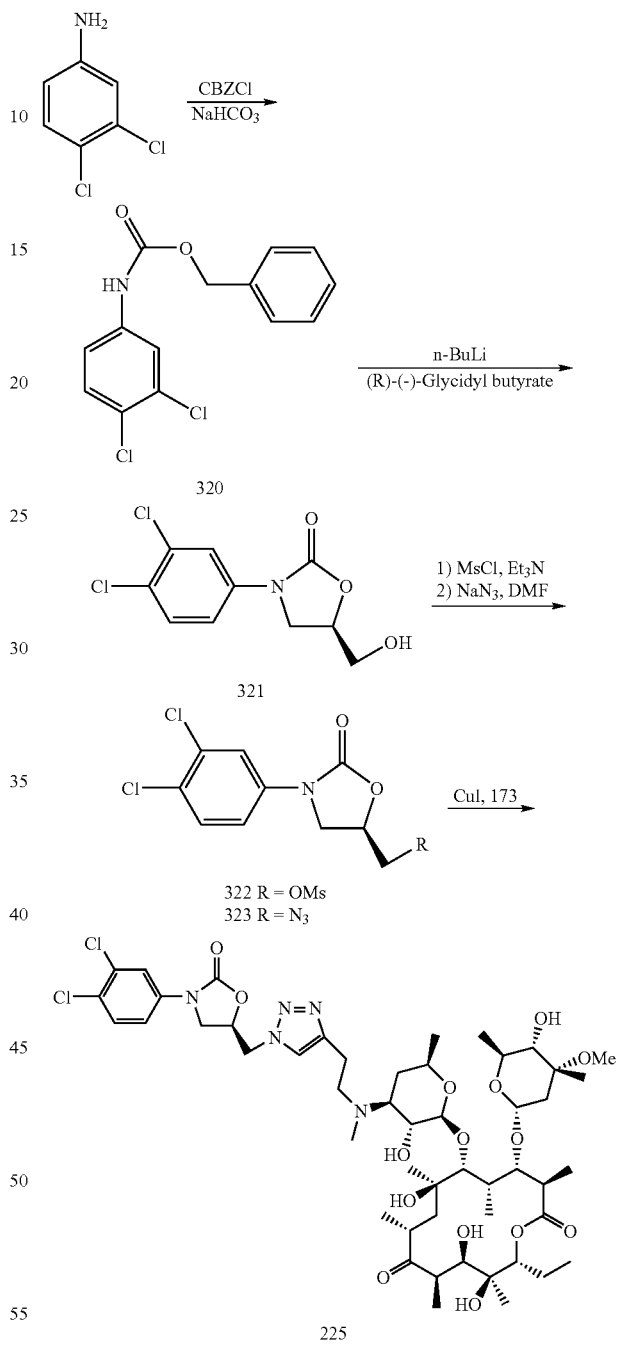

Synthesis of Carbamate 320

Sodium bicarbonate (2.60 g, 24.7 mmol) was dissolved in water (22 mL) and 3,4-dichloroaniline (2.0 g, 12.34 mmol) was added. The mixture was cooled to 0° C., and benzyl chloroformate (1.76 mL, 12.34 mmol) was added. The mixture was stirred 5 min at 0° C., the cold bath removed, and then stirring was continued at room temperature overnight (~16 hours). The mixture was evaporated, and partitioned with a 1:1 mixture of ethyl acetate and water. The organic layer was washed with water, and then brine. The organic layer was dried with Na$_2$SO$_4$, and evaporated to yield 320 (3.60 g, 99% yield) of suitable purity for use in subsequent reactions. Data for 320: $^1$HNMR (300 MHz, CDCl$_3$): δ 7.18-7.14 (m, 5H), 7.42 (s, 1H), 6.98 (dd, J=11, 3 Hz, 1H), 6.48 (s, 1H), 5.06 (s, 2H).

Synthesis of Alcohol 321

Carbamate 320 (3.60 g, 12.16 mmol) was dissolved in 10 mL tetrahydrofuran, and the solution cooled to −78° C. n-Butyllithium (2.5 M in hexane, 7.6 mL, 12.16 mmol) was added slowly, and the mixture allowed to stir for 45 min at −78° C. R-(−)-Glycidyl butyrate (1.75 mL, 12.16 mmol) was added, and the mixture was stirred for 1 h at −78° C. The bath was removed and the reaction allowed to stir overnight at room temperature. The reaction was quenched with 25 mL saturated ammonium chloride solution, and partitioned with ethyl acetate and water. The aqueous layer was extracted thrice with ethyl acetate, and the combined organic layer was washed with brine, dried (Na$_2$SO$_4$), and evaporated to yield 321 (2.80 g, 88% yield) of suitable purity for use in subsequent reactions. Data for 321: $^1$NMR (300 MHz, CDCl$_3$): δ 7.59 (s, 1H), 7.33 (s, 1H), 4.68 (m, 1H), 3.91 (m, 3H), 3.67 (dd, J=16, 4 Hz, 1H).

Synthesis of Azide 323

Alcohol 321 (2.80 g, 10.68 mmol) was dissolved in 10 mL methylene chloride, and the mixture cooled to 0° C. Triethylamine (3.0 mL, 21.37 mmol) was added, followed by methanesulfonyl chloride (1.15 mL, 15.0 mmol). The mixture was allowed to warm to room temperature and stirred for 1 h. Methylene chloride (20 mL) was added, and the mixture washed twice with 1N HCl, then twice with 10% aqueous sodium carbonate, and then brine. The organic phase was dried (Na$_2$SO$_4$), and evaporated to yield mesylate 322 (3.60 g, 99% yield). Data for 322: $^1$HNMR (300 MHz, CDCl$_3$): δ 7.67 (s, 1H), 7.42 (s, 2H), 4.94 (m, 1H), 4.47 (m, 2H), 4.26 (m, 1H), 4.0 (m, 1H), 3.03 (s, 3H).

A solution of mesylate 322 (3.60 g, 10.58 mmol) in dimethylformamide (10 mL) was treated with sodium azide (2.6 g, 40.21 mmol) and the mixture heated to 80° C. for 5 h. The reaction mixture was cooled to room temperature, diluted with ethyl acetate (100 mL), and washed with brine (2×50 mL). Drying (Na$_2$SO$_4$), and evaporation provided azide 323 (2.53 g, 84% yield) as a yellow solid of suitable purity for use in subsequent reactions. Data for 323: $^1$HNMR (300 MHz, CDCl$_3$): δ 7.61 (s, 1H), 7.30 (s, 2H), 4.75 (m, 1H), 4.01 (m, 1H), 3.75 (m, 1H), 3.66 (dd, J=17, 4 Hz, 1H), 3.51 (dd, J=4, 17 Hz, 1H).

Synthesis of Triazole 225

A solution of alkyne 173 (170 mg, 0.220 mmol) in tetrahydrofuran (10 mL) was treated with azide 323 (100 mg, 0.320 mmol), N,N-diisopropylethylamine (0.05 mL, 0.22 mmol) and copper (I) iodide (0.03 g, 0.160 mmol), and the mixture was stirred under argon at room, temperature for 16 h. The reaction mixture was diluted with ethyl acetate (50 mL), and washed with brine (2×50 mL). The organic phase was dried and evaporated. The residue was purified by preparative thin layer chromatography using (80% CH$_2$Cl$_2$, 20% MeOH, 1% NH$_4$OH) to provide triazole 225 (180 mg, 77% yield) as a white solid. Data for 225: MS (ESI) m/z 1075 (M+H)$^+$; $^1$HNMR (300 MHz, CDCl$_3$, partial): δ 7.95 (s, 1H), 7.46 (s, 1H), 7.20 (d, J=8 Hz, 1H), 7.04 (s, 2H), 5.04-4.93 (m, 1H), 4.91 (s, 2H), 4.28 (d, J=6 Hz, 1H), 3.98-3.92 (m, 2H), 3.61 (s, 1H), 3.59-3.48 (m, 1H), 3.34 (s, 1H), 3.19 (s, 1H), 3.06 (m, 1H), 2.94 (m, 1H).

Synthesis of Triazoles 226 and 227

These compounds were synthesized from the requisite anilines using the procedures described above for the synthesis of triazole 225.

Data for 226: $^1$H-NMR (300 MHz, CDCl$_3$, partial): δ 8.01 (s, 1H), 7.60 (s, 1H), 7.02 (m, 1H), 6.77 (m, 1H), 4.98-4.68 (m, 1H), 4.37 (s, 2H), 4.13-4.04 (m, 2H), 3.89 (m, 1H), 3.26 (s, 1H), 2.84 (m, 2H), 2.66 (m, 2H).

Data for 227: $^1$H-NMR (300 MHz, CDCl$_3$, partial): δ 7.50 (s, 1H), 7.00 (s, 1H), 6.82 (d, J=9 Hz, 1H), 6.64 (d, J=9 Hz, 1H), 5.02-4.89 (s, 1H), 4.53 (m, 2H), 4.34 (m, 2H), 3.19 (m, 1H), 2.96 (m, 1H), 2.93 (m, 2H), 2.86 (m, 2H).

Example 32

Synthesis of Triazole 228

Scheme 56 details the synthesis of triazole 228. 5-Aminoquinoline was converted to oxazolidinone alcohol 325 via carbamate 324. The alcohol of 325 was the transformed to azide 326, which was parlayed to triazole 228 via cycloaddition with alkyne 173.

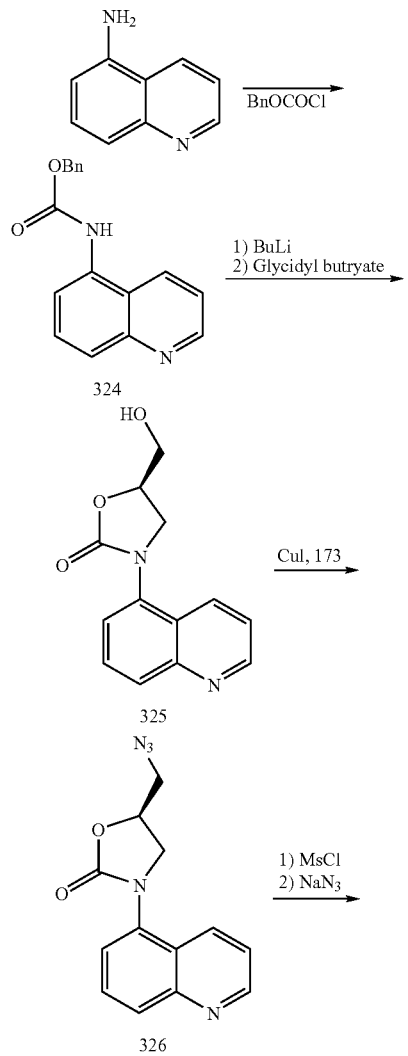

Scheme 56

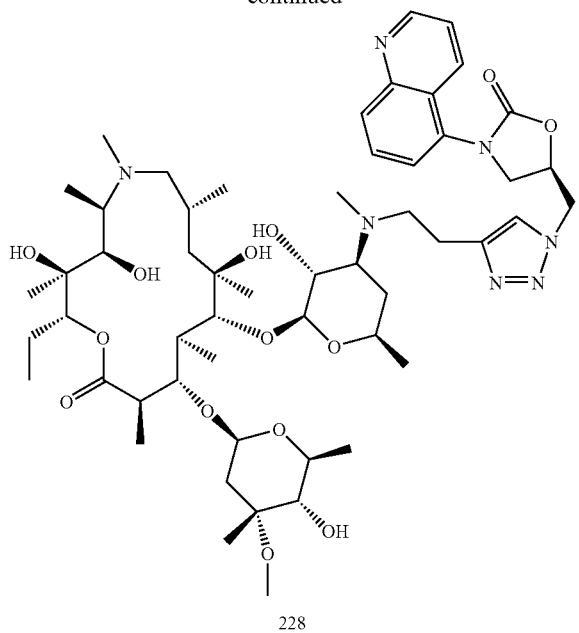

228

Synthesis of Azide 326

To a stirred 0° C. solution of 5-aminoquinoline (1.0 g, 6.9 mmol) in 2:1 acetone/water (15 mL) was added NaHCO$_3$ (1.0 g, 13.7 mmol) followed by benzyl chloroformate (1.1 mL, 7.7 mmol). The reaction mixture was allowed to warm to room temperature and stirred for 2 h then cooled to 0° C. and filtered. The filtrate was washed with water and ether and dried in a vacuum oven at 40° C. overnight. The yellow solid (carbamate 324) thus obtained (1.9 g, 100% yield) was used as-is without further purification.

To a mixture of 324 (1.9 g, 6.9 mmol) in 25 mL THF at −78° C. was added 4.3 mL (6.9 mmol) of 1.6M n-butyllithium-hexane over 5 minutes. After 30 minutes, 1 mL of (R)-glycidyl butyrate was added and the mixture allowed to stir at −78° C. for 1 hour and then at room temperature for 16 hr. Saturated ammonium chloride was added (25 mL) followed by ethyl acetate (100 mL). The layers were separated and the aqueous layer extracted with ethyl acetate (3×50 mL). The combined organic extracts were dried on MgSO$_4$, filtered and concentrated to provide 2.3 g of yellow solid which was purified by silica gel chromatography (50 mm×6" column, eluted with 1:1 hexane/EtOAc to afford alcohol 325 as a yellow solid (450 mg, 27% yield).

To a stirred solution of 325 (300 mg, 1.2 mmol) in DMF (5 mL) was added triethylamine (0.34 mL, 2.4 mmol) followed by methanesulfonyl chloride (95 µL, 1.2 mmol). The mixture was stirred at room temperature and for 2 h, and then sodium azide (1 g, 15 mmol) was added and the slurry stirred overnight. The mixture was diluted with water (100 mL) and extracted with ethyl acetate (3×50 mL). The combined organic extracts were washed with brine, dried (Na$_2$SO$_4$), filtered and concentrated to give 287 mg of azide 326 as an off-white solid which was used without further purification.

Synthesis of Triazole 228

To a stirred solution of alkyne 173 (50 mg, 64 µmol) in THF (250 µL) was added azide 326 (18 mg, 67 µmol) and cuprous iodide (5 mg, 26 µmol). The resulting mixture was degassed by alternately applying vacuum and purging with argon gas. The mixture was stirred under argon at ambient temperature for 16 h. The entire reaction mixture was then placed atop a silica gel flash chromatography column and eluted with 100:3 CH$_2$Cl$_2$/2N NH$_3$ in MeOH to afford the desired triazole adduct 228 as a white solid (50 mg, 74% yield). Data for 228: MS (ESI) m/z 322.9 (M+3H)$^{3+}$, 528.6 (M+2H)$^{2+}$, 1056.4 (M+H)$^+$, 1078.3 (M+Na)$^+$; $^1$HNMR (300 MHz, CDCl$_3$, partial): δ 9.05 (d, J=3 Hz, 1H), 8.05 (m, 2H), 7.90 (bs, 1H), 7.71 (dd, J=8, 3 Hz, 1H), 7.48 (s, 1H), 7.50 (d, J=7.0 Hz, 1H), 5.18-5.01 (m, 1H), 4.95 (d, J=5 Hz, 1H), 4.75 (d, J=4 Hz, 2H), 4.58 (dd, J=10, 2 Hz, 1H), 4.38 (d, J=7 Hz, 1H), 4.25 (t, J=9 Hz, 1H), 4.06 (dd, J=9, 6 Hz, 1H), 4.08-3.92 (m, 1H), 3.79 (d, J=7 Hz, 1H), 3.26 (s, 3H), 3.15 (dd, J=10, 7 Hz, 1H), 2.95 (t, J=10 Hz, 1H), 2.28 (s, 3H), 2.20 (s, 3H), 0.82 (m, 6H).

Example 33

Synthesis of Triazoles 229-232

Scheme 57 details the synthesis of targets 229-232. Hex-5-yn-1-ol was converted to tosylate 327 which served as an alkylating agent for amine 171. Acetylene 328 was the precursor for cycloaddition reactions with azides 326, 158, 189, and 188 to yield triazoles 229, 230, 231, and 232 respectively.

Scheme 57

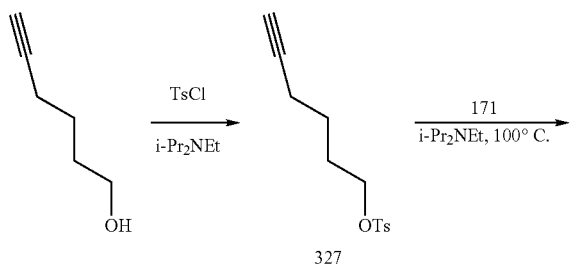

327

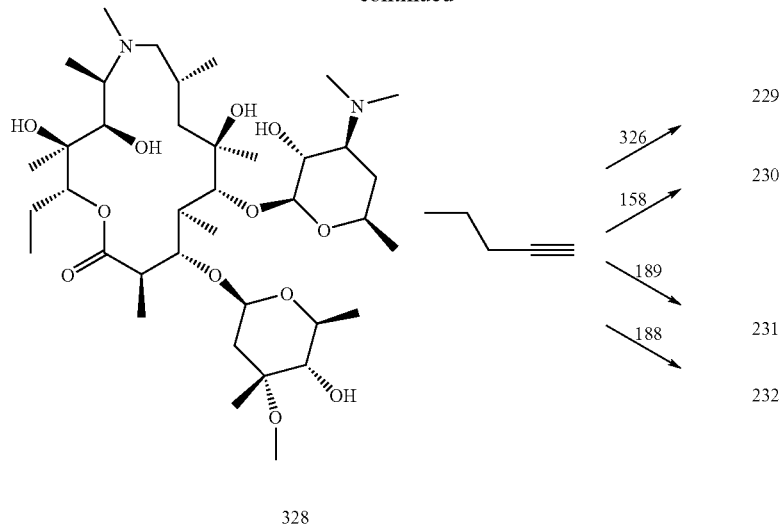

328

326 → 229
158 → 230
189 → 231
188 → 232

Synthesis of Tosylate 327

To a stirred, ice-cold solution of hex-5-yn-1-ol (1.0 g, 10.2 mmol) in ether (20 mL) was added p-toluenesulfonyl chloride (2.14 g, 11.2 mmol). Powdered KOH (1.1 g, 20.4 mmol) was then added portion-wise over 5 minutes. The slurry was stirred at 0° C. for 3 hours then poured into 100 mL water, and extracted with ether (2×50 mL). The combined organic extracts were washed with brine, dried over MgSO$_4$, filtered, and concentrated to afford 327 as a colorless oil (2.3 g, 89% yield). Data for 327: $^1$HNMR (300 MHz, CDCl$_3$): δ 7.80 (d, J=8 Hz, 2H), 7.35 (d, J=8 Hz, 2H), 4.05 (t, J=6 Hz, 2H) 2.45 (s, 3H), 2.19 (td, J=7, 3 Hz, 2H), 1.79 (pent, J=7 Hz, 2H), 1.55 (pent., J=7 Hz, 2H); $^{13}$C NMR (75 MHz, CDCl$_3$): δ 144.8, 133.0, 129.9, 127.9, 83.4, 69.9, 69.0, 27.7, 24.2, 21.6, 17.7.

Synthesis of Alkyne 328

A 20 mL vial was charged with tosylate 327 (0.20 g, 0.85 mmol), N-desmethyl azithromycin 171 (0.5 g, 0.68 mmol), and Hunig's base (10 mL), and then purged with argon gas and sealed. The solution was stirred in a 100° C. oil bath for 6 h. After cooling to room temperature, the reaction mixture was poured into saturated aqueous NaHCO$_3$ (50 mL) and extracted with CH$_2$Cl$_2$ (3×50 mL). The combined organic extracts were washed with brine, dried over K$_2$CO$_3$, filtered, and concentrated to afford 0.8 g of a white solid. Purification by silica gel flash chromatography (25 mm×6" column eluted with 50:1 CH$_2$Cl$_2$/2N NH$_3$ in MeOH) gave 328 as a white solid (0.38 g, 68% yield). Data for 328: MS (ESI) m/z 408.0 (M+2H)$^{2+}$, 815.3 (M+H)$^+$.

Synthesis of Triazole 229

To a stirred solution of alkyne 328 (50 mg, 63 μmol) in THF (250 μL) was added azide 326 (18 mg, 67 μmol) and cuprous iodide (5 mg, 26 μmol). The resulting mixture was degassed by alternately applying vacuum and purging with argon gas. The mixture was stirred under argon at ambient temperature for 16 h. The entire reaction mixture was then placed atop a silica gel flash chromatography column and eluted with 100:3 CH$_2$Cl$_2$/2N NH$_3$ in MeOH to afford the desired triazole adduct 229 as a white solid (54 mg, 76% yield). Data for 229: MS (ESI) m/z 332.2 (M+3H)$^{3+}$, 542.5 (M+2H)$^{2+}$, 1070.3 (M+H)+1092.2 (M+Na)$^+$; $^1$HNMR (300 MHz, CDCl$_3$, partial): δ 9.10 (d, J=3 Hz, 1H), 8.05 (m, 2H), 8 (bs, 1H), 7.72 (dd, J=8, 3 Hz, 1H), 7.48 (s, 1H), 7.50 (d, J=7 Hz, 1H), 5.20-5.03 (m, 1H), 4.95 (d, J=5 Hz, 1H), 4.75 (d, J=4 Hz, 2H), 4.58 (dd, J=10, 2 Hz, 1H), 4.36 (d, J=7 Hz, 1H), 4.23 (t, J=9 Hz, 1H), 4.07 (dd, J=9, 6 Hz, 1H), 4.08-3.94 (m, 1H), 3.79 (d, J=7 Hz, 1H), 3.24 (s, 3H), 3.15 (dd, J=10, 7 Hz, 1H), 2.95 (t, J=10 Hz, 1H), 2.28 (s, 3H), 2.20 (s, 3H), 0.83 (m, 6H).

Synthesis of Triazole 230

To a stirred solution of 328 (35 mg, 43 μmol) in THF (150 μL) was added Hunig's base (30 μL), azide 158 (28 mg, 86 μmol), and cuprous iodide (4 mg, 21 μmol). The mixture was degassed by alternately applying vacuum and purging with argon gas. The slurry was stirred under argon at ambient temperature for 4 h. The entire reaction mixture was then placed atop a silica gel flash chromatography column and eluted with 50:1 CH$_2$Cl$_2$/2N NH$_3$ in MeOH to afford triazole 230 as a white solid (24 mg, 50% yield). Data for 230: MS (ESI) m/z 568.8 (M+2H)$^{2+}$, 1136.4 (M+H)$^+$; $^1$HNMR (300 MHz, CDCl$_3$, partial): δ 8.45 (bs, 1H), 7.55 (s, 1H), 7.33 (dd, J=14, 2 Hz, 1H), 6.98 (dd, J=9, 2 Hz, 1H), 6.90 (dd, J=14, 9 Hz, 1H), 5.10-4.95 (m, 2H), 4.80-4.60 (m, 2H), 4.50 (d, J=7 Hz 1H), 3.32 (s, 3H), 2.32 (bs, 3H), 2.22 (bs, 3H), 0.90 (m, 6H).

Synthesis of Triazole 231

To a stirred solution of 328 (35 mg, 43 μmol) in THF (150 μL) was added Hunig's base (30 μL), azide 189 (20 mg, 86 μmol) and cuprous iodide (4 mg, 22 μmol). The resulting slurry was degassed by alternately applying vacuum and purging with argon gas. The mixture was stirred under argon at ambient temperature for 4 h. The entire reaction mixture was then placed atop a silica gel flash chromatography column and eluted with 50:1 CH$_2$Cl$_2$/2N NH$_3$ in MeOH to afford the triazole adduct 231 as a white solid (31 mg, 70% yield). Data for 231: MS (ESI) m/z 526.4 (M+2H)$^{2+}$, 1073.5 (M+Na)$^+$; $^1$HNMR (300 MHz, CDCl$_3$, partial): δ 8.6 (bs, 1H), 7.55 (s, 1H), 7.4-7.2 (m, 2H), 7.08 (dd, J=8, 2 Hz, 1H), 6.78 (td, J=6, 2 Hz, 2H), 5.1-5.0 (m, 2H), 4.8-4.6 (m, 3H), 4.4 (d, J=7 Hz, 1H), 3.95 (dd, J=9, 6 Hz, 1H), 3.31 (s, 3H), 2.32 (bs, 3H), 2.25 (s, 3H), 0.82 (m, 6H).

Synthesis of Triazole 232

To a stirred solution of 328 (50 mg, 62 µmol) in THF (150 µL) wag added azide 188 (18 mg, 65 µmol) and cuprous iodide (5 mg, 26 µmol). The resulting mixture was degassed by alternately applying vacuum and purging with argon gas. The mixture was stirred under argon at ambient temperature for 16 h. The entire reaction mixture was then placed atop a silica gel flash chromatography column and eluted with 50:1 $CH_2Cl_2/2N\ NH_3$ in MeOH to afford the desired triazole adduct 232 as a white solid (54 mg, 81% yield). Data for 232: MS (ESI) m/z 538.4 $(M+2H)^{2+}$, 1075.4 $(M+H)^+$; $^1HNMR$ (300 MHz, $CDCl_3$, partial): δ 7.87 (dd, J=7, 2 Hz, 2H), 7.70 (bs, 1H), 7.45 (dd, J=9, 2 Hz, 2H), 4.90 (d, J=4 Hz, 1H), 4.75-4.60 (m, 2H), 4.58 (d, J=9 Hz, 1H), 4.39 (d, J=7 Hz, 1H), 4.20 (d, J=5 Hz, 1H), 4.18 (t, J=9 Hz, 1H), 4.10-3.90 (m, 1H), 3.92 (dd, J=10, 6 Hz, 1H), 3.32 (s, 3H), 3.15 (dd, J=10, 7 Hz, 1H), 2.95 (t, J=10 Hz, 1H), 2.28 (s, 3H), 2.20 (s, 3H), 0.82 (m, 6H).

Example 34

Synthesis of Triazoles 233 and 234

Synthesis of Triazole 233

Compound 180 (50 mg, 49 µmol) was dissolved in EtOH (1.6 mL), and 1N HCl (aq) was then added (0.4 mL) and the solution stirred at room temperature for 12 h. The reaction mixture was diluted with 10 mL aq. 0.2N HCl and washed with $CH_2Cl_2$ (3×10 mL). The aqueous layer was then adjusted to pH 10 by addition of 2N KOH and extracted with $CH_2Cl_2$ (2×10 mL). The latter two extracts were dried on $K_2CO_3$, filtered and concentrated to afford 233 as a solid (37 mg, 87% yield). Data for 233: MS (ESI) m/z 433.4 $(M+2H)^{2+}$, 865.3 $(M+H)^+$, 887.3 $(M+Na)^+$; $^1HNMR$ (300 MHz, $CDCl_3$, partial): δ 7.59 (s, 1H), 7.35-7.20 (m, 2H), 7.05 (dd, J=8, 2 Hz, 1H), 6.78 (td, J=8, 2 Hz, 2H), 4.98 (m, 1H), 4.75-4.60 (m, 3H), 4.35 (d, J=7 Hz, 1H), 4.15-3.98 (m, 2H), 3.88 (dd, J=9, 6 Hz, 1H), 3.7 (dd, J=10, 4 Hz, 1H), 2.31 (bs, 3H), 2.10 (s, 3H), 0.82 (m, 6H).

Synthesis of Triazole 234

Compound 231 (10 mg, 8.8 µmol) was dissolved in EtOH (0.8 mL), and 1N HCl (aq) was then added (0.2 mL) and the solution stirred at room temperature for 12 h. The reaction mixture was diluted with 10 mL aq. 0.2N HCl and washed with $CH_2Cl_2$ (3×10 mL). The aqueous layer was then adjusted to pH 10 by addition of 2N KOH and extracted with $CH_2Cl_2$ (2×10 mL). The latter two extracts were dried on $K_2CO_3$, filtered, and concentrated to afford 234 as a solid (7 mg, 89% yield). Data for 234: MS (ESI) m/z 447.2 $(M+2H)^{2+}$, 893.5 $(M+H)^+$; $^1HNMR$ (300 MHz, $CDCl_3$, partial): δ 7.59 (s, 1H) 7.35-7.20 (m, 2H), 7.00 (dd, J=8, 2 Hz, 1H), 6.78 (td, J=8, 2 Hz, 2H), 5.05-4.95 (m, 1H), 4.75-4.60 (m, 3H), 4.40 (d, J=7 Hz 1H), 4.15-3.98 (m, 2H), 3.88 (dd, J=9, 6 Hz, 1H), 3.70 (dd, J=10.4, 4.43 Hz, 1H), 2.31 (bs, 3H), 2.10 (s, 3H), 0.82 (m, 6H).

Example 35

Synthesis of Triazoles 235 and 236

Scheme 58 illustrates the synthesis of triazoles 235 and 236. 2-Penten-4-yn-1-ol was converted to tosylate 329 which was used to alkylate amine 171 to yield enyne 330. The cycloaddition of alkyne 330 with azide 158 and 189 gave triazole products 235 and 236 respectively.

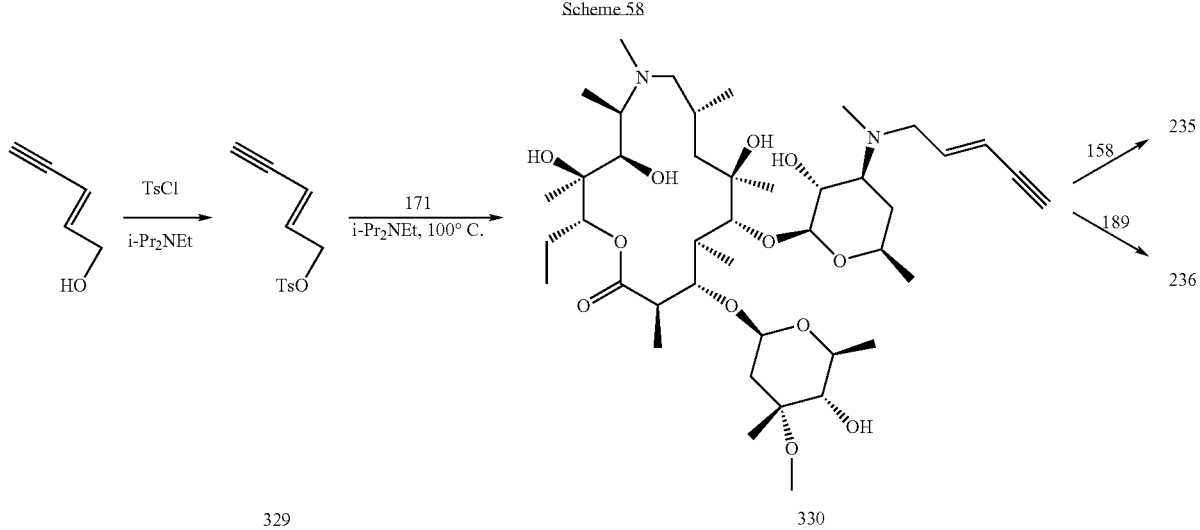

Scheme 58

Synthesis of Tosylate 329

To a stirred ice-cold solution of 2-penten-4-yn-1-ol (0.821 g, 10 mmol) in ether (25 mL) was added p-toluenesulfonyl chloride (2.0 g, 10.5 mmol). Powdered KOH (1.0 g, 17.8 mmol) was then added portionwise over 5 minutes. The slurry was stirred at 0° C. for 45 minutes. The reaction mixture was poured into 100 mL water, and extracted with ether (2×50 mL). The combined organic extracts were washed with brine, dried over $MgSO_4$, filtered, and concentrated to afford 329 as a yellow oil (2.1 g, 89% yield). Data for 329: $^1HNMR$ (300 MHz, $CDCl_3$): δ 7.80 (d, J=8 Hz, 2H), 7.35 (d, J=8 Hz, 2H), 6.12 (dt, J=16, 6 Hz, 1H), 5.70 (ddd, J=16, 2, 2 Hz, 1H), 4.60-4.50 (m, 2H), 2.95 (d, J=2, Hz 1H), 2.45 (s, 3H); $^{13}$C NMR (75 MHz, CDCl$_3$): δ 145.1, 135.9, 132.9, 130.0, 127.9, 113.9, 80.3, 79.8, 69.0, 21.66.

Synthesis of Enyne 330

A 20 mL vial was charged with tosylate 329 (0.20 g, 0.85 mmol), N-desmethyl azithromycin 171 (0.5 g, 0.68 mmol), and Hunig's base (10 mL) then purged with argon gas and sealed. The solution was stirred in a 100° C. oil bath for 1 h. After cooling to room temperature, the reaction mixture was poured into saturated aqueous NaHCO$_3$ (50 mL) and extracted with CH$_2$Cl$_2$ (3×50 mL). The combined organic extracts were washed with brine, dried over K$_2$CO$_3$, filtered, and concentrated to afford 0.72 g of a viscous yellow oil. Purification by silica gel flash chromatography (25 mm×6" column eluted with 50:1 CH$_2$Cl$_2$/2N NH$_3$ in MeOH) gave 330 as a yellow solid (0.48 g, 88% yield). Data for 330: MS (ESI) m/z 400.2 (M+2H)$^{2+}$, 799.3 (M+H)$^+$, 821.2 (M+Na)$^+$; $^1$HNMR (300 MHz, CDCl$_3$, partial): δ 8.00 (bs, 1H), 6.20 (dt, J=16, 7, Hz, 1H), 5.70-5.60 (m, 1H), 5.00 (d, J=4 Hz, 1H), 4.65 (m, 1H), 4.48 (d, J=7 Hz, 1H), 4.28 (dd, J=6, 2 Hz, 1H), 4.15-3.99 (m, 1H), 3.82 (d, J=6 Hz, 1H), 3.65 (d, J=7 Hz, 1H), 3.60-3.40 (m, 1H), 3.32 (s, 3H), 3.32-3.20 (m, 2H), 2.32 (s, 3H), 2.26 (s, 3H), 0.86 (m, 6H); $^{13}$C NMR (75 MHz, CDCl$_3$): δ 179.3, 144.4, 111.8, 103.8, 96.2, 85.1, 82.6, 79.7, 79.0, 78.5, 77.5, 75.7, 75.3, 74.4, 73.8, 71.9, 71.0, 69.4, 66.5, 65.4, 62.9, 57.0, 50.39, 45.9, 43.4, 42.0, 37.6, 37.5, 35.9, 31.8, 31.2, 28.2, 27.7, 22.8, 22.5, 22.2, 22.0, 19.3, 17.1, 16.3, 12.1, 10.3, 8.6.

Synthesis of Triazole 235

To a stirred solution of 330 (20 mg, 25 Amos) in THF (100 μL) was added Hunig's base (20 μL), azide 158 (16 mg, 50 μmol), and cuprous iodide (2.4 mg, 13 μmol). The resulting mixture was degassed by alternately applying vacuum and purging with argon gas. The slurry was stirred under argon at ambient temperature for 4 h. The entire reaction mixture was then placed atop a silica gel flash chromatography column and eluted with 50:1 CH$_2$Cl$_2$/2N NH$_3$ in MeOH to afford triazole 235 as a white solid (14 mg, 50% yield). Data for 235: MS (ESI) m/z 560.8 (M+2H)$^{2+}$, 1120.5 (M+H)$^+$; $^1$HNMR (300 MHz, CDCl$_3$, partial): δ 8.60 (bs, 1H), 7.62 (s, 1H), 7.40-7.20 (m, 1H), 7.00-6.78 (m, 2H), 6.55-6.20 (m, 2H), 5.10-4.90 (m, 2H), 4.50 (d, J=10 Hz 1H), 3.18 (s, 3H), 2.28 (bs, 3H), 2.16 (bs, 3H), 0.90 (m, 6H).

Synthesis of Triazole 236

To a stirred solution of 330 (20 mg, 25 μmol) in THF (100 μL) was added Hunig's base (20 mL), azide 189 (16 mg, 50 μmol), and cuprous iodide (2.4 mg, 13 μmol). The resulting mixture was degassed by alternately applying vacuum and purging with argon gas. The slurry was stirred under argon at ambient temperature for 4 h. The entire reaction mixture was then placed atop a silica gel flash chromatography column and eluted with 50:1 CH$_2$Cl$_2$/2N NH$_3$ in MeOH to afford the desired triazole adduct 236 as a white solid (18 mg, 70% yield). Data for 236: MS (ESI) m/z 518.2 (M+2H)$^{2+}$, 1035.2 (M+H)$^+$; $^1$HNMR (300 MHz, CDCl$_3$, partial): δ 8.70 (bs, 1H), 7.65 (s, 1H), 7.40-7.20 (m, 2H), 7.05 (dd, J=8, 2 Hz, 1H), 6.78 (td, J=8, 2 Hz, 2H), 6.60-6.20 (m, 2H), 5.10-4.90 (m, 2H), 4.40 (d, J=7 Hz 1H), 3.86 (dd, J=9, 7 Hz, 1H), 3.21 (s, 3H), 2.22 (bs, 3H), 2.16 (s, 3H), 0.82 (m, 6H).

Example 36

Synthesis of Triazoles 237-240

Scheme 59 illustrates the synthesis of triazoles 237-240. Propargyl alcohol was alkylated to afford silylether 331 and the silylether subsequently converted to tosylate 332. Alkylation of amine 171 with 332 afforded alkyne 333. Cycloaddition of 333 with azides 189 and 158 yielded triazoles 237 and 238 respectively. Hydrolysis of 237 and 238 provided triazoles 239 and 240.

Scheme 59

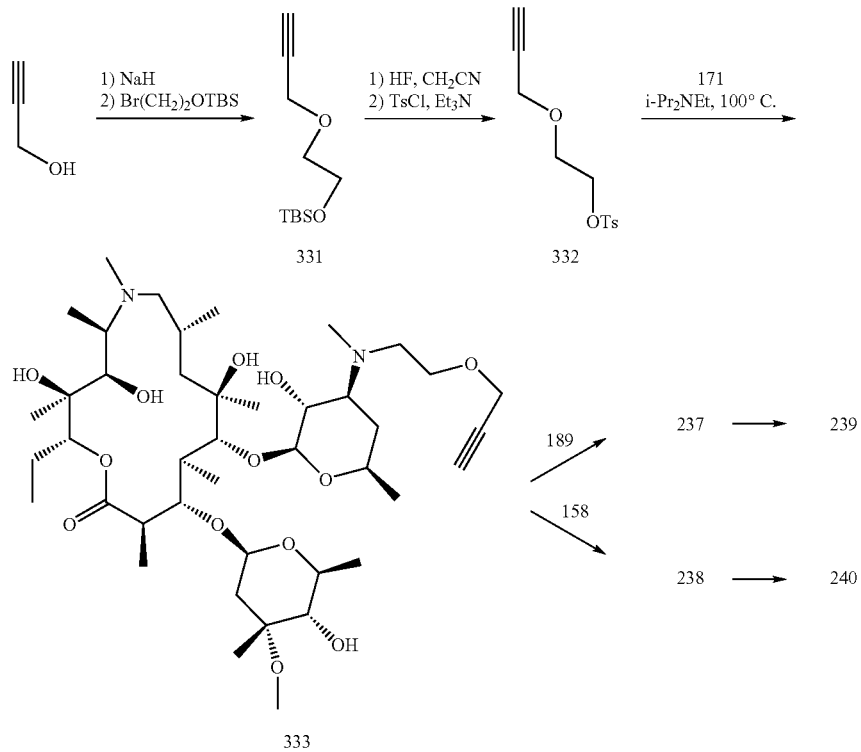

Synthesis of Silylether 331

To a stirred slurry of sodium hydride (0.28 g, 6.97 mmol) in DMF (30 mL) was added propargyl alcohol (0.41 mL, 6.97 mmol) dropwise over 5 minutes. The mixture was stirred at room temperature for 45 min., then 2-[t-butyldimethylsiloxy]-bromoethane (1.8 mL, 8.4 mmol) was added in one portion. After 16 hours the reaction mixture was poured into water (100 mL) and extracted with 1:1 hexane/ether (3×50 mL). The combined organic extracts were washed with brine, dried on $MgSO_4$, filtered and concentrated in vacuo to afford 331 as a colorless oil which was used as-is without further purification (1.38 g, 92% yield).

Synthesis of Tosylate 332

Silylether 331 (0.86 g, 4 mmol) was dissolved in acetonitrile (20 mL) in a plastic culture tube and cooled to 0° C. Aqueous HF (48% w/w, 1 mL) was then added and the solution stirred at 0° C. for 3 hours. The reaction mixture was poured slowly into 100 mL saturated aqueous $NaHCO_3$ and extracted with ether (3×50 mL). The combined organic extracts were washed with brine, dried ($K_2CO_3$), filtered, and concentrated to afford a colorless oil (0.5 g). This oil was dissolved in anhydrous $CH_2Cl_2$ (5 mL), cooled to 0° C., and then Hunig's base was added (2 mL) followed by tosyl chloride (0.76 g, 4.0 mmol). The reaction mixture was allowed to warm to room temperature and stirred for 6 hours. The solution was diluted with $CH_2Cl_2$ (50 mL) and washed with saturated aqueous $NaHCO_3$ and brine. The aqueous washes were back-extracted with $CH_2Cl_2$ (50 mL). The combined organic extracts were dried on $MgSO_4$, filtered, and; concentrated to give 332 as a colorless oil (0.81 g, 80% yield). Data for 332: $^1$HNMR (300 MHz, $CDCl_3$): δ 7.74 (m, 2H), 7.27 (m, 2H), 4.12 (t, J=5 Hz, 2H), 4.05 (d, J=2 Hz, 2H), 3.66 (t, J=5 Hz, 2H), 2.38 (s, 3H), 2.34 (t, J=2 Hz, 1H); $^{13}$C NMR (75 MHz, $CDCl_3$): δ 144.8, 133.0, 129.8, 128.0, 78.9, 75.0, 68.8, 67.1, 58.4, 21.6.

Synthesis of Alkyne 333

A 20 mL vial was charged with tosylate 332 (0.20 g, 0.82 mmol), N-desmethyl azithromycin 171 (0.5 g, 0.68 mmol), and Hunig's base (10 mL) and then purged with argon gas and sealed. The solution was stirred in a 100° C. oil bath for 6 h. After cooling to room temperature, the reaction mixture was poured into saturated aqueous $NaHCO_3$ (50 mL) and extracted with $CH_2Cl_2$ (3×50 mL). The combined organic extracts were washed with brine, dried over $K_2CO_3$, filtered, and concentrated to afford 0.65 g of an off-white solid. Purification by silica gel flash chromatography (25 mm×6" column eluted with 50:1 $CH_2Cl_2$/2N $NH_3$ in MeOH) gave 333 as a white solid (0.22 g, 37% yield). Data for 333: MS (ESI) m/z 409.2 $(M+2H)^{2+}$, 817.0 $(M+H)^+$; $^1$HNMR (300 MHz, $CDCl_3$, partial): δ 7.50 (bs, 1H), 4.87 (d, J=4 Hz, 1H), 4.55 (dd, J=10, 2 Hz, 1H), 4.35 (d, J=7 Hz, 1H), 4.20 (dd, J=7, 2 Hz, 1H), 4.06 (d, J=2 Hz, 2H), 4.05-3.90 (m, 1H), 3.57 (d, J=7 Hz, 1H), 3.51 (t, J=6 Hz, 1H), 3.38 (d, J=6 Hz, 1H), 3.24 (s, 3H), 3.15 (dd, J=10, 7 Hz, 1H), 2.93 (t, J=10 Hz, 1H), 2.24 (s, 3H), 2.23 (s, 3H), 0.86 (m, 6H); $^{13}$C NMR (75 MHz,): δ 177.8, 106.84, 95.05, 82.3, 79.3, 76.0, 74.3, 73.1, 70.6, 69.9, 69.5, 65.8, 62.35, 60.34, 52.1, 44.6, 41.9, 37.3, 36.5, 36.1, 29.6, 26.7, 25.8, 21.2, 20.8, 18.6, 16.1, 15.9, 14.2, 10.9, 7.8.

Synthesis of Triazole 237

To a stirred solution of 333 (50 mg, 61 μmol) in THF (150 μL) was added Hunig's base (30 μL), azide 189 (20 mg, 86 μmol), and cuprous iodide (6 mg, 33 μmol). The resulting mixture was degassed by alternately applying vacuum and purging with argon gas. The slurry was stirred under argon at ambient temperature for 4 h. The entire reaction mixture was then placed atop a silica gel flash chromatography column and eluted with 50:1 $CH_2Cl_2$/2N $NH_3$ in MeOH to afford the desired triazole adduct 237 as a white solid (31 mg, 70% yield). Data for 237: MS (ESI) m/z 527.4 $(M+2H)^{2+}$, 1075.4 $(M+H)^+$; $^1$HNMR (300 MHz, $CDCl_3$, partial): δ 8.10 (bs, 1H), 7.72 (s, 1H), 7.40-7.20 (m, 2H), 7.05 (dd, J=8, 2 Hz, 1H), 6.78 (td, J=6, 2 Hz, 2H), 5.10-4.90 (m, 2H), 4.80-4.60 (m, 4H), 4.40 (d, J=7 Hz, 1H), 4.22 (d, J=4 Hz, 1H), 4.09 (t, J=9 Hz, 1H), 4.10-3.95 (m, 1H), 3.89 (dd, J=9, 6 Hz, 1H), 3.34 (s, 3H), 3.16 (dd, J=10, 8 Hz, 1H), 2.32 (s, 3H), 2.30 (s, 3H), 0.90 (m, 6H).

Synthesis of Triazole 238

To a stirred solution of 333 (35 mg, 43 μmol) in THF (150 μL) was added Hunig's base (30 μL), azide 158 (28 mg, 86 μmol), and cuprous iodide (4 mg, 21 μmol). The mixture was degassed by alternately applying vacuum and purging with argon gas. The mixture was stirred under argon at ambient temperature for 4 h. The entire reaction mixture was then placed atop a silica gel flash chromatography column and eluted with 50:1 $CH_2Cl_2$/2N $NH_3$ in MeOH to afford the desired triazole adduct as a white solid (24 mg, 50% yield). Data for 238: MS (ESI) m/z 569.9 $(M+2H)^{2+}$, 11.60.4 $(M+Na)^+$; $^1$HNMR (300 MHz, $CDCl_3$, partial): δ 8.05 (bs, 1H), 7.80 (s, 1H), 7.33 (dd, J=14, 2 Hz, 1H), 7.05 (dd, J=9, 2 Hz, 1H), 6.88 (t, J=9 Hz, 1H), 5.18-5.00 (m, 2H), 4.80-4.60 (m, 4H), 4.50 (d, J=7 Hz 1H), 4.13 (t, J=9 Hz, 1H), 3.92 (dd, J=9, 6 Hz, 1H), 3.34 (s, 3H), 2.32 (s, 3H), 2.30 (s, 3H), 0.90 (m, 6H).

Synthesis of Triazole 239

Compound 237 (10 mg, 9.8 μmol) was dissolved in EtOH (0.8 mL) and 1N HCl (aq) was then added (0.2 mL) and the solution stirred at room temperature for 16 h. The reaction mixture was diluted with 10 mL aq. 0.2N HCl and washed with $CH_2Cl_2$ (3×10 mL). The aqueous layer was then adjusted to pH 10 by addition of 2N KOH and extracted with $CH_2Cl_2$ (2×10 mL). The latter two extracts were dried on-$K_2CO_3$, filtered and concentrated to afford triazole 239 as a solid (7 mg, 80% yield). Data for 239: MS (ESI) m/z 448.3 $(M+2H)^{2+}$, 895.3 $(M+H)^+$.

Synthesis of Triazole 240

Compound 238 (10 mg, 8.7 μmol) was dissolved in EtOH (1.6 mL) and 1N HCl (aq) was then added (0.4 mL) and the solution stirred at room temperature for 12 h. The reaction mixture was diluted with 10 mL aq. 0.2N HCl and washed with $CH_2Cl_2$ (3×10 mL). The aqueous layer was then adjusted to pH 10 by addition of 2N KOH and extracted with $CH_2Cl_2$ (2×10 mL). The latter two extracts were dried on $K_2CO_3$, filtered and concentrated to afford triazole 240 as a solid (6 mg, 87% yield). Data for 240: MS (ESI) m/z 434.4 $(M+2H)^+$, 867.2 $(M+H)^+$, 889.3 $(M+Na)^+$.

Example 37

Synthesis of Ketolides 237-240

Scheme 60 depicts the synthesis of triazoles 241 and 242. Alkyne 197 was protected as diacetate 334, and then 334 was treated with sodium hexamethyldisilylazide and carbonyldiimidazole to provide imidazole carbamate 335. Michael addition of ammonia to 335 was followed by closure of the amine group onto the imidazole carbamate to afford carbamate 336. Seleective hydrolysis of 336 afforded alcohol 337 which was subsequently oxidized with the Dess-Martin periodinane to yield ketolide 338. Deprotection of 338 gave alkyne 339, which was treated with azides 158 and 189 to provide triazoles 241 and 242 respectively.
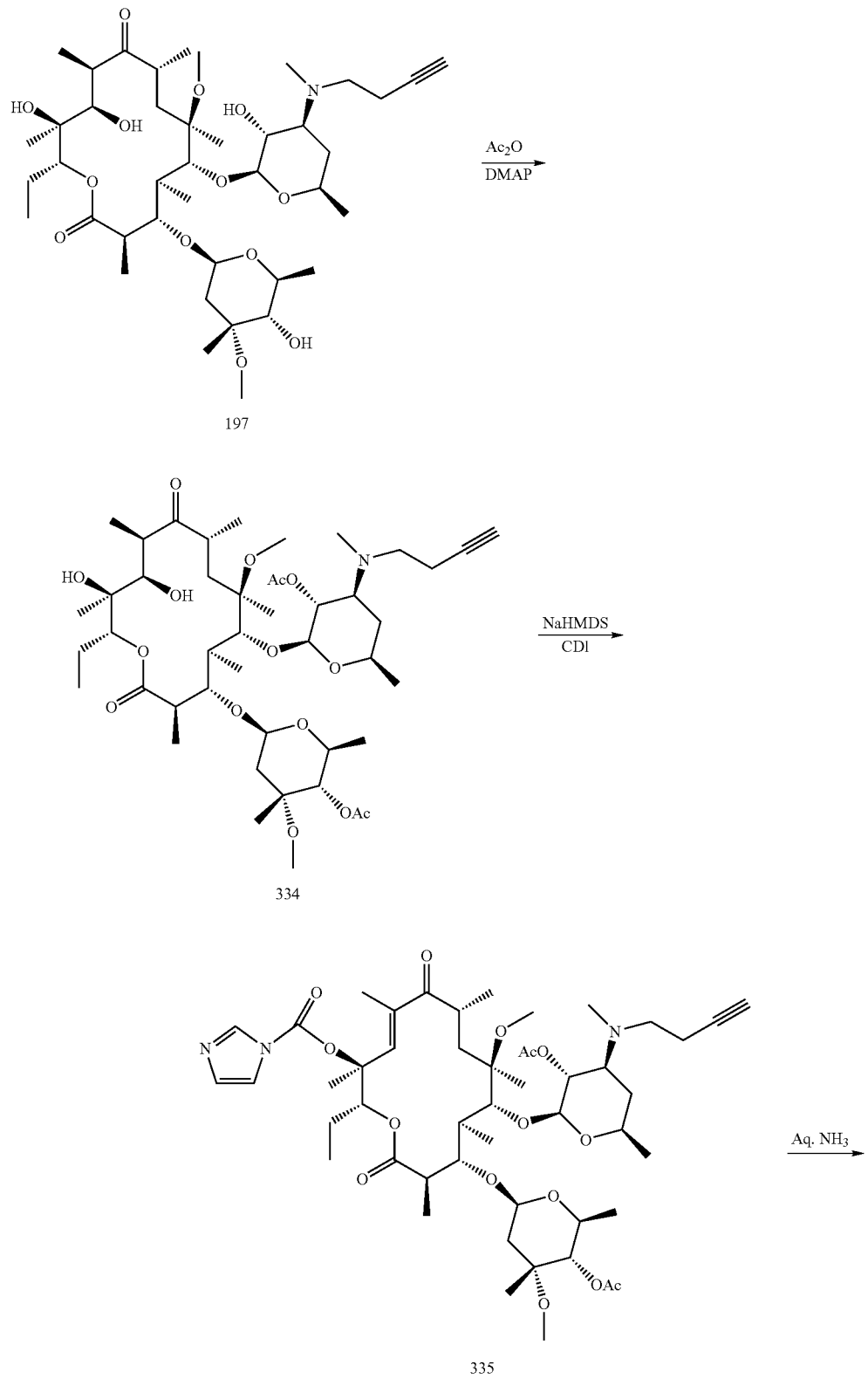
Scheme 60

-continued
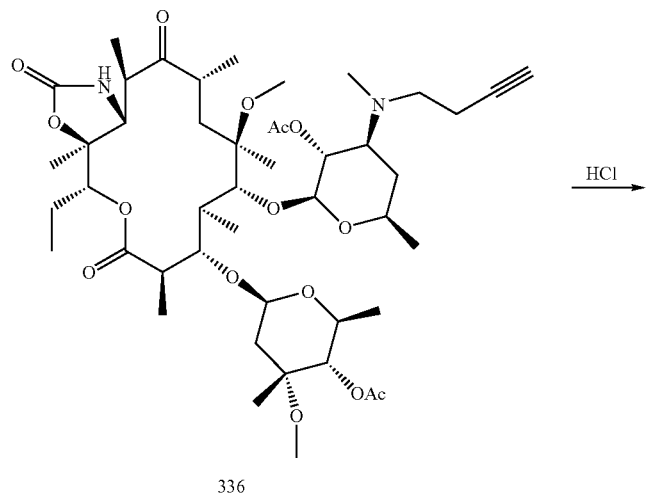
336
HCl →
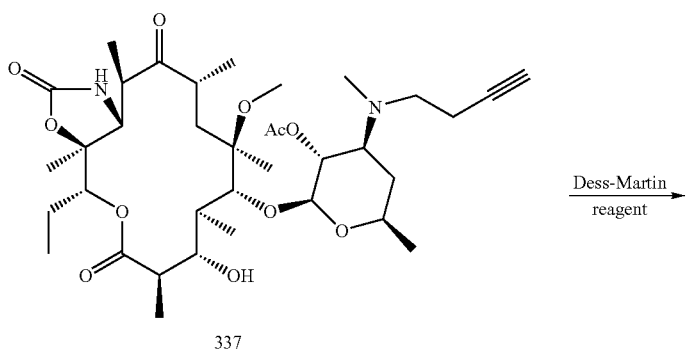
337
Dess-Martin reagent →
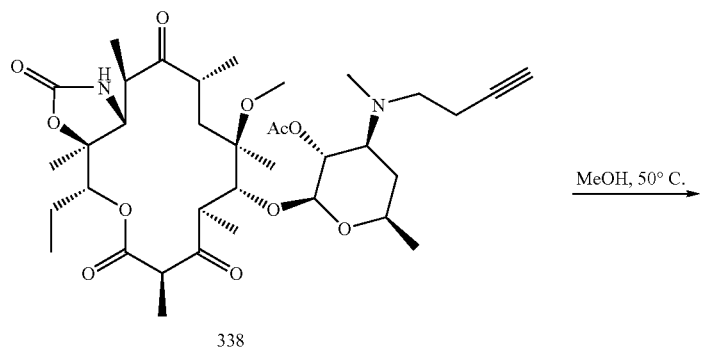
338
MeOH, 50° C. →
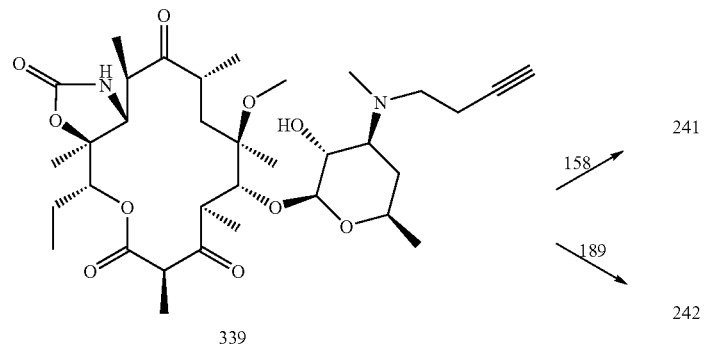
339
158 → 241
189 → 242

Synthesis of Diacetate 334

Alkyne 197 (1.50 g, 1.90 mmol) was dissolved in 5 mL methylene chloride and the mixture cooled to 0° C. Dimethylaminopyridine (47 mg, 0.38 mmol) and triethylamine (0.8 mL, 5.7 mmol) were added, followed by acetic anhydride (0.54 mL, 5.7 mmol). The mixture was allowed to warm to room temperature and stirred for 1.5 h. Methylene chloride (50 mL) was added and the mixture washed with sat. aqueous $NaHCO_3$, and then brine. The organic phase was dried ($K_2CO_3$) and evaporated to afford 1.9 g of a white solid. The crude solid was purified by silica gel flash chromatography (25 mm×6" column eluted with 40:1 $CH_2Cl_2$/2N $NH_3$ in MeOH) to afford 334 as a white solid (1.4 g, 86% yield). Data for 334: MS (ESI) m/z 870.2 $(M+H)^+$, 892.3 $(M+Na)^+$.

Synthesis of Imidazole Carbamate 335

A solution of 334 (0.8 g, 0.92 mmol) in 5.0 mL THF was cooled to −40° C., NaHMDS (1.2 mL of a 1.0 M THF soln.) was added dropwise to the stirred solution over 5 min., and the mixture was stirred at −40° C. for 40 min. A solution of carbonyldiimidazole (0.60 g, 3.7 mmol) in 8 mL of a 5:3 mixture of THF and DMF was then added over a period of 30 minutes by syringe-pump. Ten minutes after the addition was complete the cold bath was removed and the reaction mixture was allowed to warm to room temperature. After 16 h the reaction mixture was diluted with EtOAc (20 mL) and the washed with sat. aqueous $NaHCO_3$ and brine. The organic phase was dried ($Na_2SO_4$), filtered, and evaporated to afford 335 as an off-white solid which was used without further purification (0.92 g, 100% yield). Data for 335: MS (ESI) m/z 968.4 $(M+Na)^+$.

Synthesis of Carbamate 336

A solution of 335 (0.94 g, 0.92 mmol) in acetonitrile (10 mL) was treated with 15% aqueous ammonia (2 mL) and the mixture stirred at room temperature for 40 hours. The reaction mixture was diluted with EtOAc (50 mL), and washed with sat. aqueous $NaHCO_3$ and brine, the aqueous washes were back-extracted twice with 50 mL portions of EtOAc. The combined organic extracts were dried ($Na_2SO_4$) and evaporated to afford 1.3 g of an off-white solid. Purification by silica gel flash chromatography (25 mm×6" column eluted with 1:3 acetone/hexanes) gave 260 mg of 336 (31% yield) along with 100 mg of its C-10 epimer and 450 mg of a mixture of the two. Data for 336: MS (ESI) m/z 895.2 $(M+H)^+$, 917.3 $(M+Na)^+$.

Synthesis of Alcohol 337

A solution of 336 (209 mg, 0.221 mmol) in 0.1 N aqueous HCl (5 mL) was stirred at room temperature for 8 h. The reaction mixture was neutralized with with saturated aqueous $NaHCO_3$ (50 mL) and extracted with methylene chloride (3×25 mL). The combined organic extracts were washed with brine, dried ($K_2CO_3$), filtered, and evaporated to give 190 mg of a white solid. The crude product was chromatographed on silica gel using a 3:1 hexane/acetone as the eluant to provide 337 (145 mg, 94% yield) as a white solid. Data for 337: MS (ESI) m/z 695.2 $(M+H)^+$, 717.1 $(M+Na)^+$.

Synthesis of Ketolide 338

To a stirred solution of 337 (80 mg, 0.115 mmol) in methylene chloride at 0° C. was added Dess-Martin periodinane (59 mg, 0.138 mmol). The reaction mixture was stirred at ambient temperature for 12 hours then placed directly on a silica gel chromatography column and eluted with 3:1 hexane/acetone to afford ketolide 338 (62 mg, 78% yield) as a white solid. Data for 338: MS (ESI) m/z 693.1 $(M+H)^+$, 715.3 $(M+Na)^+$.

Synthesis of Alkyne 339

A methanol solution of 338 (62 mg, 0.090 mmol) was stirred at 50° C. for 16 h. The reaction mixture was concentrated in vacuo to give 339 as a white solid (55 mg, 94% yield) which was used without further purification. Data for 339: MS (ESI) m/z 651.2 $(M+H)^+$, 673.1 $(M+Na)^+$.

Synthesis of Triazole 241

To a stirred solution of 339 (20 mg, 31 μmol) in THF (310 mL) was added Hunig's base (26 μL), azide 158 (14.8 mg, 46 μmol), and cuprous iodide (5.8 mg, 31 μmol). The resulting mixture was stirred at ambient temperature for 4 h. The entire reaction mixture was then placed atop a silica gel flash chromatography column and eluted with 50:1 $CH_2Cl_2$/2N $NH_3$ in MeOH to afford the desired triazole adduct 241 as a white solid (26 mg, 86% yield). Data for 241: MS (ESI) m/z 972.3 $(M+H)^+$, 994.3 $(M+Na)^+$; $^1$HNMR (300 MHz, $CDCl_3$, partial): δ 7.60 (s, 1H), 7.41 (dd, J=14, 2 Hz, 1H), 7.00-6.60 (m, 2H), 6.75 (bs, 1H), 5.72 (dd, J=10, 3 Hz 1H), 5.01-4.90 (m, 1H), 4.75-4.52 (m, 3H), 4.33-4.05 (m, 3H), 2.18 (s, 3H), 0.90 (t, J=7 Hz, 3H).

Synthesis of Triazole 242

To a stirred solution of 339 (18 mg, 28 μmol) in THF (310 μL) was added Hunig's base (24 μL), azide 189 (10 mg, 42 μmol) and cuprous iodide (5.3 mg, 28 μmol). The resulting mixture was stirred at ambient temperature for 4 h. The entire reaction mixture was then placed atop a silica gel flash chromatography column and eluted with 50:1 $CH_2Cl_2$/2N $NH_3$ in MeOH to afford the desired triazole adduct 242 as a white solid (21 mg, 85% yield). Data for 242: MS (ESI) m/z 887.3 $(M+H)^+$, 909.3 $(M+Na)^+$; $^1$HNMR (300 MHz, $CDCl_3$, partial): δ 7.65 (s, 1H), 7.55-7.30 (m, 2H), 7.10 (dd, J=8, 2 Hz, 1H), 6.82-6.70 (m, 1H), 6.75 (bs, 1H), 5.70 (dd, J=10, 3 Hz 1H), 5.18-4.99 (m, 1H), 4.80-4.52 (m, 3H), 4.33-4.05 (m, 3H), 2.20 (bs, 3H), 0.90 (t, J=7 Hz, 3H).

Example 38

Synthesis of Isoxazolines 243-245

Scheme 61 depicts the synthesis of isoxazolines 243-245. Known hydroxyiminoyl chloride 340 (*J. Med. Chem.* 2003, 46, 284) was converted to isoxazoline alcohol 341. The alcohol group of 341 was transformed to the azide 342, an intermediate used in subsequent aromatic substitution chemistry with nucleophiles to produce azides 343, 344 and 345. Azide 345 was acylated to provide azide 346. The cycloaddition of azides 343, 344, and 346 with alkyne 173 yielded target isoxazolines 243, 245, and 244 respectively.

Scheme 61

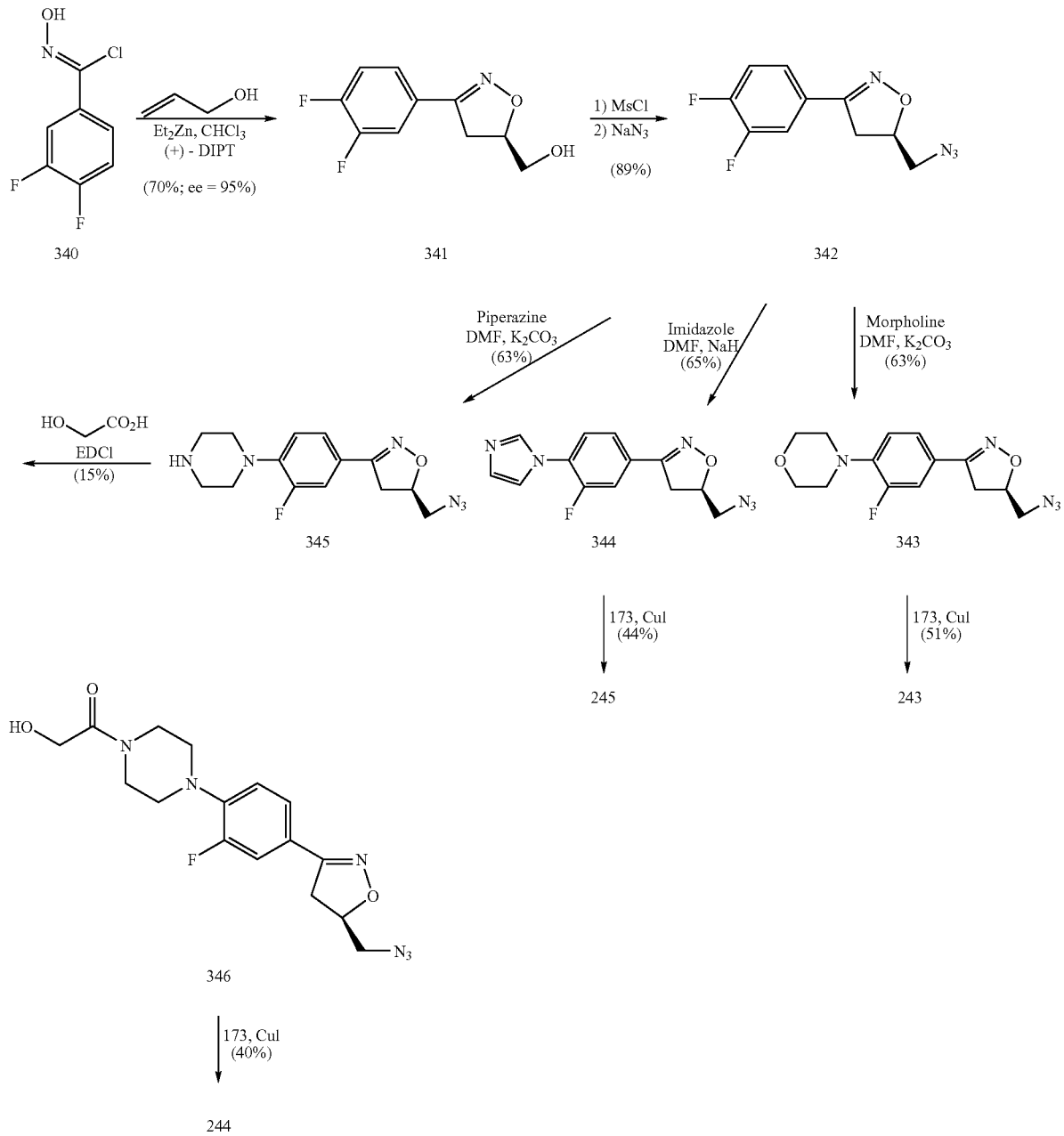

Synthesis of Alcohol 341

To a solution of allyl alcohol (15.6 mL, 0.23 mol) in 600 mL chloroform was added a 1M solution of diethyl zinc in hexanes (276 mL, 0.276 mol) between −10° C. to 0° C. After stirring for 10 min, (+)-diisopropyl L-tartrate (9.68 mL, 45.9 mmol) was added and the solution was stirred at 0° C. for 1 h. Dioxane (24 mL, 0.282 mol) was added followed by hydroxyiminoyl chloride 340 (40 g. 0.209 mol) and the solution was stirred at −5° C. to 0° C. for 1½ h, then poured into 1 M citric acid/ice (400 mL) and extracted with dichloromethane (2×200 mL). The combined organic extract was washed with water (100 mL), brine (100 mL), dried ($Na_2SO_4$) and evaporated to a volume of 50 mL. 1-Chlorobutane (250 mL) was added and again the solution evaporated to a volume of 50 mL. The beige suspension was filtered, washed with 1-chlorobutane (2×10 mL) and dried to afford 14.5 g of alcohol 341. The remaining supernatant was evaporated and purified by flash-chromatography (eluant: hexanes-ethyl acetate 2:1) yielding and additional 22.0 g of alcohol 341. The combined portions of alcohol 341 were recrystallized from 120 mL 1-chlorobutane-hexanes 4:1, yielding pure alcohol 341 (31.1 g, 70% yield, ee: 95% as determined by Mosher ester). Data for 341: $^1$HNMR (300 MHz, $CDCl_3$): δ 7.55-7.45 (m, 1H), 7.39-7.12 (m, 2H), 4.95-4.83 (m, 1H), 3.91 (dd, J=1, 2 Hz, 1H), 3.69 ((dd, J=1, 2 Hz, 1H), 3.40-3.21 (m, 2H), 2.20 (br s, 1H).

Synthesis of Azide 342

To a solution of 341 (3.0 g, 14.1 mmol) in 60 mL dichloromethane was added Et$_3$N (3.53 mL, 25.2 mmol) followed by MsCl (1.31 mL, 16.9 mmol) at 0° C. The mixture was stirred at 0° C. for 30 min, then poured into 30 mL water/ice and extracted with dichloromethane (2×50 mL). The combined organic extract was washed with water (2×30 mL), brine (30 mL), dried (Na$_2$SO$_4$) and evaporated. The residue was dissolved in 50 mL DMF, and NaN$_3$ (1.83 g., 28.1 mmol) was added and the mixture stirred at 80° C. for 2 h. The mixture was poured into 30 mL water/ice and extracted with ethyl acetate (2×50 mL). The combined organic extract was washed with water (2×30 mL), brine (30 mL), dried (Na$_2$SO$_4$) and evaporated. The residual oil was crystallized with 20 mL 1-chlorobutane-hexanes 2:1, yielding azide 342 (3.0 g, 89%). Data for 342: $^1$HNMR (300 MHz, CDCl$_3$): δ 7.50-7.41 (m, 1H), 7.35-7.05 (m, 2H), 4.92-4.81 (m, 1H), 3.51-3.05 (m, 4H).

Synthesis of Azide 343

A mixture of 342 (400 mg, 1.68 mmol) and K$_2$CO$_3$ (302 mg, 2.18 mmol) in 6 mL morpholine was stirred at 120° C. for 48 h, then poured into 20 mL water/ice and extracted with ethyl acetate (2×10 mL). The combined organic extract was washed with water (2×10 mL), brine (10 mL), dried (Na$_2$SO$_4$) and evaporated. The residue was purified by flash-chromatography (eluant: hexanes-ethyl acetate 2:1) yielding azide 343 (320 mg, 63%). Data for 343: MS (ESI) m/z 306 (M+H)$^+$; $^1$HNMR (300 MHz, CDCl$_3$): δ 7.38-7.23 (m, 2H), 6.80-6.78 (m, 1H), 4.90-4.75 (m, 1H), 3.83-3.75 (m, 4H), 3.48-3.25 (m, 4H), 3.18-3.02 (m, 4H).

Synthesis of Azide 344

To a solution of imidazole (214 mg, 3.15 mmol) in 5 mL DMF was added NaH (60% dispersion in paraffin oil, 100 mg, 2.52 mmol) at 0° C. After stirring the mixture for 30 min, the azide 342 (0.5 g, 2.1 mmol) was added. The mixture was stirred at room temperature overnight and then 60° C. for 2 h, and then poured into 40 mL water/ice and extracted with ethyl acetate (3×20 mL). The combined organic extract was washed with water (3×20 mL), brine (10 mL), dried (Na$_2$SO$_4$) and evaporated. The residue was purified by flash-chromatography (eluant: ethyl acetate followed by ethyl acetate-MeOH 20:1) yielding azide 344 (390 mg, 65%). Data for 344: $^1$HNMR (300 MHz, CDCl$_3$): δ 7.92 (s, 1H), 7.72-7.45 (m, 3H), 7.39-7.23 (m, 2H), 5.10-4.96 (m, 1H), 3.69-3.41 (m, 3H), 3.31-3.20 (m, 1H).

Synthesis of Azide 345

A mixture of azide 342 (1.0 g, 4.2 mmol), K$_2$CO$_3$ (755 mg, 5.5 mmol) and piperazine (15 g, 175 mmol) was dissolved in 9 mL DMF. The mixture was stirred at 120° C. for 3 h, then poured into 50 mL water/ice and extracted with ethyl acetate-isopropanol 95:5 (3×30 mL). The combined organic extract was washed with water (3×20 mL), brine (10 mL), dried (Na$_2$SO$_4$) and evaporated. The residue was purified by flash-chromatography (eluant: ethyl acetate-MeOH 3:1) yielding azide 345 (793 mg, 63%). Data for 345: $^1$HNMR (300 MHz, CDCl$_3$): δ 7.52-7.39 (m, 2H), 7.08-6.95 (m, 1H), 5.05-4.9 (m, 1H), 3.63-3.41 (m, 3H), 3.33-3.10 (m, 9H), 1.85 (br s, 1H).

Synthesis of Azide 346

To a solution of azide 345 (300 mg, 0.99 mmol) in 6 ml dichloromethane-DMF 2:1 was added glycolic acid (97.8 mg, 1.29 mmol), 1-(3-dimethylaminopropyl)-3-ethylcarbodiimide hydrochloride (EDCI) (284 mg, 1.48 mmol) and diisopropyl ethylamine (0.344 mL, 1.98 mmol) at 0° C. The solution was stirred at room temperature over the weekend and then poured into 20 mL 5% aqueous Na$_2$CO$_3$/ice and extracted with ethyl acetate (2×15 mL). The combined organic extract was washed with water (2×10 mL), 10 mL 1 M aqueous HCl, water (2×10 mL), brine (10 mL), dried (Na$_2$SO$_4$) and; evaporated. The residue was purified by flash-chromatography (eluant: ethyl acetate) yielding azide 346 (51 mg, 15%). Data for 346: $^1$HNMR (300 MHz, CDCl$_3$): δ 7.39-7.25 (m, 2H), 6.91-6.80 (m, 1H), 4.91-4.79 (m, 1H), 4.15 (s, 2H), 3.83-3.75 (m, 2H), 3.50-3.26 (m, 5H), 3.18-3.04 (m, 5H).

Synthesis of Isoxazoline 243

To a solution of alkyne 173 (100 mg, 0.127 mmol) in 4 mL acetonitrile was added azide 343 (39 mg, 0.127 mmol), 2,6-lutidine (0.0163 mL, 0.139 mmol) and CuI (24 mg, 0.127 mmol). The mixture was stirred overnight at room temperature, then poured into 10 mL 5% aqueous NH$_3$/ice and extracted with ethyl acetate (3×20 mL). The combined organic extract was washed with water (2×10 mL), brine (10 mL), dried (Na$_2$SO$_4$) and evaporated. The residue was purified by flash-chromatography (eluant: ethyl acetate-MeOH 5:1) yielding 243 (71 mg, 51%). Data for 243: MS (ESI) m/z 1092 (M+H)$^+$; $^1$HNMR (300 MHz, CDCl$_3$, partial): δ 8.31-8.21 (br s, 1H), 7.51 (s, 1H), 7.31-7.12 (m, 2H), 6.81 (t, J=1 Hz, 1H), 5.05-4.90 (s, 1H), 4.65-3.90 (m, 5H), 3.81-3.74 (m, 2H).

Synthesis of Isoxazoline 244

To a solution of alkyne 173 (100 mg, 0.127 mmol) in 4 mL acetonitrile was added azide 346 (46 mg, 0.127 mmol), 2,6-lutidine (0.0163 mL, 0.139 mmol) and CuI (14.5 mg, 0.076 mmol). The mixture was stirred overnight at room temperature, then poured into 10 mL-5% aqueous NH$_3$/ice and extracted with ethyl acetate (3×20 mL). The combined organic extract was washed with water (2×10 mL), bane (10 mL), dried (Na$_2$SO$_4$) and evaporated. The residue was purified by flash-chromatography (eluant: ethyl acetate-MeOH 5:1) yielding 244 (58 mg, 40%). Data for 244: MS (ESI) m/z 1049 (M+H)$^+$; $^1$HNMR (300 MHz, CDCl$_3$, partial): δ 7.54 (s, 1H), 7.31-7.13 (m, 2H), 7.85-7.72 (m, 1H), 5.10-4.95 (m, 1H).

Synthesis of Isoxazoline 245

To a solution of alkyne 173 (100 mg, 0.127 mmol) in 4 mL acetonitrile was added 344 (36.3 mg, 0.127 mmol), 2,6-lutidine (0.0163 mL, 0.139 mmol) and CuI (24 mg, 0.127 mmol). The mixture was stirred overnight at room temperature, then poured into 10 mL 5% aqueous NH$_3$/ice and extracted with ethyl acetate (3×20 mL). The combined organic extract was washed with water (2×10 mL), brine (10 mL), dried (Na$_2$SO$_4$) and evaporated. The residue was purified by flash-chromatography (eluant: ethyl acetate-MeOH 5:1) yielding 245 (60 mg, 44%). Data for 245: MS (ESI) m/z 1073 (M+H)$^+$; $^1$HNMR (300 MHz, CDCl$_3$, partial): δ 7.8 (s, 1H), 7.50-7.30 (m, 3H), 7.21-7.14 (m, 3H), 5.19-4.95 (m, 2H), 4.68-3.90 (m, 7H).

Example 39

Synthesis of Isoxazolines 246-250

Scheme 62 depicts the synthesis of isoxazolines 246-250. Hydroxyiminoyl chloride 347 was converted to isoxazoline alcohol 348 as described in the literature (*J. Med. Chem.* 2003, 46, 284). The alcohol group of 348 was transformed to the azide 349, which was treated with alkyne 173 to afford isoxazoline 246. Azide 349 was coupled to substituted boronic acids to afford azides 354 and 355, which were treated with alkyne 173 to afford isoxazolines 248 and 249.

Alcohol 348 was coupled to substituted boronic acids to provide alcohols 350 and 351, which were subsequently converted to azides 352 and 353. The cycloaddition of 352 and 353 with alkyne 173 gave isoxazolines 250 and 247 respectively.

biphenyl (47 mg, 0.156 mmol) and KF (678 mg, 11.7 mmol) in THF (10 mL) at room temperature was degassed by bubbling argon through the mixture. The mixture was then stirred at room temperature for 15 h. The red suspension was poured into 10 mL sat. $Na_2CO_3$ and 100 ml water. The

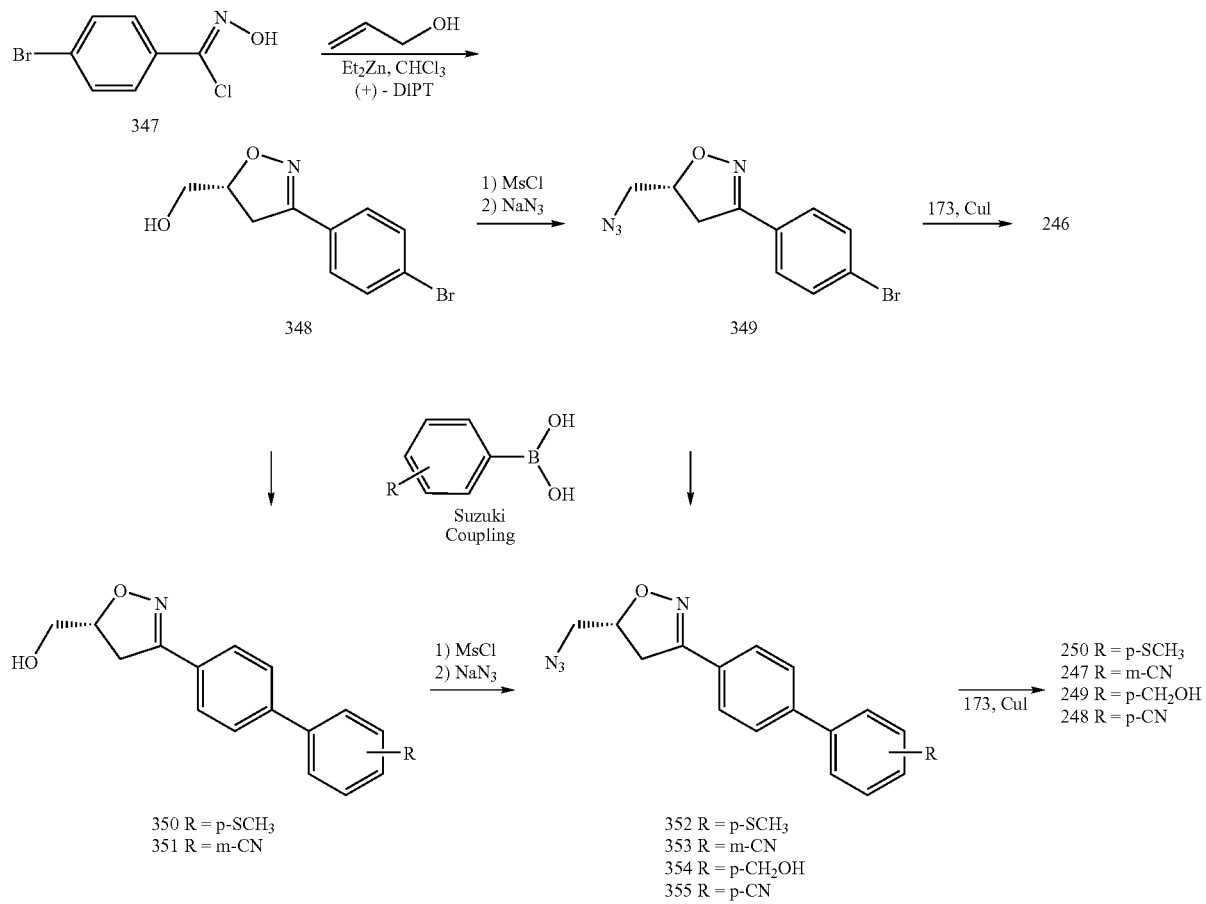

Synthesis of Azide 349

To a solution of alcohol 348 (2.00 g, 7.81 mmol) in $CH_2CH_2$ (40 mL) at 0° C. was added $Et_3N$ (2.20 mL, 15.6 mmol), followed by the dropwise addition of MsCl (911 µL, 11.7 mmol). The mixture was stirred at 0° C. for 30 min, then poured into 30 mL water/ice and extracted with $Et_2O$ (50 mL×3). The combined organic extract was washed with water (50 mL×3), dried over $MgSO_4$, and evaporated to give 2.70 g of the intermediate mesylate of suitable purity to be used in the next step. The mesylate (2.70 g) was dissolved in DMF (30 mL), $NaN_3$ (2.10 g, 31.238 mmol) was added, and the mixture stirred at 80° C. for 2.5 h. The mixture was poured into water/ice (150 mL) and $Et_2O$ (300 mL). The organic extract was washed with water (150 mL×3), dried over $MgSO_4$, and concentrated to afford azide 349 as a white crystalline solid (2.10 g, 96% yield). Data for 349: $^1$HNMR (300 MHz, $CDCl_3$): δ 7.54 (s, 4H), 4.93 (dddd, J=10, 8, 5, 5 Hz, 1H), 3.56 (dd, J=13, 5 Hz, 1H), 3.45 (dd, J=13, 5 Hz, 1H), 3.42 (dd, J=17, 11 Hz, 1H), 3.21 (dd, J=17, 7 Hz, 1H).

Synthesis of Alcohol 350

A mixture of alcohol 348 (1.00 g, 3.91 mmol), 4-methylthiophenyl boronic acid (1.10 g, 5.86 mmol), palladium acetate (18 mg, 0.078 mmol), 2-(di-tert-butylphosphino) mixture was extracted with 15% isopropyl alcohol in $CH_2CH_2$ (200 mL×3). The combined organic layer was washed with water (100 mL×3), dried over $MgSO_4$, and evaporated to provide 350 (1.2 g, 100% yield). Data for 350: $^1$HNMR (300 MHz, $CDCl_3$): δ 7.73 (d, J=8 Hz, 2H), 7.62 (d, J=8 Hz, 2H), 7.55 (d, J=8 Hz, 2H), 7.33 (d, J=8 Hz, 2H), 4.90 (dddd, J=13, 8, 5, 3 Hz, 1H), 3.90 (ddd, J=12, 6, 3 Hz, 1H), 3.71 (ddd, J=12, 8, 5 Hz, 1H), 3.43 (dd, J=17, 11 Hz, 1H), 3.32 (dd, J=17, 8 Hz, 2H), 2.53 (s, 3H), 1.90 (dd, J=8, 6 Hz, 1H).

Synthesis of Alcohol 351

Alcohol 351 was synthesized by the same procedure as reported for alcohol 350 using 3-cyanophenyl boronic acid (956 mg, 5.86 mmol). The mixture was extracted with $CH_2CH_2$ (100 mL×3). The residue was isolated by flash-chromatography on silica gel (2/100 MeOH/$CH_2CH_2$ as eluant), to afford alcohol 351 (1.0 g, 92% yield). Data for 351: $^1$HNMR (300 MHz, $CDCl_3$): δ 7.90-7.77 (m, 4H), 7.69-7.54 (m, 4H), 4.92 (dddd, J=11, 8, 5, 3 Hz, 1H), 3.92 (ddd, J=12, 6, 3 Hz, 1H), 3.72 (ddd, J=12, 8, 5 Hz, 1H), 3.45 (dd, J=17, 11 Hz, 1H), 3.34 (dd, J=17, 8 Hz, 1H), 1.92 (dd, J=8, 6 Hz, 1H).

Synthesis of Azide 352

To a suspension of alcohol 350 (2.00 g, 6.68 mmol) in CH$_2$CH$_2$ (40 mL) at 0° C. was added Et$_3$N (1.90 mL, 13.4 mmol), and then MsCl (776 μL, 10.0 mmol) dropwise. The mixture was stirred at room temperature for 2 h and then refluxed for 3 h. The mixture was cooled to room temperature and EtOAc/Hexane (150 mL/50 mL) was added. The white solid was collected, washed with water (30 mL×3), and dried under vacuum to afford 2 g of crude mesylate. The crude mesylate obtained above (0.50 g, 1.33 mmol) was suspended in DMF (8 mL), NaN$_3$ (348 mg, 5.30 mmol) was added and the mixture stirred at 80° C. for 4 h. The mixture was poured into water/ice (50 mL), extracted by EtOAc (30 mL×4), dried over MgSO$_4$, the residue was isolated by chromatography on silica gel (40/60 EtOAc/hexane as eluant) to afford azide 352 (305 mg, 71% yield) as a white powder. Data for 352: $^1$HNMR (300 MHz, CDCl$_3$): δ 7.73 (d, J=8 Hz, 2H), 7.62 (d, J=8 Hz, 2H), 7.55 (d, J=8 Hz, 2H), 7.33 (d, J=8 Hz, 2H), 4.94 (m, 1H), 3.55 (dd, J=13, 5 Hz, 1H), 3.48 (m, 2H), 3.25 (dd, J=17, 7 Hz, 1H), 2.97 (s, 3H).

Synthesis of Azide 353

To a solution of alcohol 351 (1.00 g, 3.59 mmol) in CH$_2$CH$_2$ (20 mL) at 0° C. was added Et$_3$N (1.00 mL, 7.19 mmol), followed by the dropwise addition of MsCl (419 μL, 5.39 mmol). The mixture was stirred at 0° C. for 30 min, and then at room temperature for 2 h. The mixture was poured into 100 mL water/ice and EtOAc/hexane 150 mL/50 mL). The combined organic extract was washed with water (100 mL×3), dried over MgSO$_4$, and evaporated to give 1.20 g of the crude mesylate which was used directly in the next step without further purification. The mesylate (1.20 g) was dissolved in DMF (20 mL), and NaN$_3$ (884 mg, 13.47 mmol) was added, and the mixture was stirred at 80 for 2.5 h. The mixture was poured into water/ice (150 mL) and EtOAc (250 mL). The organic extract was washed with water (100 mL×3), dried over MgSO$_4$, and evaporated. The residue was separated by chromatography on silica gel (30/70 EtOAc/hexane as eluant) to afford azide 353 (836 mg, 77% yield) as a white crystalline solid. Data for 353: $^1$HNMR (300 MHz, CDCl$_3$): δ 7.90-7.77 (m, 4H), 7.69-7.50 (m, 4H), 4.97 (dddd, J=15, 7, 5, 5 Hz, 1H), 3.57 (dd, J=13, 5 Hz, 1H), 3.50 (m, 2H), 3.26 (dd, J=17, 7 Hz, 1H).

Synthesis of Azide 354

A mixture of azide 349 (300 mg, 1.07 mmol), 4-(hydroxymethyl)phenyl boronic acid (286 mg, 1.60 mmol), palladium acetate (5 mg, 0.021 mmol), 2-(di-tert-butylphosphino)biphenyl. (13 mg, 0.043 mmol) and KF (188 mg, 3.20 mmol) in THF (4 mL) at was degassed by bubbling argon through the mixture. The mixture was then stirred at room temperature for 15 h. The red suspension was poured into 5 mL sat. Na$_2$CO$_3$ and 20 mL water. The mixture was extracted with 5% MeOH/CH$_2$CH$_2$ (200 mL). The combined organic layer was washed by water (1100 mL×3), dried over MgSO$_4$, and evaporated. The residue was purified by chromatography on silica gel (1.5/100 MeOH/CH$_2$CH$_2$ as eluant) to afford azide 354 (220 mg, 67% yield). Data for 354: $^1$HNMR (300 MHz, CDCl$_3$): δ 7.75 (d, J=8 Hz, 2H), 7.65 (d, J=8 Hz, 2H), 7.62 (d, J=8 Hz, 2H), 7.47 (d, J=8 Hz, 2H), 4.95 (dddd, J=10, 8, 5, 5 Hz, 1H), 4.76 (d, J=6 Hz, 2H), 3.55 (dd, J=13, 5 Hz, 1H), 3.50 (dd, J=17, 11 Hz, 2H), 3.25 (dd, J=17, 7 Hz, 1H), 1.71 (dd, J=5, 5 Hz, 1H).

Synthesis of Azide 355

A mixture of azide 349 (300 mg, 1.07 mmol), 4-cyanophenyl boronic acid (261 mg, 1.60 mmol), palladium acetate (5 mg, 0.021 mmol), 2-(di-tert-butylphosphino)biphenyl (13 mg, 0.043 mmol) and KF (188 mg, 3.20 mmol) in THF (4 mL) at room temperature was degassed by bubbling argon through the mixture. The mixture was then stirred at room temperature for 15 h. The red suspension was poured into 5 mL sat. Na$_2$CO$_3$ and 20 mL water. The mixture was extracted with CH$_2$CH$_2$ (50 mL×3). The combined organic layer was washed by water (100 mL×3), dried over MgSO$_4$, and evaporated. The residue was purified by chromatography on silica gel (30/70 EtOAc/hexane as eluant) to afford azide 355 (300 mg, 93% yield). Data for 355: $^1$HNMR (300 MHz, CDCl$_3$): δ 7.83-7.63 (m, 8H), 4.97 (dddd, J=16, 7, 5, 5 Hz, 1H), 3.58 (dd, J=13, 5 Hz, 1H), 3.50 (dd, J=16, 10 Hz, 1H), 3.40 (dd, J=13, 5 Hz, 1H), 3.27 (dd, J=16, 7 Hz, 1H).

General Procedure for the Synthesis of Isoxazolines 246-250

To a mixture of alkyne 173 (100 mg, 0.127 mmol), the appropriate azide (0.140 mmol, 1.1 eq) in acetonitrile (4.0 mL) at room temperature under argon was added 2,6-lutidine (22 μL, 0.191 mmol, 1.1 eq), followed by the addition of copper (I) iodide (12 mg, 0.064 mmol). The mixture was stirred at room temperature for 1.5 to 6 h. After the reaction was complete, 1 mL 5% NH$_4$OH was added. The mixture was stirred at room temperature for 10 min. The acetonitrile was removed under vacuum. The aqueous phase was extracted with CH$_2$Cl$_2$ (30 mL×3), dried over Na$_2$SO$_4$, and evaporated. The residue was purified by chromatography on silica gel (20/80 to 30/70 MeOH/EtOAc) to provide isoxazolines 246 (116 mg, 85% yield), 247 (120 mg, 87% yield), 248 (120 mg, 87% yield), 249 (72 mg, 52% yield), and 250 (93 mg, 66% yield).

Data for 246: MS (ESI) m/z 1067.6 (M−H)$^+$; $^1$HNMR (300 MHz, CDCl$_3$, partial): δ 7.56 (s, 1H), 7.53 (d, J=9 Hz, 2H), 7.74 (d, J=9 Hz, 2H), 5.12 (br s, 1H), 4.71-4.52 (m, 4H), 4.43 (d, J=7 Hz, 1H), 4.29 (br s, 1H), 4.08 (m, 1H), 3.69-3.16 (m, 10H), 3.03 (dd, J=10, 10 Hz, 1H).

Data for 247: MS (ESI) m/z 1090.5 (M)$^+$; $^1$HNMR (300 MHz, CDCl$_3$, partial): δ 7.88 (s, 1H), 7.83 (d, J=8 Hz, 1H), 7.75-7.55 (m, 7H), 5.17 (br s, 1H), 5.09 (br s, 1H), 4.80-4.60 (m, 4H), 4.41 (d, J=7 Hz, 1H), 4.26 (br s, 1H), 4.09 (m, 1H), 3.68-3.18 (m, 10H).

Data for 248: MS (ESI) m/z 1090.3 (M)$^+$; $^1$HNMR (300 MHz, CDCl$_3$, partial): δ 7.77-7.60 (m, 9H), 5.17 (br s, 1H), 5.09 (br s, 1H), 4.71-4.55 (m, 4H), 4.41 (d, J=7 Hz, 1H), 4.26 (br s, 1H), 4.09 (m, 1H), 3.67-3.20 (m, 4H).

Data for 249: MS (ESI) m/z 1095.4 (M)$^+$; $^1$HNMR (300 MHz, CDCl$_3$, partial): δ 7.69-7.57 (m, 7H), 7.46 (d, J=8 Hz, 2H), 5.12 (d, J=4 Hz, 2H), 4.70-4.54 (m, 4H), 4.42 (d, J=7 Hz, 1H), 4.28 (br s, 1H), 4.08 (m, 1H), 3.69-3.20 (m, 10H).

Data for 250: MS (ESI) m/z 1111.4 (M)$^+$; $^1$HNMR (300 MHz, CDCl$_3$, partial): δ 7.68-7.50 (m, 7H), 7.35 (d, J=8 Hz, 2H), 5.12 (br s, 1H), 4.71-4.54 (m, 4H), 4.43 (d, J=8 Hz, 1H), 4.29 (br s, 1H), 4.07 (m, 1H), 3.69-3.20 (m, 10H), 3.03 (dd, J=10, 10 Hz, 1H).

Example 40

Synthesis of Isoxazolines 251 and 252

Scheme 63 depicts the synthesis of isoxazoline 251. Hydroxyiminoyl chloride 357 was made from the oxime (356) of 3,5-dichlorobenzaldehyde. The cycloaddition of 357 and allyl alcohol (via the intermediate nitrile oxide) afforded racemic isoxazoline alcohol 358. The alcohol was converted to azide 360 via the mesylate 359. The cycloaddition of 360 with alkyne 173 yielded isoxazoline 251 (as a diasteromeric mixture). Isoxazoline 252 was synthesized (also as a diastereomeric mixture) by carrying 3,5-difluorobenzaldehyde through the sequence of Scheme 63.

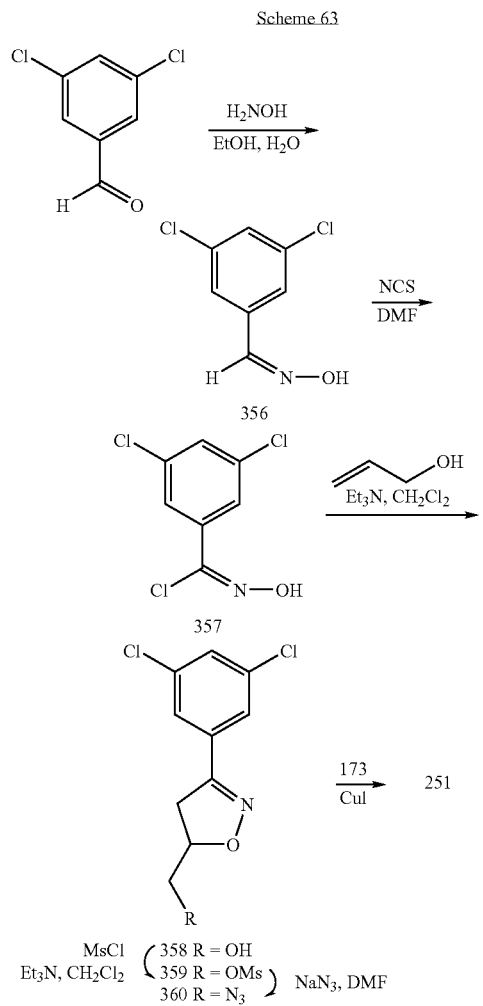

Synthesis of Oxime 356

A solution of 3,5-dichlorobenzaldehyde (2.0 g, 11.42 mmol) and hydroxylamine hydrochloride (0.87 g, 12.57 mmol) in ethanol (40 mL) and water (80 mL) was cooled to 4° C., and NaOH (50% (w/w), 2.3 mL) was added. The reaction mixture was stirred for 3 h at room temperature. The reaction mixture was then neutralized to pH 6.0, and partitioned with methylene chloride and water. The aqueous layer was extracted twice with methylene chloride, and the combined organic layer was washed with brine, dried (Na$_2$SO$_4$), and evaporated to yield; 356 (2.15 g, 99% yield) as a white solid. Data for 356: $^1$HNMR (300 MHz, CDCl$_3$): δ 8.11 (s, 1H), 7.45 (s, 1H), 7.34 (s, 1H).

Synthesis of Hydroximinoyl Chloride 357

To a solution of oxime 356 (2.15 g, 11.31 mmol) in dimethylformamide (10 mL) was added N-chlorosuccinimide (1.5 g, 11.31 mmol). The reaction mixture was warmed to 50° C. for 1 h. The reaction was then diluted with ethyl acetate (50 mL), and washed with brine, dried (Na$_2$SO$_4$), and evaporated to yield 357 (2.60 g, 100% yield). Data for 357: $^1$HNMR (300 MHz, CDCl$_3$): δ 7.8 (s, 1H), 7.50 (s, 1H), 7.17 (s, 1H).

Synthesis of Isoxazoline Alcohol 358

To a solution of hydroximinoyl chloride 357 (1.50 g, 6.68 mmol) in methylene chloride (50 mL) was added allyl alcohol (0.45 mL, 6.68 mmol). The mixture was cooled to 0° C., and triethylamine (1.0 mL, 6.68 mmol) was added. The reaction mixture was slowly warmed to room temperature, stirred for 16 h, quenched with water (50 mL), and extracted twice with methylene chloride. The combined organic layer was washed with brine, dried over Na$_2$SO$_4$, and evaporated to yield; 358 (1.60 g, 100% yield). Data for 358: $^1$HNMR (300 MHz, CDCl$_3$): δ 7.47 (s, 2H), 7.32 (s, 1H), 4.84 (m, 1H), 3.82 (dd, J=15, 3 Hz, 1H), 3.62 (dd, J=16, 4 Hz, 1H), 3.23 (m, 2H).

Synthesis of Mesylate 359

Alcohol 358 (1.60 g, 6.50 mmol) was dissolved in 5 mL methylene chloride, and the mixture cooled to 0° C. Triethylamine (1.8 mL, 13.0 mmol) was added, followed by methanesulfonyl chloride (0.7 mL, 9.10 mmol). The mixture was allowed to warm to room temperature and stirred for 1 h. Methylene chloride (20 mL) was added, and the mixture washed twice with 1N HCl, then twice with 10% aqueous sodium carbonate, and then brine. The organic phase was dried (Na$_2$SO$_4$), and evaporated to yield mesylate 359 (1.60 g, 99% yield). Data for 359: $^1$HNMR (300 MHz, CDCl$_3$): δ 7.67 (s, 2H), 7.56 (s, 1H), 5.22 (m, 1H), 4.51 (m, 2H), 3.60 (m, 1H), 3.40 (dd, J=7, 15 Hz, 1H), 3.25 (s, 3H).

Synthesis of Azide 360

A solution of mesylate 359 (1.60 g, 6.15 mmol) in dimethylformamide (10 mL) was treated with sodium azide (1.6 g, 24.60 mmol) and the mixture heated to 80° C. for 3 h. The reaction mixture was cooled to room temperature, diluted with ethyl acetate (50 mL), and washed with brine (2×50 mL). Drying (Na$_2$SO$_4$), and evaporation provided azide 360 (1.28, 77% yield) as a yellow oil of suitable purity for use in subsequent reactions. Data for 360: $^1$HNMR (300 MHz, CDCl$_3$): δ 7.45 (s, 2H), 7.39 (s, 1H), 3.51 (dd, J=17, 4 Hz, 1H), 3.35-3.20 (m, 2H), 3.13 (m, 1H).

Synthesis of Isoxazoline 251

A solution of alkyne 173 (170 mg, 0.220 mmol) in tetrahydrofuran (10 mL) was treated with azide 360 (0.08 g, 0.324 mmol), N,N-diisopropylethylamine (0.05 mL, 0.22 mmol) and copper (I) iodide (0.03 g, 0.160 mmol), and the mixture was stirred under argon at room temperature for 16 h. The reaction mixture was diluted with ethyl acetate (50 mL), and washed with brine (2×50 mL). The organic phase was dried and evaporated. The residue was purified by preparative thin layer chromatography (using 80% CH$_2$Cl$_2$, 20% MeOH, 1% NH$_4$OH as eluant) to provide isoxazoline 251 (197 mg, 86% yield) as a yellow solid. Data for 251: $^1$HNMR (300 MHz, CDCl$_3$, partial): δ 7.36 (s, 2H), 7.22 (s, 1H), 4.96 (m, 2H), 4.24 (m, 2H) 4.10 (m, 1H), 3.52-3.15 (m, 2H), 3.06 (s, 1H), 2.59 (m, 2H).

Synthesis of Isoxazoline 252

This compound was made from alkyne 173 and the requisite 3,5-difluoro azide using the same procedures reported above for the synthesis of isoxazoline 251. Data for 252: ¹H-NMR (300 MHz, CDCl₃, partial): δ 7.50 (s, 1H), 7.10 (d, J=3 Hz, 2H), 6.86 (m, 1H), 5.10 (m, 1H), 5.08 (m, 1H), 4.66 (m, 1H), 4.61 (m, 2H), 4.41 (m, 1H), 4.20 (m, 1H), 4.10 (m, 1H), 3.68 (m, 2H), 3.32-3.22 (m, 2H), 2.84 (t, 2H).

Example 41

Synthesis of Triazoles 361-367

Scheme 64 depicts the synthesis of triazoles 361 and 362. Azide 416 was treated with alkynes 173 and 174 to produce triazoles 361 and 362 respectively.

Scheme 64

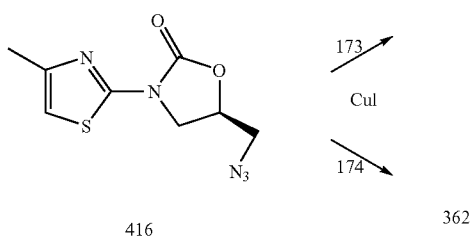

Synthesis of Azide 416

Azide 416 was synthesized from 2-amino-3-methyl-thiazole using the chemistry reported in the literature (Brickner, S. J. et al. *J. Med. Chem.* 1996, 39, 673). Data for 416: ¹HNMR (300 MHz, CDCl₃): δ 6.59 (s, 1H), 4.92-4.87 (m, 1H), 4.34 (t, J=9 Hz, 1H), 4.12 (dd, J=6, 3 Hz, 1H), 3.73 (dd, J=3, 12 Hz, 1H), 3.61 (dd, J=3, 12 Hz, 1H), 2.35 (s, 3H).

Synthesis of Triazole 361

To a mixture of alkyne 173 (150 mg, 0.191 mmol), azide 416 (55 mg, 0.229 mmol) and copper (I) iodide (18.3 mg, 0.096 mmol) was added THF (10 mL) and the mixture was repeatedly degassed and flushed with argon. Then i-Pr₂NEt (0.05 mL) was introduced and the mixture was stirred at room temperature for 1 h. The reaction mixture was poured into NH₄Cl (30 mL) and stirred for few minutes. Then NH₄OH (3 mL) was added and the mixture was extracted with methylene chloride (3×40 ml). The combined organic layer was dried (Na₂SO₄), concentrated and flash chromatographed over silica gel (methylene chloride: MeOH: NH₄OH=12:1:0.025) to provide 150 mg of the product. Data for 361: MS (ESI) no/z 514 (M+2H)²⁺; ¹HNMR (300 MHz, CDCl₃, partial): δ 7.59 (s, 1H), 6.56 (s, 1H), 5.22-5.10 (m, 2H), 4.79-4.62 (m, 4H), 4.46-4.39 (m, 2H), 4.28 (br d, J=3 Hz, 1H), 0.91-0.87 (m, 6H).

Synthesis of Triazole 362

The cycloaddition of alkyne 174 (150 mg, 0.187 mmol) and azide 416 (49.2 mg, 0.206 mmol) was performed under similar conditions as described above for the synthesis of 361 to afford 169 mg of 362. Data for 362: MS (ESI) m/z 521 (M+2H)₂; ¹H NMR (300 MHz, CDCl₃, partial): δ 7.49 (s, 1H), 6.56 (s, 1H), 5.18-5.12 (m, 2H), 3.34 (s, 3H), 3.03 (t, J=9 Hz, 1H), 0.91-0.87 (m, 6H).

Synthesis of Triazole 363

Triazole 363 (117 mg) was synthesized from alkyne 174 (100 mg, 0.125 mmol) and azide 189 (29.7 mg, 0.126 mmol) following the same procedure as described above for compound 361. Data for 363: MS (ESI) m/z 519 (M+2H)²⁺; ¹H NMR (300 MHz, CDCl₃, partial): δ 7.52 (s, 1H), 7.35-7.28 (m, 2H), 7.08 (br d, J=8 Hz, 1H), 6.84 (dd, J=2, 8 Hz, 1H), 5.10-5.01 (m, 2H), 4.29 (d, J=3 Hz, 1H), 3.23 (t, J=8 Hz, 1H), 3.03 (t, J=9 Hz, 2H), 0.91-0.87 (m, 6H).

Synthesis of Triazole 364

Triazole 364 (141 mg) was synthesized from alkyne 174 (150 mg, 0.187 mmol) and azide 277 (57.5 mg, 0.206 mmol) following the same procedure as described above for compound 361. Data for 364: MS (ESI) nz/z 541 (M+2H)²⁺; ¹H NMR (300 MHz, CDCl₃, partial): δ 7.52 (s, 1H), 7.22 (d, J=2 Hz, 1H), 6.93 (dd, J=2, 8 Hz, 1H), 6.83 (t, J=9 Hz, 1H), 5.09 (d, J=5 Hz, 1H), 5.05-4.98 (m, 1H), 4.45 (d, J=7 Hz, 1H), 3.88 (dd, J=6, 3 Hz, 1H), 3.34 (s, 3H), 3.03 (t, J=9 Hz, 1H), 0.91-0.87 (m, 6H).

Synthesis of Triazole 365

Triazole 365 (200 mg) was synthesized from alkyne 174 (150 mg, 0.187 mmol) and azide 266 (63.6 mg, 0.206 mmol) following the same procedure as described above for compound 361. Data for 365: MS (ESI) m/z 556 (M+2H)²⁺; ¹H NMR (300 MHz, CDCl₃, partial): δ 7.52 (s, 1H), 7.28-7.23 (m, 1H), 6.98-6.91 (m, 2H), 5.12 (d, J=5 Hz, 1H), 5.04-5.02 (m, 1H), 4.45 (d, J=7 Hz, 1H), 4.28 (br d, J=3 Hz, 1H), 4.13-4.05 (m, 2H), 3.88 (dd, J=6, 3 Hz, 1H), 3.74 (t, J=5 Hz, 2H), 3.34 (s, 3H), 3.03 (t, J=9 Hz, 1H), 0.91-0.87 (m, 6H).

Synthesis of Triazole 366

The required 3,5-difluorophenyl oxazolidinone azide was synthesized from 3,5-difluoroaniline using the same procedure as that used for the synthesis of azide 189. Triazole 366 (157 mg) was synthesized from alkyne 174 (150 mg, 0.187 mmol) and the 3,5-difluorophenyl oxazolidinone azide (52.3 mg, 0.206 mmol) following the same procedure as described above for compound 361. Data for 366: MS (ESI) m/z 528.6 (M+2H)²⁺, 1055.8 (M+H)⁺; ¹H NMR (300 MHz, CDCl₃, partial): δ 7.50 (s, 1H), 7.02 (dd, J=2, 9 Hz, 2H), 6.62-6.55 (m, 1H), 5.14 (d, J=5 Hz, 1H), 5.10-5.02 (m, 1H), 4.81 (d, J=6 Hz, 1H), 4.72 (d, J=4 Hz, 2H), 4.45 (d, J=7 Hz, 1H), 3.93 (dd, J=6, 3 Hz, 1H), 3.34 (s, 3H), 3.23 (dd, J=7, 3 Hz, 1H), 3.03 (t, J=10 Hz, 1H), 0.91-0.86 (m, 6H).

Synthesis of Triazole 367

Triazole 367 (200 mg) was synthesized from alkyne 174 (150 mg, 0.187 mmol) and azide 323 (59.1 mg, 0.206 mmol) following the same procedure as described above for compound 361. Data for 367: MS (ESI) m/z 545 (M+2H)²⁺; ¹H NMR (300 MHz, CDCl₃, partial): δ 7.58 (d, J=3 Hz, 1H), 7.50 (s, 1H), 7.40 (d, J=9 Hz, 1H), 7.28-7.24 (m, 1H), 5.14 (d, J=4 Hz, 1H), 5.10-5.02 (m, 1H), 4.44 (d, J=7 Hz, 1H), 4.29 (br d, J=2 Hz, 1H), 3.95 (dd, J=6, 3 Hz, 1H), 3.34 (s, 3H), 3.23 (dd, J=7, 3 Hz, 1H), 3.03 (t, J=9 Hz, 1H), 0.91-0.86 (m, 6H).

Example 42

Synthesis of Triazoles 368-370

Scheme 65 depicts the synthesis of triazoles 368-370. The required azides 420, 424, and 428 were synthesized using standard methods from the appropriate anilines. The cycloaddition of these azides with alkyne 173 afforded triazoles 368-370.

Scheme 65

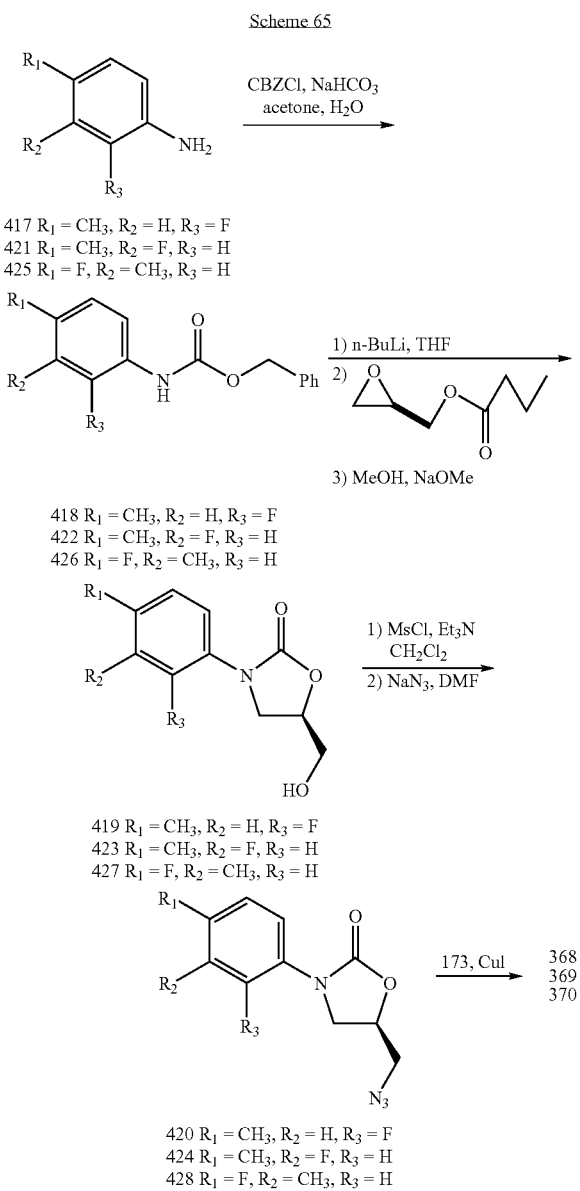

417 $R_1 = CH_3, R_2 = H, R_3 = F$
421 $R_1 = CH_3, R_2 = F, R_3 = H$
425 $R_1 = F, R_2 = CH_3, R_3 = H$

418 $R_1 = CH_3, R_2 = H, R_3 = F$
422 $R_1 = CH_3, R_2 = F, R_3 = H$
426 $R_1 = F, R_2 = CH_3, R_3 = H$

419 $R_1 = CH_3, R_2 = H, R_3 = F$
423 $R_1 = CH_3, R_2 = F, R_3 = H$
427 $R_1 = F, R_2 = CH_3, R_3 = H$

420 $R_1 = CH_3, R_2 = H, R_3 = F$
424 $R_1 = CH_3, R_2 = F, R_3 = H$
428 $R_1 = F, R_2 = CH_3, R_3 = H$

Synthesis of Azides 420, 424, 428

The azides were synthesized from the substituted anilines using the chemistry reported in the literature (Brickner, S. J. et al. *J. Med. Chem.* 1996, 39, 673).

Data for 420: MS (ESI) m/z 291.9 (M+H+CH$_3$CN)$^+$, $^1$H-NMR, (300 MHz, CDCl$_3$): δ 7.31 (t, J=8 Hz, 1H), 6.96-6.91 (m, 2H), 4.76 (m, 1H), 4.01 (t, J=9 Hz, 1H), 3.73 (m, 1H), 3.63 (dd, J=13, 4 Hz, 1H), 3.50 (dd, J=14, 5 Hz, 1H), 2.31 (s, 3H).

Data for 424: $^1$H-NMR, (300 MHz, CDCl$_3$): δ 7.28 (dd, J=12, 2 Hz, 1H), 7.08-7.00 (m, 2H), 4.71 (m, 1H), 3.98 (t, J=9 Hz, 1H), 3.74 (m, 1H), 3.63 (dd, J=13, 4 Hz, 1H), 3.50 (dd, J=14, 5 Hz, 1H), 2.16 (d, J=2 Hz, 3H).

Data for 428: $^1$H-NMR, (300 MHz, CDCl$_3$) δ 7.29 (m, 1H), 7.19 (m, 1H), 6.92 (t, J=9 Hz, 1H), 4.69 (m, 1H), 3.98 (t, J=9 Hz, 1H), 3.75 (m, 1H), 3.62 (dd, J=13, 4 Hz, 1H), 3.50 (dd, J=13, 5 Hz, 1H), 2.21 (s, 3H).

Synthesis of Triazole 368

This compound was obtained from the reaction of alkyne 173 (0.115 g, 0.148 mole) with azide 420 (0.048 g, 0.192 mmol) in the presence of CuI (0.023 g, 0.111 mmol) in THF (5 mL) and Hunig's base (0.05 mL) at room temperature within 30 min. The reaction was poured into a mixture containing saturated NH$_4$Cl/NH$_4$OH (pH=9.5, 30 mL) and extracted with CH$_2$Cl$_2$ (3×30 mL). The combined organic layer was dried over Na$_2$SO$_4$ and the solvent evaporated. The crude was purified on silica gel eluting with CH$_2$Cl$_2$/MeOH/NH$_4$OH 18:1:0.05 to 15:1:0.05 to 12:1:0.05 to give 368 as a white solid (0.146 g, 95% yield). Data for 368: MS (ESI) m/z 1037.1 (M+H)$^+$; $^1$H-NMR (300 MHz, CDCl$_3$, partial): δ 7.59 (s, 1H), 7.05 (t, J=8 Hz, 1H), 6.89-6.84 (m, 2H), 5.02 (m, 2H), 4.37 (d, J=7 Hz, 1H), 4.22 (d, J=2 Hz, 1H), 4.07 (m, 2H), 3.78 (m, 1H), 3.60 (m, 2H), 0.82 (m, 6H).

Synthesis of Triazole 369

This compound was obtained from the reaction of alkyne 173 (0.115 g, 0.148 mmol) with azide 424 (0.048 g, 0.192 mmol) in the presence of CuI (0.023 g, 0.111 mmol) in THF (5 mL) and Hunig's base (0.02 mL) at room temperature within 30 min. The reaction was worked-up as described for the synthesis of 368 and purified on silica gel eluting with CHCl$_3$/MeOH/NH$_4$OH 15:1:0.05 to give 369 as a white solid (0.121 g, 79% yield). Data for 369: MS (ESI) m/z 1037.8 (M+H)$^+$; $^1$H-NMR (300 MHz, CDCl$_3$, partial): δ 7.61 (s, 1H), 7.24 (m, 1H), 7.11 (t, J=8 Hz, 1H), 6.95 (m, 1H), 5.08 (d, J=4 Hz, 1H), 5.02 (m, 1H), 4.69 (m, 3H), 4.57 (m, 1H), 4.42 (d, J=7 Hz, 1H), 4.27 (d, J=3 Hz, 1H), 4.10 (m, 2H), 3.91 (m, 1H), 3.65 (m, 2H), 0.88 (m, 6H).

Synthesis of Triazole 370

This compound was obtained from the reaction of alkyne 173 (0.115 g, 0.148 mmol) with azide 428 (0.048 g, 0.192 mmol) in the presence of CuI (0.023 g, 0.111 mmol) in THF (5 mL) and Hunig's base (0.02 mL) at room temperature within 30 min. The reaction was worked-up as described for the synthesis of 368 and purified on silica gel eluting with CHCl$_3$/MeOH/NH$_4$OH 15:1:0.05 to give 370 as a white solid (0.129 g, 84% yield). Data for 370: MS (ESI) m/z 1037.8 (M+H)$^+$; $^1$H-NMR (300 MHz, CDCl$_3$, partial): δ 7.62 (s, 1H), 7.23-7.16 (m, 2H), 6.98 (t, J=9 Hz, 1H), 5.08-5.04 (m, 2H), 4.72 (m, 3H), 4.44 (d, J=7 Hz, 1H), 4.29 (m, 2H), 4.11 (m, 2H), 3.93 (m, 1H), 3.66 (m, 2H), 0.90 (m, 6H).

Example 43

Synthesis of Triazoles 371 and 372

Scheme 66 depicts the synthesis of triazoles 371 and 372. The silylethers 429 and 430 were synthesized from the available carboxylic acids, and were transformed into azides 435 and 436. The cycloaddition of 435 and 436 yielded triazoles 371 and 372 respectively.

Scheme 66

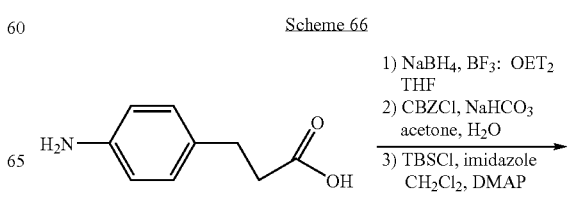

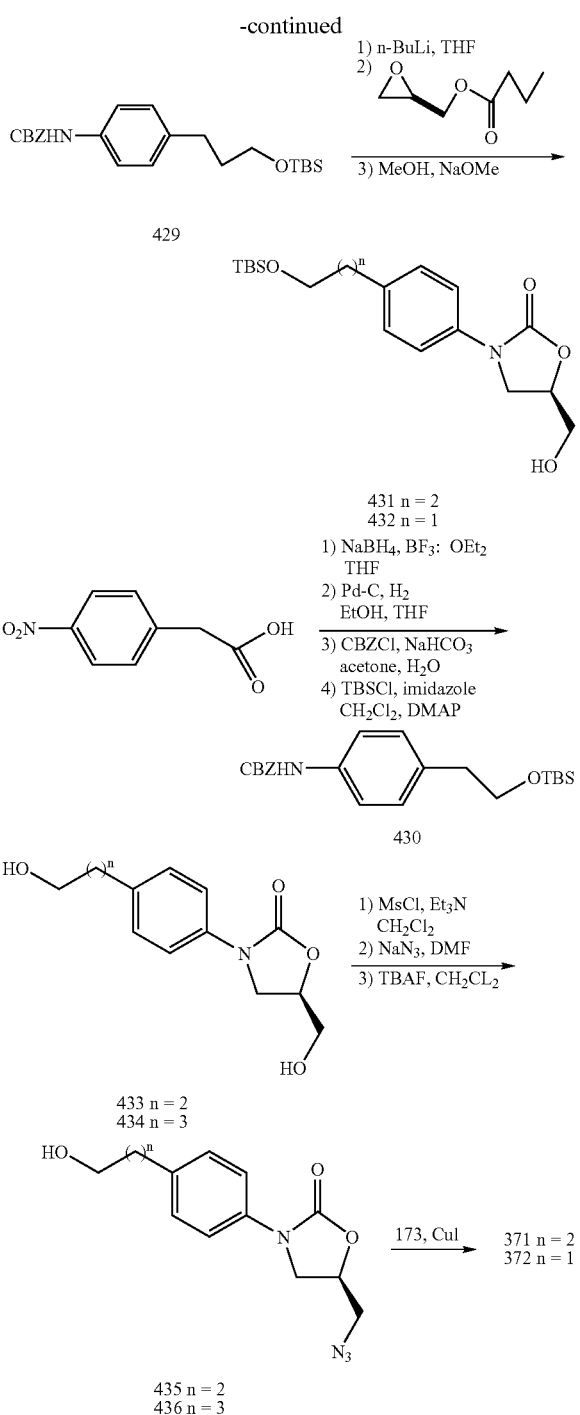

Synthesis of Silylethers 429 and 430

3-(4-Amino-phenyl)-propionic acid was reduced to the corresponding amino alcohol as described in the literature (Anhowry et al., *J. Chem. Soc. Perkin Trans.* 11-974, 191-192). The crude amino alcohol was sequentially protected with CBZ- and TBS-groups as described below for compound 437. The crude was purified on silica gel (eluting with EtOAc/Hexanes, 1:7) to give compound 429 as colorless oil (about 74% yield, three steps).

(4-Nitro-phenyl)-acetic acid was reduced to the nitro-alcohol as described in the literature (Anhowry et al., *J. Chem. Soc. Perkin Trans. I* 1974, 191-192). Catalytic hydrogenation afforded the corresponding amino alcohol. Subsequent CBZ- and TBS-group protection, as described below for compound 437, followed by purification on a silica gel column (eluting with EtOAc/Hexanes, 1:8 to 1:7) gave compound 430 as white solid (about 78% yield, 4 steps).

Synthesis of Azides 435 and 436

Silylethers 429 and 430 were converted to azides 435 and 436 using the chemistry reported in the literature (Brickner, S. J. et al. *J. Med. Chem.* 1996, 39, 673), followed by desilylation using standard conditions.

Synthesis of Triazoles 371 and 372

Triazole 371 was obtained from the reaction of alkyne 173 (0.120 g, 0.154 mmol) with azide 435 (0.051 g, 0.185 mmol) in the presence of CuI (0.023 g, 0.111 mmol) in THF (5 mL) and Hunig's base (0.02 mL) at room temperature within 30 min. The reaction was worked-up as described for the synthesis of triazole 368 and purified on silica gel (eluting with $CH_2Cl_2$/MeOH/$NH_4OH$ 15:1:0.05 to 14:1:0.05) to give 371 as a white solid (0.124 g, 76% yield). Data for 371: MS (ESI) m/z 1063.9 $(M+H)^+$; $^1$H-NMR (300 MHz, $CDCl_3$, partial): δ 7.63 (s, 1H), 7.32 (d, J=8 Hz, 2H), 7.19 (d, J=8 Hz, 2H), 5.05 (m, 2H), 4.72 (m, 3H), 4.45 (d, J=7 Hz, 2H), 4.28 (d, J=4 Hz, 1H), 4.15 (m, 2H), 3.92 (m, 1H), 0.90 (m, 6H).

Triazole 372 was obtained from the reaction of alkyne 173 (0.120 g, 0.154 mmol) with azide 436 (0.049 g, 0.185 mmol) in the presence of CuI (0.023 g, 0.111 mmol) in THF (5 mL) and Hunig's base (0.02 mL) at room temperature within 30 min. The reaction was worked-up as described for the synthesis of triazole 368 and purified on silica gel (eluting with $CH_2Cl_2$/MeOH/$NH_4OH$ 15:1:0.05 to 14:1:0.05) to give 372 as a white solid (0.116 g, 72% yield). Data for 372: MS (ESI) m/z 1050.0 $(M+H)^+$; $^1$H-NMR (300 MHz, $CDCl_3$, partial): δ 7.59 (s, 1H), 7.31 (d, J=8 Hz, 2H), 7.18 (d, J=8 Hz, 2H), 5.02 (m, 2H), 4.66 (m, 3H), 4.51 (m, 1H), 4.40 (d, J=6 Hz, 2H), 4.24 (m, 1H), 4.1m, 2H), 3.61 (m, 2H), 0.86 (m, 6H).

Example 44

Synthesis of Triazole 373

Scheme 67 depicts the synthesis of triazole 373. Trans 4-aminocyclohexanol was converted to carbamate 437 prior to further manipulation into azide 439. The cycloaddition of 439 with alkyne 173 afforded triazole 373.

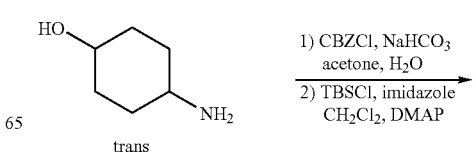

Scheme 67

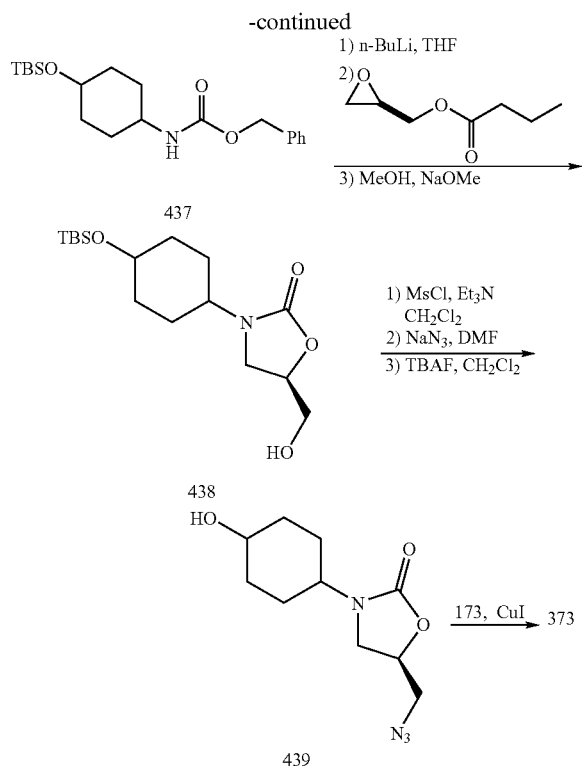

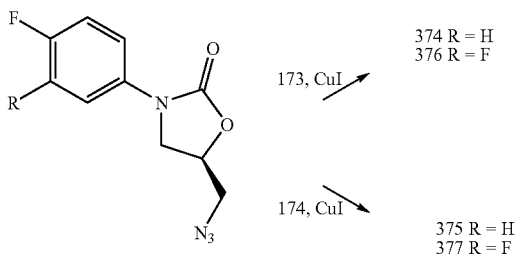

Synthesis of Carbamate 437

Trans 4-aminocyclohexanol was protected with a CBZ-group as described in the literature (Brickner, S. J. et al. *J. Med. Chem.* 1996, 39, 673) and protected with a TBS-group as described in the literature (Green, T. W.; Wuts, P. G. M., Protective Groups in Organic Synthesis, 1991, John Wiley & Sons, Inc., pp 77-83) to give crude compound 437 which was used without further purification.

Synthesis of Azide 439

Carbamate 437 was converted to azide 439 using the chemistry reported in the literature (Brickner, S. J. et al. *J. Med. Chem.* 1996, 39, 673).

Synthesis of Triazole 373

Triazole 373 was obtained from the reaction of alkyne 173 (0.140 g; 0.180 mmol) with azide 439 (0.050 g, 0.210 mmol) in the presence of CuI (0.023 g, 0.111 mmol) in THF (5 mL) and Hunig's base (0.05 mL) at room temperature within 30 min. The reaction was worked-up as described for the synthesis of triazole 368 and purified on silica gel (eluting with CH$_2$Cl$_2$/MeOH/NH$_4$OH 14:1:0.075) to give triazole 373 as a white solid (0.135 g, 73% yield). Data for 373: MS (ESI) m/z 1027.8 (M+H)$^+$; $^1$H-NMR (300 MHz, CDCl$_3$, partial): δ 7.50 (s, 1H), 5.13 (m, 2H), 4.90 (m, 2H), 4.61 (m, 4H), 4.12 (m, 3H), 0.90 (m, 6H).

Example 45

Synthesis of Triazoles 374-377

Scheme 68 depicts the synthesis of triazoles 374-377. The cycloaddition of fluoroaryl azides 440 and 441 with alkynes 0.173 and 174 provided triazoles 374-377.

Synthesis of Azides 440 and 441

The azides were synthesized from the substituted anilines using the chemistry reported in the literature (Brickner, S. J. et al. *J. Med. Chem.* 1996, 39, 673).

Synthesis of Triazole 374

This compound was obtained from the reaction of alkyne 173 (0.250 g, 0.318 mmol) with azide 440 (0.090 g, 0.381 mmol) in the presence of CuI (0.031 g, 0.150 mmol) in THF (10 mL) and Hunig's base (0.1 mL) at room temperature within 30 min. The reaction was worked-up as described for the synthesis of 368 and purified on silica gel eluting with CH$_2$Cl$_2$/MeOH/NH$_4$OH 15:1:0.05 to give 374 as a white solid (0.294 g, 90% yield). Data for 374: MS (ESI) m/z 1023.7 (M+H)$^+$; $^1$H-NMR (300 MHz, CDCl$_3$, partial): δ 7.55 (s, 1H), 7.30 (m, 2H), 6.97 (t, J=9 Hz, 2H), 4.99 (m, 2H), 4.36 (d, J=7 Hz, 1H), 4.22 (d, J=3 Hz, 1H), 4.07 (m, 2H), 3.84 (m, 1H), 3.59 (m, 2H), 0.82 (m, 6H).

Synthesis of Triazole 375

This compound was obtained from the reaction of alkyne 174 (0.150 g, 0.187 mmol) with azide 440 (0.068 g, 0.288 mmol) in the presence of CuI (0.023 g, 0.111 mmol) in THF (5 mL) and Hunig's base (0.05 mL) at room temperature within 30 min. The reaction was worked-up as described for the synthesis of 368 and purified on silica gel eluting with CH$_2$Cl$_2$/MeOH/NH$_4$OH 15:1:0.05 to 12:1:0.05 to give 375 as a white solid (0.139 g, 72% yield). Data for 375: MS (ESI) m/z 1037.7 (M+H)$^+$; $^1$H-NMR (300 MHz, CDCl$_3$): δ 7.46 (s, 1H), 7.27 (m, 2H), 6.97 (m, 2H), 5.05 (d, J=5 Hz, 1H), 4.96 (m, 1H), 4.65 (m, 4H), 4.38 (d, J=7 Hz, 1H), 4.22 (d, J=3 Hz, 1H), 4.05 (m, 2H), 3.87 (m, 1H), 3.56 (m, 2H), 0.83 (m, 6H).

Synthesis of Triazole 376

This compound was obtained from the reaction of alkyne 173 (0.140 g, 0.180 mmol) with azide 441 (0.053 g, 0.210 mmol) in the presence of CuI (0.023 g, 0.111 mmol) in THF (5 mL) and Hunig's base (0.05 mL) at room temperature within 30 min. The reaction was worked-up as described for the synthesis of 368 and purified on silica gel eluting with CH$_2$Cl$_2$/MeOH/NH$_4$OH 15:1:0.05 to 15:1:0.1 to give 376 as a white solid (0.183 g, 98% yield). Data for 376: MS (ESI) m/z 1041.7 (M+H)$^+$; $^1$H-NMR (300 MHz, CDCl$_3$, partial): δ 7.61 (s, 1H), 7.48 (m, 1H), 7.13 (m, 1H), 7.00 (m, 1H), 5.07 (m, 2H), 4.72 (m, 3H), 4.43 (d, J=7 Hz, 1H), 4.29 (m, 2H), 4.14 (m, 2H), 3.85 (m, 1H), 3.66 (m, 2H), 0.88 (m, 6H).

Synthesis of Triazole 377

Alkyne 174 (150 mg, 0.187 mmol) and azide 441 (52.3 mg, 0.206 mmol) were treated with copper (I) iodide under similar conditions as reported above for the synthesis of triazole 361 to afford 170 mg of 377. Data for 377: MS (ESI) m/z 528.5 (M+2H)$^{2+}$, 1055.7 (M+H)$^+$; $^1$H NMR (300 MHz, CDCl$_3$, partial): δ 7.51 (s, 1H), 7.49-7.42 (m, 1H), 7.14 (dd, J=9, 9 Hz, 1H), 6.99-6.96 (m, 1H), 5.13 (d, J=5 Hz, 1H), 5.07-5.02 (m, 1H), 4.44 (d, J=7 Hz, 1H), 3.95 (dd, J=6, 3 Hz, 1H), 3.48 (s, 3H), 3.34 (s, 3H), 3.03 (t, J=9 Hz, 1H), 0.92-0.87 (m, 6H).

Example 46

Synthesis of Triazole 378

Scheme 69 depicts the synthesis of triazole 378. The reductive amination reaction of 4-iodobenzylamine and quinoline-4-carboxaldehyde yielded amine 442 which was converted to the BOC derivative 443. Palladium-catalyzed conversion of iodide 443 to the corresponding pinacol boronate ester was followed by in situ Suzuki coupling with iodoaryl azide 253 to yield azide 444. The cycloaddition of 444 with alkyne 173 gave triazole 378.

dried (Na$_2$SO$_4$), and evaporated to provide iodide 442 (0.83 mg, 69% yield) as a yellow oil. Data for 442: MS (ESI) m/z 375 (M+H)$^+$; $^1$HNMR (300 MHz, CDCl$_3$): δ 8.80 (d, J=5 Hz, 1H), 8.07 (d, J=8 Hz, 1H), 7.94 (d, J=8 Hz, 1H), 7.65-7.58 (m, 1H), 7.59 (d, J=8 Hz, 2H), 7.52-7.42 (m, 1H), 7.37 (d, J=5 Hz, 1H), 7.05 (d, J=8 Hz, 2H), 4.13 (s, 2H), 3.76 (s, 2H).

Synthesis of Iodide 443

A solution of iodide 442 (0.66 g, 1.8 mmol) in methylene chloride (15 mL) was treated with di-tert-butyl dicarbonate (0.42 mL, 3.2 mmol), and heated to reflux for 0.5 h. The reaction mixture was evaporated, and the residue purified by flash chromatography (SiO$_2$, 15-50% ethyl acetate/methylene chloride) to provide iodide 443 (0.72 g, 86% yield) as a colorless oil. Data for 443: MS (ESI) m/z 475 (M+H)$^+$; $^1$HNMR (300 MHz, CDCl$_3$): δ 8.85 (d, J=4 Hz, 1H), 8.12 (d, J=8 Hz, 1H), 7.98-7.82 (m, 1H), 7.72-7.66 (m, 1H), 7.61 (d, J=8 Hz, 2H), 7.54-7.48 (m, 1H), 7.16 (d, J=5 Hz, 1H), 6.98-6.85 (m, 2H), 4.88-4.80 (m, 2H), 4.43-4.29 (m, 2H), 1.49-1.42 (m, 9H).

Synthesis of Azide 444

A solution of iodide 443 (0.22 g, 0.46 mmol) in dioxane (2.5 mL) was treated with triethylamine (0.19 ml, 1.4 mmol), pinacol borane (0.090 mL, 0.61 mmol), and Pd(dp-

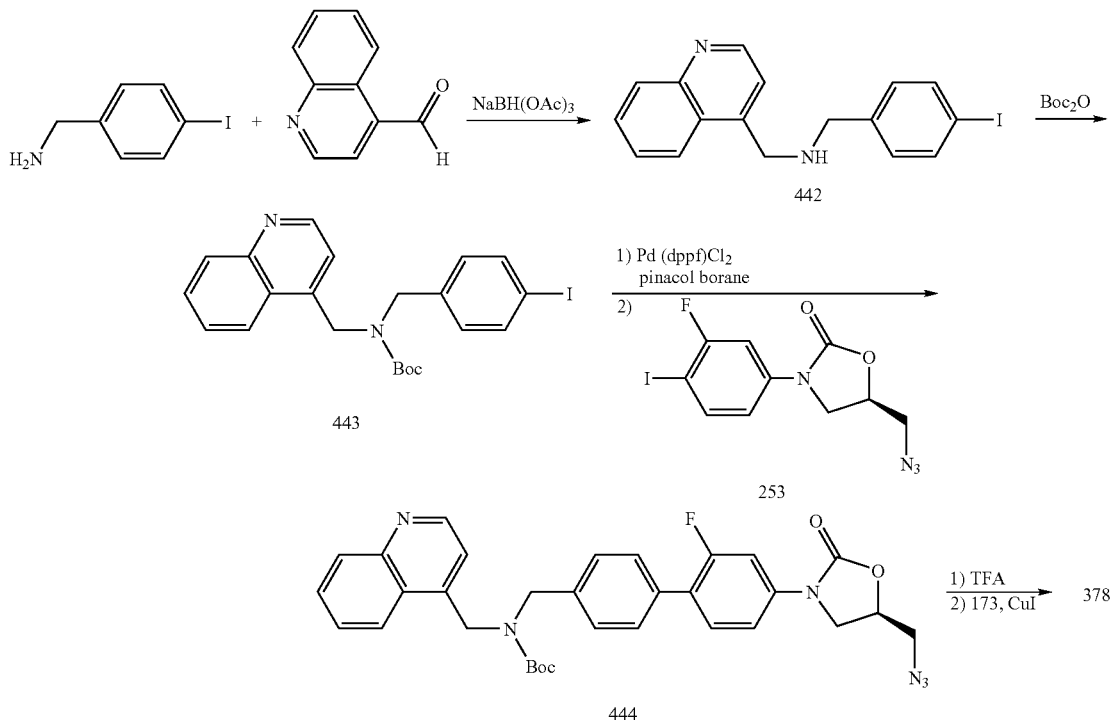

Scheme 69

Synthesis of Amine 442

A solution of 4-iodobenzylamine (0.93 g, 4.0 mmol) in methanol (10 mL) was treated with quinoline-4-carboxaldehyde (0.50 g, 3.2 mmol), acetic acid (0.2 mL) and sodium triacetoxyborohydride (1.7 g, 8.0 mmol), and the mixture was stirred under argon at 23° C. for 3 h. The reaction mixture was diluted with ethyl acetate (150 mL), washed with saturated aqueous sodium bicarbonate (2×100 mL), pf)Cl$_2$ (10 mg, 0.012 mmol) and heated to 80° C. for 3 h. The reaction mixture was cooled to room temperature, diluted with ethanol (0.83 mL) and H$_2$O (0.83 mL), treated with potassium carbonate (0.19 g, 1.4 mmol), azide 253 (0.17 g, 0.46 mmol), and Pd(dppf)Cl$_2$ (10 mg, 0.012 mmol), and heated to 80° C. for 3 h. The reaction mixture was cooled to room temperature, diluted with methylene chloride (50 mL), washed with saturated aqueous sodium bicarbonate (2×50 mL), dried (Na$_2$SO$_4$), and evaporated. Flash chromatography (SiO$_2$, 50-100% ethyl acetate/methylene chloride) provided azide 444 (0.18 g, 67% yield) as a yellow oil. Data for 444: $^1$HNMR (300 MHz, CD$_3$OD/CDCl$_3$): δ 8.76 (d, J=5 Hz, 1H), 8.04-8.00 (m, 2H), 7.77-7.69 (m, 1H), 7.62-7.43 (m, 8H), 7.33-7.25 (m, 1H), 4.89-4.83 (m, 1H), 4.28 (s, 2H), 4.22-4.12 (m, 1H), 3.94 (s, 2H), 3.92-3.88 (m, 1H), 3.79-3.72 (m, 1H), 3.62-3.56 (m, 1H).

Synthesis of Triazole 378

A solution of azide 444 (0.090 g, 0.15 mmol) in dichloromethane (4.0 mL) was treated with trifluoroacetic acid (4.0 mL) and stirred at 23° C. for 1 h. The solvent was removed under reduced pressure, and the residue dissolved in chloroform (100 mL) and washed with 10% aqueous potassium carbonate (100 mL), dried (Na$_2$SO$_4$), and evaporated to provide 50 mg of deprotected amine as an orange solid.

A solution of this crude amine (0.0430 g, 0.089 mmol) and alkyne 173 (0.056 g, 0.071 mmol) in tetrahydrofuran (1.5 mL) was treated with N,N-diisopropylethylamine (0.015 mL, 0.089 mmol) and copper (I) iodide (2.0 mg, 0.0089 mmol) and stirred under argon at 23° C. for 1 h. The reaction mixture was diluted with saturated aqueous ammonium hydroxide (10 mL) and extracted with dichloromethane (3×20 mL). The combined organic fractions were dried (Na$_2$SO$_4$) and evaporated, and the residue purified by preparative thin-layer chromatography (PTLC, SiO$_2$, ammonium hydroxide/methanol/ethyl acetate/dichloromethane 0.5:10:15:74.5) to provide 378 (44 mg, 48% yield) as a white powder. Data for 378: MS (ESI) m/z 1270 (M+H)$^+$; $^1$HNMR (300 MHz, CDCl$_3$, partial): δ 8.89 (d, J=5 Hz, 1H), 8.12 (d, J=9 Hz, 1H), 8.06 (d, J=8 Hz, 1H), 7.72-7.68 (m, 1H), 7.62 (s, 1H), 7.19-7.17 (m, 1H), 4.30 (s, 2H), 3.96 (s, 2H), 3.33 (s, 3H), 2.33 (s, 3H), 2.26 (s, 3H), 0.88-0.86 (m, 6H).

Example 47

Synthesis of Triazole 379

Scheme 70 depicts the synthesis of triazole 379. Azide 300 was converted to hydroxyamidine 445 which was subsequently cyclized with triethylorthoformate to oxadiazole azide 446. The cycloaddition of 446 with alkyne 173 yielded triazole 379.

Scheme 70

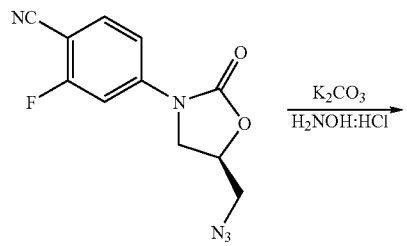

300

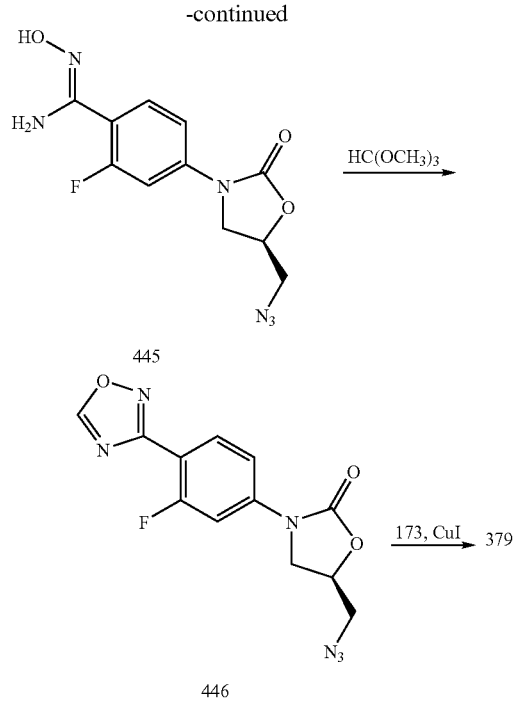

Synthesis of Azide 446

A solution of azide 300 (300 mg, 1.1 mmol) in ethanol (5.5 mL) was treated with potassium carbonate (152 mg, 1.1 mmol) and hydroxylamine hydrochloride (153 mg, 2.2 mmol) and refluxed for 3 h. The reaction was cooled to 23° C. and the solvent was evaporated in vacuo. The crude hydroxyamidine was added to triethylorthoformate (5.5 mL) and the reaction was refluxed for 2 h, cooled to 23° C. and stirred for 48 h, and then refluxed for 1 h. The reaction was then cooled to 23° C. and diluted with ethyl acetate (20 mL). The organic layer was washed with 1 M hydrochloric acid (20 mL). Drying (Na$_2$SO$_4$) and evaporation provided oxadiazole azide 446 (80 mg, 0.26 mmol, 24% yield). Data for 446: $^1$HNMR (300 MHz, CDCl$_3$): δ 8.80 (s, 1H), 8.12 (t, J=8 Hz, 1H), 7.66 (dd, J=13, 2 Hz, 1H), 7.43 (dd, J=9, 2 Hz, 1H), 4.91-4.81 (m, 1H), 4.17-4.11 (m, 1H), 3.93 (dd, J=9, 6 Hz, 1H), 3.77 (dd, J=4, 13, 1H), 3.63 (dd, J=4, 13, 1H).

Synthesis of Triazole 379

A solution of alkyne 173 (135 mg, 0.17 mmol) and azide 446 (65 mg, 0.21 mmol) in tetrahydrofuran (1.3 mL) was treated with diisopropylethylamine (0.037 mL, 0.21 mmol) and then degassed by application of vacuum and introduction of argon. Copper (I) iodide (4 mg, 0.021 mmol) was added, and the reaction was again degassed. The reaction was stirred under argon at 23° C. for 1 h, and then purified by flash chromatography (SiO$_2$, ammonium hydroxide/methanol/dichloromethane (0.05:1:12)) to provide 379 (153 mg, 0.14 mmol, 82% yield) as a white powder. Data for 379: MS (ESI) m/z 1091.8 (M+H)$^+$; $^1$HNMR (300 MHz, CDCl$_3$, partial): δ 8.80 (s, 1H), 8.18-8.136 (m, 1H), 7.69 (s, 1H), 7.65 (dd, J=13, 2, 1H), 7.37-7.33 (m, 1H), 4.82-4.80 (m, 1H), 4.67 (dd, J=10, 2 Hz, 1H), 3.41 (s, 3H), 0.98-0.93 (m, 6H).

Example 48

Synthesis of Triazole 380

The required 3,5-difluoroaryl oxazolidinone azide was synthesized from 3,5-difluoroaniline using the chemistry reported in the literature (Brickner, S. J. et al. *J. Med. Chem.* 1996, 39, 673).

Example 49

Synthesis of Triazoles 381 and 382

Scheme 71 depicts the synthesis of triazoles 381 and 382. Amine 171 was converted to carbamate 447 prior to cycloaddition with azide 158 to afford triazole 381. Amine 171 was demethylated to yield amine 448, which was subsequently transformed to carbamate 449 and ultimately triazole 382.

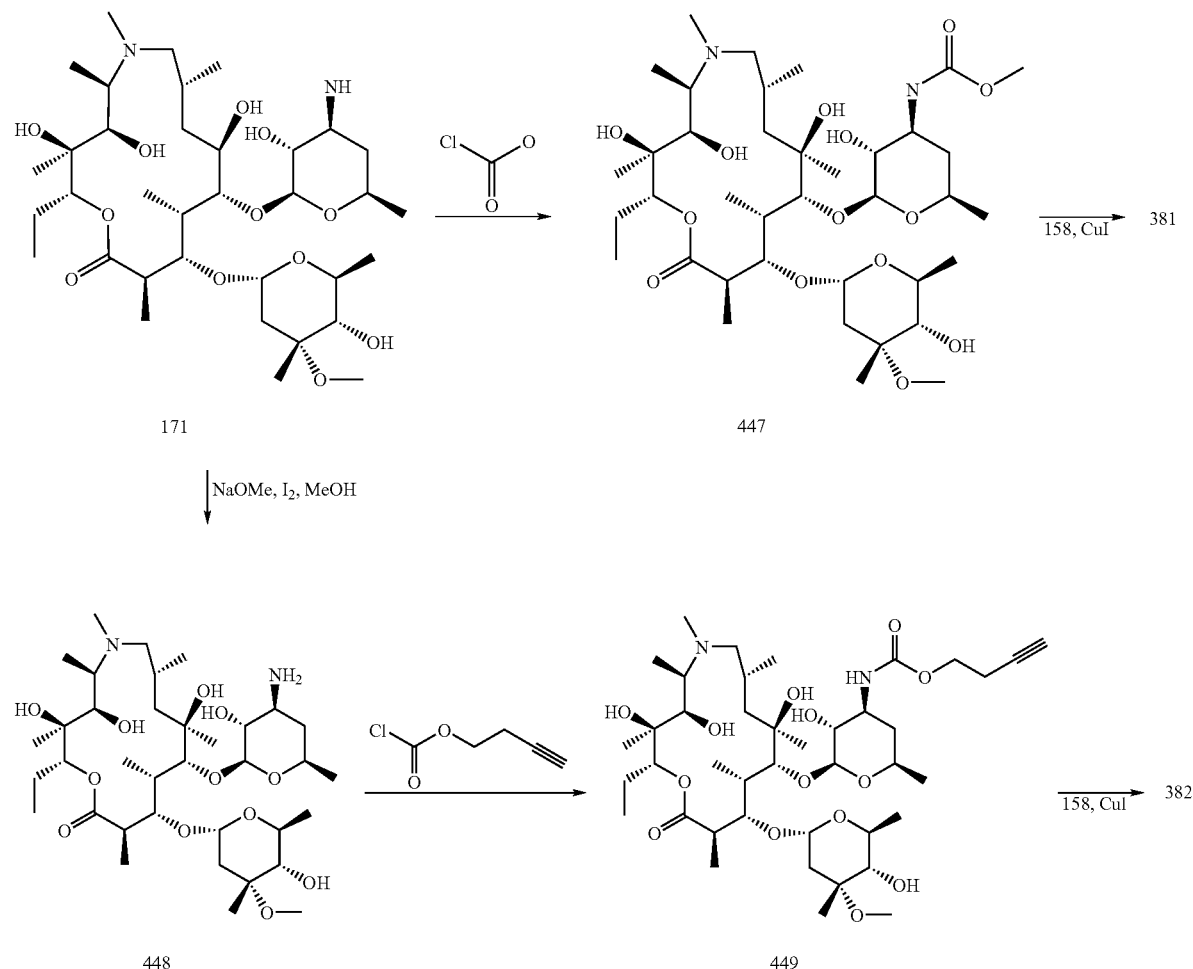

Scheme 71

Alkyne 328 (70 mg, 86 µmol), the above azide (33 mg, 129 µmol), and CuI (2 mg, 8 µmol) were reacted under the conditions described for the synthesis of triazole 228 to afford triazole 380 as a white solid (92.6 mg, 85 µmol). Data for 380: MS (ESI) m/z 543 (M+2H)$^{2+}$; $^1$HNMR (300 MHz, CDCl$_3$, partial): δ 7.99 (bs, 1H), 7.42 (s, 1H). 7.00-6.92 (m, 2H), 6.51 (tt, J=9, 2 Hz, 1H), 5.06-4.99 (m, 1H), 4.94 (d, J=6 Hz, 1H), 4.66 (d, J=5 Hz, 2H), 4.59 (dd, J=9, 2 Hz, 1H), 4.38 (d, J=7 Hz, 1H), 4.22 (dd, J=6, 2 Hz, 1H), 4.10 (t, J=8 Hz, 1H), 4.10-4.00 (m, 1H), 3.87-3.82 (m, 2H), 3.61-3.57 (m, 2H), 3.53-3.41 (m, 2H), 3.33 (s, 3H), 3.16 (dd, J=10, 4 Hz, 1H), 2.96 (t, J=10 Hz, 1H), 2.85-2.73 (m, 5H), 2.31 (s, 3H), 2.19 (s, 3H), 0.83 (d, J=6 Hz, 3H), 0.81 (t, J=7 Hz, 3H).

Synthesis of Carbamate 447

To a stirred solution of 171 (0.72 g, 1.0 mmol) in CH$_2$Cl$_2$ (10 mL) and Hunig's base (1 mL), was added dropwise a CH$_2$Cl$_2$ solution of 4-butynyl chloroformate (135 mg, 1.01 mmol in 2 mL). The mixture was stirred at rt for 16 h, then diluted to 50 mL with CH$_2$Cl$_2$ and washed with sat. aq. NaHCO$_3$ (50 mL) and brine (25 mL). The organic fraction was dried over K$_2$CO$_3$, filtered and concentrated to give 0.9 g of a foam which was purified by silica gel chromatography (25 mm×6" column eluted with 50:1 CH$_2$Cl$_2$/2N NH$_3$ in MeOH) to afford carbamate 447 as a white solid (0.68 g, 0.83 mmol). Data for 447: MS (ESI) m/z 815 (M+H)$^+$; $^1$HNMR (300 MHz, CDCl$_3$, partial): δ 8.72 (bs, 1H), 5.07 (d, J=4 Hz, 1H), 4.95 (d, J=7 Hz, 1H), 3.32 (s, 3H), 2.90 (s, 3H), 2.31 (s, 3H), 1.34-1.27 (m, 8H), 1.27-1.15 (m, 10H), 1.10-0.99 (m, 9H), 0.92-0.84 (m, 6H).

Synthesis of Triazole 381

Alkyne 447 (60 mg, 72 μmol), azide 158 (35 mg, 108 μmol), and CuI (2 mg, 8 μmol) were reacted under the conditions described for the synthesis of compound 228 to afford triazole 381 as a white solid (67 mg, 65 μmol). Data for 381: MS (ESI) m/z 1137 (M+H)+; $^1$HNMR (300 MHz, CDCl$_3$, partial): δ 8.9 (bs, 1H), 7.63 (s, 1H), 7.05-6.92 (m, 1H), 6.82 (t, J=9 Hz, 1H), 5.10-4.90 (m, 2H), 4.80-4.00 (m, 7H), 3.90-3.81 (m, 3H), 3.70-3.58 (m, 2H), 3.41-3.25 (m, 3H) 3.20 (pent, J=6, 1H), 3.10-2.96 (m, 4H), 2.92-2.38 (m, 5H), 2.29 (s, 3H), 2.10-1.40 (m, 51H), 1.25-1.04 (m, 15H), 0.93 (d, J=8, 3H), 0.94-0.83 (m, 6H).

Synthesis of Amine 448

To a stirred solution of desmethyl azithromycin 171 (10.0 g, 13.6 mmol) in methanol (200 mL) was added sodium methoxide (1.33 g, 25 mmol). The mixture was cooled to 0° C. prior to the addition of iodine (3.55 g, 14 mmol). The mixture was stirred at 0° C. for 1.5 h, then warmed to rt over 1 h. The reaction mixture was poured into ice water (1L) and the solution was adjusted to pH 12 by addition of KOH which led to the precipitation of a white solid. After sitting at 0° C. for 1 h, the solid was filtered to give 7.2 g of crude product which was recrystallized from boiling methanol to give 3.8 g of product as white crystals. Data for 448: MS (ESI) m/z 361.24 (M+2H)$^{2+}$; $^1$HNMR (300 MHz, CDCl$_3$, partial): δ 8.48 (bs, 1H), 5.18 (bs, 1H), 4.95 (d, J=4 Hz, 1H), 4.60 (dd, J=10, 2 Hz, 1H), 4.30 (d, J=8 Hz, 1H), 4.18 (dd, J=5, 2 Hz, 1H), 4.06-3.96 (m, 1H), 3.60-3.48 (m, 3H), 3.27 (s, 3H) 2.28 (s, 3H).

Synthesis of Carbamate 449

3'-N-bis-demethyl azithromycin 448 (180 mg, 0.25 mmol) was treated with 4-butynyl chlorofomate (35 mg, 0.25 mmol) under the same conditions described for the synthesis of 447 to afford carbamate 449 as a white solid (157 mg, 0.19 mmol). Data for 449: MS (ESI) m/z 1123 (M+H)+; $^1$HNMR (300 MHz, CDCl$_3$, partial): δ 8.18 (bs, 1H), 4.92 (d, J=4 Hz, 1H), 4.78 (d, J=4 Hz, 1H), 4.39 (d, J=6 Hz, 1H), 4.15 (t, J=7 Hz, 2H), 4.05-3.92 (m, 1H), 3.28 (s, 3H), 2.30 (s, 3H), 1.68 (d, J=8 Hz, 1H), 151 (dd, J=8, 3 Hz, 1H), 1.28-1.12 (m, 8H), 1.27-1.15 (m, 10H), 1.05 (d, J=7 Hz, 3H), 1.00 (s, 3H), 0.91 (d, J=7 Hz, 3H), 0.92-0.84 (m, 6H).

Synthesis of Triazole 382

Alkyne 449 (40 mg, 49 μmol), azide 158 (24 mg, 73 μmol), and CuI (2 mg, 8 μmol) were reacted under the conditions described for the synthesis of compound 228 to afford triazole 382 as a white solid (67 mg, 65 μmol). Data for 382: MS (ESI) m/z 1135 (M+H)+; $^1$HNMR (300 MHz, CDCl$_3$, partial): δ 8.30 (bs, 1H), 7.54 (s, 1H), 7.11-7.02 (m, 2H), 6.82-6.70 (m, 2H), 5.41 (d, J=5 Hz, 1H), 5.05-4.90 (m, 2H) 4.68 (d, J=4 Hz, 1H), 4.59 (d, J=6 Hz, 1H), 3.28 (s, 3H), 2.25 (s, 3H), 1.69 (d, J=8 Hz, 1H), 1.31-1.01 (m, 15H), 0.95 (d, J=8, 3H), 0.80 (t, J=8, 3H).

Example 50

Synthesis of Triazoles 383 and 384

Scheme 72 depicts the synthesis of triazoles 383 and 384. 4-Nitrobenzenesulfonyl chloride was convereted to sulfonamide 450 which was manipulated to carbamate 452 by standard chemistry. Oxazolidinone formation followed by azide formation gave 455. The cycloaddition of 455 with alkynes 173 and 174 rendered triazoles 383 and 384 respectively.

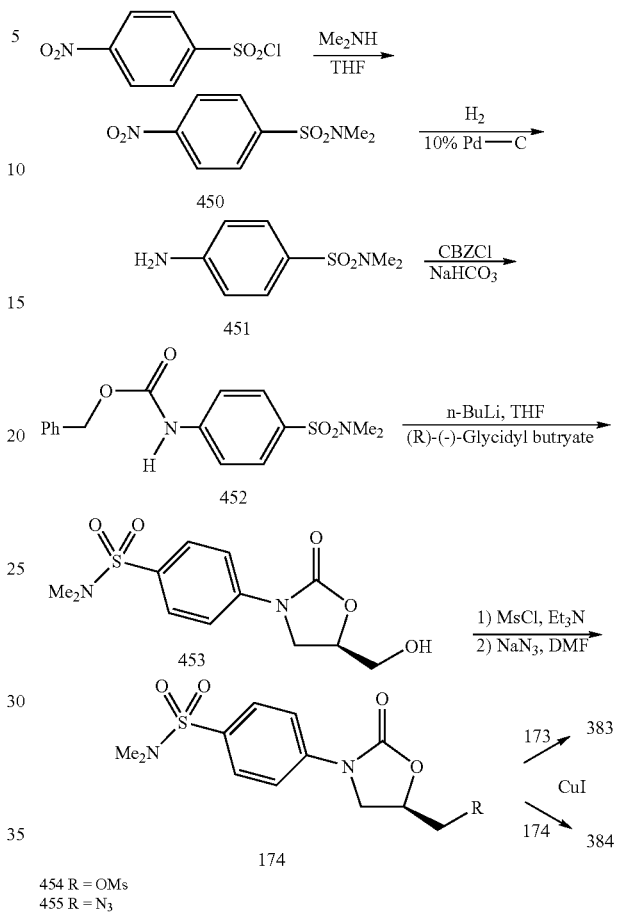

Scheme 72

Synthesis of Azide 455

4-Nitrobenzenesulfonyl chloride (2.22 g, 10 mmol) was added to a solution of dimethylamine (10 mL, 2.0 M in THF, 20 mmol) at 0° C. The reaction was stirred at 0° C. for 1 h and then at room temperature for additional 1 h. The THF was removed under vacuum, more water was added, and the precipitate was collected by filtration and dried to afford 450 (2.20 g, 96% yield). Data for 450: $^1$HNMR (300 MHz, CDCl$_3$-CD$_3$OD): δ 8.33 (d, J=9 Hz, 2H), 7.90 (d, J=9 Hz, 2H), 2.70 (s, 6H).

To a solution of sulfonamide 450 (2.2 g, 9.6 mmol) in methanol (30 mL) was added 10% Pd—C (0.25 g) and the resulting mixture was stirred at room temperature for 6 h under 1 atm hydrogen atmosphere. The Pd—C was removed by filtration on celite. The filtered solution was evaporated to provide 451 (1.8 g, 94% yield) as a white solid. Data for 451: $^1$HNMR (300 MHz, CDCl$_3$): δ 7.43 (d, J=9 Hz, 2H), 6.59 (d, J=9 Hz, 2H), 2.53 (s, 6H).

Benzyl chloroformate (1.4 mL, 9.6 mmol) was added dropwise to a solution of aniline 451 (1.60 g, 8.0 mmol), and NaHCO$_3$ (2.70 g, 21 mmol) in a mixture of THF (5 mL) and water (3 mL) at 0° C. After stirring at 0° C. for 2 h and room temperature for 4 h, the reaction mixture was diluted with ethyl acetate (30 mL). The organic layer was washed with brine (3×50 mL), dried (MgSO$_4$) and concentrated to provide 2.35 g of white solid 452 in a yield of 93%. Data for 452: ¹HNMR (300 MHz, CDCl₃): δ 7.79 (d, J=9 Hz, 2H), 7.64 (d, J=9 Hz, 2H), 7.50-7.45 (m, 5H), 7.02 (br s, 1H), 5.30 (s, 2H), 2.76 (s, 6H).

To a solution of CBZ-protected amine 452 (1.0 g, 3 mmol) in THF (20 mL) was added n-BuLi (3.3 mL, 1.6 M in hexane, 5.28 mmol) at −78° C. and the mixture was stirred for 30 min. (R)-(−)-Glycidyl butyrate (0.53 mL, 3.75 mmol) was added, the reaction was stirred at −78° C. for 3 h and was then warmed to room temperature and stirred overnight. The reaction was carefully quenched with saturated NH₄Cl and extracted with EtOAc. The organic phase was washed with brine, dried (MgSO₄) and concentrated. The crude product was recrystallized from ethyl acetate to give alcohol 453 as a white crystalline solid (0.45 g, 50% yield). Data for 453: MS (ESI) m/z 300.9 (M+H)⁺; ¹HNMR (300 MHz, CDCl₃): δ 7.83 (d, J=9 Hz, 2H), 7.78 (d, J=9 Hz, 2H), 4.86 (m, 1H), 4.19-4.07 (m, 3H), 3.85 (dd, J=4, 13 Hz, 1H), 2.75 (s, 6H).

To a solution of alcohol 453 (200 mg, 0.67 mmol) and Et₃N (101 mg, 1.0 mmol) in CH₂Cl₂ (5 mL) was added methanesulfonyl chloride (92 mg, 0.80 mmol) at 0° C. The mixture was stirred at room temperature for 30 min. The CH₂Cl₂ solution was washed with brine, dried (MgSO₄), concentrated and crystallized from EtOAc to afford mesylate 454 (238 mg, 94% yield). Data for 454: MS (ESI) m/z 378.9 (M+H)⁺; ¹HNMR (300 MHz, CDCl₃): δ 7.80 (d, J=9 Hz, 2H), 7.73 (d, J=9 Hz, 2H), 4.98 (m, 1H), 4.54 (dd, J=4, 12 Hz, 1H), 4.46 (dd, J=4, 12 Hz, 1H), 4.23 (t, J=9 Hz, 1H), 4.04 (dd, J=6, 9 Hz, 1H), 3.11 (s, 3H), 2.70 (s, 6H).

A mixture of 454 (200 mg, 0.52 mmol) and sodium azide (137 mg, 2.11 mmol) in DMF (4 mL) was heated at 80° C. for 3 h. The reaction mixture was diluted with EtOAc, washed with brine, dried (MgSO₄), concentrated and crystallized from EtOAc/MeOH to afford azide 455 (149 mg, 88% yield). Data for 455: ¹HNMR (300 MHz, DMSO): δ 7.72 (d, J=9 Hz, 2H), 7.67 (d, J=9 Hz, 2H), 4.83 (m, 1H), 4.11 (t, J=9 Hz, 1H), 3.77-3.58 (m, 3H), 2.58 (s, 6H).

Synthesis of Triazole 383

A mixture of alkyne 173 (118 mg, 0.15 mmol), azide 455 (54 mg, 0.165 mmol) and copper (I) iodide (28.5 mg, 0.15 mmol) in THF (5 mL) was repeatedly degassed and flushed with argon. Hunig's base (0.26 mL) was introduced and the mixture stirred at room temperature for 12 h. The reaction mixture was poured into saturated NH₄Cl (30 mL) and stirred for 15 minutes. The mixture was extracted with CH₂Cl₂, washed with brine, dried over MgSO₄ and concentrated. Chromatography on silica gel (25:1:0.05 CH₂Cl₂/MeOH/NH₃—H₂O as eluant) provided 383 (145 mg, 87% yield) as a white foam. Data for 383: MS (ESI) m/z 1112.7 (M+H)⁺, 557.1 (100%); ¹HNMR (300 MHz, CDCl₃, partial): δ 7.70 (d, J=9 Hz, 2H), 7.61 (s, 1H), 7.60 (d, J=9 Hz, 2H), 3.32 (s, 3H), 2.66 (s, 6H), 2.28 (s, 3H), 2.26 (s, 3H), 0.87 (t, J=8 Hz, 3H).

Synthesis of Triazole 384

A mixture of alkyne 174 (120 mg, 0.15 mmol), azide 445 (54 mg, 0.165 mmol) and copper (I) iodide (28.5 mg, 0.15 mmol) in THF (5 mL) was repeatedly degassed and flushed with argon. Hunig's base (0.26 mL) was introduced and the mixture stirred at room temperature for 12 h. The reaction mixture was poured into saturated NH₄Cl (30 mL) and stirred for 15 minutes. The mixture was extracted with CH₂Cl₂, washed with brine, dried over MgSO₄ and concentrated. Chromatography on silica gel (25:1:0.05 CH₂Cl₂/MeOH/NH₃—H₂O as eluant) provided 384 (150 mg, 89% yield) as a white foam. Data for 384: MS (ESI) m/z 1126.7 (M+H)⁺, 564.1 (100%); ¹HNMR (300 MHz, CDCl₃, partial): δ 7.74 (d, J=9 Hz, 2H), 7.60 (d, J=9 Hz, 2H), 7.52 (s, 1H), 3.33 (s, 3H), 2.68 (s, 6H), 2.32 (s, 3H), 2.23 (s, 3H), 0.89 (t, J=8 Hz, 3H).

Example 51

Synthesis of Triazoles 385-389

Scheme 73 depicts the synthesis of triazole 385. 3-Chloro-4-methoxyaniline was converted to carbamate 456 which was subsequently parlayed to azide 459. The cycloaddition of 459 with alkyne 173 afforded triazole 385. The same chemistry depicted in Scheme 73 was used to synthesize triazoles 386-389 from the appropriate anilines.

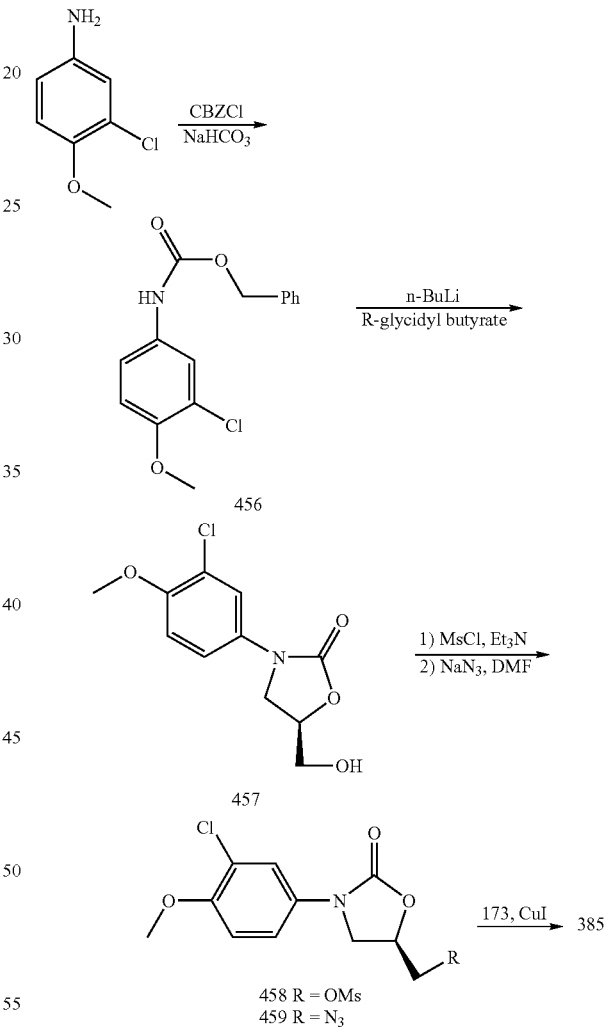

Scheme 73

Synthesis of Azide 459

Sodium bicarbonate (2.69 g, 25.4 mmol) was dissolved in water (22 mL) and (45 mL) acetone. To this solution p-anisidine (2.0 g, 12.7 mmol) was added. The mixture was cooled to 0° C., and benzyl chloroformate (1.81 mL, 12.70 mmol) was added. The mixture was stirred 5 min at 0° C., the cold bath removed, and then stirring was continued at room temperature overnight (~16 hours). The mixture was evaporated, and partitioned with a 1:1 mixture of ethyl acetate and water. The organic layer was washed with water, and then brine. The organic layer was dried with Na₂SO₄, and evaporated to yield carbamate 456 (3.20 g, 86% yield) of suitable purity for use in subsequent reactions. Data for 456: ¹HNMR (300 MHz, CDCl₃): δ 7.50 (s, 1H), 7.30 (m, 5H), 7.10 (d, J=5 Hz, 1H), 6.80 (d, J=8 Hz, 1H), 5.15 (s, 2H), 3.84 (s, 3H).

Carbamate 456 (1.0 g, 3.43 mmol) was dissolved in 50 mL tetrahydrofuran, and the solution cooled to −78° C. n-Butyllithium (2.5 M in hexane, 2.1 mL, 3.43 mmol) was added slowly, and the mixture allowed to stir for 45 min at −78° C. R-Glycidyl butyrate (0.5 mL, 3.5 mmol) was added, and the mixture was stirred for 1 h at −78° C. The bath was removed and the reaction allowed to stir overnight at room temperature. The reaction was quenched with 10 mL saturated ammonium chloride solution, and partitioned with ethyl acetate and water. The aqueous layer was extracted thrice with ethyl acetate, and the combined organic layer was washed with brine, dried (Na₂SO₄), and evaporated to yield alcohol 457 (0.5 g, 63% yield) of suitable purity for use in subsequent reactions. Data for 457: ¹HNMR (300 MHz, CDCl₃): δ 7.49 (s, 1H), 7.35 (m, 1H), 6.84 (d, J=5 Hz, 1H), 4.71 (m, 1H), 3.95 (n, 2H).

Alcohol 457 (0.5 g, 1.94 mmol) was dissolved in 5 mL methylene chloride, and the mixture cooled to 0° C. Triethylamine (0.54 mL, 3.88 mmol) was added, followed by methanesulfonyl chloride (0.2 mL, 2.72 mmol). The mixture was allowed to warm to room temperature and stirred for 1 hr. Methylene chloride (10 mL) was added, and the mixture washed twice with 1N HCl, then twice with 10% aqueous sodium carbonate, and then brine. The organic phase was dried (Na₂SO₄), and evaporated to yield mesylate 458 (0.60 g, 92% yield).

A solution of mesylate 458 (0.60 g, 1.79 mmol) in dimethylformamide (5 mL) was treated with sodium azide (0.46 g, 7.15 mmol) and the mixture heated to 80° C. for 5 h. The reaction mixture was cooled to room temperature, diluted with ethyl acetate (50 mL), and washed with brine (2×50 mL). Drying (Na₂SO₄), and evaporation provided azide 459 (0.45 g, 90% yield) as a yellow solid of suitable purity for use in subsequent reactions. Data for 459: ¹HNMR (300 MHz, CDCl₃): δ 7.50 (s, 1H), 7.35 (dd, J=2, 5 Hz, 1H), 6.87 (d, J=9 Hz, 1H), 4.75 (m, 1H), 4.0 (t, J=9 Hz. 1H), 3.75 (dd, J=9, 13 Hz, 1H), 3.52 (dd, J=5, 13 Hz, 1H).

Synthesis of Triazole 385

A solution of but-3-ynyl-methyl-amino azithromycin 173 (100 mg, 0.127 mmol) in tetrahydrofuran (5 mL) was treated with azide 459 (53.0 mg, 0.19 mmol), N,N-diisopropylethylamine (0.026 mL, 0.15 mmol) and copper (1) iodide (0.018 g, 0.095 mmol), and the mixture was stirred under argon at room temperature for 16 h. The reaction mixture was diluted with ethyl acetate (50 mL), and washed with brine (2×50 mL). The organic phase was dried and evaporated. The residue was purified by preparative thin layer chromatography (using 80% CH₂Cl₂, 20% MeOH, 1% NH₄OH as eluant) to provide triazole 385 (64 mg, 50% yield) as a white solid. Data for 385: ¹HNMR (300 MHz, CDCl₃, partial): δ 7.60 (s, 1H), 7.40 (s, 1H), 7.10 (s, 1H), 6.80 (d, J=3 Hz, 1H), 4.95 (m, 1H), 4.60 (m, 1H), 4.40 (m, 1H), 4.20 (m, 1H), 4.0 (m, 1H), 3.50 (m, 1H), 3.20 (s, 2H).

Synthesis of Triazoles 386-389

The azides required for the synthesis of triazoles 386-389 were synthesized from the appropriate amines using the chemistry reported in the literature (Brickner, S. J. et al. *J. Med. Chem.* 1996, 39, 673). The azides were treated with alkyne 173, using the conditions reported above for the synthesis of triazole 385, to afford the targets 386-389.

Data for 386: ¹H-NMR (300 MHz, CDCl₃, partial): δ 7.50 (s, 1H), 5.0 (s, 1H), 4.80 (m, 1H), 4.60 (m, 2H), 4.47 (m, 2H), 3.98-4.20 (m, 5H), 3.60 (m, 2H), 3.25 (d, J=6 Hz, 3H), 2.20 (m, 3H).

Data for 387: ¹H-NMR (300 MHz, CDCl₃, partial): δ 7.46 (s, 1H), 7.37 (d, J=2 Hz, 2H), 7.20 (m, 2H), 5.10 (s, 1H), 5.00 (m, 2H), 4.70 (m, 2H), 4.45 (d, J=3 Hz, 1H), 4.20 (s, 1H), 4.15 (m, 3H).

Data for 388: ¹H-NMR (300 MHz, CDCl₃, partial): δ 9.0 (s, 1H), 7.50 (m, 4H), 5.0 (m, 2H), 4.70 (m, 3H), 4.30 (d, J=2 Hz, 1H), 4.20 (s, 1H), 4.10 (m, 1H), 4.0 (m, 1H), 3.98 (m, 1H), 3.60 (m, 2H), 3.20 (m, 3H), 2.98 (t, J=7 Hz, 1H).

Data for 389: ¹H-NMR (300 MHz, CDCl₃, partial): δ 9.20 (s, 1H), 7.50 (s, 1H), 7.30 (m, 2H), 6.80 (m, 1H), 5.10 (d, J=5 Hz, 1H), 4.98 (m, 1H), 4.80 (d, J=3 Hz, 1H), 4.60 (m, 2H), 4.30 (d, J=2 Hz, 1H), 4.20 (s, 1H), 4.0 (m, 2H), 3.80 (s, 3H), 3.60 (m, 2H), 3.27 (s, 3H), 3.11 (app t, J=7 Hz, 1H).

Example 52

Synthesis of Triazole 390

Scheme 74 depicts the synthesis of triazole 390. The cycloaddition of dibromo hydroxyformimine and allyl alcohol provided bromo isoxazoline 460 which was then converted into alcohol 461. The alcohol of 461 was transformed to the azide 462 which underwent cycloaddition to alkyne 173 to afford triazole 390.

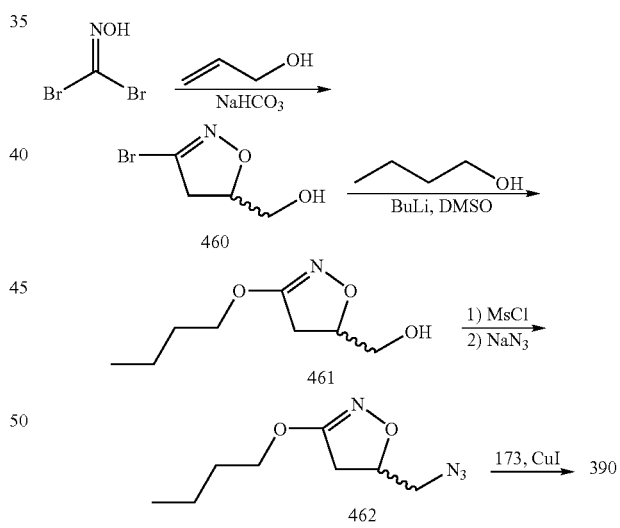

Scheme 74

Synthesis of Isoxazoline 460

A mixture of dibromo hydroxyformimine (1 g, 4.93 mmol), allyl alcohol (1.68 mL, 24.7 mmol), NaHCO₃ (1.58 g, 18.7 mmol) in 1.5 mL water and 18 mL ethyl acetate was stirred over night at room temperature. The mixture was then poured into 20 mL of water and extracted, with ethyl acetate (2×20 mL). The combined organic extract was washed with brine (10 mL), dried (Na₂SO₄) and evaporated, yielding 460 (828 mg, 93%). Data for 460: ¹HNMR (300 MHz, CDCl₃): δ 4.80-4.65 (m, 1H), 3.85-3.74 (m, 1H), 3.61-3.52 (m, 1H), 3.22-3.05 (m, 2H), 1.95-1.75 (br s, 1H).

Synthesis of Alcohol 461

To a solution of 1-butanol (5.1 mL, 55.6 mmol) in 25 mL DMSO was added a 2.5 M n-BuLi solution in hexanes (3.9 mL, 9.72 mmol). The mixture was stirred at room temperature for 20 min, then a solution of 460 (500 mg, 2.78 mmol) in 2 mL DMSO was added. The mixture was stirred at room temperature for 3 h, poured into 50 mL water/ice and extracted with ethyl acetate (3×40 mL). The combined organic extract was washed with water (4×20 mL), brine (20 mL), dried ($Na_2SO_4$) and evaporated. The residue was purified by flash-chromatography (eluant: hexanes-ethyl acetate 2:1) yielding 461 (165 mg, 34%). Data for 461: $^1$HNMR (300 MHz, $CDCl_3$): δ 4.69-4.60 (m, 1H), 4.09-4.00 (m, 2H), 3.78-3.69 (m, 1H), 3.59-3.51 (m, 1H), 2.99-2.78 (m, 2H), 1.68-1.55 (m, 2H), 1.40-1.25 (m, 2H), 0.90-0.82 (m, 3H).

Synthesis of Azide 462

To a solution of 461 (165 mg, 0.95 mmol) in 3 mL dichloromethane was added $Et_3N$ (0.24 mL, 1.72 mmol) followed by MsCl (0.089 mL, 1.14 mmol) at 0° C. The mixture was stirred at 0° C. for 1 h, poured into 10 mL water/ice and extracted with dichloromethane (2×10 mL). The combined organic extract was washed with water (2×10 mL), brine (10 mL), dried ($Na_2SO_4$) and evaporated. The residue was dissolved in 3 mL DMF, $NaN_3$ (124 mg, 1.91 mmol) was added, and the mixture was stirred at 80° C. for 2 h. The mixture was poured into 10 mL water/ice and extracted with ethyl acetate (2×10 mL). The combined organic extract was washed with water (2×10 mL), brine (10 mL), dried ($Na_2SO_4$) and evaporated. The residue was purified by flash-chromatography (eluant: hexanes-ethyl acetate 3:1) yielding 462 (155 mg, 82%). Data for 462: $^1$HNMR (300 MHz, $CDCl_3$): δ 4.98-4.85 (m, 1H), 4.31-4.25 (m, 2H), 3.72-3.51 (m, 2H), 3.25-3.15 (m, 1H), 3.05-2.91 (m, 1H), 1.92-1.81 (m, 2H), 1.62-1.50 (m, 2H), 1.15-1.05 (m, 3H).

Synthesis of Triazole 390

To a solution of alkyne 173 (150 mg, 0.191 mmol) in 6 mL acetonitrile was added 462 (37.8 mg, 0.191 mmol), 2,6-lutidine (0.025 mL, 0.209 mmol) and CuI (18.2 mg, 0.095 mmol). The mixture was stirred over night at room temperature, then poured into 10 mL 5% aqueous $NH_3$/ice and extracted with $CH_2Cl_2$/isopropanol 95:5 (3×20 mL). The combined organic extract was washed with brine (10 mL), dried ($Na_2SO_4$) and evaporated. The residue was purified by flash-chromatography (eluant: ethyl acetate-MeOH 5:1) yielding 390 (131 mg, 70%). Data for 390: MS (ESI) m/z 985 (M+H)$^+$; $^1$HNMR (300 MHz, $CDCl_3$, partial): δ 8.25-8.05 (br s, 1H) 7.66 (s, 1H), 5.12-4.90 (m, 3H).

Example 53

Synthesis of Triazoles 391-393

Scheme 75 depicts the synthesis of triazole 391. The oxime of 2,4-dichlorobenzaldehyde was converted to hydroxyiminoyl chloride 464 prior to cycloaddition to alcohol 465. Conversion of alcohol 465 to azide 466 and final cycloaddition to alkyne 173 afforded triazole 391. Triazoles 392 and 393 were synthesized in the same manner as compound 391.

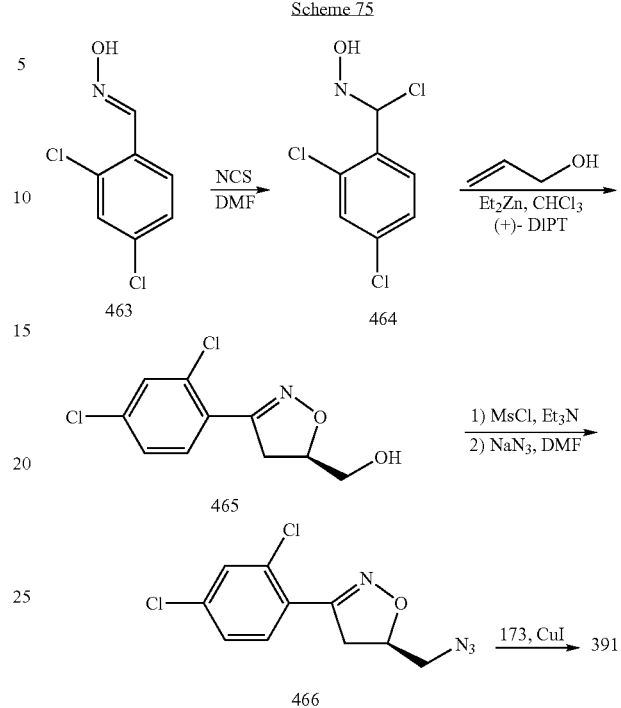

Scheme 75

Synthesis of Oxime 463

To a suspension of 2,4-dichlorobenzenecarboxaldehyde (7.73 g, 44.2 mmol) in 100 mL 95% aqueous EtOH was added $HCl.H_2NOH$ (3.69 g, 53.0 mmol) followed by a solution of NaOH (2.3 g, 57.4 mmol) in 4 mL of water at 0° C. The suspension was stirred at room temperature overnight, poured into 300 mL ice/water and extracted with ethyl acetate (2×100 mL). The combined organic extract was washed with water (2×80 mL), brine (80 mL), dried ($Na_2SO_4$) and evaporated yielding 463 (8.2 g, 97%). Data for 463: $^1$HNMR (300 MHz, $CDCl_3$): δ 8.52 (s, 1H), 7.80-8.75 (m, 1H), 7.43-7.40 (m, 1H), 7.29-7.20 (m, 1H).

Synthesis of Hydroxyiminoyl Chloride 464

To a solution of 463 (7.0 g, 36.8 mmol) in 30 mL DMF was added in portions N-chlorosuccinimide (5.4 g, 40.5 mmol) at 20-30° C. The mixture was stirred at room temperature for 1 h, then poured into 200 mL ice/water and extracted with ethyl acetate (2×100 mL). The combined organic extract was washed with water (3×80 mL), brine (80 mL), dried ($Na_2SO_4$) and evaporated yielding 464 (7.1 g, 86%). Data for 464: $^1$HNMR (300 MHz, $CDCl_3$): δ 8.64 (s, 1H), 7.38-7.15 (m, 3H).

Synthesis of Alcohol 465

To a solution of allyl alcohol (1.33 mL, 19.6 mmol) in 58 mL $CHCl_3$ was added a 1 M diethylzinc solution in hexanes (23.2 mL, 23.2 mmol) at −5 to 0° C. After stirring for 10 min, (+)-diisopropyl tartrate (0.75 mL, 3.56 mmol) was added and the solution was stirred for 1 h at 0° C. The milky solution was cooled to −20° C. and 14 mL $CHCl_3$ and dioxane (1.97 mL, 23.2 mmol) was added. Then 464 (4.00 g, 17.8 mmol) was added in portions at −20 to −15° C. The solution was stirred for 4 h at −10° C., then poured into 200 mL 1M citric acid/ice and extracted with $CHCl_3$ (3×100 mL). The combined organic extract was washed with brine (80 mL), dried ($Na_2SO_4$) and evaporated. The residue was purified by flash-chromatography (eluant: ethyl acetate-hexanes 2:3), yielding crude 465, which was recrystallized from 1-chlorobutane, yielding pure 465 (2.6 g, 60%). Data for 465: $^1$HNMR (300 MHz, CDCl$_3$): δ 7.76 (d, J=5 Hz, 1H), 7.61 (s, 1H), 7.49-7.42 (m, 1H), 5.10-5.01 (m, 1H), 4.07 (dd, J=3, 12 Hz, 1H), 4.03 (dd, J=3, 12 Hz, 1H), 3.73-3.52 (m, 2H), 2.18 (br s, 1H).

Synthesis of Azide 466

To a solution of 465 (1.0 g, 4.1 mmol) in 20 mL dichloromethane was added Et$_3$N (1.0 mL, 7.3 mmol) followed by MsCl (0.37 mL, 4.9 mmol) at 0° C. The mixture was stirred at 0° C. for 1 h, poured into 50 mL water/ice and extracted with dichloromethane (2×40 mL). The combined organic extract was washed with water (2×20 mL), brine (20 mL), dried (Na$_2$SO$_4$) and evaporated. The residue was dissolved in 17 mL DMF, NaN$_3$ (0.53 g, 8.1 mmol) was added, and the mixture was stirred at 80° C. for 2 h. The mixture was poured into 50 mL water/ice and extracted with ethyl acetate (2×50 mL). The combined organic extract was washed with water (3×20 mL), brine (20 mL), dried (Na$_2$SO$_4$) and evaporated. The residue was purified by flash-chromatography (eluant: hexanes-ethyl acetate 2:3) yielding 466 (1.1 g, 98%). Data for 466: $^1$HNMR (300 MHz, CDCl$_3$,): δ 7.65 (d, J=8 Hz, 1H), 7.61 (d, J=1 Hz, 1H), 7.23-7.17 (m, 1H), 4.90-4.82 (m, 1H), 3.61-3.21 (m, 4H).

Synthesis of Triazole 391

To a solution of alkyne 173 (150 mg, 0.191 mmol) in 6 mL acetonitrile was added azide 466 (52 mg, 0.191 mmol), 2,6-lutidine (0.025 mL, 0.209 mmol) and CuI (18.2 mg, 0.095 mmol). The mixture was stirred overnight at room temperature, poured into 10 mL 5% aqueous NH$_3$/ice and extracted with CH$_2$Cl$_2$/isopropanol 95:5 (3×20 mL). The combined organic extract was washed with brine (10 mL), dried (Na$_2$SO$_4$) and evaporated. The residue was purified by flash-chromatography (eluant: ethyl acetate-MeOH 5:1) yielding 391 (157 mg, 78%). Data for 391: MS (ESI) m/z 1057 (M+H)$^+$; $^1$HNMR (300 MHz, CDCl$_3$, partial): δ 8.30-8.10 (br s, 1H), 7.52 (s, 1H), 7.39-7.20 (m, 3H), 5.15-5-02 (m, 1H).

Synthesis of Triazole 392

To a suspension of 4-chloro-3-fluorobenzaldehyde (5.00 g, 31.5 mmol) in 90 mL 95% aqueous EtOH was added HCl.H$_2$NOH (2.63 g, 37.8 mmol) followed by a solution of NaOH (1.90 g, 47.3 mmol) in 3 mL of water at 0° C. The suspension was stirred at room temperature for 3 h, then poured into 200 mL ice/water and extracted with ethyl acetate (2×100 mL). The combined organic extract was washed with water (2×80 mL), brine (80 mL), dried Na$_2$SO$_4$) and evaporated. The residue was dissolved in 25 mL DMF and N-chlorosuccinimide (4.23 g, 34.7 mmol) was added in portions at 30-40° C. The mixture was stirred at room temperature for 1 h, then poured into 200 mL ice/water and extracted with ethyl acetate (2×100 mL). The combined organic extract was washed with water (3×80 mL), brine (80 mL), dried (Na$_2$SO$_4$) and evaporated yielding the hydroxyiminoyl chloride (3.71 g., 62%). Data: $^1$HNMR (300 MHz, CDCl$_3$,): δ 8.15 (s, 1H), 7.60-7.51 (m, 2H), 7.41-7.32 (m, 1H).

To a solution of allyl alcohol (1.16 mL, 17.0 mmol) in 50 mL CHCl$_3$ at −5 to 0° C. was added a 1M diethylzinc solution in hexanes (20.1 mL, 20.1 mmol). After stirring for 10 min, (+)-diisopropyl tartrate (0.65 mL, 3.09 mmol) was added and the solution was stirred for 1 h at 0° C. The milky solution was cooled to −20° C. and 12 mL CHCl$_3$ and dioxane (1.70 mL, 20.1 mmol) was added. Then the above hydroxyiminoyl chloride (3.21 g, 15.4 mmol) was added in portions at −20 to −15° C. The solution was stirred for 3 h at −15° C., then poured into 200 mL 1M citric acid/ice and extracted with CHCl$_3$ (3×100 mL). The combined organic extract was washed with brine (80 mL), dried (Na$_2$SO$_4$) and evaporated. The residue was purified by flash-chromatography (eluant: ethyl acetate-hexanes 1:2 and 1:2), yielding crude material which was recrystallized twice from 1-chlorobutane, yielding the expected isoxazoline alcohol (1.5 g, 42%). Data: $^1$HNMR (300 MHz, CDCl$_3$,): δ 7.48-7.21 (m, 3H), 4.82-4-74 (m, 1H), 3.82-3.76 (m, 1H), 3.58-3.53 (m, 1H), 3.27-3.09 (m, 2H).

To a solution of the above alcohol (1.0 g, 4.4 mmol) in 20 mL dichloromethane was added Et$_3$N (1.1 mL, 7.8 mmol) followed by MsCl (0.41 mL, 5.2 mmol) at 0° C. The mixture was stirred at 0° C. for 1 h, then poured into 50 mL water/ice and extracted with dichloromethane (2×40 mL). The combined organic extract was washed with water (2×20 mL), brine (20 mL), dried (Na$_2$SO$_4$) and evaporated. The residue was dissolved in 15 mL DMF, NaN$_3$ (0.57 g, 8.7 mmol) was added and the mixture was stirred at 80° C. for 2 h. The mixture was poured into 50 mL water/ice and extracted with ethyl acetate (2×50 mL). The combined organic extract was washed with water (3×20 mL), brine (20 mL), dried (Na$_2$SO$_4$) and evaporated. The residue was purified by flash-chromatography (eluant: hexanes-ethyl acetate 2:3) yielding the expected azide (1.1 g, 95%). Data: $^1$HNMR (300 MHz, CDCl$_3$): δ 7.43-7.29 (m, 3H), 4.93-4.84 (m, 1H), 3.54-3.27 (m, 3H), 3.18-3.30 (m, 1H).

To a solution of alkyne 173 (150 mg, 0.191 mmol) in 6 mL acetonitrile was added the above azide (49.5 mg, 0.191 mmol), 2,6-lutidine (0.0245 mL, 0.209 mmol) and CuI (18.2 mg, 0.095 mmol). The mixture was stirred overnight at room temperature, poured into 10 mL 5% aqueous NH$_3$/ice and extracted with CH$_2$Cl$_2$/isopropanol 95:5 (3×20 mL). The combined organic extract was washed with brine (10 mL), dried (Na$_2$SO$_4$) and evaporated. The residue was purified by flash-chromatography (eluant: ethyl acetate-MeOH 5:1) yielding 392 (138 mg, 70%). Data for 392: MS (ESI) m/z 1042 (M+H)$^+$; $^1$HNMR (300 MHz, CDCl$_3$, partial): δ 8.45-8.32 (br s, 1H), 7.28-7.19 (m, 2H), 7.13-7.10 (m, 1H), 5.05-4.82 (m, 2H).

Synthesis of Triazole 393

To a solution of alkyne 173 (150 mg, 0.191 mmol) in 6 mL acetonitrile was added azide 342 (45.4 mg, 0.191 mmol), 2,6-lutidine (0.025 mL, 0.209 mmol) and CuI (18.2 mg, 0.095 mmol). The mixture was stirred overnight at room temperature, then poured into 10 mL 5% aqueous NH$_3$/ice and extracted with CH$_2$Cl$_2$/isopropanol 95:5 (3×20 mL). The combined organic extract was washed with brine (10 mL), dried (Na$_2$SO$_4$) and evaporated. The residue was purified by flash-chromatography (eluant: ethyl acetate-MeOH 5:1) yielding 393 (118 mg, 60%). Data for 393: MS (ESI) m/z 1025 (M+H)$^+$; $^1$HNMR (300 MHz, CDCl$_3$, partial): δ 8.00 (brs, 1H), 7.52 (m, 3H), 5.11-4.95 (m, 1H), 4.95-4.82 (m, 2H).

Example 54

Synthesis of Triazoles 394-403

Scheme 76 depicts the synthesis of azides 469, 482-487, 489, 491, and 495 required for the synthesis of triazoles 394-403. The azides were then treated with alkyne 173 to afford the final targets.

Scheme 76

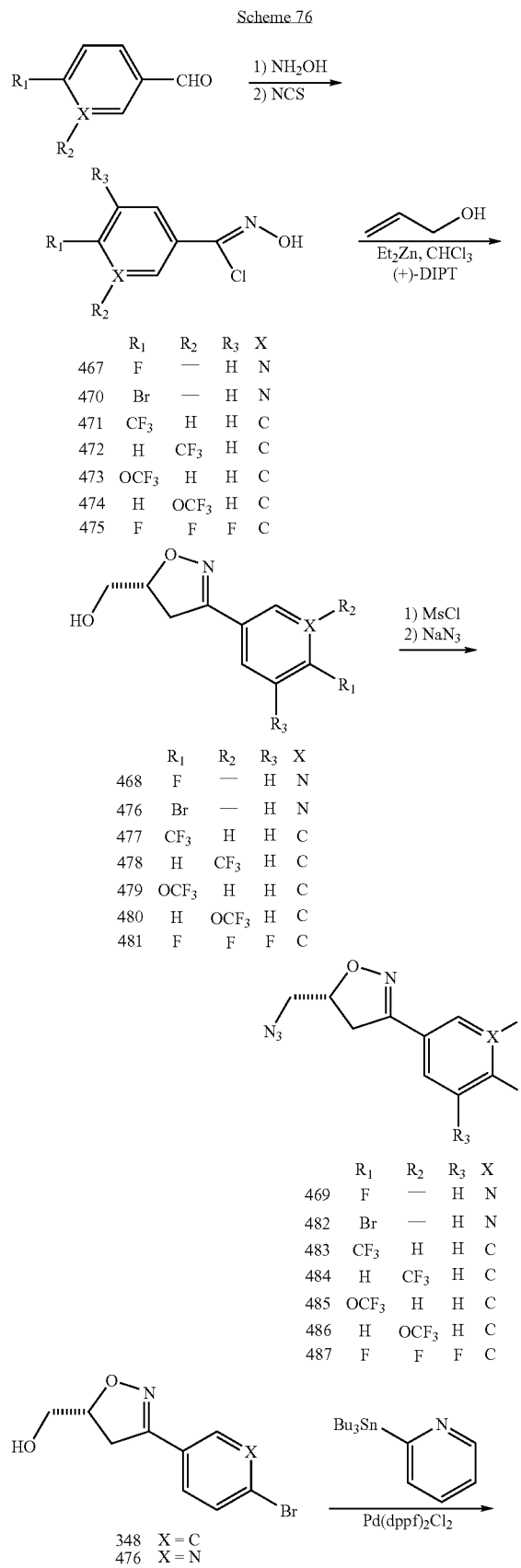

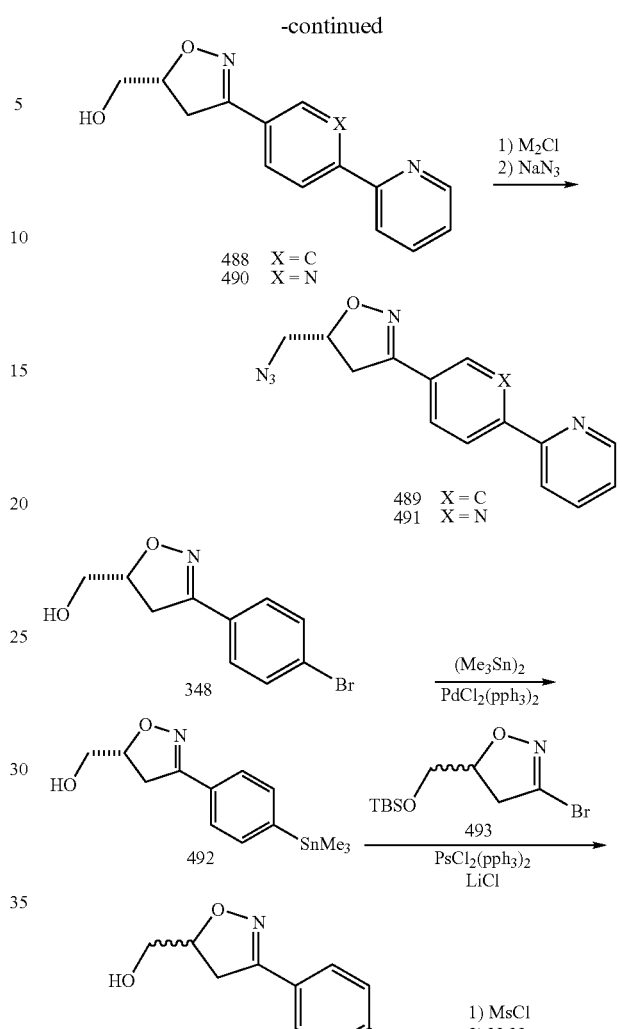

Synthesis of Hydroxyiminoyl Chloride 467

To a solution of 3-formyl-6-fluoropyridine (1.77 g, 9.36 mmol) in EtOH (10 mL) at 0° C. was added water (5 mL), then hydroxylamine (1.00 g, 14.0 mmol), followed by the addition of NaOH (2.20 mL, 50% w/w). The mixture was stirred at 0° C. for 15 min. The EtOH was evaporated, then EtOAc (50 mL) was added. HCl (1M) was used to the adjust pH to 6. The aqueous phase was extracted with EtOAc (30 mL×2), and the organic extracts were dried by $Na_2SO_4$. The concentrated residue (1.50 g) was used in the next step without further purification.

To a solution of the crude intermediate above (1.50 g, in DMF (20 mL) at room temperature was added N-chlorosuccinimide (1.80 g, 13.1 mmol) in two portions. The mixture was stirred at 45-50° C. for 1 h, then brine (50 mL) and saturated aqueous $Na_2CO_3$ (3 mL) was added. The mixture was extracted with EtOAc/Hexane (200 mL, 1/1).

The organic layer was washed by brine (200 mL), dried by MgSO$_4$, to give hydroximinoyl chloride 467 (1.45 g, 60% yield). Data for 467: $^1$HNMR (300 MHz, CDCl$_3$): δ 8.72 (d, J=3 Hz, 1H), 8.45 (s, 1H), 8.30-8.20 (m, 1H), 7.00 (dd, J=9, 3 Hz, 1H).

Synthesis of Hydroxyiminoyl Chlorides 470-475

These hydroxyiminoyl chlorides were synthesized from the appropriate aryl aldehyde using the above procedure for the synthesis of 467.

Data for 470: $^1$HNMR (300 MHz, CDCl$_3$): δ 9.27 (s, 1H), 8.86 (d, J=3 Hz, 1H), 7.90-7.70 (m, 1H), 7.54 (d, J=8 Hz, 1H).

Data for 471: $^1$HNMR (300 MHz, CDCl$_3$): δ 8.16 (s, 1H), 7.94 (d, J=8 Hz, 2H), 7.67 (d, J=8 Hz, 2H).

Data for 472: $^1$HNMR (300 MHz, CDCl$_3$): δ 8.53 (s, 1H), 8.02 (d, J=8 Hz, 1H), 7.70 (d, J=8 Hz, 1H), 7.56 (d, J=8 Hz, 1H).

Data for 475: $^1$HNMR (300 MHz, CDCl$_3$): δ 8.08 (s, 1H), 7.58-7.22 (m, 1H).

Synthesis of Alcohol 468

To a solution of allyl alcohol (661 μL, 9.62 mmol) in CHCl$_3$ (30 mL) at 0° C. was added diethylzinc (12.03 mL, 12.03 mmol). After the mixture was stirred at 0° C. for 15 min, (+)-diisopropyl tartrate (855 μL, 4.01 mmol) in CHCl$_3$ (5.0 mL) was added. The mixture was stirred at 0° C. for 1 h, then hydroxyiminoyl chloride 467 (1.40 g, 8.02 mmol) in CHCl$_3$ (10.0 mL) was added dropwise over 10 min. The mixture was stirred at 0° C. for 2 h, then sat. aqueous NH$_4$Cl (20 mL) and citric acid (6 mL, 1 M) was added. The mixture was extracted with CH$_2$Cl$_2$ (50 mL×4), and the organic extracts were dried by Na$_2$SO$_4$. The residue was purified by flash-chromatography (eluant: 2.5/100 MeOH/CH$_2$Cl$_2$), to provide 468 (1.40 g, 89% yield; >95% ee). Data for 468: $^1$HNMR (300 MHz, CDCl$_3$): δ 8.39 (d, J=3 Hz, 1H), 8.25-8.15 (m, 1H), 7.00 (dd, J=9, 3 Hz, 1H), 4.98-4.88 (m, 1H), 3.94 (dd, J=12, 3 Hz, 1H), 3.72 (dd, J=12, 4 Hz, 1H), 3.69-3.25 (m, 2H).

Synthesis of Alcohols 476-481

These alcohols were synthesized from the appropriate hydroxyiminoyl chlorides using the above procedure for the synthesis of 468.

Data for 476: $^1$HNMR (300 MHz, CDCl$_3$): δ 8.54 (d, J=3 Hz, 1H), 7.92 (dd, J=11, 3 Hz, 1H), 7.55 (d, J=8 Hz, 1H), 4.99-4.90 (m, 1H), 3.94 (dd, J=12, 3 Hz, 1H), 3.71 (dd, J=12, 4 Hz, 1H), 3.47-3.93 (m, 2H).

Data for 477: $^1$HNMR (300 MHz, CDCl$_3$): δ 7.77 (d, J=8 Hz, 2H), 7.65 (d, J=8 Hz, 2H), 4.93 (dddd, J=13, 8, 4, 3 Hz, 1H), 3.93 (dd, J=13, 3 Hz, 1H), 3.70 (dd, J=13, 4 Hz, 1H), 3.40 (dd, J=17, 11 Hz, 1H), 3.32 (dd, J=17, 8 Hz, 1H).

Data for 478: $^1$HNMR (300 MHz. CDCl$_3$): δ7.87 (d, J=8 Hz, 1H), 7.84 (d, J=8 Hz, 1H), 7.65 (d, J=8 Hz, 1H), 7.52 (d, J=8 Hz, 1H), 4.93 (dddd, J=13, 8, 3, 3 Hz, 1H), 3.92 (dd, J=13, 3 Hz, 1H), 3.70 (dd, J=13, 4 Hz, 1H), 3.43 (dd, J=11, 7 Hz, 1H), 3.33 (dd, J=11, 8 Hz, 1H).

Data for 479: $^1$HNMR (300 MHz, CDCl$_3$): δ 7.76 (d, J=7 Hz, 2H), 7.31 (d, J=7 Hz, 2H), 4.96 (dddd, J=13, 8, 4, 3 Hz, 1H), 3.96 (dd, J=12, 3 Hz, 1H), 3.75 (dd, J=12, 5 Hz), 3.44 (dd, J=17, 10 Hz, 1H), 3.34 (dd, J=17, 8 Hz, 1H).

Data for 480: $^1$HNMR (300 MHz, CDCl$_3$): δ 7.58 (d, J=8 Hz, 1H), 7.54 (s, 1H), 7.44 (d, J=8 Hz, 1H), 7.31-7.24 (m, 1H), 4.92 (dddd, J=12, 8, 4, 3 Hz, 1H), 3.94 (dd, J=5, 3 Hz, 1H), 3.90 (dd, J=5, 3 Hz, 1H), 3.72 (dd, J=8, 4 Hz, 1H), 3.68 (dd, J=8, 4 Hz, 1H).

Data for 481: $^1$HNMR (300 MHz, CDCl$_3$): δ 7.27 (s, 1H), 7.20 (s, 1H), 4.83 (dddd, J=12, 8, 3, 3 Hz, 1H), 3.87 (dd, J=12, 3 Hz, 1H), 3.67 (dd, J=12, 4 Hz, 1H), 3.37-3.17 (m, 2H).

Synthesis of Azide 469

To a solution of alcohol 468 (700 mg, 3.57 mmol) in CH$_2$Cl$_2$ (20 mL) at 0° C. was added Et$_3$N, followed by the addition of MsCl (416 μL, 5.35 mmol). The mixture was stirred at 0° C. for 30 min, then EtOAc (100 mL) was added, and the mixture was washed with brine (100 mL×2), dried with MgSO$_4$, and evaporated to afford the crude mesylate (800 mg).

A mixture of the above mesylate (800 mg, 3.57 mmol) and NaN$_3$ in DMF (15 mL) was stirred at 80° C. for 3 h, then the mixture was poured into water (50 mL), extracted with Et$_2$O (30 mL×3), dried with Na$_2$SO$_4$, and evaporated to afford azide 469 (540 mg, 68% yield). Data for 469: $^1$HNMR (300 MHz, CDCl$_3$): δ 8.39 (s, 1H), 8.30-8.20 (m, 1H), 7.03 (dd, J=8, 3 Hz, 1H), 4.40-4.30 (m, 1H), 3.60 (dd, J=10, 5 Hz, 1H), 3.55-3.35 (m, 2H), 3.25 (dd, J=16, 7 Hz, 1H).

Synthesis of Azides 482-487

These azides were synthesized from the appropriate alcohols using the above procedure for the synthesis of 469.

Data for 482: $^1$HNMR (300 MHz, CDCl$_3$): δ 8.46 (d, J=3 Hz, 1H), 7.88 (dd, J=9, 2 Hz, 1H), 7.49 (dd, J=9, 2 Hz, 1H), 5.00-4.80 (m, 1H), 3.53 (dd, J=10, 4 Hz, 1H), 3.53-3.30 (m, 2H), 3.16 (dd, J=17, 7 Hz, 1H).

Data for 483: $^1$HNMR (300 MHz, CDCl$_3$): δ 7.79 (d, J=8 Hz, 2H), 7.68 (d, J=8 Hz, 2H), 5.13-5.02 (m, 1H), 4.43 (dd, J=11, 4 Hz, 1H), 4.37 (dd, J=11, 5 Hz, 1H), 3.53 (dd, J=17, 11 Hz, 1H), 3.33 (dd, J=9, 7 Hz, 1H).

Data for 484: $^1$HNMR (300 MHz, CDCl$_3$): δ 7.87 (dd, J=9, 9 Hz, 1H), 7.70 (d, J=8 Hz, 1H), 7.56 (dd, J=8, 8 Hz, 1H), 5.13-5.02 (m, 1H), 4.46-4.30 (m, 2H), 3.53 (dd, J=17, 11 Hz, 1H), 3.36 (dd, J=9, 7 Hz, 1H).

Data for 485: $^1$HNMR (300 MHz, CDCl$_3$): δ 7.65 (d, J=9 Hz, 2H), 7.19 (d, J=8 Hz, 2H), 4.93-4.85 (m, 1H), 3.50 (dd, J=13, 5 Hz, 1H), 3.43-3.30 (m, 2H), 3.15 (dd, J=13, 7 Hz, 1H).

Data for 486: $^1$HNMR (300 MHz, CDCl$_3$): δ 7.67-750 (m, 4H), 4.94-4.84 (m, 1H), 3.50 (dd, J=13, 5 Hz, 1H), 3.45-3.25 (m, 2H), 3.20 (dd, J=13, 7 Hz, 1H).

Data for 487: $^1$HNMR (300 MHz, CDCl$_3$): δ 7.67-750 (m, 4H), 4.94-4.84 (m, 1H), 3.50 (dd, J=13, 5 Hz, 1H), 3.45-3.25 (m, 2H), 3.20 (dd, J=13, 7 Hz, 1H).

Synthesis of Alcohol 488

A mixture of alcohol 348 (310 mg, 1.21 mmol), 3-(tributyl)stannylpyridine (446 mg, 1.21 mmol), Pd(dppf)$_2$Cl$_2$ (59 mg, 0.072 mmol), copper (I) chloride (12 mg), lithium chloride (305 mg, 7.20 mmol) in DMSO (3.0 mL) was degassed by argon and then was stirred at 60° C. for 16 h. The reaction was quenched by the addition of H$_2$O (50 mL), NH$_4$OH (0.2 mL), EtOAc (150 mL) and CH$_2$Cl$_2$ (20 mL). The mixture was passed through celite. The organic layer was washed with water (50 mL×3), dried with Na$_2$SO$_4$, and the residue was purified by flash-chromatography (eluant: MeOH/CH$_2$Cl$_2$, 2/100), to give 488 (265 mg). Data for 488: $^1$HNMR (300 MHz, CDCl$_3$): δ 8.88 (s, 1H), 8.63 (d, J=4 Hz, 1H), 7.92 (d, J=8 Hz, 1H), 7.89 (d, J=8 Hz, 2H), 7.64 (d, J=8 Hz, 1H), 7.41 (dd, J=8, 5 Hz, 1H), 4.92 (dddd, J=12, 8, 3, 3 Hz, 1H), 3.92 (dd, J=12, 3 Hz, 1H), 3.72 (dd, J=12, 5 Hz, 1H), 3.44 (dd, J=17, 11 Hz, 1H), 3.33 (dd, J=17, 8 Hz, 1H).

Synthesis of Azide 489

The azide was synthesized using the same procedure as described above for the synthesis of azide 469. Data for 489:

¹HNMR (300 MHz, CDCl₃): δ 8.85 (s, 1H), 8.60 (m, 1H), 7.85 (d, J=8 Hz, 1H), 7.73 (d, J=9 Hz, 2H), 7.58 (d, J=9 Hz, 2H), 7.36 (s, 1H), 4.96-4.84 (m, 1H), 3.54 (dd, J=13, 5 Hz, 1H), 3.45-3.35 (m, 2H), 3.20 (dd, J=13, 7 Hz, 1H).

Synthesis of Alcohol 490

This compound was synthesized from alcohol 476 using the procedure described above for the synthesis of 488. Data for 490: ¹HNMR (300 MHz, CDCl₃): δ 9.17 (s, 1H), 8.86 (d, J=2 Hz, 1H), 8.62 (s, 1H), 8.30 (d, J=8 Hz, 1H), 8.08 (dd, J=8, 2 Hz, 1H), 7.76 (d, J=8 Hz, 1H), 7.37 (dd, J=8, 5 Hz, 1H), 4.93-4.84 (m 1H), 3.88 (d, J=10 Hz, 1H), 3.66 (d, J=10 Hz, 1H), 3.44-3.20 (m, 2H).

Synthesis of Azide 491

This azide was synthesized from alcohol 490 using the same procedure described above for the synthesis of azide 469. Data for 491: ¹HNMR (300 MHz, CDCl₃): δ 8.82 (s, 1H), 8.30-8.20 (m, 2H), 8.28-8.18 (m, 2H), 7.76 (d, J=9 Hz, 1H), 7.40 (s, 1H), 4.96-4.86 (m, 1H), 3.59-3.20 (m, 4H), 3.20 (dd, J=13, 7 Hz, 1H).

Synthesis of Silylether 493

To a solution of alcohol 460 (360 mg, 2.00 mmol) in DMF (8.0 mL) at 0° C. was added t-butyldimethylsilyl chloride (461 mg, 3.00 mmol), followed by the addition of imidazole (275 mg, 4.0 mmol). The mixture was stirred at 0° C. for 1 h and room temperature for 16 h. Water (50 mL) was added, and the mixture was extracted with 30% EtOAc in hexane (50 mL×3). The organic phase was washed with water (50 mL×2), dried by Na₂SO₄, and evaporated. The residue was purified by flash-chromatography (eluant: EtOAc/hexane, 5/95), to afford 493 (580 mg, 98% yield). Data for 493: ¹HNMR (300 MHz, CDCl₃, ppm): δ 4.70-4.61 (m, 1H), 3.69 (dd, J=11, 4 Hz, 1H), 3.62 (dd, J=11, 4 Hz, 1H), 0.81 (s, 9H), 0.01 (s, 6H).

Synthesis of Azide 495

Alcohol 348 (1.00 g, 3.90 mmol) and PdCl₂(dppf)₂ (546 mg, 0.762 mmol) were dissolved in dioxane (11 mL) and hexanmethylditin (1.42 g, 4.30 mmol) was added. The mixture was stirred at 85° C. for 16 h, then sat. aqueous NaHCO₃ (20 mL) was added, followed by EtOAc (20 mL). The aqueous phase was extracted with EtOAc (40 mL×3), and the organic phase was dried by Na₂SO₄. The residue was purified by flash-chromatography (eluant: EtOAc/hexane, 35/65) to afford stannane 492 (740 mg, 56% yield). Data for 492: ¹HNMR (300 MHz, CDCl₃): δ 7.13 (d, J=6 Hz, 2H), 7.05 (d, J=6 Hz, 2H), 4.70-4.60 (m, 1H), 3.70-3.61 (m, 3H), 3.51-3.41 (m, 1H), 3.17 (dd, J=17, 11 Hz, 1H), 3.05 (dd, J=17, 8 Hz, 1H), 1.73 (dd, J=8, 6 Hz, 1H), 0.09 (s, 9H).

To a suspension of stannane 492 (340 mg, 1.00 mmol), bromide 493 (353 mg, 1.20 mmol) and lithium chloride (254 mg, 6.00 mmol) in DMSO (2.5 mL) was added PdCl₂(dppf)₂ (49 mg, 0.06 mmol). The mixture was stirred at 70° C. for 16 h, then water (50 mL) was added. The mixture was extracted with EtOAc (40 mL×3), and the extracts were dried by Na₂SO₄. The residue was purified by flash-chromatography eluant: EtOAc/hexane, 35/65) to afford alcohol 494 (21 mg, 63% yield). Data for 494: ¹HNMR (300 MHz, CDCl₃): δ 7.56 (d, J=8 Hz, 2H), 7.22 (d, J=8 Hz, 2H), 4.90-4.81 (m, 1H), 3.87 (dd, J=16, 3 Hz, 3H), 3.68 (dd, J=16, 5 Hz, 1H), 3.38 (dd, J=17, 8 Hz, 1H), 3.25 (dd, J=17, 8 Hz, 1H), 2.38 (s, 3H).

Azide 495 was synthesized from alcohol 494 using the same procedure described above for the synthesis of azide 469. Data for 495: ¹HNMR (300 MHz, CDCl₃): δ 7.50 (d, J=8 Hz, 2H), 7.15 (d, J=8 Hz, 2H), 4.86-4.76 (m, 1H), 3.45-3.30 (m, 3H), 3.13 (dd, J=17, 7 Hz, 1H).

General Procedure for the Synthesis of Triazoles 394-403

To a mixture of alkyne 173 (100 mg, 0.127 mmol) and the appropriate azide (0.140 mmol, 1.1 eq) in acetonitrile (4.0 mL) at room temperature under argon was added 2,6-lutidine (22 μL, 0.191 mmol, 1.1 eq), followed by addition of copper (I) iodide (12 mg, 0.064 mmol). The mixture was stirred at room temperature for 1.5 to 6 h. After the reaction was complete, 1 mL 5% NH₄OH was added. The mixture was stirred at room temperature for 10 min. The reaction solvent (CH₃CN) was removed under vacuum. The aqueous phase was extracted with CH₂Cl₂ (30 mL×3), and the organic phase was dried over Na₂SO₄. The residue was separated by flash-chromatography (eluant: 20/80 to 30/70 MeOH/EtOAc) on silica gel to afford the desired product.

Data for 394: MS (ESI) m/z 1008.4 (M)⁺; ¹HNMR (300 MHz, CDCl₃, partial): δ 8.37 (s, 1H), 8.37-8.00 (m, 1H), 7.60 (s, 1H), 7.00 (dd, J=9, 3 Hz, 1H), 4.45 (d, J=6 Hz, 1H), 4.29 (br s, 1H), 2.24 (s, 3H), 1.04 (d, J=9 Hz, 3H).

Data for 395: MS (ESI) m/z 1070.2 (M)⁺; ¹HNMR (300 MHz, CDCl₃, partial): δ 8.45 (s, 1H), 7.73 (dd, J=4, 2 Hz, 1H), 7.47 (d, J=4 Hz, 1H), 4.45 (d, J=6 Hz, 1H), 4.29 (br s, 1H), 2.20 (s, 3H), 0.98 (d, J=9 Hz, 3H).

Data for 396: MS (ESI) m/z 1043.7 (M)⁺; ¹HNMR (300 MHz, CDCl₃, partial): δ 7.48 (s, 1H), 7.16 (d, J=7 Hz, 2H), 7.14 (d, J=7 Hz, 2H), 4.36 (d, J=7 Hz, 1H), 4.22 (s, 1H), 2.21 (s, 3H), 0.96 (d, J=8 Hz, 3H).

Data for 397: MS (ESI) m/z 1073.8 (M)⁺; ¹HNMR (300 MHz, CDCl₃, partial): δ 7.64 (d, J=8 Hz, 2H), 7.24 (d, J=8 Hz, 2H), 4.40 (d, J=9 Hz, 1H), 4.28 (s, 1H), 2.27 (s, 3H), 1.04 (d, J=9 Hz, 3H).

Data for 398: MS (ESI) m/z 1073.8 (M)⁺; ¹HNMR (300 MHz, CDCl₃, partial): δ 7.53 (s, 1H), 7.43-7.34 (m, 3H), 7.22 (s, 1H), 4.36 (d, J=7 Hz, 1H), 4.21 (s, 1H), 2.20 (s, 3H), 0.96 (d, J=8 Hz, 3H).

Data for 399: MS (ESI) m/z 1057.8 (M)⁺; ¹HNMR (300 MHz, CDCl₃, partial): δ 7.64 (d, J=8 Hz, 2H), 7.58 (d, J=8 Hz, 1H), 7.51 (br s, 1H), 4.55 (t, J=5 Hz, 2H), 4.36 (d, J=10 Hz, 1H), 4.21 (s, 1H), 2.25 (s, 3H), 0.95 (d, J=8 Hz, 3H).

Data for 400: MS (ESI) m/z 1057.8 (M)⁺; ¹HNMR (300 MHz, CDCl₃, partial): δ 7.78 (s, 1H), 7.70 (d, J=8 Hz, 1H), 7.60 (d, J=8 Hz, 1H), 7.53-7.44 (m, 2H), 4.46 (d, J=7 Hz, 1H), 4.21 (s, 1H), 2.20 (s, 3H), 0.96 (d, J=8 Hz, 3H).

Data for 401: MS (ESI) m/z 1003.8 (M)⁺; ¹HNMR (300 MHz, CDCl₃, partial): δ 7.60 (s, 1H), 7.48 (d, J=8 Hz, 2H), 7.19 (d, J=8 Hz, 2H), 4.43 (d, J=7 Hz, 1H), 4.22 (s, 1H), 2.27 (s, 3H), 1.04 (d, J=8 Hz, 3H).

Data for 402: MS (ESI) m/z 1066.9 (M)⁺; ¹HNMR (300 MHz, CDCl₃, partial): δ 8.79 (s, 1H), 8.56 (d, J=4 Hz, 1H), 7.82 (dt, J=8, 2 Hz, 1H), 7.65 (d, J=8 Hz, 2H), 7.56 (d, J=8 Hz, 2H), 7.53 (s, 1H), 7.33 (dd, J=8, 4 Hz, 1H), 4.37 (d, J=7 Hz, 1H), 4.21 (s, 1H), 2.20 (s, 3H), 0.97 (d, J=8 Hz, 3H).

Data for 403: MS (ESI) m/z 1067.8 (M)⁺; ¹HNMR (300 MHz, CDCl₃, partial): δ 9.16 (s, 1H), 8.62 (d, J=4 Hz, 1H), 7.82 (dt, J=8, 2 Hz, 1H), 7.96 (dd, J=6, 2 Hz, 1H), 7.74 (d, J=8 Hz, 1H), 7.51 (s, 1H), 7.37 (dd, J=8, 5 Hz, 1H) 4.36 (d, J=7 Hz, 1H), 4.21 (s, 1m), 2.20 (s, 3H), 0.96 (d, J=8 Hz, 3H).

Example 55

Synthesis of Triazoles 404 and 405

Synthesis of Azide 404

This compound (189 mg) was synthesized from alkyne 174 (150 mg, 0.187 mmol) and azide 349 (58 mg, 0.206 mmol) using the same procedure described above for the synthesis of triazole 361. Data for 404: MS (ESI) m/z 542 (M+2H)²⁺; ¹H NMR (300 MHz, CDCl₃, partial): δ 7.53-

7.50 (m, 3H), 7.45-7.42 (m, 2H), 5.17-5.11 (m, 1H), 5.08 (d, J=4 Hz, 1H), 4.69-4.66 (m, 1H), 4.61 (t, J=5 Hz, 2H), 4.45 (d, J=7 Hz, 1H), 3.33 (s, 3H), 3.03 (t, J=9 Hz, 1H), 2.21 (t, J=5 Hz, 4H), 0.89 (m, 6H).

Synthesis of Azide 405

This compound (175 mg) was made from alkyne 174 (150 mg, 0.187 mmol) and azide 503 (49 mg, 0.206 mmol; see Example 58 for the synthesis of 503) using the same procedure described above for the synthesis of triazole 361. Data for 405: MS (ESI) m/z 520.5 (M+2H)$^{2+}$; $^1$H NMR (300 MHz, CDCl$_3$, partial): δ 7.49 (s, 1H), 7.12-7.05 (m, 2H), 6.91-6.82 (m, 1H), 5.21-5.13 (m, 1H), 5.12 (d, J=5 Hz, 1H), 4.61 (t, J=4 Hz, 2H), 4.44 (d, J=7 Hz, 1H), 4.29 (br d, J=3 Hz, 1H), 4.13-4.03 (m, 1H), 3.69 (d, J=6 Hz, 1H), 3.65 (d, J=7 Hz, 1H), 3.03 (t, J=10 Hz, 1H), 0.91-0.87 (m, 6H).

Example 56

Synthesis of Triazoles 406-409

These triazoles were synthesized using the procedure described above for the synthesis of triazole 228.

Synthesis of Triazole 406

Alkyne 174 (70 mg, 86 µmol), azide 355 (39 mg, 129 µmol), and CuI (2 mg, 8 µmol) afforded triazole 406 as a white solid (94.1 mg, 83 µmol). Data for 406: MS (ESI) m/z 568 (M+2H)$^{2+}$; $^1$HNMR (300 MHz, CDCl$_3$, partial): δ 9.46 (br s, 1H), 7.69-7.53 (m, 8H), 7.44 (s, 1H), 5.20-5.04 (m, 3H), 4.70-4.58 (m, 2H), 4.41 (d, 1=6 Hz, 1H), 4.20 (br s, 1H), 4.12-4.00 (m, 1H), 3.61 (d, J=3 Hz, 1H), 3.56 (d, J=7 Hz, 1H), 3.33 (s, 3H), 3.05-2.93 (m, 2H), 2.29 (s, 3H), 2.18 (s, 3H), 2.10 (d, J=9 Hz, 1H), 1.34-1.14 (m, 17H), 0.91-0.84 (m, 6H): $^{13}$CNMR (75 MHz, CDCl$_3$): δ 178.9, 156.3, 148.4, 144.4, 141.0, 132.7, 128.9, 127.6, 127.5, 127.4, 122.3, 118.6, 111.6, 102.9, 94.5, 83.3, 79.2, 78.2, 77.7, 74.2, 73.7, 73.0, 70.6, 70.1, 68.8, 65.9, 65.5, 62.4, 53.1, 52.4, 49.5, 45.3, 42.3, 37.4, 36.8, 36.2, 34.7, 29.6, 27.8, 27.6, 26.9, 26.8, 25.4, 22.0, 21.6, 21.3, 21.2, 18.2, 16.2, 14.5, 11.2, 8.8, 7.9.

Synthesis of Triazole 407

Alkyne 174 (70 mg, 86 µmol), azide 349 (36 mg, 129 µmol), and CuI (2 mg, 8 µmol) afforded triazole 407 as a white solid (89 mg, 80 µmol). Data for 407: MS (ESI) m/z 556, 557 (M+2H)$^{2+}$; $^1$HNMR (300 MHz, CDCl$_3$, partial): δ 9.38 (br s, 1H), 7.54-7.41 (m, 5H), 7.44 (s, 1H), 5.20-4.90 (m, 3H), 4.70-4.58 (m, 3H), 4.49 (d, J=6 Hz, 1H), 4.28 (br s, 1H), 4.12-4.00 (m, 1H), 3.61 (d, J=3 Hz, 1H), 3.32 (s, 3H), 3.05-2.93 (m, 2H), 2.30 (s, 3H), 2.17 (s, 3H), 2.15 (d, J=9 Hz, 1H), 1.33-1.27 (m, 6H), 1.27-1.15 (m, 10H), 1.10-1.00 (m, 8H), 0.91-0.84 (m, 6H): $^{13}$CNMR (75 MHz, CDCl$_3$): δ 178.8, 156.0, 148.4, 132.0, 128.1, 127.6, 124.8, 122.3, 102.9, 94.5, 83.3, 79.2, 78.2, 77.7, 74.3, 73.7, 73.0, 70.6, 70.1, 68.8, 65.9, 65.5, 62.4, 53.4, 53.1, 52.4, 49.5, 45.3, 42.2, 37.2, 36.8, 36.2, 34.7, 29.6, 27.8, 27.6, 26.9, 26.8, 25.4, 22.0, 21.6, 21.4, 21.3, 18.2, 16.2, 14.6, 11.2, 8.9, 7.4.

Synthesis of Triazole 408

Alkyne 174 (70 mg, 86 µmol), azide 158 (39 mg, 129 µmol), and CuI (2 mg, 8 µmol) afforded triazole 408 as a white solid (93 mg, 85 µmol). Data for 408: MS (ESI) m/z 560 (M+2H)$^{2+}$; $^1$HNMR (300 MHz, CDCl$_3$, partial): δ 7.70 (br s, 1H), 7.50 (s, 1H), 7.31 (dd, J=14, 2 Hz, 1H), 7.21 (dd, J=8, 2 Hz, 1H), 6.89 (t, J=9 Hz, 3H), 5.14-5.05 (m, 1H), 4.97 (d, J=4 Hz, 1H), 4.65-4.45 (m, 3H), 4.45 (d, J=7 Hz, 1H), 4.28 (dd, J=6, 2 Hz, 1H), 4.13-3.97 (m, 1H), 3.87-3.80 (m, 4H), 3.68-3.61 (m, 3H), 3.32 (s, 3H), 2.28 (s, 3H), 2.18 (d, J=9 Hz, 1H), 2.13 (s, 3H), 1.35-1.15 (m, 18H), 1.10-1.02 (m, 9H), 0.91-0.82 (m, 6H): $^{13}$CNMR (75 MHz, CDCl$_3$): δ 178.3, 153.3, 148.3, 133.4, 122.5, 122.3, 118.2, 114.5, 114.2, 103.0, 95.4, 84.0, 79.0, 78.1, 77.6, 77.5, 77.1, 76.6, 73.5, 72.8, 70.7, 70.0, 68.7, 66.7, 65.6, 65.5, 61.8, 53.1, 52.4, 50.4, 50.3, 49.4, 44.9, 42.5, 40.9, 37.4, 36.8, 36.6, 35.0, 29.7, 27.8, 27.3, 26.9, 26.7, 25.4, 21.9, 21.6, 21.4, 18.4, 16.3, 15.5, 11.2, 8.9, 7.4.

Synthesis of Triazole 409

Alkyne 174 (70 mg, 86 µmol), the azide 503 (31 mg, 129 µmol; see Example 58 for the synthesis of 503), and CuI (2 mg, 8 µmol) afforded triazole 409 as a white solid (93 mg, 85 µmol). Data for 409: MS (ESI) m/z 527 (M+2H)$^{2+}$; $^1$HNMR (300 MHz, CDCl$_3$ partial): δ 8.95 (br s, 1H), 7.47 (s, 1H), 7.12-7.03 (m, 2H), 6.71 (tt, J=9, 2 Hz, 1H), 5.21-5.09 (m, 2H), 4.62 (d, J=6 Hz, 1H), 4.48 (t, J=10 Hz, 1H), 4.45 (d, J=7 Hz, 1H), 4.29 (br s, 1H), 4.15-4.00 (m, 1H), 3.66 (d, J=5 Hz, 1H), 3.62 (d, J=7 Hz, 1H), 3.32 (s, 3H), 3.02 (t, J=11 Hz, 1H), 2.29 (s, 3H), 2.18 (d, J=10 Hz, 1H), 2.13 (s, 3H), 1.77 (d, J=9 Hz, 1H), 1.33-1.26 (m, 6H), 1.27-1.15 (m, 10H), 1.10-0.99 (m, 9H), 0.92-0.84 (m, 6H): $^{13}$CNMR (75 MHz, CDCl$_3$, partial): δ 178.7, 155.2, 148.4, 131.6, 122.2, 109.9, 109.8, 109.6, 109.5, 105.7, 02.9, 94.6, 83.4, 79.6, 78.1, 77.9, 76.6, 74.3, 73.9, 73.6, 72.9, 70.6, 70.1, 68.8, 65.8, 65.5, 62.3, 53.1, 52.3, 49.4, 45.2, 42.4, 42.0, 37.0, 36.8, 36.3, 34.8, 29.6, 27.8, 27.5, 27.0, 26.7, 25.4, 21.9, 21.6, 21.3, 21.2, 18.2, 16.2, 11.2, 7.5.

Example 57

Synthesis of Triazoles 410 and 411

These triazoles were synthesized using the chemistry illustrated for triazole 410 shown in Scheme 77. Racemic azide 499 was used to generate triazole 410 as a mixture of diastereomers.

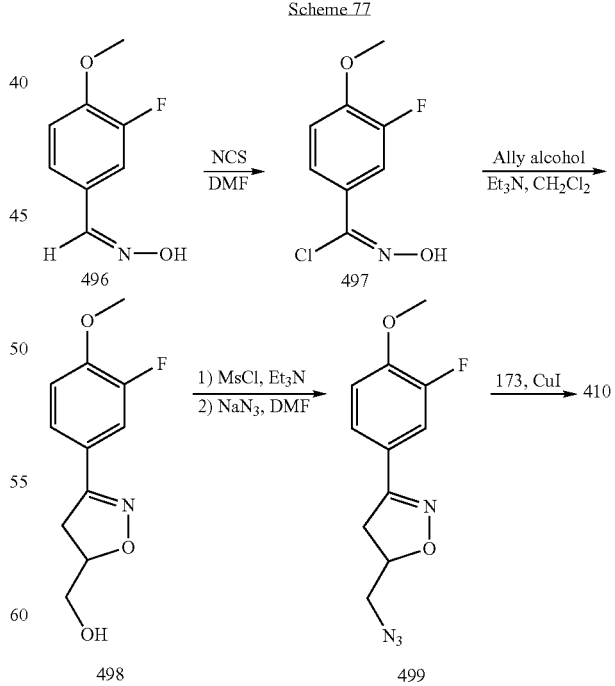

Scheme 77

Synthesis of Azide 499

A solution of 3-fluoro-4-methoxybenzaldehyde (2.0 g, 12.97 mmol) and hydroxylamine hydrochloride (1.0 g, 14.27 mmol) in ethanol (40 mL) and water (80 mL) was cooled to 4° C., and 2.3 mL NaOH (50% w/w) was added. The reaction mixture was stirred for 3 h at room temperature. The reaction mixture was adjusted to pH 6.0, and partitioned with methylene chloride and water. The aqueous layer was extracted twice with methylene chloride, and the combined organic layer was washed with brine, dried (Na$_2$SO$_4$), and evaporated to yield 496 (1.97 g, 90%) as a white solid. Data for 496: $^1$HNMR (300 MHz, CDCl$_3$): δ 7.84 (s, 1H), 7.04 (d, J=3 Hz, 1H), 6.74 (app t, J=8 Hz, 1H).

To a solution of oxime 496 (1.97 g, 11.64 mmol) in dimethylformamide (10 mL) was added N-chlorosuccinimide (1.5 g, 11.64 mmol). The reaction mixture was warmed to 50° C. for 1 h. The reaction was diluted with ethyl acetate (50 mL), and washed with brine. The organic phase was dried (Na$_2$SO$_4$), and evaporated to yield 497 (2.37 g, 100% yield). Data for 497: $^1$HNMR (300 MHz, CDCl$_3$): δ 8.02 (s, 1H), 7.60 (m, 1H), 6.94 (t, J=3 Hz, 1H).

To a solution of hydroximinoyl chloride 497 (1.00 g, 4.91 mmol) in methylene chloride (5 mL) was added allyl alcohol (0.3 mL, 4.91 mmol). The mixture was cooled to 0° C., and triethylamine (0.68 mL, 4.91 mmol) was added. The reaction mixture was slowly warmed to room temperature, stirred for 16 h, then quenched with water (20 mL), and extracted twice with methylene chloride. The combined organic layer was washed with brine, dried over (Na$_2$SO$_4$), and evaporated to yield 498 (0.76 g, 70% yield). Data for 498: $^1$HNMR (300 MHz, CDCl$_3$): δ 7.40 (m, 1H), 7.30 (m, 1H), 6.80 (m, 1H), 4.80 (m, 1H), 3.60 (s, 3H), 3.20 (m, 2H).

Alcohol 498 (0.7 g, 3.10 mmol) was dissolved in 10 mL methylene chloride, and the mixture cooled to 0° C. Triethylamine (0.86 mL, 6.2 mmol) was added, followed by methanesulfonyl chloride (0.34 mL, 4.35 mmol). The mixture was allowed to warm to room temperature and stirred for 1 h. Methylene chloride (10 mL) was added, and the mixture washed twice with 1N HCl, then twice with 10% aqueous sodium carbonate, and then brine. The organic phase was dried (Na$_2$SO$_4$), and evaporated to yield the expected mesylate (0.77 g, 86% yield). Data: $^1$HNMR (300 MHz, CDCl$_3$): δ 7.40 (m, 1H), 7.20 (d, J=3 Hz, 1H), 6.85 (m, 1H), 4.90 (m, 1H), 3.00 (s, 3H).

A solution of the above mesylate (0.77 g, 2.30 mmol) in dimethylformamide (5 mL) was treated with sodium azide (0.66 g, 10.15 mmol) and the mixture heated to 80° C. for 3 h. The reaction mixture was cooled to room temperature, diluted with ethyl acetate (50 mL), and washed with brine (2×50 mL). Drying (Na$_2$SO$_4$), and evaporation provided azide 499 (0.52, 83% yield) as a yellow oil of suitable purity for use in subsequent reactions.

Synthesis of Triazole 410

A solution of alkyne 173 (100 mg, 0.127 mmol) in tetrahydrofuran (10 mL) was treated with azide 499 (0.05 g, 0.19 mmol), N,N-diisopropylethylamine (0.03 mL, 0.15 mmol) and copper (1) iodide (0.02 g, 0.127 mmol), and the mixture was stirred under argon at room temperature for 16 h. The reaction mixture was diluted with ethyl acetate (50 mL), and washed with brine (2×50 mL). The organic phase was dried and evaporated. The residue was purified by preparative thin layer chromatography (using 90% CH$_2$Cl$_2$, 0% MeOH, 0.1% NH$_4$OH as eluant) to provide 410 (71 mg, 77% yield) as a yellow solid. Data for 410: $^1$HNMR (300 MHz, CDCl$_3$, partial): δ 7.50 (s, 1H), 7.32 (m, 1H), 7.10 (s, 1H), 6.80 (t, J=3 Hz, 1H), 5.0 (m, 1H), 4.60-4.35 (m, 2H), 4.01 (m, 1H), 3.6 (m, 1H).

Synthesis of Triazole 411

This compound was made from alkyne 173 and the required 3-(4-chlorophenoxy)phenyl isoxazoline azide (synthesized from 3-(4-chlorophenoxy)benzaldehyde using the same procedure described above for the synthesis of azide 499) using the same procedure described above for the synthesis of triazole 410. Data for 411: $^1$H-NMR (300 MHz, CDCl$_3$, partial): δ 7.50 (s, 1H), 7.10-7.30 (m, 4H), 6.90 (s, 1H), 6.80 (s, 1H), 5.02 (m, 1H), 4.50-4.70 (m, 2H), 4.35 (d, J=3 Hz, 1H), 4.0 (m, 1H), 3.60 (t, J=7 Hz, 2H).

Example 58

Synthesis of Triazoles 412-414

These triazoles were synthesized using the chemistry illustrated for triazole 412 shown in Scheme 78. Hydroxyiminoyl chloride 501 was converted to chiral, non-racemic alcohol 502 which was transformed to azide 503. The cycloaddition of alkyne 173 with azide 503 yielded triazole 412.

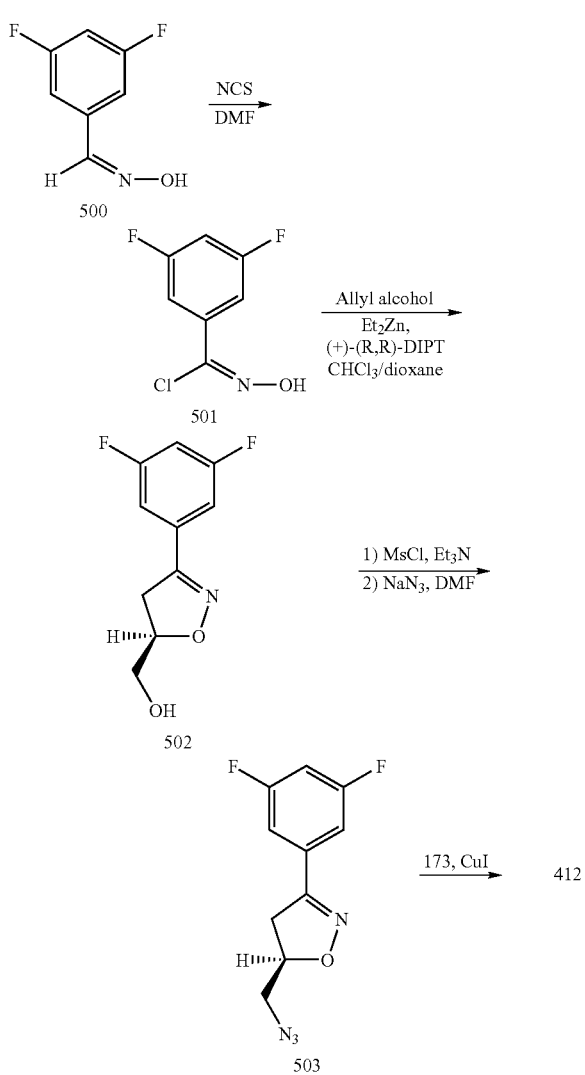

Synthesis of Azide 503

A solution of 3,5-difluorobenzaldehyde (2.0 g. 14.0 mmol) and hydroxylamine hydrochloride (1.07 g, 15.4 mmol) in ethanol (40 mL) and water (80 mL) was cooled to 4° C. and 2.3 mL NaOH (50% w/w) was added. The reaction mixture was stirred for 3 h at room temperature. The reaction mixture was adjusted to pH 6.0, and partitioned with methylene chloride and water. The aqueous layer was extracted twice with methylene chloride, and the combined organic layer was washed with brine, dried ($Na_2SO_4$), and evaporated to yield 500 (2.01 g, 91% yield) as a white solid. Data for 500: $^1$HNMR (300 MHz, $CDCl_3$): δ 7.82 (s, 1H), 6.80 (m, 1H), 6.60 (m, 1H).

To a solution of oxime 500 (2.01 g, 12.7 mmol) in dimethylformamide (10 mL) was added N-chlorosuccinimide (1.7 g, 12.7 mmol). The reaction mixture was warmed to 50° C. for 1 h. The reaction was diluted with ethyl acetate (50 mL), and washed with brine. The organic phase was dried ($Na_2SO_4$), and evaporated to yield 501 (2.45 g, 100% yield). Data for 501: $^1$HNMR (300 MHz, $CDCl_3$): δ 8.0 (s, 1H), 7.40 (d, J=2 Hz, 1H), 6.80 (m, 1H).

To a solution of allyl alcohol (0.7 mL, 10.30 mmol) in 20 mL $CHCl_3$ was added a 1 M diethylzinc solution in hexane (12.4 mL, 12.40 mmol) at −5 to 0° C. After stirring for 10 min, (+)-diisopropyl tartrate (0.5 mL, 2.10 mmol) was added and the solution was stirred for 1 h at 0° C. The milky solution was cooled to −20° C. and 20 mL $CHCl_3$ and dioxane (5 mL) was added. Then hydroximinoyl chloride 501 (1.80 g, 9.40 mmol) was added in portions at −20 to −15° C. The solution was stirred for 3 h at −150° C., then poured into 100 mL saturated aqueous $NH_4Cl$ and extracted with $CHCl_3$ (3×100 mL). The combined organic extract was washed with brine, dried $Na_2SO_4$, and evaporated. The residue was purified by flash-chromatography (eluting with 30% ethyl acetate/hexane), to afford crude material which was recrystallized from ethyl acetate and hexane to yield 502 (0.75 g, 75% yield). Data for 502: $^1$HNMR (300 MHz; $CDCl_3$): δ 7.20 (m, 2H), 6.80 (m, 1H), 4.96 (m, 1H), 3.90 (m, 1H), 3.70 (m, 1H), 3.30 (m, 2H), 2.10 (m, 1H).

Alcohol 502 (0.74 g, 3.47 mmol) was dissolved in 10 mL methylene chloride, and the mixture cooled to 0° C. Triethylamine (1.0 mL, 6.94 mmol) was added, followed by methanesulfonyl chloride (0.4 mL, 4.85 mmol). The mixture was allowed to warm to room temperature and stirred for 1 h. Methylene chloride (10 mL) was added, and the mixture washed twice with 1 N HCl, then twice with 10% aqueous sodium carbonate, and then brine. The organic phase was dried ($Na_2SO_4$), and evaporated to yield the mesylate (0.93 g, 92% yield). Data: $^1$HNMR (300 MHz, $CDCl_3$): δ 7.15 (m, 2H), 6.85 (m, 1H), 5.01 (m, 1H) 4.33 (m, 2H); 3.00 (s, 3H).

A solution of the above mesylate (0.93 g, 3.19 mmol) in dimethylformamide (10 mL) was treated with sodium azide (0.83 g, 12.7 mmol) and the mixture heated to 80° C. for 3 h. The reaction mixture was cooled to room temperature, diluted with ethyl acetate (50 mL), and washed with brine (2×50 mL). Drying ($Na_2SO_4$), and evaporation provided azide 503 (0.65, 86% yield) as a yellow oil of suitable purity for use in subsequent reactions. Data for 503: $^1$HNMR (300 MHz, $CDCl_3$): δ 7.20 (m, 2H), 6.80 (m, 1H), 4.95 (m, 1H), 3.54 (dd, J=4, 15 Hz, 1H), 3.00 (dd, J=7, 10 Hz, 1H).

Synthesis of Triazole 412

A solution of alkyne 173 (100 mg, 0.127 mmol) in tetrahydrofuran (10 mL) was treated with azide 503 (0.045 g, 0.19 mmol), N,N-diisopropylethylamine (0.03 mL, 0.15 mmol) and copper (I) iodide (0.02 g, 0.127 mmol), and the mixture was stirred under argon at room temperature for 16 h. The reaction mixture was diluted with ethyl acetate (50 mL), and washed with brine (2×50 mL). The organic phase was dried and evaporated. The residue was purified by preparative thin layer chromatography (using 80% $CH_2Cl_2$, 20% MeOH, 0.1% $NH_4OH$ as eluant) to provide 412 (96 mg, 74% yield) as a yellow solid. Data for 412: $^1$HNMR (300 MHz, $CDCl_3$, partial): δ 8.50 (s, 1H), 7.10 (m, 1H), 7.00 (m, 1H), 6.80 (m, 1H), 5.10 (m, 1H), 4.70-4.50 (m, 2H), 4.01 (m, 1H), 3.80 (m, 1H).

Synthesis of Triazole 413

This compound was made from alkyne 173 and the required 3,5-dichlorophenyl isoxazoline azide (produced from 3,5-dichlorobenzaldehyde as described above for the synthesis of azide 503) using the same procedure described above for the synthesis of 412. Data for 413: $^1$H-NMR (300 MHz, $CDCl_3$, partial): δ 9.20 (s, 1H), 7.50 (m, 1H), 7.35 (m, 1H), 5.10 (m, 2H), 4.90 (m, 1H), 4.60 (d, J=5 Hz, 1H), 4.50 (m, 2H), 4.40 (d, J=3 Hz, 1H), 4.00 (m, 1H), 3.60 (m, 2H), 3.20 (s, 3H).

Synthesis of Triazole 414

This compound was made from alkyne 173 and the required piperonyl isoxazoline azide (produced from piperonaldehyde as described above for the synthesis of azide 503) using the same procedure described above for the synthesis of 412. Data for 414: $^1$H-NMR (300 MHz, $CDCl_3$, partial): δ 8.80 (s, 1H), 7.30 (m, 1H), 7.20 (s, 1H), 7.00 (m, 1H), 6.80 (m, 1H), 6.0 (s, 1H), 4.95 (m, 2H), 4.80-4.20 (m, 8H), 4.00 (m, 1H), 3.70 (t, J=3 Hz, 3H).

Example 59

Synthesis of Thiazole 415

Scheme 79 depicts the synthesis of thiazole 415. Mesylate 504 was converted to nitrile 505 which was then hydrolyzed to afford amide 506. Amide 506 was treated with Lawesson's reagent to give the thioamide 507, which was subsequently converted to thiazole 509 by heating in the presence of acyl bromide 508. Alkyation of amine 171 then provided thiazole 415.

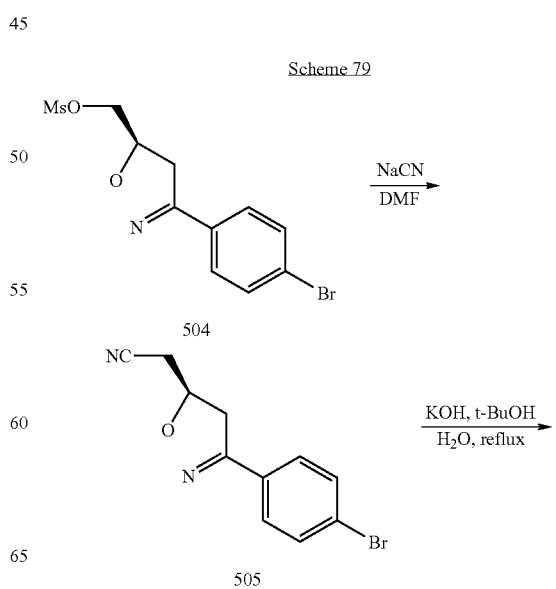

Scheme 79

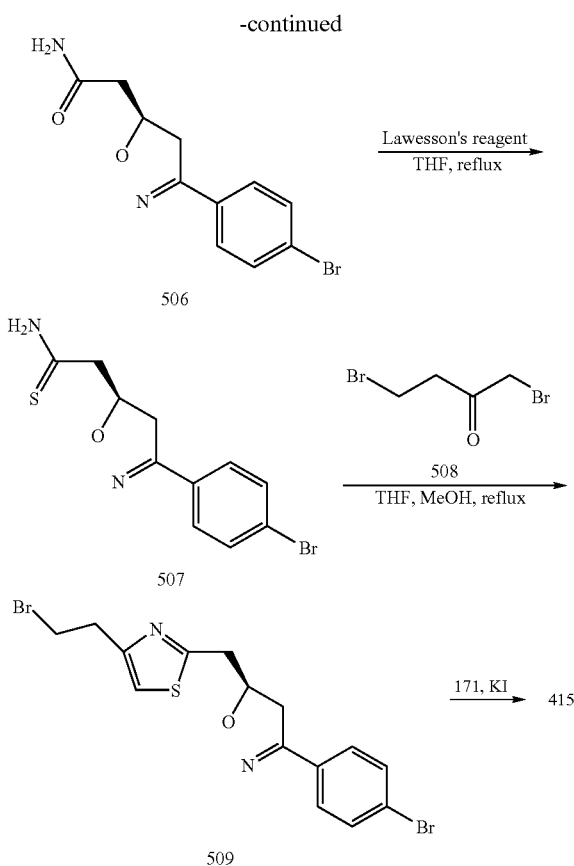

Synthesis of Bromide 509

Under an argon atmosphere, a mixture of mesylate 504 (1.67 g, 5 mmol; for a synthesis see Example 39) and NaCN (1.25 g, 25 mmol) in 15 mL of DMF was heated at 120° C. for 2 h. The reaction mixture was diluted with EtOAc, washed with brine, dried (MgSO$_4$), concentrated and crystallized in EtOAc/hexane to afford nitrile 505 (1.20 g, 90% yield). Data for 505: $^1$HNMR (300 MHz, CDCl$_3$): δ 7.56 (d, J=9 Hz, 2H), 7.53 (d, J=9 Hz, 2H), 5.05 (m, 1H), 3.60 (dd, J=11, 17 Hz, 1H), 3.25 (dd, J=6, 17 Hz, 1H), 2.51 (dd, J=5, 17 Hz, 1H), 2.73 (dd, J=7, 17 Hz, 1H).

A mixture of nitrile 505 (1.0 g, 3.77 mmol) and KOH (0.5 g, 8.93 mmol) in 16 mL of tert-butanol and 2 mL of water was heated to reflux for 2 h. The reaction mixture was cooled to room temperature and diluted with water. The desired amide 506 was collected by filtration (0.85 g, 80% yield). Data for 506: $^1$HNMR (300 MHz, DMSO): δ 7.66 (d, J=8 Hz, 2H), 7.61 (d, J=8 Hz, 2H), 7.43 (s, 1H), 6.97 (s, 1H), 4.99 (m, 1H), 3.52 (dd, J=11, 17 Hz, 1H), 3.15 (dd, J=7, 17 Hz, 1H), 2.51 (dd, J=7.14 Hz, 1H), 2.39 (dd, J=7, 14 Hz, 1H).

A mixture of 506 (220 mg, 0.78 mmol) and Lawesson's reagent (187 mg, 0.46 mmol) in THF (3 mL) was refluxed under argon for 2 h. The reaction was diluted with EtOAc, washed with brine, dried over MgSO$_4$ and concentrated under vacuum. Recrystallization of the crude product from EtOAc afforded 507 (180 mg, 77% yield). Data for 507: MS (ESI) m/z 298.8 (M+H)$^+$; $^1$HNMR (300 MHz, CDCl$_3$): δ 7.56 (d, J=9 Hz, 2H), 7.52 (d, J=9 Hz, 2H), 7.46 (br s, 2H), 5.15 (m, 1H), 3.52 (dd, J=10, 17 Hz, 1H), 3.27 (dd, J=8, 17 Hz, 1H), 3.12 (d, J=12 Hz, 2H).

To a solution of 508 (190 mg, 0.83 mmol; prepared as in Eur. J. Org. Chem. 2001, pp. 3789-3795) in THF (8 mL) and MeOH (2 mL) was added 507 (150 mg, 0.50 mmol). After refluxing for 2 h, the reaction was concentrated and crystallized in CH$_2$Cl$_2$ to provide 509 (163 mg, 77% yield). Data for 509: MS (ESI) m/z 430.7 (M+H)$^+$; $^1$HNMR (300 MHz, CDCl$_3$): δ 7.56 (d, J=9 Hz, 2H), 7.52 (d, J=9 Hz, 2H), 7.41 (s, 1H), 5.26 (m, 1H), 4.02 (dd, J=4, 15 Hz, 1H), 3.85-3.75 (m, 3H), 3.69-3.47 (m, 4H).

Synthesis of Thiazole 415

A mixture of 509 (56 mg, 0.13 mmol), amine 171 (96 mg, 0.13 mmol), Hunig's base (170 mg, 1.3 mmol) and KI (22 mg, 0.13 mmol) in THF (4 mL) was refluxed for 24 h. The THF was removed under vacuum and the residue was dissolved in EtOAc. The solution was washed with brine, dried over MgSO$_4$, concentrated and purified by chromatography on silica gel (eluant: 25:1:0.1/CH$_2$Cl$_2$:MeOH:NH$_3$H$_2$O) to provide thiazole 415 (52 mg, 37% yield). Data for 415: MS (ESI) m/z 1083.7 (M+H)$^+$, 542.2 (100%); $^1$HNMR (300 MHz, CDCl$_3$, partial): δ 7.46 (s, 4H), 6.78 (s, 1H), 5.10 (m, 1H), 3.24 (s, 3H), 0.83 (t, J=7 Hz, 3H).

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound having the formula:

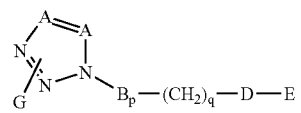

or a pharmaceutically acceptable salt, ester, or prodrug thereof, wherein

A at each occurrence, is carbon;

B is selected from the group consisting of O, NR$^2$, S(O)$_r$, C=O, C=S, and C=NOR$^3$, p is 0;

q, at each occurrence, independently is 0 or 1;

r is 0, 1, or 2;

R$^2$, at each occurrence, independently is selected from the group consisting of:

a) hydrogen, b) S(O)$_r$R$^4$, c) formyl, d) C$_{1-8}$ alkyl, e) C$_{2-8}$ alkenyl, f) C$_{2-8}$ alkynyl, g) C$_{1-8}$ alkoxy, h) C$_{1-8}$ alkylthio, i) C$_{1-8}$ acyl, j) saturated, unsaturated, or aromatic C$_{3-8}$ carbocycle, and k) saturated, unsaturated, or aromatic 5-10 membered heterocycle containing one or more heteroatoms selected from the group consisting of nitrogen, oxygen, and sulfur, wherein any of d)-k) optionally is substituted with one or more moieties selected from the group consisting of carbonyl, aryl, substituted aryl, heteroaryl, substituted heteroaryl, F, Cl, Br, I, CN, NO$_2$, —NR$^3$R$^3$, —OR$^3$, —S(O)$_r$R$^4$, —S(O)$_r$NR$^3$R$^3$, —C(O)R$^3$, —C(O)OR$^3$, —OC(O)R$^3$, —C(O)NR$^3$R$^3$, and —OC(O)NR$^3$R$^3$;

alternatively, two R$^2$ groups, taken together with the atom to which they are bonded, form i) 5-8 membered saturated or unsaturated carbocycle, or ii) 5-8 membered saturated or unsaturated heterocycle containing one or more atoms selected from the group consisting of nitrogen, oxygen, and sulfur, wherein i)-ii) optionally is substituted with one or more moieties selected from the group consisting of carbonyl, F, Cl, Br, I, CN, NO$_2$, —NR$^3$R$^3$, —OR$^3$, —S(O)$_r$R$^4$, —S(O)$_r$NR$^3$R$^3$, —C(O)R$^3$, —C(O)OR$^3$, —OC(O)R$^3$, —C(O)NR$^3$R$^3$, —OC(O)NR$^3$R$^3$, C$_{1-6}$ acyl, aryl, substituted aryl, heteroaryl, and substituted heteroaryl;

R$^3$, at each occurrence, independently is selected from the group consisting of:
a) hydrogen, b) C$_{1-8}$ alkyl, c) C$_{2-8}$ alkenyl, d) C$_{2-8}$ alkynyl, e) C$_{1-8}$ acyl, f) saturated, unsaturated, or aromatic C$_{3-8}$ carbocycle, and g) saturated, unsaturated, or aromatic 5-10 membered heterocycle containing one or more heteroatoms selected from the group consisting of nitrogen, oxygen, and sulfur,
wherein any of b)-h) optionally is substituted with one or more moieties selected from the group consisting of carbonyl, F, Cl, Br, I, CN, NO$_2$, —NR$^6$R$^6$, —OR$^6$, —S(O)$_r$R$^6$, —S(O)$_r$NR$^6$R$^6$, —C(O)R$^6$, —C(O)OR$^6$, —OC(O)R$^6$, —C(O)NR$^6$R$^6$, —OC(O)NR$^6$R$^6$, C$_{1-6}$ acyl, aryl, substituted aryl, heteroaryl, and substituted heteroaryl;

alternatively, two R$^3$ groups, taken together with the atom to which they are bonded, form i) a 5-7 membered saturated or unsaturated carbocycle, or ii) a 5-7 membered saturated or unsaturated heterocycle containing one or more atoms selected from the group consisting of nitrogen, oxygen, and sulfur,
wherein i)-ii) optionally is substituted with one or more moieties selected from the group consisting of carbonyl, F, Cl, Br, I, CN, NO$_2$, —NR$^6$R$^6$, —OR$^6$, S(O)$_r$R$^6$, —S(O)$_r$NR$^6$R$^6$, —C(O)R$^6$, —C(O)OR$^6$, —OC(O)R$^6$, —C(O)NR$^6$R$^6$, —OC(O)NR$^6$R$^6$, C$_{1-6}$ acyl, aryl, substituted aryl, heteroaryl, and substituted heteroaryl;

R$^4$ is selected from the group consisting of:
a) hydrogen, b) —NR$^3$R$^3$, c) —NR$^3$OR$^3$, d) —NR$^3$NR$^3$R$^3$ e) —NHC(O)R$^3$, f) —C(O)NR$^3$R$^3$, g) —N$_3$, h) C$_{1-8}$ alkyl, i) C$_{2-8}$ alkenyl, j) C$_{2-8}$ alkynyl, k) saturated, unsaturated, or aromatic C$_{3-8}$ carbocycle, and l) saturated, unsaturated, or aromatic 5-10 membered heterocycle containing one or more heteroatoms selected from the group consisting of nitrogen, oxygen, and sulfur,
wherein any of h)-l) optionally is substituted with one or more moieties selected from the group consisting of carbonyl, F, Cl, Br, I, CN, NO$_2$, —NR$^3$R$^3$, —OR$^3$, —SR$^3$, —S(O)$_r$R$^5$, —S(O)$_r$NR$^3$R$^3$, —C(O)R$^3$, —C(O)OR$^3$, —OC(O)R$^3$, —C(O)NR$^3$R$^3$, —OC(O)NR$^3$R$^3$, C$_{1-6}$ alkyl, C$_{1-6}$ alkenyl, C$_{1-6}$ alkynyl, C$_{1-6}$ acyl, aryl, substituted aryl, heteroaryl, and substituted heteroaryl;

R$^5$ is selected from the group consisting of:
a) hydrogen, b) —NR$^3$R$^3$, c) —NR$^3$OR$^3$, d) —NR$^3$NR$^3$R$^3$ e) —NHC(O)R$^3$, f) —C(O)NR$^3$R$^3$, g) —N$_3$, h) C$_{1-8}$ alkyl, i) C$_{2-8}$ alkenyl, j) C$_{2-8}$ alkynyl, k) saturated, unsaturated, or aromatic C$_{3-8}$ carbocycle, and l) saturated, unsaturated, or aromatic 5-10 membered heterocycle containing one or more heteroatoms selected from the group consisting of nitrogen, oxygen, and sulfur,
wherein any of h)-l) optionally is substituted with one or more moieties selected from the group consisting of F, Cl, Br, I, CN, NO$_2$, —NR$^3$R$^3$, —OR$^3$, —SR$^3$—C(O)R$^3$, —C(O)OR$^3$, —OC(O) R$^3$, —C(O)NR$^3$R$^3$, —OC(O)NR$^3$R$^3$, C$_{1-6}$ alkyl, C$_{1-6}$ alkenyl, C$_{1-6}$ alkynyl, C$_{1-6}$ acyl, aryl, substituted aryl, heteroaryl, and substituted heteroaryl;

R$^6$, at each occurrence, independently is selected from the group consisting of:
hydrogen, C$_{1-6}$ alkyl, C$_{1-6}$ alkenyl, C$_{1-6}$ alkynyl, C$_{1-6}$ acyl, aryl, substituted aryl, heteroaryl, substituted heteroaryl;

alternatively, two R$^6$ groups taken together are —(CH$_2$)$_s$—,
wherein s is 1, 2, 3, 4, or 5;

D-E is:

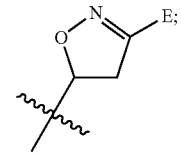

E is selected from the group consisting of:

a) 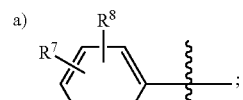

b) 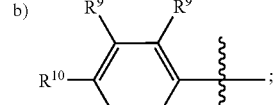

c) 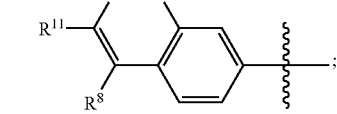

d) 5-10 membered aromatic heterocycle containing one or more heteroatoms selected from the group consisting of nitrogen, oxygen, and sulfur, and optionally substituted with one or more R$^{13}$ groups; and
e) C$_{5-10}$ aromatic carbocycle, optionally substituted with one or more R$^{13}$ groups;

R$^7$ is selected from the group consisting of:
a) hydrogen, b) carbonyl, c) formyl, d) F, e) Cl, f) Br, g) I, h) CN, i) NO$_2$, j) OR$^3$, k) —S(O)$_r$R$^5$, l) —S(O)$_t$N═R$^2$, m) —C(O)R$^2$, n) —C(O)OR$^3$, o) —OC(O)R$^2$, p) —C(O)NR$^2$R$^2$, q) —OC(O)NR$^2$R$^2$, r) —C(=NR$^{12}$)R$^2$, s) —C(R$^2$)(R$^2$)OR$^3$, t) —C(R$^2$)(R$^2$)OC(O)R$^2$, u) —C(R$^2$)(OR$^3$)(CH$_2$)$_r$NR$^2$R$^2$, v) —NR$^2$R$^2$, w) —NR$^2$OR$^3$, x) —N(R$^2$)C(O)R$^2$, y) —N(R$^2$)C(O)OR$^3$, z) —N(R$^2$)C(O)NR$^2$R$^2$, aa) —N(R$^2$)S(O)$_r$R$^5$, bb) —C(OR$^6$)(OR$^6$)R$^2$, cc) —C(R$^2$)(R$^3$)NR$^2$R$^2$, dd) —C(R$^2$)(R$^3$)NR$^2$R$^{12}$, ee) =NR$^{12}$, ff) —C(S)NR$^2$R$^2$, gg) —N(R$^2$)C(S)R$^2$, hh) —OC(S)NR$^2$R$^2$, ii) —N(R$^2$)C(S)OR$^3$, jj) —N(R$^2$)C(S)NR$^2$R$^2$, kk) —SC(O)R$^2$, ll) C$_{1-8}$ alkyl, mm) C$_{2-8}$ alkenyl, nn) C$_{2-8}$ alkynyl, oo) C$_{1-8}$ alkoxy, pp) C$_{1-8}$ alkylthio, qq) C$_{1-8}$ acyl, rr) saturated, unsaturated, or aromatic C$_{5-10}$ carbocycle, and ss) saturated, unsaturated, or aromatic 5-10 membered heterocycle containing one or more heteroatoms selected from the group consisting of nitrogen, oxygen, and sulfur, wherein any of ll)-ss) optionally is substituted with one or more moieties selected from the group consisting of:

carbonyl; formyl; F; Cl; Br; I; CN; NO$_2$; OR$^3$; —S(O)$_r$R$^5$; —S(O)$_r$N=R$^2$, —C(O)R$^2$; —C(O)OR$^3$; —OC(O)R$^2$; —C(O)NR$^2$R$^2$; —OC(O)NR$^2$R$^2$; —C(=NR$^{10}$)R$^2$; —C(R$^2$)(R$^2$)OR$^3$; —C(R$^2$)(R$^2$)OC(O)R$^2$; —C(R$^2$)(OR$^3$)(CH$_2$)$_r$NR$^2$R$^2$; —NR$^2$R$^2$; —NR$^2$OR$^3$; —NR$^2$C(O)R$^2$; —NR$^2$C(O)OR$^3$; —NR$^2$C(O)NR$^2$R$^2$; —NR$^2$S(O)$_r$R$^5$; —C(OR$^6$)(OR$^6$)R$^2$; —C(R$^2$)(R$^3$)NR$^2$R$^2$; —C(R$^2$)(R$^3$)NR$^2$R$^{12}$; =NR$^{12}$; —C(S)NR$^2$R$^2$; —NR$^2$C(S)R$^2$; —OC(S)NR$^2$R$^2$; —NR$^2$C(S)OR$^3$; —NR$^2$C(S)NR$^2$R$^2$; —SC(O)R$^2$; C$_{2-5}$ alkenyl; C$_{2-5}$ alkynyl; C$_{1-8}$ alkoxy; C$_{1-8}$ alkylthio; C$_{1-8}$ acyl; saturated, unsaturated, or aromatic C$_{5-10}$ carbocycle, optionally substituted with one or more R$^8$ groups; and saturated, unsaturated, or aromatic 5-10 membered heterocycle containing one or more heteroatoms selected from the group consisting of nitrogen, oxygen, and sulfur, and optionally substituted with one or more R$^8$ groups;

R$^8$ is selected from the group consisting of:

hydrogen; F; Cl; Br; I; CN; NO$_2$; OR$^6$; aryl; substituted aryl; heteroaryl; substituted heteroaryl; and C$_{1-6}$ alkyl, optionally substituted with one or more moieties selected from the group consisting of aryl, substituted aryl, heteroaryl, substituted heteroaryl, F, Cl, Br, I, CN, NO$_2$, and OR$^6$;

alternatively, R$^7$ and R$^8$ taken together are —O(CH$_2$)$_r$O—;

R$^9$, at each occurrence, independently is selected from the group consisting of:

hydrogen, F, Cl, Br, I, CN, OR$^3$, NO$_2$, —NR$^2$R$^2$, C$_{1-6}$ alkyl, C$_{1-6}$ acyl, and C$_{1-6}$ alkoxy;

R$^{10}$ is selected from the group consisting of:

a) saturated, unsaturated, or aromatic C$_{5-10}$ carbocycle,
b) saturated, unsaturated, or aromatic 5-10 membered heterocycle containing one or more heteroatoms selected from the group consisting of nitrogen, oxygen, and sulfur, c) —X—C$_{1-6}$ alkyl-saturated, unsaturated, or aromatic 5-10 membered heterocycle containing one or more heteroatoms selected from the group consisting of nitrogen, oxygen, and sulfur, d) saturated, unsaturated, or aromatic 10-membered bicyclic ring system optionally containing one or more heteroatoms selected from the group consisting of nitrogen, oxygen, and sulfur, e) saturated, unsaturated, or aromatic 13-membered tricyclic ring system optionally containing one or more heteroatoms selected from the group consisting of nitrogen, oxygen, and sulfur, and f) R$^9$, wherein any of a)-e) optionally is substituted with one or more R$^{13}$ groups, and X is O or NR$^3$;

alternatively, R$^{10}$ and one R$^9$ group, taken together with the atoms to which they are bonded, form a 5-7 membered saturated or unsaturated carbocycle, optionally substituted with one or more R$^{13}$ groups; or a 5-7 membered saturated or unsaturated heterocycle containing one or more atoms selected from the group consisting of nitrogen, oxygen, and sulfur, and optionally substituted with one or more R$^{13}$ groups;

R$^{11}$ at each occurrence, independently is selected from the group consisting of:

hydrogen; an electron-withdrawing group; aryl; substituted aryl; heteroaryl; substituted heteroaryl; and C$_{1-6}$ alkyl, optionally substituted with F, Cl, or Br;

alternatively, any R$^{11}$ and R$^8$, taken together with the atoms to which they are bonded, form a 5-7 membered saturated or unsaturated carbocycle, optionally substituted with one or more R$^{13}$ groups; or a 5-7 membered saturated or unsaturated heterocycle containing one or more atoms selected from the group consisting of nitrogen, oxygen, and sulfur, and optionally substituted with one or more R$^{13}$ groups;

R$^{12}$ is selected from the group consisting of:

—NR$^2$R$^2$, —OR$^3$, —OC(O)R$^2$, —OC(O)OR$^3$, —NR$^2$C(O)R$^2$, —NR$^2$C(O)NR$^2$R$^2$, —NR$^2$C(S)NR$^2$R$^2$, and —NR$^2$C(=NR$^2$)NR$^2$R$^2$;

R$^{13}$, at each occurrence, independently is selected from the group consisting of:

a) hydrogen, b) carbonyl, c) formyl d) F, e) Cl, f) Br, g) I, h) CN, i) NO$_2$, j) OR$^3$, k) —S(O)$_r$R$^5$, l) —S(O)$_r$N=R$^3$, m) —C(O)R$^2$, n) —C(O)OR$^3$, o) —OC(O)R$^2$ p) —C(O)NR$^2$R$^2$, q) —OC(O)NR$^2$R$^2$, r) —C(=NR$^{12}$)R$^2$, s) —C(R$^2$)(R$^2$)OR$^3$, t) —C(R$^2$)(R$^2$)OC(O)R$^2$, u) —C(R$^2$)(OR$^3$)(CH$_2$)$_r$NR$^2$R$^2$, v) —NR$^2$R$^2$, w) —NR$^2$OR$^3$, x) —N(R$^2$)C(O)R$^2$, y) —N(R$^2$)C(O)OR$^3$, z) —N(R$^2$)C(O)NR$^2$R$^2$, aa) —N(R$^2$)S(O)$_r$R$^5$, bb) —C(OR$^6$)(OR$^6$)R$^2$, cc) —C(R$^2$)(R$^3$)NR$^2$R$^2$, dd) —C(R$^2$)(R$^3$)NR$^2$R$^{12}$, ee) =NR$^{12}$, ff) —C(S)NR$^2$R$^2$, gg) —N(R$^2$)C(S)R$^2$, hh) —OC(S)NR$^2$R$^2$, ii) —N(R$^2$)C(S)OR$^3$, jj) —N(R$^2$)C(S)NR$^2$R$^2$, kk) —SC(O)R$^2$, ll) C$_{1-8}$ alkyl, mm) C$_{2-8}$ alkenyl, nn) C$_{2-8}$ alkynyl, oo) C$_{1-8}$ alkoxy, pp) C$_{1-8}$ alkylthio, qq) C$_{1-8}$ acyl, rr) saturated, unsaturated, or aromatic C$_{5-10}$ carbocycle, ss) saturated, unsaturated, or aromatic 5-10 membered heterocycle containing one or more heteroatoms selected from the group consisting of nitrogen, oxygen, and sulfur, tt) saturated, unsaturated, or aromatic 10-membered bicyclic ring system optionally containing one or more heteroatoms selected from the group consisting of nitrogen, oxygen, and sulfur, and uu) saturated, unsaturated, or aromatic 13-membered tricyclic ring system optionally containing one or more heteroatoms selected from the group consisting of nitrogen, oxygen, and sulfur, wherein any of ll)-uu) optionally is substituted with one or more moieties selected from the group consisting of:

carbonyl; formyl; F; Cl; Br; I; CN; NO$_2$; OR$^3$; —S(O)$_r$R$^5$; —S(O)$_r$N=R$^2$, —C(O)R$^2$; —C(O)OR$^3$; —OC(O)R$^2$; —C(O)NR$^2$R$^2$; —OC(O)NR$^2$R$^2$; —C(=NR$^{12}$)R$^2$; —C(R$^2$)(R$^2$)OR$^3$;

—C(R²)(R²)OC(O)R²; —C(R²)(OR³)(CH₂)ᵣNR²R²; —NR²R²; —NR²OR³; —NR²C(O)R²; —NR²C(O)OR³; —NR²C(O)NR²R²; —NR²S(O)ᵣR⁵; —C(OR⁶)(OR⁶)R²; —C(R²)(R³)NR²R²; —C(R²)(R³)NR²R¹²; =NR¹²; —C(S)NR²R²; —NR²C(S)R²; —OC(S)NR²R²; —NR²C(S)OR³; —NR²C(S)NR²R²; —SC(O)R²; C₁₋₈ alkyl, C₂₋₈ alkenyl; C₂₋₈ alkynyl; C₁₋₈ alkoxy; C₁₋₈ alkylthio; C₁₋₈ acyl; saturated, unsaturated, or aromatic C₃₋₁₀ carbocycle optionally substituted with one or more R⁷ groups; and saturated, unsaturated, or aromatic 3-10 membered heterocycle containing one or more heteroatoms selected from the group consisting of nitrogen, oxygen, and sulfur, and substituted with one or more R⁷ groups;

G is selected from the group consisting of:

a)
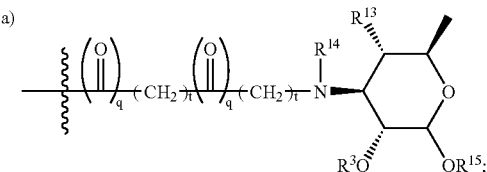

b)
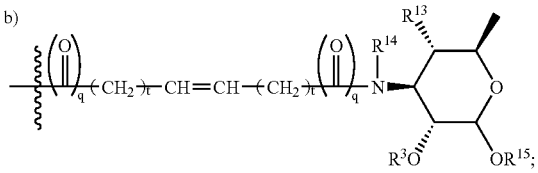

and c)
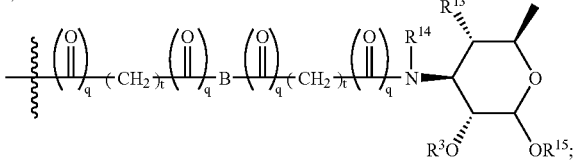

t, at each occurrence, independently is 0, 1, 2, or 3;

R¹⁴ is selected from the group consisting of:
a) hydrogen, b) C₁₋₆-alkyl, c) C₂₋₆ alkenyl, d) C₂₋₆ alkynyl, e) —C(O)—R³, f) —C(O)—C₁₋₆ alkyl-R³, g) —C(O)—C₂₋₆ alkenyl-R³, h) —C(O)—C₂₋₆ alkynyl-R³, i) —C₁₋₆ alkyl-J-R³, j) —C₂₋₆ alkenyl-J-R³; and k) —C₂₋₆ alkynyl-J-R³;
wherein
(i) any of b)-d) optionally is substituted with one or more substituents selected from the group consisting of:
F, Cl, Br, I, aryl, substituted aryl, heteroaryl, substituted heteroaryl, —OR³, —O—C₁₋₆ alkyl-R², —O—C₂₋₆ alkenyl-R², —O—C₂₋₆ alkynyl-R², and —NR²R²; and
(ii) J is selected from the group consisting of:
—OC(O)—, —OC(O)O—, —OC(O)NR²—, —C(O)NR²—, —NR²C(O)—, —NR²C(O)O—, —NR²C(O)NR²—, —NR²C(NH)NR²—, and S(O)ᵣ; and R¹⁵ is selected from the group consisting of:
hydrogen; C₁₋₁₀ alkyl, optionally substituted with one or more R¹³ groups; C₁₋₆ acyl, optionally substituted with one or more R¹³ groups; aryl; substituted aryl; heteroaryl; substituted heteroaryl; arylalkyl; substituted arylalkyl; and a macrolide.

2. The compound according to claim 1, having the formula:

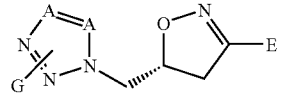

wherein A, E, and G are as defined in claim 1.

3. The compound according to claim 1, wherein E has the formula:

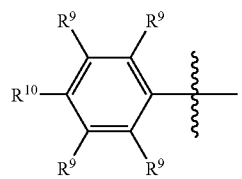

wherein R⁹ and R¹⁰, at each occurrence, are as defined in claim 1.

4. The compound according to claim 1, wherein E has the formula:

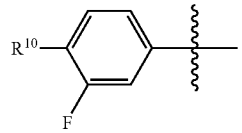

wherein R¹⁰ is as defined in claim 1.

5. The compound according to claim 3, wherein R¹⁰ has the formula:

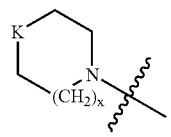

wherein
K is selected from the group consisting of O, NR², and S(O)ᵣ, and
x is 0, 1, 2, or 3.

6. The compound according to claim 5, wherein K is oxygen.

7. The compound according to claim 5, wherein x is 1.

8. The compound according to claim 1, wherein G has the formula:

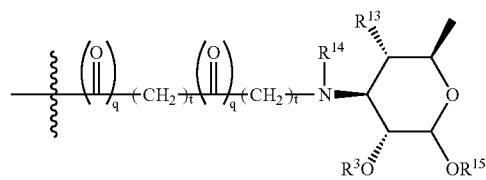

and R¹⁵ is a macrolide.

9. The compound according to claim 1, wherein G has the formula:

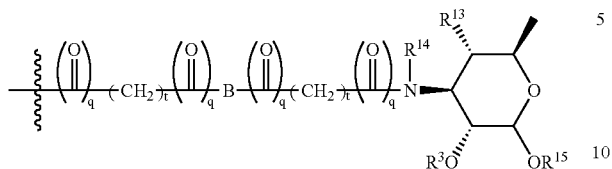

and $R^{15}$ is a macrolide.

10. The compound according to claim 1, wherein G has the formula:

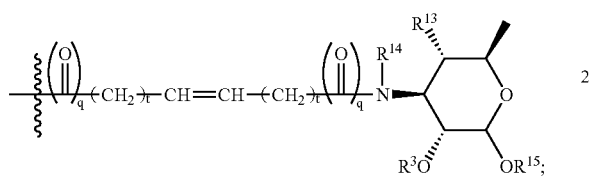

and $R^{15}$ is a macrolide.

11. The compound according to claim 1, wherein $R^{15}$ is selected from the group consisting of:

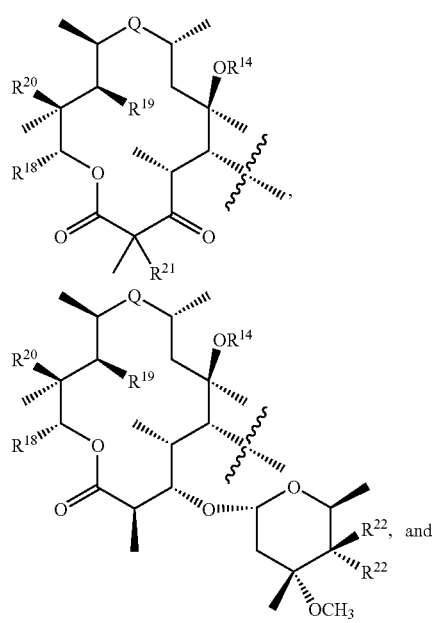

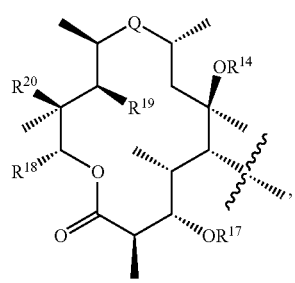

and pharmaceutically acceptable salts, esters and prodrugs thereof wherein $R^{17}$ is selected from the group consisting of:
hydrogen, hydroxy protecting group, $R^3$, and —V—W—$R^{13}$,
wherein
V is —C(O), —C(O)O—, —C(O)$NR^2$—, or absent, and
W is $C_{1-6}$ alkyl, or absent;
alternatively $R^{17}$ and $R^{14}$, taken together with the atoms to which they are bonded, form:

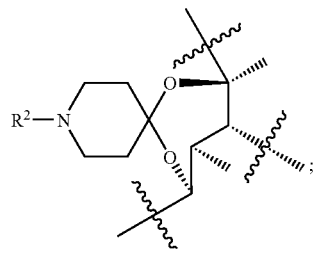

Q is selected from the group consisting of:
—$NR^2CH_2$—, —$CH_2$—$NR^2$—, —C(O)—, —C(=$NR^2$)—, —C(=$NOR^3$)—, —C(=N—$NR^2R^2$)—, —CH($OR^3$)—, and —CH($NR^2R^2$)—;

$R^{18}$ is selected from the group consisting of:
i) $C_{1-6}$ alkyl, ii) $C_{2-6}$ alkenyl, and iii) $C_{2-6}$ alkynyl;
wherein any of i)-iii) optionally is substituted with one or more moieties selected from the group consisting of —$OR^3$, aryl, substituted aryl, heteroaryl, and substituted heteroaryl;

$R^{19}$ is selected from the group consisting of:
a) —$OR^{17}$, b) $C_{1-6}$ alkyl, c) $C_{2-6}$ alkenyl, d) $C_{2-6}$ alkynyl, e) —$NR^2R^2$, f) —C(O)$R^3$, g) —C(O)—$C_{1-6}$ alkyl-$R^{13}$, h) —C(O)—$C_{2-6}$ alkenyl-$R^{13}$, and i) —C(O)—$C_{2-6}$ alkynyl-$R^{13}$,
wherein any of b)-d) optionally is substituted with one or more $R^{13}$ groups;
alternatively, $R^{14}$ and $R^{19}$, taken together with the atoms to which they are bonded, form:

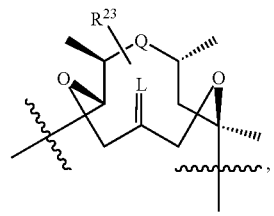

wherein
L is CH or N, and
$R^{23}$ is —$OR^3$, or $R^3$;
$R^{20}$ is —$OR^{17}$;
alternatively, $R^{19}$ and $R^{20}$, taken together with the atoms to which they are bonded, form a 5-membered ring by attachment to each other through a linker selected from the group consisting of:
—OC($R^2$)($R^2$)O—, —OC(O)O—, —OC(O)$NR^2$—, —$NR^2$C(O)O—, —OC(O)$NOR^3$—, —N($OR^3$)C(O)O—, —OC(O)N—$NR^2R$ —, —N($NR^2R^2$)C(O)O—, —OC(O)$CHR^2$—, —$CHR^2$C(O)O—, —OC(S)O—, —OC(S)$NR^2$—, —$NR^2$C(S)O—, —OC(S)

NOR³—, —N(OR³)C(S)O—, —OC(S)N—
NR²R²—, —N(NR²R²)C(S)O—, —OC(S)CHR²—,
and —CHR²C(S)O—;

alternatively, Q, $R^{19}$, and $R^{20}$, taken together with the atoms to which they are bonded, form:

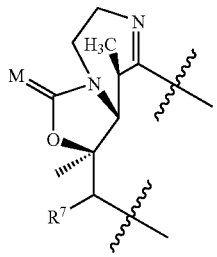

wherein

M is O or $NR^2$;

$R^{21}$ is selected from the group consisting of:
hydrogen, F, Cl, Br, and $C_{1-6}$ alkyl;

$R^{22}$, at each occurrence, independently is selected from the group consisting of:
hydrogen, —OR³, —O-hydroxy protecting group, —O—$C_{1-6}$ alkyl-J-$R^{13}$, —O—$C_{2-6}$ alkenyl-J-$R^{13}$, —O—$C_{1-6}$ alkynyl-J-$R^{13}$, and —NR²R²;

alternatively, two $R^{22}$ groups taken together are =O, =N—OR³, or =N—NR²R²; and $R^2$, $R^3$, $R^{13}$, $R^{14}$, and J are as described in claim 1.

12. The compound according to claim 1, wherein G has the formula selected from the group consisting of:

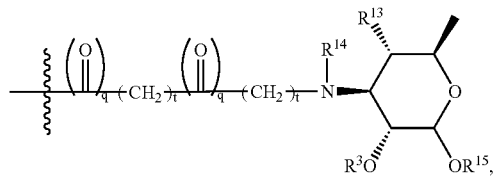

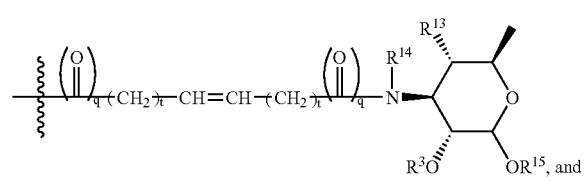

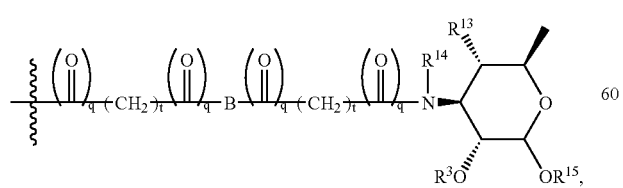

and $R^{15}$ has the formula selected from the group consisting of:

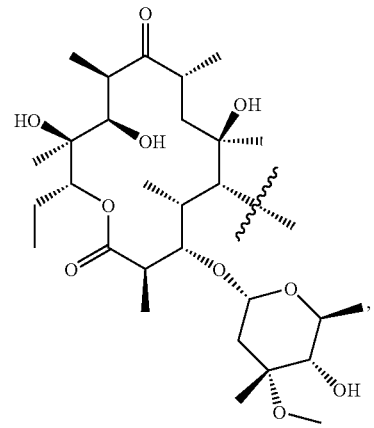

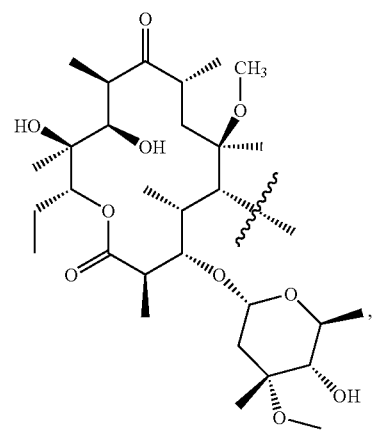

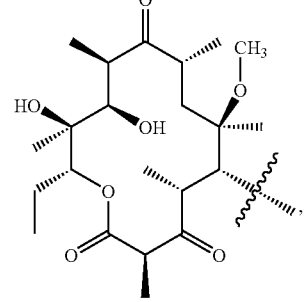

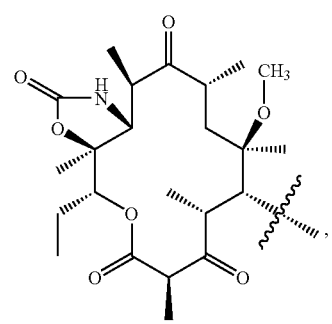

413
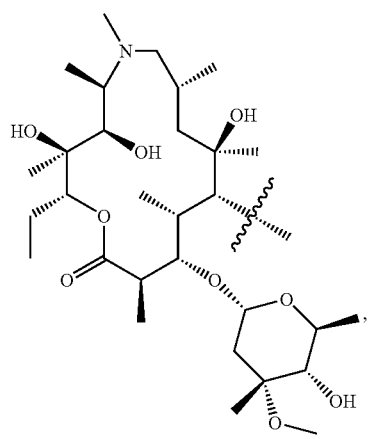
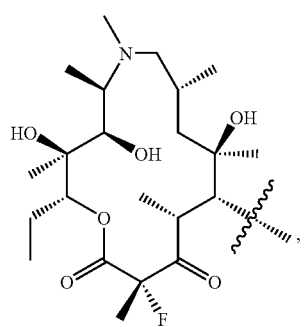
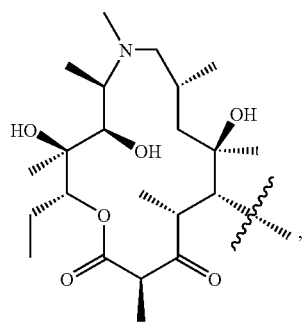
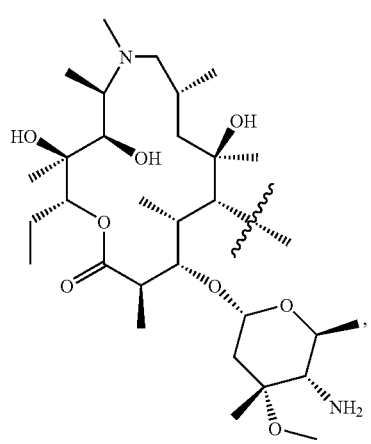
414
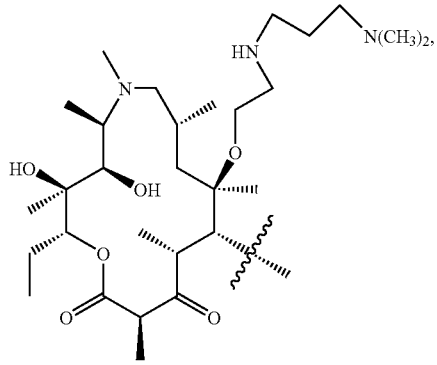
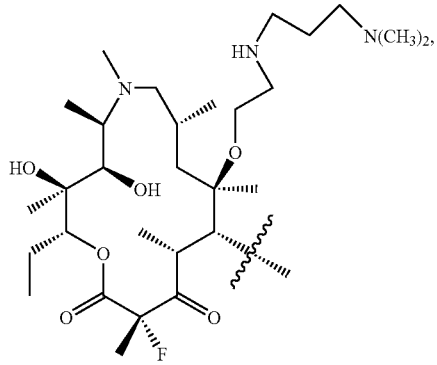
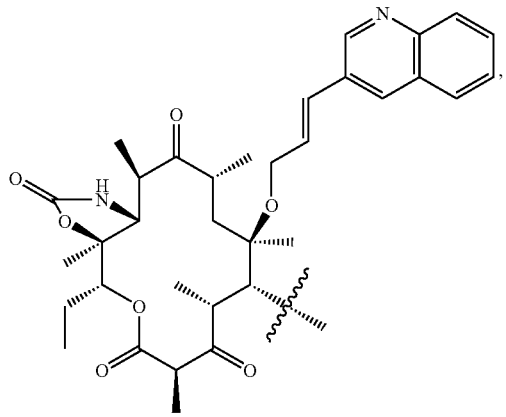
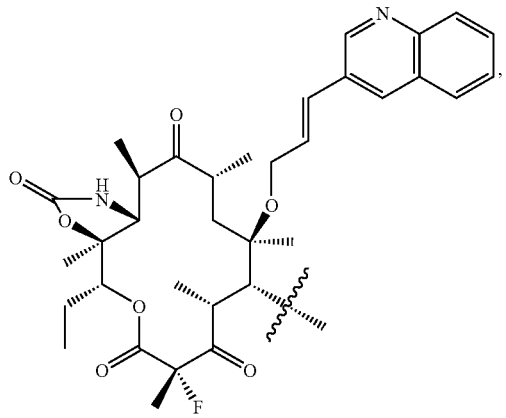

415
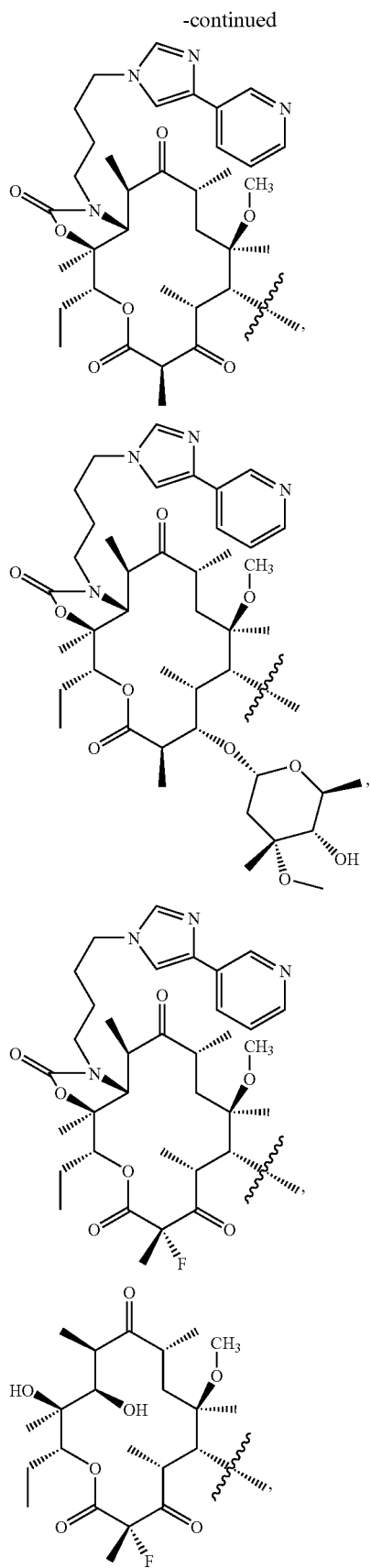
416
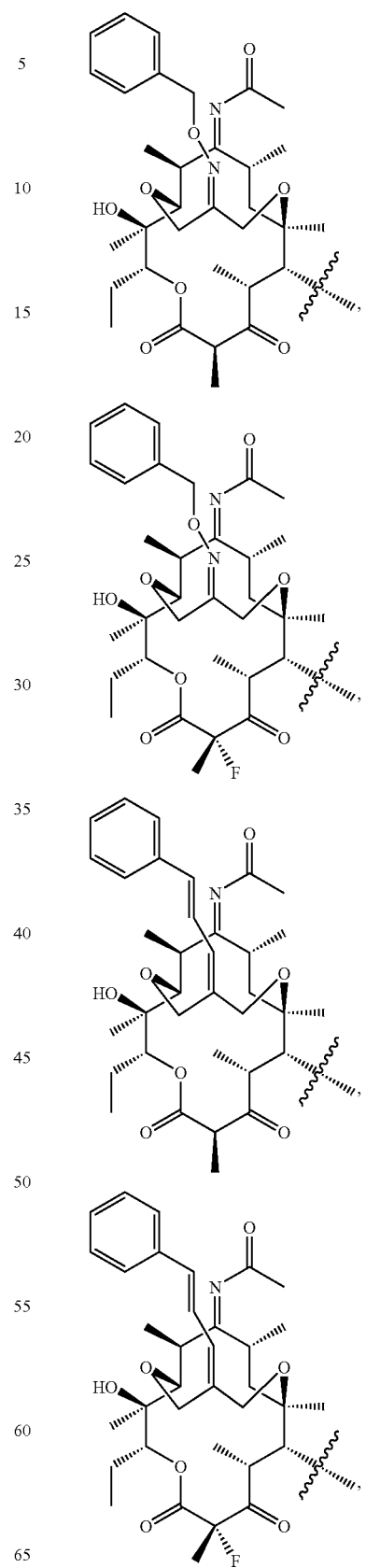

-continued
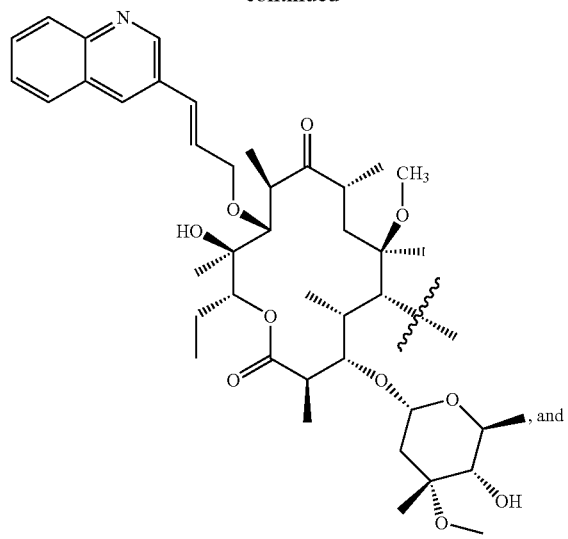, and
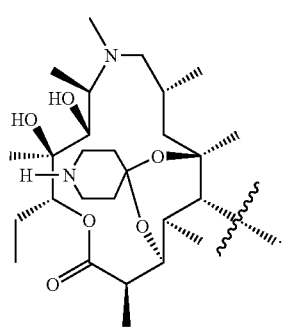
13. The compound according to claim 1, wherein G has the formula:
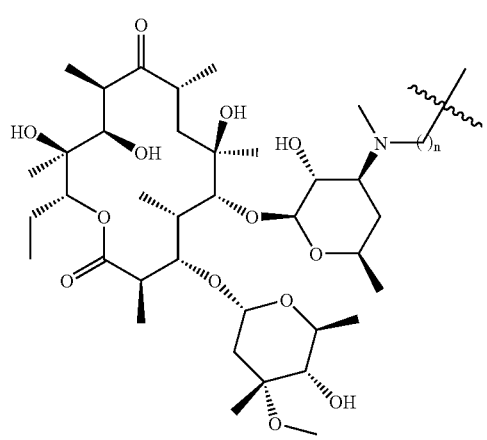
wherein n=1, 2, 3, or 4.
14. The compound according to claim 1, wherein G has the formula:
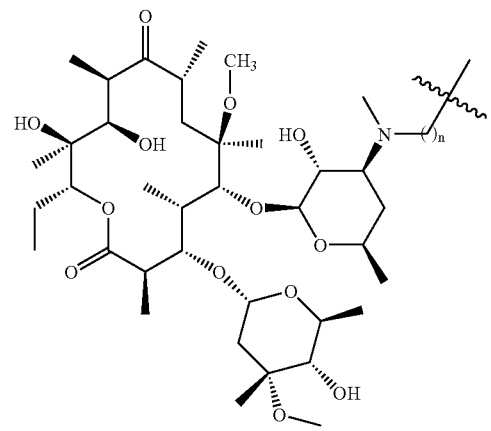
wherein n=1, 2, 3, or 4.
15. The compound according to claim 1 wherein G has the formula selected from the group consisting of:
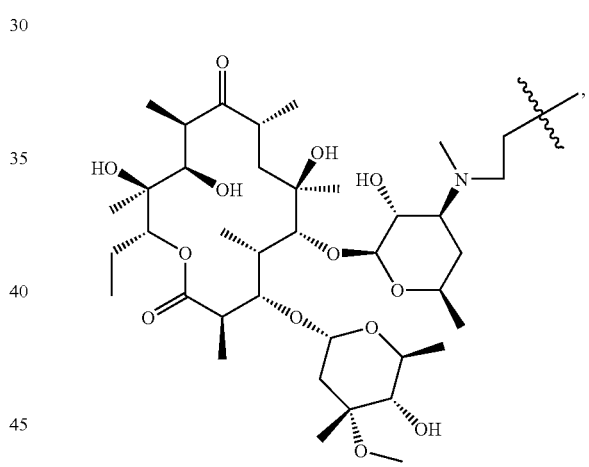
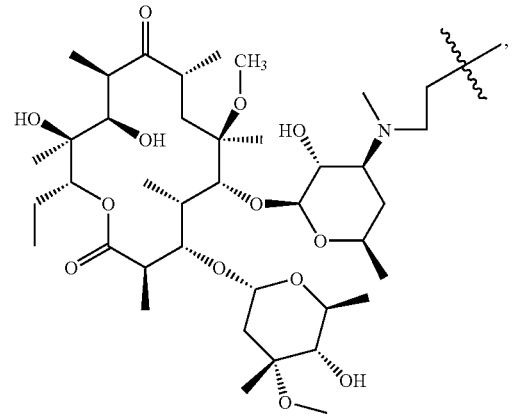

419
-continued
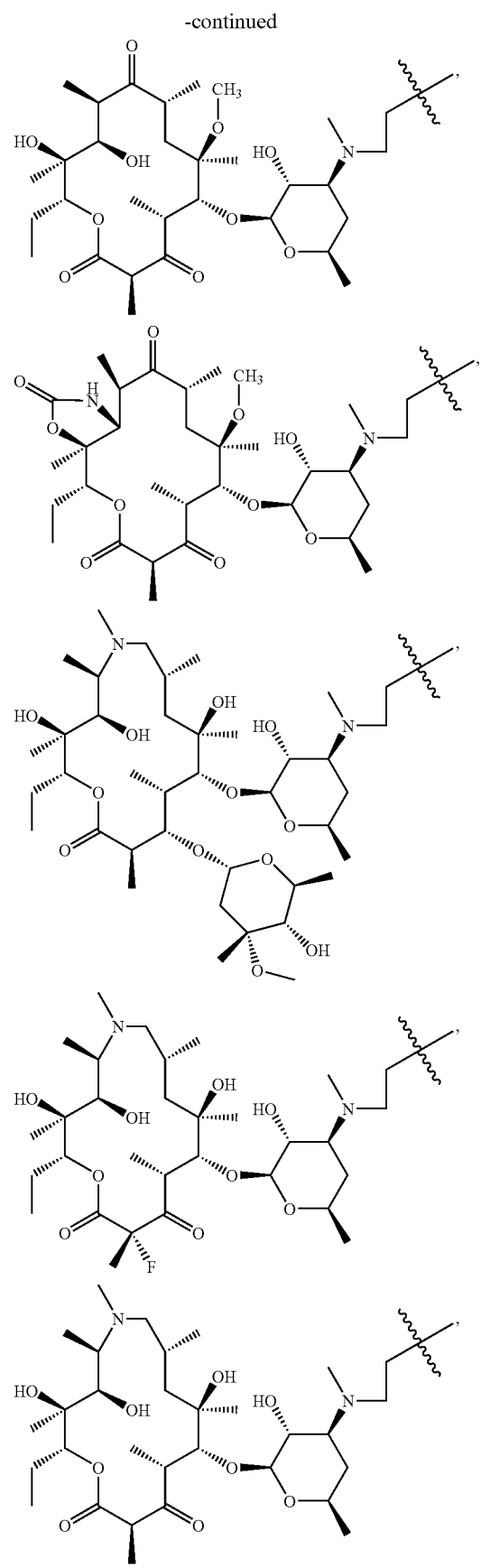
420
-continued
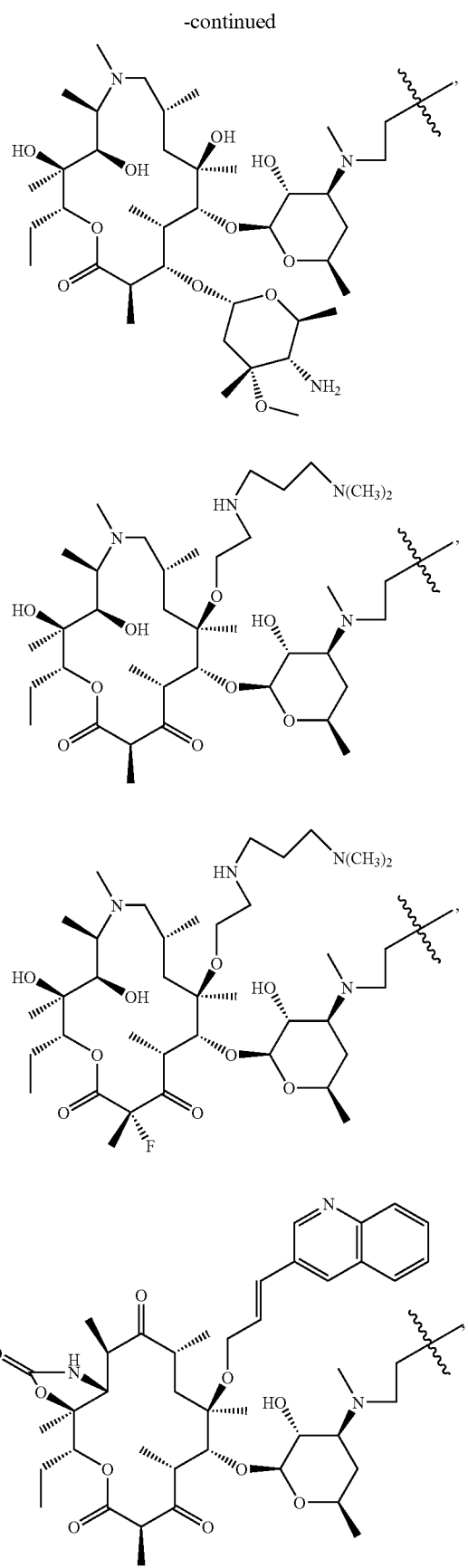

421 422
-continued -continued
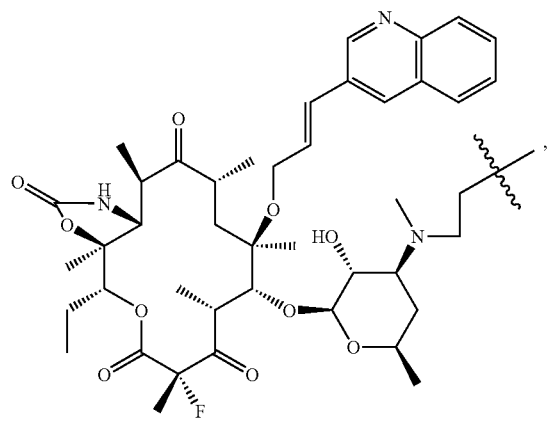
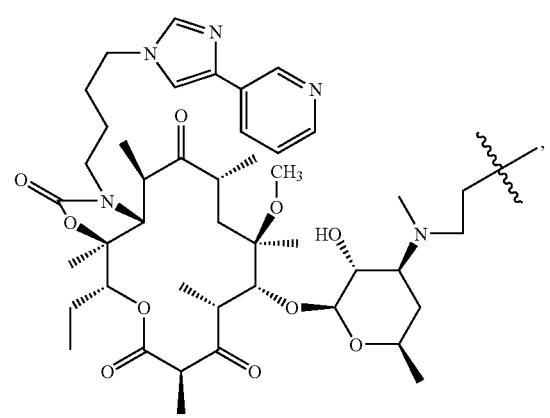
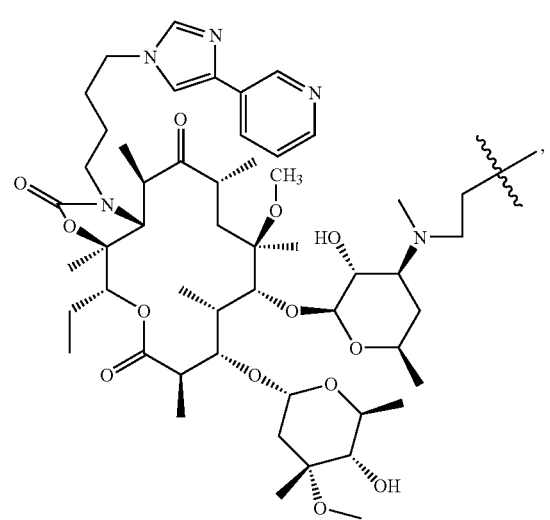
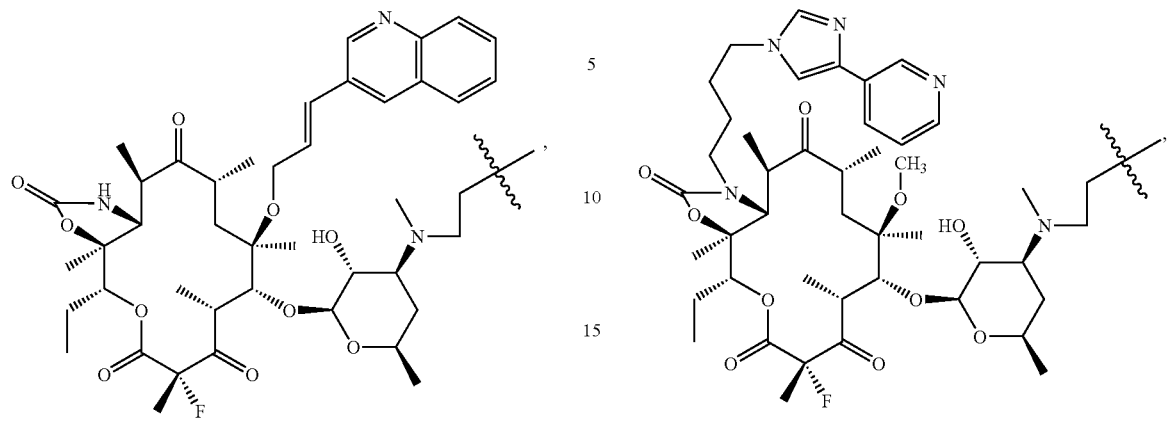

423
-continued
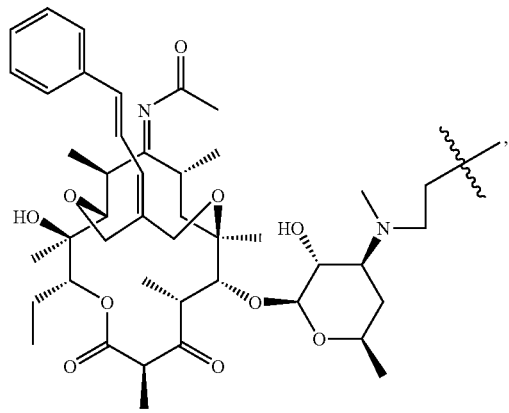
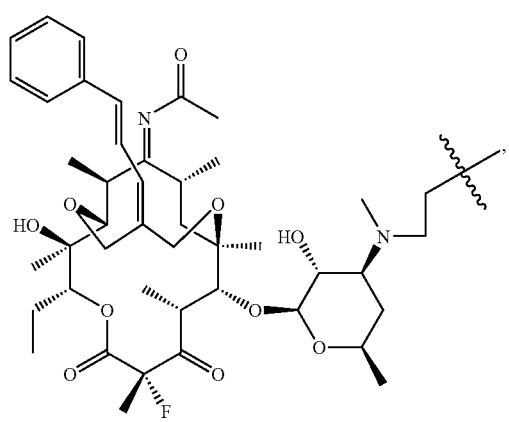
424
-continued
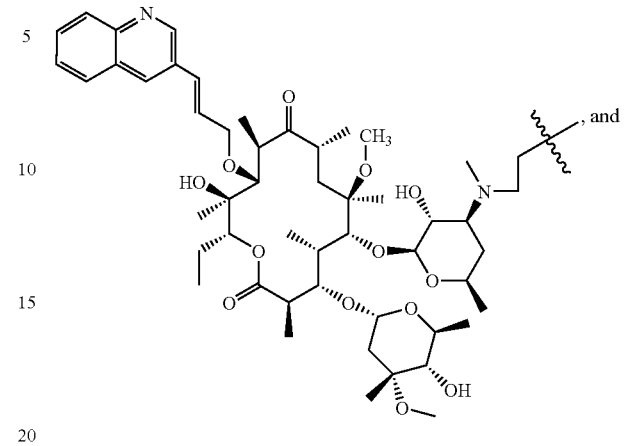
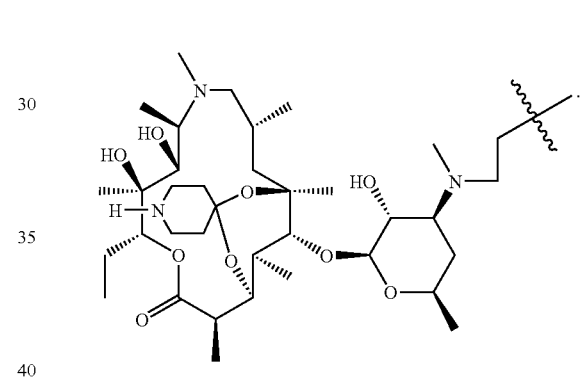
16. A compound having the structure corresponding to any of the structures listed below:
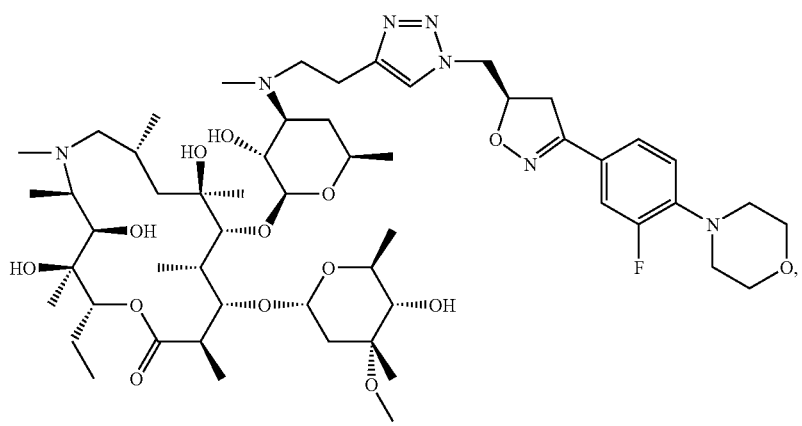

-continued
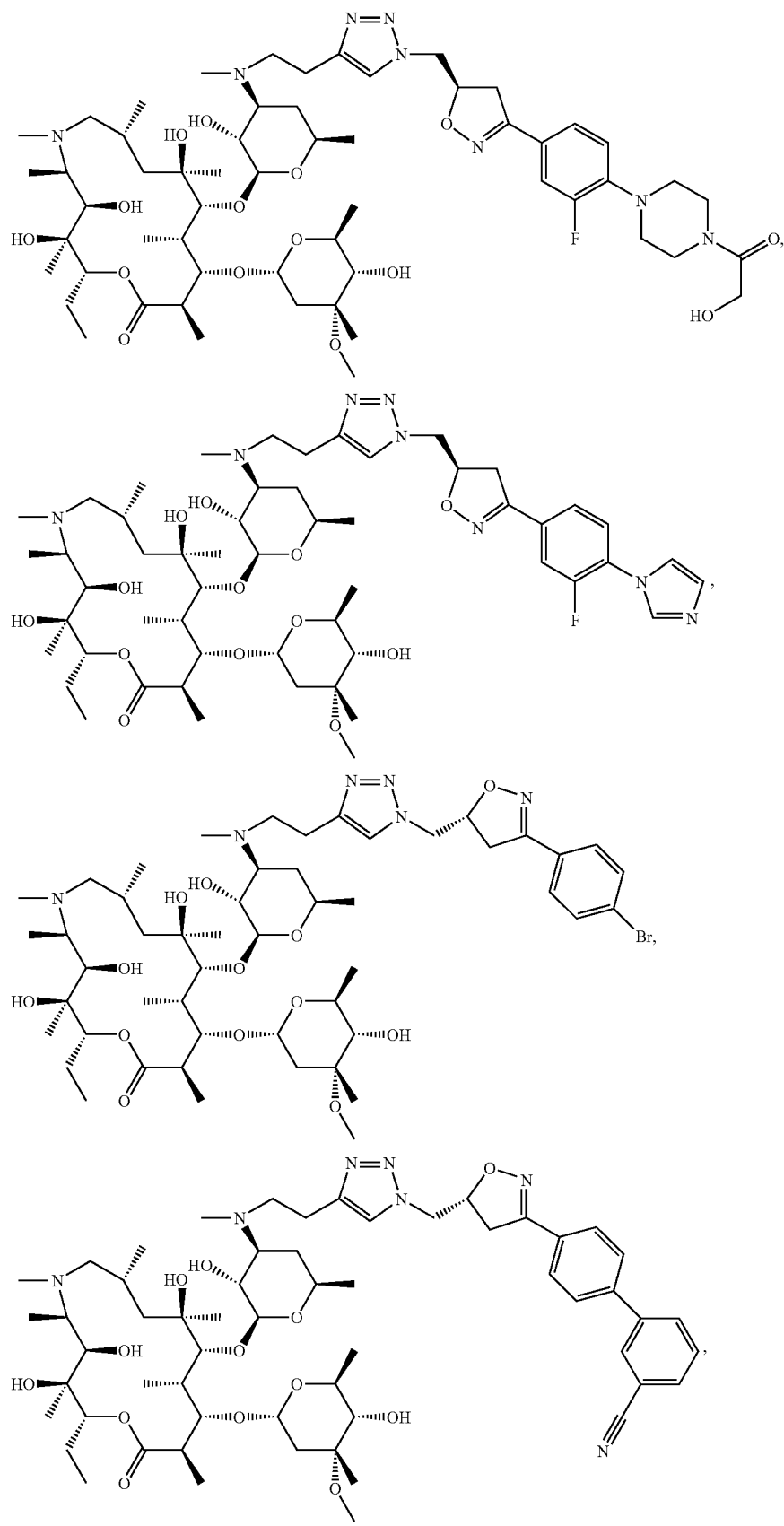

-continued
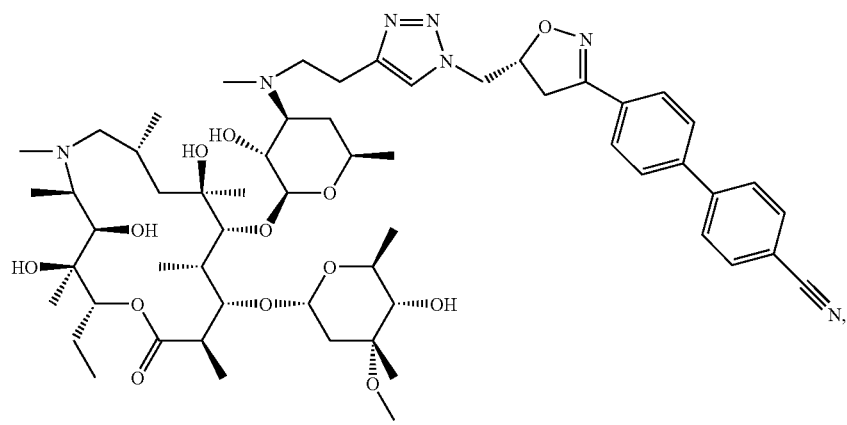
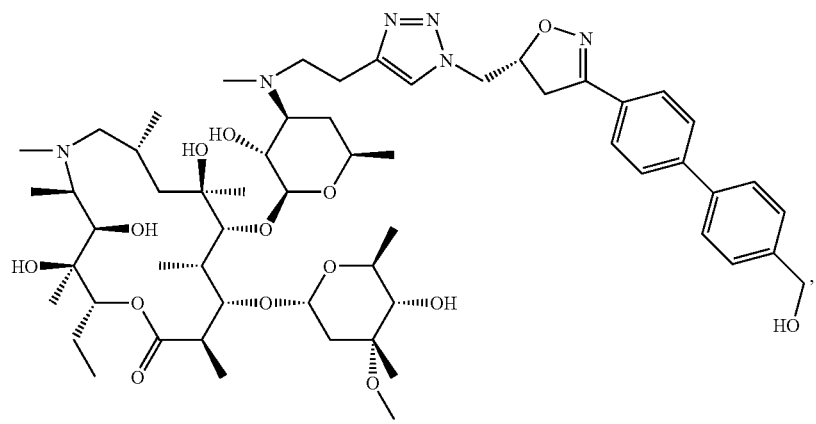
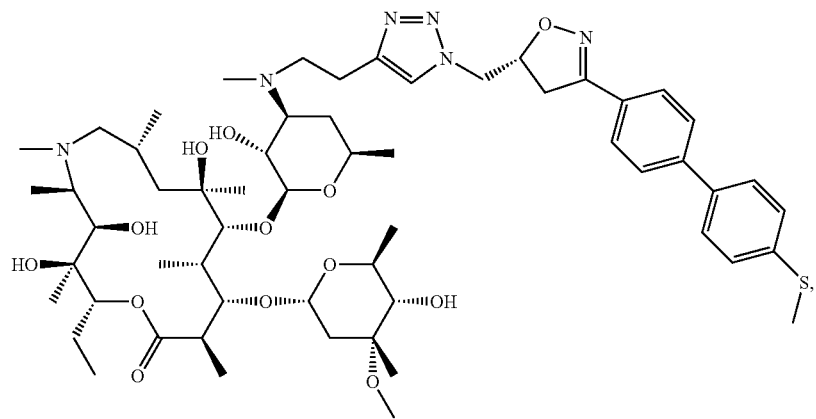

-continued
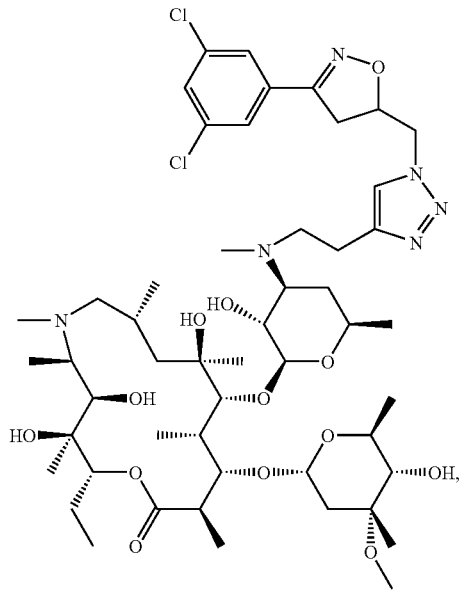
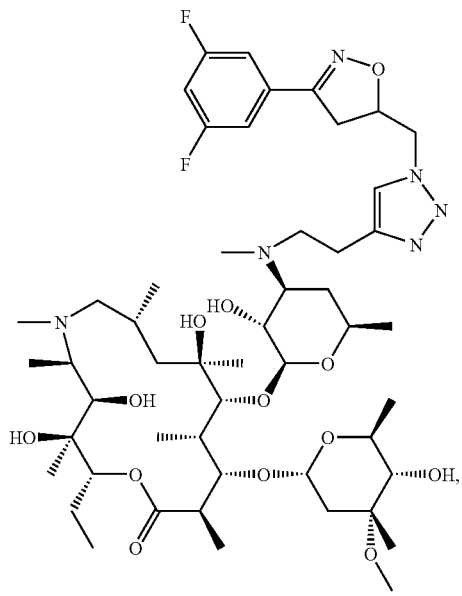
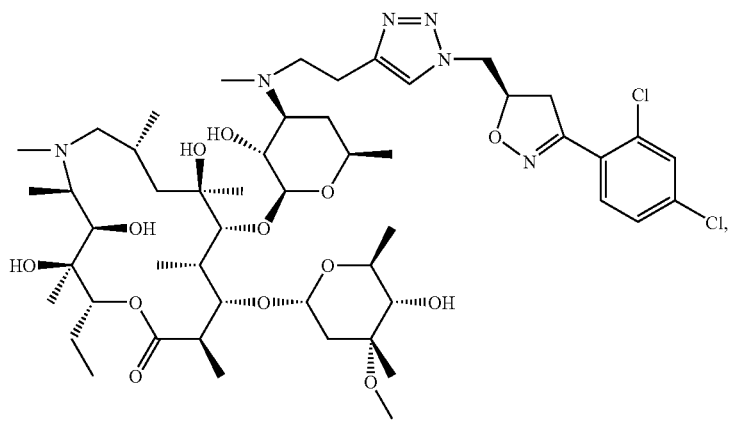

-continued
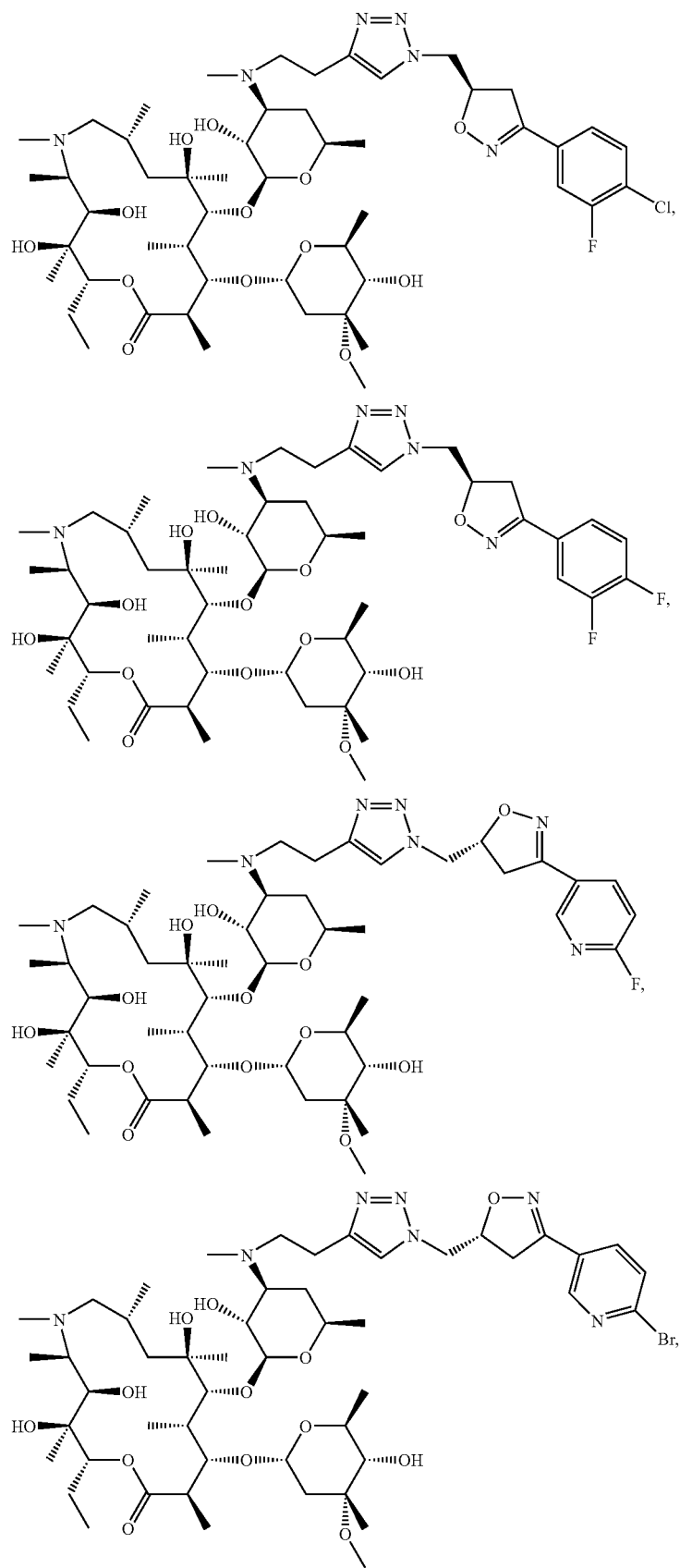

-continued
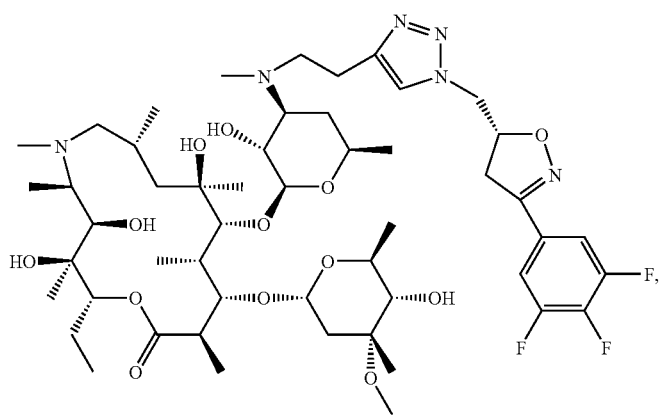
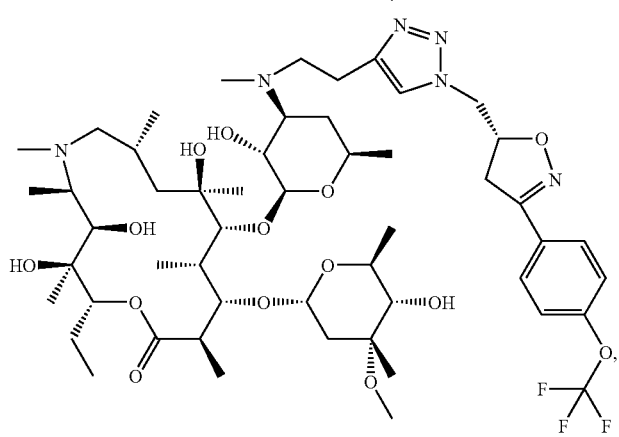
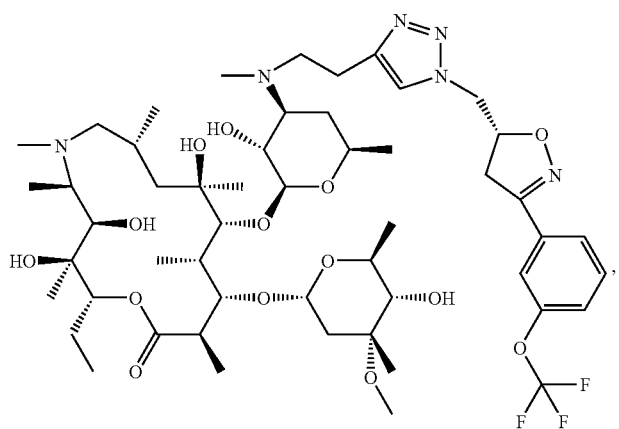
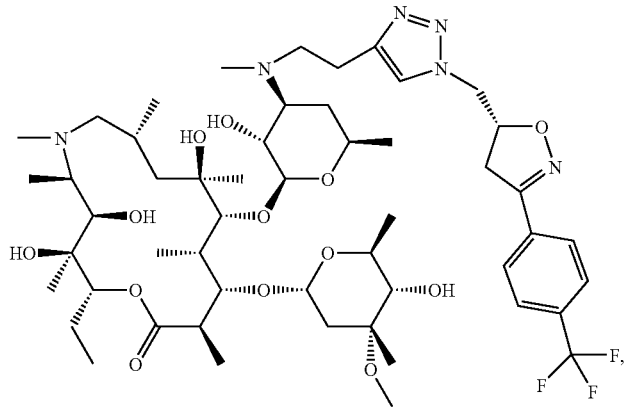

-continued
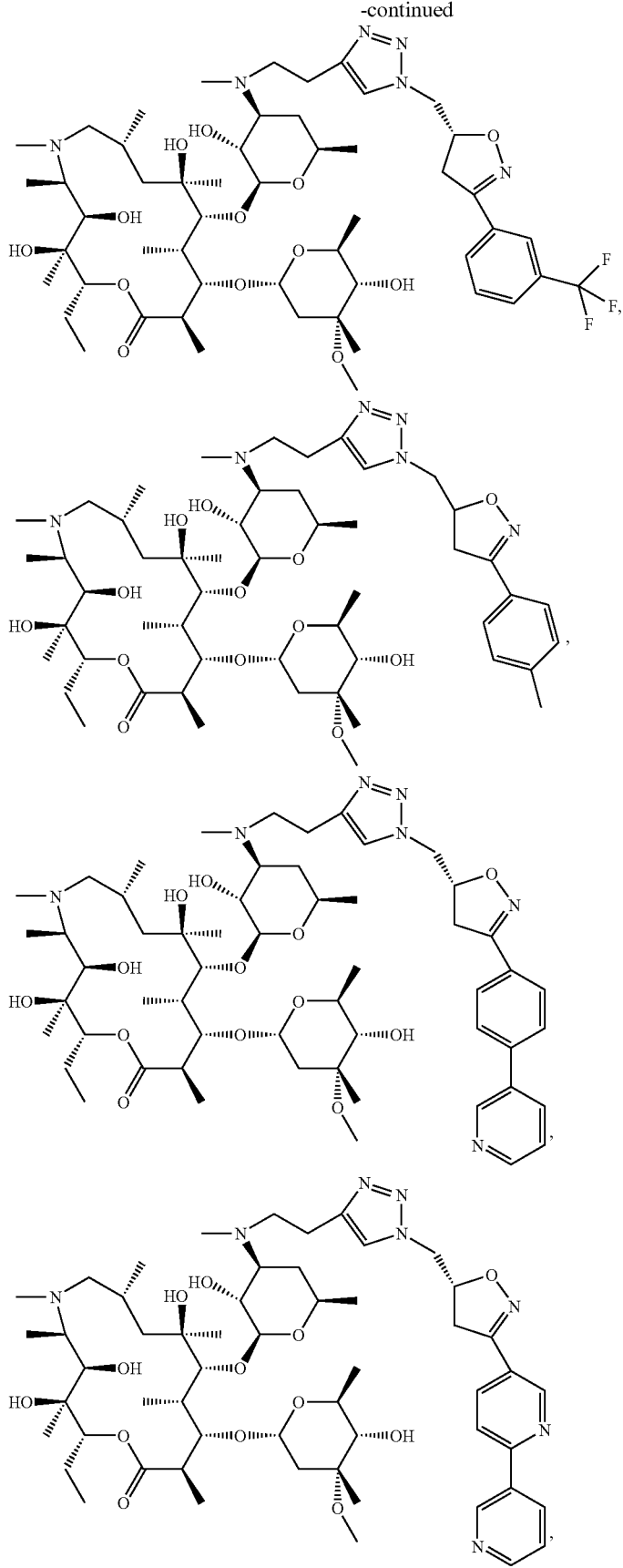

-continued
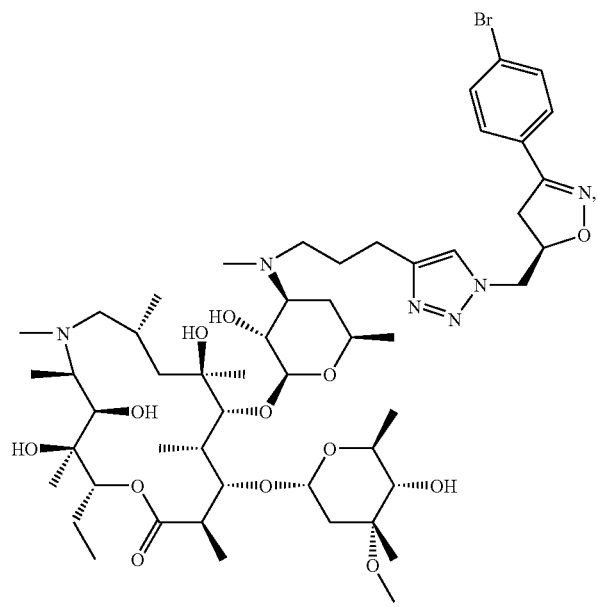
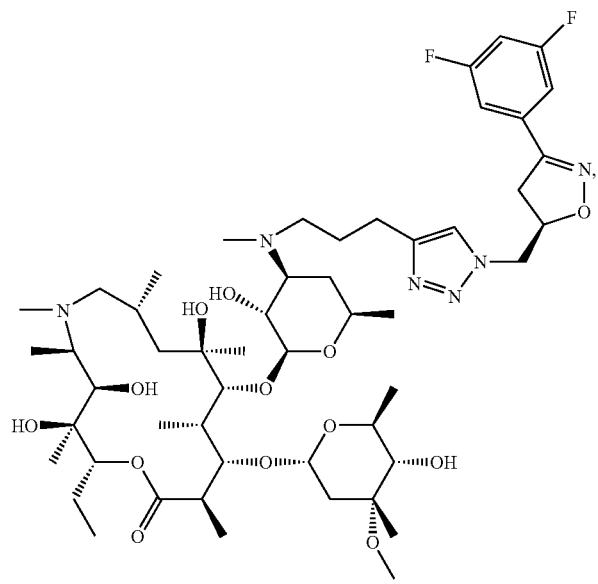

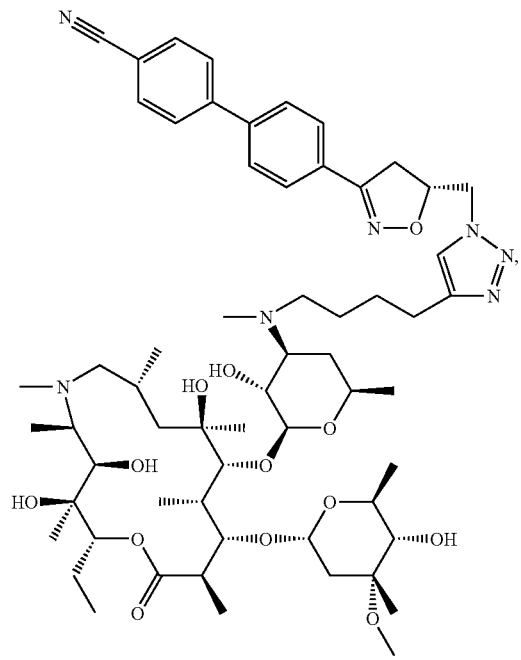
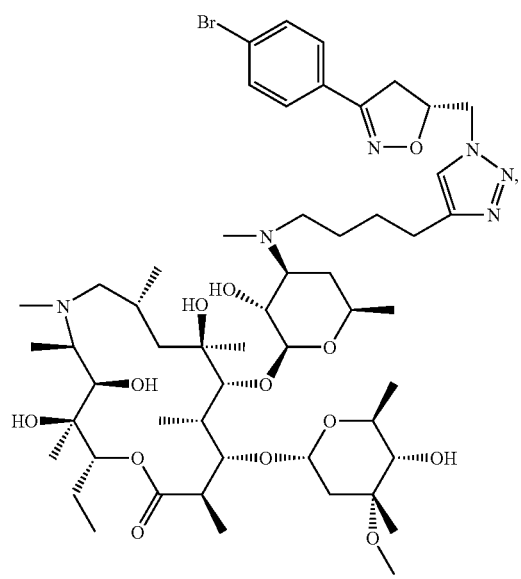

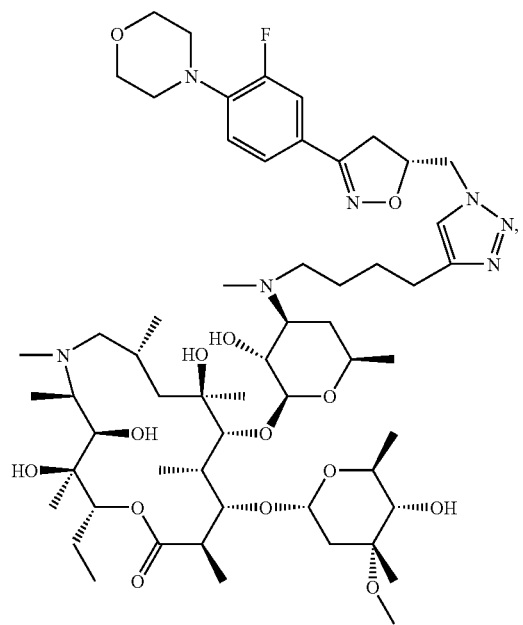
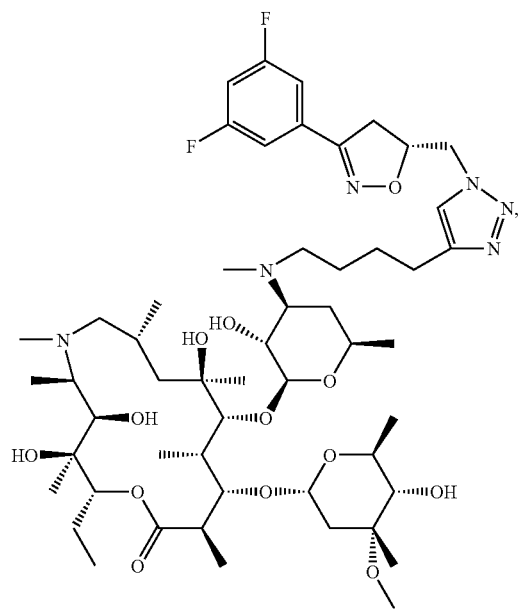

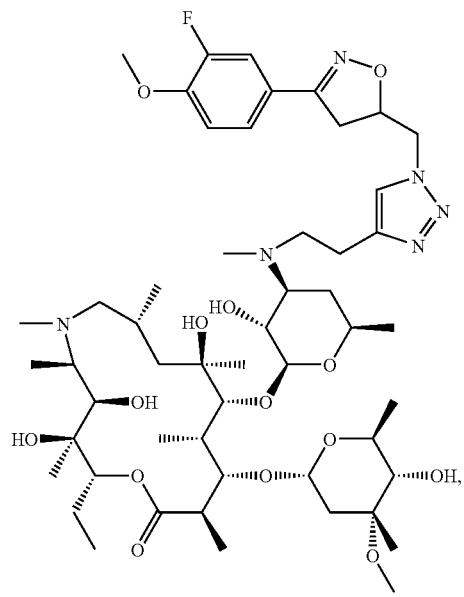
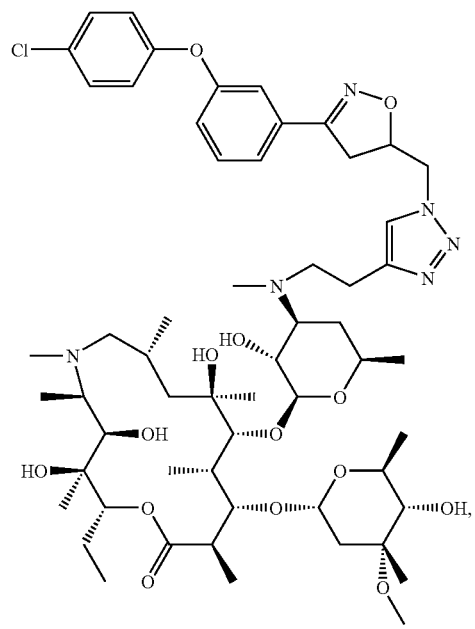

-continued
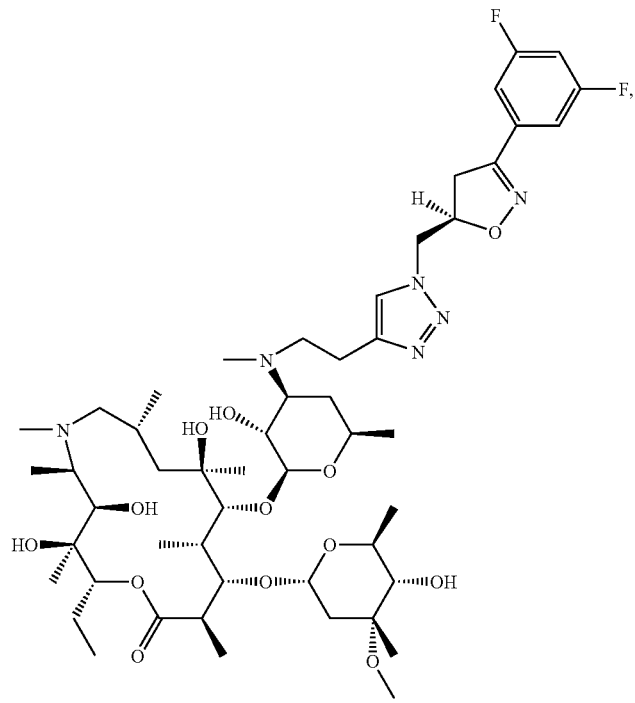
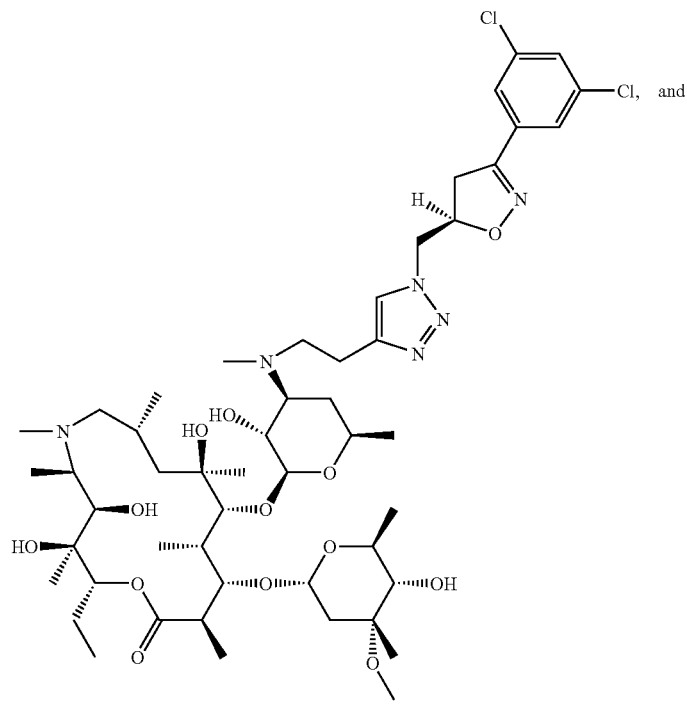

-continued

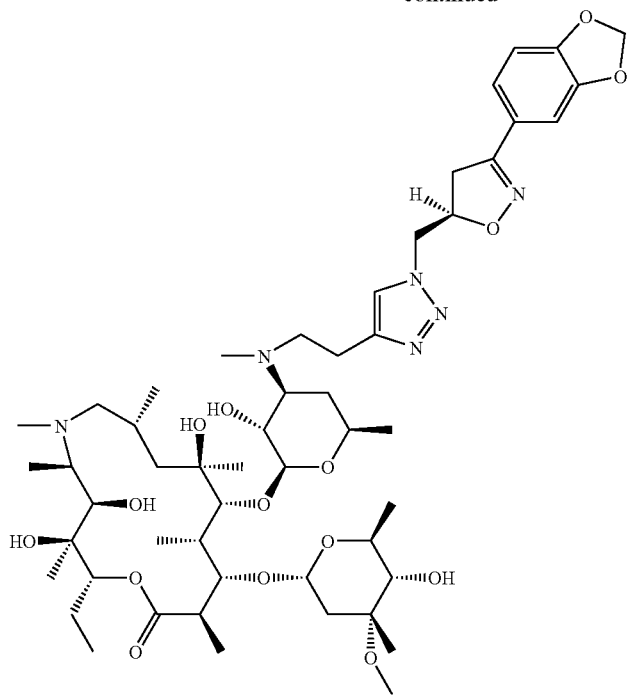

17. A pharmaceutical composition comprising a compound according to claim 1 and a pharmaceutically acceptable carrier.

18. A pharmaceutical composition comprising a compound according to claim 8 and a pharmaceutically acceptable carrier.

19. A pharmaceutical composition comprising a compound according to claim 9 and a pharmaceutically acceptable carrier.

20. A pharmaceutical composition comprising a compound according to claim 1 and a pharmaceutically acceptable carrier.

21. A pharmaceutical composition comprising a compound according to claim 16 and a pharmaceutically acceptable carrier.

* * * * *